US012522594B2

(12) United States Patent
Gutcher et al.

(10) Patent No.: US 12,522,594 B2
(45) Date of Patent: *Jan. 13, 2026

(54) 2-HETEROARYL-3-OXO-2,3-DIHYDROPYRIDAZINE-4-CARBOXAMIDES FOR THE TREATMENT OF CANCER

(71) Applicant: Deutsches Krebsforschungszentrum, Heidelberg (DE)

(72) Inventors: Ilona Gutcher, Berlin (DE); Ulrike Röhn, Berlin (DE); Norbert Schmees, Berlin (DE); Ludwig Zorn, Berlin (DE); Lars Röse, Berlin (DE); Benjamin Bader, Berlin (DE); Christina Kober, Lollar (DE); Rafael Carretero, Heidelberg (DE); Detlef Stöckigt, Potsdam (DE); Horst Irlbacher, Berlin (DE); Michael Platten, Heidelberg (DE)

(73) Assignee: Deutsches Krebsforschungszentrum (DE)

( * ) Notice: Subject to any disclaimer, the term of this patent is extended or adjusted under 35 U.S.C. 154(b) by 584 days.

This patent is subject to a terminal disclaimer.

(21) Appl. No.: 16/485,049

(22) PCT Filed: Feb. 2, 2018

(86) PCT No.: PCT/EP2018/052627

§ 371 (c)(1),
(2) Date: Aug. 9, 2019

(87) PCT Pub. No.: WO2018/146010

PCT Pub. Date: Aug. 16, 2018

(65) Prior Publication Data

US 2024/0294505 A1 Sep. 5, 2024

(30) Foreign Application Priority Data

Feb. 9, 2017 (EP) .................................... 17155406
Nov. 21, 2017 (EP) .................................... 17202882

(51) Int. Cl.
*C07D 417/04* (2006.01)
*A61K 31/501* (2006.01)
(Continued)

(52) U.S. Cl.
CPC .......... *C07D 417/04* (2013.01); *A61K 31/501* (2013.01); *A61K 31/506* (2013.01); *A61K 45/06* (2013.01); *A61P 35/00* (2018.01); *C07D 237/14* (2013.01); *C07D 401/04* (2013.01); *C07D 401/14* (2013.01); *C07D 403/04* (2013.01); *C07D 405/14* (2013.01); *C07D 409/04* (2013.01); *C07D 409/14* (2013.01); *C07D 413/04* (2013.01)

(58) Field of Classification Search
CPC .. C07D 417/04; C07D 401/04; C07D 401/14; C07D 403/04; C07D 405/14; C07D 409/04; C07D 409/14; C07D 413/04; A61P 35/00
See application file for complete search history.

(56) References Cited

U.S. PATENT DOCUMENTS 5,418,233 A 5/1995 Linz
6,358,964 B1 3/2002 Baraldi
(Continued)

FOREIGN PATENT DOCUMENTS

EP 1130015 A1 9/2001
EP 1319659 A1 6/2003
(Continued)

OTHER PUBLICATIONS

Andersson, P. et al. (2002). "A constitutively active dioxin/aryl hydrocarbon receptor induces stomach tumors," PNAS 99(15): 9990-9995.
Bui, L-C. et al. (2009). "Nedd9/Hef1/Cas-L mediates the effects of environmental pollutants on cell migration and plasticity," Oncogene 28: 3642-3651.
(Continued)

*Primary Examiner* — Erich A Leeser
(74) *Attorney, Agent, or Firm* — Morrison & Foerster LLP

(57) ABSTRACT

The present invention covers 2-heteroaryl-3-oxo-2,3-dihydropyridazine-4-carboxamide compounds of general formula (I), in which X, $R^1$, $R^2$, $R^3$, $R^4$ and $R^5$ are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of cancer or conditions with dysregulated immune responses or other disorders associated with aberrant AHR signaling, as a sole agent or in combination with other active ingredients.

(I)

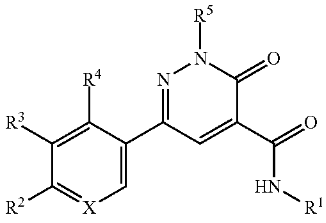

15 Claims, 1 Drawing Sheet

Specification includes a Sequence Listing.

(51) Int. Cl.

| | |
|---|---|
| ***A61K 31/506*** | (2006.01) |
| ***A61K 45/06*** | (2006.01) |
| ***A61P 35/00*** | (2006.01) |
| ***C07D 237/14*** | (2006.01) |
| ***C07D 401/04*** | (2006.01) |
| ***C07D 401/14*** | (2006.01) |
| ***C07D 403/04*** | (2006.01) |
| ***C07D 405/14*** | (2006.01) |
| ***C07D 409/04*** | (2006.01) |
| ***C07D 409/14*** | (2006.01) |
| ***C07D 413/04*** | (2006.01) |

(56) References Cited

U.S. PATENT DOCUMENTS

| | | | | |
|---|---|---|---|---|
| 11,040,035 | B2 | 6/2021 | Schmees et al. | |
| 11,304,946 | B2 | 4/2022 | Lefranc et al. | |
| 11,459,312 | B2 | 10/2022 | Zorn et al. | |
| 11,524,944 | B2 | 12/2022 | Lefranc et al. | |
| 11,591,311 | B2 | 2/2023 | Gutcher et al. | |
| 11,795,164 | B2 * | 10/2023 | Gutcher | A61P 35/00 |
| 2009/0048258 | A1 | 2/2009 | Ogino et al. | |
| 2013/0338201 | A1 | 12/2013 | Song | |
| 2014/0023623 | A1 | 1/2014 | Peled et al. | |
| 2023/0113037 | A1 | 4/2023 | Lefranc et al. | |
| 2024/0174683 | A1 | 5/2024 | Lücking et al. | |

FOREIGN PATENT DOCUMENTS

| | | | | |
|---|---|---|---|---|
| EP | 1611121 | B1 | 8/2007 | |
| EP | 1845081 | A1 | 10/2007 | |
| EP | 1953147 | A1 | 8/2008 | |
| FR | 2847253 | A1 | 5/2004 | |
| WO | 0222587 | A1 | 3/2002 | |
| WO | 2004046117 | A1 | 6/2004 | |
| WO | 2006053903 | A2 | 5/2006 | |
| WO | 2006084017 | A2 | 8/2006 | |
| WO | 2007040565 | A2 | 4/2007 | |
| WO | 2007058392 | A1 | 5/2007 | |
| WO | 2007128723 | A1 | 11/2007 | |
| WO | 2008009963 | A2 | 1/2008 | |
| WO | 2008058995 | A2 | 5/2008 | |
| WO | 2008080056 | A2 | 7/2008 | |
| WO | WO 2008/080056 | * | 7/2008 | C07D 237/14 |
| WO | 2009069100 | A1 | 6/2009 | |
| WO | 2009142732 | A2 | 11/2009 | |
| WO | 2010051188 | A1 | 5/2010 | |
| WO | 2010059401 | A2 | 5/2010 | |
| WO | 2012015914 | A2 | 2/2012 | |
| WO | 2015143164 | A1 | 9/2015 | |
| WO | 2017202816 | A1 | 11/2017 | |
| WO | 2018146010 | A1 | 8/2018 | |
| WO | 2019090198 | A1 | 5/2019 | |
| WO | 2019101641 | A1 | 5/2019 | |
| WO | 2019101642 | A1 | 5/2019 | |
| WO | 2019101643 | A1 | 5/2019 | |
| WO | 2019101647 | A1 | 5/2019 | |
| WO | 2020061377 | A1 | 3/2020 | |
| WO | 2020102506 | A1 | 5/2020 | |
| WO | 2021028382 | A1 | 2/2021 | |
| WO | 2021074279 | A1 | 4/2021 | |
| WO | 2021249913 | A1 | 12/2021 | |
| WO | 2022167627 | A1 | 8/2022 | |

OTHER PUBLICATIONS

Dinatale, B.C. et al. (2010). "Kynurenic Acid Is a Potent Endogenous Aryl Hydrocarbon Receptor Ligand that Synergistically Induces Interleukin-6 in the Presence of Inflammatory Signaling," Toxicological Sciences 115(1): 89-97.

Esser, C. et al. (2009). "The aryl hydrocarbon receptor in immunity," Trends in Immunology 30(9): 447-454.

Gramatzki, D. et al. (2009). "Aryl hydrocarbon receptor inhibition downregulates the TGF-β/Smad pathway in human glioblastoma cells," Oncogene 28: 2593-2605.

Liu, X. et al. (2010). "Selective inhibition of IDO1 effectively regulates mediators of antitumor immunity," Blood 115(17): 3520-3530.

Metz, R. et al. (2007). "Novel Tryptophan Catabolic Enzyme IDO2 Is the Preferred Biochemical Target of the Antitumor Indoleamine 2,3-Dioxygenase Inhibitory Compound D-1-Methyl-Tryptophan," Cancer Res 67(15): 7082-7087.

Mezrich, J.D. et al. (2010). "An Interaction between Kynurenine and the Aryl Hydrocarbon Receptor Can Generate Regulatory T Cells," J Immunol 185(6): 3190-3198.

Muller, A.J. et al. (2005). "Inhibition of indoleamine 2,3-dioxygenase, an immunoregulatory target of the cancer suppression gene Bin1, potentiates cancer chemotherapy," Nature Medicine 11(3): 312-319.

Nguyen, L.P. et al. (2008). "The Search for Endogenous Activators of the Aryl Hydrocarbon Receptor," Chem. Res. Toxicol. 21: 102-116.

Nguyen, N.T. et al. (2010). "Aryl hydrocarbon receptor negatively regulates dendritic cell immunogenicity via a kynurenine-dependent mechanism," PNAS 107(46): 19961-19966.

Nguyen, N.T. et al. (2014). "Aryl hydrocarbon receptor and kynurenine: recent advances in autoimmune disease research," Frontiers in Immunology 5(551): 1-6.

Opitz, C.A. et al. (2011). "An endogenous tumour-promoting ligand of the human aryl hydrocarbon receptor," Nature 478: 197-203.

Reyes, H. et al. (1992). "Identification of the Ah Receptor Nuclear Translocator Protein (Arnt) as a Component of the DNA Binding Form of the Ah Receptor," Science 256: 1193-1195.

Uyttenhove, C. et al. (2003). "Evidence for a tumoral immune resistance mechanism based on tryptophan degradation by indoleamine 2,3-dioxygenase," Nature Medicine 9(10): 1269-1274.

Wang, C. et al. (2014). "Activation of the aryl hydrocarbon receptor affects activation and function of human monocyte-derived dendritic cells," Clinical and Experimental Immunology 117: 521-530.

Wei, P. et al. (2014). "An aryl hydrocarbon receptor ligand acts on dendritic cells and T cells to suppress the Th17 response in allergic rhinitis patients," Laboratory Investigation 94: 528-535.

Yamada, T. et al. (2016). "Constitutive aryl hydrocarbon receptor signaling constrains type I interferon-mediated antiviral innate defense," Nature Immunology 17(6): 687-694.

Baird, D. D. et al. (Jan. 2003) "High Cumulative Incidence of Uterine Leiomyoma in Black and White Women: Ultrasound Evidence," Am J Obstet Gynecol. 188(1):100-107.

Bauer, J.F. et al. (2008). "Polymorphism—A Critical Consideration in Pharmaceutical Development, Manufacturing, and Stability," Journal of Validation Technology:15-23.

Berge, S.M. et al. (Jan. 1977). "Pharmaceutical Salts," Journal of Pharmaceutical Sciences 66(1):1-19.

Bianchi-Smiraglia, A. et al. (2018). "Inhibition of the Aryl Hydrocarbon Receptor/Polyamine Biosynthesis Axis Suppresses Multiple Myeloma," J Clin Invest. 128(10):4682-4696.

Bushuev, M.B. et al. (2011). "Zinc(II) and Cadmium(II) Complexes Based on 2-(3,5-dimethyl-1H-pyrazol-1-yl)-6-(4-methoxyphenyl)pyrimidine-4-carboxylic acid: Synthesis, Structure, and Luminescence," Inorganic Chemistry Communications 14:749-752.

CAS RN 329745-38-2, STN Entry Date: Apr. 2, 2001. "5-Chloro-2-(4-chlorophenyl)-[1,2,4]triazolo[1,5-c]quinazoline," located at https://pubchem.ncbi.nlm.nih.gov/compound/156067872, last visited on Jul. 28, 2025, 9 pages.

David, M. et al. (2016). "Myoma-associated Pain Frequency and Intensity: A Retrospective Evaluation of 1548 Myoma Patients," European Journal of Obstetrics & Gynecology and Reproductive Biology 199:137-140.

Downes, E. et al. (2010). "The Burden of Uterine Fibroids in Five European Countries," European Journal of Obstetrics & Gynecology and Reproductive Biology 152:96-102.

Francis, J. E. et al. (1988). "Structure-Activity Profile of a Series of Novel Triazoloquinazoline Adenosine," Journal of Medicinal Chemistry 31(5):1014-1020.

Francis, J.E. et al. (Jan. 1, 1991). "Synthesis and Benzodiazepine Binding Activity of a Series of Novel [1,2,4]Triazolo[1,5-c]quinazolin-5(6H)-ones," J. Med. Chem. 34(1):281-290.

(56) References Cited

OTHER PUBLICATIONS

Gelotte, K. et al. (Sep./Oct. 1990). "An Efficient Synthesis of the Novel Triazoloquinazoline Adenosine Antagonist," Journal of Heterocyclic Chemistry 27(6):1549-1552.
Gineinah, M. M. et al. (2000). "Synthesis and Antiinflammatory Evaluation of New 2- and 3-Substitutes 1,2,4-Triazolo 4,3-c] and [1,5-c]Quinazoline Derivatives," Med Chem Res 10(4):243-252.
Golub, T.R. et al. (Oct. 15, 1999). "Molecular Classification of Cancer: Class Discovery and Class Prediction by Gene Expression Monitoring," Science 286:531-537.
International Search Report and Written Opinion of the International Searching Authority mailed Apr. 11, 2020, for International Patent Application No. PCT/EP2020/072377, filed Aug. 10, 2020, 10 pages.
International Search Report and Written Opinion, mailed Jun. 24, 2022, for PCT Application No. PCT/EP2022/052794, filed Feb. 4, 2022, 9 pages.
International Search Report dated Apr. 1, 2019 for International Application No. PCT/EP2018/081545 filed Nov. 16, 2018 3 pages.
International Search Report mailed Feb. 11, 2019 for PCT Application No. PCT/EP2018/081576 filed Nov. 16, 2018, 4 pages.
International Search Report mailed Jan. 2, 2019 for PCT Application No. PCT/EP2018/081543 filed Nov. 16, 2018, 3 pages.
International Search Report mailed on Jan. 15, 2019, for PCT Patent Application No. PCT/EP2018/081546 filed on Nov. 16, 2018, 3 pages.
International Search Report mailed on Mar. 29, 2018, for PCT Application No. PCT/EP2018/052627, filed on Feb. 2, 2018, 3 pages.
Kawaguchi, K. et al. (1991) "Immunohistochemical Analysis of Oestrogen Receptors, Progesterone Receptors and Ki-67 in Leiomyoma and Myometrium During the Menstrual Cycle and Pregnancy," Virchows Archiv A Pathol. Anal. 419:309-315.
Keir, M.E. et al. (2008, e-pub. Jan. 2, 2008). "PD-1 and Its Ligands in Tolerance and Immunity," Annu. Rev. Immunol. 26:677-704.
Lala. P.K. et al. (1998). "Role of Nitric Oxide in Tumor Progression: Lessons from Experimental Tumors," Cancer and Metastasis Reviews 17(1):91-106.
Patani, G.A. et al. (1996). "Bioisosterism: A Rational Approach in Drug Design," Chemical Reviews 96(8):3147-3176.
Tsibris, J. C. M. et al. (Jul. 2002). "Insights from Gene Arrays on the Development and Growth Regulation of Uterine Leiomyomata," Fertility and Sterility 78(1):114-121.
Wang, Y. et al. (Mar. 2010). "Kynurenine is a Novel Endothelium-derived Relaxing Factor Produced During Inflammation," Nat Med. 16(3):279-285, 18 pages.
Written Opinion mailed on Mar. 29, 2018, for PCT Application No. PCT/EP2018/052627, filed on Feb. 2, 2018, 5 pages.
Yang, J-H. et al. (Apr. 2011). "Impact of Submucous Myoma on the Severity of Anemia," Fertility and Sterility 95(5):1769-1772.e1.

* cited by examiner

Fig. 1

<SEQ ID No.: 1>

DIQMTQSPSSLSASVGDRVTITCRASQDVSTAVAWYQQKPGKAPKLLIYSASFLYSGVPS
RFSGSGSGTDFTLTISSLQPEDFATYYCQQYLYHPATFGQGTKVEIKRADAAPTVSIFPP
SSEQLTSGGASVVCFLNNFYPKDINVKWKIDGSERQNGVLNSWTDQDSKDSTYSMSSTLT
LTKDEYERHNSYTCEATHKTSTSPIVKSFNRNEC

Fig. 2

<SEQ ID No.: 2>

EVQLVESGGGLVQPGGSLRLSCAASGFTFSDSWIHWVRQAPGKGLEWVAWISPYGGSTYY
ADSVKGRFTISADTSKNTAYLQMNSLRAEDTAVYYCARRHWPGGFDYWGQGTLVTVSSAK
TTPPSVYPLAPGSAAQTNSMVTLGCLVKGYFPEPVTVTWNSGSLSSGVHTFPAVLQSDLY
TLSSSVTVPSSTWPSETVTCNVAHPASSTKVDKKIVPRDCGCKPCICTVPEVSSVFIFPP
KPKDVLTITLTPKVTCVVVDISKDDPEVQFSWFVDDVEVHTAQTQPREEQFNSTFRSVSE
LPIMHQDWLNGKEFKCRVNSAAFPAPIEKTISKTKGRPKAPQVYTIPPPKEQMAKDKVSL
TCMITDFFPEDITVEWQWNGQPAENYKNTQPIMDTDGSYFVYSKLNVQKSNWEAGNTFTC
SVLHEGLHNHHTEKSLSHSPGK

SEQUENCE LISTING

```
<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
<223> OTHER INFORMATION: light chain of the TPP-3911 (humanized murine
      antibody)

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95
```

-continued

```
Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 2
<211> LENGTH: 442
<212> TYPE: PRT
<213> ORGANISM: Artificial Sequence
<220> FEATURE:
<223> OTHER INFORMATION: heavy chain of the TPP-3911 (humanized murine antibody)

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240
```

-continued

| | | | | | | | | | | | | | | | |
|---|---|---|---|---|---|---|---|---|---|---|---|---|---|---|---|
| Lys | Pro | Lys | Asp | Val | Leu | Thr | Ile | Thr | Leu | Thr | Pro | Lys | Val | Thr | Cys |
| | | | | 245 | | | | | 250 | | | | | 255 | |
| Val | Val | Val | Asp | Ile | Ser | Lys | Asp | Asp | Pro | Glu | Val | Gln | Phe | Ser | Trp |
| | | | 260 | | | | | 265 | | | | | 270 | | |
| Phe | Val | Asp | Asp | Val | Glu | Val | His | Thr | Ala | Gln | Thr | Gln | Pro | Arg | Glu |
| | | 275 | | | | | 280 | | | | | 285 | | | |
| Glu | Gln | Phe | Asn | Ser | Thr | Phe | Arg | Ser | Val | Ser | Glu | Leu | Pro | Ile | Met |
| | 290 | | | | | 295 | | | | | 300 | | | | |
| His | Gln | Asp | Trp | Leu | Asn | Gly | Lys | Glu | Phe | Lys | Cys | Arg | Val | Asn | Ser |
| 305 | | | | | 310 | | | | | 315 | | | | | 320 |
| Ala | Ala | Phe | Pro | Ala | Pro | Ile | Glu | Lys | Thr | Ile | Ser | Lys | Thr | Lys | Gly |
| | | | | 325 | | | | | 330 | | | | | 335 | |
| Arg | Pro | Lys | Ala | Pro | Gln | Val | Tyr | Thr | Ile | Pro | Pro | Pro | Lys | Glu | Gln |
| | | | 340 | | | | | 345 | | | | | 350 | | |
| Met | Ala | Lys | Asp | Lys | Val | Ser | Leu | Thr | Cys | Met | Ile | Thr | Asp | Phe | Phe |
| | | 355 | | | | | 360 | | | | | 365 | | | |
| Pro | Glu | Asp | Ile | Thr | Val | Glu | Trp | Gln | Trp | Asn | Gly | Gln | Pro | Ala | Glu |
| | 370 | | | | | 375 | | | | | 380 | | | | |
| Asn | Tyr | Lys | Asn | Thr | Gln | Pro | Ile | Met | Asp | Thr | Asp | Gly | Ser | Tyr | Phe |
| 385 | | | | | 390 | | | | | 395 | | | | | 400 |
| Val | Tyr | Ser | Lys | Leu | Asn | Val | Gln | Lys | Ser | Asn | Trp | Glu | Ala | Gly | Asn |
| | | | | 405 | | | | | 410 | | | | | 415 | |
| Thr | Phe | Thr | Cys | Ser | Val | Leu | His | Glu | Gly | Leu | His | Asn | His | His | Thr |
| | | | 420 | | | | | 425 | | | | | 430 | | |
| Glu | Lys | Ser | Leu | Ser | His | Ser | Pro | Gly | Lys | | | | | | |
| | | 435 | | | | | 440 | | | | | | | | |

2-HETEROARYL-3-OXO-2,3-DIHYDROPYRIDAZINE-4-CARBOXAMIDES FOR THE TREATMENT OF CANCER

CROSS REFERENCE TO RELATED APPLICATIONS

This application is the national stage of International Application No. PCT/EP2018/052627, filed internationally on Feb. 2, 2018, which claims the benefit of European Application Nos. 17155406.6, filed Feb. 9, 2017 and 17202882.1, filed Nov. 21, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052036500SUBSEQLIST.TXT, date recorded: Jun. 14, 2023, size: 6,180 bytes).

The present invention covers 2-heteroaryl-3-oxo-2,3-dihydropyridazine-4-carboxamide compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular cancer or conditions with dysregulated immune responses, as a sole agent or in combination with other active ingredients.

BACKGROUND

The AHR (Aryl Hydrocarbon Receptor) is a ligand-activated transcription factor, belonging to the basic helix-loop-helix/Per-Arnt-Sim (bHLH/PAS) family, and is located in the cytosol. Upon ligand binding, the AHR translocates to the nucleus where it heterodimerises with ARNT (AHR Nuclear Translocator) upon which it interacts with DREs (Dioxin Response Elements) of AHR-responsive genes to regulate their transcription. The AHR is best known for binding to environmental toxins and inducing the metabolic machinery, such as cytochrome P 450 enzymes (e.g. CYP1A1, CYP1A2 and CYP1B1), required for their elimination (Reyes et al., Science, 1992, 256(5060):1193-5). Activation of AHR by xenobiotics has demonstrated its role in numerous cellular processes such as embryogenesis, tumourigenesis and inflammation.

AHR is expressed in many cells of the immune system, including dendritic cells (DCs), macrophages, T cells and NK cells, and plays an important role in immunoregulation (Nguyen et al., Front Immunol, 2014, 5:551). The classic exogenous AHR ligands TCDD and 3-methylcholanthrene, for example, are known to induce profound immunosuppression, promote carcinogenesis and induce tumour growth (Gramatzki et al., Oncogene, 2009, 28(28):2593-605; Bui et al., Oncogene, 2009, 28(41):3642-51; Esser et al., Trends Immunol, 2009, 30:447-454). In the context of immunosuppression, AHR activation promotes regulatory T cell generation, inhibits Th1 and Th17 differentiation, directly and indirectly, and decreases the activation and maturation of DCs (Wang et al., Clin Exp Immunol, 2014, 177(2):521-30; Mezrich et al., J Immunol, 2010, 185(6): 3190-8; Wei et al., Lab Invest, 2014, 94(5):528-35; Nguyen et al., PNAS, 2010, 107(46):19961-6). AHR activation modulates the innate immune response and constitutive AHR expression has been shown to negatively regulate the type-I interferon response to viral infection (Yamada et al., Nat Immunol, 2016). Additionally, mice with a constitutively active AHR spontaneously develop tumours (Andersson et al., PNAS, 2002, 99(15):9990-5).

In addition to xenobiotics, the AHR can also bind metabolic products of tryptophan degradation. Tryptophan metabolites, such as kynurenine and kynurenic acid, are endogenous AHR ligands that activate the AHR under physiological conditions (DiNatale et al., Toxicol Sci, 2010, 115(1):89-97; Mezrich et al., J Immunol, 2010, 185(6): 3190-8; Opitz et al., Nature, 2011, 478(7368):197-203). Other endogenous ligands are known to bind the AHR although their physiological roles are currently unknown (Nguyen & Bradfield, Chem Res Toxicol, 2008, 21(1):102-116).

The immunosuppressive properties of kynurenine and tryptophan degradation are well described and are implicated in cancer-associated immunosuppression. The enzymes indoleamine-2,3-dioxygenases 1 and 2 (IDO1/IDO2) as well as tryptophan-2,3-dioxygenase 2 (TDO2) are responsible for catalysing the first and rate-limiting step of tryptophan metabolism. IDO1/2-mediated degradation of tryptophan in tumours and tumour-draining lymph nodes reduces anti-tumour immune responses and inhibition of IDO can suppress tumour formation in animal models (Uyttenhove et al., Nat Med, 2003, 9(10):1269-74; Liu et al., Blood, 2005, 115(17): 3520-30; Muller et al., Nat Med, 11(3):312-9; Metz, Cancer Res, 2007, 67(15):7082-7).

TDO2 is also strongly expressed in cancer and can lead to the production of immunosuppressive kynurenine. In glioma, activation of the AHR by kynurenine, downstream of TDO-mediated tryptophan degradation, enhances tumour growth as a consequence of inhibiting anti-tumour immune responses as well as directly promoting tumour cell survival and motility (Opitz et al., Nature, 2011, 478(7368):197-203). AHR ligands generated by tumour cells therefore act in both an autocrine and paracrine fashion on tumour cells and lymphocytes, respectively, to promote tumour growth.

The present invention covers 2-heteroaryl-3-oxo-2,3-dihydropyridazine-4-carboxamide compounds of general formula (I) which inhibit the AHR.

STATE OF THE ART

WO 2010/059401 relates to compounds and compositions for expanding the number of CD34+ cells for transplantation. In particular, WO 2010/059401 relates inter alia to heterocyclic compounds capable of down-regulating the activity and/or expression of AHR.

WO 2012/015914 relates to compositions and methods for modulating AHR activity. In particular, WO 2012/015914 relates inter alia to heterocyclic compounds that modulate AHR activity for use in therapeutic compositions.

WO 2007/058392 relates to novel heterocyclic compounds and a pharmaceutical use thereof. In particular, WO 2007/058392 relates inter alia to heterocyclic compounds having an hepatitis C virus cell infection inhibitory activity.

WO 2002/022587 relates to novel compounds exhibiting inhibitory activities against AMPA receptor and/or kainate receptor. In particular, WO 2002/022587 relates inter alia to pyridazinone and triazinone compounds.

U.S. Pat. No. 5,418,233 relates to heterobiaryl derivatives inhibiting cell-cell aggregation and cell-matrix interactions. In particular, U.S. Pat. No. 5,418,233 relates to heterobiaryl derivatives which are histamine receptor antagonists.

WO 2015/143164 relates to antimicrobial agents and screening methods. In particular, WO 2015/143164 relates inter alia to pyridazinone compounds as antibiotics.

WO 2009/142732 relates to substituted pyridazinone derivatives and their use as $H_3$ antagonists/inverse agonists.

However, the state of the art does not describe the 2-heteroaryl-3-oxo-2,3-dihydropyridazine-4-carboxamide compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively inhibit AHR for which data are given in biological experimental section and may therefore be used for the treatment or prophylaxis of cancer or other conditions where exogenous and endogenous AHR ligands induce dysregulated immune responses, uncontrolled cell growth, proliferation and/or survival of tumour cells, immunosuppression in the context of cancer, inappropriate cellular immune responses, or inappropriate cellular inflammatory responses or diseases which are accompanied with uncontrolled cell growth, proliferation and/or survival of tumour cells, immunosuppression in the context of cancer inappropriate cellular immune responses, or inappropriate cellular inflammatory responses, particularly in which the uncontrolled cell growth, proliferation and/or survival of tumour cells, immunosuppression in the context of cancer, inappropriate cellular immune responses, or inappropriate cellular inflammatory responses is mediated by AHR, such as, for example, liquid and solid tumours, and/or metastases thereof, e.g. head and neck tumours including brain tumours and brain metastases, tumours of the thorax including non-small cell and small cell lung tumours, gastrointestinal tumours including colon, colorectal and pancreatic tumours, liver tumours, endocrine tumours, mammary and other gynecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

(I)

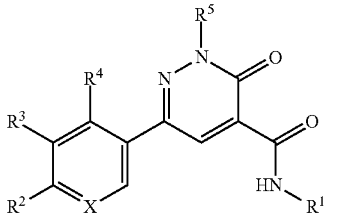

in which $R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally once with $C_1$-$C_3$-alkyl and/or one to three times with halogen, or $C_3$-$C_6$-cycloalkyl-$C_1$-$C_3$-alkyl substituted once with hydroxy and optionally once with $C_1$-$C_3$-alkyl and/or one to three times with halogen, or ($C_3$-$C_6$-cycloalkyl)$_2$-$C_1$-$C_3$-alkyl substituted once with hydroxy and optionally once with $C_1$-$C_3$-alkyl and/or one to three times with halogen, or 4- to 6-membered heterocycloalkyl substituted once with hydroxy and optionally once with $C_1$-$C_3$-alkyl and/or one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

their polymorphs, enantiomeres, diastereomeres, racemates, tautomeres, N-oxides, hydrates and solvates, as well as their physiological acceptable salts and solvates of these salts, as well as mixtures of the same.

Further, it covers their use in combination with other anti cancer medications such as immunotherapeutics, targeted anti cancer agents or chemotherapy.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom. Commonly, it is possible for the number of optional substituents, when present, to be 1, 2 or 3.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen" means a fluorine, chlorine, bromine or iodine, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethyl-propyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl. Particularly, said group has 1, 2, 3 or 4 carbon atoms ("$C_1$-$C_4$-haloalkyl"), more particularly 1, 2 or 3 carbon atoms ("$C_1$-$C_3$-haloalkyl"), e.g. a fluoromethyl, difluoromethyl or trifluoromethyl group.

The term "$C_2$-$C_6$-hydroxyalkyl" means a linear or branched, saturated, monovalent hydrocarbon group in which the term "$C_2$-$C_6$-alkyl" is defined supra, and in which 1 or 2 hydrogen atoms are replaced with a hydroxy group, e.g. a 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methylpropyl, 2-hydroxy-2-methyl-propyl, 1-hydroxy-2-methylpropyl group.

The term "$C_1$-$C_4$-alkoxy" means a linear or branched, saturated, monovalent group of formula ($C_1$-$C_4$-alkyl)-O—, which means methoxy, ethoxy, n-propoxy, isopropoxy, n-butoxy, sec-butoxy, isobutoxy or tert-butoxy.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is a monocyclic hydrocarbon ring, e.g. a cyclopropyl, cyclobutyl, cyclopentyl or cyclohexyl.

The term "$C_2$-$C_7$-alkylene" means a linear or branched, saturated, bivalent hydrocarbon group in which the term "$C_2$-$C_7$-alkyl" is as defined supra, and in which 2 hydrogen atoms from different carbon atoms are removed to form a biradical group.

The term "4- to 6-membered heterocycloalkyl" means a monocyclic, saturated heterocycle with 4, 5 or 6 ring atoms in total, which contains one or two identical or different ring heteroatoms from the series N and O, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl or oxetanyl, for example; or a 5-membered ring, such as tetrahydrofuranyl, 1,3-dioxolanyl, pyrrolidinyl, imidazolidinyl, pyrazolidinyl, 1,2-oxazolidinyl or 1,3-oxazolidinyl, for example; or a 6-membered ring, such as tetrahydropyranyl, piperidinyl, morpholinyl, piperazinyl, 1,3-dioxanyl, 1,4-dioxanyl or 1,2-oxazinanyl, for example.

Particularly, "4- to 6-membered heterocycloalkyl" means a 4- to 6-membered heterocycloalkyl as defined supra containing one ring oxygen atom and optionally one further ring heteroatom from the series: N, O. More particularly, "5- or 6-membered heterocycloalkyl" means a monocyclic, saturated heterocycle with 5 or 6 ring atoms in total, containing one ring oxygen atom.

The term "monocyclic heteroaryl" means a monovalent, aromatic ring having 5 or 6 ring atoms (a "5- or 6-membered heteroaryl" group), which contains at least one ring heteroatom and optionally one or two further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a isothiazolyl, pyrazolyl, pyridinyl, pyridazinyl or pyrimidinyl group.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x Na", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible crystallized and polymorphic forms of the inventive compounds, whereby the polymorphs are existing either as a single polymorph form or are existing as a mixture of several polymorphs in all concentrations.

In accordance with a second embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$,
 $C_1$-$C_4$-alkoxy or $C_3$-$C_6$-cycloalkyl and optionally one to three times with halogen, or
 $C_3$-$C_6$-cycloalkyl substituted once with hydroxy and optionally one to three times with halogen, or
 $C_3$-$C_6$-cycloalkyl-$C_1$-$C_3$-alkyl substituted once with hydroxy and optionally one to three times with halogen, or
 $(C_3$-$C_6$-cycloalkyl$)_2$-$C_1$-$C_3$-alkyl substituted once with hydroxy and optionally one to three times with halogen, or
 4- to 6-membered heterocycloalkyl substituted once with hydroxy and optionally one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or
 together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

their polymorphs, enantiomeres, diastereomeres, racemates, tautomeres, N-oxides, hydrates and solvates, as well as their physiological acceptable salts and solvates of these salts, as well as mixtures of the same.

In accordance with a third embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$,
 $C_1$-$C_4$-alkoxy or $C_3$-$C_6$-cycloalkyl and optionally one to three times with halogen, or
 $C_3$-$C_6$-cycloalkyl substituted once with hydroxy and optionally once with $C_1$-$C_3$-alkyl and/or one to three times with halogen, or
 $C_3$-$C_6$-cycloalkyl-$C_1$-$C_3$-alkyl substituted once with hydroxy and optionally once with $C_1$-$C_3$-alkyl and/or one to three times with halogen, or
 $(C_3$-$C_6$-cycloalkyl$)_2$-$C_1$-$C_3$-alkyl substituted once with hydroxy and optionally once with $C_1$-$C_3$-alkyl and/or one to three times with halogen, or
 4- to 6-membered heterocycloalkyl substituted once with hydroxy and optionally once with $C_1$-$C_3$-alkyl and/or one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_3$-$C_6$-cycloalkyl, $C_1$-$C_4$-alkoxy, halogen or cyano;

X represents CH or N;

their polymorphs, enantiomeres, diastereomeres, racemates, tautomeres, N-oxides, hydrates and solvates, as well as their physiological acceptable salts and solvates of these salts, as well as mixtures of the same.

In accordance with a fourth embodiment of the first aspect, the present invention covers compounds of general formula (I), supra, in which:

$R^1$ represents $C_2$-$C_5$-hydroxyalkyl, wherein said $C_2$-$C_5$-hydroxyalkyl groups are optionally substituted once with cyano, —$COOCH_3$, —$CONH_2$, methoxy or cyclopropyl and optionally one to three times with fluoro, or
 $C_4$-$C_6$-cycloalkyl substituted once with hydroxy and optionally once with methyl and/or one to two times with fluoro, or
 $C_3$-$C_4$-cycloalkyl-methyl substituted once with hydroxy, or
 5- or 6-membered heterocycloalkyl substituted once with hydroxy, said heterocycloalkyl contains one oxygen atom;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen or fluoro;

$R^4$ represents hydrogen or fluoro;

$R^5$ represents monocyclic heteroaryl, which is optionally substituted one to three times, independently from each other, with $R^6$;

$R^6$ represents methyl, difluoromethyl, methoxy, halogen or cyano;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or
 together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

their polymorphs, enantiomeres, diastereomeres, racemates, tautomeres, N-oxides, hydrates and solvates, as well as their physiological acceptable salts and solvates of these salts, as well as mixtures of the same.

In accordance with a fifth embodiment of the first aspect, the present invention covers compounds of general formula (I), supra, in which:

$R^1$ represents $C_2$-$C_5$-hydroxyalkyl, wherein said $C_2$-$C_5$-hydroxyalkyl groups are optionally substituted once with cyano, —$COOCH_3$, —$CONH_2$, methoxy or cyclopropyl and optionally one to three times with fluoro, or $C_4$-$C_6$-cycloalkyl substituted once with hydroxy and optionally once with methyl and/or one to two times with fluoro, or $C_3$-$C_4$-cycloalkyl-methyl substituted once with hydroxy, or 5- or 6-membered heterocycloalkyl substituted once with hydroxy, said heterocycloalkyl contains one oxygen atom;

$R^2$ represents chloro, dimethylamino, methyl, fluoromethyl, difluoromethyl, trifluoromethyl, difluoromethoxy or trifluoromethoxy;

$R^3$ represents hydrogen;

$R^4$ represents hydrogen or fluoro;

$R^5$ represents a group selected from:

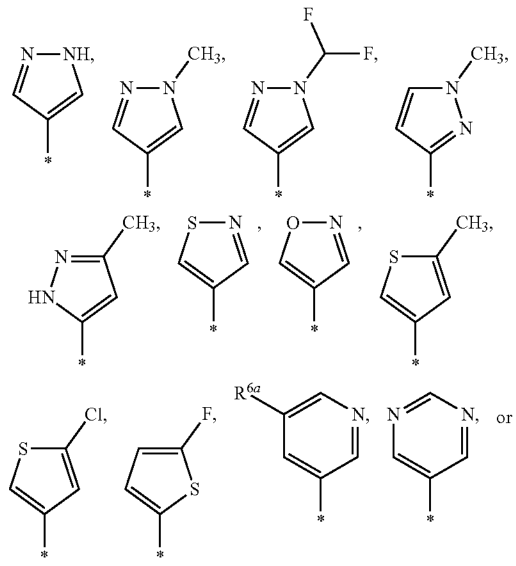

or

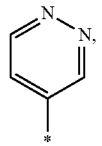

wherein * indicates the point of attachment of said group with the rest of the molecule;

$R^{6a}$ represents hydrogen, methyl, fluoro or chloro;

X represents CH or N;

their polymorphs, enantiomeres, diastereomeres, racemates, tautomeres, N-oxides, hydrates and solvates, as well as their physiological acceptable salts and solvates of these salts, as well as mixtures of the same.

In accordance with a sixth embodiment of the first aspect, the present invention covers compounds of general formula (Ia):

(Ia)

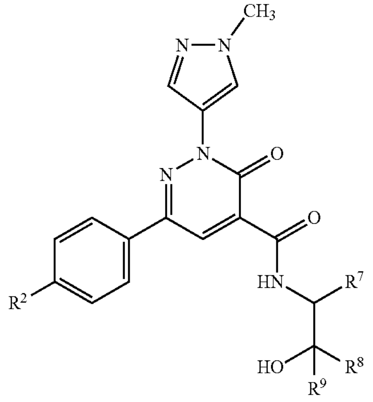

in which $R^2$ represents chloro, dimethylamino, methyl, fluoromethyl, difluoromethyl, trifluoromethyl, difluoromethoxy or trifluoromethoxy;

$R^7$ represents hydrogen, methyl, fluoromethyl, difluoromethyl, trifluoromethyl, hydroxymethyl, methoxymethyl, ethyl, isopropyl, cyclopropyl, cyano, —$COOCH_3$ or —$CONH_2$;

$R^8$ represents hydrogen, methyl, fluoromethyl, difluoromethyl, trifluoromethyl, hydroxymethyl or methoxymethyl, wherein one of $R^7$ and $R^8$ is different from hydrogen, or together $R^7$ and $R^8$ form a cyclopentyl or cyclohexyl ring, which is optionally substituted one to two times with fluoro, or a heterocycloalkyl ring, which contains one oxygen atom;

$R^9$ represents hydrogen or methyl, or together $R^8$ and $R^9$ form a cyclopropyl or cyclobutyl ring;

their polymorphs, enantiomeres, diastereomeres, racemates, tautomeres, N-oxides, hydrates and solvates, as well as their physiological acceptable salts and solvates of these salts, as well as mixtures of the same.

In accordance with a seventh embodiment of the first aspect, the present invention covers compounds of general formula (Ib):

(Ib)

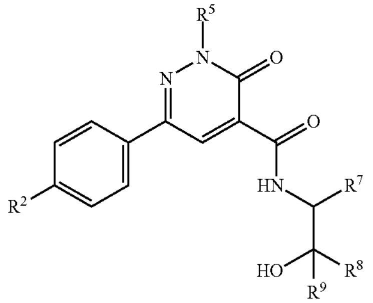

in which $R^2$ represents chloro, dimethylamino, methyl, fluoromethyl, difluoromethyl, trifluoromethyl, difluoromethoxy or trifluoromethoxy;

$R^5$ represents a group selected from:

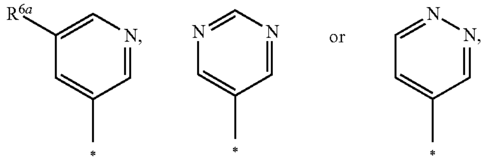

wherein * indicates the point of attachment of said group with the rest of the molecule;

$R^{6a}$ represents hydrogen, methyl, fluoro or chloro;

$R^7$ represents hydrogen, methyl, fluoromethyl, difluoromethyl, trifluoromethyl, hydroxymethyl, methoxymethyl, ethyl, isopropyl or cyclopropyl;

$R^8$ represents hydrogen, methyl, fluoromethyl, difluoromethyl, trifluoromethyl, hydroxymethyl or methoxymethyl, wherein one of $R^7$ and $R^8$ is different from hydrogen, or together $R^7$ and $R^8$ form a cyclopentyl or cyclohexyl ring, which is optionally substituted one to two times with fluoro, or a heterocycloalkyl ring, which contains one oxygen or sulphur atom;

$R^9$ represents hydrogen or methyl, or together $R^8$ and $R^9$ form a cyclopropyl or cyclobutyl ring;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally once with $C_1$-$C_3$-alkyl and/or one to three times with halogen, or $C_3$-$C_6$-cycloalkyl-$C_1$-$C_3$-alkyl substituted once with hydroxy and optionally once with $C_1$-$C_3$-alkyl and/or one to three times with halogen, or ($C_3$-$C_6$-cycloalkyl)$_2$-$C_1$-$C_3$-alkyl substituted once with hydroxy and optionally once with $C_1$-$C_3$-alkyl and/or one to three times with halogen, or 4- to 6-membered heterocycloalkyl substituted once with hydroxy and optionally once with $C_1$-$C_3$-alkyl and/or one to three times with halogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_5$-hydroxyalkyl, wherein said $C_2$-$C_5$-hydroxyalkyl groups are optionally substituted once with cyano, —$COOCH_3$, —$CONH_2$, methoxy or cyclopropyl and optionally one to three times with fluoro, or $C_4$-$C_6$-cycloalkyl substituted once with hydroxy and optionally once with methyl and/or one to two times with fluoro, or $C_3$-$C_4$-cycloalkyl-methyl substituted once with hydroxy, or 5- or 6-membered heterocycloalkyl substituted once with hydroxy, said heterocycloalkyl contains one oxygen atom;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally one to three times with halogen, or $C_3$-$C_6$-cycloalkyl-$C_1$-$C_3$-alkyl substituted once with hydroxy and optionally one to three times with halogen, or ($C_3$-$C_6$-cycloalkyl)$_2$-$C_1$-$C_3$-alkyl substituted once with hydroxy and optionally one to three times with halogen, or 4- to 6-membered heterocycloalkyl substituted once with hydroxy and optionally one to three times with halogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $C_1$-$C_4$-alkoxy or $C_3$-$C_6$-cycloalkyl and optionally one to three times with halogen, or $C_3$-$C_6$-cycloalkyl substituted once with hydroxy and optionally once with methyl and/or one to three times with halogen, or $C_3$-$C_6$-cycloalkyl-$C_1$-$C_3$-alkyl substituted once with hydroxy and optionally one to three times with halogen, or ($C_3$-$C_6$-cycloalkyl)$_2$-$C_1$-$C_3$-alkyl substituted once with hydroxy and optionally one to three times with halogen, or 4- to 6-membered heterocycloalkyl substituted once with hydroxy and optionally one to three times with halogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_6$-hydroxyalkyl, wherein said $C_2$-$C_6$-hydroxyalkyl groups are optionally substituted once with $C_1$-$C_2$-alkoxy or cyclopropyl and optionally one to three times with halogen, or $C_4$-$C_6$-cycloalkyl substituted once with hydroxy and optionally once with methyl and/or one to three times with halogen, or $C_3$-$C_6$-cycloalkyl-methyl substituted once with hydroxy and optionally one to three times with halogen, or ($C_3$-$C_6$-cycloalkyl)$_2$-methyl substituted once with hydroxy and optionally one to three times with halogen, or 5- or 6-membered heterocycloalkyl substituted once with hydroxy and optionally one to three times with halogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_5$-hydroxyalkyl, wherein said $C_2$-$C_5$-hydroxyalkyl groups are optionally substituted once with methoxy or cyclopropyl and optionally one to three times with fluoro, or $C_4$-$C_6$-cycloalkyl substituted once with hydroxy and optionally once with methyl and/or one to two times with fluoro, or $C_3$-$C_4$-cycloalkyl-methyl substituted once with hydroxy, or 5- or 6-membered heterocycloalkyl substituted once with hydroxy, said heterocycloalkyl contains one oxygen atom;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^1$ represents $C_2$-$C_5$-hydroxyalkyl, wherein said $C_2$-$C_5$-hydroxyalkyl groups are optionally substituted once with methoxy or cyclopropyl and optionally one to three times with fluoro, or $C_4$-$C_6$-cycloalkyl substituted once with hydroxy and optionally once with methyl or one to two times with fluoro, or $C_3$-$C_4$-cycloalkyl-methyl substituted once with hydroxy, or 5- or 6-membered heterocycloalkyl substituted once with hydroxy, said heterocycloalkyl contains one oxygen atom;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^2$ represents chloro, cyano, dimethylamino, methyl, fluoromethyl, difluoromethyl, trifluoromethyl, methoxy, difluoromethoxy or trifluoromethoxy;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^2$ represents chloro, dimethylamino, methyl, fluoromethyl, difluoromethyl, trifluoromethyl, difluoromethoxy or trifluoromethoxy;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^3$ represents hydrogen, fluoro, chloro or methyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^3$ represents hydrogen or fluoro;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^3$ represents hydrogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^4$ represents hydrogen or fluoro;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^4$ represents hydrogen;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^5$ represents monocyclic heteroaryl, which is optionally substituted one to three times, independently from each other, with $R^6$;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^5$ represents a group selected from:

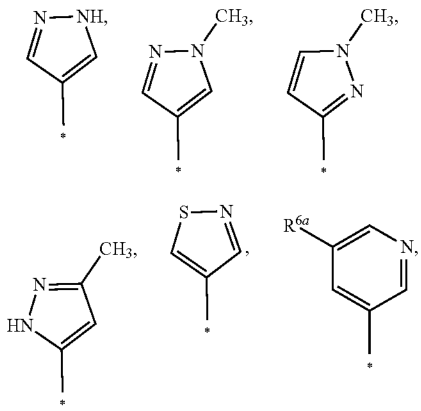

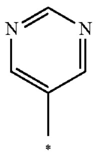

or

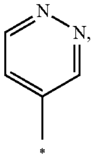

wherein * indicates the point of attachment of said group with the rest of the molecule;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^5$ represents a group selected from:

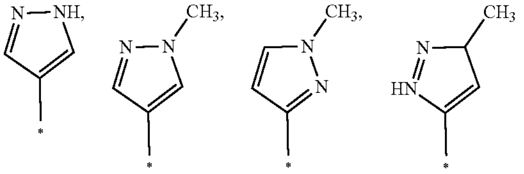

or

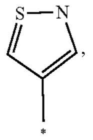

wherein * indicates the point of attachment of said group with the rest of the molecule;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^5$ represents a group selected from:

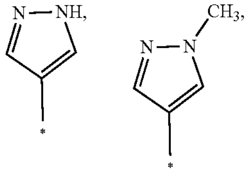

or

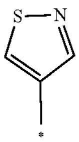

wherein * indicates the point of attachment of said group with the rest of the molecule;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^5$ represents a group selected from:

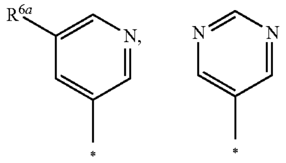

or

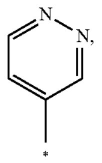

wherein * indicates the point of attachment of said group with the rest of the molecule;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents $C_1$-$C_4$-alkyl, $C_3$-$C_6$-cycloalkyl, $C_1$-$C_4$-alkoxy, halogen or cyano;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^6$ represents methyl, methoxy, halogen or cyano;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{6a}$ represents hydrogen, methyl, fluoro or chloro;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{10}$ represents $C_1$-$C_4$-alkyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{10}$ represents methyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{11}$ and $R^{12}$ are the same or different and represent, independently from each other, hydrogen or $C_1$-$C_3$-alkyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

$R^{11}$ and $R^{12}$ are the same or different and represent, independently from each other, hydrogen or methyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

X represents CH or N;

their polymorphs, enantiomeres, diastereomeres, racemates, tautomeres, N-oxides, hydrates and solvates, as well as their physiological acceptable salts and solvates of these salts, as well as mixtures of the same.

In accordance with a further embodiment of the first aspect, the present invention covers compounds of general formula (I), supra, in which:

X represents CH;

their polymorphs, enantiomeres, diastereomeres, racemates, tautomeres, N-oxides, hydrates and solvates, as well as their physiological acceptable salts and solvates of these salts, as well as mixtures of the same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (VII). The present invention covers the compounds of general formula (I) which are disclosed in the Example Section of this text, infra.

The compounds according to the invention of general formula (I) can be prepared according to the following scheme 1. The scheme and procedures described below illustrate synthetic routes to the compounds of general formula (I) of the invention and are not intended to be limiting. It is clear to the person skilled in the art that the order of transformations as exemplified in scheme 1 can be modified in various ways. The order of transformations exemplified in this scheme is therefore not intended to be limiting. In addition, interconversion of any of the substituents $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metallation, metal-catalysed coupling reactions, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Scheme 1 shows a route for the preparation of compounds of general formula (I) in which X, $R^1$, $R^2$, $R^3$, $R^4$, $R^5$ and $R^6$ have the meaning as given for general formula (I), supra. Ketomalonates represented as intermediates according to formula (III) are in some few instances commercially available or can be synthesized from alpha-halo-acetophenones (II) according to procedures known to the person skilled in the art. Related alpha-halo-acetophenones are usually commercially available. Conversion of such alpha-halo-acteophenones with malonic acid esters in the presence of a suitable base in a suitable solvent results in the formation of non-commercial ketomalonates according to formula (III). R in formula (III), (V) and (VI) represents a suitable alkyl group such as methyl, ethyl, propyl or other homologous groups. A suitable solvent can be, but should not be restricted to, acetonitril, DMF, DMA, DMSO of THF, or even mixtures of these or other solvents. A suitable base can be, but should not be restricted to, potassium carbonate, sodium hydride, caesium carbonate of potassium hexamethylendisilazane.

Formation of dihydropyridazinones according to formula (V) from intermediates (III) and suitable aryl-hydrazines (IV), which are in many cases commercially available, can be accomplished by reaction of these components in a suitable solvent at elevated temperature. A suitable solvent can be, but should not be restricted to, ethanol or acetic acid.

Scheme 1: Route for the preparation of compounds of general formula (I) in which X, $R^1$, $R^2$, $R^3$, $R^4$, AND $R^5$ have the meaning as given for general formula (I), supra and Hal represents halogen and R represents C1-C4-alkyl.

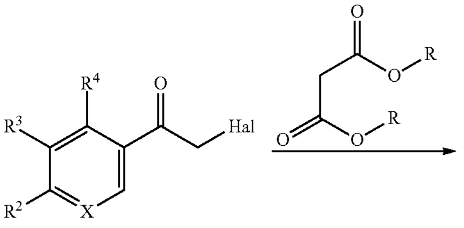

(II)

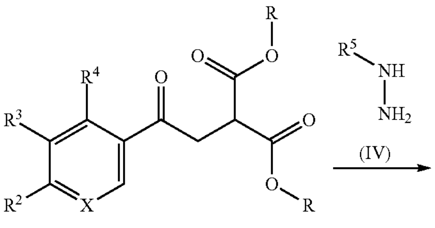

(III)

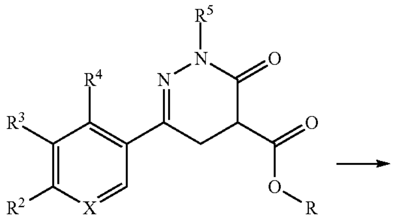

(V)

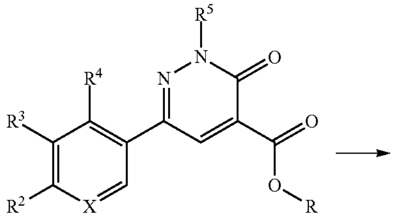

(VI)

-continued

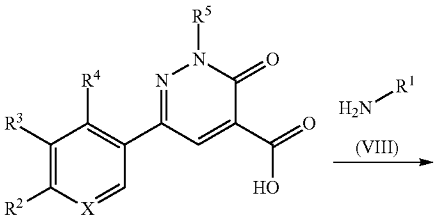

(VII)

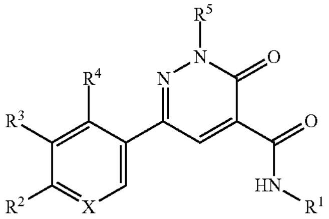

(I)

Dihydropyridazinones according to formula (V) can be transferred to pyridazinones according to formula (VI). This can be accomplished by the use of a suitable reagents such as copper dichloride at elevated temperature.

The resulting pyridazinones according to formula (VI) with an ester functional group can be converted by methods known to the person skilled in the art, for example by basic hydrolysis with, for example, aqueous alkali metal hydroxides, or by acidic hydrolysis using, for example, hydrogen chloride in dioxane or trifluoroacetic acid, to the pyridazinone carboxylic acids (VII).

These acids can be converted by coupling with amines of the formula (VIII) in which $R^1$ is as defined for the general formula (I). Coupling agents and methods for such syntheses of carboxamides from carboxylic acids and amines are known to the person skilled in the art. Examples which may be mentioned here include the use of HATU, HBTU, PyBOB or T3P with the addition of a suitable base. The conversion of the carboxylic acids to their amides is described in general terms in reference books.

Scheme 2: Route for the preparation of compounds of general formula (I) in which X, $R^1$, $R^2$, $R^3$, $R^4$ and $R^5$ have the meaning as given for general formula (I), supra and Hal represents halogen, R represents C1-C4-alkyl and R′ and R″ represent simultaneously H or C1-C4-alkyl or form together a C2-C7-alkylene group as part of a 1,2- or 1,3-diol boronic ester or a $-CO-CH_2-(NCH_3)-CH_2-CO-$ group.

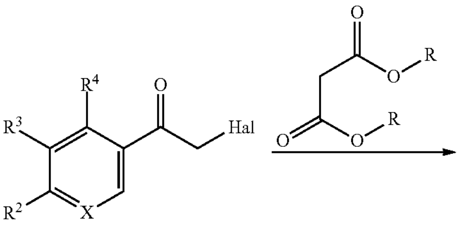

(II)

-continued

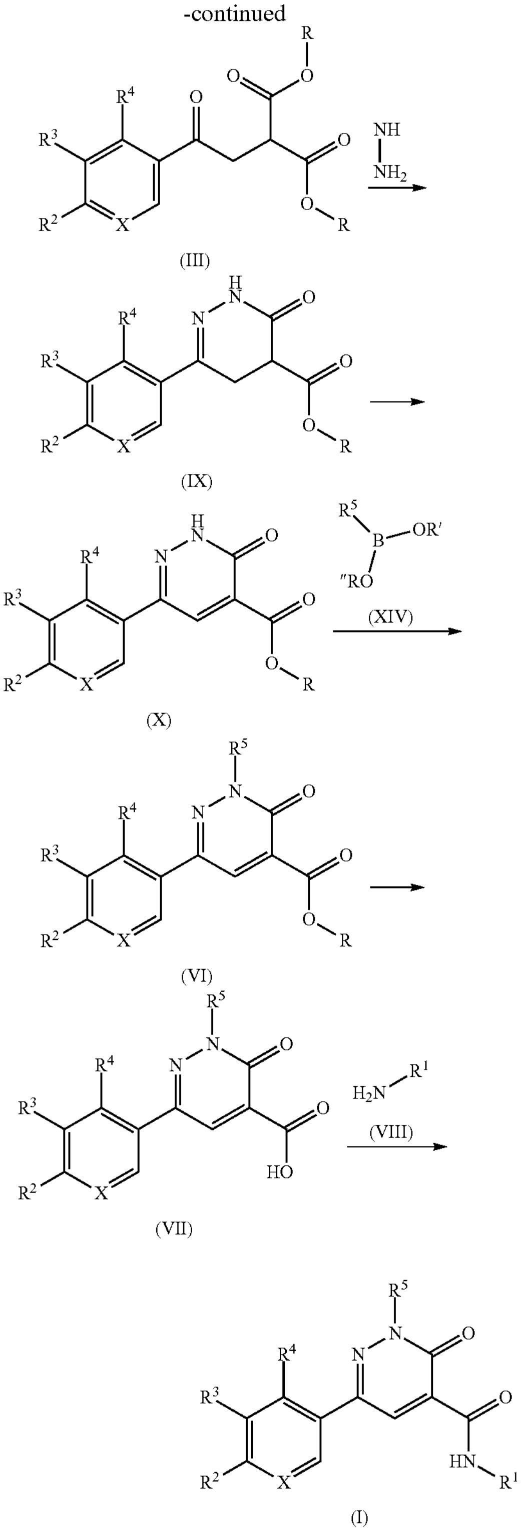

(III)

(IX)

(X)

(VI)

(VII)

(I)

Ketomalonates represented as intermediates according to formula (III) are in some few instances commercially available or can be synthesized from alpha-halo-acetophenones (II) according to procedures known to persons skilled in the art. Related alpha-halo-acetophenones are usually commercially available. Conversion of such alpha-halo-acteophenones with malonic acid esters in the presence of a suitable base in a suitable solvent results in the formation of non-commercial ketomalonates according to formula (III). R in formula (III), (IX), (X) and (VI) represents a suitable alkyl group such as methyl, ethyl, propyl or other homologous groups. A suitable solvent can be, but should not be restricted to, acetonitril, DMF, DMA, DMSO of THF, or even mixtures of these or other solvents. A suitable base can be, but should not be restricted to, potassium carbonate, sodium hydride, caesium carbonate of potassium hexamethylendisilazane.

Formation of dihydropyridazinones according to formula (IX) from intermediates (III) and hydrazine, can be accomplished by reaction of these components in a suitable solvent at elevated temperature. A suitable solvent can be, but should not be restricted to, ethanol or acetic acid.

Dihydropyridazinones according to formula (IX) can be transferred to pyridazinones according to formula (X). This can be accomplished by the use of a suitable reagent. A suitable reagent can be, but should not be restricted to, copper dichloride at elevated temperature.

Substituted pyridazinones according to formula (VI) can be prepared by Chan-Lam coupling reactions of pyridazinones according to formula (X) using boron derivatives as boronic acids, boronic acid pinacolates and tetrafluoroborates with suitable solvents at room temperature or elevated temperatures. A suitable solvent can be, but should not be restricted to, acetonitrile, dichloromethane, pyridine or DMF. A suitable catalyst can be, but should not be restricted to copper (II) acetate. Suitable basic additives can be, but should not be restricted to, trimethylamine, 2,2-bipyridine, sodium carbonate or caesium carbonate.

The resulting substituted pyridazinones according to formula (VI) with an ester functional group can be converted by methods known to the person skilled in the art, for example by basic hydrolysis with, for example, aqueous alkali metal hydroxides, or by acidic hydrolysis using, for example, hydrogen chloride in dioxane or trifluoroacetic acid, into the pyridazinone carboxylic acids (VII).

These can be converted by coupling with amines of the formula (VIII) in which $R^1$ is defined as for the general formula (I). Coupling agents and methods for such syntheses of carboxamides from carboxylic acids and amines are known to the person skilled in the art. Examples which may be mentioned here include the use of HATU, HBTU, PyBOB or T3P with the addition of a suitable base. The conversion of the carboxylic acids to their amides is described in general terms in reference books.

Scheme 2a: Route for the preparation of intermediates of general formula (X) in which X, $R^1$, $R^2$, $R^3$ and $R^4$ have the meaning as given for general formula (I), supra, and R represents $C_1$-$C_4$-alkyl.

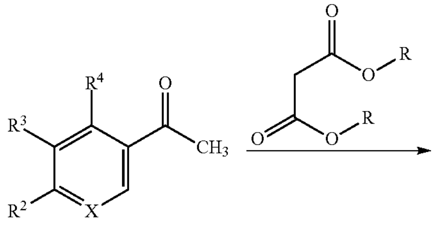

(IIa)

-continued

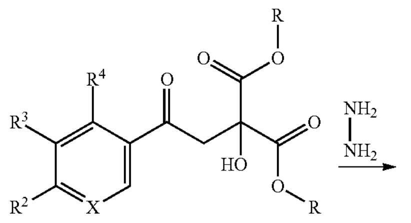

(IIIa)

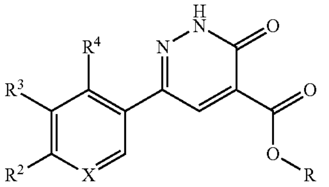

(X)

Compounds of general formula (IIa) are commercially available and can be reacted with dialkyl ketomalonate in which R represents $C_1$-$C_4$-alkyl. Diethyl ketomalonate as reagent is commercially available. Dialkyl ketomalonates can be prepared from the corresponding dialkyl malonates with tosylazide and dioxirane (see e.g.: Synth. Commun. 1994, 24, 695) or bromine and potassium acetate (see e.g.: J. Org. Chem. 1981, 46, 2598). The acetophenones of general formula (IIa) and the dialkyl ketomalonates are heated neat at 95-100° C. or with a solvent, e.g. pyridine, under reflux at 120° C. Then, the intermediates of formula (IIIa) are reacted with hydrazine hydrate in acetic acid under reflux or hydrazinium dihydrochloride in ethanol under reflux to give the intermediates (X).

Scheme 3: Additional route for the preparation of compounds of general formula (I) in which X, $R^1$, $R^2$, $R^3$, $R^4$ and $R^5$ have the meaning as given for general formula (I), supra, and R represents $C_1$-$C_4$-alkyl and R′ and R″ represent simultaneously H or $C_1$-$C_4$-alkyl or form together a $C_2$-$C_7$-alkylene group as part of 1,2- or 1,3-diol boronic ester or a $-CO-CH_2-(NCH_3)-CH_2-CO-$ group.

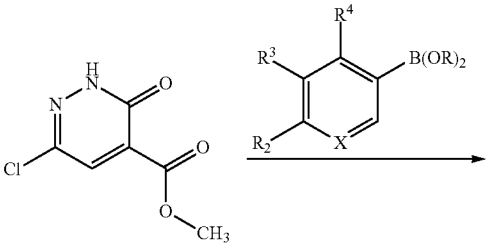

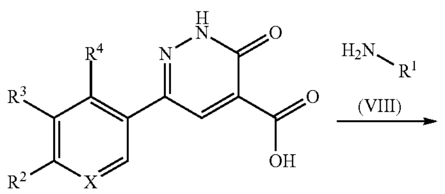

(XI)

-continued

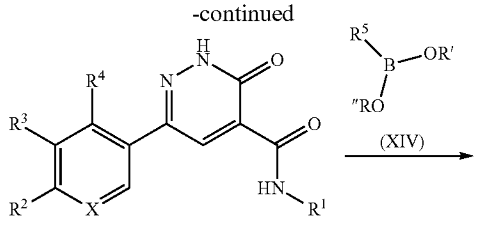

(XII)

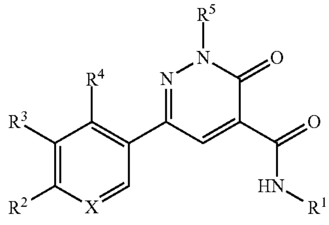

(I)

Methyl 6-chloro-3-oxo-2,3-dihydropyridazine-4-carboxylate [CAS 89581-64-6] is commercially available. Conversion of methyl 6-chloro-3-oxo-2,3-dihydropyridazine-4-carboxylate with organoboron derivatives (boronic acids, boronic acid pinacolates, mida boronates, organotrifluoroborate salts) in the presence of a suitable palladium (0) catalyst, a suitable base and in a suitable solvent at room temperature or elevated temperatures leads to the formation of 6-aryl substituted 3-oxo-2,3-dihydropyridazine-4-carboxylic acids of formula (XI). Organoboron derivatives used are commercially available or can be synthesized from organohalides. Methods for such syntheses are known to the person skilled in the art. A suitable catalyst can be, but should not be restricted to, palladium-phosphine complexes as $Pd(PPh_3)_4$, $PdCl_2(PPh_3)_2$, or palladium catalysts which can be prepared in situ from the precursors such as $Pd(OAc)_2$ or $Pd_2(dba)_3 \cdot CHCl_3$, with appropriate amounts of phosphines or palladacycle catalysts as e.g. the 2nd generation RuPhos precatalyst, chloro(2-dicyclohexylphosphino-2',6'-diisopropoxy-1,1'-biphenyl)[2-(2'-amino-1,1'-biphenyl)]palladium(II), RuPhos-Pd-G2. A suitable base can be, but should not be restricted to, potassium phosphate, potassium carbonate, potassium tert.-butylate, cesium carbonate and triethylamine. A suitable solvent can be, but should not be restricted to, dioxane, toluene, THE and dimethylformamide or even mixtures of these or other solvents.

The 3-oxo-2,3-dihydropyridazine-4-carboxylic acids (XI) can be converted to the amides (XII) by coupling with amines of the formula (VIII). Coupling agents and methods for such syntheses of carboxamides from carboxylic acids and amines are known to the person skilled in the art. Examples which may be mentioned here include the use of HATU, HBTU, PyBOB or T3P with the addition of a suitable base. The conversion of the carboxylic acids to their amides is described in general terms in reference books.

Substituted pyridazinones of formula (I) can be prepared by Chan-Lam coupling reactions using boronic acid derivatives (boronic acids, boronic acid pinacolates, mida boronates and organotrifluoroborate salts) in suitable solvents at room temperature or elevated temperatures. A suitable solvent can be, but should not be restricted to, acetonitrile, dichloromethane, pyridine and DMF. A suitable catalyst can be, but should not be restricted to, copper (II) acetate. Suitable basic additives can be, but should not be restricted to, trimethylamine, 2,2-bipyridine, sodium carbonate or caesium carbonate.

Scheme 4: Additional route for the preparation of compounds of general formula (I) in which X, $R^1$, $R^2$, $R^3$, $R^4$ and $R^5$ have the meaning as given for general formula (I), supra, and R represents $C_1$-$C_4$-alkyl and R′ and R″ represent simultaneously H or $C_1$-$C_4$-alkyl or form together a $C_2$-$C_7$-alkylene group as part of a 1,2- or 1,3-diol boronic ester or a $-CO-CH_2-(NCH_3)-CH_2-CO-$ group.

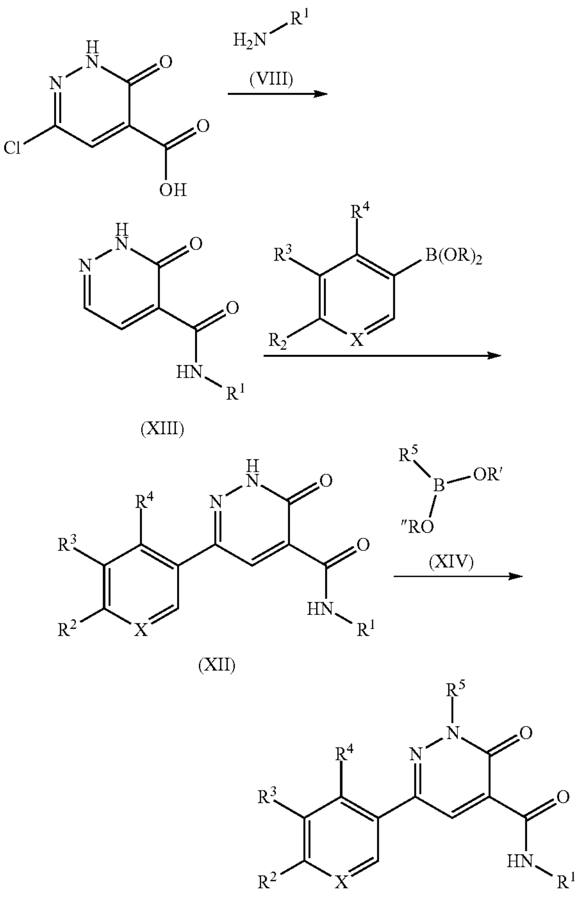

(I)

6-Chloro-3-oxo-2,3-dihydropyridazine-4-carboxylic acid [CAS 50681-26-0] is commercially available and can be converted by coupling with amines of the formula (VIII) to amides of formula (XIII). Coupling agents and methods for such syntheses of carboxamides from carboxylic acids and amines are known to the person skilled in the art. Examples which may be mentioned here include the use of HATU, HBTU, PyBOB or T3P with the addition of a suitable base.

6-Chloro-3-oxo-2,3-dihydropyridazine-4-carboxamides (XIII) can be transformed with organoboron derivatives (boronic acids, boronic acid pinacolates, mida boronates, organotrifluoroborate salts) in the presence of a suitable palladium (0) catalyst, a suitable base and in a suitable solvent at room temperature or elevated temperatures to 6-aryl substituted 3-oxo-2,3-dihydropyridazine-4-carboxamides of formula (XII). Organoboron derivatives used are commercially available or can be synthesized from organohalides. Methods for such syntheses are known to the person skilled in the art. A suitable catalyst can be, but should not be restricted to palladium-phosphine complexes as $Pd(PPh_3)_4$, $PdCl_2(PPh_3)_2$ or palladium catalysts which can be prepared in situ from the precursors such as $Pd(OAc)_2$ or $Pd_2(dba)_3$·$CHCl_3$, with appropriate amounts of phosphines or palladacycle catalysts as e.g. the 2nd generation RuPhos precatalyst, chloro(2-dicyclohexylphosphino-2',6'-diisopropoxy-1,1'-biphenyl)[2-(2'-amino-1,1'-biphenyl)]palladium(II), RuPhos-Pd-G2. A suitable base can be, but should not be restricted to potassium phosphate, potassium carbonate, potassium tert.-butylate, cesium carbonate and triehylamine. A suitable solvent can be, but should not be restricted to, dioxane, toluene, THE and dimethylformamide or even mixtures of these or other solvents.

Substituted pyridazinones according to formula (I) can be prepared by Chan-Lam coupling reactions of 6-aryl substituted 3-oxo-2,3-dihydropyridazine-4-carboxamides according to formula (XII) using boronic acid derivatives (boronic acids, boronic acid pinacolates, mida boronates and organotrifluoroborate salts) with suitable solvents at room temperature or elevated temperatures. A suitable solvent can be, but should not be restricted to, acetonitrile, dichloromethane, pyridine and DMF. A suitable catalyst can be, but should not be restricted to copper (II) acetate. Suitable basic additives can be, but should not be restricted to, trimethylamine, 2,2-bipyridine, sodium carbonate or caesium carbonate.

The compounds are either commercially available or can be prepared according to procedures available from the public domain, as understandable to the person skilled in the art. Specific examples are described in the Experimental Section.

In accordance with a second aspect, the present invention covers methods of preparing compounds of general formula (I) as defined supra, said methods comprising the step of allowing an intermediate compound of general formula (VII):

(VII)

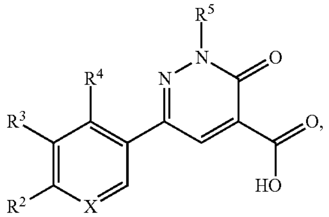

in which $R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

X represents CH or N;

to react with a compound of general formula (VIII)

(VIII)

$$H_2N—R^1,$$

in which $R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally one to three times with halogen, or $C_3$-$C_6$-cycloalkyl-$C_1$-$C_3$-alkyl substituted once with hydroxy and optionally one to three times with halogen, or $(C_3$-$C_6$-cycloalkyl$)_2$-$C_1$-$C_3$-alkyl substituted once with hydroxy and optionally one to three times with halogen, or 4- to 6-membered heterocycloalkyl substituted once with hydroxy and optionally one to three times with halogen;

$R^{10}$ represents $C_1$-$C_4$-alkyl;

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

thereby giving a compound of general formula (I):

(I)

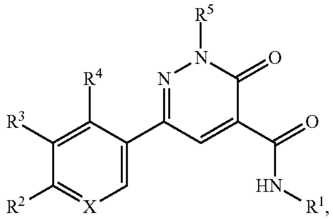

in which X, $R^1$, $R^2$, $R^3$, $R^4$ and $R^5$ are as defined supra.

The present invention covers methods of preparing compounds of the present invention of general formula (I), said methods comprising the steps as described in the Experimental Section herein.

In accordance with a third aspect, the present invention covers intermediate compounds which are useful for the preparation of the compounds of general formula (I), supra.

Particularly, the inventions covers the intermediate compounds of general formula (VII):

(VII)

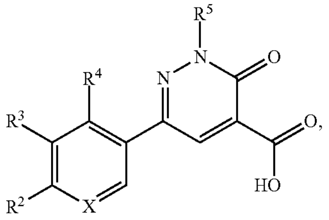

in which $R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

X represents CH or N;

In accordance with a forth aspect, the present invention covers the use of said intermediate compounds for the preparation of a compound of general formula (I) as defined supra.

Particularly, the inventions covers the use of intermediate compounds of general formula (VII)

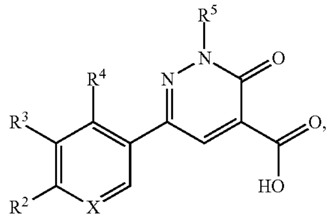

in which $R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

$R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

X represents CH or N;

for the preparation of a compound of general formula (I) as defined supra.

In accordance with a fifth aspect, the present invention covers methods of preparing compounds of general formula (I) as defined supra, said methods comprising the step of allowing an intermediate compound of general formula (XII):

(XII)

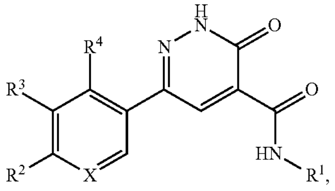

in which (XII), $R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally one to three times with halogen, or $C_3$-$C_6$-cycloalkyl-$C_1$-$C_3$-alkyl substituted once with hydroxy and optionally one to three times with halogen, or $(C_3$-$C_6$-cycloalkyl$)_2$-$C_1$-$C_3$-alkyl substituted once with hydroxy and optionally one to three times with halogen, or 4- to 6-membered heterocycloalkyl substituted once with hydroxy and optionally one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

to react with a compound of general formula (XIV):

(XIV)

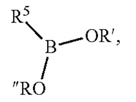

in which $R^5$ represents monocyclic heteroaryl, which is optionally substituted one to three times, independently from each other, with $R^6$;

$R^6$ represents $C_1$-$C_4$-alkyl, $C_1$-$C_4$-haloalkyl, $C_3$-$C_6$-cycloalkyl, $C_1$-$C_4$-alkoxy, halogen or cyano;

R', R' represent simultaneously H or $C_1$-$C_4$-alkyl or form together a $C_2$-$C_7$-alkylene group as part of a 1,2- or 1,3-diol boronic ester or a —CO—$CH_2$—($NCH_3$)—$CH_2$—CO— group;

thereby giving a compound of general formula (I):

(I)

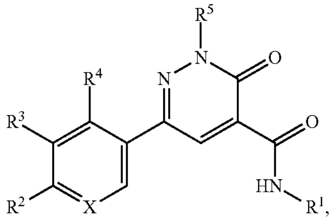

in which X, $R^1$, $R^2$, $R^3$, $R^4$ and $R^5$ are as defined supra.

The present invention covers methods of preparing compounds of the present invention of general formula (I), said methods comprising the steps as described in the Experimental Section herein.

In accordance with a sixth aspect, the present invention covers intermediate compounds which are useful for the preparation of the compounds of general formula (I), supra.

Particularly, the inventions covers the intermediate compounds of general formula (XII):

(XII)

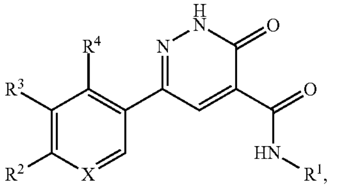

in which $R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally one to three times with halogen, or $C_3$-$C_6$-cycloalkyl-$C_1$-$C_3$-alkyl substituted once with hydroxy and optionally one to three times with halogen, or ($C_3$-$C_6$-cycloalkyl)$_2$-$C_1$-$C_3$-alkyl substituted once with hydroxy and optionally one to three times with halogen, or 4- to 6-membered heterocycloalkyl substituted once with hydroxy and optionally one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

In accordance with a seventh aspect, the present invention covers the use of said intermediate compounds for the preparation of a compound of general formula (I) as defined supra.

Particularly, the inventions covers the use of intermediate compounds of general formula (XII):

(XII)

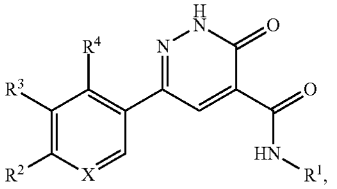

in which $R^1$ represents $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally one to three times with halogen, or $C_3$-$C_6$-cycloalkyl-$C_1$-$C_3$-alkyl substituted once with hydroxy and optionally one to three times with halogen, or ($C_3$-$C_6$-cycloalkyl)$_2$-$C_1$-$C_3$-alkyl substituted once with hydroxy and optionally one to three times with halogen, or 4- to 6-membered heterocycloalkyl substituted once with hydroxy and optionally one to three times with halogen;

$R^2$ represents chloro, cyano, dimethylamino, methyl, fluoromethyl, difluoromethyl, trifluoromethyl, methoxy, difluoromethoxy or trifluoromethoxy;

$R^3$ represents hydrogen, fluoro, chloro or methyl;

$R^4$ represents hydrogen or fluoro;

X represents CH or N;

$R^{10}$ represents $C_1$-$C_4$-alkyl;

$R^{11}$ and $R^{12}$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;

for the preparation of a compound of general formula (I) as defined supra.

The present invention covers the intermediate compounds which are disclosed in the Example Section of this text, infra.

The present invention covers any sub-combination within any embodiment or aspect of the present invention of intermediate compounds of general formula (VII), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit AHR and it is possible therefore that said compounds be used for the treatment or prophylaxis of diseases, preferably cancer or conditions with dysregulated immune responses or other disorders associated with aberrant AHR signaling, in humans and animals.

Disorders and conditions particularly suitable for treatment with an AHR inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers.

Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with: 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors, e.g. aPD-1/-L1 axis antagonists.

PD-1, along with its ligands PD-L1 and PD-L2, function as negative regulators of T cell activation. AHR suppresses immune cell function while increasing cancer cell proliferation and motility. PD-L1 is overexpressed in many cancers and overexpression of PD-1 often occurs concomitantly in tumor infiltrating T cells. Thus results in attenuation of T cell activation and evasion of immune surveillance, which contributes to impaired antitumor immune responses. (Keir M E et al. (2008) Annu. Rev. Immunol. 26:677).

Simultaneously targeting both the PD-1/-L1 axis and AHR enhances antitumor immune responses more than in an additive manner, leading to a reduction of tumor growth that is unexpected.

Thus, compositions comprising a PD-1/-L1 axis antagonist and an AHR antagonist are surprisingly effective in enhancing an immune response and in the treatment of cancer.

In addition, the inventive compounds can also be used as a therapeutic in a variety of other disorders wherein AHR is involved such as, cardiovascular and lung diseases.

Accordingly, the compounds according to the invention are suitable for the treatment and/or prophylaxis in particular of cardiovascular, inflammatory and fibrotic disorders and of renal disorders, in particular of acute and chronic renal insufficiency, and also of acute and chronic renal failure.

Accordingly, the compounds according to the invention can be used in medicaments for the treatment and/or prophylaxis of cardiovascular, inflammatory and fibrotic disorders, renal disorders, in particular of acute and chronic renal insufficiency, and also of acute and chronic renal failure.

For the purpose of the present invention the term renal insufficiency comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoidnephrosis); membranous glomerulonephritis; focal segmental glomerulosclerosis (FSGS); membrane-proliferative glomerulonephritis; crescentic glomerulonephritis; mesangioproliferative glomerulonephritis (IgA nephritis, Berger's disease); post-infectious glomerulonephritis; secondary glomerulonephritides: diabetes mellitus, lupus erythematosus, amyloidosis, Goodpasture syndrome, Wegener granulomatosis, Henoch-Schonlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or acquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis. The present invention also comprises the use of the compounds according to the invention for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

The present invention also comprises the use of the compounds according to the invention for the treatment and/or prevention of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

The compounds according to the invention are further suitable for the treatment and/or prevention of polycystic kidney disease (PCKD) and of the syndrome of inappropriate ADH secretion (SIADH).

Furthermore, the compounds according to the invention are also suitable for the treatment and/or prophylaxis of metabolic syndrome, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In addition, the compounds according to the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Picks syndrome, Parkinson's disease, progressive dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In addition, the compounds according to the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds according to the invention can also be used for treatment and/or prophylaxis of autoimmune diseases.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

The compounds according to the invention are also suitable for controlling postoperative scarring, for example as a result of glaucoma operations.

The compounds according to the invention can also be used cosmetically for ageing and keratinized skin.

Moreover, the compounds according to the invention are suitable for treatment and/or prophylaxis of hepatitis, neoplasms, osteoporosis, glaucoma and gastroparesis.

The present invention further provides for the use of the compounds according to the invention for treatment and/or prophylaxis of disorders, especially the disorders mentioned above.

The present invention further provides for the use of the compounds according to the invention for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention further provides a method for treatment and/or prophylaxis of disorders, in particular the disorders mentioned above, using an effective amount of at least one of the compounds according to the invention.

The present invention further provides a method for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

In another embodiment, the inventive compounds can also be used to treat or to prevent uterine fibroids (uterine leiomyoma or uterine myoma) in women.

Uterine fibroids are benign tumors of the myometrium, the smooth muscle layer of the uterus. Uterine fibroids grow slowly during a women's life, and their growth is dependent on the female sexual hormones estradiol and progesterone [Kawaguchi K et al. Immunohistochemical analysis of oestrogen receptors, progesterone receptors and Ki-67 in leiomyoma and myometrium during the menstrual cycle and pregnancy Virchows Arch A Pathol Anat Histopathol. 1991; 419(4):309-15.], therefore the highest prevalence of uterine fibroids with approx. 70% and >80% in white and afro-american women, respectively, is found from 35 years of age onwards to menopause, when they shrink due to reduced hormone levels [Baird D D et al. High cumulative incidence of uterine leiomyoma in black and white women: Ultrasound evidence Am J Obstet Gynecol. 2003 January; 188(1):100-7.]. Approx 30% and 45% of white and afro-american women, respectively, do show clinically relevant symptoms due to their fibroids, which are heavy menstrual bleeding and pain, which is related to the menstrual cycle [David M et al. Myoma-associated pain frequency and intensity: a retrospective evaluation of 1548 myoma patients. Eur J Obstet Gynecol Reprod Biol. 2016 April; 199:137-40]. Heavy menstrual bleeding in this respect is defined by a blood loss of more than 80 mL in a menstrual bleeding period [Fraser I S et al. The FIGO Recommendations on Terminologies and Definitions for Normal and Abnormal Uterine Bleeding, Semin Reprod Med 2011; 29(5): 383-390]. Submucosal position of the uterine fibroids, e.g. those located directly below the endometrium, seems to have an even more severe effect on uterine bleeding, which may result in anemia in affected women [Yang J H et al. Impact of submucous myoma on the severity of anemia. Fertil Steril. 2011 April; 95(5):1769-72]. Furthermore, uterine fibroids, due to their symptoms, do severely affect the quality of life of affected women [Downes E et al. The burden of uterine fibroids in five European countries. Eur J Obstet Gynecol Reprod Biol. 2010 September; 152(1):96-102].

So far, it is not understood how uterine fibroids do cause heavy menstrual bleeding. Disregulated genes in uterine fibroids, in comparison to normal myometrium, can give a hint to understand the underlying mechanisms. In published and internal studies, we found TDO2, Tryptophan 2,3-dioxygenase, being highly upregulated [Tsibris J C et al. Insights from gene arrays on the development and growth regulation of uterine leiomyomata. Fertil Steril. 2002 July; 78(1):114-21.]. TDO2 metabolizes the substrate L-Tryptophan to L-Kynurenine, which can be further metabolized to kynurenic acid. Both, L-Kynurenine and Kynurenic acid are physiological ligands and activators for the arylhydrocarbon receptor AHR [Opitz C A et al. An endogenous tumour-promoting ligand of the human aryl hydrocarbon receptor Nature. 2011 Oct. 5; 478(7368):197-203].

L-Kynurenine controls at least two physiological processes which are dysregulated in uterine fibroids. L-Kynurenine, synthesized by an upregulation of IDO (Indoleamine-2,3-dyoxygenase) or TDO2, and acting via the AHR receptor, suppresses the immune system and thus prevents immune cells from recognizing and clearing the tumor cells [Munn D H Blocking IDO activity to enhance anti-tumor immunity. Front Biosci (Elite Ed). 2012 Jan. 1; 4:734-45]. Furthermore, an upregulation of L-Kynurenine leads to a vasodilation of vessels, and thus can directly increase blood loss and bleeding [Wang Y et al. Kynurenine is an endothelium-derived relaxing factor produced during inflammation Nature Medicine 16, 279-285 (2010)].

In summary, the upregulation of L-Kynurenine through activation of its physiological receptor AHR seems to support uterine fibroid growth by local suppression of the immune system, and might cause heavy menstrual bleeding by vasodilation of endometrial vessels in proximity to the tumor.

Therefore, a systemic or local application of compounds from the present invention inhibiting activation of the AHR and thus blocking the effect of uterine fibroid derived L-Kynurenine presents a new and valid treatment option for uterine fibroids.

Compounds of the present invention can be utilized to inhibit, block, reduce or decrease AHR activation by exogenous and/or endogenous ligands for the reduction of tumour growth and the modulation of dysregulated immune responses e.g. to block immunosuppression and increase immune cell activation and infiltration in the context of cancer and cancer immunotherapy; This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating a variety of other disorders wherein AHR is involved such as, but not limited to, inflammation, vaccination for infection & cancer, viral infections, obesity and diet-induced obesity, adiposity, metabolic disorders, hepatic steatosis and uterine fibroids.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as liquid and solid tumours.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant AHR signaling.

The pharmaceutical activity of the compounds according to the invention can be explained by their activity as AHR inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant AHR signaling, particularly liquid and solid tumours.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular cancer or conditions with dysregulated immune responses or other disorders associated with aberrant AHR signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant AHR signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant AHR signaling, particularly liquid and solid tumours.

In accordance with a further aspect, the present invention covers a method of treatment or prophylaxis of diseases, in particular cancer or conditions with dysregulated immune responses or other disorders associated with aberrant AHR signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant AHR signaling generic name disorders, particularly liquid and solid tumours.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant AHR signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, quin=quintet, br=broad signal, m=multiplet. NMR signals: shift in [ppm]. Combinations of multiplicity could be e.g. dd=doublet from doublet.

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

TABLE 1

| Abbreviations | |
|---|---|
| ACN | acetonitrile |
| AcOH | acetic acid |
| $CDCl_3$ | deuterochloroform |
| DAD | diode array detector |
| DEA | diethylamine |
| DMF | N,N-dimethylformamide |
| DMSO-d6 | deuterated dimethyl sulphoxide |
| DMSO | dimethyl sulphoxide |
| ELSD | evaporative light scattering detector |
| ESIpos | electrospray ionization positive |
| Expl. | example |
| HATU | (7-aza-1H-benzotriazol-1-yl)-1,1,3,3-tetramethyluronium hexafluorophosphate |
| HBTU | O-benzotriazole-N,N,N',N'-tetramethyluronium hexafluorophosphate |
| HPLC | high-pressure liquid chromatography |
| KA | kynurenic acid |
| LCMS | liquid chromatography coupled with mass spectrometry |
| LPS | lipopolysaccharide |
| mL | milliliter |
| min. | minute(s) |
| MTBE | methyl tert-butyl ether |
| PBMC | peripheral blood mononuclear cells |
| PyBOB | (benzotriazol-1-yl)oxytripyrrolidinophosphonium hexafluorophosphate |
| RP-HPLC | reverse-phase high-pressure liquid chromatography |
| Rt | retention time |
| rt | room temperature |
| sat. | saturated |
| T3P | 2,4,6-tripropyl-1,3,5,2,4,6-trioxatriphosphorinane 2,4,6-trioxide |
| THF | tetrahydrofurane |
| TFA | trifluoroacetic acid |
| TLC | thin layer chromatography |
| TNFα | tumour necrosis factor alpha |
| μM | micromolar |
| UPLC | Ultra high performance chromatography |

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or IsoleraFour®) and eluents such as gradients of hexane/ethyl acetate or DCM/methanol. In some cases, the compounds may be purified by preparative HPLC using for example a Waters autopurifier equipped with a diode array detector and/or on line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

EXPERIMENTAL SECTION—INTERMEDIATES

Intermediate 1

Di-tert-butyl 1-(1-methyl-1H-pyrazol-4-yl)hydrazine-1,2-dicarboxylate

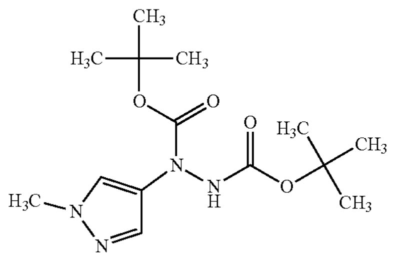 [SMILES: Cn1cc(N(NC(=O)OC(C)(C)C)C(=O)OC(C)(C)C)cn1]

To a solution of 1.5 g 4-bromo-1-methyl-1H-pyrazole in 30 mL tetrahydrofurane (30 mL) cooled to −78° C. was added 1.7 mL n-butyllithium (2M in THE). After stirring at −78° C. for 30 minutes, a solution of 2.1 g di-tert-butyl azodicarboxylate in 10 mL tetrahydrofurane was added dropwise. After 1 h, the reaction mixture was warmed up to −20° C. and quenched with ice. After warming to ambient temperature, the mixture was filtered and rinsed with tetrahydrofurane. The resulting solid was taken up in a mixture of dichloromethane and water, and the mixture was phase separated. After evaporation in vacuo, the residue was subjected to column chromatography (petroleum ether/ethyl acetate 2:1) to yield 800 mg di-tert-butyl 1-(1-methyl-1H-pyrazol-4-yl)hydrazine-1,2-dicarboxylate.

$^1$H-NMR: (300 MHz, 25° C., Methanol-$d_4$): δ [ppm]=1.44 (s, 18H); 3.77 (s, 3H); 7.17-7.28 (m, 1H); 7.61-7.67 (m, 1H); 9.60 (s, 1H).

Intermediate 2

4-Hydrazinyl-1-methyl-1H-pyrazole trifluoroacetate (1:1

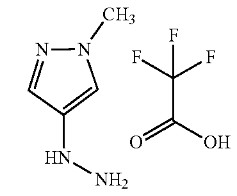

A mixture of 800 mg intermediate 1 in 15 mL dichloromethane and 1 mL trifluoroacetic acid was stirred at room temperature for 3 hours. The mixture was evaporated to dryness to give 750 mg (crude) of the product which can be used in next step directly without further purification.

$^1$H-NMR: (300 MHz, 25° C., DMSO-$d_6$): δ [ppm]=3.79 (s, 3H); 7.33 (s, 1H); 7.57 (s, 1H); 9.49 (br s, 3H).

Intermediate 3

Dimethyl [2-(4-methylphenyl)-2-oxoethyl]propanedioate

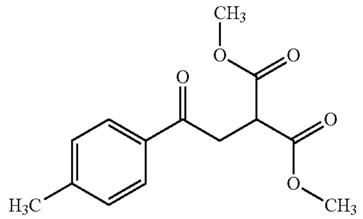

A solution of 49.6 g 2-bromo-1-(4-methylphenyl)ethanone in 300 mL of acetone was added dropwise at rt to a solution of 10 g dimethyl malonate in 120 mL of acetone. The reaction mixture was stirred at room temperature for 4 hs. Then, the solvent was removed in vacuo. The residue was purified by column chromatography (petroleum ether/ethyl acetate 10:1) to yield 10.3 g dimethyl [2-(4-methylphenyl)-2-oxoethyl]propanedioate.

$^1$H-NMR: (400 MHz, 25° C., DMSO-$d_6$): δ [ppm]=2.38 (s, 3H); 3.60 (d, 2H); 3.68 (s, 6H); 3.97 (t, 1H); 7.34 (d, 2H); 7.89 (d, 2H).

Intermediate 4

Methyl 6-(4-methylphenyl)-2-(1-methyl-1H-pyrazol-4-yl)-3-oxo-2,3,4,5-tetrahydropyridazine-4-carboxylate

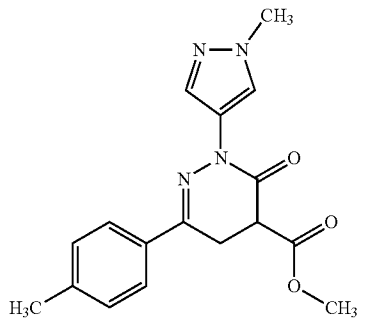

A mixture of 818 mg intermediate 3 and 700 mg intermediate 2 in 20 mL ethanol was stirred at 80° C. for 2 hours. Then the solvent was removed in vacuo. The residue was purified by column chromatography (petroleum ether/ethyl acetate 3:2) to yield 500 mg methyl 6-(4-methylphenyl)-2-(1-methyl-1H-pyrazol-4-yl)-3-oxo-2,3,4,5-tetrahydropyridazine-4-carboxylate.

$^1$H-NMR: (400 MHz, 25° C., $CDCl_3$): δ [ppm]=2.41 (s, 3H); 3.14 (dd, 1H); 3.51 (dd, 1H); 3.76 (dd, 1H); 3.79 (s, 3H); 3.91 (s, 3H); 7.27 (d, 2H, signal partly below $CDCl_3$ signal); 7.74 (d, 2H); 7.87 (s, 1H); 8.00 (s, 1H).

Intermediate 5

Methyl 6-(4-methylphenyl)-2-(1-methyl-1H-pyrazol-4-yl)-3-oxo-2,3-dihydropyridazine-4-carboxylate

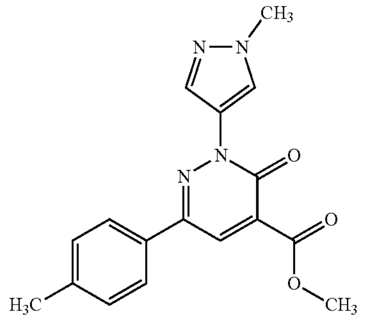

A mixture of 450 mg intermediate 4 and 371 mg copper (II) chloride in 20 mL of acetonitrile was stirred at 90° C. for 2 hours. After evaporation in vacuo, the residue was purified by column chromatography (dichloromethane/methanol 20:1) to yield 380 mg methyl 6-(4-methylphenyl)-2-(1-methyl-1H-pyrazol-4-yl)-3-oxo-2,3-dihydropyridazine-4-carboxylate.

$^1$H-NMR: (400 MHz, 25° C., DMSO-$d_6$): δ [ppm]=2.37 (s, 3H); 3.88 (s, 3H); 3.91 (s, 3H); 7.34 (d, 2H); 7.93 (d, 2H); 8.08 (s, 1H); 8.40 (s, 1H); 8.49 (s, 1H).

Intermediate 6

6-(4-Methylphenyl)-2-(1-methyl-1H-pyrazol-4-yl)-3-oxo-2,3-dihydropyridazine-4-carboxylic acid

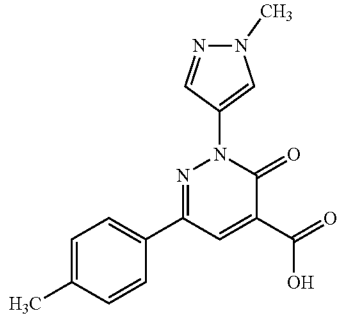 [SMILES: Cc1ccc(-c2cc(C(=O)O)c(=O)n(-c3cnn(C)c3)n2)cc1]

A mixture of 380 mg intermediate 5 in 30 mL of acetonitrile was treated with 147 mg lithium hydroxide, dissolved in 2 mL of water. The reaction mixture was stirred at room temperature for 3 hours. Then the pH value was adjusted to 5-6 with hydrochloric acid (10%). The solids were collected by filtration, washed three times with water and dried in an oven to yield 310 mg 6-(4-methylphenyl)-2-(1-methyl-1H-pyrazol-4-yl)-3-oxo-2,3-dihydropyridazine-4-carboxylic acid.

$^1$H-NMR: (400 MHz, 25° C., DMSO-$d_6$): δ [ppm]=2.37 (s, 3H); 3.91 (s, 3H); 7.32 (d, 2H); 7.89 (d, 2H); 7.95 (s, 1H); 8.04 (s, 1H); 8.40 (s, 1H).

Intermediate 7

6-(4-Methylphenyl)-2-(1-methyl-1H-pyrazol-4-yl)-3-oxo-2,3-dihydropyridazine-4-carbonyl chloride

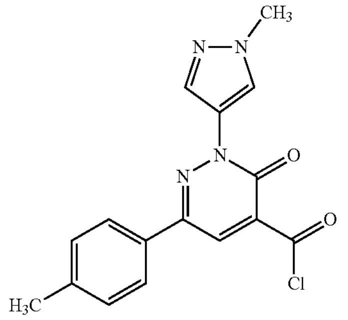 [SMILES: Cc1ccc(-c2cc(C(=O)Cl)c(=O)n(-c3cnn(C)c3)n2)cc1]

110 mg oxalylchloride were slowly added to a solution of 180 mg intermediate 6 in 10 mL of dichloromethane and 0.1 mL N,N-dimethylformamide. The reaction mixture was stirred at 0° C. for 1 h. The mixture was evaporated to dryness to give 260 mg crude 6-(4-methylphenyl)-2-(1-methyl-1H-pyrazol-4-yl)-3-oxo-2,3-dihydropyridazine-4-carbonyl chloride which was used into next step directly without further purification.

Intermediate 8

Dimethyl [2-(4-chlorophenyl)-2-oxoethyl]malonate

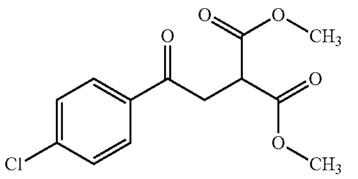 [SMILES: COC(=O)C(CC(=O)c1ccc(Cl)cc1)C(=O)OC]

2-Chloro-1-(4-chlorophenyl)ethanone (25 g, 107.1 mmol) was dissolved in acetone (500 mL). Then, dimethyl malonate (31.1 g, 235.4 mmol) and potassium carbonate (22.2 g, 160.6 mmol) were added at rt. It was stirred at rt overnight. The reaction mixture was reduced under vacuum to half its volume. Then, the residue was poured into water. The layers were separated and the aqueous phase was extracted twice with ethyl acetate. The combined organic layers were washed with water and concentrated aqueous sodium chloride solution, dried over sodium sulfate and concentrated. The crude product was purified by flash chromatography (silica gel, hexane/ethyl acetate, gradient) yielding 12.21 g (36%) of the title product.

$^1$H-NMR (400 MHz, DMSO-$d_6$): δ [ppm]=3.63 (d, 2H), 3.68 (s, 6H), 3.97 (t, 1H), 7.59-7.64 (m, 2H), 7.99-8.03 (m, 2H).

Intermediate 9

Methyl 6-(4-chlorophenyl)-2-(1-methyl-1H-pyrazol-4-yl)-3-oxo-2,3,4,5-tetrahydropyridazine-4-carboxylate

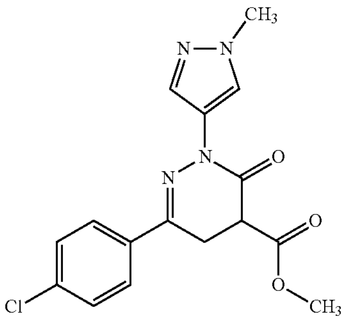 [SMILES: COC(=O)C1CC(c2ccc(Cl)cc2)=NN(c2cnn(C)c2)C1=O]

Dimethyl [2-(4-chlorophenyl)-2-oxoethyl]malonate (1360 mg, 4.78 mmol) and sodium acetate (1037 mg, 12.65 mmol) were dissolved in acetic acid (40 mL). Then, 4-hydrazino-1-methyl-1H-pyrazole dihydrochloride (780 mg, 4.22 mmol) was added portion wise. It was stirred for 1 h at rt and 20 h at 50° C. The reaction mixture was cooled down and concentrated on a rotary evaporator under reduced pressure. Ethyl acetate and water were added to dissolve the residue. Concentrated aqueous sodium hydrogen carbonate solution was added, the phases were separated, and the aqueous layer was extracted with ethyl acetate (four times with 80 mL). The combined organic layers were washed twice with water, dried over magnesium sulfate, and concentrated. The residue was purified by flash chromatography (silica gel, hexane/ethyl acetate, gradient) to afford 530 mg (36%) of the title product.

$^1$H-NMR (400 MHz, DMSO-$d_6$): δ [ppm]=3.35-3.46 (m, 2H), 3.68 (s, 3H), 3.85 (s, 3H), 4.03 (dd, 1H), 7.52-7.57 (m, 2H), 7.75 (d, 1H), 7.92-7.96 (m, 2H), 8.08 (s, 1H).

Intermediate 10

Methyl 6-(4-chlorophenyl)-2-(1-methyl-1H-pyrazol-4-yl)-3-oxo-2,3-dihydropyridazine-4-carboxylate

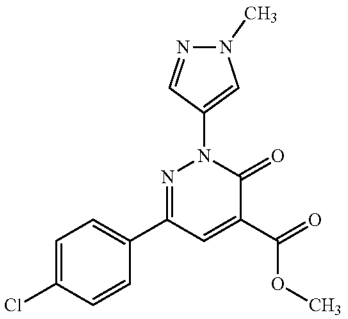 [SMILES: COC(=O)c1cc(-c2ccc(Cl)cc2)nn(-c2cnn(C)c2)c1=O]

Methyl 6-(4-chlorophenyl)-2-(1-methyl-1H-pyrazol-4-yl)-3-oxo-2,3,4,5-tetrahydropyridazine-4-carboxylate (600 mg, 1.730 mmol) was dissolved in acetonitrile (40 mL). Copper dichloride (698 mg, 5.191 mmol) was added. It was stirred for 4 h at 90° C. It was cooled down and concentrated on a rotary evaporator. Water was added, the remaining solid was filtered by suction, washed five times with water, and dried under vacuum at 50° C. to yield 741 mg of the title compound which was used without further purification in the next step.

$^1$H-NMR (400 MHz, DMSO-$d_6$): δ [ppm]=3.88 (s, 3H), 3.91 (s, 3H), 7.59 (d, 2H), 8.05-8.13 (m, 3H), 8.44 (s, 1H), 8.52 (br s, 1H).

Intermediate 11

6-(4-Chlorophenyl)-2-(1-methyl-1H-pyrazol-4-yl)-3-oxo-2,3-dihydropyridazine-4-carboxylic acid

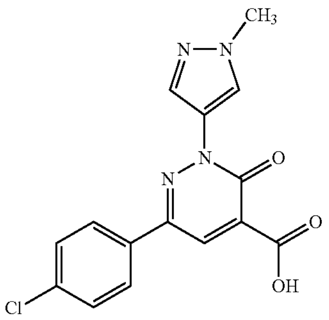 [SMILES: Cn1cc(-n2nc(-c3ccc(Cl)cc3)cc(C(=O)O)c2=O)cn1]

Methyl 6-(4-chlorophenyl)-2-(1-methyl-1H-pyrazol-4-yl)-3-oxo-2,3-dihydropyridazine-4-carboxylate (600 mg, 1.74 mmol) was dissolved in acetonitrile (60 mL). A solution of lithium hydroxide (125 mg, 5.221 mmol) in water (1.90 mL) was added at rt. It was stirred for 10 h at 40° C. Water was added and the pH was adjusted to 4 with 2N HCl. The precipitate was filtered off under suction, washed three times with water and dried under vacuum at 50° C. obtaining 520 mg (90%) of the title compound which was used without further purification in the next step.

$^1$H-NMR (400 MHz, DMSO-$d_6$): δ [ppm]=3.91 (s, 3H), 7.54 (br d, 2H), 7.78 (s, 1H), 8.00-8.07 (m, 3H), 8.41 (s, 1H).

Intermediate 12

Methyl 6-(4-chlorophenyl)-3-oxo-2,3,4,5-tetrahydropyridazine-4-carboxylate

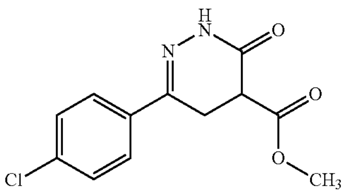 [SMILES: COC(=O)C1CC(c2ccc(Cl)cc2)=NNC1=O]

Dimethyl [2-(4-chlorophenyl)-2-oxoethyl]malonate (16.30 g, 57.25 mmol) was dissolved in acetic acid (203 mL). A solution of hydrazidine in THF (80 mL, 1.0M, 80 mmol) was added at rt. It was stirred for 5.5 h at 75° C. and at rt overnight. Then, it was stirred at 75° C. After 2.5 h a solution of hydrazine in THF (24 mL, 1.0M, 24 mmol) was added and stirring at 75° C. was continued for 1.5 hours. The reaction mixture was cooled down and water (1 L) was added. The precipitate was filtered off under suction, washed with water and dried under vacuum at 50° C. obtaining 12.14 g (80%) of the title compound which was used without further purification in the next step.

$^1$H-NMR (400 MHz, DMSO-$d_6$): δ [ppm]=3.16 (dd, 1H), 3.26 (dd, 1H), 3.67 (s, 3H), 3.75 (dd, 1H), 7.47-7.52 (m, 2H), 7.75-7.79 (m, 2H), 11.31 (s, 1H).

Intermediate 13

Methyl 6-(4-chlorophenyl)-3-oxo-2,3-dihydropyridazine-4-carboxylate

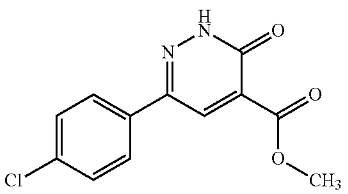 [SMILES: COC(=O)c1cc(-c2ccc(Cl)cc2)n[nH]c1=O]

Methyl 6-(4-chlorophenyl)-3-oxo-2,3,4,5-tetrahydropyridazine-4-carboxylate (4.97 g, 18.64 mmol) was dissolved in acetonitrile (350 mL). Copper dichloride (6.26 g, 46.59 mmol) was added and it was stirred for 5.5 h at 70° C. Then, additional copper dichloride (0.626 g, 4.66 mmol) was added and the stirring at 70° C. was continued for 1 h. The reaction mixture was cooled down and concentrated on a rotary evaporator to half its volume. Water was added (300 mL) and the reaction mixture was stirred for 10 min. The precipitate was filtered by suction, washed three times with water and dried at 50° C. under vacuum to give 4.793 g (97%) of the title compound.

$^1$H-NMR (400 MHz, DMSO-$d_6$): δ [ppm]=3.85 (s, 3H), 7.53-7.58 (m, 2H), 7.89-7.93 (m, 2H), 8.38 (s, 1H), 13.70 (s, 1H).

Intermediate 14

Dimethyl {2-oxo-2-[4-(trifluoromethyl)phenyl]ethyl}malonate

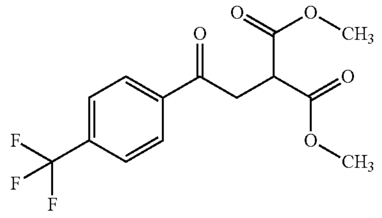 [SMILES: COC(=O)C(CC(=O)c1ccc(C(F)(F)F)cc1)C(=O)OC]

Dimethyl malonate (9.894 g, 74.89 mmol) and potassium carbonate (7.763 g, 56.17 mmol) were added to acetone (140 mL). Under cooling (0-5° C.) a solution of 2-bromo-1-[4-(trifluoromethyl)phenyl]ethanone (10 g, 37.4 mmol) in acetone (60 mL) was added dropwise. It was stirred 2 h at 0-5° C. and at rt overnight. The volatile compounds were removed on a rotavap. Water and ethyl acetate were added, the layers were separated and the aqueous phase was extracted twice with ethyl acetate. The combined organic layers were washed with concentrated aqueous sodium chloride solution, dried over magnesium sulfate and concentrated. The crude product was purified by flash chromatography (silica gel, hexane/ethyl acetate, gradient) affording 8.03 g (67%) of the title product.

$^1$H-NMR (400 MHz, CHLOROFORM-$d_3$): β [ppm]=3.65 (d, 2H), 3.79 (s, 6H), 4.10 (t, 1H), 7.73-7.77 (m, 2H), 8.07-8.11 (m, 2H).

Intermediate 15

Methyl 3-oxo-6-[4-(trifluoromethyl)phenyl]-2,3,4,5-tetrahydropyridazine-4-carboxylate

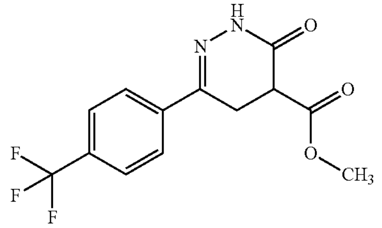 [SMILES: COC(=O)C1CC(c2ccc(C(F)(F)F)cc2)=NNC1=O]

Dimethyl {2-oxo-2-[4-(trifluoromethyl)phenyl]ethyl}malonate (5.68 g, 17.55 mmol) was dissolved in acetic acid (64 mL). A solution of hydrazidine in THF (35 mL, 1.0M, 35 mmol) was added at rt. It was stirred for 3.5 h at 75° C. Then, a solution of hydrazine in THF (3.5 mL, 1.0M, 3.5 mmol) was added and stirring at 75° C. was continued for 1 h. The reaction mixture was cooled down and water (0.6 L) was added. The precipitate was filtered off under suction, washed with water and dried under vacuum at 50° C. yielding 4.06 g (76%) of the title compound which was used without further purification in the next step.

$^1$H-NMR (400 MHz, DMSO-$d_6$): δ [ppm]=3.23 (dd, 1H), 3.28-3.36 (m, 1H and water signal), 3.68 (s, 3H), 3.79 (dd, 1H), 7.80 (d, 2H), 7.96 (d, 2H), 11.43 (s, 1H).

Intermediate 16

Methyl 3-oxo-6-[4-(trifluoromethyl)phenyl]-2,3-dihydropyridazine-4-carboxylate

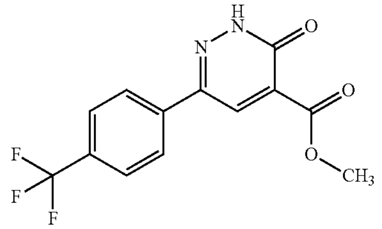 [SMILES: COC(=O)c1cc(-c2ccc(C(F)(F)F)cc2)n[nH]c1=O]

Methyl 3-oxo-6-[4-(trifluoromethyl)phenyl]-2,3,4,5-tetrahydropyridazine-4-carboxylate (4.06 g, 13.52 mmol) was dissolved in acetonitrile (180 mL). Copper dichloride (4.55 g, 33.81 mmol) was added and it was stirred for 2.5 h at 90° C. The reaction mixture was cooled down and concentrated on a rotary evaporator to half its volume. Water was added (350 mL) and the reaction mixture was stirred for 10 min. The precipitate was filtered by suction, washed three times with water and dried at 50° C. under vacuum to afford 3.67 g (91%) of the title compound.

$^1$H-NMR (400 MHz, DMSO-$d_6$): δ [ppm]=3.86 (s, 3H), 7.86 (d, 2H), 8.11 (d, 2H), 8.45 (s, 1H), 13.83 (s, 1H).

Intermediate 17

Methyl 2-(1-methyl-1H-pyrazol-4-yl)-3-oxo-6-[4-(trifluoromethyl)phenyl]-2,3-dihydropyridazine-4-carboxylate

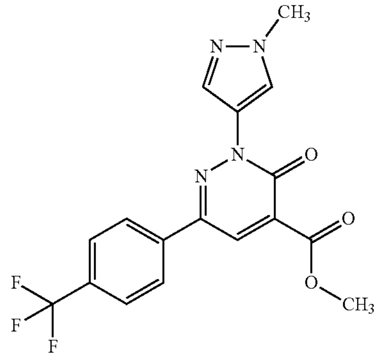 [SMILES: COC(=O)c1cc(-c2ccc(C(F)(F)F)cc2)nn(-c2cnn(C)c2)c1=O]

Methyl 3-oxo-6-[4-(trifluoromethyl)phenyl]-2,3-dihydropyridazine-4-carboxylate (0.5 g, 1.68 mmol) was dissolved in DMF (26.6 mL). 1-Methyl-4-(4,4,5,5-tetramethyl-1,3,2-dioxaborolan-2-yl)-1H-pyrazole (698 mg, 3.53 mmol), 2,2'-bipyridine (655 mg, 4.19 mmol), cesium hydrogen carbonate (390 mg, 2.01 mmol), and anhydrous copper diacetate (380.7 mg, 2.10 mmol) were added. It was stirred for 21 h at rt. 1-Methyl-4-(4,4,5,5-tetramethyl-1,3,2-dioxaborolan-2-yl)-1H-pyrazole (349 mg, 1.68 mmol) was added and stirring was continued at rt overnight. Water (5 mL) was added and the pH was adjusted to 3 with 2N HCl (3.5 mL). The precipitate was filtered, washed three times with water, and dried at 50° C. under vacuum to afford 594 mg (63%) of the title compound.

$^1$H-NMR (400 MHz, DMSO-$d_6$): δ [ppm]=3.89 (s, 3H), 3.92 (s, 3H), 7.88 (br d, 2H), 8.11 (s, 1H), 8.28 (br d, 2H), 8.52 (s, 1H), 8.52 (s, 1H).

Intermediate 18

2-(1-Methyl-1H-pyrazol-4-yl)-3-oxo-6-[4-(trifluoromethyl)phenyl]-2,3-dihydropyridazine-4-carboxylic acid

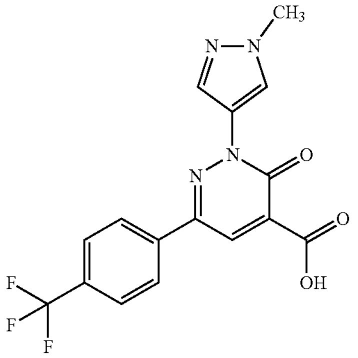 [SMILES: Cn1cc(-n2nc(-c3ccc(C(F)(F)F)cc3)cc(C(=O)O)c2=O)cn1]

Methyl 2-(1-methyl-1H-pyrazol-4-yl)-3-oxo-6-[4-(trifluoromethyl)phenyl]-2,3-dihydropyridazine-4-carboxylate (590 mg, 1.56 mmol) was dissolved in acetonitrile (54 mL). A solution of lithium hydroxide (112 mg, 4.70 mmol) in water (1.7 mL) was added at rt. It was stirred for 3 h at rt. Water (100 mL) was added and the pH was adjusted to 6 with 2N HCl. The precipitate was filtered off under suction, washed with water and dried under vacuum at 50° C. yielding 345 mg (45%) of the title compound which was used without further purification in the next step.

$^1$H-NMR (400 MHz, DMSO-$d_6$): δ [ppm]=3.93 (br s, 3H), 7.47-8.39 (m, 7H).

Intermediate 19

6-(4-Chlorophenyl)-2-(1-cyclobutyl-1H-pyrazol-4-yl)-3-oxo-2,3-dihydropyridazine-4-carboxylic acid

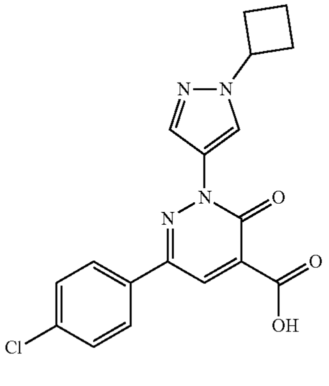 [SMILES: O=C(O)c1cc(-c2ccc(Cl)cc2)nn(-c2cnn(C3CCC3)c2)c1=O]

Step 1: Methyl 6-(4-chlorophenyl)-3-oxo-2,3-dihydropyridazine-4-carboxylate (0.5 g, 1.89 mmol) was dissolved in DMF (15 mL). 1-Cyclobutyl-4-(4,4,5,5-tetramethyl-1,3,2-dioxaborolan-2-yl)-1H-pyrazole (1406 mg, 5.67 mmol), 2,2'-bipyridine (737.7 mg, 4.72 mmol), sodium hydrogen carbonate (318 mg, 3.78 mmol), and anhydrous copper diacetate (429 mg, 3.79 mmol) were added. It was stirred for 96 h at rt. Water was added and the pH was adjusted to 3 with 2N HCl. The precipitate was filtered, washed three times with water, and dried at 50° C. under vacuum to afford 370 mg (36%) of the methyl ester which was used in the successive step without further purification.

Step 2: The ester (293 mg, 0.76 mmol) was dissolved in acetonitrile (16.7 mL). A solution of lithium hydroxide (55 mg, 2.28 mmol) in water (0.65 mL) was added at rt. It was stirred at rt overnight. Water was added and the pH was adjusted to 6 with 2N HCl. The precipitate was filtered off under suction, washed with water and dried under vacuum at 50° C. yielding 93 mg (33%) of the title compound which was used without further purification in the next step.

LC-MS (Instrument: Waters Acquity UPLC-MS SOD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.64 min; MS (ESIpos): m/z=371.3 $[M+H]^+$ Intermediate 20

Dimethyl {2-oxo-2-[4-(trifluoromethoxy)phenyl]ethyl}malonate

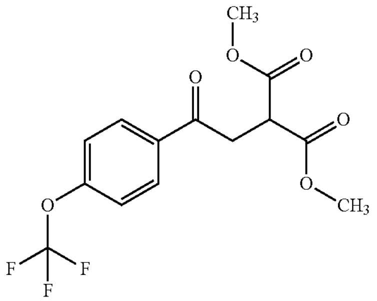 [SMILES: COC(=O)C(CC(=O)c1ccc(OC(F)(F)F)cc1)C(=O)OC]

4.1 g dimethyl malonate and 3.2 g potassium carbonate were added to a solution of 4.4 g 2-bromo-1-[4-(trifluoromethoxy)phenyl]ethan-1-one in 110 mL of acetone. The reaction mixture was stirred at room temperature overnight and then quenched with water. Acetone was evaporated and the remaining aqueous phase was extracted three times with ethyl acetate. The combined organic phases were washed with brine, dried over sodium sulfate, filtrated and concentrated. The residue was purified by column chromatography (hexane/ethyl acetate gradient with up to 30% ethyl acetate) to yield 4.9 g dimethyl {2-oxo-2-[4-(trifluoromethoxy)phenyl]ethyl}malonate.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.22 min; MS (ESIpos): m/z=335 $[M+H]^+$ $^1$H NMR (400 MHz, DMSO-$d_6$) δ [ppm]=3.33 (s, 6H), 3.62-3.67 (m, 2H), 3.99 (t, 1H), 7.52 (dd, 2H), 8.11-8.16 (m, 2H).

Intermediate 21

Methyl 2-(1-methyl-1H-pyrazol-4-yl)-3-oxo-6-[4-(trifluoromethoxy)phenyl]-2,3,4,5-tetrahydropyridazine-4-carboxylate

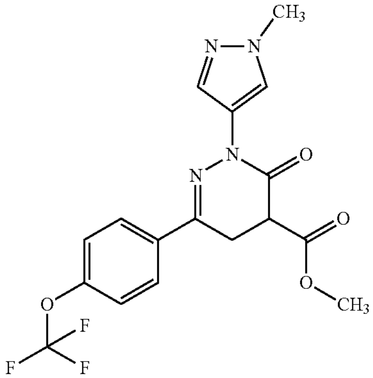 [SMILES: COC(=O)C1CC(c2ccc(OC(F)(F)F)cc2)=NN(c2cnn(C)c2)C1=O]

A mixture of 954 mg dimethyl {2-[4-(difluoromethoxy)phenyl]-2-oxoethyl}malonate, 1111 mg 4-hydrazino-1-methyl-1H-pyrazole dihydrochloride and 1053 mg sodium acetate in 27 mL of AcOH was stirred at rt for 14 h and 50° C. for 6 h. The reaction mixture was concentrated and the residue was taken up in water and ethyl acetate followed by the addition of saturated aqueous sodium bicarbonate solution. The phases were separated and the aqueous phase was extracted three times with ethyl acetate. The combined organic phases were washed with brine, dried over sodium sulfate, filtrated and evaporated to dryness. The residue was purified by column chromatography (hexane/ethyl acetate gradient with up to 80% ethyl acetate) to yield 559 mg methyl 2-(1-methyl-1H-pyrazol-4-yl)-3-oxo-6-[4-(trifluoromethoxy)phenyl]-2,3,4,5-tetrahydropyridazine-4-carboxylate.

$^1$H NMR (400 MHz, DMSO-$d_6$) δ [ppm]=3.40-3.43 (m, 2H), 3.69 (s, 3H), 3.85 (s, 3H), 4.04 (t, 1H), 7.48 (d, 2H), 7.75 (s, 1H), 8.04 (d, 2H), 8.08 (s, 1H).

Intermediate 22

Methyl 2-(1-methyl-1H-pyrazol-4-yl)-3-oxo-6-[4-(trifluoromethoxy)phenyl]-2,3-dihydropyridazine-4-carboxylate

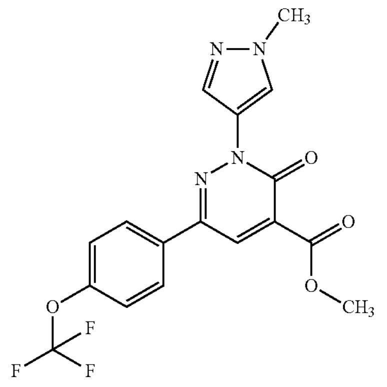 [SMILES: COC(=O)c1cc(-c2ccc(OC(F)(F)F)cc2)nn(-c2cnn(C)c2)c1=O]

A mixture of 686 mg methyl 2-(1-methyl-1H-pyrazol-4-yl)-3-oxo-6-[4-(trifluoromethoxy)phenyl]-2,3,4,5-tetrahydropyridazine-4-carboxylate and 698 mg copper(II) chloride in 23 mL of acetonitrile was stirred at 50° C. for 2 hours and 90° C. for 3 h. After evaporation in vacuum, the residue was suspended in water and the precipitate was filtered off to yield 528 mg methyl 2-(1-methyl-1H-pyrazol-4-yl)-3-oxo-6-[4-(trifluoromethoxy)phenyl]-2,3-dihydropyridazine-4-carboxylate.

$^1$H NMR (400 MHz, DMSO-$d_6$) δ [ppm]=3.89 (s, 3H), 3.92 (s, 3H), 7.52 (d, 2H), 8.09 (s, 1H), 8.15-8.20 (m, 2H), 8.46 (s, 1H), 8.51 (s, 1H).

Intermediate 23

2-(1-Methyl-1H-pyrazol-4-yl)-3-oxo-6-[4-(trifluoromethoxy)phenyl]-2,3-dihydropyridazine-4-carboxylic acid

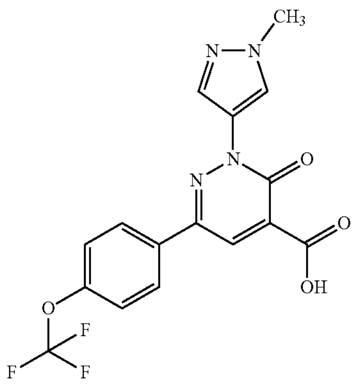 [SMILES: Cn1cc(-n2nc(-c3ccc(OC(F)(F)F)cc3)cc(C(=O)O)c2=O)cn1]

A mixture of 528 mg methyl 2-(1-methyl-1H-pyrazol-4-yl)-3-oxo-6-[4-(trifluoromethoxy)phenyl]-2,3-dihydropyridazine-4-carboxylate and 1.7 mL 2N aqueous sodium hydroxide solution in 7 mL tetrahydrofurane was stirred at rt for 14 hours. Then the pH value was adjusted to 3 with 1M hydrochloric acid and the precipitate was filtered off, washed with water and dried in vacuum to yield 458 mg 2-(1-methyl-1H-pyrazol-4-yl)-3-oxo-6-[4-(trifluoromethoxy)phenyl]-2,3-dihydropyridazine-4-carboxylic acid.

$^1$H NMR (400 MHz, DMSO-$d_6$) δ [ppm]=3.92 (s, 3H), 7.51 (d, 2H), 8.11 (s, 1H), 8.17-8.24 (m, 2H), 8.42 (s, 1H), 8.52 (s, 1H).

Intermediate 24

Dimethyl {2-[4-(difluoromethyl)phenyl]-2-oxoethyl}propanedioate

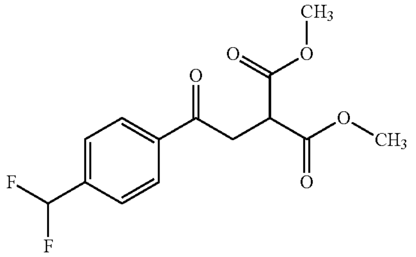 [SMILES: COC(=O)C(CC(=O)c1ccc(C(F)F)cc1)C(=O)OC]

A mixture of 2.5 g 2-bromo-1-[4-(difluoromethyl)phenyl]ethanone (CAS 1227004-73-0), 4.6 mL dimethyl malonate and 2.1 g potassium carbonate in 70 mL acetone was stirred at rt for 14 hours. After full conversion (TLC) the reaction mixture was poured into water and the acetone was evaporated under reduced pressure. The resulting solution was extracted with ethyl acetate three times, the combined organic phases were washed with water and brine and the solvent was evaporated in vacuo. The residue was purified by column chromatography (hexanes/ethyl acetate gradient to 40% ethyl acetate) to yield 1.45 g dimethyl {2-[4-(difluoromethyl)phenyl]-2-oxoethyl}propanedioate.

$^1$H-NMR (400 MHz, DMSO-$d_6$) δ[ppm]=3.64-3.70 (m, 8H); 4.00 (t, 1H); 7.15 (t, 1H); 7.74 (d, 2H); 8.12 (d, 2H).

Intermediate 25

Methyl 6-[4-(difluoromethyl)phenyl]-2-(1-methyl-1H-pyrazol-4-yl)-3-oxo-2,3,4,5-tetra-hydropyridazine-4-carboxylate

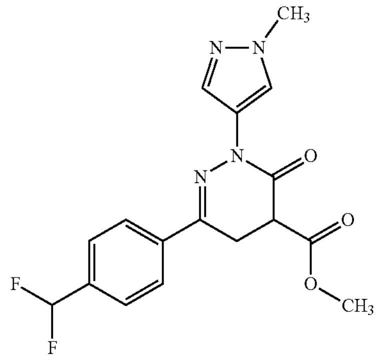 [SMILES: COC(=O)C1CC(c2ccc(C(F)F)cc2)=NN(c2cnn(C)c2)C1=O]

A mixture of 75 mg dimethyl {2-[4-(difluoromethyl)phenyl]-2-oxoethyl}propanedioate, 44 mg 4-hydrazino-1-methyl-1H-pyrazole dihydrochloride and 53 mg sodium acetate in 2.5 mL of AcOH was stirred at rt for 1 h and 50° C. for 24 h. Further 88 mg of 4-hydrazino-1-methyl-1H-pyrazole dihydrochloride were added and the reaction mixture was stirred at 50° C. for 6 hours. The reaction mixture was concentrated and the residue was taken up in water and ethyl acetate followed by the addition of saturated aqueous sodium bicarbonate solution. The phases were separated and the aqueous phase was extracted three times with ethyl acetate. The combined organic phases were washed with brine, dried over sodium sulfate, filtrated and evaporated to dryness. The residue was purified by HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 24 mg methyl 6-[4-(difluoromethyl)phenyl]-2-(1-methyl-1H-pyrazol-4-yl)-3-oxo-2,3,4,5-tetra-hydro-pyridazine-4-carboxylate.

$^1$H NMR (400 MHz, DMSO-$d_6$) δ [ppm]=3.43 (dd, 2H), 3.69 (s, 3H), 3.85 (s, 3H), 4.02-4.08 (m, 1H), 7.11 (t, 1H), 7.68 (d, 2H), 7.76 (s, 1H), 8.06 (d, 2H), 8.09 (s, 1H).

Intermediate 26

Methyl 6-[4-(difluoromethyl)phenyl]-2-(1-methyl-1H-pyrazol-4-yl)-3-oxo-2,3-dihydropyridazine-4-carboxylate

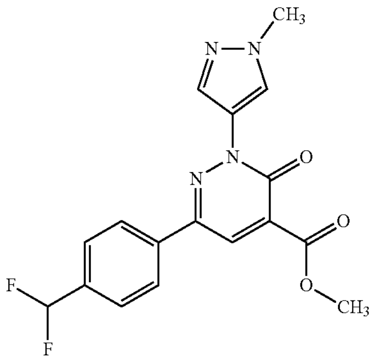 [SMILES: COC(=O)c1cc(-c2ccc(C(F)F)cc2)nn(-c2cnn(C)c2)c1=O]

A mixture of 495 mg methyl 6-[4-(difluoromethyl)phenyl]-2-(1-methyl-1H-pyrazol-4-yl)-3-oxo-2,3,4,5-tetra-hydropyridazine-4-carboxylate and 551 mg copper(II) chloride in 15 mL of acetonitrile was stirred at 90° C. for 2 hours. After evaporation in vacuum, the residue was suspended in water and the precipitate was filtered off to yield 451 mg methyl 6-[4-(difluoromethyl)phenyl]-2-(1-methyl-1H-pyrazol-4-yl)-3-oxo-2,3-dihydropyridazine-4-carboxylate.

$^1$H NMR (400 MHz, DMSO-$d_6$) δ [ppm]=3.89 (s, 3H), 3.92 (s, 3H), 7.13 (t, 1H), 7.72 (d, 2H), 8.11 (s, 1H), 8.20 (d, 2H), 8.48 (s, 1H), 8.52 (s, 1H).

Intermediate 27

6-[4-(Difluoromethyl)phenyl]-2-(1-methyl-1H-pyrazol-4-yl)-3-oxo-2,3-dihydropyridazine-4-carboxylic acid

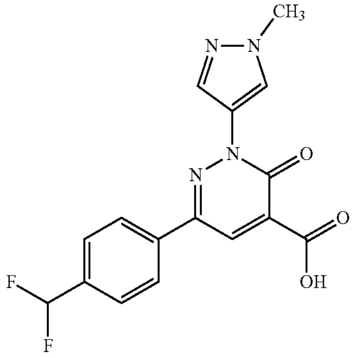 [SMILES: Cn1cc(-n2nc(-c3ccc(C(F)F)cc3)cc(C(=O)O)c2=O)cn1]

A mixture of 451 mg methyl 6-[4-(difluoromethyl)phenyl]-2-(1-methyl-1H-pyrazol-4-yl)-3-oxo-2,3-dihydropyridazine-4-carboxylate and 6 mL 1N aqueous sodium hydroxide solution in 19 mL tetrahydrofurane was stirred at rt for 48 hours. Then the pH value was adjusted to 3 with 1M hydrochloric acid and the precipitate was filtered off, washed with water and dried in vacuum to yield 190 mg 6-[4-(difluoromethyl)phenyl]-2-(1-methyl-1H-pyrazol-4-yl)-3-oxo-2,3-dihydropyridazine-4-carboxylic acid.

$^1$H NMR (400 MHz, DMSO-$d_6$) δ [ppm]=3.93 (s, 3H), 7.13 (t, 1H), 7.72 (d, 2H), 8.13 (s, 1H), 8.23 (d, 2H), 8.49 (s, 1H), 8.54 (s, 1H).

Intermediate 28

Dimethyl {2-[6-(difluoromethyl)pyridin-3-yl]-2-oxoethyl}malonate

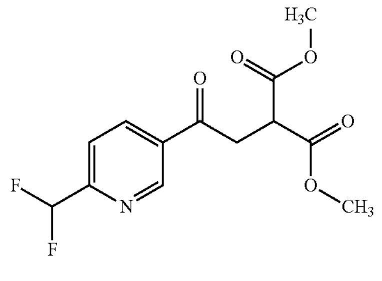 [SMILES: COC(=O)C(CC(=O)c1ccc(C(F)F)nc1)C(=O)OC]

A mixture of 5 g 2-bromo-1-[6-(difluoromethyl)pyridin-3-yl]ethanone, 4.5 mL dimethyl malonate and 4.1 g potassium carbonate in 140 mL acetone was stirred at rt for 14 hours. After full conversion (TLC) the reaction mixture was poured into water and the acetone was evaporated under reduced pressure. The resulting solution was extracted with ethyl acetate three times, the combined organic phases were washed with water and brine and the solvent was evaporated in vacuo. The residue was purified by column chromatography (dichloromethane/methanol gradient to 20% methanol) to yield 1.1 g dimethyl {2-[6-(difluoromethyl)pyridin-3-yl]-2-oxoethyl}malonate.

$^1$H NMR (400 MHz, DMSO-$d_6$) δ[ppm]=3.69 (s, 6H), 3.74 (d, 2H), 4.01 (t, 1H), 7.07 (t, 1H), 7.87 (d, 1H), 8.53 (dd, 1H), 9.24 (d, 1H).

Intermediate 29

Methyl 6-[6-(difluoromethyl)pyridin-3-yl]-2-(1-methyl-1H-pyrazol-4-yl)-3-oxo-2,3,4,5-tetrahydropyridazine-4-carboxylate

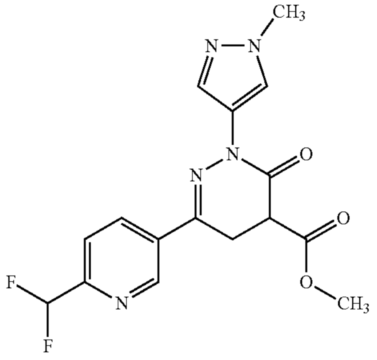 [SMILES: COC(=O)C1CC(c2ccc(C(F)F)nc2)=NN(c2cnn(C)c2)C1=O]

A mixture of 424 mg dimethyl {2-[6-(difluoromethyl)pyridin-3-yl]-2-oxoethyl}malonate, 549 mg 4-hydrazino-1-methyl-1H-pyrazole dihydrochloride and 520 mg sodium acetate in 13 mL of AcOH was stirred at rt for 1 hour and 50° C. for 2 h. The reaction mixture was concentrated and the residue was taken up in water and ethyl acetate followed by the addition of saturated aqueous sodium bicarbonate solution. The phases were separated and the aqueous phase was extracted three times with ethyl acetate. The combined organic phases were washed with brine, dried over sodium sulfate, filtrated and evaporated to dryness. The residue was purified by column chromatography (dichloromethane/methanol gradient to 8% methanol) to yield 240 mg methyl 6-[6-(difluoromethyl)pyridin-3-yl]-2-(1-methyl-1H-pyrazol-4-yl)-3-oxo-2,3,4,5-tetrahydropyridazine-4-carboxylate.

$^1$H NMR (400 MHz, DMSO-$d_6$) δ [ppm]=3.39-3.56 (m, 2H), 3.70 (s, 3H), 3.85 (s, 3H), 4.05-4.12 (m, 1H), 7.04 (t, 1H), 7.77-7.83 (m, 2H), 8.12 (s, 1H), 8.49 (dd, 1H), 9.19 (d, 1H).

Intermediate 30

Methyl 6-[6-(difluoromethyl)pyridin-3-yl]-2-(1-methyl-1H-pyrazol-4-yl)-3-oxo-2,3-dihydropyridazine-4-carboxylate

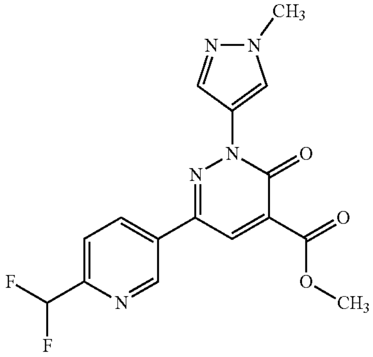 [SMILES: COC(=O)c1cc(-c2ccc(C(F)F)nc2)nn(-c2cnn(C)c2)c1=O]

A mixture of 240 mg methyl 6-[6-(difluoromethyl)pyridin-3-yl]-2-(1-methyl-1H-pyrazol-4-yl)-3-oxo-2,3,4,5-tetrahydropyridazine-4-carboxylate and 266 mg copper(II) chloride in 9 mL of acetonitrile was stirred at 90° C. for 2 hours. After evaporation in vacuum, the residue was suspended in water and the precipitate was filtered off and dried to yield 184 mg methyl 6-[6-(difluoromethyl)pyridin-3-yl]-2-(1-methyl-1H-pyrazol-4-yl)-3-oxo-2,3-dihydropyridazine-4-carboxylate.

$^1$H NMR (400 MHz, DMSO-$d_6$) δ[ppm]=3.89 (s, 3H), 3.91 (s, 3H), 7.05 (t, 1H), 7.83 (d, 1H), 8.13 (s, 1H), 8.54 (d, 2H), 8.63 (dd, 1H), 9.33 (d, 1H).

Intermediate 31

6-[6-(Difluoromethyl)pyridin-3-yl]-2-(1-methyl-1H-pyrazol-4-yl)-3-oxo-2,3-dihydropyridazine-4-carboxylic acid

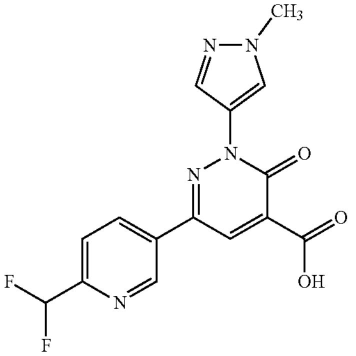 [SMILES: Cn1cc(-n2nc(-c3ccc(C(F)F)nc3)cc(C(=O)O)c2=O)cn1]

A mixture of 133 mg methyl 6-[6-(difluoromethyl)pyridin-3-yl]-2-(1-methyl-1H-pyrazol-4-yl)-3-oxo-2,3-dihydropyridazine-4-carboxylate and 0.46 mL 2N aqueous sodium hydroxide solution in 2 mL tetrahydrofurane was stirred at rt for 14 h. Then the pH value was adjusted to 3 with 1M hydrochloric acid and the precipitate was filtered off, washed with water and dried in vacuum to yield 103 mg 6-[6-(difluoromethyl)pyridin-3-yl]-2-(1-methyl-1H-pyrazol-4-yl)-3-oxo-2,3-dihydropyridazine-4-carboxylic acid.

$^{1}H$ NMR (400 MHz, DMSO-$d_6$) δ [ppm]=3.93 (s, 3H), 6.91-7.21 (m, 1H), 7.84 (d, 1H), 8.16 (s, 1H), 8.55 (d, 2H), 8.66 (dd, 1H), 9.36 (d, 1H).

Intermediate 32

5-Bromo-2-(difluoromethyl)pyridine

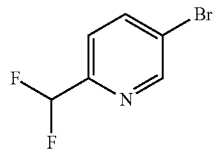

Into a 2000-mL 4-necked round-bottom flask, was placed a solution of 5-bromopyridine-2-carbaldehyde (30 g, 161.29 mmol, 1.00 equiv) in dichloromethane (800 mL). This was followed by the addition of DAST (diethylaminosulfur trifluoride) (40 g, 1.08 mol, 6.69 equiv) dropwise with stirring at 0° C. The resulting solution was stirred for 12 hours at room temperature. The reaction was then quenched by the addition of water. The pH value of the solution was adjusted to 8 with sodium carbonate (2 mol/L). The resulting solution was extracted with 3×500 mL of dichloromethane and the organic layers were combined. The resulting mixture was washed with 1×300 mL of $H_2O$. The resulting mixture was washed with 1×300 mL of brine. The mixture was dried over anhydrous sodium sulfate and concentrated under vacuum. The residue was applied onto a silica gel column with ethyl acetate/petroleum ether (1:10). This resulted in 18 g (54%) of 5-bromo-2-(difluoromethyl)pyridine as yellow oil.

Intermediate 33

1-[6-(difluoromethyl)pyridin-3-yl]ethanone

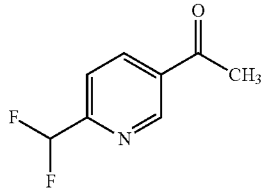

Into a 500-mL 4-necked round-bottom flask, was placed a solution of 5-bromo-2-(difluoromethyl)pyridine (18 g, 86.54 mmol, 1.00 equiv) in dioxane (180 mL), tributyl(1-ethoxyethenyl)stannane (35 g, 96.91 mmol, 1.12 equiv), tetrakis(triphenylphosphane) palladium (3 g, 2.60 mmol, 0.03 equiv). The resulting solution was stirred for 2 h at 100° C. The reaction mixture was cooled with a water bath. The reaction was then quenched by the addition of 250 mL of (2N) HCl. The pH value of the solution was adjusted to 8 with sodium carbonate (2 mol/L). The resulting solution was extracted with 3×500 mL of ethyl acetate and the organic layers were combined. The resulting mixture was washed with 1×200 mL of $H_2O$. The resulting mixture was washed with 1×200 mL of brine. The mixture was dried over anhydrous sodium sulfate and concentrated under vacuum. The residue was applied onto a silica gel column with ethyl acetate/petroleum ether (1:10). This resulted in 10 g (68%) of 1-[6-(difluoromethyl)pyridin-3-yl]ethan-1-one as yellow oil.

Intermediate 34

Diethyl {2-[6-(difluoromethyl)pyridin-3-yl]-2-oxo-ethyl}(hydroxy)malonate

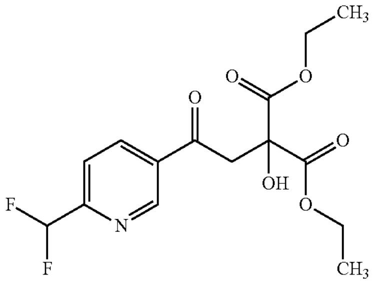 [SMILES: CCOC(=O)C(O)(CC(=O)c1ccc(C(F)F)nc1)C(=O)OCC]

Into a 100-mL round-bottom flask, was placed 1-[6-(difluoromethyl)pyridin-3-yl]ethan-1-one (10 g, 58.43 mmol, 1.00 equiv) and 1,3-diethyl 2-oxopropanedioate (15 g, 86.13 mmol, 1.47 equiv). The resulting solution was stirred for 24 h at 130° C. The resulting mixture was concentrated under vacuum. This resulted in 24 g (crude) of 1,3-diethyl 2-[2-[6-(difluoromethyl)pyridin-3-yl]-2-oxo-ethyl]-2-hydroxypropanedioate as red oil which was used without further purification.

Intermediate 35

Ethyl 6-[6-(difluoromethyl)pyridin-3-yl]-3-oxo-2,3-dihydropyridazine-4-carboxylate

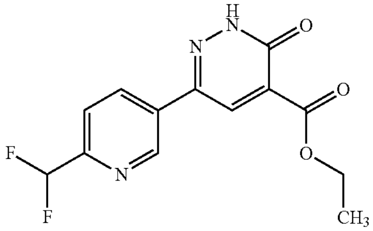 [SMILES: CCOC(=O)c1cc(-c2ccc(C(F)F)nc2)n[nH]c1=O]

Into a 500-mL round-bottom flask, was placed a solution of 1,3-diethyl 2-[2-[6-(difluoromethyl)pyridin-3-yl]-2-oxo-ethyl]-2-hydroxypropanedioate (24 g, 69.51 mmol, 1.00 equiv) in ethanol (200 mL) and hydrazine (15 mL). The resulting solution was stirred for 12 h at 80° C. The reaction was then quenched by the addition of water. The resulting solution was extracted with 3×300 mL of ethyl acetate and the organic layers were combined. The resulting mixture was washed with 1×100 mL of water. The resulting mixture was washed with 1×100 mL of brine. The mixture was dried over anhydrous sodium sulfate and concentrated under vacuum. The residue was applied onto a silica gel column with ethyl acetate/petroleum ether (2:1). This resulted in 2.8 g (14%) of ethyl 6-[6-(difluoromethyl)pyridin-3-yl]-3-oxo-2,3-dihydropyridazine-4-carboxylate as a yellow solid.

$^1$H-NMR (300 MHz, DMSO-$d_6$) δ [ppm]=13.84 (s, 1H), 9.17 (s, 1H), 8.46 (m, 2H), 7.83 (m, 1H), 7.03 (t, 1H), 4.35 (m, 2H), 1.33 (t, 3H).

Intermediate 36

Methyl 6-(4-chlorophenyl)-3-oxo-2-(pyridin-3-yl)-2,3,4,5-tetrahydropyridazine-4-carboxylate

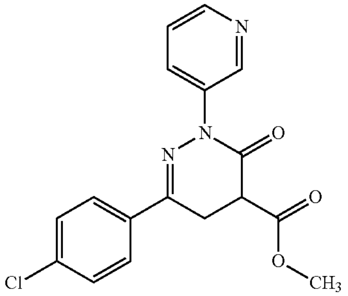 [SMILES: COC(=O)C1CC(c2ccc(Cl)cc2)=NN(c2cccnc2)C1=O]

Dimethyl [2-(4-chlorophenyl)-2-oxoethyl]malonate (1.88 g, 6.60 mmol) and sodium acetate (3.25 g, 39.62 mmol) were dissolved in acetic acid (50 mL). Then, 3-hydrazinopyridine hydrochloride (1:1) (0.961 g, 6.60 mmol) was added portion wise. It was stirred for 24 h at rt. Additional 3-hydrazinopyridine hydrochloride (1:1) (0.961 g, 6.60 mmol) was added and stirring was continued for 24 h at rt. Then, 3-hydrazinopyridine hydrochloride (1:1) (0.961 g, 6.60 mmol) was added again and it was stirred for 24 h at rt. Finally, it was stirred for 7 h at 80° C. The reaction mixture was cooled down and concentrated on a rotary evaporator under reduced pressure. Ethyl acetate and water were added to dissolve the residue. Concentrated aqueous sodium hydrogen carbonate solution was added, the phases were separated, and the aqueous layer was extracted three times with ethyl acetate. The combined organic layers were washed three times with water, dried over magnesium sulfate, and concentrated. The residue was purified by RP-HPLC (column: YMC-Triart C18 5 μm 100×50 mm, mobile phase: (water+0.1 vol % formic acid (99%))/acetonitrile, gradient) to yield 398 mg (18%) of the title product.

$^1$H-NMR (400 MHz, DMSO-$d_6$): δ [ppm]=3.43 (dd, 1H), 3.50 (dd, 1H), 3.71 (s, 3H), 4.11 (dd, 1H), 7.51 (ddd, 1H), 7.51-7.56 (m, 2H), 7.86-7.90 (m, 2H), 7.97 (ddd, 1H), 8.50 (dd, 1H), 8.77 (d, 1H).

Intermediate 37

6-(4-Chlorophenyl)-3-oxo-2-(pyridin-3-yl)-2,3-dihydropyridazine-4-carboxylic acid

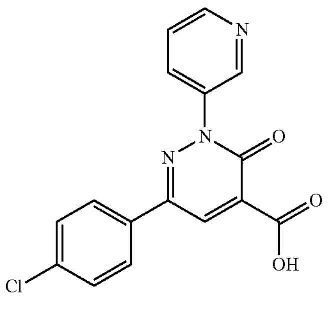 [SMILES: O=C(O)c1cc(-c2ccc(Cl)cc2)nn(-c2cccnc2)c1=O]

Step 1: Methyl 6-(4-chlorophenyl)-3-oxo-2-(pyridin-3-yl)-2,3,4,5-tetrahydropyridazine-4-carboxylate (1.0 g, 2.909 mmol) was dissolved in acetonitrile (60 mL). Copper dichloride (1.173 g, 8.727 mmol) was added. It was stirred for 4 h at 90° C. It was cooled down and concentrated on a rotary evaporator. Water was added, the remaining solid was filtered by suction, washed five times with water, and dried under vacuum at 50° C. for 24 h yielding 1.262 g of methyl 6-(4-chlorophenyl)-3-oxo-2-(pyridin-3-yl)-2,3-dihydropyridazine-4-carboxylate which was used without further purification in the next step.

Step 2: Methyl 6-(4-chlorophenyl)-3-oxo-2-(pyridin-3-yl)-2,3-dihydropyridazine-4-carboxylate (1.00 g, 2.93 mmol) was dissolved in acetonitrile (100 mL). A solution of lithium hydroxide (210 mg, 8.778 mmol) in water (3.2 mL) was added at rt. It was stirred for 10 h at 40° C. Water was added and the pH was adjusted to 6-7 with 0.5N HCl. The precipitate was filtered off under suction, washed three times with water and dried under vacuum at 50° C. yielding 910 mg (95%) of the title compound which was used without further purification in the next step.

$^1$H-NMR (400 MHz, DMSO-$d_6$): δ [ppm]=7.54 (br d, 2H), 7.59 (dd, 1H), 7.90-7.99 (m, 3H), 8.11 (br d, 1H), 8.63 (br d, 1H), 8.88 (br d, 1H).

Intermediate 38

Diethyl 2-(2-(4-chlorophenyl)-2-oxoethyl)-2-hydroxymalonate

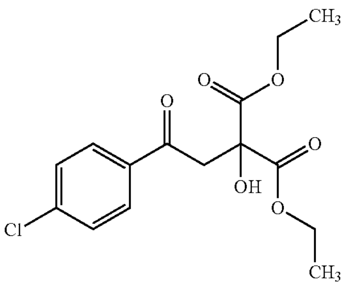

A mixture of 4-chloro acetophenone (30 g, 194.8 mmol) and diethyl ketomalonate (45 mL, 292.2 mmol) was heated at 130° C. for 48 h. The reaction was monitored by TLC and upon completion the reaction mixture was cooled and triturated with pentane to afford diethyl 2-(2-(4-chlorophenyl)-2-oxoethyl)-2-hydroxymalonate (50 g, 79%, LC-MS 98%) as a pale yellow liquid.

Intermediate 39

Ethyl 6-(4-chlorophenyl)-3-oxo-2,3-dihydropyridazine-4-carboxylate

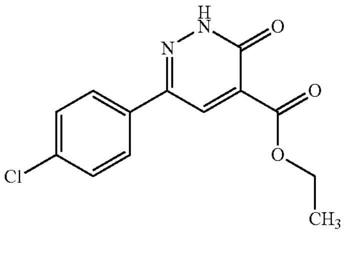 [SMILES: CCOC(=O)c1cc(-c2ccc(Cl)cc2)n[nH]c1=O]

A mixture of diethyl 2-(2-(4-chlorophenyl)-2-oxoethyl)-2-hydroxymalonate (50 g, 152.43 mmol) and hydrazine dihydrochloride (19.2 g, 182.9 mmol) in ethanol (500 mL) was heated under ref lux for 16 h. The reaction was monitored by TLC. After completion, the reaction mixture was cooled and concentrated under reduced pressure. Reaction mixture was poured into sat. sodium bicarbonate solution (500 mL) and extracted with ethyl acetate (3×600 mL). The combined organic layer were washed with water, brine, dried over $Na_2SO_4$, filtered and concentrated under reduced pressure to give crude product. The crude product was purified by column chromatography (silica gel, eluent EtOAc/hexane 30:70) to afford ethyl 6-(4-chlorophenyl)-3-oxo-2,3-dihydropyridazine-4-carboxylate (21 g, 42%, LC-MS 95%) as a pale yellow solid.

$^1$H NMR (400 MHz, DMSO-$d_6$) δ [ppm]=1.31 (t, 3H), 4.31 (q, 2H), 7.53-7.60 (m, 2H), 7.87-7.95 (m, 2H), 8.34 (s, 1H), 13.68 (br s, 1H).

Intermediate 40

Methyl 6-(4-chlorophenyl)-2-(5-fluoropyridin-3-yl)-3-oxo-2,3-dihydropyridazine-4-carboxylate

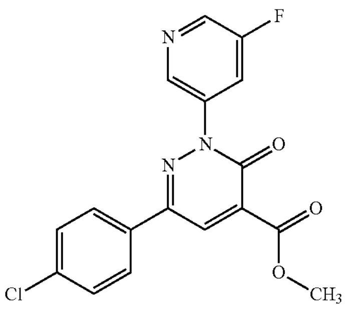 [SMILES: COC(=O)c1cc(-c2ccc(Cl)cc2)nn(-c2cncc(F)c2)c1=O]

Methyl 6-(4-chlorophenyl)-3-oxo-2,3-dihydropyridazine-4-carboxylate (682.3 mg, 2.578 mmol) was dissolved in DMF (27 mL). 3-Fluoro-5-(4,4,5,5-tetramethyl-1,3,2-dioxaborolan-2-yl)pyridine (1150 mg, 5.156 mmol), 2,2'-bipyridine (1007 mg, 6.445 mmol), sodium carbonate (328 mg, 3.093 mmol), and anhydrous copper diacetate (585 mg, 3.222 mmol) were added. It was stirred for 5 h at 40° C. The reaction mixture was cooled down, water was added and the pH was adjusted to 3 with 2N HCl. The precipitate was filtered, washed with water, and dried at 50° C. under vacuum. The crude material was purified by flash chromatography (silica gel, hexane/ethyl acetate, gradient) to afford 174 mg (13%) of the title compound.

$^1$H-NMR (400 MHz, DMSO-$d_6$): δ [ppm]=3.89 (s, 3H), 7.57-7.61 (m, 2H), 7.99-8.04 (m, 2H), 8.23 (ddd, 1H), 8.54 (s, 1H), 8.72 (dd, 1H), 8.86 (br t, 1H).

Intermediate 41

6-(4-Chlorophenyl)-2-(5-fluoropyridin-3-yl)-3-oxo-2,3-dihydropyridazine-4-carboxylic acid

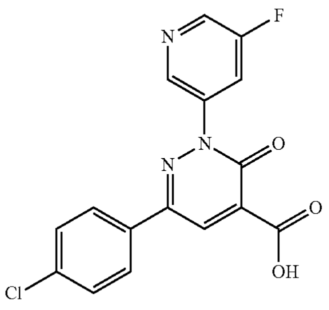 [SMILES: O=C(O)c1cc(-c2ccc(Cl)cc2)nn(-c2cncc(F)c2)c1=O]

Methyl 6-(4-chlorophenyl)-2-(5-fluoropyridin-3-yl)-3-oxo-2,3-dihydropyridazine-4-carboxylate (170 mg, 0.473 mmol) was dissolved in THE (8 mL). A solution of lithium hydroxide (34 mg, 1.418 mmol) in water (0.40 mL) was added at rt. It was stirred for 24 h at rt. Water was added and the pH was adjusted to 6 with 2N HCl. The precipitate was filtered off under suction, washed with water and dried under vacuum at 50° C. yielding 157 mg (96%) of the title compound which was used without further purification in the next step.

$^1$H-NMR (400 MHz, DMSO-$d_6$): δ [ppm]=7.56-7.60 (m, 2H), 8.01-8.06 (m, 2H), 8.24 (dt, 1H), 8.51 (s, 1H), 8.73 (d, 1H), 8.87 (s, 1H).

Intermediate 42

Methyl 3-oxo-2-(pyridin-3-yl)-6-[4-(trifluoromethyl)phenyl]-2,3-dihydropyridazine-4-carboxylate

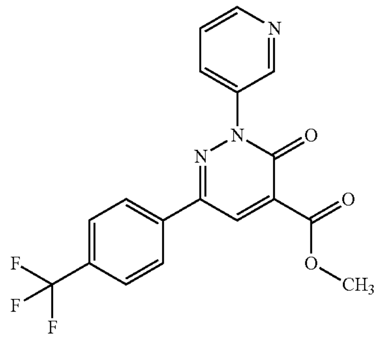 [SMILES: COC(=O)c1cc(-c2ccc(C(F)(F)F)cc2)nn(-c2cccnc2)c1=O]

Methyl 3-oxo-6-[4-(trifluoromethyl)phenyl]-2,3-dihydropyridazine-4-carboxylate (2 g, 6.71 mmol) was dissolved in DMF (90 mL). 3-(4,4,5,5-Tetramethyl-1,3,2-dioxaborolan-2-yl)pyridine (2.75 g, 13.41 mmol), 2,2'-bipyridine (2.62 g, 16.77 mmol), sodium carbonate (0.85 g, 8.02 mmol), and anhydrous copper diacetate (1.52 g, 8.37 mmol) were added. It was stirred for 3 h at 60° C. The reaction mixture was cooled down with an ice bath, water (240 mL) was added and the pH was adjusted to 3 with 2N HCl (20 mL). The precipitate was filtered, washed with water, and dried at 50° C. under vacuum to afford 1.8 g (72%) of the title compound.

$^1$H-NMR (400 MHz, DMSO-$d_6$): δ [ppm]=3.89 (s, 3H), 7.62 (dd, 1H), 7.88 (d, 2H), 8.15-8.21 (m, 3H), 8.60 (s, 1H), 8.68 (br d, 1H), 8.93 (br s, 1H).

Intermediate 43

3-Oxo-2-(pyridin-3-yl)-6-[4-(trifluoromethyl)phenyl]-2,3-dihydropyridazine-4-carboxylic acid

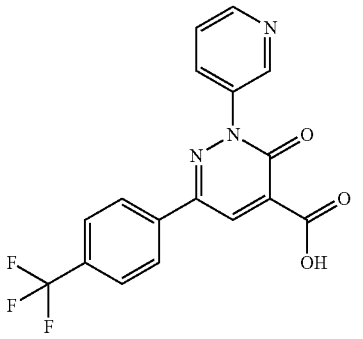 [SMILES: O=C(O)c1cc(-c2ccc(C(F)(F)F)cc2)nn(-c2cccnc2)c1=O]

Methyl 3-oxo-2-(pyridin-3-yl)-6-[4-(trifluoromethyl)phenyl]-2,3-dihydropyridazine-4-carboxylate (1.80 g, 4.80 mmol) was dissolved in THE (28 mL). A solution of lithium hydroxide (345 mg, 23.95 mmol) in water (5 mL) was added at rt. It was stirred at rt overnight. Water (100 mL) was added and the pH was adjusted to 6 with 2N HCl (4.5 mL). To the reaction mixture were added methylene chloride (50 mL) and chloroform (50 mL) The organic layer was separated and discarded. The precipitate was filtered off under suction, washed with water and dried under vacuum at 50° C. affording 1036 mg (60%) of the title compound which was used without further purification in the next step.

$^1$H-NMR (400 MHz, DMSO-$d_6$): δ [ppm]=7.60 (dd, 1H), 7.84 (d, 2H), 8.02 (s, 1H), 8.10-8.18 (m, 3H), 8.64 (d, 1H), 8.89 (d, 1H).

Intermediate 44

Diethyl hydroxy{2-oxo-2-[4-(trifluoromethoxy)phenyl]ethyl}malonate

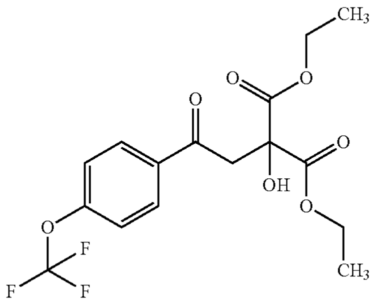 [SMILES: CCOC(=O)C(O)(CC(=O)c1ccc(OC(F)(F)F)cc1)C(=O)OCC]

A mixture of 1-(4-(trifluoromethoxy)phenyl)ethanone (20 g, 98.03 mmol) and diethyl ketomalonate (23 mL, 147.02 mmol) was heated at 130° C. for 48 h and the reaction was monitored by TLC. Upon completion, the reaction mixture was cooled to 0-5° C. and triturated with pet-ether to afford diethyl 2-hydroxy-2-(2-oxo-2-(4-(trifluoromethoxy) phenyl) ethyl) malonate 3 (35 g, 94%, LC-MS 98%) as a pale yellow liquid.

Intermediate 45

Ethyl 3-oxo-6-[4-(trifluoromethoxy)phenyl]-2,3-dihydropyridazine-4-carboxylate

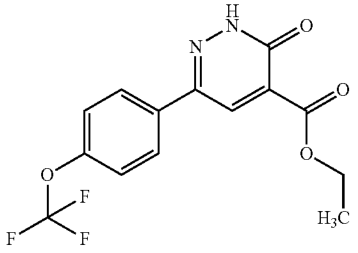 [SMILES: CCOC(=O)c1cc(-c2ccc(OC(F)(F)F)cc2)n[nH]c1=O]

A mixture of diethyl 2-hydroxy-2-(2-oxo-2-(4-(trifluoromethoxy) phenyl) ethyl) malonate (35 g, 92.5 mmol) and hydrazine dihydrochloride (10.6 g, 101.31 mmol) in ethanol (350 mL) was heated under ref lux for 16 h and the reaction was monitored by TLC. After completion the reaction mixture was cooled to rt and concentrated under reduced pressure, the pH was adjusted to 7 using sat. aqueous sodium bicarbonate solution (150 mL) and extracted into ethyl acetate (3×350 mL). The combined organic layers were washed with water, brine, dried over sodium sulfate, filtered and concentrated under reduced pressure to give crude product. The crude product was purified by column chromatography (silica gel, eluent EtOAc/hexane 30:70) to afford ethyl 3-oxo-6-(4-(trifluoromethoxy) phenyl)-2,3-dihydropyridazine-4-carboxylate (12 g, 40%, LC-MS 97%) as an off-white solid.

$^1$H NMR (400 MHz, DMSO-$d_6$) δ [ppm]=1.31 (t, 3H), 4.31 (q, 2H), 7.49 (d, 2H), 7.97-8.04 (m, 2H), 8.35 (s, 1H), 13.70 (br s, 1H).

Intermediate 46

3-Oxo-2-(pyridin-3-yl)-6-[4-(trifluoromethoxy)phenyl]-2,3-dihydropyridazine-4-carboxylic acid

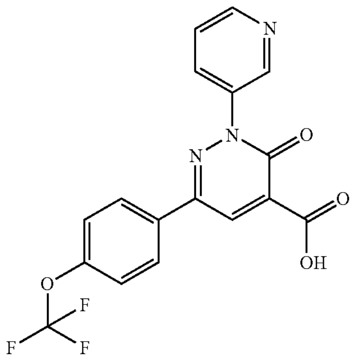 [SMILES: O=C(O)c1cc(-c2ccc(OC(F)(F)F)cc2)nn(-c2cccnc2)c1=O]

Ethyl 3-oxo-6-[4-(trifluoromethoxy)phenyl]-2,3-dihydropyridazine-4-carboxylate (2 g, 6.1 mmol) was dissolved in DMF (80 mL). Pyridin-3-yl boronic acid (1.5 g, 12.2 mmol), 2,2'-bipyridine (4.76 g, 30.46 mmol), sodium carbonate (0.775 g, 7.3 mmol), and anhydrous copper diacetate (2.76 g, 15.23 mmol) were added. The reaction mixture was stirred for 4 h at 80° C., cooled down followed by the addition of 6 mL aqueous 2N sodium hydroxide solution. Water was added and the precipitate was filtered off and dried in vacuum to yield 2.5 g of the title compound.

LC-MS (Instrument: Waters Acquity UPLC-MS SQD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.14 min; MS (ESIpos): m/z=378.4 $[M+H]^+$ Intermediate 47

Methyl 6-[4-(difluoromethyl)phenyl]-3-oxo-2,3,4,5-tetrahydropyridazine-4-carboxylate

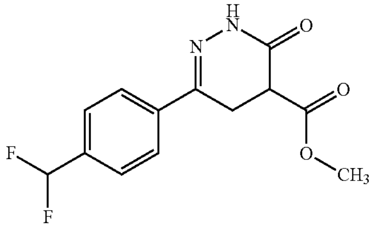 [SMILES: COC(=O)C1CC(c2ccc(C(F)F)cc2)=NNC1=O]

A mixture of 2.9 g dimethyl {2-[4-(difluoromethyl)phenyl]-2-oxoethyl}propanedioate and 13.5 mL hydrazine in THF (1M) in acetic acid was stirred at 70° C. for 4 h. Additional 10 mL hydrazine in THF (1M) was added and the reaction mixture was stirred at 70° C. for 4 hours. Water was added and the precipitate formed was filtered off and dried in vacuum to yield 2.1 g of the title compound.

$^1H$ NMR (400 MHz, DMSO-$d_6$) δ [ppm]=3.15-3.32 (m, 2H), 3.65-3.69 (m, 3H), 3.77 (dd, 1H), 7.08 (t, 1H), 7.63 (d, 2H), 7.89 (d, 2H), 11.36 (s, 1H).

Intermediate 48

Methyl 6-[4-(difluoromethyl)phenyl]-3-oxo-2,3-dihydropyridazine-4-carboxylate

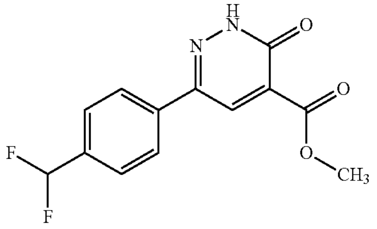 [SMILES: COC(=O)c1cc(-c2ccc(C(F)F)cc2)n[nH]c1=O]

A mixture of 2089 mg methyl 6-[4-(difluoromethyl)phenyl]-3-oxo-2,3,4,5-tetrahydropyridazine-4-carboxylate and 2487 mg copper(II) chloride in 215 mL of acetonitrile was stirred at 50° C. for 1 hour. After evaporation in vacuum, the residue was suspended in water and the precipitate was filtered off to yield 1420 mg methyl 6-[4-(difluoromethyl)phenyl]-3-oxo-2,3-dihydropyridazine-4-carboxylate.

$^1H$ NMR (400 MHz, DMSO-$d_6$) δ [ppm]=3.85 (s, 3H), 7.12 (t, 1H), 7.69 (d, 2H), 8.03 (d, 2H), 8.42 (s, 1H), 13.76 (s, 1H).

Intermediate 49

6-[4-(Difluoromethyl)phenyl]-3-oxo-2-(pyridin-3-yl)-2,3-dihydropyridazine-4-carboxylic acid

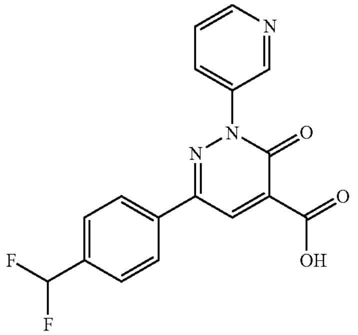 [SMILES: O=C(O)c1cc(-c2ccc(C(F)F)cc2)nn(-c2cccnc2)c1=O]

Methyl 6-[4-(difluoromethyl)phenyl]-3-oxo-2,3-dihydropyridazine-4-carboxylate (700 mg, 2.5 mmol) was dissolved in DMF (32 mL). Pyridin-3-yl boronic acid (614 mg, 5 mmol), 2,2'-bipyridine (1.95 g, 12.5 mmol), sodium carbonate (318 mg, 3 mmol), and anhydrous copper diacetate (1.13 g, 6.24 mmol) were added. The reaction mixture was stirred for 5 hours at 80° C., cooled down followed by the addition of water. The pH was adjusted to 9 by adding 1M aqueous sodium hydroxide solution and the precipitate was filtered off and dried in vacuum to yield 481 mg of the title compound.

$^1H$ NMR (400 MHz, DMSO-$d_6$) δ [ppm]=7.10 (t, 1H), 7.59 (br s, 1H), 7.66 (d, 2H), 7.76 (s, 1H), 8.06 (d, 2H), 8.13 (br d, 1H), 8.63 (br s, 1H), 8.91 (br s, 1H).

Intermediate 50

6-(4-Methylphenyl)-3-oxo-2,3-dihydropyridazine-4-carboxylic acid

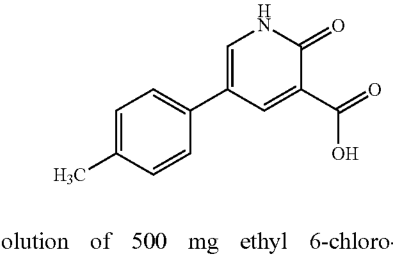

A solution of 500 mg ethyl 6-chloro-3-hydroxypyridazine-4-carboxylate and 436 mg 4-tolylboronic acid in 20 mL dioxane was treated with tripotassium phosphate (15 mL of a 0.5M solution in water) and second generation RuPhos Pd precatalyst (CAS No. [1375325-68-0]; 383 mg), heated to 100° C. and stirred for 4 hours. The reaction mixture was cooled to room temperature, the formed precipitate filtered off, washed with 1,4-dioxane (2 mL) and dried. The obtained material was taken up with water and freeze-dried to give the title compound (406 mg) which was used in the next step without further purification.

$^1H$ NMR (400 MHz, DMSO-$d_6$) δ[ppm]=2.35 (s, 3H), 7.29 (d, 2H), 7.89 (d, 2H), 8.06 (s, 1H).

Intermediate 51

6-(4-Methylphenyl)-3-oxo-2-(pyridin-3-yl)-2,3-dihydropyridazine-4-carboxylic acid

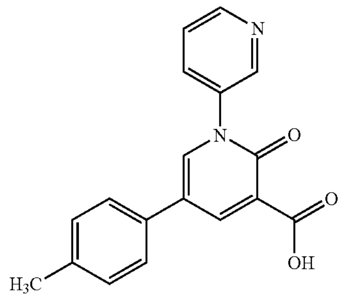 [SMILES: Cc1ccc(-c2cc(C(=O)O)c(=O)n(-c3cccnc3)c2)cc1]

6-(4-Methylphenyl)-3-oxo-2,3-dihydropyridazine-4-carboxylic acid (50 mg) was dissolved in DMF (3 mL). 3-(4,4,5,5-Tetramethyl-1,3,2-dioxaborolan-2-yl)pyridine (89 mg), 2,2-bipyridine (170 mg), sodium carbonate (28 mg), and anhydrous copper diacetate (99 mg) were added. The reaction mixture was stirred for 4 hours at 70° C. The reaction mixture was filtrated and purified by RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 85%/B 15%→A 45%/B 55%; flow: 150 mL/min; UV-detection: 254 nm) to yield 17 mg of 6-(4-methylphenyl)-3-oxo-2-(pyridin-3-yl)-2,3-dihydropyridazine-4-carboxylic acid.

LC-MS (Instrument: Waters Acquity UPLC-MS SOD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=0.58 min; MS (ESIpos): m/z=308.5 $[M+H]^+$ Intermediate 52

Diethyl [2-(4-chloro-2-fluorophenyl)-2-oxoethyl](hydroxy)malonate

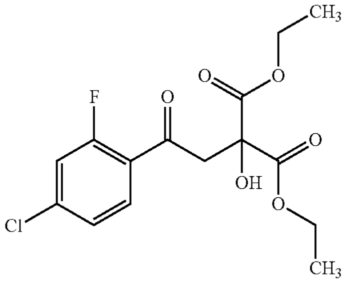 [SMILES: CCOC(=O)C(O)(CC(=O)c1ccc(Cl)cc1F)C(=O)OCC]

Into a 100-mL round-bottom flask, was placed 1-(4-chloro-2-fluorophenyl)ethan-1-one (10 g, 57.94 mmol, 1.00 equiv) and 1,3-diethyl 2-oxopropanedioate (15 mL). The resulting solution was stirred for 24 hours at 130° C. The resulting mixture was concentrated under vacuum. This resulted in 24 g (crude) of 1,3-diethyl 2-[2-(4-chloro-2-fluorophenyl)-2-oxoethyl]-2-hydroxypropanedioate as a black oil which was used without further purification.

Intermediate 53

Ethyl 6-(4-chloro-2-fluorophenyl)-3-oxo-2,3-dihydropyridazine-4-carboxylate

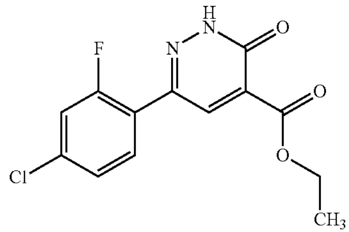 [SMILES: CCOC(=O)c1cc(-c2ccc(Cl)cc2F)n[nH]c1=O]

Into a 500-mL round-bottom flask, was placed a solution of 1,3-diethyl 2-[2-(4-chloro-2-fluorophenyl)-2-oxoethyl]-2-hydroxypropanedioate (24 g, 69.22 mmol, 1.00 equiv) in ethanol (250 mL) and hydrazine (15 mL). The resulting solution was stirred for 12 h at 80° C. The reaction was then quenched by the addition of 200 mL of water. The resulting solution was extracted with 2×200 mL of ethyl acetate and the organic layers were combined. The resulting mixture was washed with 1×100 mL of water. The resulting mixture was washed with 1×100 mL of brine. The mixture was dried over anhydrous sodium sulfate, filtrated and concentrated under vacuum. The residue was applied onto a silica gel column with ethyl acetate/petroleum ether (2:1). This resulted in 2.9 g (14%) of ethyl 6-(4-chloro-2-fluorophenyl)-3-oxo-2,3-dihydropyridazine-4-carboxylate as a pink solid.

$^1H$ NMR (400 MHz, DMSO-$d_6$) δ[ppm]=1.29 (t, 3H), 4.30 (q, 2H), 7.44 (dd, 1H), 7.63 (dd, 1H), 7.74 (t, 1H), 8.10 (d, 1H), 13.84 (s, 1H).

Intermediate 54

6-(4-Chloro-2-fluorophenyl)-3-oxo-2-(pyridin-3-yl)-2,3-dihydropyridazine-4-carboxylic acid

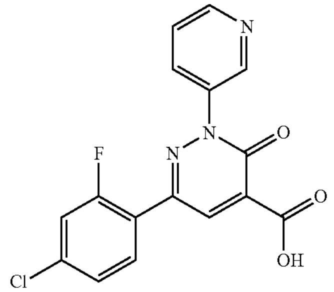 [SMILES: O=C(O)c1cc(-c2ccc(Cl)cc2F)nn(-c2cccnc2)c1=O]

Ethyl 6-(4-chloro-2-fluorophenyl)-3-oxo-2,3-dihydropyridazine-4-carboxylate (500 mg) was dissolved in DMF (22 mL). 3-(4,4,5,5-Tetramethyl-1,3,2-dioxaborolan-2-yl)pyridine (691 mg), 2,2'-bipyridine (1.31 g), sodium carbonate (214 mg), and anhydrous copper diacetate (765 mg) were added. The reaction mixture was stirred for 5 h at 80° C. After cooling down, 1M NaOH (1.7 mL) was added and the reaction mixture was stirred at rt for 48 hours. 1M aqueous hydrochloric acid was added until the product precipitated. The precipitate was filtered off and dried in vacuum to yield 418 mg of 6-(4-chloro-2-fluorophenyl)-3-oxo-2-(pyridin-3-yl)-2,3-dihydropyridazine-4-carboxylic acid which was used without further purification.

LC-MS (Instrument: Waters Acquity UPLC-MS SQD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.04 min; MS (ESI-pos): m/z=346.3 $[M+H]^+$ Intermediate 55

3-(4-Chlorophenyl)-6-oxo-6H-1,4'-bipyridazine-5-carboxylic acid

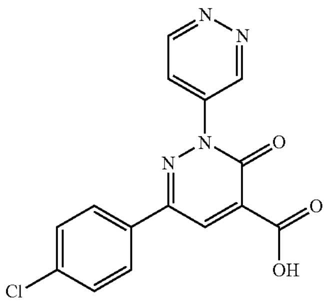 [SMILES: O=C(O)c1cc(-c2ccc(Cl)cc2)nn(-c2ccnnc2)c1=O]

Ethyl 6-(4-chlorophenyl)-3-oxo-2,3-dihydropyridazine-4-carboxylate (500 mg) was dissolved in DM (23 mL). 4-(4,4,5,5-Tetramethyl-1,3,2-dioxaborolan-2-yl)pyridazine (739 mg), 2,2'-bipyridine (1.12 g), sodium carbonate (228 mg), and anhydrous copper diacetate (815 mg) were added. The reaction mixture was stirred at rt for 14 hours followed by the addition of 1.8 mL aqueous 2N sodium hydroxide solution. Water was added and the precipitate was filtered off and dried in vacuum to yield 438 mg of the title compound.

LC-MS (Instrument: Waters Acquity UPLC-MS SQD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.90 min; MS (ESI-pos): m/z=329.2 $[M+H]^+$ Intermediate 56

3-Oxo-6-[6-(trifluoromethyl)pyridin-3-yl]-2,3-dihydropyridazine-4-carboxylic acid

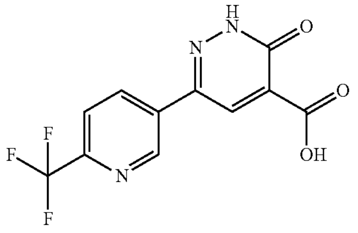 [SMILES: O=C(O)c1cc(-c2ccc(C(F)(F)F)nc2)n[nH]c1=O]

A solution of ethyl 6-chloro-3-hydroxypyridazine-4-carboxylate (CAS No. [61404-41-9]; 450 mg, 2.22 mmol) and [6-(trifluoromethyl)pyridin-3-yl]boronic acid (CAS No. [868662-36-6]; 1.30 eq., 551 mg, 2.89 mmol) in 1,4-dioxane (17 mL) was treated with tripotassium phosphate (3.00 eq, 6.7 mmol, 13.3 mL of a 0.5M solution in water) and second generation RuPhos Pd precatalyst (CAS No. [1375325-68-0]; 0.20 eq, 345 mg, 444 μmol), heated to 100° C. and stirred for 4.5 h. The reaction mixture was cooled to room temperature, the formed precipitate filtered off, washed with 1,4-dioxane (2 mL) and dried. The obtained material was taken up with water and freeze-dried to give the title compound (555 mg) which was used in the next step without further purification.

$^1H$ NMR (400 MHz, DMSO-$d_6$) δ [ppm]=7.98 (d, 1H), 8.30 (s, 1H), 8.68 (br d, 1H), 9.39 (s, 1H).

Intermediate 57

N-[(2S)-1-hydroxypropan-2-yl]-3-oxo-6-[6-(trifluoromethyl)pyridin-3-yl]-2,3-dihydropyridazine-4-carboxamide

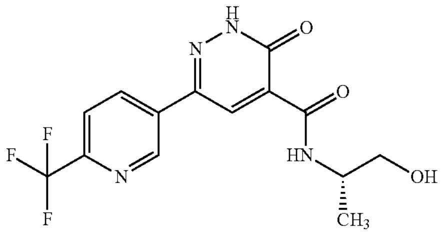 [SMILES: C[C@@H](CO)NC(=O)c1cc(-c2ccc(C(F)(F)F)nc2)n[nH]c1=O]

A suspension of crude 3-oxo-6-[6-(trifluoromethyl)pyridin-3-yl]-2,3-dihydropyridazine-4-carboxylic acid (486 mg, 0.852 mmol) in DMF (6 mL) was treated with a solution of (2S)-2-aminopropan-1-ol (CAS No. [2749-11-3]; 2.00 eq 128 mg, 1.70 mmol) in DMF (6 mL), N,N-diisopropyl ethylamine (4.50 eq, 670 μL, 3.80 mmol) and 2,4,6-tripropyl-1,3,5,2,4,6-trioxatriphosphinane 2,4,6-trioxide (CAS No. [68957-94-8]; 1.50 eq, 1.28 mmol, 750 μL of a 50 wt % solution in DMF) and stirred at room temperature for one week. The reaction mixture was concentrated under reduced pressure and the obtained residue purified by preparative reversed-phase HPLC followed by lyophilization to give the title compound (150 mg).

$^1$H-NMR (400 MHz, DMSO-$d_6$) δ[ppm]=1.17 (d, 3H), 3.41-3.49 (m, 2H), 3.98-4.08 (m, 1H), 4.94 (br s, 1H), 8.03 (d, 1H), 8.59 (dd, 1H), 8.65 (s, 1H), 9.28 (d, 1H), 9.62 (br d, 1H), 13.82 (br s, 1H).

Intermediate 58

Diethyl [2-(4-cyanophenyl)-2-oxoethyl](hydroxy) malonate

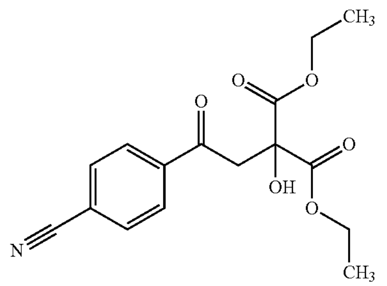 [SMILES: CCOC(=O)C(O)(CC(=O)c1ccc(C#N)cc1)C(=O)OCC]

Into a 100-mL round-bottom flask, was placed 4-acetylbenzonitrile (10 g, 68.89 mmol, 1.00 equiv) and 1,3-diethyl 2-oxopropanedioate (15 g, 86.13 mmol, 1.25 equiv). The resulting solution was stirred for 24 h at 130° C. The resulting mixture was concentrated under vacuum. This resulted in 25 g (114%) of 1,3-diethyl 2-[2-(4-cyanophenyl)-2-oxoethyl]-2-hydroxypropanedioate as black oil which was used without further purification.

Intermediate 59

Ethyl 6-(4-cyanophenyl)-3-oxo-2,3-dihydropyridazine-4-carboxylate

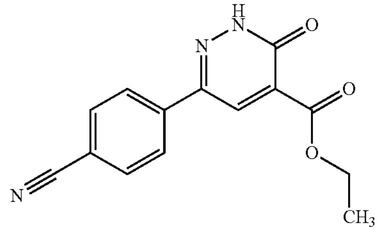 [SMILES: CCOC(=O)c1cc(-c2ccc(C#N)cc2)n[nH]c1=O]

Into a 500-mL round-bottom flask, was placed a solution of 1,3-diethyl 2-[2-(4-cyanophenyl)-2-oxoethyl]-2-hydroxypropanedioate (25 g, 78.29 mmol, 1.00 equiv) in ethanol (200 mL) and hydrazine (15 mL). The resulting solution was stirred for 12 h at 80° C. The reaction was then quenched by the addition of 200 mL of water. The resulting solution was extracted with 2×200 mL of ethyl acetate and the organic layers were combined. The resulting mixture was washed with 1×100 mL of water. The resulting mixture was washed with 1×100 mL of brine. The mixture was dried over anhydrous sodium sulfate and concentrated under vacuum. The residue was applied onto a silica gel column with ethyl acetate/petroleum ether (2:1). This resulted in 6 g (28%) of ethyl 6-(4-cyanophenyl)-3-oxo-2,3-dihydropyridazine-4-carboxylate as a yellow solid.

$^1$H NMR (400 MHz, DMSO-$d_6$) δ[ppm]=1.31 (t, 3H), 4.31 (q, 2H), 7.92-8.00 (m, 2H), 8.08 (d, 2H), 8.42 (s, 1H), 13.84 (s, 1H).

Intermediate 60

6-(4-Cyanophenyl)-3-oxo-2-(pyridin-3-yl)-2,3-dihydropyridazine-4-carboxylic acid

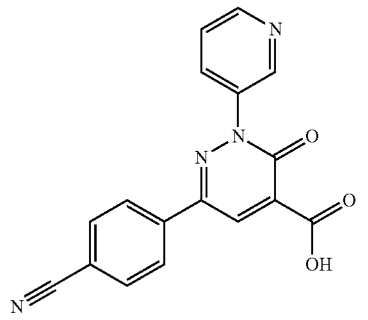 [SMILES: N#Cc1ccc(-c2cc(C(=O)O)c(=O)n(-c3cccnc3)n2)cc1]

Ethyl 6-(4-cyanophenyl)-3-oxo-2,3-dihydropyridazine-4-carboxylate (500 mg) was dissolved in DMF (24 mL). 3-(4,4,5,5-Tetramethyl-1,3,2-dioxaborolan-2-yl)pyridine (762 mg), 2,2'-bipyridine (1.45 g), sodium carbonate (236 mg), and anhydrous copper diacetate (843 mg) were added. The reaction mixture was stirred at 80° C. for 5 h followed by the addition of 1.8 mL aqueous 2N sodium hydroxide solution. Water was added and the precipitate was filtered off and dried in vacuum to yield 632 mg of the title compound.

LC-MS (Instrument: Waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.81 min; MS (ESI-pos): m/z=319.3 $[M+H]^+$ Intermediate 61

Methyl 6-(4-chlorophenyl)-3-oxo-2-(pyrimidin-5-yl)-2,3-dihydropyridazine-4-carboxylate

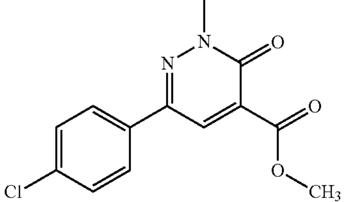

Methyl 6-(4-chlorophenyl)-3-oxo-2,3-dihydropyridazine-4-carboxylate (50 mg, 0.189 mmol) was dissolved in DMF (3 mL). 5-(4,4,5,5-Tetramethyl-1,3,2-dioxaborolan-2-yl)pyrimidine (77.9 mg, 0.378 mmol), 2,2'-bipyridine (73.8 mg, 0.472 mmol), sodium hydrogen carbonate (31.7 mg, 0.378 mmol), and anhydrous copper diacetate (42.9 mg, 0.236 mmol) were added. It was stirred at rt overnight. Water was added and the pH was adjusted to 3 with 2N HCl. The precipitate was filtered, washed with water, and dried at 50° C. under vacuum to yield 39.7 mg (61%) of the title compound.

$^1$H-NMR (400 MHz, DMSO-$d_6$): δ [ppm]=3.89 (s, 3H), 7.59 (br d, 2H), 8.04 (br d, 2H), 8.57 (s, 1H), 9.20-9.33 (m, 3H).

Intermediate 62

6-(4-Chlorophenyl)-3-oxo-2-(pyrimidin-5-yl)-2,3-dihydropyridazine-4-carboxylic acid

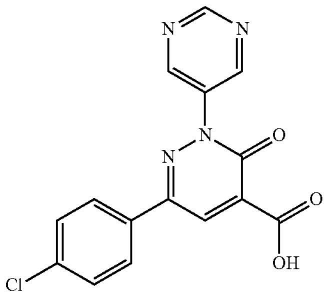 [SMILES: O=C(O)c1cc(-c2ccc(Cl)cc2)nn(-c2cncnc2)c1=O]

Methyl 6-(4-chlorophenyl)-3-oxo-2-(pyrimidin-5-yl)-2,3-dihydropyridazine-4-carboxylate (275 mg, 0.802 mmol) was dissolved in acetonitrile (13.6 mL). A solution of lithium hydroxide (57.6 mg, 2.41 mmol) in water (0.45 mL) was added at rt. It was stirred for 24 hat 40° C.

Water was added and the pH was adjusted to 6-7 with 0.5N HCl. The precipitate was filtered off under suction, washed three times with water and dried under vacuum at 50° C. to afford 251 mg (95%) of the title compound which was used without further purification in the next step.

$^1$H-NMR (400 MHz, DMSO-$d_6$): δ [ppm]=7.54 (d, 2H), 7.87 (s, 1H), 7.99 (d, 2H), 9.23 (s, 2H), 9.29 (s, 1H).

Intermediate 63

Methyl 6-(4-chlorophenyl)-3-oxo-2-(1-{[2-(trimethylsilyl)ethoxy]methyl}-1H-pyrazol-4-yl)-2,3-dihydropyridazine-4-carboxylate

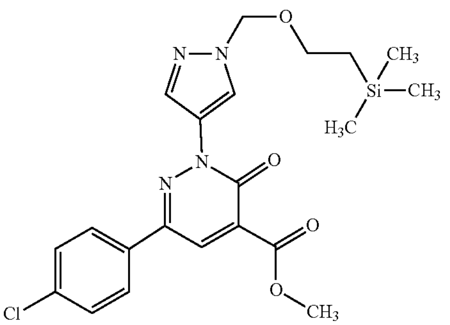 [SMILES: COC(=O)c1cc(-c2ccc(Cl)cc2)nn(-c2cnn(COCC[Si](C)(C)C)c2)c1=O]

Batch 1: Methyl 6-(4-chlorophenyl)-3-oxo-2,3-dihydropyridazine-4-carboxylate (200 mg) was dissolved in DMF (12 mL). 4-(4,4,5,5-Tetramethyl-1,3,2-dioxaborolan-2-yl)-1-{[2-(trimethylsilyl)ethoxy]methyl}-1H-pyrazole (490 mg), 2,2'-bipyridine (295 mg), cesium carbonate (295 mg), and anhydrous copper diacetate (172 mg) were added. It was stirred for 5 h at rt. Water was added and the pH was adjusted to 3 with 2N HCl. The volatiles were removed under vacuum on a rotavap. Water was added and the aqueous phase was extracted three times with chloroform. The combined organic layers were dried over magnesium sulfate and concentrated affording 265 mg of a crude product which was purified together with the second batch.

Batch 2: Methyl 6-(4-chlorophenyl)-3-oxo-2,3-dihydropyridazine-4-carboxylate (544 mg) was dissolved in acetonitrile (5.4 mL). 4-(4,4,5,5-Tetramethyl-1,3,2-dioxaborolan-2-yl)-1-{[2-(trimethylsilyl)ethoxy]methyl}-1H-pyrazole (1 g), pyridine (333 μL), N,N-diethylethanamine (573 μL), anhydrous copper diacetate (747 mg), and molecular sieves (544 mg, 0.4 nm, particle size: <50 μm) were added. It was stirred for one day at rt. 4-(4,4,5,5-Tetramethyl-1,3,2-dioxaborolan-2-yl)-1-{[2-(trimethylsilyl)ethoxy]methyl}-1H-pyrazole (320 mg) was added and stirring was continued for another day at rt. Kieselgel was added and the volatiles were removed under vacuum. It was prepurified by flash chromatography (silica gel, hexane/ethyl acetate, gradient) to yield 427 mg of a product which was combined with the first batch and purified by flash chromatography (silica gel, hexane/ethyl acetate 7:3) affording 220 mg of the title compound.

$^1$H-NMR (400 MHz, DMSO-$d_6$): δ [ppm]=−0.04 (s, 9H), 0.83-0.88 (m, 2H), 3.55-3.61 (m, 2H), 3.88 (s, 3H), 5.49 (s, 2H), 7.57-7.61 (m, 2H), 8.07-8.12 (m, 2H), 8.21 (s, 1H), 8.46 (s, 1H), 8.69 (s, 1H).

Intermediate 64

6-(4-Chlorophenyl)-3-oxo-2-(1-{[2-(trimethylsilyl)ethoxy]methyl}-1H-pyrazol-4-yl)-2,3-dihydropyridazine-4-carboxylic acid

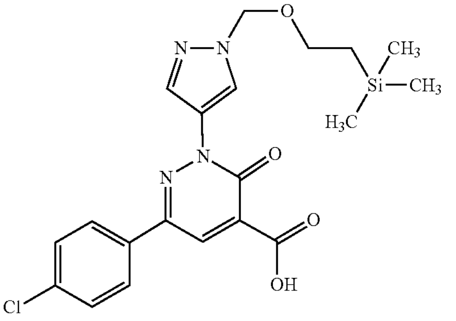 [SMILES: C[Si](C)(C)CCOCn1cc(-n2nc(-c3ccc(Cl)cc3)cc(C(=O)O)c2=O)cn1]

Methyl 6-(4-chlorophenyl)-3-oxo-2-(1-{[2-(trimethylsilyl)ethoxy]methyl}-1H-pyrazol-4-yl)-2,3-dihydropyridazine-4-carboxylate (50 mg) was dissolved in acetonitrile (1 mL) and THE (1 mL). Lithium hydroxide (7.8 mg) and water (0.118 mL) were added and it was stirred at rt overnight. The reaction mixture was concentrated to half of its volume and water was added (150 mL). The pH was adjusted to 3 with 2N HCl (7.5 mL). The precipitate was filtered off under suction, washed with water and dried under vacuum at 50° C. yielding 36 mg of the title compound which was used without further purification in the next step.

$^1$H-NMR (400 MHz, DMSO-$d_6$): δ [ppm]=−0.04 (s, 9H), 0.83-0.89 (m, 2H), 3.56-3.61 (m, 2H), 5.50 (s, 2H), 7.57-

7.61 (m, 2H), 8.10-8.15 (m, 2H), 8.23 (s, 1H), 8.46 (s, 1H), 8.70 (s, 1H), 13.86 (br s, 1H).

Intermediate 65

6-(4-Chlorophenyl)-3-oxo-2-(1H-pyrazol-4-yl)-2,3-dihydropyridazine-4-carboxylic acid

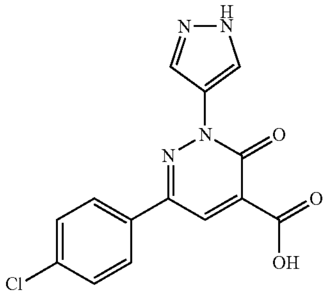 [SMILES: O=C(O)c1cc(-c2ccc(Cl)cc2)nn(-c2cn[nH]c2)c1=O]

Process 1, step 1: Methyl 6-(4-chlorophenyl)-3-oxo-2-(1-{[2-(trimethylsilyl)ethoxy]methyl}-1H-pyrazol-4-yl)-2,3-dihydropyridazine-4-carboxylate (220 mg) was dissolved in ethanol (1.85 mL). Hydrochloric acid in dioxane (1.85 mL, 4M in dioxane) was added and it was stirred for 2 h at 70° C. The reaction mixture was allowed to reach rt and was concentrated to dryness to obtain 169 mg of methyl 6-(4-chlorophenyl)-3-oxo-2-(1H-pyrazol-4-yl)-2,3-dihydropyridazine-4-carboxylate. This material was used without further purification in the next step.

Process 2, step 1:6-(4-Chlorophenyl)-3-oxo-2-(1-{[2-(trimethylsilyl)ethoxy]methyl}-1H-pyrazol-4-yl)-2,3-dihydropyridazine-4-carboxylic acid (34 mg) was dissolved in ethanol (0.29 mL). Hydrochloric acid in dioxane (0.29 mL, 4M in dioxane) was added and it was stirred for 2 h at 70° C. The reaction mixture was allowed to reach rt and stirring was continued at rt overnight. The reaction mixture was concentrated to dryness to afford 27 mg of a mixture of ethyl 6-(4-chlorophenyl)-3-oxo-2-(1H-pyrazol-4-yl)-2,3-dihydropyridazine-4-carboxylate and 6-(4-chlorophenyl)-3-oxo-2-(1H-pyrazol-4-yl)-2,3-dihydropyridazine-4-carboxylic acid. This material was used without further purification in the next step.

Step 2: The crude material from process 1 and process 2 were combined in acetonitrile (5 mL). Lithium hydroxide (80 mg) and water (0.6 mL) were added and it was stirred at rt for 1 h. Water was added (5 mL) and the pH was adjusted to 3 with 2N HCl (1.2 mL). The precipitate was filtered off under suction, washed with water and dried under vacuum at 50° C. yielding 186 mg of the title compound which was used without further purification in the next step.

$^1$H-NMR (400 MHz, DMSO-$d_6$): δ [ppm]=7.56-7.61 (m, 2H), 8.09-8.14 (m, 2H), 8.34 (br s, 2H), 8.44 (s, 1H), 13.45 (br s, 2H).

Intermediate 66

6-[4-(Dimethylamino)phenyl]-3-oxo-2,3-dihydropyridazine-4-carboxylic acid

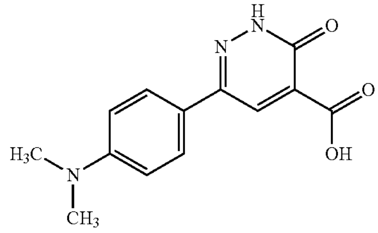 [SMILES: CN(C)c1ccc(-c2cc(C(=O)O)c(=O)[nH]n2)cc1]

A solution of ethyl 6-chloro-3-hydroxypyridazine-4-carboxylate (200 mg) and 4-(dimethylamino)-benzolboronsäure (212 mg) in 1,4-dioxane (8 mL) was treated with tripotassium phosphate (6 mL of a 0.5M solution in water) and second generation RuPhos Pd precatalyst (153 mg), heated to 75° C. and stirred for 6 h. The reaction mixture was cooled to room temperature, treated with water and the pH was adjusted to 3 by the addition of 1M HCl. The formed precipitate was filtered off, washed with water. The precipitate was dissolved in ethyl acetate and the filtrate was extracted three times with ethyl acetate. The combined organic phases were washed with brine, separated, dried over sodium sulfate, filtrated and ethyl acetate was evaporated. The residue was subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 59 mg 6-[4-(dimethylamino)phenyl]-3-oxo-2,3-dihydropyridazine-4-carboxylic acid.

$^1$H NMR (400 MHz, DMSO-$d_6$) δ[ppm]=2.98 (s, 6H), 6.79 (d, 2H), 7.77 (d, 2H), 8.44 (s, 1H).

Intermediate 67

6-[4-(Dimethylamino)phenyl]-N-[(2S)-1-hydroxypropan-2-yl]-3-oxo-2,3-dihydropyridazine-4-carboxamide

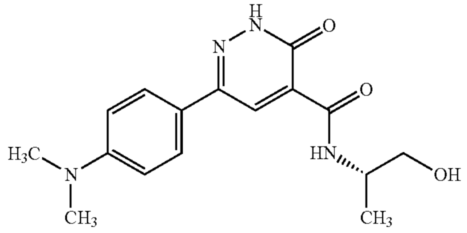 [SMILES: C[C@@H](CO)NC(=O)c1cc(-c2ccc(N(C)C)cc2)n[nH]c1=O]

A solution of 59 mg intermediate 6-[4-(dimethylamino)phenyl]-3-oxo-2,3-dihydropyridazine-4-carboxylic acid, 34 mg (2S)-2-amino-1-propanol, 174 mg HATU, 0.16 mL ethyldiisopropylamine and 1 mg 4-dimethylaminopyridine in 3 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 11 mg 6-[4-(dimethylamino) phenyl]-N-[(2S)-1-hydroxypropan-2-yl]-3-oxo-2,3-dihydropyridazine-4-carboxamide.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.84 min; MS (ESIpos): m/z=317.3 $[M+H]^+$ Intermediate 68

Methyl 6-(4-chlorophenyl)-2-(1-methyl-1H-pyrazol-3-yl)-3-oxo-2,3,4,5-tetrahydropyridazine-4-carboxylate

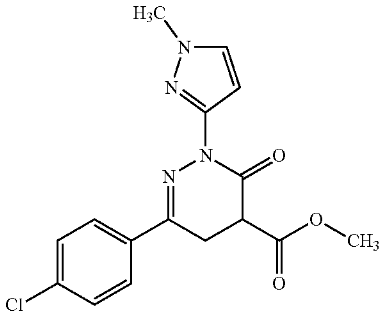 [SMILES: COC(=O)C1CC(c2ccc(Cl)cc2)=NN(c2ccn(C)n2)C1=O]

Dimethyl [2-(4-chlorophenyl)-2-oxoethyl]malonate (200 mg) and sodium acetate (259 mg) were dissolved in acetic acid (7 mL). Then, 3-hydrazinyl-1-methyl-1H-pyrazole trihydrochloride (327 mg) was added portion wise. It was stirred at rt overnight and for 1 h at 50° C. The reaction mixture was cooled down, treated with water and lyophilized. The residue and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 119 mg methyl 6-(4-chlorophenyl)-2-(1-methyl-1H-pyrazol-3-yl)-3-oxo-2,3,4,5-tetrahydropyridazine-4-carboxylate.

$^1$H NMR (400 MHz, DMSO-$d_6$) δ [ppm]=3.37-3.46 (m, 2H), 3.69 (s, 3H), 3.83 (s, 3H), 3.99-4.06 (m, 1H), 6.30 (d, 1H), 7.49-7.56 (m, 2H), 7.71 (d, 1H), 7.78-7.83 (m, 2H).

Intermediate 69

Methyl 6-(4-chlorophenyl)-2-(1-methyl-1H-pyrazol-3-yl)-3-oxo-2,3-dihydropyridazine-4-carboxylate

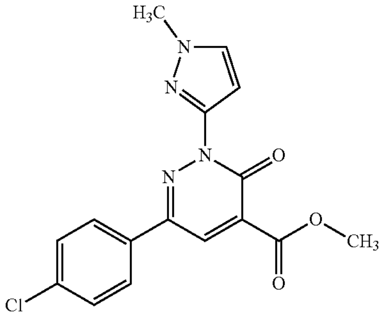 [SMILES: COC(=O)c1cc(-c2ccc(Cl)cc2)nn(-c2ccn(C)n2)c1=O]

Methyl 6-(4-chlorophenyl)-2-(1-methyl-1H-pyrazol-3-yl)-3-oxo-2,3,4,5-tetrahydropyridazine-4-carboxylate (119 mg) was dissolved in acetonitrile (5 mL). Copper dichloride (138 mg) was added. It was stirred for 1 h at 90° C. The reaction mixture was cooled down, taken up in water and extracted three times with ethyl acetate. The combined organic phases were washed with brine, dried over sodium sulfate, filtrated and evaporated to dryness to yield 112 mg of the title compound which was used without further purification in the next step.

$^1$H NMR (400 MHz, DMSO-$d_6$) δ [ppm]=3.87 (s, 3H), 3.90 (s, 3H), 6.56 (d, 1H), 7.55-7.60 (m, 2H), 7.83 (d, 1H), 7.92-7.96 (m, 2H), 8.48 (s, 1H)

Intermediate 70

6-(4-Chlorophenyl)-2-(1-methyl-1H-pyrazol-3-yl)-3-oxo-2,3-dihydropyridazine-4-carboxylic acid

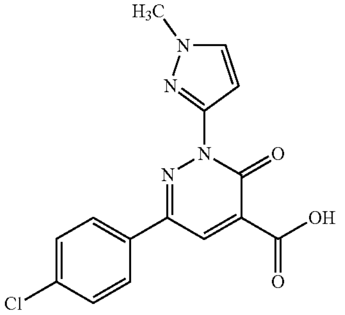

Methyl 6-(4-chlorophenyl)-2-(1-methyl-1H-pyrazol-3-yl)-3-oxo-2,3-dihydropyridazine-4-carboxylate (112 mg) was dissolved in tetrahydrofurane (5 mL). A solution of sodium hydroxide (65 mg) in water (0.8 mL) was added and the reaction mixture was stirred at rt for 14 h. Water was added and the pH was adjusted to 3 with 2N HCl. The precipitate was filtered off under suction, washed three times with water and dried under lyophilization obtaining 94 mg of the title compound which was used without further purification in the next step.

$^1$H NMR (400 MHz, DMSO-$d_6$) δ [ppm] 3.91 (s, 3H), 6.57 (d, 1H), 7.57 (d, 2H), 7.84 (d, 1H), 7.96 (d, 2H), 8.48 (s, 1H).

Intermediate 71

Methyl 6-(4-chlorophenyl)-2-(3-methyl-1H-pyrazol-5-yl)-3-oxo-2,3,4,5-tetrahydropyridazine-4-carboxylate

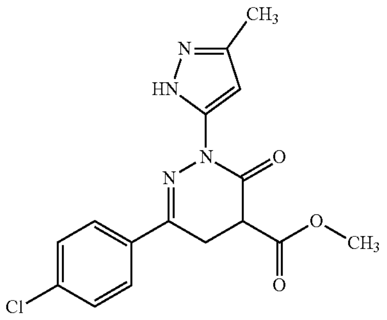 [SMILES: COC(=O)C1CC(c2ccc(Cl)cc2)=NN(c2cc(C)n[nH]2)C1=O]

Dimethyl [2-(4-chlorophenyl)-2-oxoethyl]malonate (200 mg) and sodium acetate (259 mg) were dissolved in acetic acid (7 mL). Then, 5-hydrazinyl-3-methyl-1H-pyrazole hydrochloride (220 mg) was added portion wise. It was stirred at rt overnight and for 1 h at 50° C. The reaction mixture was cooled down, treated with water and lyophilized. The residue and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 126 mg methyl 6-(4-chlorophenyl)-2-(3-methyl-1H-pyrazol-5-yl)-3-oxo-2,3,4,5-tetrahydropyridazine-4-carboxylate.

LC-MS (Instrument: Waters Acquity UPLC-MS SQD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.07 min; MS (ESIpos): m/z=347.3 $[M+H]^+$ Intermediate 72

Methyl 6-(4-chlorophenyl)-2-(3-methyl-1H-pyrazol-5-yl)-3-oxo-2,3-dihydropyridazine-4-carboxylate

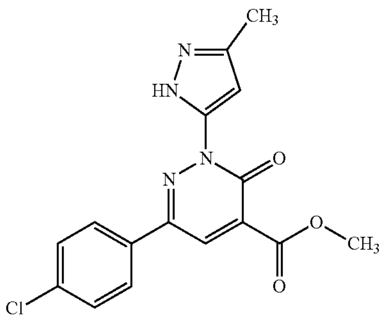 [SMILES: COC(=O)c1cc(-c2ccc(Cl)cc2)nn(-c2cc(C)n[nH]2)c1=O]

Methyl 6-(4-chlorophenyl)-2-(3-methyl-1H-pyrazol-5-yl)-3-oxo-2,3,4,5-tetrahydropyridazine-4-carboxylate (126 mg) was dissolved in acetonitrile (5 mL). Copper dichloride (146 mg) was added. It was stirred for 1 h at 90° C. The reaction mixture was cooled down, treated with water and the precipitate formed was filtered off, washed with water and dried by lyophilization to give 132 mg of the title compound which was used without further purification in the next step.

LC-MS (Instrument: Waters Acquity UPLC-MS SQD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.08 min; MS (ESIpos): m/z=345.3 $[M+H]^+$ Intermediate 73

6-(4-Chlorophenyl)-2-(3-methyl-1H-pyrazol-5-yl)-3-oxo-2,3-dihydropyridazine-4-carboxylic acid

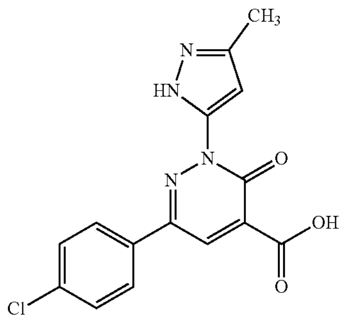 [SMILES: Cc1cc(-n2nc(-c3ccc(Cl)cc3)cc(C(=O)O)c2=O)[nH]n1]

Methyl 6-(4-chlorophenyl)-2-(3-methyl-1H-pyrazol-5-yl)-3-oxo-2,3-dihydropyridazine-4-carboxylate (132 mg) was dissolved in tetrahydrofurane (6 mL). A solution of sodium hydroxide (76 mg) in water (0.96 mL) was added and the reaction mixture was stirred at rt for 14 h. Water was added and the pH was adjusted to 3 with 2N HCl. The precipitate was filtered off under suction, washed three times with water and dried under lyophilization obtaining 80 mg of the title compound which was used without further purification in the next step.

$^1H$ NMR (400 MHz, DMSO-$d_6$) δ [ppm]=2.30 (s, 3H), 6.35 (br s, 1H), 7.57 (d, 2H), 7.97 (br d, 2H), 8.48 (br s, 1H)

Intermediate 74

Methyl 6-(4-chlorophenyl)-3-oxo-2-(1,2-thiazol-4-yl)-2,3-dihydropyridazine-4-carboxylate

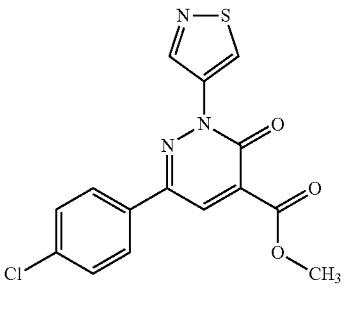 [SMILES: COC(=O)c1cc(-c2ccc(Cl)cc2)nn(-c2cnsc2)c1=O]

Methyl 6-(4-chlorophenyl)-3-oxo-2,3-dihydropyridazine-4-carboxylate (500 mg) was provided in acetonitrile (5 mL). Powdered molecular sieve (500 mg, 4 A, 50 μm), 4-(4,4,5,5-tetramethyl-1,3,2-dioxaborolan-2-yl)-1,2-thiazole (483 mg), pyridine (153 μL), triethylamine (263 μL), and anhydrous copper diacetate (343 mg) were added. It was stirred for 3 h at rt. 4-(4,4,5,5-Tetramethyl-1,3,2-dioxaborolan-2-yl)-1,2-thiazole (211.1 mg), pyridine (104 μL), triethylamine (179 μL), and anhydrous copper diacetate (343 mg) were added. It was stirred for 16 h at rt. Silica gel was added and the volatiles were removed under vacuum. It was purified by flash chromatography (silica gel, hexane/ethyl acetate, gradient) to yield 317 mg of the title compound.

$^1$H-NMR (400 MHz, DMSO-$d_6$): δ [ppm]=3.89 (s, 3H), 7.57-7.62 (m, 2H), 8.05-8.10 (m, 2H), 8.52 (s, 1H), 9.14 (s, 1H), 9.58 (s, 1H).

Intermediate 75

6-(4-Chlorophenyl)-3-oxo-2-(1,2-thiazol-4-yl)-2,3-dihydropyridazine-4-carboxylic

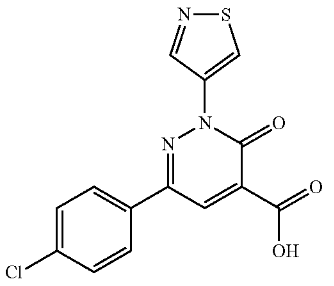 [SMILES: O=C(O)c1cc(-c2ccc(Cl)cc2)nn(-c2cnsc2)c1=O]

Methyl 6-(4-chlorophenyl)-3-oxo-2-(1,2-thiazol-4-yl)-2,3-dihydropyridazine-4-carboxylate (423 mg) was suspended in acetonitrile (11 mL). Lithium hydroxide (87 mg) dissolved in water (1.31 mL) was added. The pH was determined (pH=4) and again lithium hydroxide (87 mg) was added. It was stirred for 1 h at rt. Water (5 mL) was added and the pH was adjusted to 3 with 2N HCl (1.2 mL). The precipitate was filtered off under suction, washed with water and dried under vacuum at 50° C. providing 340 mg of the title compound which was used without further purification in the next step.

$^1$H-NMR (400 MHz, DMSO-$d_6$): δ [ppm]=7.58 (d, 2H), 8.08 (d, 2H), 8.41 (br s, 1H), 9.15 (br s, 1H), 9.59 (br s, 1H).

Intermediate 76

Diethyl hydroxy{2-oxo-2-[4-(trifluoromethyl)phenyl]ethyl}malonate

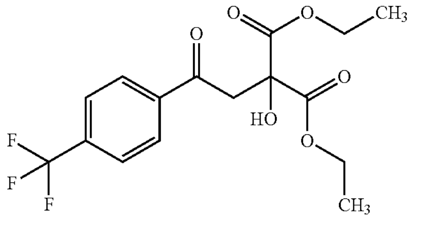 [SMILES: CCOC(=O)C(O)(CC(=O)c1ccc(C(F)(F)F)cc1)C(=O)OCC]

1-[4-(Trifluoromethyl)phenyl]ethanone (50 g, 0.266 mol) and diethyl oxomalonate (66.0 g, 0.379 mol) were stirred at 120° C. for 48 h. The reaction mixture was cooled to rt and the solid was filtered and washed with petrol ether (300 mL) affording 70 g (73%) of the title compound.

$^1$H-NMR (400 MHz, DMSO-$d_6$): δ [ppm]=1.19 (t, 6H), 3.76 (s, 2H), 4.18 (q, 4H), 6.47 (s, 1H), 7.91 (d, 2H), 8.15 (d, 2H).

Intermediate 77

Ethyl 3-oxo-6-[4-(trifluoro methyl)phenyl]-2,3-dihydropyridazine-4-carboxylate

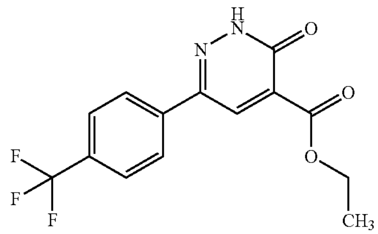 [SMILES: CCOC(=O)c1cc(-c2ccc(C(F)(F)F)cc2)n[nH]c1=O]

Diethyl hydroxy{2-oxo-2-[4-(trifluoromethyl)phenyl]ethyl}malonate (70 g, 0.193 mol) and hydrazine dihydrochloride (22.3 g, 0.212 mol) in ethanol (600 mL) were heated at 70° C. for 24 h. After completion, the reaction mixture was cooled to rt and concentrated under reduced pressure. The crude product was purified by column chromatography (silica gel, hexane/ethyl acetate 50%) to yield 35.0 g (58%) of the title compound.

$^1$H-NMR (400 MHz, DMSO-$d_6$): δ [ppm]=1.31 (t, 3H), 4.32 (q, 2H), 7.86 (d, 2H), 8.11 (d, 2H), 8.42 (s, 1H), 13.81 (s, 1H).

Intermediate 78

Ethyl 3-oxo-2-(1,2-thiazol-4-yl)-6-[4-(trifluoromethyl)phenyl]-2,3-dihydropyridazine-4-carboxylate

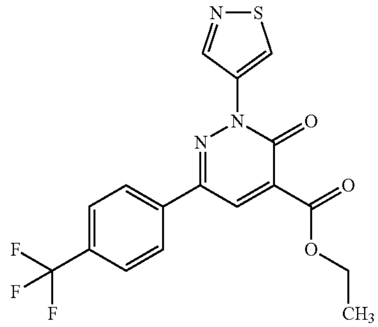 [SMILES: CCOC(=O)c1cc(-c2ccc(C(F)(F)F)cc2)nn(-c2cnsc2)c1=O]

Ethyl 3-oxo-6-[4-(trifluoromethyl)phenyl]-2,3-dihydropyridazine-4-carboxylate (1.20 g, 3.84 mmol) was suspended in acetonitrile (24 mL). 4-(4,4,5,5-Tetramethyl-1,3,2-dioxaborolan-2-yl)-1,2-thiazole (1.05 g, 5.00 mmol), pyridine (622 μL, 7.69 mmol), N,N-diethylethanamine (1.07 mL, 7.69 mmol), and anhydrous copper diacetate (907 mg, 5.00 mmol) were added. It was stirred for 28 h at rt. Water was added and the pH was adjusted to 3 with 2N HCl. The precipitate was filtered, washed tree times with water, and dried at 50° C. under vacuum to give 1.915 g of the title compound which was used without further purification in the next step.

$^1$H-NMR (400 MHz, DMSO-$d_6$): δ [ppm]=1.34 (t, 3H), 4.37 (q, 2H), 7.90 (d, 2H), 8.27 (d, 2H), 8.56 (s, 1H), 9.15 (s, 1H), 9.60 (s, 1H).

Intermediate 79 3-Oxo-2-(1,2-thiazol-4-yl)-6-[4-(trifluoromethyl)phenyl]-2,3-dihydropyridazine-4-carboxylic acid

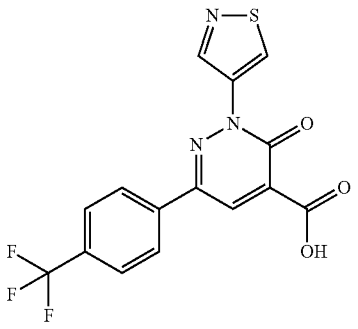 [SMILES: O=C(O)c1cc(-c2ccc(C(F)(F)F)cc2)nn(-c2cnsc2)c1=O]

To ethyl 3-oxo-2-(1,2-thiazol-4-yl)-6-[4-(trifluoromethyl) phenyl]-2,3-dihydropyridazine-4-carboxylate (1.91 g, 3.88 mmol) in acetonitrile (35 mL) was added lithium hydroxide (278 mg, 11.63 mmol) in water (4.2 mL). It was stirred for 2 h at rt. Water (5 mL) was added and the pH was adjusted to 3 with hydrochloric acid (3 mL, 2N). The precipitate was filtered, washed with water and dried under vacuum at 50° C. affording 1.3 g of the title compound and starting material.

The precipitate (465 mg) was stirred at 60° C. in aqueous sodium hydroxide solution. The solid material was filtered warm and washed with water. The residue was dried, suspended in water (20 mL) and the pH was adjusted to 3 with 2M hydrochloric acid. The solid material was collected, washed with water and dried under vacuum at 50° C. yielding 195 mg (11%) of the title compound. The first filtrate was acidified with 2M hydrochloric acid to pH 4, the precipitate was collected, washed with water and dried under vacuum at 50° C. to obtain 180 mg (10%) of the title compound.

The remaining impure material (720 mg) was stirred in aqueous sodium hydroxide solution for 1 h at rt. The pH was adjusted to 3 with hydrochloric acid (2 mL, 2M) and it was stirred for 0.5 h at rt. The solid was filtered, washed three times with water, dried under vacuum at 50° C. to give 660 mg (37%) of the title compound.

$^1$H-NMR (400 MHz, DMSO-$d_6$): δ [ppm]=7.88 (br d, 2H), 8.28 (br d, 2H), 8.59 (br s, 1H), 9.16 (br s, 1H), 9.62 (br s, 1H), 13.94 (br s, 1H).

Intermediate 80

Ethyl 3-oxo-6-[4-(trifluoro methyl)phenyl]-2-(1-{[2-(trimethylsilyl)ethoxy]methyl}-1H-pyrazol-4-yl)-2, 3-dihydro

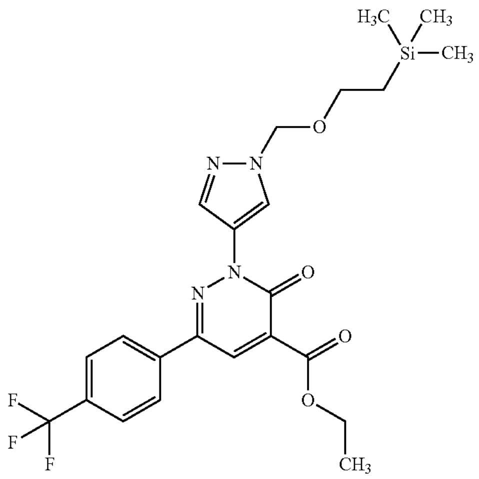 [SMILES: CCOC(=O)c1cc(-c2ccc(C(F)(F)F)cc2)nn(-c2cnn(COCC[Si](C)(C)C)c2)c1=O]

Ethyl 3-oxo-6-[4-(trifluoromethyl)phenyl]-2,3-dihydropyridazine-4-carboxylate (1.00 g, 3.20 mmol) was suspended in acetonitrile (10 mL). 4-(4,4,5,5-Tetramethyl-1,3,2-dioxaborolan-2-yl)-1-{[2-(trimethylsilyl)ethoxy]methyl}-1H-pyrazole (1.35 g, 4.16 mmol), pyridine (0.52 mL, 6.41 mmol), N,N-diethylethanamine (0.893 mL, 6.41 mmol), and anhydrous copper diacetate (756 mg, 4.16 mmol) were added. It was stirred for 4 days at rt. 1 equivalent of 4-(4,4,5,5-tetramethyl-1,3,2-dioxaborolan-2-yl)-1-{[2-(trimethylsilyl)ethoxy]methyl}-1H-pyrazole was added. It was stirred for 1 day at rt, 1 day at 50° C., 8 h at 60° C. and overnight at 50° C. The reaction mixture was cooled down and purified by column chromatography (silica gel, hexane/ethyl acetate 75:25) to yield 1.44 g (88%) of the title compound.

$^1$H-NMR (400 MHz, DMSO-$d_6$): δ [ppm]=−0.04 (s, 9H), 0.83-0.89 (m, 2H), 1.34 (t, 3H), 3.55-3.63 (m, 2H), 4.36 (q, 2H), 5.50 (s, 2H), 7.89 (d, 2H), 8.23 (s, 1H), 8.29 (d, 2H), 8.51 (s, 1H), 8.72 (s, 1H).

Intermediate 81

3-Oxo-2-(1H-pyrazol-4-yl)-6-[4-(trifluoromethyl) phenyl]-2,3-dihydropyridazine-4-carboxylic acid

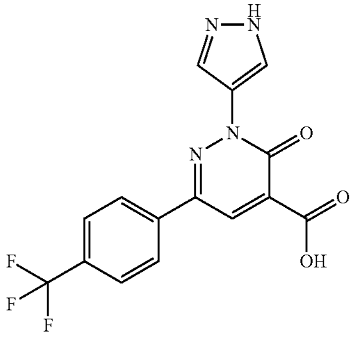 [SMILES: O=C(O)c1cc(-c2ccc(C(F)(F)F)cc2)nn(-c2cn[nH]c2)c1=O]

Step 1: Ethyl 3-oxo-6-[4-(trifluoromethyl)phenyl]-2-(1-{[2-(trimethylsilyl)ethoxy]methyl}-1H-pyrazol-4-yl)-2,3-dihydropyridazine-4-carboxylate (1.38 g, 3.20 mmol) was suspended in ethanol (11.3 mL). Hydrochloride in dioxane (11.3 mL, 4M) was added and stirred for 5 h at 70° C. Overnight it was stirred at rt and then for 5 h at 70° C. The reaction mixture was cooled down and concentrated to dryness giving 1.01 g which was used without further purification in the next step.

Step 2: The intermediate (1.01 g) from step 1 was suspended in acetonitrile (24 mL). Lithium hydroxide (192 mg, 8.01 mmol) in water (6 mL) was added and it was stirred for 3 h at rt. Water (5 mL) was added and the pH was adjusted to 3 with hydrochloric acid (1.2 mL, 2N). The precipitate was filtered, washed with water and dried under vacuum at 50° C. affording 695 mg (73%) of the title compound which was used without further purification in the next step.

$^1$H-NMR (400 MHz, DMSO-$d_6$): δ [ppm]=7.87 (d, 2H), 8.27-8.43 (m, 5H), 13.38 (br s, 2H).

Intermediate 82

2-[1-(Difluoromethyl)-1H-pyrazol-4-yl]-3-oxo-6-[4-(trifluoromethyl)phenyl]-2,3-dihydropyridazine-4-carboxylic acid

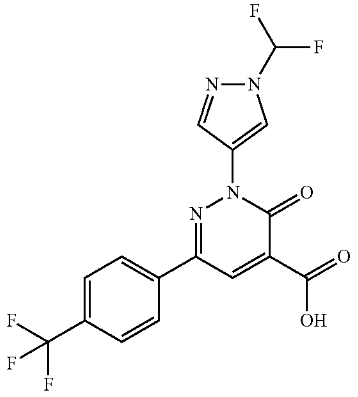 [SMILES: O=C(O)c1cc(-c2ccc(C(F)(F)F)cc2)nn(-c2cnn(C(F)F)c2)c1=O]

Step 1: Methyl 3-oxo-6-[4-(trifluoromethyl)phenyl]-2,3-dihydropyridazine-4-carboxylate (0.40 g, 1.34 mmol) was suspended in acetonitrile (7 mL). Molecular sieves (400 mg, 0.4 nm, particle size: <50 μm), 1-(difluoromethyl)-4-(4,4,5,5-tetramethyl-1,3,2-dioxaborolan-2-yl)-1H-pyrazole (491 mg, 2.01 mmol), pyridine (0.217 mL, 2.68 mmol), N,N-diethylethanamine (0.374 mL, 2.68 mmol), and anhydrous copper diacetate (487 mg, 2.68 mmol) were added. It was stirred for 24 h at rt. 1-(Difluoromethyl)-4-(4,4,5,5-tetramethyl-1,3,2-dioxaborolan-2-yl)-1H-pyrazole (300 mg, 1.23 mmol) was added and stirred for 3 days at rt. It was diluted with water and acidified with hydrochloric acid (2N). The solid material was filtered off and dried under vacuum at 50° C. obtaining 1.21 g of intermediate 1 with molecular sieves which was used without further purification in the next step.

Step 2: The intermediate (1.01 g) from step 1 was suspended in acetonitrile (30 mL). Lithium hydroxide (96.2 mg, 4.02 mmol) in water (2 mL) was added and it was stirred for 20 h at 40° C. The reaction mixture was diluted with water (30 mL) and filtered over diatomaceous earth. The filtrate was adjusted to pH 4 with hydrochloric acid (2N). The precipitate was filtered, washed with water three times and dried under vacuum at 50° C. yielding 380 mg (71%) of the title compound.

$^1$H-NMR (400 MHz, DMSO-$d_6$): δ [ppm]=7.89 (d, 2H), 7.93 (t, 1H), 8.34 (d, 2H), 8.48-8.57 (m, 2H), 9.01 (s, 1H), 13.88 (br s, 1H).

Intermediate 83

6-(4-Chlorophenyl)-2-(5-fluoro-2-thienyl)-3-oxo-2,3-dihydropyridazine-4-carboxylic acid

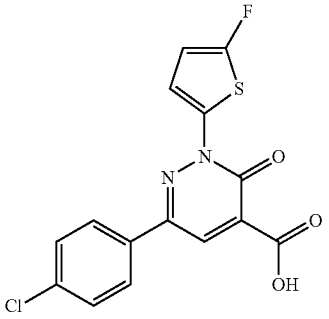 [SMILES: O=C(O)c1cc(-c2ccc(Cl)cc2)nn(-c2ccc(F)s2)c1=O]

Step 1: Methyl 6-(4-chlorophenyl)-3-oxo-2,3-dihydropyridazine-4-carboxylate (0.20 g, 0.756 mmol) was suspended in acetonitrile (8 mL). 2-(5-Fluoro-2-thienyl)-4,4,5,5-tetramethyl-1,3,2-dioxaborolane (569 mg, 2.49 mmol), pyridine (0.122 mL, 1.51 mmol), N,N-diethylethanamine (0.211 mL, 1.51 mmol), and anhydrous copper diacetate (275 mg, 1.51 mmol) were added. It was stirred for 5 h at rt an 120 h at 50° C. The reaction mixture was diluted with buffer solution (15 mL, pH 7), stirred and the precipitate was filtered, washed three times with water and dried under vacuum at 50° C. to obtain 446 mg of crude material which was used without further purification in the next step. Step 2: The intermediate (446 mg) from step 1 was suspended in acetonitrile (13 mL). Lithium hydroxide (146 mg, 6.11 mmol) in water (2.5 mL) was added and it was stirred for 24 h at rt. The reaction mixture was diluted with water (30 mL), the pH was adjusted to 3 with hydrochloric acid (2N), and the precipitate was filtered, washed with water three times and dried under vacuum at 50° C. obtaining 335 mg which was used without further purification in the next step.

LC-MS (Instrument: Waters Acquity UPLC-MS SQD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.73 min; MS (ESIpos): m/z=351.2 $[M+H]^+$ Intermediate 84

Methyl 6-(4-chlorophenyl)-2-(5-methyl-3-thienyl)-3-oxo-2,3-dihydropyridazine-4-carboxylate

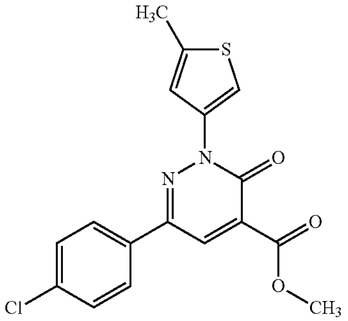

Methyl 6-(4-chlorophenyl)-3-oxo-2,3-dihydropyridazine-4-carboxylate (0.10 g, 0.378 mmol) was suspended in acetonitrile (2 mL). 4,4,5,5-Tetramethyl-2-(5-methyl-3-thienyl)-1,3,2-dioxaborolane (127 mg, 0.567 mmol), pyridine (0.061 mL, 0.756 mmol), N,N-diethylethanamine (0.105 mL, 0.756 mmol), and anhydrous copper diacetate (137 mg, 0.756 mmol) were added. It was stirred for 5 h at rt and 23 h at 50° C. A second batch synthesized under analogous conditions—but stirred for 24 h at 50° C.—was combined with this batch and then poured into a buffer solution of pH 7. It was stirred for a short period, the precipitate was filtered, washed twice with water and dried under vacuum at 50° C. yielding 460 mg of the title compound which was used without further purification in the next step.

$^1$H-NMR (400 MHz, DMSO-$d_6$): δ [ppm]=3.88 (s, 3H), 7.37 (s, 1H), 7.59 (d, 2H), 7.71 (d, 1H), 8.03 (d, 2H), 8.45 (s, 1H).

Intermediate 85

6-(4-Chlorophenyl)-2-(5-methyl-3-thienyl)-3-oxo-2,3-dihydropyridazine-4-carboxylic acid

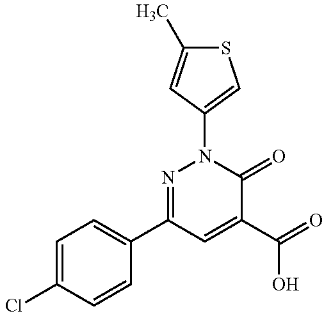 [SMILES: Cc1cc(-n2nc(-c3ccc(Cl)cc3)cc(C(=O)O)c2=O)cs1]

Methyl 6-(4-chlorophenyl)-2-(5-methyl-3-thienyl)-3-oxo-2,3-dihydropyridazine-4-carboxylate (272 mg, 0.754 mmol) was dissolved in acetonitrile (6.8 mL). Lithium hydroxide (54.2 mg, 2.262 mmol) in water (1.36 mL) was added and it was stirred for 24 h at 50° C. The reaction mixture was cooled down, diluted with water (15 mL), the pH was adjusted to 3 with hydrochloric acid (2N), and the precipitate was filtered, washed with water twice and dried under vacuum at 50° C. affording 225 mg (86%) which was used without further purification in the next step.

LC-MS (Instrument: Waters Acquity UPLC-MS SQD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.78 min; MS (ESIpos): m/z=347.2 $[M+H]^+$ Intermediate 86

Methyl 6-(4-chlorophenyl)-2-(5-chloro-3-thienyl)-3-oxo-2,3-dihydropyridazine-4-carboxylate

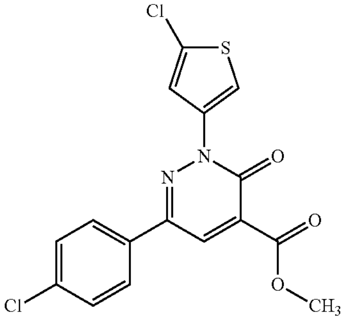 [SMILES: COC(=O)c1cc(-c2ccc(Cl)cc2)nn(-c2csc(Cl)c2)c1=O]

Methyl 6-(4-chlorophenyl)-3-oxo-2,3-dihydropyridazine-4-carboxylate (0.20 g, 0.756 mmol) was suspended in acetonitrile (6 mL). 2-(5-Chloro-3-thienyl)-4,4,5,5-tetramethyl-1,3,2-dioxaborolane (277 mg, 1.133 mmol), pyridine (0.122 mL, 1.511 mmol), N,N-diethylethanamine (0.211 mL, 1.511 mmol), and anhydrous copper diacetate (275 mg, 1.511 mmol) were added. It was stirred for 24 h at 50° C. The reaction mixture was cooled down and buffer solution pH 7 (10 mL) was added. It was stirred for a short period of time, the precipitate was filtered, washed twice with water and dried under vacuum at 50° C. affording 520 mg of the title compound which was used without further purification in the next step. 70 mg of this batch was purified by HPLC to obtain 25 mg of the title compound.

$^1$H-NMR (400 MHz, DMSO-$d_6$): δ [ppm]=3.88 (s, 3H), 7.57-7.61 (m, 2H), 7.69 (d, 1H), 8.03-8.07 (m, 2H), 8.10 (d, 1H), 8.47 (s, 1H).

Intermediate 87

6-(4-Chlorophenyl)-2-(5-chloro-3-thienyl)-3-oxo-2,3-dihydropyridazine-4-carboxylic acid

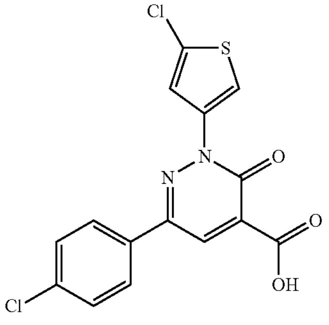 [SMILES: O=C(O)c1cc(-c2ccc(Cl)cc2)nn(-c2csc(Cl)c2)c1=O]

Methyl 6-(4-chlorophenyl)-2-(5-chloro-3-thienyl)-3-oxo-2,3-dihydropyridazine-4-carboxylate (288 mg, 0.755 mmol) was dissolved in acetonitrile (8.3 mL). Lithium hydroxide (54.3 mg, 2.266 mmol) in water (1.60 mL) was added and it was stirred for 4 h at 50° C. The reaction mixture was cooled down, diluted with water (15 mL), the pH was adjusted to 3 with hydrochloric acid (2N), and the precipitate was filtered, washed with water twice and dried under vacuum at 45° C. affording 300 mg which was used without further purification in the next step.

LC-MS (Instrument: Waters Acquity UPLC-MS SQD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.75 min; MS (ESIpos): m/z=367.2 $[M+H]^+$ Intermediate 88

Methyl 6-(4-chlorophenyl)-2-[1-(difluoromethyl)-1H-pyrazol-4-yl]-3-oxo-2,3-dihydropyridazine-4-carboxylate

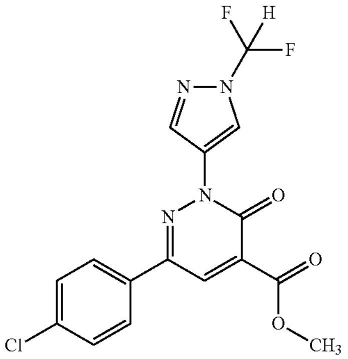 [SMILES: COC(=O)c1cc(-c2ccc(Cl)cc2)nn(-c2cnn(C(F)F)c2)c1=O]

Methyl 6-(4-chlorophenyl)-3-oxo-2,3-dihydropyridazine-4-carboxylate (0.10 g, 0.378 mmol) was suspended in acetonitrile (1 mL). Molecular sieves (100 mg, 0.4 nm, particle size: <50 μm), 1-(difluoromethyl)-4-(4,4,5,5-tetramethyl-1,3,2-dioxaborolan-2-yl)-1H-pyrazole (138 mg, 0.567 mmol), pyridine (0.061 mL, 0.756 mmol), N,N-diethylethanamine (0.105 mL, 0.756 mmol), and anhydrous copper diacetate (137 mg, 0.756 mmol) were added. It was stirred for 48 h at rt, 1-(difluoromethyl)-4-(4,4,5,5-tetramethyl-1,3,2-dioxaborolan-2-yl)-1H-pyrazole (100 mg, 0.410 mmol) was added, and stirred for 72 h at rt. It was diluted with water and acidified slightly. The precipitate was filtered and dried under vacuum at 50° C. giving 315 mg of the title compound which was used without further purification in the next step.

$^1$H-NMR (400 MHz, DMSO-$d_6$): δ [ppm]=3.89 (s, 3H), 7.58-7.62 (m, 2H), 7.91 (t, 1H), 8.11-8.15 (m, 2H), 8.50 (s, 1H), 8.50 (s, 1H), 8.98 (s, 1H).

Intermediate 89

6-(4-Chlorophenyl)-2-[1-(difluoromethyl)-1H-pyrazol-4-yl]-3-oxo-2,3-dihydropyridazine-4-carboxylic acid

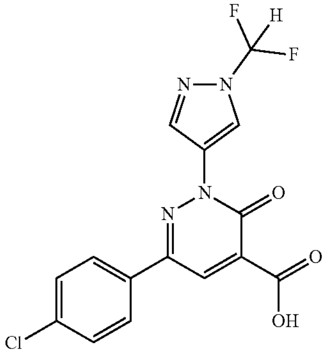 [SMILES: O=C(O)c1cc(-c2ccc(Cl)cc2)nn(-c2cnn(C(F)F)c2)c1=O]

Methyl 6-(4-chlorophenyl)-2-[1-(difluoromethyl)-1H-pyrazol-4-yl]-3-oxo-2,3-dihydropyridazine-4-carboxylate (646 mg, 1.697 mmol) was suspended in acetonitrile (35 mL). Lithium hydroxide (122 mg, 5.09 mmol) in water (2 mL) was added and it stirred for 20 h at 40° C. The reaction mixture was cooled down, diluted with water (30 mL), and filtered over diatomaceous earth. The filtrate was adjusted to pH 4 with hydrochloric acid (2N), and the precipitate was filtered, washed three times with water and dried under vacuum at 50° C. to yield 360 mg which was used without further purification in the next step.

$^1$H-NMR (400 MHz, DMSO-$d_6$): δ [ppm]=7.57-7.62 (m, 2H), 7.92 (t, 1H), 8.12-8.17 (m, 2H), 8.47 (s, 1H), 8.51 (s, 1H), 8.99 (s, 1H), 13.86 (br s, 1H).

Intermediate 90

Di-tert-butyl 1-(1,2-oxazol-4-yl)hydrazine-1,2-dicarboxylate

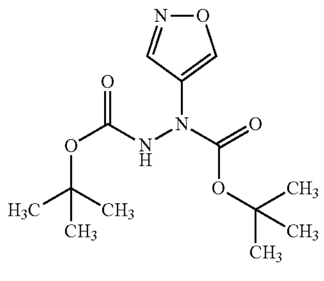 [SMILES: CC(C)(C)OC(=O)NN(C(=O)OC(C)(C)C)c1cnoc1]

To a solution of diethyl ether (30 mL) at −78° C. was added n-butyllithium (2.5 M in hexane, 21.6 mL, 54 mmol), dropwise. 4-Bromo-1,2-oxazole (4.00 g, 27.0 mmol), was added and the mixture stirred for 30 minutes. A solution of di-tert-butyl (E)-diazene-1,2-dicarboxylate, (9.33 g, 40.6 mmol), in diethyl ether (30 mL) was added dropwise and the mixture stirred for 1 hour at −78° C. The reaction mixture was added to water (200 mL) and extracted with dichloromethane (twice 200 mL). The combined organic phases were dried over sodium sulfate, filtered and concentrated.

The crude residue was purified by column chromatography (silica gel, heptane/ethyl acetate 4:1 to 11:9) to give 1.99 g (16%) of the title product.

$^1H$ NMR (400 MHz, $CDCl_3$): δ [ppm]=1.40-1.60 (m, 18H), 6.68 (s, 1H), 8.40 (s, 1H), 8.63 (s, 1H).

Intermediate 91

4-Hydrazino-1,2-oxazole hydrochloride

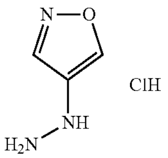

Hydrochloric acid (4 M in 1,4-dioxane, 10.0 mL, 40.0 mmol) was added to a solution of di-tert-butyl 1-(1,2-oxazol-4-yl)hydrazine-1,2-dicarboxylate (2.64 g, 8.82 mmol), in 1,4-dioxane (10 mL) and the mixture was heated at 50° C. for 5 hours. The mixture was concentrated under vacuum to give 863 mg (76%) of the title compound.

$^1H$ NMR (400 MHz, MeOD-$d_3$): δ [ppm]=8.42 (s, 1H), 8.63 (s, 1H).

Intermediate 92

Methyl 6-(4-chlorophenyl)-2-(1,2-oxazol-4-yl)-3-oxo-2,3,4,5-tetrahydropyridazine-4-carboxylate

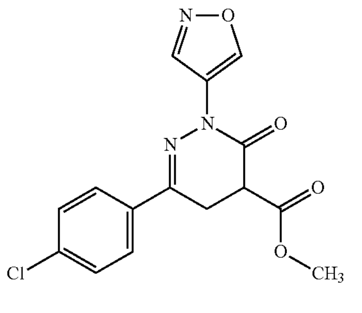 [SMILES: COC(=O)C1CC(c2ccc(Cl)cc2)=NN(c2cnoc2)C1=O]

A mixture of dimethyl [2-(4-chlorophenyl)-2-oxoethyl] malonate (494 mg, 1.74 mmol), 4-hydrazino-1,2-oxazole hydrochloride (588 mg, 3.47 mmol), and sodium acetate, (641 mg, 7.81 mmol), in acetic acid (11.8 mL) was stirred at room temperature for 96 hours. The reaction mixture was concentrated and added to water (200 mL). The solids were collected by filtration and dried under vacuum to give 567 mg (98%) of the title compound.

$^1H$-NMR (400 MHz, DMSO-$d_6$): δ [ppm]=3.34-3.49 (m, 2H), 3.67 (s, 3H), 4.06-4.13 (m, 1H), 7.53 (d, 2H), 7.99 (d, 2H), 9.07 (s, 1H), 9.32 (s, 1H).

Intermediate 93

Methyl 6-(4-chlorophenyl)-2-(1,2-oxazol-4-yl)-3-oxo-2,3-dihydropyridazine-4-carboxylate

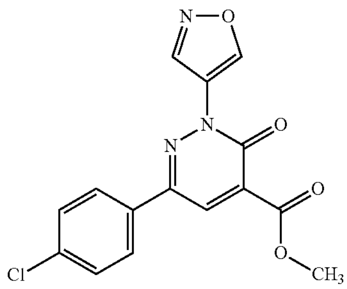 [SMILES: COC(=O)c1cc(-c2ccc(Cl)cc2)nn(-c2cnoc2)c1=O]

To a solution of methyl 6-(4-chlorophenyl)-2-(1,2-oxazol-4-yl)-3-oxo-2,3,4,5-tetrahydropyridazine-4-carboxylate (586 mg, 1.76 mmol), in acetonitrile (10.5 mL) was added copper(II) chloride (1.18 g, 8.78 mmol) and the mixture heated at 50° C. for 2 hours. The mixture was cooled to room temperature and stood for 16 hours. The mixture was heated at 50° C. for 16 hours. The mixture was concentrated and added to water. The solids were collected by filtration and dried to give 563 mg (97%) of the title compound.

$^1H$ NMR (400 MHz, DMSO-$d_6$): δ [ppm]=3.61 (s, 3H), 7.56 (d, 2H), 8.12 (d, 2H), 8.50 (s, 1H), 9.39 (s, 1H), 9.72 (s, 1H).

Intermediate 94

6-(4-Chlorophenyl)-2-(1,2-oxazol-4-yl)-3-oxo-2,3-dihydropyridazine-4-carboxylic acid

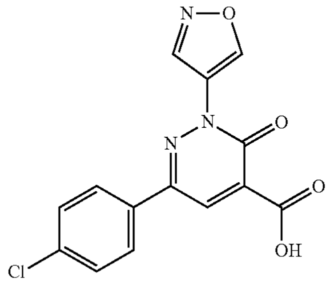 [SMILES: O=C(O)c1cc(-c2ccc(Cl)cc2)nn(-c2cnoc2)c1=O]

To a solution of methyl 6-(4-chlorophenyl)-2-(1,2-oxazol-4-yl)-3-oxo-2,3-dihydropyridazine-4-carboxylate (383 mg, 1.16 mmol) in 1,4-dioxane (10 mL) was added hydrochloric acid (2 M in water, 10.0 mL, 20.0 mmol), and the mixture heated at 100° C. for 48 hours. The mixture was cooled to rt and the solids collected by filtration and dried under vacuum to give 246 mg (67%) of the title compound which was used in the next step without further purification.

$^1H$ NMR (400 MHz, DMSO-$d_6$): δ [ppm]=7.56 (d, 2H), 8.14 (d, 2H), 8.46 (br s, 1H), 9.38 (s, 1H), 9.72 (br s, 1H).

Intermediate 95

Ethyl 3-oxo-2-(1,2-thiazol-4-yl)-6-[6-(trifluoromethyl)pyridin-3-yl]-2,3-dihydropyridazine-4-carboxylate

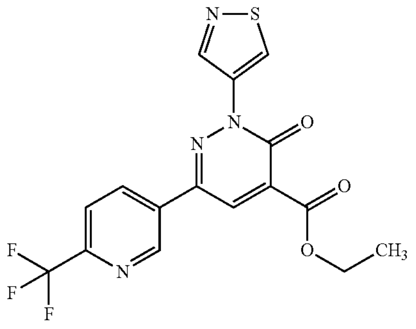 [SMILES: CCOC(=O)c1cc(-c2ccc(C(F)(F)F)nc2)nn(-c2cnsc2)c1=O]

Ethyl 3-oxo-6-[6-(trifluoromethyl)pyridin-3-yl]-2,3-dihydropyridazine-4-carboxylate (475 mg, 1.52 mmol) was suspended in acetonitrile (10 mL). 4-(4,4,5,5-Tetramethyl-1,3,2-dioxaborolan-2-yl)-1,2-thiazole (480 mg, 2.28 mmol), pyridine (0.245 mL, 3.03 mmol), N,N-diethylethanamine (0.423 mL, 3.03 mmol), and anhydrous copper diacetate (358 mg, 1.97 mmol) were added. It was stirred for 24 h at rt. 4-(4,4,5,5-Tetramethyl-1,3,2-dioxaborolan-2-yl)-1,2-thiazole (100 mg, 0.474 mmol) was added and stirred for 24 h at rt. Buffer solution pH 7 (50 mL) was added and stirred for a short period. The precipitate was filtered, washed twice with water and dried under vacuum at 45° C. affording 630 mg of the title compound which was used without further purification in the next step.

$^1$H-NMR (400 MHz, DMSO-$d_6$): δ [ppm]=1.34 (t, 3H), 4.38 (q, 2H), 8.07 (d, 1H), 8.63 (s, 1H), 8.73 (dd, 1H), 9.19 (s, 1H), 9.42 (d, 1H), 9.64 (s, 1H).

Intermediate 96

3-Oxo-2-(1,2-thiazol-4-yl)-6-[6-(trifluoromethyl)pyridin-3-yl]-2,3-dihydropyridazine-4-carboxylic acid

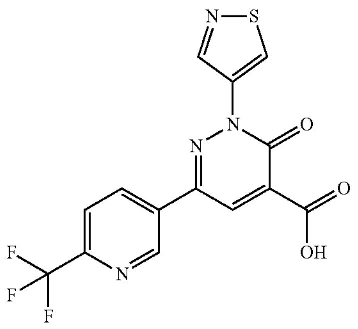

Ethyl 3-oxo-2-(1,2-thiazol-4-yl)-6-[6-(trifluoromethyl)pyridin-3-yl]-2,3-dihydropyridazine-4-carboxylate (625 mg, 1.58 mmol) was suspended in THE (19 mL). Lithium hydroxide (113 mg, 4.73 mmol) in water (2.3 ml) was added and stirred at rt for 24 h. Water (100 mL) was added and the pH was adjusted to 4 with hydrochloric acid (0.5N). It was stirred for a short period, the precipitate was filtered, washed three times with water and dried at 45° C. under vacuum to obtain 585 mg of the title compound which was used without further purification in the next step.

$^1$H-NMR (400 MHz, DMSO-$d_6$): δ [ppm]=7.99 (br s, 1H), 8.47 (br s, 1H), 9.14 (br s, 1H).

LC-MS (Instrument: Waters Acquity UPLC-MS SOD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.59 min; MS (ESIpos): m/z=369.1 [M+H]$^+$ Intermediate 97

Dimethyl {2-[4-(fluoromethyl)phenyl]-2-oxoethyl}malonate

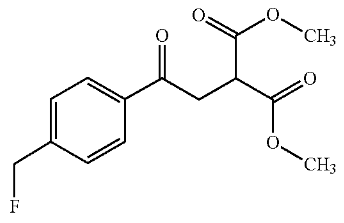 [SMILES: COC(=O)C(CC(=O)c1ccc(CF)cc1)C(=O)OC]

2-Bromo-1-[4-(fluoromethyl)phenyl]ethanone (5.5 g, 23.80 mmol) was dissolved in acetone (120 mL). Dimethyl malonate (6.94 g, 52.50 mmol) and potassium carbonate (5.0 g, 36.18 mmol) were added. It was stirred at rt overnight. The volume was reduced by half under vacuum on a rotavap. Then it was poured into water (550 mL) containing some brine. The layers were separated and the aqueous phase was extracted three times with ethyl acetate (200 mL). The combined organic layers were washed with water and concentrated aqueous sodium chloride solution, dried over magnesium sulfate and concentrated. A second batch prepared under analogues conditions (0.5 g starting material bromidoketone) was added and the volatiles were removed under high vacuum at 70° C. The crude product was purified by flash chromatography (hexane/ethyl acetate) affording 5.59 g (76%) of the title product.

$^1$H-NMR (400 MHz, DMSO-$d_6$): δ [ppm]=3.65 (d, 2H), 3.68 (s, 6H), 3.99 (t, 1H), 5.54 (d, 2H), 7.56 (d, 2H), 8.04 (d, 2H).

Intermediate 98

Methyl 6-[4-(fluoromethyl)phenyl]-3-oxo-2,3,4,5-tetrahydropyridazine-4-carboxylate

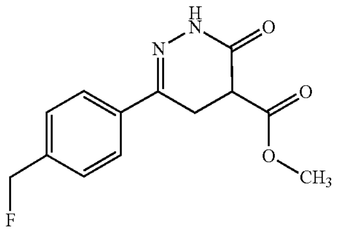 [SMILES: COC(=O)C1CC(c2ccc(CF)cc2)=NNC1=O]

Dimethyl {2-[4-(fluoromethyl)phenyl]-2-oxoethyl}malonate (2.50 g, 8.86 mmol) was dissolved in acetic acid (31.4 mL). A solution of hydrazine in THF (14 mL, 1.0M, 14 mmol) was added at rt. Then, it was stirred at 85° C. overnight. The reaction mixture was cooled down and a solution of hydrazine in THF (2.1 mL, 1.0M, 2.1 mmol) was added. It was stirred at 75° C. for 3 h and at rt for 120 h. Water (150 mL) was added and it was stirred for a while. The precipitate was filtered off under suction, washed three times with water and dried under vacuum at 50° C. yielding 1.781 g (76%) of the title compound which was used without further purification in the next step.

$^1$H-NMR (400 MHz, DMSO-$d_6$): δ [ppm]=3.19 (dd, 1H), 3.29 (dd, 1H), 3.67 (s, 3H), 3.75 (dd, 1H), 5.45 (d, 2H), 7.47 (dd, 2H), 7.78-7.82 (m, 2H), 11.29 (s, 1H).

Intermediate 99

Methyl 6-[4-(fluoromethyl)phenyl]-3-oxo-2,3-dihydropyridazine-4-carboxylate

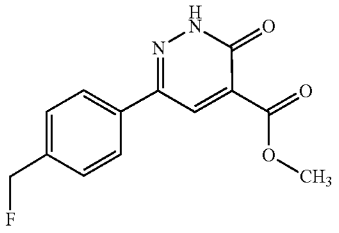 [SMILES: COC(=O)c1cc(-c2ccc(CF)cc2)n[nH]c1=O]

Methyl 6-[4-(fluoromethyl)phenyl]-3-oxo-2,3,4,5-tetrahydropyridazine-4-carboxylate (1.00 g, 3.78 mmol) was dissolved in acetonitrile (20 mL). Copper dichloride (1.60 g, 11.90 mmol) was added and it was stirred for 1 h at 90° C. The reaction mixture was cooled down and poured into water (150 mL). It was stirred for 10 min. The precipitate was filtered by suction, washed three times with water and dried at 50° C. under vacuum to yield 1.02 g of the title compound which was used without further purification in the next step.

$^1$H-NMR (400 MHz, DMSO-$d_6$): δ [ppm]=3.85 (s, 3H), 5.48 (d, 2H), 7.53 (br d, 2H), 7.93 (br d, 2H), 8.39 (s, 1H), 13.69 (br s, 1H).

Intermediate 100

Methyl 6-[4-(fluoromethyl)phenyl]-2-(1-methyl-1H-pyrazol-4-yl)-3-oxo-2,3-dihydropyridazine-4-carboxylate

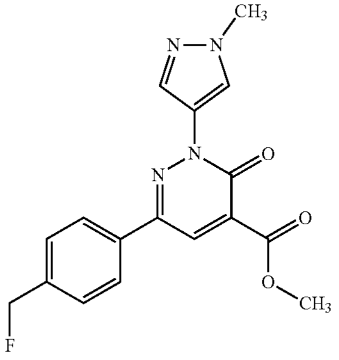 [SMILES: COC(=O)c1cc(-c2ccc(CF)cc2)nn(-c2cnn(C)c2)c1=O]

Methyl 6-[4-(fluoromethyl)phenyl]-3-oxo-2,3-dihydropyridazine-4-carboxylate (0.940 g, 3.58 mmol) was suspended in acetonitrile (10 mL). Anhydrous sodium sulfate (0.950 g, 6.68 mmol), 1-methyl-4-(4,4,5,5-tetramethyl-1,3,2-dioxaborolan-2-yl)-1H-pyrazole (1.2 g, 5.77 mmol), pyridine (0.58 mL, 7.17 mmol), N,N-diethylethanamine (1 mL, 7.17 mmol), and anhydrous copper diacetate (1.3 g, 7.17 mmol) were added. It was stirred at rt for 2 days. 1-Methyl-4-(4,4,5,5-tetramethyl-1,3,2-dioxaborolan-2-yl)-1H-pyrazole (0.522 g, 2.51 mmol) and anhydrous copper diacetate (651 mg, 3.58 mmol) were added and stirred at rt for 4 days. It was diluted with dichloromethane and silica gel was added. The volatiles were removed under vacuum. The residue was purified by flash chromatography (silica gel, dichloromethane/ethanol 95:5) yielding 1.05 g (85%) of the title compound.

$^1$H-NMR (400 MHz, DMSO-$d_6$): δ [ppm]=3.89 (s, 3H), 3.92 (s, 3H), 5.51 (d, 2H), 7.54-7.59 (m, 2H), 8.07-8.12 (m, 3H), 8.45 (s, 1H), 8.51 (s, 1H).

Intermediate 101

6-[4-(Fluoromethyl)phenyl]-2-(1-methyl-1H-pyrazol-4-yl)-3-oxo-2,3-dihydropyridazine-4-carboxylic acid

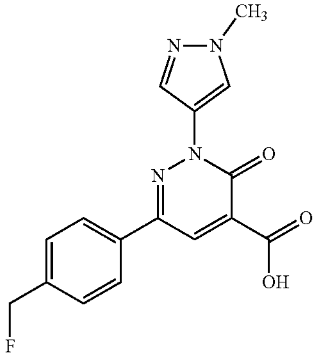 [SMILES: Cn1cc(-n2nc(-c3ccc(CF)cc3)cc(C(=O)O)c2=O)cn1]

Methyl 6-[4-(fluoromethyl)phenyl]-2-(1-methyl-1H-pyrazol-4-yl)-3-oxo-2,3-dihydropyridazine-4-carboxylate (1.05 g, 3.07 mmol) was suspended in THE (50.5 mL). Lithium hydroxide (221 mg, 9.20 mmol) in water (2.5 mL) was added and stirred at rt for 1 h. The pH was adjusted to 3 with hydrochloric acid (4 mL, 2N). The precipitate was filtered, washed three times with water and dried under vacuum at 50° C. obtaining 352 mg (35%) of the title compound which was used without further purification in the next step.

$^1$H-NMR (400 MHz, DMSO-$d_6$): δ [ppm]=3.93 (s, 3H), 5.51 (d, 2H), 7.55-7.59 (m, 2H), 8.11-8.15 (m, 3H), 8.46 (s, 1H), 8.53 (s, 1H), 13.88 (br s, 1H).

Intermediate 102

Methyl 6-[4-(fluoromethyl)phenyl]-3-oxo-2-(pyridin-3-yl)-2,3-dihydropyridazine-4-carboxylate

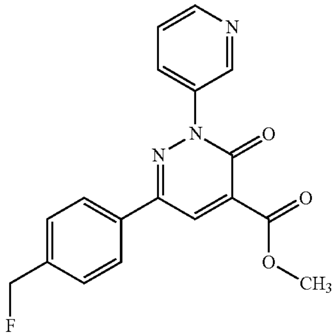 [SMILES: COC(=O)c1cc(-c2ccc(CF)cc2)nn(-c2cccnc2)c1=O]

Methyl 6-[4-(fluoromethyl)phenyl]-3-oxo-2,3-dihydropyridazine-4-carboxylate (0.725 g, 2.77 mmol) was suspended in acetonitrile (7.4 mL). Anhydrous sodium sulfate (0.725 g, 5.10 mmol), 3-(4,4,5,5-tetramethyl-1,3,2-dioxaborolan-2-yl)pyridine (851 mg, 4.15 mmol), pyridine (448 µL, 5.53 mmol), N,N-diethylethanamine (771 µL, 5.53 mmol), and anhydrous copper diacetate (1.004 g, 5.53 mmol) were added. It was stirred at rt overnight. The pH was adjusted to 3 with hydrochloric acid (2N). The precipitate was filtered, washed three times with water (1 mL) and dried under vacuum at 50° C. overnight. The solids were triturated with dichloromethane/methanol 1:1, filtered and dried under vacuum at 50° C. affording 942 mg of the title compound which was used without further purification in the next step.

$^1$H-NMR (400 MHz, DMSO-$d_6$): δ [ppm]=3.88 (s, 3H), 5.50 (d, 2H), 7.56 (br d, 2H), 8.00 (br d, 2H), 8.40-8.69 (m, 1H).

Intermediate 103

6-[4-(Fluoromethyl)phenyl]-3-oxo-2-(pyridin-3-yl)-2,3-dihydropyridazine-4-carboxylic acid

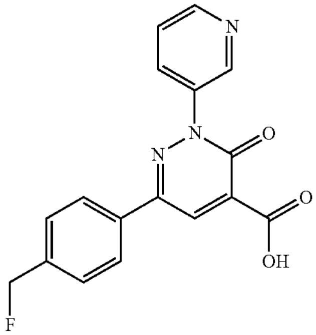 [SMILES: O=C(O)c1cc(-c2ccc(CF)cc2)nn(-c2cccnc2)c1=O]

Methyl 6-[4-(fluoromethyl)phenyl]-3-oxo-2-(pyridin-3-yl)-2,3-dihydropyridazine-4-carboxylate (915 mg, 2.70 mmol) was suspended in acetonitrile (24 mL). Lithium hydroxide (194 mg, 8.09 mmol) in water (2.91 mL) was added. An additional amount of water (3 mL) was added. It was stirred at rt overnight. The reaction mixture was diluted with water (30 mL), stirred for 30 minutes and then the pH was adjusted to 3 with hydrochloric acid (4 mL, 2N). The precipitate was filtered, washed with water and dried under vacuum at 50° C. to afford 728 mg (78%) of the title compound which was used without further purification in the next step.

LC-MS (Instrument: Waters Acquity UPLC-MS SQD 3001; column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; injection: 2 µL; DAD scan: 210-400 nm; ELSD): $R_t$=0.53 min; MS (ESIpos): m/z=326.4 $[M+H]^+$ Intermediate 104

6-(4-Chlorophenyl)-3-oxo-2-(pyridin-3-yl)-N-(4,4,4-trifluoro-3-hydroxybutan-2-yl)-2,3-dihydropyridazine-4-carboxamide

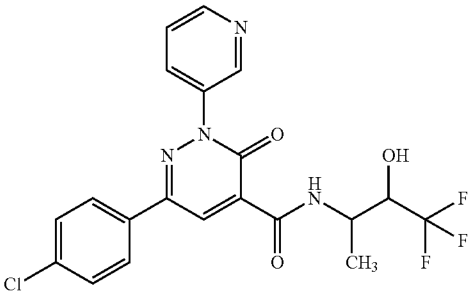 [SMILES: CC(NC(=O)c1cc(-c2ccc(Cl)cc2)nn(-c2cccnc2)c1=O)C(O)C(F)(F)F]

6-(4-Chlorophenyl)-3-oxo-2-(pyridin-3-yl)-2,3-dihydropyridazine-4-carboxylic acid (245 mg, 0.75 mmol) was dissolved in anhydrous DMF (10 mL). 3-Amino-1,1,1-trifluorobutan-2-ol hydrochloride 1:1 (174.5 mg, 0.97 mmol), N-ethyl-N-isopropylpropan-2-amine (0.59 mL, 3.36 mmol), and propane phosphonic acid anhydride (T3P, 0.71 g, 50% in DMF, 1.12 mmol) were successively added. It was stirred at rt overnight. The crude reaction mixture was purified by RP-HPLC (column: X-Bridge C18 5 μm 100×30 mm, mobile phase: (water+0.1 vol % formic acid (99%))/acetonitrile, gradient) to yield 52.8 mg (16%) of the title compound.

LC-MS (Instrument: Waters Acquity UPLC-MS SQD 3001; column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.22 min; MS (ESI-pos): m/z=454.3 $[M+H]^+$ Intermediate 105

6-(4-Chlorophenyl)-2-(5-chloropyridin-3-yl)-3-oxo-2,3-dihydropyridazine-4-carboxylic acid

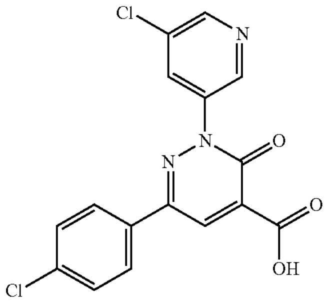 [SMILES: O=C(O)c1cc(-c2ccc(Cl)cc2)nn(-c2cncc(Cl)c2)c1=O]

Ethyl 6-(4-chlorophenyl)-3-oxo-2,3-dihydropyridazine-4-carboxylate (250 mg, 0.9 mmol) was dissolved in DMF (12 mL). (5-Chloropyridin-3-yl)boronic acid (282 mg, 1.79 mmol), 2,2'-bipyridine (700.5 mg, 4.48 mmol), sodium carbonate (0.114 g, 1.076 mmol), and anhydrous copper diacetate (407 mg, 2.24 mmol) were added. The reaction mixture was stirred for 4 h at 80° C., cooled down followed by the addition of 2.7 mL of aqueous 2N sodium hydroxide solution. It was stirred overnight, water was added and the precipitate was filtered off and dried in vacuum to yield 402 mg of the title compound.

LC-MS (Instrument: Waters Acquity UPLC-MS SOD 3001; column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.25 min; MS (ESI-pos): m/z=364.0 $[M+H]^+$ Intermediate 106

6-(4-Chlorophenyl)-2-(5-methylpyridin-3-yl)-3-oxo-2,3-dihydropyridazine-4-carboxylic acid

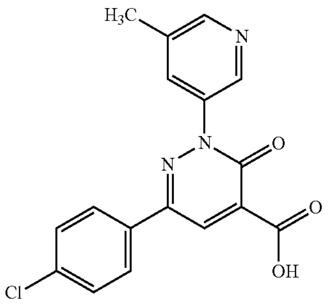 [SMILES: Cc1cncc(-n2nc(-c3ccc(Cl)cc3)cc(C(=O)O)c2=O)c1]

Ethyl 6-(4-chlorophenyl)-3-oxo-2,3-dihydropyridazine-4-carboxylate (250 mg, 0.9 mmol) was dissolved in DMF (12 mL). 5-Methylpyridine-3-boronic acid (245.7 mg, 1.79 mmol), 2,2'-bipyridine (700.5 mg, 4.48 mmol), sodium carbonate (0.114 g, 1.076 mmol), and anhydrous copper diacetate (407 mg, 2.24 mmol) were added. The reaction mixture was stirred for 4 h at 80° C., cooled down followed by the addition of 2.7 mL aqueous 2N sodium hydroxide solution. It was stirred overnight, water was added and the precipitate was filtered off and dried in vacuum to yield 317 mg of the title compound.

LC-MS (Instrument: Waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.12 min; MS (ESI-pos): m/z=342.2 $[M+H]^+$ Intermediate 107

Dimethyl {2-[4-(difluoromethoxy)phenyl]-2-oxoethyl}malonate

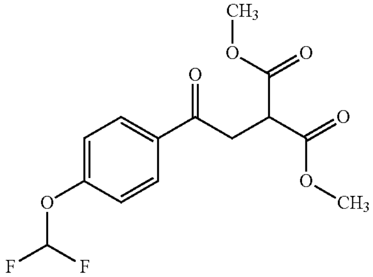 [SMILES: COC(=O)C(CC(=O)c1ccc(OC(F)F)cc1)C(=O)OC]

4.5 g of dimethyl malonate and 3.6 g of potassium carbonate were added to a solution of 4.8 g of 2-bromo-1-[4-(difluoromethoxy)phenyl]ethan-1-one in 120 mL of acetone. The reaction mixture was stirred at room temperature overnight and then quenched with water. Acetone was evaporated and the remaining aqueous phase was extracted three times with ethyl acetate. The combined organic phases were washed with brine, dried over sodium sulfate, filtrated and concentrated. The residue was purified by column chromatography (hexane/ethyl acetate gradient with up to 40% ethyl acetate) to yield 4.3 g of dimethyl {2-[4-(difluoromethoxy)phenyl]-2-oxoethyl}malonate.

$^1H$ NMR (400 MHz, DMSO-$d_6$) δ ppm=3.60-3.65 (m, 2H), 3.68 (s, 6H), 3.98 (t, 1H), 7.22-7.66 (m, 3H), 8.05-8.11 (m, 2H).

Intermediate 108

Methyl 6-[4-(difluoromethoxy)phenyl]-2-(1-methyl-1H-pyrazol-4-yl)-3-oxo-2,3,4,5-tetrahydro-pyridazine-4-carboxylate

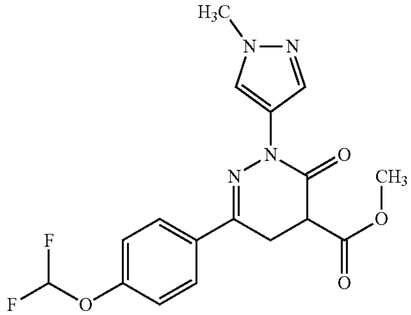 [SMILES: COC(=O)C1CC(c2ccc(OC(F)F)cc2)=NN(c2cnn(C)c2)C1=O]

A mixture of dimethyl {2-[4-(difluoromethoxy)phenyl]-2-oxoethyl}malonate (1 g, 3.16 mmol), 4-hydrazino-1-methyl-1H-pyrazole dihydrochloride (1.23 g, 6.32 mmol) and sodium acetate (1.17 g, 14.23 mmol) in 30 mL of acetic acid was stirred at 45° C. for 3 h and at rt overnight. Further 4-hydrazino-1-methyl-1H-pyrazole dihydrochloride (1 g, 3.16 mmol) was added and the reaction mixture was stirred at 45° C. for 2 hours. Then the reaction mixture was taken up in water, the precipitate was filtered off and dried in vacuum to yield 1.05 g (88%) of the title compound.

$^1H$ NMR (400 MHz, DMSO-$d_6$) δ ppm=3.35-3.45 (m, 2H), 3.68 (s, 3H), 3.85 (s, 3H), 3.99-4.05 (m, 1H), 7.24-7.30 (m, 2H), 7.36 (t, 1H), 7.75 (d, 1H), 7.94-8.03 (m, 2H), 8.08 (s, 1H).

Intermediate 109

Methyl 6-[4-(difluoromethoxy)phenyl]-2-(1-methyl-1H-pyrazol-4-yl)-3-oxo-2,3-dihydropyridazine-4-carboxylate

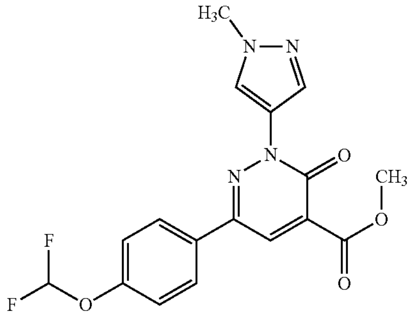 [SMILES: COC(=O)c1cc(-c2ccc(OC(F)F)cc2)nn(-c2cnn(C)c2)c1=O]

A mixture of methyl 6-[4-(difluoromethoxy)phenyl]-2-(1-methyl-1H-pyrazol-4-yl)-3-oxo-2,3,4,5-tetrahydro-pyridazine-4-carboxylate (1.05 g, 2.77 mmol) and copper(II) chloride (1.12 g, 8.3 mmol) in 37.5 mL of acetonitrile was stirred at 90° C. for 3 hours. The reaction mixture was taken up in water and the precipitate was filtered off to yield 1.08 g (quant.) of the title compound.

$^1H$ NMR (400 MHz, DMSO-$d_6$) δ ppm=3.88 (s, 3H), 3.92 (s, 3H), 7.29-7.34 (m, 2H), 7.38 (t, 1H), 8.08-8.10 (m, 1H), 8.10-8.14 (m, 2H), 8.44 (s, 1H), 8.50 (s, 1H).

Intermediate 110

6-[4-(Difluoromethoxy)phenyl]-2-(1-methyl-1H-pyrazol-4-yl)-3-oxo-2,3-dihydropyridazine-4-carboxylic acid

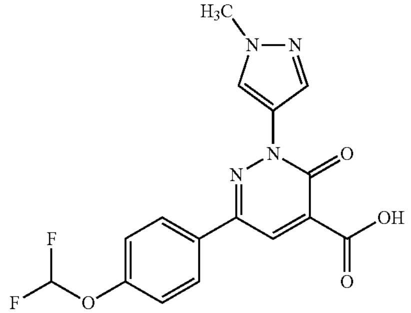 [SMILES: Cn1cc(-n2nc(-c3ccc(OC(F)F)cc3)cc(C(=O)O)c2=O)cn1]

Methyl 6-[4-(difluoromethoxy)phenyl]-2-(1-methyl-1H-pyrazol-4-yl)-3-oxo-2,3-dihydropyridazine-4-carboxylate (3.8 g, 10.1 mmol) was dissolved in THF (50 mL). A 2M solution of sodium hydroxide (12.6 mL, 25.2 mmol) was added at rt and the mixture was stirred overnight, diluted with water and treated with 1 M HCl. The pH was adjusted to 3 and the precipitate was filtered off under suction, washed three times with water and dried under vacuum to yield 276 mg (50%) of the title compound.

$^1H$ NMR (400 MHz, DMSO-$d_6$) δ ppm=3.92 (s, 3H), 7.38 (t, 1H), 7.29-7.34 (m, 2H), 8.09-8.18 (m, 3H), 8.43-8.48 (m, 1H), 8.50-8.55 (m, 1H).

Intermediate 111

6-(4-Chlorophenyl)-3-oxo-2,3-dihydropyridazine-4-carboxylic acid

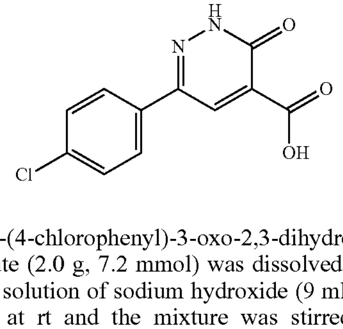

Ethyl 6-(4-chlorophenyl)-3-oxo-2,3-dihydropyridazine-4-carboxylate (2.0 g, 7.2 mmol) was dissolved in THF (37 mL). A 2M solution of sodium hydroxide (9 mL, 18 mmol) was added at rt and the mixture was stirred overnight, diluted with water and treated with 2M HCl. The pH was adjusted to 3 and the precipitate was filtered off under suction, washed three times with water and dried under vacuum to yield 1.79 g (99%) of the title compound.

$^1$H NMR (400 MHz, DMSO-$d_6$) δ ppm=7.55-7.59 (d, 2H), 7.95-7.99 (d, 2H), 8.50 (s, 1H), 14.1 (br s, 2H).

Intermediate 112

6-(4-Chlorophenyl)-N-[(2R)-3-hydroxy-3-methylbutan-2-yl]-3-oxo-2,3-dihydropyridazine-4-carboxamide

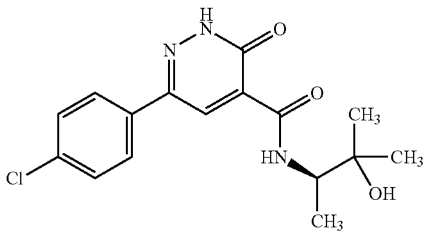 [SMILES: C[C@@H](NC(=O)c1cc(-c2ccc(Cl)cc2)n[nH]c1=O)C(C)(C)O]

6-(4-Chlorophenyl)-3-oxo-2,3-dihydropyridazine-4-carboxylic acid (1425 mg, 5.68 mmol) was dissolved in anhydrous DMF (30 mL). (3R)-3-amino-2-methyl-butan-2-ol hydrochloride 1:1 (1191 mg, 8.53 mmol), N-ethyl-N-isopropylpropan-2-amine (4.46 mL, 25.6 mmol), and propane phosphonic acid anhydride (T3P, 5.43 g, 50% in DMF, 8.53 mmol) were successively added. It was stirred at rt overnight followed by the addition of water and saturated ammonium chloride solution. The newly formed precipitate was filtered off, washed with water and dried in vacuum to yield 626 mg (33%) of the title compound.

$^1$H NMR (400 MHz, DMSO-$d_6$) δ ppm=1.09-1.11 (m, 3H), 1.13 (d, 3H), 1.15 (s, 3H), 3.85-3.97 (m, 1H), 4.65 (br s, 1H), 7.57 (d, 2H), 7.93 (d, 2H), 8.53 (s, 1H), 9.73 (s, 1H), 13.86 (br s, 1H).

Intermediate 113

3-Oxo-6-[4-(trifluoromethoxy)phenyl]-2,3-dihydropyridazine-4-carboxylic acid

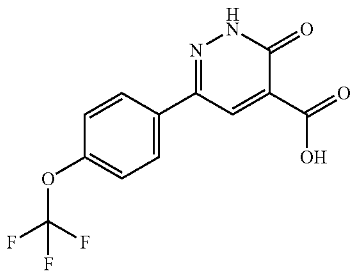 [SMILES: O=C(O)c1cc(-c2ccc(OC(F)(F)F)cc2)n[nH]c1=O]

The synthesis was performed in analogy to intermediate 111 from ethyl 3-oxo-6-[4-(trifluoromethoxy)phenyl]-2,3-dihydropyridazine-4-carboxylate.

LC-MS (Instrument: Waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.07 min; MS (ESIpos): m/z=301.2 $[M+H]^+$ Intermediate 114

N-[(2R)-3-Hydroxy-3-methylbutan-2-yl]-3-oxo-6-[4-(trifluoromethoxy)phenyl]-2,3-dihydropyridazine-4-carboxamide

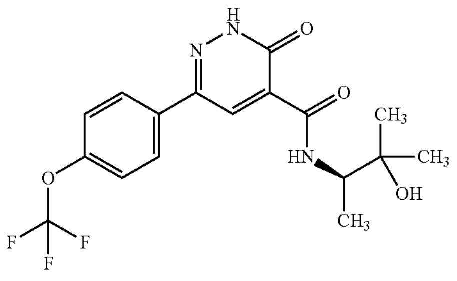 [SMILES: C[C@@H](NC(=O)c1cc(-c2ccc(OC(F)(F)F)cc2)n[nH]c1=O)C(C)(C)O]

The synthesis was performed in analogy to intermediate 112 from 3-oxo-6-[4-(trifluoromethoxy)phenyl]-2,3-dihydropyridazine-4-carboxylic acid.

$^1$H NMR (400 MHz, DMSO-$d_6$) δ ppm=1.10 (s, 3H), 1.13 (d, 3H), 1.15 (s, 3H), 3.85-3.97 (m, 1H), 4.64 (s, 1H), 7.42-7.56 (m, 2H), 7.97-8.09 (m, 2H), 8.55 (s, 1H), 9.75 (br d, 1H), 14.02 (br s, 1H).

Intermediate 115

Dimethyl {2-[4-(dimethylamino)phenyl]-2-oxoethyl}malonate

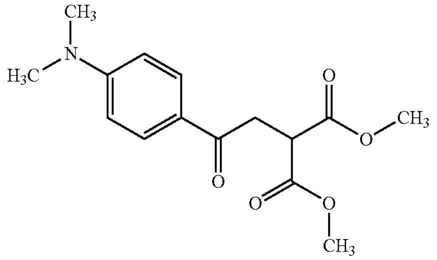

Dimethyl malonate (5.45 g, 41.3 mmol) and potassium carbonate (4.3 g, 31 mmol) were added to a solution of 4-(dimethylamino)phenacyl bromid (5.0 g, 20.6 mmol) in 145 mL of acetone. The reaction mixture was stirred at room temperature overnight and then quenched with water. The precipitate was filtered off, washed with water and dried in vacuum to yield 4.66 g (77%) of the title compound.

$^1$H NMR (400 MHz, DMSO-$d_6$) δ ppm=3.02 (s, 6H), 3.48 (d, 2H), 3.67 (s, 6H), 3.93 (t, 1H), 6.72 (d, 2H), 7.81 (d, 2H).

Intermediate 116

Methyl 6-[4-(dimethylamino)phenyl]-2-(1-methyl-1H-pyrazol-4-yl)-3-oxo-2,3,4,5-tetrahydro-pyridazine-4-carboxylate

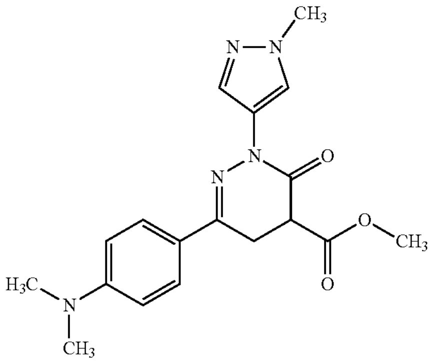

A mixture of dimethyl {2-[4-(dimethylamino)phenyl]-2-oxoethyl}malonate (500 mg, 1.7 mmol), 4-hydrazino-1-methyl-1H-pyrazole dihydrochloride (336 mg, 2.2 mmol) and sodium acetate (629 mg, 7.6 mmol) in 14 mL of AcOH was stirred at rt overnight followed by 50° C. for 1 h. Further 4-hydrazino-1-methyl-1H-pyrazole dihydrochloride (258 mg, 1.7 mmol) was added and the reaction mixture was stirred at rt overnight followed by 50° C. for 5 h. Then the reaction mixture was taken up in water and the mixture was extracted three times with ethyl acetate. The combined organic phases were washed with brine, filtered (MN 617 WA filter paper) and concentrated in vacuum to yield 516 mg (85%) of the title compound.

LC-MS (Instrument: Waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.05 min; MS (ESIpos): m/z=356.5 $[M+H]^+$ Intermediate 117

Methyl 6-[4-(dimethylamino)phenyl]-2-(1-methyl-1H-pyrazol-4-yl)-3-oxo-2,3-dihydropyridazine-4-carboxylate

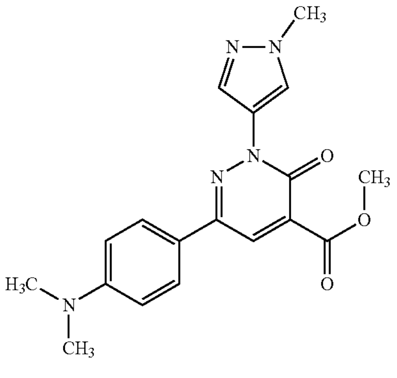

A mixture of methyl 6-[4-(dimethylamino)phenyl]-2-(1-methyl-1H-pyrazol-4-yl)-3-oxo-2,3,4,5-tetrahydro-pyridazine-4-carboxylate (516 mg, 1.45 mmol) and iodine (737 mg, 2.9 mmol) in 11 mL of acetic acid was stirred at rt for 48 hours. Additional iodine (368.5 mg, 1.45 mmol) was added and the mixture was stirred at rt for 24 h. The reaction mixture was taken up in saturated sodium thiosulfate solution and ethyl acetate. The phases were separated and the organic phase was washed with saturated sodium thiosulfate solution and brine, filtered (MN 617 WA filter paper) and concentrated in vacuum to yield 936 mg (purity 55%) of the title compound.

LC-MS (Instrument: Waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.7 min; MS (ESIpos): m/z=354.4 $[M+H]^+$ Intermediate 118

6-[4-(Dimethylamino)phenyl]-2-(1-methyl-1H-pyrazol-4-yl)-3-oxo-2,3-dihydropyridazine-4-carboxylic acid

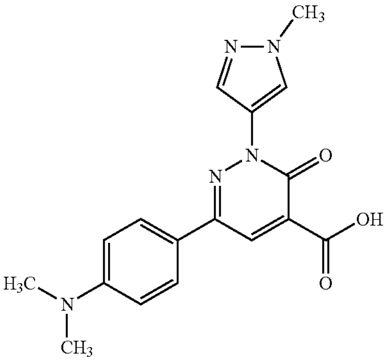 [SMILES: CN(C)c1ccc(-c2cc(C(=O)O)c(=O)n(-c3cnn(C)c3)n2)cc1]

Methyl 6-[4-(dimethylamino)phenyl]-2-(1-methyl-1H-pyrazol-4-yl)-3-oxo-2,3-dihydropyridazine-4-carboxylate (936 mg, 1.45 mmol, 55%) was dissolved in THE (5 mL). A 2M solution of sodium hydroxide (1.5 mL, 3.0 mmol) was added at rt and the mixture was stirred overnight, diluted with water and treated with 1M HCl. The pH was adjusted to 3 followed by the addition of ethyl acetate. The phases were separated and the aqueous phase was extracted three times with ethyl acetate. The combined organic phases were washed with brine, filtered (MN 617 WA filter paper) and concentrated in vacuum to yield 99 mg (20%) of the title compound.

LC-MS (Instrument: waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.11 min; MS (ESIpos): m/z=340.3 $[M+H]^+$ Intermediate 119

Ethyl 3-oxo-2-(1,2-thiazol-4-yl)-6-[4-(trifluoromethoxy)phenyl]-2,3-dihydropyridazine-4-carboxylate

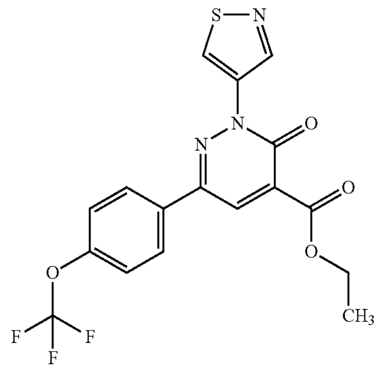 [SMILES: CCOC(=O)c1cc(-c2ccc(OC(F)(F)F)cc2)nn(-c2cnsc2)c1=O]

Ethyl 3-oxo-6-[4-(trifluoromethoxy)phenyl]-2,3-dihydropyridazine-4-carboxylate (207 mg, 0.63 mmol) was dissolved in acetonitrile (6 mL) followed by the addition of molecular sieves (4 Å, powder, 0.176 g), 4-(tetramethyl-1,3,2-dioxaborolan-2-yl)-1,2-thiazole (200 mg, 0.95 mmol), triethylamine (0.18 mL, 1.26 mmol), pyridine (0.10 mL, 1.26 mmol) and anhydrous copper diacetate (229.5 mg, 1.26 mmol). The reaction mixture was stirred for 4 h at 80° C., filtered through celite, concentrated and purified by column chromatography (hexane/ethyl acetate gradient with up to 50% ethyl acetate) to yield 95 mg (36%) of the title compound.

$^1$H NMR (400 MHz, DMSO-$d_6$) δ ppm=1.34 (t, 3H), 4.36 (q, 2H), 7.53 (dd, 2H), 8.18 (d, 2H), 8.51 (s, 1H), 9.14 (s, 1H), 9.59 (s, 1H).

Intermediate 120

3-Oxo-2-(1,2-thiazol-4-yl)-6-[4-(trifluoromethoxy)phenyl]-2,3-dihydropyridazine-4-carboxylic acid

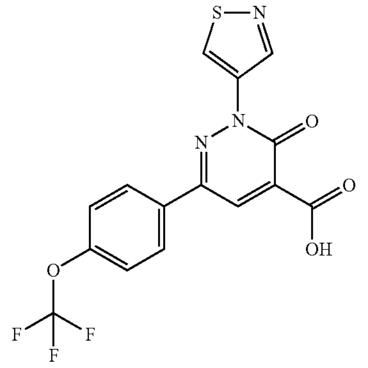 [SMILES: O=C(O)c1cc(-c2ccc(OC(F)(F)F)cc2)nn(-c2cnsc2)c1=O]

Ethyl 3-oxo-2-(1,2-thiazol-4-yl)-6-[4-(trifluoromethoxy)phenyl]-2,3-dihydropyridazine-4-carboxylate (90 mg, 0.22 mmol) was dissolved in THF (2 mL). A 2M solution of sodium hydroxide (0.33 mL, 0.66 mmol) was added at rt and the mixture was stirred overnight, diluted with water and treated with 1M HCl. The pH was adjusted to 3 and the precipitate was filtered off, washed with water and dried in vacuum to yield 74 mg (88%) of the title compound.

$^1$H NMR (400 MHz, DMSO-$d_6$) δ ppm=7.48-7.55 (m, 2H), 8.20 (d, 2H), 8.50 (s, 1H), 9.15 (s, 1H), 9.60 (s, 1H).

Intermediate 121

Methyl 6-[4-(difluoromethoxy)phenyl]-3-oxo-2,3,4,5-tetrahydropyridazine-4-carboxylate

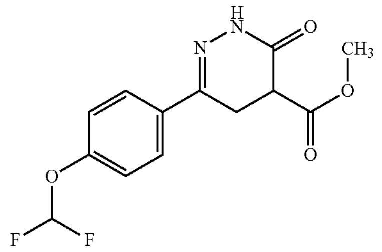 [SMILES: COC(=O)C1CC(c2ccc(OC(F)F)cc2)=NNC1=O]

A mixture of dimethyl {2-[4-(difluoromethoxy)phenyl]-2-oxoethyl}malonate (709 mg, 2.24 mmol), hydrazine in THF (1 M, 4.5 mL, 4.5 mmol) and sodium acetate (828 mg, 10.1 mmol) in 21 mL of AcOH was stirred at rt overnight followed by 6 h at 50° C. Further hydrazine in THF (1 M, 6.7 mL, 6.7 mmol) was added and the reaction mixture was stirred at 80° C. for 3 hours. Then the reaction mixture was taken up in water, the precipitate was filtered off and dried in vacuum to yield 334 mg (50%) of the title compound.

$^1$H NMR (400 MHz, DMSO-$d_6$) δ ppm=3.13-3.30 (m, 2H), 3.67 (s, 3H), 3.71-3.77 (m, 1H), 7.20-7.25 (m, 2H), 7.31 (t, 1H), 7.81 (d, 2H), 11.27 (s, 1H).

Intermediate 122

Methyl 6-[4-(difluoromethoxy)phenyl]-3-oxo-2,3-dihydropyridazine-4-carboxylate

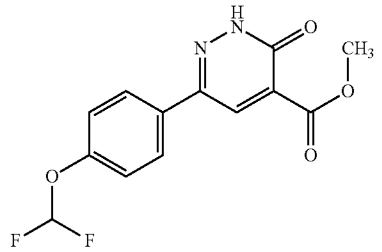 [SMILES: COC(=O)c1cc(-c2ccc(OC(F)F)cc2)n[nH]c1=O]

A mixture of methyl 6-[4-(difluoromethoxy)phenyl]-3-oxo-2,3,4,5-tetrahydropyridazine-4-carboxylate (1.3 g, 4.4 mmol) and copper(II) chloride (1.77 g, 13.2 mmol) in 60 mL of acetonitrile was stirred at 90° C. for 4 hours. The reaction mixture was taken up in water and the precipitate was filtered off to yield 1.13 g (87%) of the title compound.

$^1$H NMR (400 MHz, DMSO-$d_6$) δ ppm=3.85 (s, 3H), 7.29 (br d, 2H), 7.34 (t, 1H), 7.94 (d, 2H), 8.37 (s, 1H), 13.66 (s, 1H).

Intermediate 123

6-[4-(Difluoromethoxy)phenyl]-3-oxo-2-(pyridin-3-yl)-2,3-dihydropyridazine-4-carboxylic acid

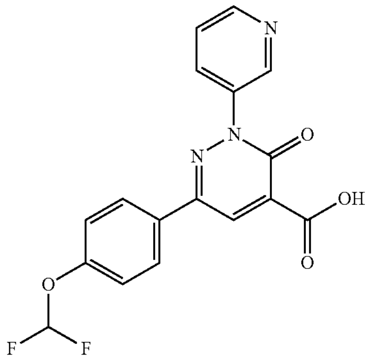 [SMILES: O=C(O)c1cc(-c2ccc(OC(F)F)cc2)nn(-c2cccnc2)c1=O]

Methyl 6-[4-(difluoromethoxy)phenyl]-3-oxo-2,3-dihydropyridazine-4-carboxylate (550 mg, 1.86 mmol) was dissolved in DMF (12 mL) followed by the addition of pyridin-3-ylboronic acid (456 mg, 3.7 mmol), 2,2'-bipyridine (1.45 g, 9.3 mmol), sodium carbonate (236 mg, 2.23 mmol) and anhydrous copper diacetate (843.1 mg, 4.6 mmol). The reaction mixture was stirred for 4 h at 80° C. followed by 48 h at rt. Then 2M sodium hydroxide solution (1.86, 3.7 mmol) was added and the mixture was stirred at rt for 3 h followed by the addition of water. The precipitate formed was filtered off, washed with water and dried in vacuum to yield 610 mg (91%) of the title compound.

LC-MS (Instrument: waters Acquity UPLC-MS SOD 3001; column: Acquity UPLC BEH C18 1.7 50×2.1 mm; eluent A: water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.07 min; MS (ESIpos): m/z=360.2 $[M+H]^+$ Intermediate 124

Diethyl hydroxy{2-oxo-2-[6-(trifluoromethyl)pyridin-3-yl]ethyl}malonate

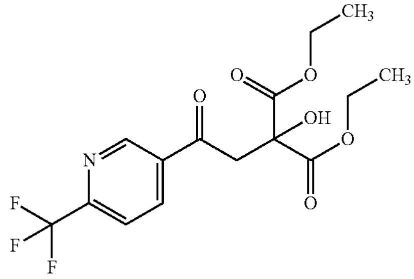 [SMILES: CCOC(=O)C(O)(CC(=O)c1ccc(C(F)(F)F)nc1)C(=O)OCC]

Into a 100-mL round-bottom flask, was placed 1-[6-(trifluoromethyl)pyridin-3-yl]ethanone (10 g, 52.87 mmol) and 1,3-diethyl 2-oxopropanedioate (15.65 g, 89.9 mmol). The resulting solution was stirred for 24 h at 130° C. followed by the addition of more 1,3-diethyl 2-oxopropanedioate (13.81 g, 79.30 mmol) and heating for another 13 h at 130° C. The resulting mixture was cooled down to rt and poured into pentane. The precipitate was filtered off, washed with pentane and water yielding 22.6 g (crude) of diethyl hydroxy{2-oxo-2-[6-(trifluoromethyl)pyridin-3-yl]ethyl}malonate which was used without further purification.

Intermediate 125

Ethyl 3-oxo-6-[6-(trifluoro methyl)pyridin-3-yl]-2,3-dihydropyridazine-4-carboxylate

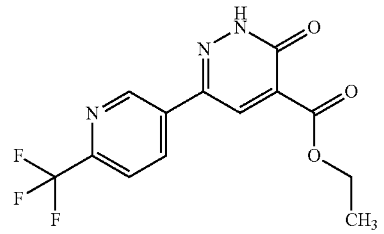 [SMILES: CCOC(=O)c1cc(-c2ccc(C(F)(F)F)nc2)n[nH]c1=O]

To a solution of diethyl hydroxy{2-oxo-2-[6-(trifluoromethyl)pyridin-3-yl]ethyl}malonate (22.6 g, 62.2 mmol) in ethanol (255 mL) was added hydrazine hydrochloride (7.2 g, 68.5 mmol). The resulting solution was stirred for 24 h at 80° C. The reaction was then quenched by the addition of water. The resulting precipitate was filtered off and dried in vacuum to give 13.26 g (68%) of ethyl 3-oxo-6-[6-(trifluoromethyl)pyridin-3-yl]-2,3-dihydropyridazine-4-carboxylate.

$^1H$ NMR (400 MHz, DMSO-$d_6$) δ ppm=1.32 (t, 3H), 4.33 (q, 2H), 8.01-8.06 (m, 1H), 8.47-8.51 (m, 1H), 8.52-8.57 (m, 1H), 9.23-9.26 (m, 1H), 13.92 (s, 1H).

Intermediate 126

Ethyl 2-(5-fluoropyridin-3-yl)-3-oxo-6-[6-(trifluoromethyl)pyridin-3-yl]-2,3-dihydropyridazine-4-carboxylate

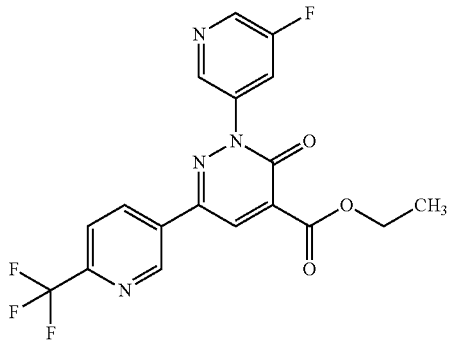 [SMILES: CCOC(=O)c1cc(-c2ccc(C(F)(F)F)nc2)nn(-c2cncc(F)c2)c1=O]

Ethyl 3-oxo-6-[6-(trifluoromethyl)pyridin-3-yl]-2,3-dihydropyridazine-4-carboxylate (5 g, 15.96 mmol) was dissolved in acetonitrile (141 mL) followed by the addition of (5-fluoropyridin-3-yl)boronic acid (3.37 g, 23.94 mmol), triethylamine (4.45 mL, 31.9 mmol), pyridine (2.58 mL, 31.9 mmol) and anhydrous copper diacetate (7.25 g, 39.9 mmol). The reaction mixture was stirred for 3 h at 80° C. followed by the addition of water. The solution was adjusted to pH 3 by adding 1 M aqueous hydrochloric acid followed by extraction with ethyl acetate three times. The combined organic phases were washed with brine, dried over sodium sulfate, filtrated and concentrated to receive 5.6 g (86%) of the title compound.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.15 min; MS (ESI-pos): m/z=409.2 $[M+H]^+$ Intermediate 127

2-(5-Fluoropyridin-3-yl)-3-oxo-6-[6-(trifluoromethyl)pyridin-3-yl]-2,3-dihydropyridazine-4-carboxylic acid

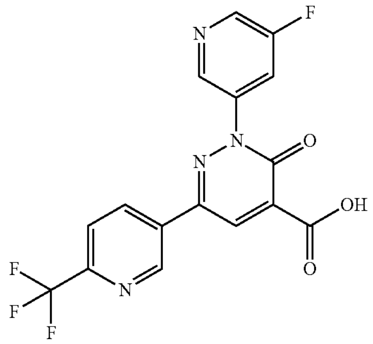 [SMILES: O=C(O)c1cc(-c2ccc(C(F)(F)F)nc2)nn(-c2cncc(F)c2)c1=O]

Ethyl 2-(5-fluoropyridin-3-yl)-3-oxo-6-[6-(trifluoromethyl)pyridin-3-yl]-2,3-dihydropyridazine-4-carboxylate (5.6 g, 13.7 mmol) was dissolved in tetrahydrofurane (100 mL) followed by the addition of 20.5 mL (41.1 mmol) of aqueous 2N sodium hydroxide solution. The reaction mixture was stirred overnight at rt. Water was added to the reaction mixture and the pH was adjusted to pH 3 with 1 M aqueous hydrochloric acid. The precipitate was filtered off and dried in vacuum to yield 3.19 g (70%) of the title compound.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.00 min; MS (ESI-pos): m/z=381.6 $[M+H]^+$ Intermediate 128

Diethyl hydroxy{2-oxo-2-[5-(trifluoromethyl)pyridin-2-yl]ethyl}malonate

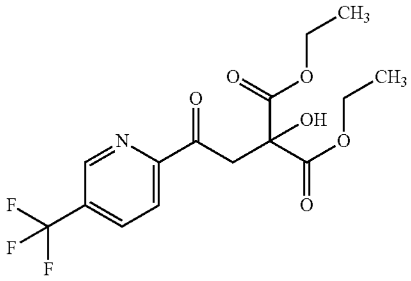 [SMILES: CCOC(=O)C(O)(CC(=O)c1ccc(C(F)(F)F)cn1)C(=O)OCC]

1-[5-(Trifluoromethyl)pyridin-2-yl]ethanone (3.8 g, 20.1 mmol) and diethyl ketomalonate (7.0 g, 40.2 mmol) were mixed and stirred at 130° C. for 24 h. After cooling to rt, the mixture was taken up in ethyl acetate and water. The phases were separated and the aqueous phase was extracted three times with ethyl acetate. The combined organic phases were washed with brine, filtered (MN 617 WA filter paper) and concentrated. The crude product was purified by flash chromatography (silica gel, hexane/ethyl acetate, gradient) to afford 4.64 g (64%) of the title compound.

$^1$H NMR (400 MHz, DMSO-$d_6$) δ ppm=1.18 (t, 6H), 3.91 (q, 2H), 4.17 (q, 4H), 6.50 (s, 1H), 8.12 (d, 1H), 8.42-8.47 (m, 1H), 9.17 (dd, 1H).

Intermediate 129

Ethyl 3-oxo-6-[5-(trifluoro methyl)pyridin-2-yl]-2,3-dihydropyridazine-4-carboxylate

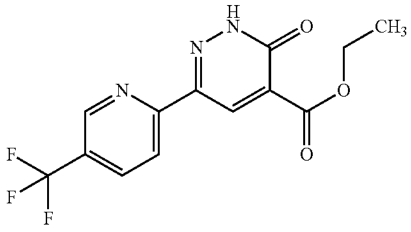 [SMILES: CCOC(=O)c1cc(-c2ccc(C(F)(F)F)cn2)n[nH]c1=O]

Diethyl hydroxy{2-oxo-2-[5-(trifluoromethyl)pyridin-2-yl]ethyl}malonate (4.6 g, 12.66 mmol) and hydrazine dihydrochlorid (1.79, 17.1 mmol) were dissolved in ethanol (52 mL) and stirred at reflux for 9 h. After addition of water a precipitate formed and was filtered off, washed with water and dried in vacuum to yield 3.19 g (81%) of the title compound.

$^1$H NMR (400 MHz, DMSO-$d_6$) b ppm 1.31 (t, 3H), 4.32 (q, 2H), 8.24-8.29 (m, 1H), 8.35 (dd, 1H), 8.67 (s, 1H), 9.07-9.11 (m, 1H), 13.94 (s, 1H).

Intermediate 130

3-Oxo-6-[5-(trifluoromethyl)pyridin-2-yl]-2,3-dihydropyridazine-4-carboxylic acid

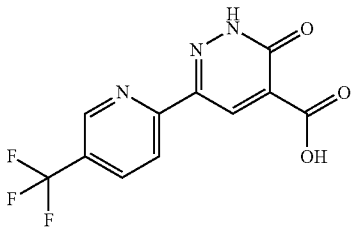 [SMILES: O=C(O)c1cc(-c2ccc(C(F)(F)F)cn2)n[nH]c1=O]

3.0 g of a crude mixture containing an unknown amount of ethyl 3-oxo-6-[5-(trifluoromethyl)-pyridin-2-yl]-2,3-dihydropyridazine-4-carboxylate was dissolved in tetrahydrofurane (50 mL) followed by the addition of 9.2 mL (18.4 mmol) of aqueous 2N sodium hydroxide solution. The reaction mixture was stirred overnight at rt. Water was added to the reaction mixture and the pH was adjusted to pH 3 with 1M aqueous hydrochloric acid. The precipitate was filtered off and dried in vacuum to yield 1.05 g of a crude mixture containing the title compound.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=1.04 min; MS (ESIpos): m/z=286.1 $[M+H]^+$ Intermediate 131

N-[(2S)-1-Hydroxypropan-2-yl]-3-oxo-6-[5-(trifluoromethyl) pyridin-2-yl]-2,3-dihydropyridazine-4-carboxamide

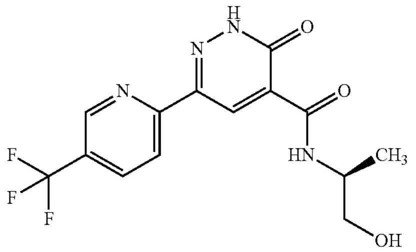 [SMILES: C[C@@H](CO)NC(=O)c1cc(-c2ccc(C(F)(F)F)cn2)n[nH]c1=O]

1.051 g of a crude mixture containing an unknown amount of 3-oxo-6-[5-(trifluoromethyl)pyridin-2-yl]-2,3-dihydropyridazine-4-carboxylic acid and 312 mg (4.15 mmol) of alaninol were dissolved in 16 mL of DMF and treated with HATU (2.1 g, 5.54 mmol), N,N-diisopropylethylamine (1.07 g, 8.3 mmol) and 4-dimethylaminopyridine (16.9 mg, 0.14 mmol). The reaction mixture was stirred overnight and taken up in water and ethyl acetate. The phases were separated and the organic phase was washed with brine, filtered (MN 617 WA filter paper) and concentrated. The crude product was purified by flash chromatography (silica gel, hexane/ethyl acetate, gradient) to afford 383 mg of the title compound.

LC-MS (Instrument: Waters Acquity UPLC-MS SOD 3001; column: Acquity UPLC BEH C18 1.7 50×2.1 mm; eluent A: Water+0.1 vol % formic acid (99%) eluent B: acetonitrile; gradient: 0-1.6 min 1-99% B, 1.6-2.0 min 99% B; flow 0.8 mL/min; temperature: 60° C.; injection: 2 μL; DAD scan: 210-400 nm; ELSD): $R_t$=0.93 min; MS (ESIpos): m/z=343.5 $[M+H]^+$

EXPERIMENTAL SECTION—EXAMPLES

The following examples describe the embodiment of the instant invention, not restricting the invention to these examples only.

Example 1

N-(1-Hydroxy-3-methylbutan-2-yl)-6-(4-methylphenyl)-2-(1-methyl-1H-pyrazol-4-yl)-3-oxo-2,3-dihydropyridazine-4-carboxamide

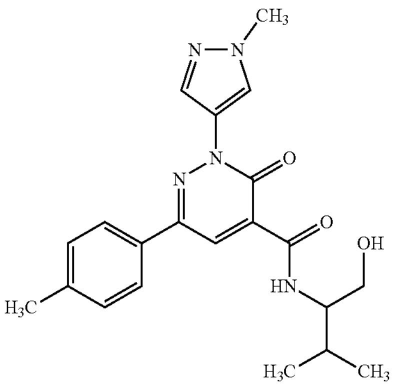 [SMILES: Cc1ccc(-c2cc(C(=O)NC(CO)C(C)C)c(=O)n(-c3cnn(C)c3)n2)cc1]

A solution of 100 mg intermediate 6, 33.2 mg 2-amino-3-methylbutan-1-ol, 184 mg HATU and 125 mg ethyldiisopropylamine in 5 mL of DMF was stirred at room temperature for 2 hour. Then the reaction was quenched by water, and the mixture was extracted with ethylacetate. The organic phase was dried over sodium sulfate and evaporated to dryness. The residue was subjected to RP-HPLC ((column: X-Bridge C18 5 μm 100×30 mm, mobile phase: acetonitrile/water (0.1 vol % formic acid)-gradient)) to yield 25.3 mg N-(1-hydroxy-3-methylbutan-2-yl)-6-(4-methylphenyl)-2-(1-methyl-1H-pyrazol-4-yl)-3-oxo-2,3-dihydropyridazine-4-carboxamide.

$^1$H-NMR: (400 MHz, 25° C., Methanol-$d_4$): δ [ppm]=1.00-1.07 (m, 6H); 2.02-2.13 (m, 1H); 2.41 (s, 3H); 3.67-3.75 (m, 2H); 3.95-4.01 (m+s, 4H); 7.34 (d, 2H); 7.88 (d, 2H); 8.15 (s, 1H); 8.49 (s, 1H); 8.64 (s, 1H).

Example 2

N-(1-Hydroxy-3-methylbutan-2-yl)-6-(4-methylphenyl)-2-(1-methyl-1H-pyrazol-4-yl)-3-oxo-2,3-dihydropyridazine-4-carboxamide, Enantiomer 1

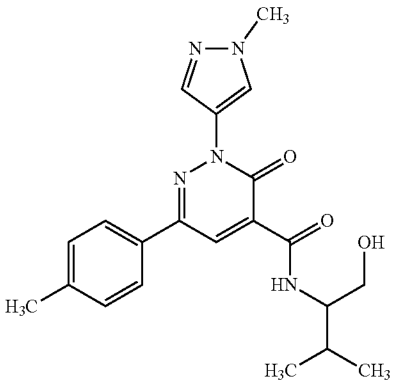 [SMILES: Cc1ccc(-c2cc(C(=O)NC(CO)C(C)C)c(=O)n(-c3cnn(C)c3)n2)cc1]

HPLC-separation of 24 mg N-(1-hydroxy-3-methylbutan-2-yl)-6-(4-methylphenyl)-2-(1-methyl-1H-pyrazol-4-yl)-3-oxo-2,3-dihydropyridazine-4-carboxamide (example 1) on a chiral column (Chiralpak IB 5 μm 250×30 mm, eluent: hexanes/ethanol gradient with 20-50% ethanol, flow 40 mL/min) yielded 6 mg N-(1-hydroxy-3-methylbutan-2-yl)-6-(4-methylphenyl)-2-(1-methyl-1H-pyrazol-4-yl)-3-oxo-2,3-dihydropyridazine-4-carboxamide, enantiomer 1.

$^1$H-NMR (400 MHz, DMSO-$d_6$): δ [ppm]=0.90-0.96 (m, 6H); 1.95-2.03 (m, 1H); 2.39 (s, 3H); 3.43-3.50 (m, 1H); 3.53-3.60 (m, 1H); 3.81-3.90 (m, 1H); 3.93 (s, 3H); 4.82 (t, 1H); 7.36 (d, 2H); 7.95 (d, 2H); 8.10 (s, 1H); 8.56 (s, 1H); 8.57 (s, 1H); 9.55 (d, 1H).

Chiral HPLC: Rt=3.65 min

Instrument: Agilent HPLC 1260; column: Chiralpak IB 3 μm 100×4.6 mm; eluent: hexanes/ethanol 50:50, flow 1.4 mL/min; temperature: 25° C.; DAD scan: 254 nm Example 3

N-(1-Hydroxy-3-methylbutan-2-yl)-6-(4-methylphenyl)-2-(1-methyl-1H-pyrazol-4-yl)-3-oxo-2,3-dihydropyridazine-4-carboxamide, Enantiomer 2

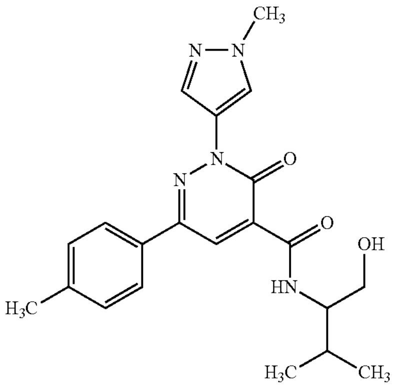 [SMILES: Cc1ccc(-c2cc(C(=O)NC(CO)C(C)C)c(=O)n(-c3cnn(C)c3)n2)cc1]

The separation of 24 mg example 1, according to example 2, additionally yielded 6 mg N-(1-hydroxy-3-methylbutan-2-yl)-6-(4-methylphenyl)-2-(1-methyl-1H-pyrazol-4-yl)-3-oxo-2,3-dihydropyridazine-4-carboxamide, enantiomer 2.

$^1$H-NMR (300 MHz, DMSO-$d_6$): δ [ppm]=0.90-0.96 (m, 6H); 1.95-2.03 (m, 1H); 2.39 (s, 3H); 3.43-3.50 (m, 1H); 3.53-3.60 (m, 1H); 3.81-3.90 (m, 1H); 3.93 (s, 3H); 4.82 (t, 1H); 7.36 (d, 2H); 7.95 (d, 2H); 8.10 (s, 1H); 8.56 (s, 1H); 8.57 (s, 1H); 9.55 (d, 1H).

Chiral HPLC: Rt=6.15 min

Instrument: Agilent HPLC 1260; column: Chiralpak IB 3 μm 100×4.6 mm; eluent: hexanes/ethanol 50:50, flow 1.4 mL/min; temperature: 25° C.; DAD scan: 254 nm Example 4

N-(1-Hydroxybutan-2-yl)-6-(4-methylphenyl)-2-(1-methyl-1H-pyrazol-4-yl)-3-oxo-2,3-dihydropyridazine-4-carboxamide

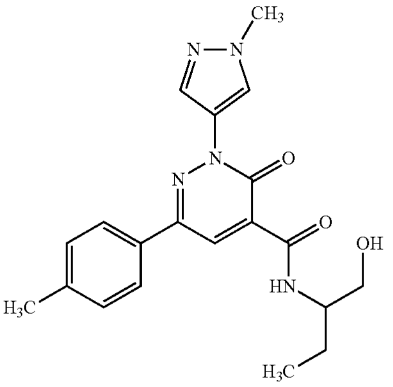 [SMILES: CCC(CO)NC(=O)c1cc(-c2ccc(C)cc2)nn(-c2cnn(C)c2)c1=O]

A solution of 100 mg intermediate 7, 40.7 mg 2-aminobutan-1-ol and 85 μL triethylamine in 10 mL of dichloromethane was stirring under ice-water bath for 10 min. Then the reaction was quenched by water, and the mixture was extracted with dichloromethane. The organic phase was dried over sodium sulfate filtered and evaporated to dryness. The residue was subjected to flash chromatography (ethyl acetate/petroleum ether 1:2) to yield 34 mg N-(1-hydroxybutan-2-yl)-6-(4-methylphenyl)-2-(1-methyl-1H-pyrazol-4-yl)-3-oxo-2,3-dihydropyridazine-4-carboxamide.

$^1$H-NMR: (400 MHz, 25° C., Methanol-$d_4$): δ [ppm]=1.02 (t, 3H); 1.59-1.83 (m, 2H); 2.41 (s, 3H); 3.68 (d, 2H); 3.96 (s, 3H); 4.01-4.07 (m, 1H); 7.34 (d, 2H); 7.87 (d, 2H); 8.15 (s, 1H); 8.48 (s, 1H); 8.62 (s, 1H).

Example 5

N-(1-Hydroxybutan-2-yl)-6-(4-methylphenyl)-2-(1-methyl-1H-pyrazol-4-yl)-3-oxo-2,3-dihydro-pyridazine-4-carboxamide, Enantiomer 1

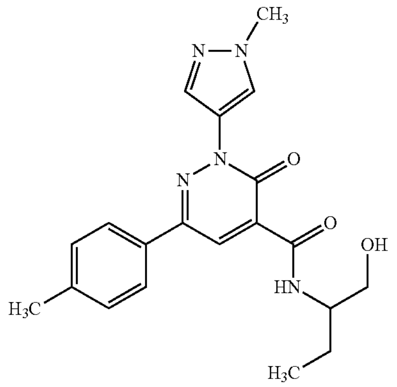 [SMILES: CCC(CO)NC(=O)c1cc(-c2ccc(C)cc2)nn(-c2cnn(C)c2)c1=O]

HPLC-separation of 33 mg N-(1-hydroxybutan-2-yl)-6-(4-methylphenyl)-2-(1-methyl-1H-pyrazol-4-yl)-3-oxo-2,3-dihydropyridazine-4-carboxamide (example 4) on a chiral column (Chiralpak IC 5 μm 250×30 mm, eluent: hexanes (0.1% diethylamine)/(ethanol/methanol 50:50) gradient with 20-50% (ethanol/methanol 50:50), flow 40 mL/min) yielded 8 mg N-(1-hydroxybutan-2-yl)-6-(4-methylphenyl)-2-(1-methyl-1H-pyrazol-4-yl)-3-oxo-2,3-dihydropyridazine-4-carboxamide, enantiomer 1.

$^1$H-NMR (400 MHz, DMSO-$d_6$): δ [ppm]=0.91 (t, 3H); 1.47-1.56 (m, 1H); 1.64-1.72 (m, 1H); 2.39 (s, 3H); 3.34-3.49 (m, 1H); 3.51-3.56 (m, 1H); 3.87-3.95 (m+s, 4H); 4.89 (t, 1H); 7.36 (d, 2H); 7.95 (d, 2H); 8.11 (s, 1H); 8.56 (s, 2H); 9.51 (d, 1H).

Chiral HPLC: Rt=4.68 min

Instrument: Agilent HPLC 1260; column: Chiralpak IC 3 μm 100×4.6 mm; eluent: hexanes (0.1% diethylamine)/(ethanol/methanol 50:50) gradient with 20-50% (ethanol/methanol 50:50), flow 1.4 mL/min; temperature: 25° C.; DAD scan: 254 nm Example 6

N-(1-Hydroxybutan-2-yl)-6-(4-methylphenyl)-2-(1-methyl-1H-pyrazol-4-yl)-3-oxo-2,3-dihydro-pyridazine-4-carboxamide, Enantiomer 2

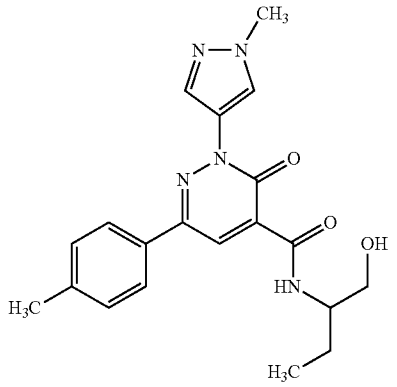 [SMILES: CCC(CO)NC(=O)c1cc(-c2ccc(C)cc2)nn(-c2cnn(C)c2)c1=O]

The separation of 33 mg example 4, according to example 5, additionally yielded 8 mg N-(1-hydroxybutan-2-yl)-6-(4-methylphenyl)-2-(1-methyl-1H-pyrazol-4-yl)-3-oxo-2,3-dihydropyridazine-4-carboxamide, enantiomer 2.

$^1$H-NMR (400 MHz, DMSO-$d_6$): δ [ppm]=0.91 (t, 3H); 1.47-1.56 (m, 1H); 1.64-1.72 (m, 1H); 2.39 (s, 3H); 3.34-3.49 (m, 1H); 3.51-3.56 (m, 1H); 3.87-3.95 (m+s, 4H); 4.89 (t, 1H); 7.36 (d, 2H); 7.95 (d, 2H); 8.11 (s, 1H); 8.56 (s, 2H); 9.51 (d, 1H).

Chiral HPLC: Rt=6.25 min

Instrument: Agilent HPLC 1260; column: Chiralpak IC 3 μm 100×4.6 mm; eluent: hexanes (0.1% diethylamine)/(ethanol/methanol 50:50) gradient with 20-50% (ethanol/methanol 50:50), flow 1.4 mL/min; temperature: 25° C.; DAD scan: 254 nm Example 7

N-(1-Hydroxypropan-2-yl)-6-(4-methylphenyl)-2-(1-methyl-1H-pyrazol-4-yl)-3-oxo-2,3-dihydro-pyridazine-4-carboxamide

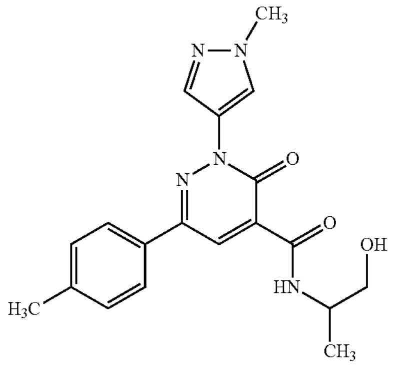 [SMILES: Cc1ccc(-c2cc(C(=O)NC(C)CO)c(=O)n(-c3cnn(C)c3)n2)cc1]

A solution of 100 mg intermediate 7, 34.3 mg 2-amino-propan-1-ol and 85 μL triethylamine in 10 mL of dichloromethane was stirring under ice-water bath for 10 min. Then the reaction was quenched by water, and the mixture was extracted with dichloromethane. The organic phase was dried over sodium sulfate filtered and evaporated to dryness. The residue was subjected to flash chromatography (ethyl acetate/petroleum ether 1:2) to yield 40.8 mg N-(1-hydroxy-propan-2-yl)-6-(4-methylphenyl)-2-(1-methyl-1H-pyrazol-4-yl)-3-oxo-2,3-dihydropyridazine-4-carboxamide.

$^1$H-NMR: (400 MHz, 25° C., Methanol-$d_4$): δ [ppm]=1.30 (d, 3H); 2.41 (s, 3H); 3.61-3.69 (m, 2H); 3.95 (s, 3H); 4.15-4.23 (m, 1H); 7.33 (d, 2H); 7.85 (d, 2H); 8.13 (s, 1H); 8.46 (s, 1H); 8.60 (s, 1H).

Example 8

N-[(2S)-1-Hydroxypropan-2-yl]-6-(4-methyl phenyl)-2-(1-methyl-1H-pyrazol-4-yl)-3-oxo-2,3-dihydropyridazine-4-carboxamide

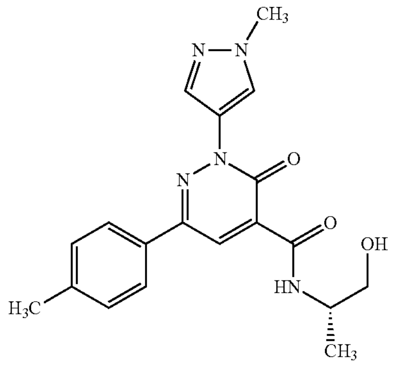 [SMILES: Cc1ccc(-c2cc(C(=O)N[C@@H](C)CO)c(=O)n(-c3cnn(C)c3)n2)cc1]

A: A solution of 80 mg intermediate 6, 38 mg (2S)-2-aminopropan-1-ol, 147 mg HATU and 0.135 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 3% methanol) to yield 20 mg N-[(2S)-1-hydroxypropan-2-yl]-6-(4-methylphenyl)-2-(1-methyl-1H-pyrazol-4-yl)-3-oxo-2,3-dihydropyridazine-4-carboxamide.

B: HPLC-separation of 39 mg N-(1-hydroxypropan-2-yl)-6-(4-methylphenyl)-2-(1-methyl-1H-pyrazol-4-yl)-3-oxo-2,3-dihydropyridazine-4-carboxamide (example 7) on a chiral column (Chiralpak IC 5 μm 250×30 mm, eluent: hexanes (0.1% diethylamine)/(ethanol/methanol 50:50) gradient with 20-50% (ethanol/methanol 50:50), flow 40 mL/min) yielded 9 mg N-[(2S)-1-hydroxypropan-2-yl]-6-(4-methylphenyl)-2-(1-methyl-1H-pyrazol-4-yl)-3-oxo-2,3-dihydropyridazine-4-carboxamide.

$^1$H-NMR (400 MHz, $CDCl_3$): δ [ppm]=1.34 (d, 3H); 2.43 (s, 3H); 2.85 (dd, 1H); 3.70 (ddd, 1H); 3.80 (ddd, 1H); 3.98 (s, 3H); 4.26-4.34 (m, 1H); 7.32 (d, 2H); 7.82 (d, 2H); 8.14 (s, 1H); 8.33 (s, 1H); 8.71 (s, 1H); 9.87 (d, 1H).

Chiral HPLC: Rt=5.28 min

Instrument: Agilent HPLC 1260; column: Chiralpak IC 3 μm 100×4.6 mm; eluent: hexanes (0.1% diethylamine)/(ethanol/methanol 50:50) gradient with 20-50% (ethanol/methanol 50:50), flow 1.4 mL/min; temperature: 25° C.; DAD scan: 254 nm Example 9

N-[(2R)-1-Hydroxypropan-2-yl]-6-(4-methyl phenyl)-2-(1-methyl-1H-pyrazol-4-yl)-3-oxo-2,3-dihydropyridazine-4-carboxamide

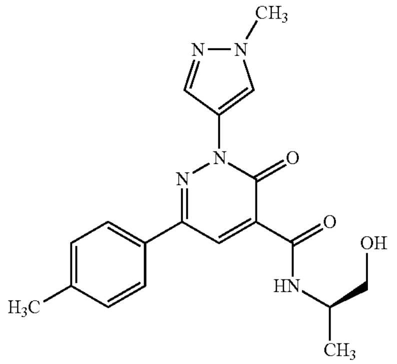 [SMILES: Cc1ccc(-c2cc(C(=O)N[C@H](C)CO)c(=O)n(-c3cnn(C)c3)n2)cc1]

The separation of 39 mg example 7, according to example 8, procedure B, additionally yielded 13 mg N-[(2R)-1-hydroxypropan-2-yl]-6-(4-methylphenyl)-2-(1-methyl-1H-pyrazol-4-yl)-3-oxo-2,3-dihydropyridazine-4-carboxamide.

$^1$H-NMR (400 MHz, $CDCl_3$): δ [ppm]=1.34 (d, 3H); 2.43 (s, 3H); 2.85 (dd, 1H); 3.70 (ddd, 1H); 3.80 (ddd, 1H); 3.98 (s, 3H); 4.26-4.34 (m, 1H); 7.32 (d, 2H); 7.82 (d, 2H); 8.14 (s, 1H); 8.33 (s, 1H); 8.71 (s, 1H); 9.87 (d, 1H).

Chiral HPLC: Rt=7.07 min

Instrument: Agilent HPLC 1260; column: Chiralpak IC 3 μm 100×4.6 mm; eluent: hexanes (0.1% diethylamine)/(ethanol/methanol 50:50) gradient with 20-50% (ethanol/methanol 50:50), flow 1.4 mL/min; temperature: 25° C.; DAD scan: 254 nm.

Example 10

6-(4-Methylphenyl)-2-(1-methyl-1H-pyrazol-4-yl)-3-oxo-N-(3,3,3-trifluoro-2-hydroxypropyl)-2,3-dihydropyridazine-4-carboxamide

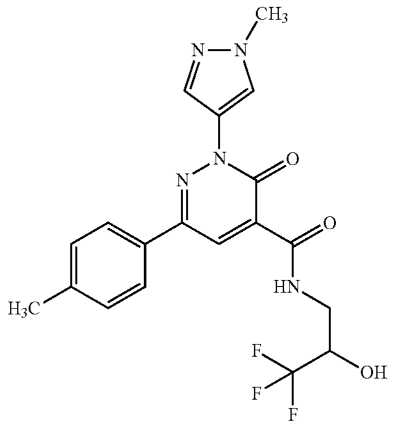 [SMILES: Cc1ccc(-c2cc(C(=O)NCC(O)C(F)(F)F)c(=O)n(-c3cnn(C)c3)n2)cc1]

A solution of 100 mg intermediate 6, 83.2 mg 3-amino-1,1,1-trifluoropropan-2-ol, 184 mg HATU and 0.17 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 2% methanol) to yield 65 mg 6-(4-methylphenyl)-2-(1-methyl-1H-pyrazol-4-yl)-3-oxo-N-(3,3,3-trifluoro-2-hydroxypropyl)-2,3-dihydropyridazine-4-carboxamide.

$^1$H-NMR (400 MHz, $CDCl_3$): δ [ppm]=2.44 (s, 3H); 3.78 (ddd, 1H); 3.90 (ddd, 1H); 3.99 (s, 3H); 4.18-4.27 (m, 1H); 4.56 (d, 1H); 7.33 (d, 2H); 7.82 (d, 2H); 8.16 (s, 1H); 8.33 (s, 1H); 8.71 (s, 1H); 10.24 (bt, 1H).

Example 11

(−)-6-(4-Methylphenyl)-2-(1-methyl-1H-pyrazol-4-yl)-3-oxo-N-(3,3,3-trifluoro-2-hydroxypropyl)-2,3-dihydropyridazine-4-carboxamide, Enantiomer 1

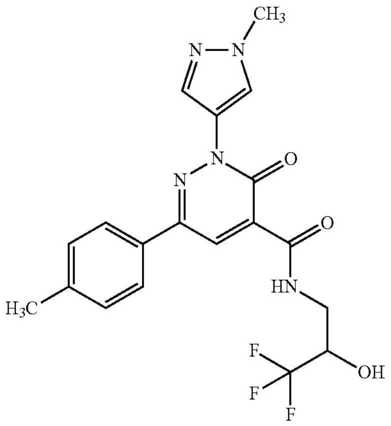 [SMILES: Cc1ccc(-c2cc(C(=O)NCC(O)C(F)(F)F)c(=O)n(-c3cnn(C)c3)n2)cc1]

HPLC-separation of 63 mg 6-(4-methylphenyl)-2-(1-methyl-1H-pyrazol-4-yl)-3-oxo-N-(3,3,3-trifluoro-2-hydroxypropyl)-2,3-dihydropyridazine-4-carboxamide (example 10) on a chiral column (Chiralpak IA 5 μm 250×30 mm, eluent: methanol (0.1% diethylamine)/ethanol 50:50, flow 30 mL/min) yielded 29 mg (−)-6-(4-methylphenyl)-2-(1-methyl-1H-pyrazol-4-yl)-3-oxo-N-(3,3,3-trifluoro-2-hydroxypropyl)-2,3-dihydropyridazine-4-carboxamide, enantiomer 1.

$^1$H-NMR (400 MHz, $CDCl_3$): δ [ppm]=2.44 (s, 3H); 3.78 (ddd, 1H); 3.90 (ddd, 1H); 3.99 (s, 3H); 4.18-4.27 (m, 1H); 4.56 (d, 1H); 7.33 (d, 2H); 7.82 (d, 2H); 8.16 (s, 1H); 8.33 (s, 1H); 8.71 (s, 1H); 10.24 (bt, 1H).

Chiral HPLC: Rt=2.69 min

Instrument: Agilent HPLC 1260; column: Chiralpak IC 3 μm 100×4.6 mm; eluent: methanol (0.1% diethylamine)/ethanol 50:50, flow 1.4 mL/min; temperature: 25° C.; DAD scan: 254 nm Optical rotation: $[\alpha]_D^{20}$=−6.7°+/−0.62° (c=1.00, methanol).

Example 12

(+)-6-(4-Methylphenyl)-2-(1-methyl-1H-pyrazol-4-yl)-3-oxo-N-(3,3,3-trifluoro-2-hydroxypropyl)-2,3-dihydropyridazine-4-carboxamide, Enantiomer 2

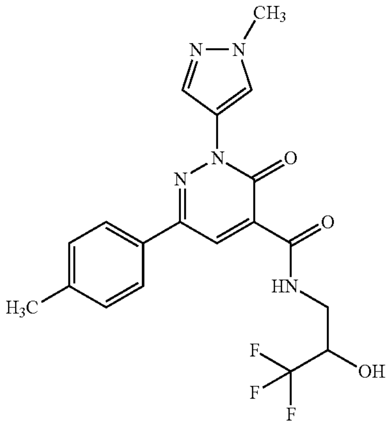 [SMILES: Cc1ccc(-c2cc(C(=O)NCC(O)C(F)(F)F)c(=O)n(-c3cnn(C)c3)n2)cc1]

The separation of 63 mg example 10, according to example 11, additionally yielded 29 mg (+)-6-(4-methylphenyl)-2-(1-methyl-1H-pyrazol-4-yl)-3-oxo-N-(3,3,3-trifluoro-2-hydroxypropyl)-2,3-dihydropyridazine-4-carboxamide, enantiomer 2.

$^1$H-NMR (400 MHz, $CDCl_3$): δ [ppm]=2.44 (s, 3H); 3.78 (ddd, 1H); 3.90 (ddd, 1H); 3.99 (s, 3H); 4.18-4.27 (m, 1H); 4.56 (d, 1H); 7.33 (d, 2H); 7.82 (d, 2H); 8.16 (s, 1H); 8.33 (s, 1H); 8.71 (s, 1H); 10.24 (bt, 1H).

Chiral HPLC: Rt=3.11 min

Instrument: Agilent HPLC 1260; column: Chiralpak IC 3 μm 100×4.6 mm; eluent: methanol (0.1% diethylamine)/ethanol 50:50, flow 1.4 mL/min; temperature: 25° C.; DAD scan: 254 nm Optical rotation: $[\alpha]_D^{20}$=5.6°+/−0.47° (c=1.00, methanol).

Example 13

N-(3,3-Difluoro-2-hydroxypropyl)-6-(4-methylphenyl)-2-(1-methyl-1H-pyrazol-4-yl)-3-oxo-2,3-dihydropyridazine-4-carboxamide

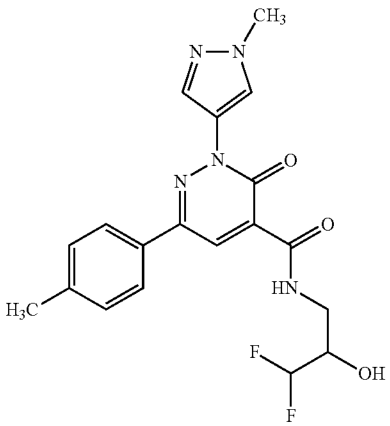 [SMILES: Cc1ccc(-c2cc(C(=O)NCC(O)C(F)F)c(=O)n(-c3cnn(C)c3)n2)cc1]

A solution of 100 mg intermediate 6, 71.6 mg 3-amino-1,1-difluoropropan-2-ol, 184 mg HATU and 0.17 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 2% methanol) to yield 55 mg N-(3,3-difluoro-2-hydroxypropyl)-6-(4-methylphenyl)-2-(1-methyl-1H-pyrazol-4-yl)-3-oxo-2,3-dihydropyridazine-4-carboxamide.

$^1$H-NMR (400 MHz, $CDCl_3$): δ [ppm]=2.43 (s, 3H); 3.67-3.77 (m, 1H); 3.84 (ddd, 1H); 3.95-4.09 (m+s, 4H); 4.11 (d, 1H); 5.79 (dt, 1H); 7.32 (d, 2H); 7.82 (d, 2H); 8.14 (s, 1H); 8.33 (s, 1H); 8.70 (s, 1H); 10.16 (bt, 1H).

Example 14

N-(3,3-Difluoro-2-hydroxypropyl)-6-(4-methylphenyl)-2-(1-methyl-1H-pyrazol-4-yl)-3-oxo-2,3-dihydropyridazine-4-carboxamide, Enantiomer 1

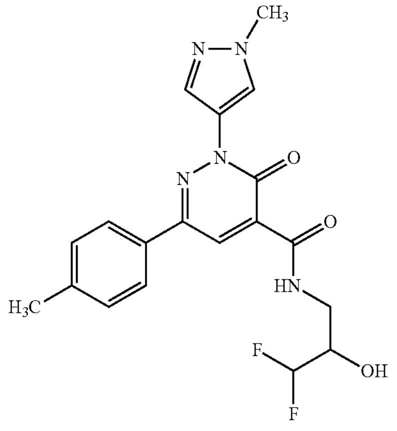 [SMILES: Cc1ccc(-c2cc(C(=O)NCC(O)C(F)F)c(=O)n(-c3cnn(C)c3)n2)cc1]

HPLC-separation of 53 mg N-(3,3-difluoro-2-hydroxypropyl)-6-(4-methylphenyl)-2-(1-methyl-1H-pyrazol-4-yl)-3-oxo-2,3-dihydropyridazine-4-carboxamide (example 13) on a chiral column (Chiralpak IA 5 μm 250×30 mm, eluent: methanol (0.1% diethylamine)/ethanol 50:50, flow 30 mL/min) yielded 24 mg N-(3,3-difluoro-2-hydroxypropyl)-6-(4-methylphenyl)-2-(1-methyl-1H-pyrazol-4-yl)-3-oxo-2,3-dihydropyridazine-4-carboxamide, enantiomer 1.

$^1$H-NMR (400 MHz, $CDCl_3$): δ [ppm]=2.43 (s, 3H); 3.67-3.77 (m, 1H); 3.84 (ddd, 1H); 3.95-4.09 (m+s, 4H); 4.11 (d, 1H); 5.79 (dt, 1H); 7.32 (d, 2H); 7.82 (d, 2H); 8.14 (s, 1H); 8.33 (s, 1H); 8.70 (s, 1H); 10.16 (bt, 1H).

Chiral HPLC: Rt=3.92 min

Instrument: Agilent HPLC 1260; column: Chiralpak IA 3 μm 100×4.6 mm; eluent: methanol (0.1% diethylamine)/ethanol 50:50, flow 1.4 mL/min; temperature: 25° C.; DAD scan: 254 nm

Example 15

N-(3,3-Difluoro-2-hydroxypropyl)-6-(4-methylphenyl)-2-(1-methyl-1H-pyrazol-4-yl)-3-oxo-2,3-dihydropyridazine-4-carboxamide, Enantiomer 2

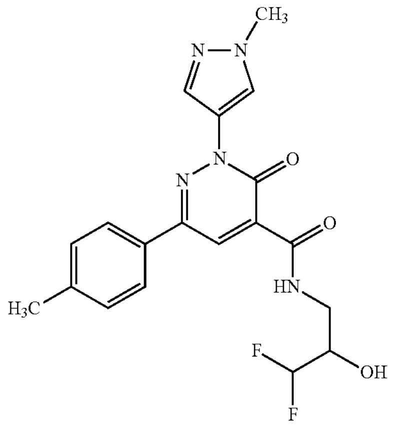 [SMILES: Cc1ccc(-c2cc(C(=O)NCC(O)C(F)F)c(=O)n(-c3cnn(C)c3)n2)cc1]

The separation of 53 mg example 13, according to example 14, additionally yielded 24 mg N-(3,3-difluoro-2-hydroxypropyl)-6-(4-methylphenyl)-2-(1-methyl-1H-pyrazol-4-yl)-3-oxo-2,3-dihydropyridazine-4-carboxamide, enantiomer 2.

$^1$H-NMR (400 MHz, $CDCl_3$): δ [ppm]=2.43 (s, 3H); 3.67-3.77 (m, 1H); 3.84 (ddd, 1H); 3.95-4.09 (m+s, 4H); 4.11 (d, 1H); 5.79 (dt, 1H); 7.32 (d, 2H); 7.82 (d, 2H); 8.14 (s, 1H); 8.33 (s, 1H); 8.70 (s, 1H); 10.16 (bt, 1H).

Chiral HPLC: Rt=4.78 min

Instrument: Agilent HPLC 1260; column: Chiralpak IA 3 μm 100×4.6 mm; eluent: methanol (0.1% diethylamine)/ethanol 50:50, flow 1.4 mL/min; temperature: 25° C.; DAD scan: 254 nm

Example 16

6-(4-Chlorophenyl)-N-[(2S)-1-hydroxy-3-methyl butan-2-yl]-2-(1-methyl-1H-pyrazol-4-yl)-3-oxo-2,3-dihydropyridazine-4-carboxamide

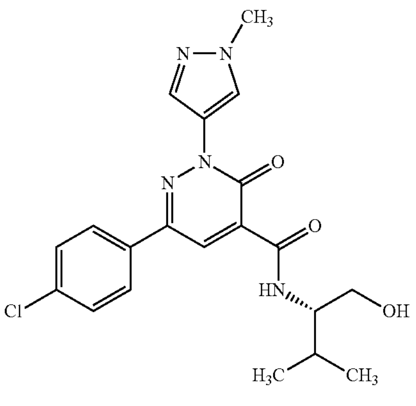 [SMILES: CC(C)[C@@H](CO)NC(=O)c1cc(-c2ccc(Cl)cc2)nn(-c2cnn(C)c2)c1=O]

A solution of 80 mg intermediate 11, 49.9 mg (2S)-2-amino-3-methylbutan-1-ol, 138 mg HATU and 0.13 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 vol % formic acid)-gradient)) to yield 45 mg 6-(4-chlorophenyl)-N-[(2S)-1-hydroxy-3-methylbutan-2-yl]-2-(1-methyl-1H-pyrazol-4-yl)-3-oxo-2,3-dihydropyridazine-4-carboxamide $^1$H-NMR (400 MHz, $CDCl_3$): δ [ppm]=1.05 (d, 3H), 1.06 (d, 3H), 2.01-2.14 (m, 1H), 2.79 (t, 1H), 3.75-3.82 (m, 1H), 3.83-3.89 (m, 1H), 3.96-4.06 (m, 4H), 7.46-7.51 (m, 2H), 7.85-7.90 (m, 2H), 8.11 (s, 1H), 8.34 (s, 1H), 8.69 (s, 1H), 9.93 (br d, 1H).

Example 17

6-(4-Chlorophenyl)-N-[(2S)-1-hydroxypropan-2-yl]-2-(1-methyl-1H-pyrazol-4-yl)-3-oxo-2,3-dihydropyridazine-4-carboxamide

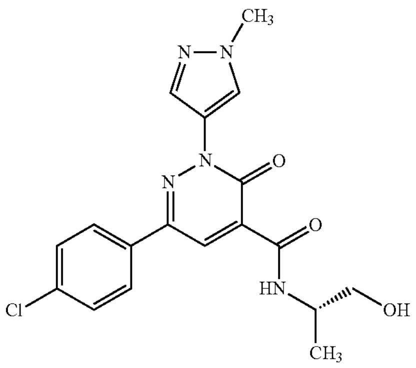 [SMILES: C[C@@H](CO)NC(=O)c1cc(-c2ccc(Cl)cc2)nn(-c2cnn(C)c2)c1=O]

A solution of 80 mg intermediate 11, 29.1 mg (2S)-2-aminopropan-1-ol, 110 mg HATU and 0.1 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 vol % formic acid)-gradient)) to yield 50 mg 6-(4-chlorophenyl)-N-[(2S)-1-hydroxypropan-2-yl]-2-(1-methyl-1H-pyrazol-4-yl)-3-oxo-2,3-dihydropyridazine-4-carboxamide $^1$H-NMR (400 MHz, $CDCl_3$): δ [ppm]=1.34 (d, 3H); 2.73-2.82 (m, 1H); 3.66-3.73 (m, 1H); 3.77-3.84 (m, 1H); 3.98 (s, 3H); 4.26-4.36 (m, 1H); 7.49 (d, 2H); 7.87 (d, 2H); 8.12 (s, 1H); 8.33 (s, 1H); 8.69 (s, 1H); 9.82 (bd, 1H).

Example 18

6-(4-Chlorophenyl)-2-(1-methyl-1H-pyrazol-4-yl)-3-oxo-N-(3,3,3-trifluoro-2-hydroxypropyl)-2,3-dihydropyridazine-4-carboxamide

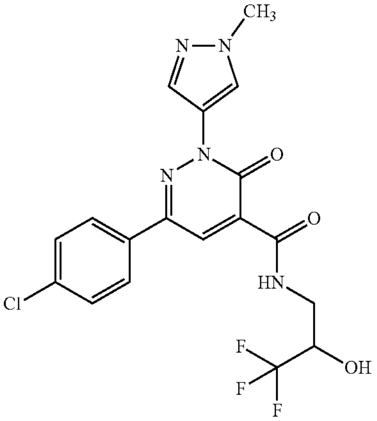 [SMILES: Cn1cc(-n2nc(-c3ccc(Cl)cc3)cc(C(=O)NCC(O)C(F)(F)F)c2=O)cn1]

A solution of 130 mg intermediate 11, 101 mg 3-amino-1,1,1-trifluoropropan-2-ol, 224 mg HATU and 0.21 mL ethyldiisopropylamine in 10 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to flash chromatography (dichloromethane/methanol gradient with up to 2% methanol) to yield 160 mg 6-(4-chlorophenyl)-2-(1-methyl-1H-pyrazol-4-yl)-3-oxo-N-(3,3,3-trifluoro-2-hydroxypropyl)-2,3-dihydropyridazine-4-carboxamide.

$^1$H-NMR (400 MHz, $CDCl_3$): δ [ppm]=3.70-3.79 (m, 1H); 3.93 (ddd, 1H); 3.98 (s, 3H); 4.21-4.28 (m, 1H); 4.64 (br s, 1H); 7.49 (d, 2H); 7.85 (d, 2H); 8.11 (s, 1H); 8.31 (s, 1H); 8.66 (s, 1H); 10.15 (bt, 1H).

Example 19

(−)-6-(4-Chlorophenyl)-2-(1-methyl-1H-pyrazol-4-yl)-3-oxo-N-(3,3,3-trifluoro-2-hydroxypropyl)-2,3-dihydropyridazine-4-carboxamide

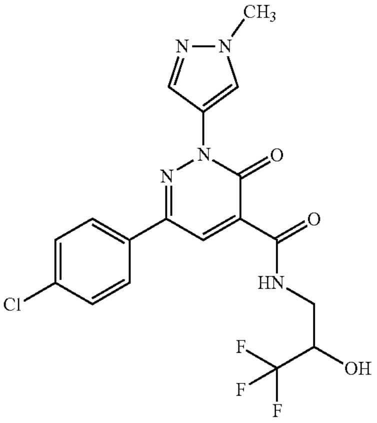 [SMILES: Cn1cc(-n2nc(-c3ccc(Cl)cc3)cc(C(=O)NCC(O)C(F)(F)F)c2=O)cn1]

HPLC-separation of 158 mg 6-(4-chlorophenyl)-2-(1-methyl-1H-pyrazol-4-yl)-3-oxo-N-(3,3,3-trifluoro-2-hydroxypropyl)-2,3-dihydropyridazine-4-carboxamide (example 18) on a chiral column (Chiralpak IA 5 μm 250×30 mm, eluent: $CO_2$/2-propanol 77:23, flow 100 mL/min, p=150 bar, T=40° C.) yielded 50 mg (−)-6-(4-chlorophenyl)-2-(1-methyl-1H-pyrazol-4-yl)-3-oxo-N-(3,3,3-trifluoro-2-hydroxypropyl)-2,3-dihydropyridazine-4-carboxamide.

$^1$H-NMR (400 MHz, $CDCl_3$): δ [ppm]=3.70-3.79 (m, 1H); 3.93 (ddd, 1H); 3.98 (s, 3H); 4.21-4.28 (m, 1H); 4.64 (br s, 1H); 7.49 (d, 2H); 7.85 (d, 2H); 8.11 (s, 1H); 8.31 (s, 1H); 8.66 (s, 1H); 10.15 (bt, 1H).

Chiral HPLC: Rt=2.76 min

Instrument: Agilent HPLC 1260; column: Chiralpak IA 3 μm 100×4.6 mm; eluent: $CO_2$/2-propanol 77:23, flow 4 mL/min, p=100 bar, T=37.5° C.; DAD scan: 254 nm Optical rotation: $[\alpha]_D^{20}$=−5.2°+/−0.35° (c=1.00, methanol).

Example 20

(+)-6-(4-Chlorophenyl)-2-(1-methyl-1H-pyrazol-4-yl)-3-oxo-N-(3,3,3-trifluoro-2-hydroxypropyl)-2,3-dihydropyridazine-4-carboxamide

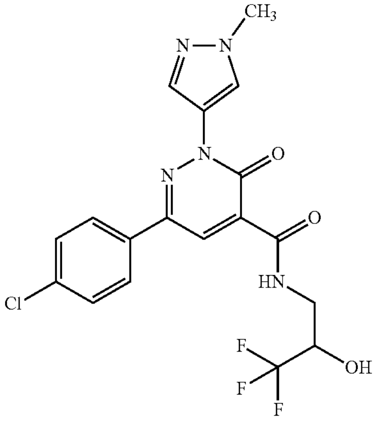 [SMILES: Cn1cc(-n2nc(-c3ccc(Cl)cc3)cc(C(=O)NCC(O)C(F)(F)F)c2=O)cn1]

The separation of 158 mg example 18, according to example 19, additionally yielded 55 mg (+)-6-(4-chlorophenyl)-2-(1-methyl-1H-pyrazol-4-yl)-3-oxo-N-(3,3,3-trifluoro-2-hydroxypropyl)-2,3-dihydropyridazine-4-carboxamide.

$^1$H-NMR (400 MHz, $CDCl_3$): δ [ppm]=3.70-3.79 (m, 1H); 3.93 (ddd, 1H); 3.98 (s, 3H); 4.21-4.28 (m, 1H); 4.64 (br s, 1H); 7.49 (d, 2H); 7.85 (d, 2H); 8.11 (s, 1H); 8.31 (s, 1H); 8.66 (s, 1H); 10.15 (bt, 1H).

Chiral HPLC: Rt=3.75 min

Instrument: Agilent HPLC 1260; column: Chiralpak IA 3 μm 100×4.6 mm; eluent: $CO_2$/2-propanol 77:23, flow 4 mL/min, p=100 bar, T=37.5° C.; DAD scan: 254 nm Optical Rotation:

$[\alpha]_D^{20}$=6.9°+/−0.23° (c=1.00, methanol).

Example 21

6-(4-Chlorophenyl)-N-(3,3-difluoro-2-hydroxypropyl)-2-(1-methyl-1H-pyrazol-4-yl)-3-oxo-2,3-dihydropyridazine-4-carboxamide

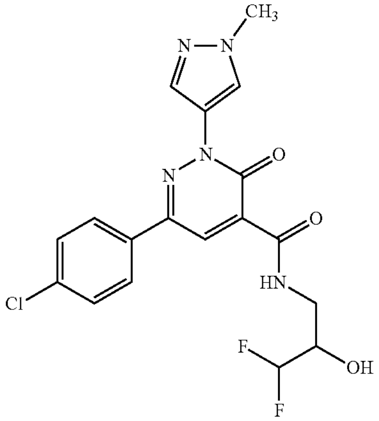 [SMILES: Cn1cc(-n2nc(-c3ccc(Cl)cc3)cc(C(=O)NCC(O)C(F)F)c2=O)cn1]

A solution of 110 mg intermediate 11, 59.1 mg 3-amino-1,1-difluoropropan-2-ol, 152 mg HATU and 0.14 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 vol % formic acid)-gradient)) to yield 65 mg 6-(4-chlorophenyl)-N-(3,3-difluoro-2-hydroxypropyl)-2-(1-methyl-1H-pyrazol-4-yl)-3-oxo-2,3-dihydropyridazine-4-carboxamide.

$^1$H-NMR (400 MHz, $CDCl_3$): δ [ppm]=3.68-3.77 (m, 1H); 3.85 (ddd, 1H); 3.96-4.08 (m+s, 5H); 5.79 (dt, 1H); 7.49 (d, 2H); 7.86 (d, 2H); 8.12 (s, 1H); 8.32 (s, 1H); 8.67 (s, 1H); 10.10 (bt, 1H).

Example 22

(−)-6-(4-Chlorophenyl)-N-(3,3-difluoro-2-hydroxypropyl)-2-(1-methyl-1H-pyrazol-4-yl)-3-oxo-2,3-dihydropyridazine-4-carboxamide

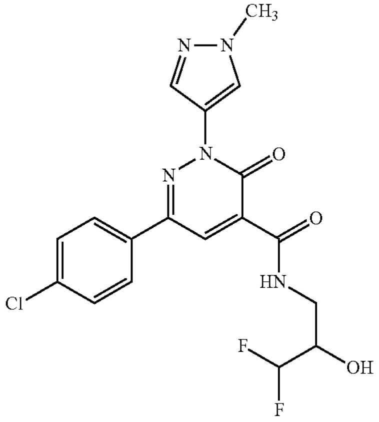 [SMILES: Cn1cc(-n2nc(-c3ccc(Cl)cc3)cc(C(=O)NCC(O)C(F)F)c2=O)cn1]

HPLC-separation of 63 mg 6-(4-chlorophenyl)-N-(3,3-difluoro-2-hydroxypropyl)-2-(1-methyl-1H-pyrazol-4-yl)-3-oxo-2,3-dihydropyridazine-4-carboxamide (example 21) on a chiral column (Chiralpak IA 5 μm 250×30 mm, eluent: $CO_2$/2-propanol 71:29, flow 100 mL/min, p=150 bar, T=40° C.) yielded 15 mg (−)-6-(4-chlorophenyl)-N-(3,3-difluoro-2-hydroxypropyl)-2-(1-methyl-1H-pyrazol-4-yl)-3-oxo-2,3-dihydropyridazine-4-carboxamide.

$^1$H-NMR (400 MHz, $CDCl_3$): δ [ppm]=3.68-3.77 (m, 1H); 3.85 (ddd, 1H); 3.96-4.08 (m+s, 5H); 5.79 (dt, 1H); 7.49 (d, 2H); 7.86 (d, 2H); 8.12 (s, 1H); 8.32 (s, 1H); 8.67 (s, 1H); 10.10 (bt, 1H).

Chiral HPLC: Rt=2.50 min

Instrument: Agilent HPLC 1260; column: Chiralpak IA 3 μm 100×4.6 mm; eluent: $CO_2$/2-propanol 71:29, flow 4 mL/min, p=100 bar, T=37.5° C.; DAD scan: 254 nm Optical rotation: $[\alpha]_D^{20}$=−6.6°+/−0.41° (c=1.00, methanol).

Example 23

(+)-6-(4-Chlorophenyl)-N-(3,3-difluoro-2-hydroxypropyl)-2-(1-methyl-1H-pyrazol-4-yl)-3-oxo-2,3-dihydropyridazine-4-carboxamide

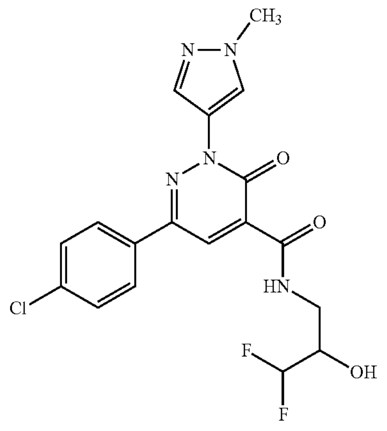 [SMILES: Cn1cc(-n2nc(-c3ccc(Cl)cc3)cc(C(=O)NCC(O)C(F)F)c2=O)cn1]

The separation of 63 mg example 21, according to example 22, additionally yielded 20 mg (+)-6-(4-chlorophenyl)-N-(3,3-difluoro-2-hydroxypropyl)-2-(1-methyl-1H-pyrazol-4-yl)-3-oxo-2,3-dihydropyridazine-4-carboxamide.

$^1$H-NMR (400 MHz, $CDCl_3$): δ [ppm]=3.68-3.77 (m, 1H); 3.85 (ddd, 1H); 3.96-4.08 (m+s, 5H); 5.79 (dt, 1H); 7.49 (d, 2H); 7.86 (d, 2H); 8.12 (s, 1H); 8.32 (s, 1H); 8.67 (s, 1H); 10.10 (bt, 1H).

Chiral HPLC: Rt=4.12 min

Instrument: Agilent HPLC 1260; column: Chiralpak IA 3 μm 100×4.6 mm; eluent: $CO_2$/2-propanol 71:29, flow 4 mL/min, p=100 bar, T=37.5° C.; DAD scan: 254 nm Optical rotation: $[\alpha]_D^{20}$=8.4°+/−0.32° (c=1.00, methanol).

Example 24

6-(4-Chlorophenyl)-N-(2-hydroxy-3-methoxypropyl)-2-(1-methyl-1H-pyrazol-4-yl)-3-oxo-2,3-dihydropyridazine-4-carboxamide

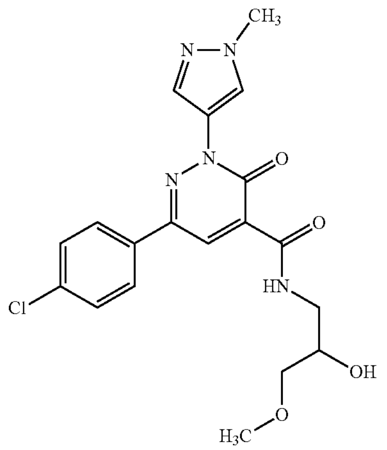 [SMILES: COCC(O)CNC(=O)c1cc(-c2ccc(Cl)cc2)nn(-c2cnn(C)c2)c1=O]

A solution of 110 mg intermediate 11, 55.9 mg 1-amino-3-methoxypropan-2-ol, 152 mg HATU and 0.14 mL ethyldiisopropylamine in 5 mL of DMF was stirred at room temperature for 14 hours. Then the reaction was quenched by water, and the mixture was extracted with dichloromethane two times. The combined organic phases were dried over sodium sulfate and evaporated to dryness. The residue was subjected to RP-HPLC ((column: X-Bridge C18 5 μm 100×30 mm, mobile phase: acetonitrile/water (0.1 vol % formic acid)-gradient)) to yield 40 mg 6-(4-chlorophenyl)-N-(2-hydroxy-3-methoxypropyl)-2-(1-methyl-1H-pyrazol-4-yl)-3-oxo-2,3-dihydropyridazine-4-carboxamide.

$^1$H-NMR (400 MHz, $CDCl_3$): δ [ppm]=3.06 (d, 1H); 3.40-3.46 (m+s, 4H); 3.47-3.60 (m, 2H); 3.74 (ddd, 1H); 3.98 (s, 3H); 4.01-4.08 (m, 1H); 7.49 (d, 2H); 7.88 (d, 2H); 8.13 (s, 1H); 8.37 (s, 1H); 8.69 (s, 1H); 9.97 (bt, 1H).

Example 25

(−)-6-(4-Chlorophenyl)-11-(2-hydroxy-3-methoxy-propyl)-2-(1-methyl-1H-pyrazol-4-yl)-3-oxo-2,3-dihydropyridazine-4-carboxamide

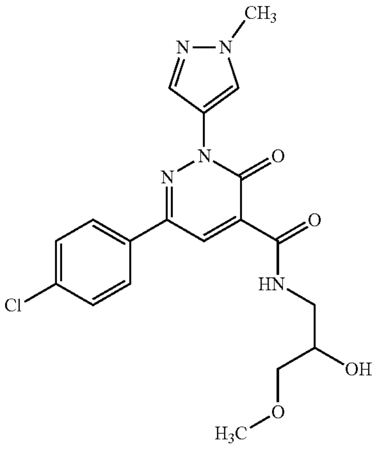 [SMILES: COCC(O)CNC(=O)c1cc(-c2ccc(Cl)cc2)nn(-c2cnn(C)c2)c1=O]

HPLC-separation of 38 mg 6-(4-chlorophenyl)-N-(2-hydroxy-3-methoxypropyl)-2-(1-methyl-1H-pyrazol-4-yl)-3-oxo-2,3-dihydropyridazine-4-carboxamide (example 24) on a chiral column (Chiralpak AD-H 5 μm 250×30 mm, eluent: acetonitrile (0.1 vol % diethylamine)/ethanol 90:10, flow 50 mL/min) yielded 18 mg (−)-6-(4-chlorophenyl)-N-(2-hydroxy-3-methoxypropyl)-2-(1-methyl-1H-pyrazol-4-yl)-3-oxo-2,3-dihydropyridazine-4-carboxamide.

$^{1}$H-NMR (400 MHz, $CDCl_3$): δ [ppm]=3.06 (d, 1H); 3.40-3.46 (m+s, 4H); 3.47-3.60 (m, 2H); 3.74 (ddd, 1H); 3.98 (s, 3H); 4.01-4.08 (m, 1H); 7.49 (d, 2H); 7.88 (d, 2H); 8.13 (s, 1H); 8.37 (s, 1H); 8.69 (s, 1H); 9.97 (bt, 1H).

Chiral HPLC: Rt=3.83 min

Instrument: Agilent HPLC 1260; column: Chiralpak AD-H 3 μm 100×4.6 mm; eluent: acetonitrile (0.1 vol % diethylamine)/ethanol 90:10, flow 1.4 mL/min, DAD scan: 254 nm Optical rotation: $[\alpha]_D^{20}$=−5.2°+/−0.44° (c=1.00, methanol).

Example 26

(+)-6-(4-Chlorophenyl)-N-(2-hydroxy-3-methoxy-propyl)-2-(1-methyl-1H-pyrazol-4-yl)-3-oxo-2,3-dihydropyridazine-4-carboxamide

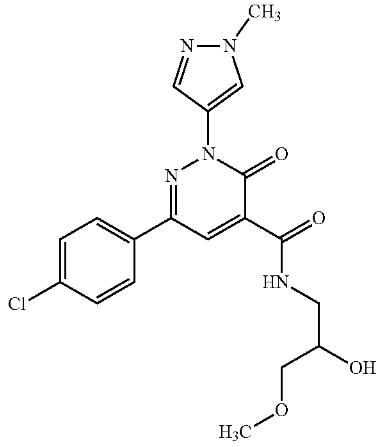 [SMILES: COCC(O)CNC(=O)c1cc(-c2ccc(Cl)cc2)nn(-c2cnn(C)c2)c1=O]

The separation of 38 mg example 24, according to example 25, additionally yielded 15 mg (+)-6-(4-chlorophenyl)-N-(2-hydroxy-3-methoxypropyl)-2-(1-methyl-1H-pyrazol-4-yl)-3-oxo-2,3-dihydropyridazine-4-carboxamide.

$^{1}$H-NMR (400 MHz, $CDCl_3$): δ [ppm]=3.06 (d, 1H); 3.40-3.46 (m+s, 4H); 3.47-3.60 (m, 2H); 3.74 (ddd, 1H); 3.98 (s, 3H); 4.01-4.08 (m, 1H); 7.49 (d, 2H); 7.88 (d, 2H); 8.13 (s, 1H); 8.37 (s, 1H); 8.69 (s, 1H); 9.97 (bt, 1H).

Chiral HPLC: Rt=4.88 min

Instrument: Agilent HPLC 1260; column: Chiralpak AD-H 3 μm 100×4.6 mm; eluent: acetonitrile (0.1 vol % diethylamine)/ethanol 90:10, flow 1.4 mL/min, DAD scan: 254 nm Optical rotation: $[\alpha]_D^{20}$=6.2°+/−0.31° (c=1.00, methanol).

Example 27

6-(4-Chlorophenyl)-N-[(2S)-2,3-dihydroxypropyl]-2-(1-methyl-1H-pyrazol-4-yl)-3-oxo-2,3-dihydro-pyridazine-4-carboxamide

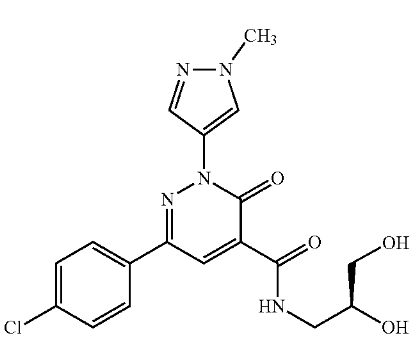 [SMILES: Cn1cc(-n2nc(-c3ccc(Cl)cc3)cc(C(=O)NC[C@H](O)CO)c2=O)cn1]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). (2S)-3-

Aminopropane-1,2-diol (27.5 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 21.5 mg (35%) of the title compound.

$^1$H-NMR (400 MHz, DMSO-$d_6$): δ [ppm]=3.20-3.30 (m, 1H), 3.30-3.36 (m, 1H and water signal), 3.38-3.44 (m, 1H), 3.58-3.67 (m, 2H), 3.93 (s, 3H), 4.70 (t, 1H), 5.03 (d, 1H), 7.58-7.62 (m, 2H), 8.08-8.13 (m, 3H), 8.55 (s, 1H), 8.59 (s, 1H), 9.63 (t, 1H).

$[\alpha]_D^{20}$=−5.5° (c=1.00, DMSO).

Example 28

6-(4-Chlorophenyl)-N-[(2R)-2,3-dihydroxypropyl]-2-(1-methyl-1H-pyrazol-4-yl)-3-oxo-2,3-dihydro-pyridazine-4-carboxamide

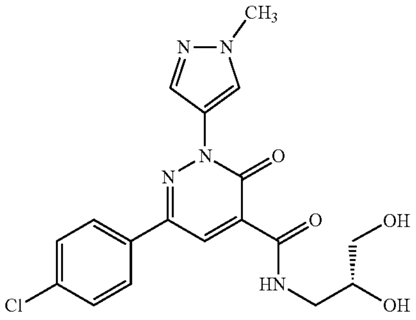 [SMILES: Cn1cc(-n2nc(-c3ccc(Cl)cc3)cc(C(=O)NC[C@@H](O)CO)c2=O)cn1]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). (2R)-3-Aminopropane-1,2-diol (27.5 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 17.5 mg (29%) of the title compound.

$^1$H-NMR (400 MHz, DMSO-$d_6$): δ [ppm]=3.21-3.30 (m, 1H), 3.30-3.36 (m, 1H and water signal), 3.38-3.44 (m, 1H), 3.58-3.67 (m, 2H), 3.93 (s, 3H), 4.70 (t, 1H), 5.03 (d, 1H), 7.58-7.62 (m, 2H), 8.08-8.13 (m, 3H), 8.55 (s, 1H), 8.59 (s, 1H), 9.63 (t, 1H).

$[\alpha]_D^{20}$=+14.3° (c=1.00, DMSO).

Example 29

6-(4-Chlorophenyl)-N-[(2S)-1-hydroxy-3-methoxy-propan-2-yl]-2-(1-methyl-1H-pyrazol-4-yl)-3-oxo-2,3-dihydropyridazine-4-carboxamide

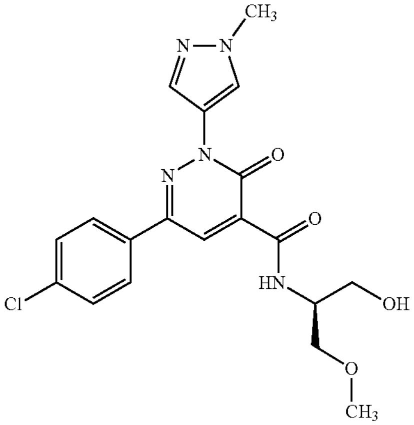 [SMILES: COC[C@H](CO)NC(=O)c1cc(-c2ccc(Cl)cc2)nn(-c2cnn(C)c2)c1=O]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). (2S)-2-Amino-3-methoxypropan-1-ol (31.8 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 33 mg (52%) of the title compound.

$^1$H-NMR (400 MHz, DMSO-$d_6$): δ [ppm]=3.30 (s, 3H), 3.44-3.61 (m, 4H), 3.93 (s, 3H), 4.10-4.19 (m, 1H), 4.99 (t, 1H), 7.58-7.62 (m, 2H), 8.08-8.12 (m, 3H), 8.56 (s, 1H), 8.60 (s, 1H), 9.64 (d, 1H).

Example 30

6-(4-Chlorophenyl)-N-[(2R)-1-hydroxy-3-methoxy-propan-2-yl]-2-(1-methyl-1H-pyrazol-4-yl)-3-oxo-2,3-dihydropyridazine-4-carboxamide

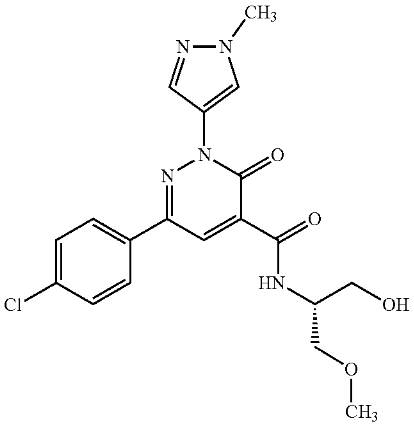 [SMILES: COC[C@@H](CO)NC(=O)c1cc(-c2ccc(Cl)cc2)nn(-c2cnn(C)c2)c1=O]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). (2R)-2-Amino-3-methoxypropan-1-ol (31.8 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 26 mg (41%) of the title compound.

$^1$H-NMR (400 MHz, DMSO-$d_6$): δ [ppm]=3.30 (s, 3H), 3.44-3.61 (m, 4H), 3.93 (s, 3H), 4.10-4.19 (m, 1H), 4.99 (t, 1H), 7.58-7.62 (m, 2H), 8.08-8.12 (m, 3H), 8.56 (s, 1H), 8.60 (s, 1H), 9.64 (d, 1H).

Example 31

6-(4-Chlorophenyl)-N-(1,3-dihydroxypropan-2-yl)-2-(1-methyl-1H-pyrazol-4-yl)-3-oxo-2,3-dihydropyridazine-4-carboxamide

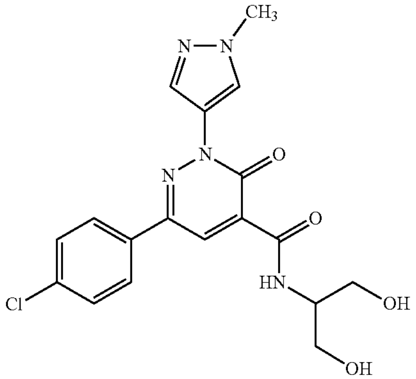 [SMILES: Cn1cc(-n2nc(-c3ccc(Cl)cc3)cc(C(=O)NC(CO)CO)c2=O)cn1]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). 2-Aminopropane-1,3-diol (27.5 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 29 mg (48%) of the title compound.

$^1$H-NMR (400 MHz, DMSO-$d_6$): δ [ppm]=3.47-3.54 (m, 2H), 3.57-3.63 (m, 2H), 3.93 (s, 3H), 3.94-4.02 (m, 1H), 4.89 (t, 2H), 7.58-7.62 (m, 2H), 8.07-8.13 (m, 3H), 8.57 (s, 1H), 8.60 (s, 1H), 9.63 (d, 1H).

Example 32

6-(4-Chlorophenyl)-N-(2-hydroxy-2-methylpropyl)-2-(1-methyl-1H-pyrazol-4-yl)-3-oxo-2,3-dihydropyridazine-4-carboxamide

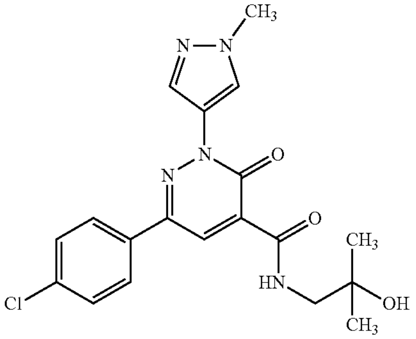 [SMILES: Cn1cc(-n2nc(-c3ccc(Cl)cc3)cc(C(=O)NCC(C)(C)O)c2=O)cn1]

6-(4-Chlorophenyl)-2-(1-methyl-1H-pyrazol-4-yl)-3-oxo-2,3-dihydropyridazine-4-carboxylic acid (50 mg, 0.15 mmol) was dissolved in anhydrous DMF (1.1 mL). 1-Amino-2-methylpropan-2-ol (27 mg, 0.30 mmol), N-ethyl-N-isopropylpropan-2-amine (0.118 mL, 0.68 mmol), and propane phosphonic acid anhydride (T3P, 132 μL, 50% in DMF, 227 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 20 mg (33%) of the title compound.

$^1$H-NMR (400 MHz, DMSO-$d_6$): δ [ppm]=1.15 (s, 6H), 3.32-3.35 (m, 2H and water signal), 3.93 (s, 3H), 4.70 (s, 1H), 7.58-7.62 (m, 2H), 8.07-8.13 (m, 3H), 8.56 (s, 1H), 8.59 (s, 1H), 9.65 (t, 1H).

Example 33

6-(4-Chlorophenyl)-2-(1-methyl-1H-pyrazol-4-yl)-3-oxo-N-[(2RS)-1,1,1-trifluoro-3-hydroxypropan-2-yl]-2,3-dihydropyridazine-4-carboxamide

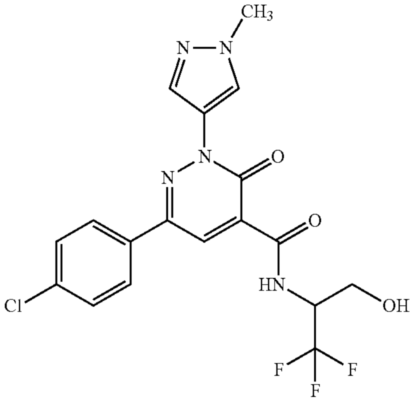 [SMILES: Cn1cc(-n2nc(-c3ccc(Cl)cc3)cc(C(=O)NC(CO)C(F)(F)F)c2=O)cn1]

6-(4-Chlorophenyl)-2-(1-methyl-1H-pyrazol-4-yl)-3-oxo-2,3-dihydropyridazine-4-carboxylic acid (100 mg, 0.30 mmol) was dissolved in anhydrous DMF (2.3 mL). (2RS)-

2-Amino-3,3,3-trifluoropropan-1-ol hydrochloride (1:1) (100 mg, 0.61 mmol), N-ethyl-N-isopropylpropan-2-amine (342 μL, 1.97 mmol), and propane phosphonic acid anhydride (T3P, 265 μL, 50% in DMF, 454 μmol) were successively added. It was stirred for 48 h at rt. The crude reaction mixture was purified by RP-HPLC (column: X-Bridge C18 5 μm 100×30 mm, mobile phase: (water+0.2 vol % aqueous ammonia (32%))/acetonitrile, gradient) to yield 35 mg (26%) of the title compound.

$^1$H-NMR (400 MHz, DMSO-$d_6$): δ [ppm]=3.68-3.76 (m, 1H), 3.81-3.88 (m, 1H), 3.93 (s, 3H), 4.81-4.93 (m, 1H), 5.45-5.49 (m, 1H), 7.58-7.63 (m, 2H), 8.10-8.14 (m, 3H), 8.59 (s, 1H), 8.65 (s, 1H), 10.12 (d, 1H).

Example 34

(−)-6-(4-Chlorophenyl)-2-(1-methyl-1H-pyrazol-4-yl)-3-oxo-N-[(2S)-1,1,1-trifluoro-3-hydroxypropan-2-yl]-2,3-dihydropyridazine-4-carboxamide

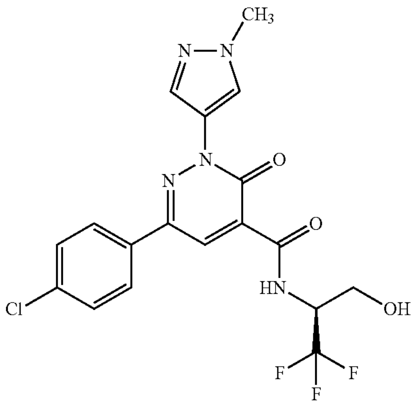 [SMILES: Cn1cc(-n2nc(-c3ccc(Cl)cc3)cc(C(=O)N[C@@H](CO)C(F)(F)F)c2=O)cn1]

6-(4-Chlorophenyl)-2-(1-methyl-1H-pyrazol-4-yl)-3-oxo-N-[(2RS)-1,1,1-trifluoro-3-hydroxypropan-2-yl]-2,3-dihydropyridazine-4-carboxamide (27.7 mg) was separated by chiral HPLC (column: Chiralpak IB 5μ 250×30 mm, mobile phase: isocratic (82:18) of carbon dioxide/2-propanol, 100 mL/min, temperature 40° C., BPR: 150 bar, UV: 254 nm) to yield 14 mg (51%) of the title compound.

$^1$H-NMR (400 MHz, DMSO-$d_6$): δ [ppm]=3.68-3.76 (m, 1H), 3.81-3.88 (m, 1H), 3.93 (s, 3H), 4.81-4.93 (m, 1H), 5.47 (br s, 1H), 7.57-7.63 (m, 2H), 8.09-8.15 (m, 3H), 8.59 (s, 1H), 8.65 (s, 1H), 10.12 (d, 1H).

Chiral HPLC: Rt=2.54 min

Instrument: Agilent HPLC 1260: Chiralpak IB 5μ 100×4.6 mm; eluent: carbon dioxide/2-propanol, isocratic: 82:18, flow: 4 mL/min, temperature: 37.5° C., BPR: 100 bar, UV: 254 nm.

$[\alpha]_D^{20}$=−34.5° (c=1.00, methanol).

Example 35

(+)-6-(4-Chlorophenyl)-2-(1-methyl-1H-pyrazol-4-yl)-3-oxo-N-[(2R)-1,1,1-trifluoro-3-hydroxypropan-2-yl]-2,3-dihydropyridazine-4-carboxamide

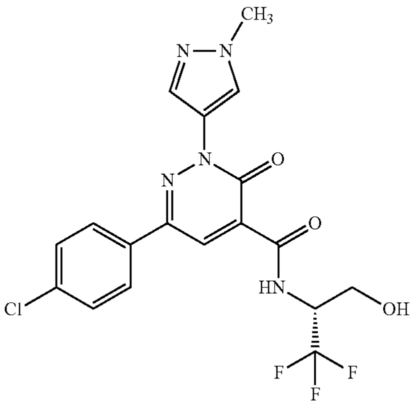 [SMILES: Cn1cc(-n2nc(-c3ccc(Cl)cc3)cc(C(=O)N[C@H](CO)C(F)(F)F)c2=O)cn1]

6-(4-Chlorophenyl)-2-(1-methyl-1H-pyrazol-4-yl)-3-oxo-N-[(2RS)-1,1,1-trifluoro-3-hydroxypropan-2-yl]-2,3-dihydropyridazine-4-carboxamide (27.7 mg) was separated by chiral HPLC (column: Chiralpak IB 5μ 250×30 mm, mobile phase: isocratic (82:18) of carbon dioxide/2-propanol, 100 mL/min, temperature 40° C., BPR: 150 bar, UV: 254 nm) to yield 14 mg (51%) of the title compound.

$^1$H-NMR (400 MHz, DMSO-$d_6$): δ [ppm]=3.68-3.76 (m, 1H), 3.84 (dt, 1H), 3.93 (s, 3H), 4.81-4.94 (m, 1H), 5.47 (t, 1H), 7.58-7.63 (m, 2H), 8.10-8.15 (m, 3H), 8.60 (s, 1H), 8.65 (s, 1H), 10.12 (d, 1H).

Chiral HPLC: Rt=3.61 min

Instrument: Agilent HPLC 1260: Chiralpak IB 5μ 100×4.6 mm; eluent: carbon dioxide/2-propanol, isocratic: 82:18, flow: 4 mL/min, temperature: 37.5° C., BPR: 100 bar, UV: 254 nm.

$[\alpha]_D^{20}$=+40.10 (c=1.00, methanol).

Example 36

2-(1-Methyl-1H-pyrazol-4-yl)-3-oxo-N-[(2R)-1,1,1-trifluoro-3-hydroxypropan-2-yl]-6-[4-(trifluoromethyl)phenyl]-2,3-dihydropyridazine-4-carboxamide

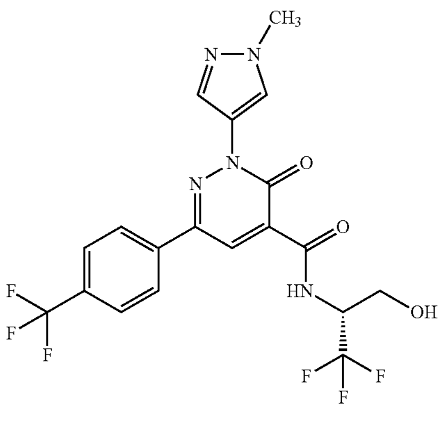 [SMILES: Cn1cc(-n2nc(-c3ccc(C(F)(F)F)cc3)cc(C(=O)N[C@H](CO)C(F)(F)F)c2=O)cn1]

2-(1-Methyl-1H-pyrazol-4-yl)-3-oxo-6-[4-(trifluoromethyl)phenyl]-2,3-dihydropyridazine-4-carboxylic acid (50 mg, 0.137 mmol) was dissolved in anhydrous DMF (1.5 mL). (2R)-2-Amino-3,3,3-trifluoropropan-1-ol hydrochloride (1:1) (35.5 mg, 0.215 mmol), N-ethyl-N-isopropylpropan-2-amine (0.108 mL, 0.62 mmol), and propane phosphonic acid anhydride (T3P, 121 μL, 50% in DMF, 207 μmol) were successively added. It was stirred at rt overnight.

The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient, twice) to yield 10.9 mg (17%) of the title compound.

$^1$H-NMR (400 MHz, DMSO-$d_6$): δ [ppm]=3.69-3.77 (m, 1H), 3.82-3.88 (m, 1H), 3.94 (s, 3H), 4.88 (dt, 1H), 5.48 (s, 1H), 7.90 (d, 2H), 8.15 (s, 1H), 8.32 (d, 2H), 8.61 (s, 1H), 8.71 (s, 1H), 10.10 (d, 1H).

Example 37

2-(1-Methyl-1H-pyrazol-4-yl)-3-oxo-N-[(2S)-3,3,3-trifluoro-2-hydroxypropyl]-6-[4-(trifluoromethyl)phenyl]-2,3-dihydropyridazine-4-carboxamide

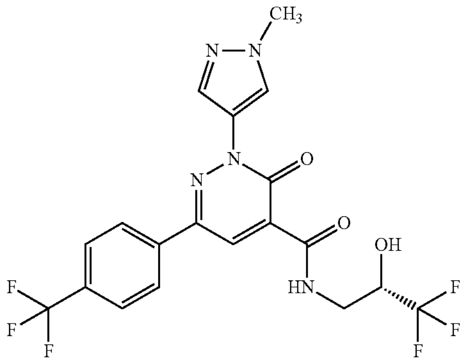 [SMILES: Cn1cc(-n2nc(-c3ccc(C(F)(F)F)cc3)cc(C(=O)NC[C@H](O)C(F)(F)F)c2=O)cn1]

2-(1-Methyl-1H-pyrazol-4-yl)-3-oxo-6-[4-(trifluoromethyl)phenyl]-2,3-dihydropyridazine-4-carboxylic acid (50 mg, 0.137 mmol) was dissolved in anhydrous DMF (1.5 mL). (2S)-3-Amino-1,1,1-trifluoropropan-2-ol (35.5 mg, 0.262 mmol), N-ethyl-N-isopropylpropan-2-amine (0.108 mL, 0.62 mmol), and propane phosphonic acid anhydride (T3P, 121 μL, 50% in DMF, 207 μmol) were successively added. It was stirred at rt overnight. The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient, twice) to yield 12.7 mg (19%) of the title compound.

$^1$H-NMR (400 MHz, DMSO-$d_6$): δ [ppm]=3.46-3.54 (m, 1H), 3.74-3.82 (m, 1H), 3.94 (s, 3H), 4.19-4.30 (m, 1H), 6.71 (s, 1H), 7.90 (d, 2H), 8.14 (s, 1H), 8.30 (d, 2H), 8.56 (s, 1H), 8.67 (s, 1H), 9.72 (t, 1H).

$[\alpha]_D^{20}$=4.1° (c=1.00, methanol).

Example 38

(−)-N-[(2R)-1-Hydroxypropan-2-yl]-2-(1-methyl-1H-pyrazol-4-yl)-3-oxo-6-[4-(trifluoromethyl)phenyl]-2,3-dihydropyridazine-4-carboxamide

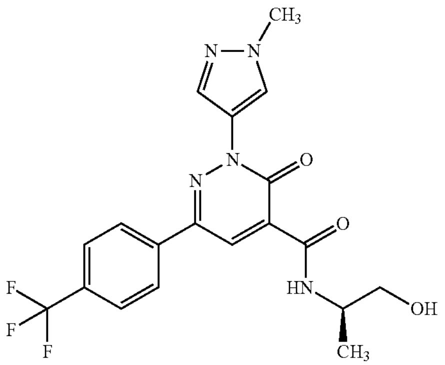 [SMILES: C[C@H](CO)NC(=O)c1cc(-c2ccc(C(F)(F)F)cc2)nn(-c2cnn(C)c2)c1=O]

2-(1-Methyl-1H-pyrazol-4-yl)-3-oxo-6-[4-(trifluoromethyl)phenyl]-2,3-dihydropyridazine-4-carboxylic acid (50 mg, 0.137 mmol) was dissolved in anhydrous DMF (1.5 mL). (2R)-2-Aminopropan-1-ol (21 mg, 0.28 mmol), N-ethyl-N-isopropylpropan-2-amine (0.108 mL, 0.62 mmol), and propane phosphonic acid anhydride (T3P, 121 μL, 50% in DMF, 207 μmol) were successively added. It was stirred at rt overnight. The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient, twice) to yield 12.5 mg (21%) of the title compound.

$^1$H-NMR (400 MHz, DMSO-$d_6$): δ [ppm]=1.19 (d, 3H), 3.43-3.52 (m, 2H), 3.93 (s, 3H), 4.01-4.11 (m, 1H), 4.97 (t, 1H), 7.90 (d, 2H), 8.13 (s, 1H), 8.30 (d, 2H), 8.58 (s, 1H), 8.65 (s, 1H), 9.52 (d, 1H).

$[\alpha]_D^{20}$=−14.0° (c=1.00, methanol).

Example 39

(+)-N-[(2S)-1-Hydroxypropan-2-yl]-2-(1-methyl-1H-pyrazol-4-yl)-3-oxo-6-[4-(trifluoromethyl)phenyl]-2,3-dihydropyridazine-4-carboxamide

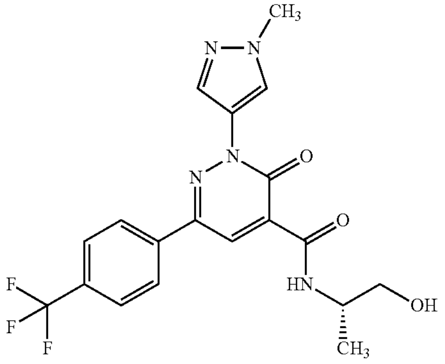 [SMILES: C[C@@H](CO)NC(=O)c1cc(-c2ccc(C(F)(F)F)cc2)nn(-c2cnn(C)c2)c1=O]

2-(1-Methyl-1H-pyrazol-4-yl)-3-oxo-6-[4-(trifluoromethyl)phenyl]-2,3-dihydropyridazine-4-carboxylic acid (45 mg, 0.124 mmol) was dissolved in anhydrous DMF (1.5 mL). (2S)-2-Aminopropan-1-ol (18.6 mg, 0.25 mmol), N-ethyl-N-isopropylpropan-2-amine (0.097 mL, 0.56 mmol), and propane phosphonic acid anhydride (T3P, 108 μL, 50% in DMF, 185 μmol) were successively added. It was stirred at rt overnight. The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient, twice) to yield 10 mg (19%) of the title compound.

$^1$H-NMR (400 MHz, DMSO-$d_6$): δ [ppm]=1.19 (d, 3H), 3.43-3.53 (m, 2H), 4.01-4.11 (m, 1H), 4.97 (t, 1H), 7.90 (d, 2H), 8.13 (s, 1H), 8.30 (d, 2H), 8.59 (s, 1H), 8.65 (s, 1H), 9.52 (d, 1H).

$[\alpha]_D^{20}$=+30.0° (c=1.00, methanol).

Example 40

6-(4-Chlorophenyl)-2-(1-cyclobutyl-1H-pyrazol-4-yl)-3-oxo-N-[(2S)-3,3,3-trifluoro-2-hydroxypropyl]-2,3-dihydropyridazine-4-carboxamide

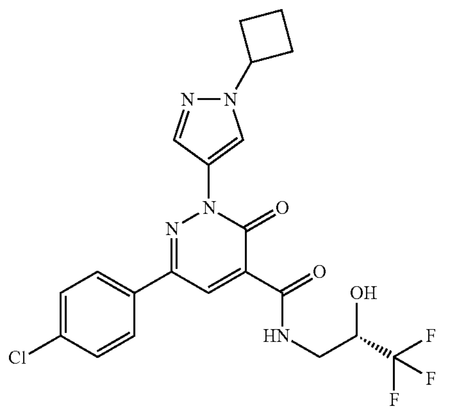 [SMILES: O=C(NC[C@H](O)C(F)(F)F)c1cc(-c2ccc(Cl)cc2)nn(-c2cnn(C3CCC3)c2)c1=O]

6-(4-Chlorophenyl)-2-(1-cyclobutyl-1H-pyrazol-4-yl)-3-oxo-2,3-dihydropyridazine-4-carboxylic acid (50 mg, 0.135 mmol) was dissolved in anhydrous DMF (1.5 mL). (25)-3-Amino-1,1,1-trifluoropropan-2-ol (35 mg, 0.27 mmol), N-ethyl-N-isopropylpropan-2-amine (0.106 mL, 0.61 mmol), and propane phosphonic acid anhydride (T3P, 118 μL, 50% in DMF, 202 μmol) were successively added. It was stirred for 1 h at rt. The crude reaction mixture was purified by RP-HPLC (column: X-Bridge C18 5 μm 100×30 mm, mobile phase: (water+0.2 vol % aqueous ammonia (32%))/acetonitrile, gradient, twice) to yield 23 mg (35%) of the title compound.

$^1$H-NMR (400 MHz, DMSO-$d_6$): δ [ppm]=1.75-1.86 (m, 2H), 2.36-2.46 (m, 2H), 2.46-2.58 (m, 2H and DMSO signal), 3.49 (ddd, 1H), 3.77 (ddd, 1H), 4.19-4.24 (m, 1H), 4.91-5.01 (m, 1H), 6.69 (s, 1H), 7.58-7.63 (m, 2H), 8.08-8.13 (m, 2H), 8.18 (s, 1H), 8.59 (s, 1H), 8.61 (s, 1H), 9.73 (t, 1H).

$[\alpha]_D^{20}$=−2.7° (c=1.00, methanol).

Example 41

6-(4-Chlorophenyl)-2-(1-cyclobutyl-1H-pyrazol-4-yl)-3-oxo-N-[(2R)-1,1,1-trifluoro-3-hydroxypropan-2-yl]-2,3-dihydropyridazine-4-carboxamide

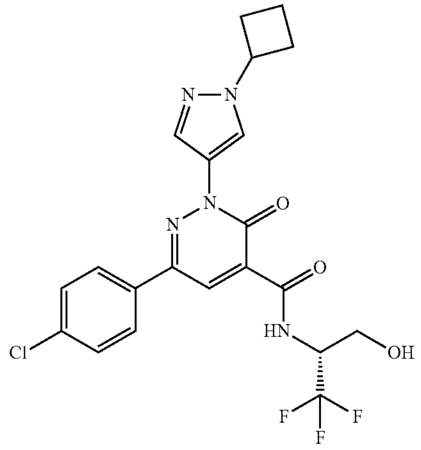 [SMILES: O=C(N[C@H](CO)C(F)(F)F)c1cc(-c2ccc(Cl)cc2)nn(-c2cnn(C3CCC3)c2)c1=O]

6-(4-Chlorophenyl)-2-(1-cyclobutyl-1H-pyrazol-4-yl)-3-oxo-2,3-dihydropyridazine-4-carboxylic acid (45 mg, 0.121 mmol) was dissolved in anhydrous DMF (1.5 mL). (2R)-2-Amino-3,3,3-trifluoropropan-1-ol hydrochloride (1:1) (40 mg, 0.24 mmol), N-ethyl-N-isopropylpropan-2-amine (0.137 mL, 0.79 mmol), and propane phosphonic acid anhydride (T3P, 106 μL, 50% in DMF, 182 μmol) were successively added. It was stirred for 1 h at rt. The crude reaction mixture was purified by RP-HPLC (column: X-Bridge C18 5 μm 100×30 mm, mobile phase: (water+0.2 vol % aqueous ammonia (32%))/acetonitrile, gradient, twice) to yield 22 mg (38%) of the title compound.

$^1$H-NMR (400 MHz, DMSO-$d_6$): δ [ppm]=1.75-1.88 (m, 2H), 2.36-2.45 (m, 2H), 2.46-2.60 (m, 2H and DMSO signal), 3.67-3.75 (m, 1H), 3.85 (dt, 1H), 4.81-5.02 (m, 2H), 5.47 (t, 1H), 7.58-7.64 (m, 2H), 8.10-8.15 (m, 2H), 8.18 (s, 1H), 8.62 (s, 1H), 8.65 (s, 1H), 10.09 (d, 1H).

$[\alpha]_D^{20}$=+36.7° (c=1.00, methanol).

Example 42

6-(4-Chlorophenyl)-2-(1-cyclobutyl-1H-pyrazol-4-yl)-N-[(2S)-1-hydroxypropan-2-yl]-3-oxo-2,3-dihydropyridazine-4-carboxamide

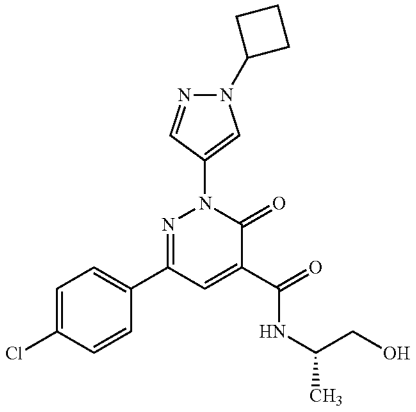 [SMILES: C[C@@H](CO)NC(=O)c1cc(-c2ccc(Cl)cc2)nn(-c2cnn(C3CCC3)c2)c1=O]

6-(4-Chlorophenyl)-2-(1-cyclobutyl-1H-pyrazol-4-yl)-3-oxo-2,3-dihydropyridazine-4-carboxylic acid (47 mg, 0.127 mmol) was dissolved in anhydrous DMF (1.5 mL). (25)-2-Aminopropan-1-ol (19 mg, 0.25 mmol), N-ethyl-N-isopropylpropan-2-amine (99.3 μL, 0.57 mmol), and propane phosphonic acid anhydride (T3P, 111 μL, 50% in DMF, 190 μmol) were successively added. It was stirred at rt overnight. The reaction mixture was concentrated under vacuum and purified by RP-HPLC (column: X-Bridge C18 5 μm 100×30 mm, mobile phase: (water+0.1 vol % formic acid (99%))/acetonitrile, gradient, DAD: 210-400 nm) to yield 15.5 mg (29%) of the title compound.

$^1$H-NMR (400 MHz, DMSO-$d_6$): δ [ppm]=1.18 (d, 3H), 1.75-1.89 (m, 2H), 2.36-2.45 (m, 2H), 2.46-2.59 (m, 2H and DMSO signal), 3.42-3.52 (m, 2H), 4.00-4.11 (m, 1H), 4.90-5.00 (m, 2H), 7.58-7.63 (m, 2H), 8.08-8.12 (m, 2H), 8.16 (s, 1H), 8.59 (s, 1H), 8.61 (s, 1H), 9.52 (d, 1H).

$[\alpha]_D^{20}$=+20.5° (c=1.00, methanol).

Example 43

6-(4-Chlorophenyl)-N-[(cis)-4-hydroxytetrahydrofuran-3-yl]-2-(1-methyl-1H-pyrazol-4-yl)-3-oxo-2,3-dihydropyridazine-4-carboxamide

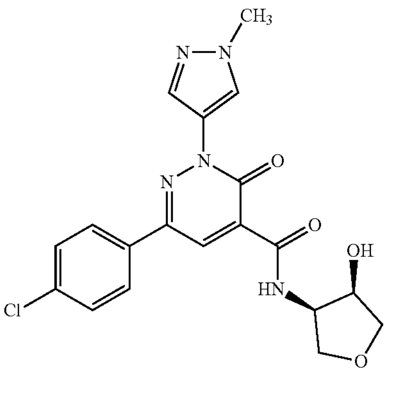 [SMILES: Cn1cc(-n2nc(-c3ccc(Cl)cc3)cc(C(=O)N[C@@H]3COC[C@@H]3O)c2=O)cn1]

A solution of 150 mg intermediate 6-(4-chlorophenyl)-2-(1-methyl-1H-pyrazol-4-yl)-3-oxo-2,3-dihydropyridazine-4-carboxylic acid, 126.6 mg cis-4-aminotetrahydro-3-furanol hydrochloride (1:1), 344.9 mg HATU, 0.32 mL ethyldiisopropylamine and 4 mg 4-dimethylaminopyridine in 3.1 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 127 mg of the title compound.

$^1$H NMR (400 MHz, DMSO-$d_6$) δ [ppm]=3.47 (t, 1H), 3.64 (dd, 1H), 3.93 (s, 3H), 3.94-3.98 (m, 1H), 4.01 (dd, 1H), 4.26-4.33 (m, 1H), 4.34-4.44 (m, 1H), 5.70 (d, 1H), 7.57-7.63 (m, 2H), 8.06-8.11 (m, 2H), 8.11 (s, 1H), 8.55 (s, 1H), 8.61 (s, 1H), 9.90 (d, 1H).

Example 44

6-(4-Chlorophenyl)-N-[(cis)-4-hydroxytetrahydrofuran-3-yl]-2-(1-methyl-1H-pyrazol-4-yl)-3-oxo-2,3-dihydropyridazine-4-carboxamide, Enantiomer 1

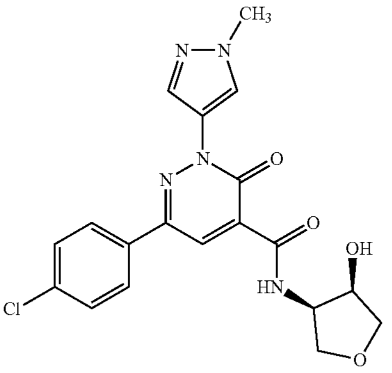 [SMILES: Cn1cc(-n2nc(-c3ccc(Cl)cc3)cc(C(=O)N[C@@H]3COC[C@@H]3O)c2=O)cn1]

HPLC-separation of 127 mg 6-(4-chlorophenyl)-N-(4-hydroxytetrahydrofuran-3-yl)-2-(1-methyl-1H-pyrazol-4-yl)-3-oxo-2,3-dihydropyridazine-4-carboxamide (example 43) on a chiral column (instrument: Labomatic HD5000, Labocord-5000; Gilson GX-241, Labcol Vario 4000, column: Chiralpak IE 5μ 250×30 mm; eluent A: tert.-butyl methyl ether; eluent B: methanol; isocratic: 50% A+50% B; flow 50.0 mL/min; UV 280 nm) yielded 48 mg of the title compound.

Chiral HPLC: Rt=2.46 min (instrument: Agilent HPLC 1260; column: Chiralpak IE 3μ100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm)

Example 45

6-(4-Chlorophenyl)-N-[(cis)-4-hydroxytetrahydrofuran-3-yl]-2-(1-methyl-1H-pyrazol-4-yl)-3-oxo-2,3-dihydropyridazine-4-carboxamide, Enantiomer 2

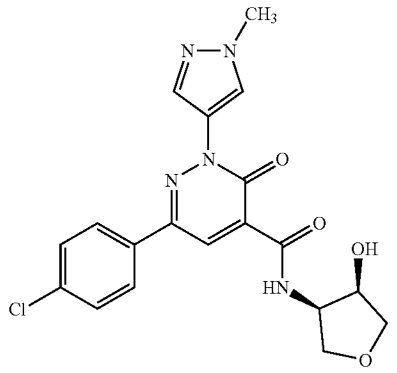 [SMILES: Cn1cc(-n2nc(-c3ccc(Cl)cc3)cc(C(=O)N[C@@H]3COC[C@@H]3O)c2=O)cn1]

The separation of 127 mg 6-(4-chlorophenyl)-N-(4-hydroxytetrahydrofuran-3-yl)-2-(1-methyl-1H-pyrazol-4-yl)-3-oxo-2,3-dihydropyridazine-4-carboxamide (example 43), according to example 44, additionally yielded 46 mg of the title compound.

Chiral HPLC: Rt=2.02 min (instrument: Agilent HPLC 1260; column: Chiralpak IE 3μ100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm).

Example 46

N-[(1S,2R)-2-Hydroxycyclohexyl]-2-(1-methyl-1H-pyrazol-4-yl)-3-oxo-6-[4-(trifluoromethoxy)phenyl]-2,3-dihydropyridazine-4-carboxamide

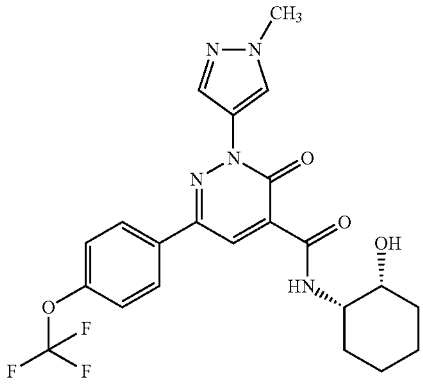 [SMILES: Cn1cc(-n2nc(-c3ccc(OC(F)(F)F)cc3)cc(C(=O)N[C@H]3CCCC[C@H]3O)c2=O)cn1]

A solution of 75 mg intermediate 2-(1-methyl-1H-pyrazol-4-yl)-3-oxo-6-[4-(trifluoromethoxy)phenyl]-2,3-dihydropyridazine-4-carboxylic acid, 63 mg (1R,2S)-2-aminocyclohexanol hydrochloride (1:1), 150 mg HATU, 0.14 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: waters Autopurification MS SingleQuad; Column: Waters Xbridge C18 5μ100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 42 mg N-[(1S,2R)-2-hydroxycyclohexyl]-2-(1-methyl-1H-pyrazol-4-yl)-3-oxo-6-[4-(trifluoromethoxy)phenyl]-2,3-dihydropyridazine-4-carboxamide.

$^1$H NMR (400 MHz, DMSO-$d_6$) δ [ppm]=1.27-1.40 (m, 2H), 1.49-1.76 (m, 6H), 3.76-3.84 (m, 1H), 3.93 (m, 4H), 4.90 (d, 1H), 7.47-7.58 (m, 2H), 8.12 (d, 1H), 8.17-8.22 (m, 2H), 8.56 (s, 1H), 8.61 (s, 1H), 9.72 (d, 1H).

Example 47

2-(1-Methyl-1H-pyrazol-4-yl)-3-oxo-N-[(2R)-1,1,1-trifluoro-3-hydroxypropan-2-yl]-6-[4-(trifluoromethoxy)phenyl]-2,3-dihydropyridazine-4-carboxamide

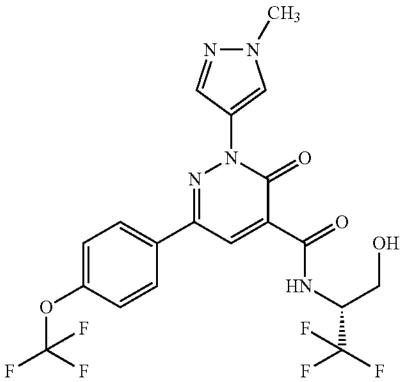 [SMILES: Cn1cc(-n2nc(-c3ccc(OC(F)(F)F)cc3)cc(C(=O)N[C@H](CO)C(F)(F)F)c2=O)cn1]

A solution of 75 mg intermediate 2-(1-methyl-1H-pyrazol-4-yl)-3-oxo-6-[4-(trifluoromethoxy)phenyl]-2,3-dihydropyridazine-4-carboxylic acid, 65.3 mg (2R)-2-amino-3,3,3-trifluoropropan-1-ol hydrochloride (1:1), 150 mg HATU, 0.14 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters Xbridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 56 mg 2-(1-methyl-1H-pyrazol-4-yl)-3-oxo-N-[(2R)-1,1,1-trifluoro-3-hydroxypropan-2-yl]-6-[4-(trifluoromethoxy)phenyl]-2,3-dihydropyridazine-4-carboxamide.

$^1$H NMR (400 MHz, DMSO-$d_6$) δ [ppm]=3.65-3.77 (m, 1H), 3.85 (m, 1H), 3.93 (s, 3H), 4.81-4.96 (m, 1H), 5.47 (t, 1H), 7.36-7.54 (m, 2H), 8.13 (d, 1H), 8.17-8.31 (m, 2H), 8.60 (s, 1H), 8.66 (s, 1H), 10.12 (d, 1H).

Example 48

6-(4-Chlorophenyl)-N-[(1S,2R)-2-hydroxycyclohexyl]-2-(1-methyl-1H-pyrazol-4-yl)-3-oxo-2,3-dihydropyridazine-4-carboxamide

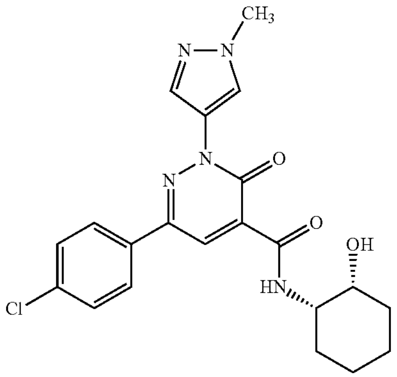 [SMILES: Cn1cc(-n2nc(-c3ccc(Cl)cc3)cc(C(=O)N[C@H]3CCCC[C@H]3O)c2=O)cn1]

A solution of 75 mg intermediate 6-(4-chlorophenyl)-2-(1-methyl-1H-pyrazol-4-yl)-3-oxo-2,3-dihydropyridazine-4-carboxylic acid, 44 mg (1R,2S)-2-aminocyclohexanol hydrochloride (1:1), 105 mg HATU, 0.14 mL ethyldiisopropylamine and 1 mg 4-dimethylaminopyridine in 1 mL of DMF was stirred at room temperature for 14 hours. Then the reaction mixture was filtered and subjected to RP-HPLC (Instrument: Waters Autopurification MS SingleQuad; Column: Waters XBridge C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 43 mg of the title compound.

$^1$H NMR (400 MHz, DMSO-$d_6$) δ[ppm]=1.28-1.41 (m, 2H), 1.49-1.76 (m, 6H), 3.80 (br s, 1H), 3.93 (s, 4H), 4.90 (br d, 1H), 7.57-7.63 (m, 2H), 8.06-8.10 (m, 2H), 8.11 (s, 1H), 8.55 (s, 1H), 8.59 (s, 1H), 9.72 (d, 1H).

Example 49

6-(4-Chlorophenyl)-N-[(1S,2S)-2-hydroxycyclopentyl]-2-(1-methyl-1H-pyrazol-4-yl)-3-oxo-2,3-dihydropyridazine-4-carboxamide

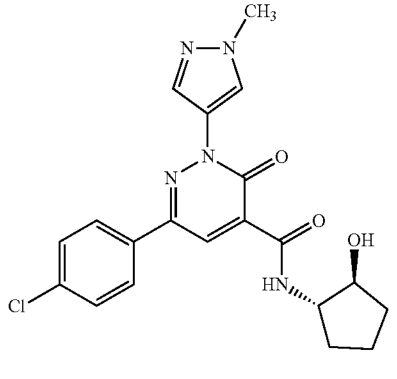 [SMILES: Cn1cc(-n2nc(-c3ccc(Cl)cc3)cc(C(=O)N[C@H]3CCC[C@@H]3O)c2=O)cn1]

A solution of 128 mg intermediate 6-(4-chlorophenyl)-2-(1-methyl-1H-pyrazol-4-yl)-3-oxo-2,3-dihydropyridazine-4-carboxylic acid (46%), 50 mg (1S,2S)-2-aminocyclopentanol hydrochloride (1:1), 135 mg HATU, 0.13 mL ethyldiisopropylamine and 1 mg 4-dimethylaminopyridine in 1 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 3 mg 6-(4-chlorophenyl)-N-[(1S,2S)-2-hydroxycyclopentyl]-2-(1-methyl-1H-pyrazol-4-yl)-3-oxo-2,3-dihydropyridazine-4-carboxamide.

$^1$H NMR (400 MHz, DMSO-$d_6$) δ[ppm]=1.38-1.58 (m, 2H), 1.60-1.79 (m, 2H), 1.80-1.89 (m, 1H), 2.03-2.18 (m, 1H), 3.93 (s, 3H), 3.94-3.99 (m, 1H), 3.99-4.07 (m, 1H), 4.97 (d, 1H), 7.55-7.65 (m, 2H), 8.07-8.14 (m, 3H), 8.52-8.60 (m, 2H), 9.44 (d, 1H).

Example 50

6-(4-Chlorophenyl)-N-[(1S,2R)-2-hydroxycyclopentyl]-2-(1-methyl-1H-pyrazol-4-yl)-3-oxo-2,3-dihydropyridazine-4-carboxamide

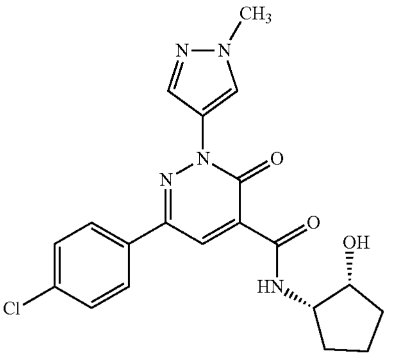 [SMILES: Cn1cc(-n2nc(-c3ccc(Cl)cc3)cc(C(=O)N[C@H]3CCC[C@H]3O)c2=O)cn1]

A solution of 75 mg intermediate 6-(4-chlorophenyl)-2-(1-methyl-1H-pyrazol-4-yl)-3-oxo-2,3-dihydropyridazine-4-carboxylic acid (61%), 38.5 mg (1R,2S)-2-aminocyclopentanol hydrochloride (1:1), 105 mg HATU, 0.1 mL ethyldiisopropylamine and 1 mg 4-dimethylaminopyridine in 1 mL of DMF was stirred at room temperature for 14 hours. Then the reaction mixture was filtered and subjected to RP-HPLC (instrument: Waters Autopurification MS SingleQuad; Column: Waters XBridge C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 16 mg 6-(4-chlorophenyl)-N-[(1S,2R)-2-hydroxycyclopentyl]-2-(1-methyl-1H-pyrazol-4-yl)-3-oxo-2,3-dihydropyridazine-4-carboxamide.

$^1$H NMR (400 MHz, DMSO-$d_6$) δ[ppm]=1.50-1.67 (m, 3H), 1.71-1.89 (m, 2H), 1.92-2.04 (m, 1H), 3.93 (s, 3H), 4.02-4.15 (m, 2H), 5.05 (br s, 1H), 7.56-7.64 (m, 2H), 8.07-8.13 (m, 3H), 8.55-8.58 (m, 1H), 8.60 (s, 1H), 9.77 (d, 1H).

Example 51

6-(4-Chlorophenyl)-N-[(trans)-2-hydroxycyclopentyl]-2-(1-methyl-1H-pyrazol-4-yl)-3-oxo-2,3-dihydropyridazine-4-carboxamide

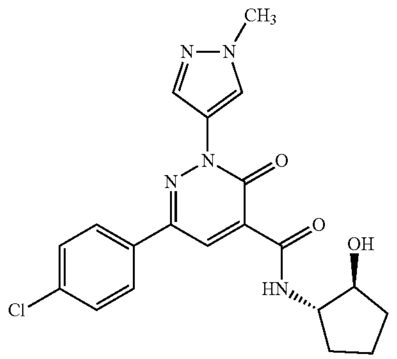 [SMILES: Cn1cc(-n2nc(-c3ccc(Cl)cc3)cc(C(=O)N[C@H]3CCC[C@@H]3O)c2=O)cn1]

A solution of 65 mg intermediate 6-(4-chlorophenyl)-2-(1-methyl-1H-pyrazol-4-yl)-3-oxo-2,3-dihydropyridazine-4-carboxylic acid, 56 mg (trans)-2-aminocyclopentanol hydrochloride (1:1), 149.5 mg HATU, 0.14 mL ethyldiisopropylamine and 1.2 mg 4-dimethylaminopyridine in 2 mL of DMF was stirred at room temperature for 14 hours. Then the reaction mixture was filtered and subjected to RP-HPLC (instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 56 mg 6-(4-chlorophenyl)-N-[(trans)-2-hydroxycyclopentyl]-2-(1-methyl-1H-pyrazol-4-yl)-3-oxo-2,3-dihydropyridazine-4-carboxamide.

$^1$H NMR (400 MHz, DMSO-$d_6$) δ [ppm]=1.41-1.57 (m, 2H), 1.61-1.78 (m, 2H), 1.80-1.91 (m, 1H), 2.04-2.16 (m, 1H), 3.93 (s, 3H), 3.94-3.99 (m, 1H), 4.00-4.08 (m, 1H), 4.97 (d, 1H), 7.56-7.64 (m, 2H), 8.08-8.13 (m, 3H), 8.53-8.58 (m, 2H), 9.44 (d, 1H).

Example 52

6-[4-(Difluoromethyl)phenyl]-N-[(trans)-2-hydroxycyclopentyl]-2-(1-methyl-1H-pyrazol-4-yl)-3-oxo-2,3-dihydropyridazine-4-carboxamide

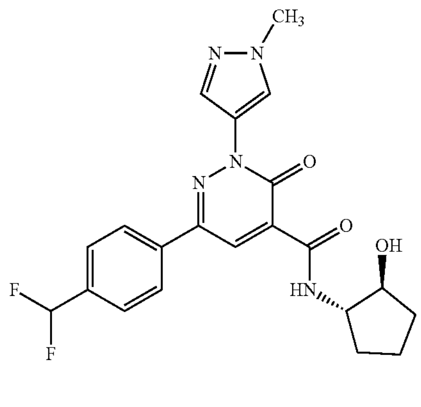 [SMILES: Cn1cc(-n2nc(-c3ccc(C(F)F)cc3)cc(C(=O)N[C@H]3CCC[C@@H]3O)c2=O)cn1]

A solution of 47 mg intermediate 6-[4-(difluoromethyl)phenyl]-2-(1-methyl-1H-pyrazol-4-yl)-3-oxo-2,3-dihydropyridazine-4-carboxylic acid, 37.4 mg (trans)-2-aminocyclopentanol hydrochloride (1:1), 103 mg HATU, 0.1 mL ethyldiisopropylamine and 1 mg 4-dimethylaminopyridine in 1 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 41 mg 6-[4-(difluoromethyl)phenyl]-N-[(trans)-2-hydroxycyclopentyl]-2-(1-methyl-1H-pyrazol-4-yl)-3-oxo-2,3-dihydropyridazine-4-carboxamide.

$^1$H NMR (400 MHz, DMSO-$d_6$) δ [ppm]=1.42-1.57 (m, 2H), 1.61-1.80 (m, 2H), 1.81-1.92 (m, 1H), 2.05-2.18 (m, 1H), 3.93 (s, 3H), 3.94-3.99 (m, 1H), 4.00-4.08 (m, 1H), 4.97 (d, 1H), 7.14 (t, 1H), 7.74 (d, 2H), 8.13 (s, 1H), 8.22 (d, 2H), 8.57 (s, 1H), 8.60 (s, 1H), 9.44 (d, 1H).

Example 53

N-[(2S)-1-Hydroxypropan-2-yl]-2-(1-methyl-1H-pyrazol-4-yl)-3-oxo-6-[4-(trifluoromethoxy)phenyl]-2,3-dihydropyridazine-4-carboxamide

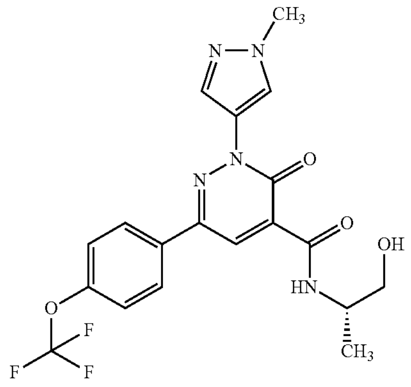 [SMILES: C[C@@H](CO)NC(=O)c1cc(-c2ccc(OC(F)(F)F)cc2)nn(-c2cnn(C)c2)c1=O]

A solution of 75 mg intermediate 2-(1-methyl-1H-pyrazol-4-yl)-3-oxo-6-[4-(trifluoromethoxy)phenyl]-2,3-dihydropyridazine-4-carboxylic acid, 65.3 mg (S)-(+)-2-amino-1-propanol, 150 mg HATU, 0.1 mL ethyldiisopropylamine and 1 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 53 mg N-[(2S)-1-hydroxypropan-2-yl]-2-(1-methyl-1H-pyrazol-4-yl)-3-oxo-6-[4-(trifluoromethoxy)phenyl]-2,3-dihydropyridazine-4-carboxamide.

$^1$H NMR (400 MHz, DMSO-$d_6$) δ [ppm]=1.19 (d, 3H), 3.42-3.51 (m, 2H), 3.93 (s, 3H), 4.00-4.13 (m, 1H), 4.96 (t, 1H), 7.53 (d, 2H), 8.12 (s, 1H), 8.16-8.24 (m, 2H), 8.57 (s, 1H), 8.60 (s, 1H), 9.53 (d, 1H).

Example 54

6-[6-(Difluoromethyl)pyridin-3-yl]-N-[(1S,2R)-2-hydroxycyclohexyl]-2-(1-methyl-1H-pyrazol-4-yl)-3-oxo-2,3-dihydropyridazine-4-carboxamide

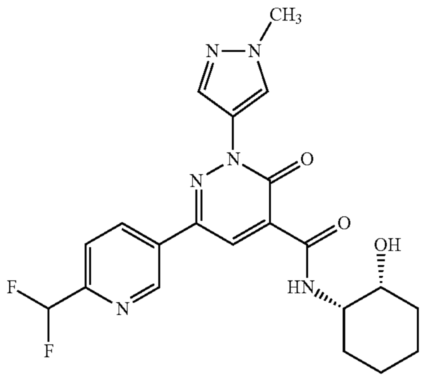 [SMILES: Cn1cc(-n2nc(-c3ccc(C(F)F)nc3)cc(C(=O)N[C@H]3CCCC[C@H]3O)c2=O)cn1]

A solution of 55 mg intermediate 6-[6-(difluoromethyl)pyridin-3-yl]-2-(1-methyl-1H-pyrazol-4-yl)-3-oxo-2,3-dihydropyridazine-4-carboxylic acid, 50.5 mg (1R,2S)-2-aminocyclohexanol hydrochloride (1:1), 120 mg HATU, 0.11 mL ethyldiisopropylamine and 1.5 mg 4-dimethylaminopyridine in 1 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 39 mg 6-[6-(difluoromethyl)pyridin-3-yl]-N-[(1S,2R)-2-hydroxycyclohexyl]-2-(1-methyl-1H-pyrazol-4-yl)-3-oxo-2,3-dihydropyridazine-4-carboxamide.

$^1$H NMR (400 MHz, DMSO-$d_6$) δ [ppm]=1.35 (br d, 2H), 1.51-1.75 (m, 6H), 3.81 (br s, 1H), 3.93 (m, 4H), 4.92 (d, 1H), 7.07 (t, 1H), 7.85 (d, 1H), 8.17 (s, 1H), 8.59 (s, 1H), 8.66 (dd, 1H), 8.70 (s, 1H), 9.36 (d, 1H), 9.70 (d, 1H).

Example 55

N-[(cis)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide

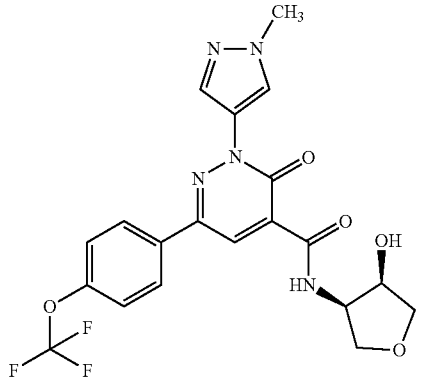 [SMILES: Cn1cc(-n2nc(-c3ccc(OC(F)(F)F)cc3)cc(C(=O)N[C@@H]3COC[C@@H]3O)c2=O)cn1]

A solution of 153 mg intermediate 2-(1-methyl-1H-pyrazol-4-yl)-3-oxo-6-[4-(trifluoromethoxy)phenyl]-2,3-dihydropyridazine-4-carboxylic acid, 112.3 mg cis-4-aminotetrahydro-3-furanol hydrochloride (1:1), 306 mg HATU, 0.28 mL ethyldiisopropylamine and 4 mg 4-dimethylaminopyridine in 3 mL of DMF was stirred at room temperature for 14 hours. Then the reaction mixture was filtered and subjected to RP-HPLC (Instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 120 mg N-[(cis)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide.

$^1$H NMR (400 MHz, DMSO-$d_6$) δ [ppm]=3.48 (t, 1H), 3.65 (dd, 1H), 3.93 (s, 3H), 3.94-3.98 (m, 1H), 4.01 (t, 1H), 4.26-4.33 (m, 1H), 4.34-4.44 (m, 1H), 5.70 (d, 1H), 7.53 (d, 2H), 8.12 (s, 1H), 8.17-8.23 (m, 2H), 8.56 (s, 1H), 8.63 (s, 1H), 9.90 (d, 1H).

Example 56

N-[(cis)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, Enantiomer 1

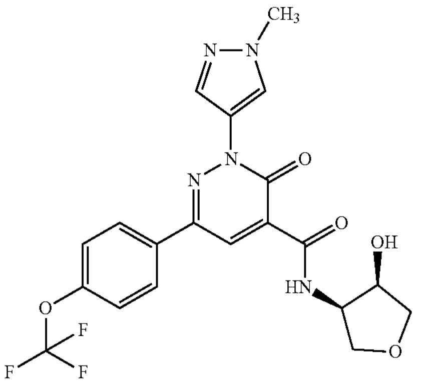 [SMILES: Cn1cc(-n2nc(-c3ccc(OC(F)(F)F)cc3)cc(C(=O)N[C@@H]3COC[C@@H]3O)c2=O)cn1]

HPLC-separation of 115 mg rac-N-[(cis)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide (example 55) on a chiral column (instrument: Labomatic HD5000, Labocord-5000; Gilson GX-241, Labcol Vario 4000, column: Chiralpak IE 5μ250×30 mm; eluent A: tert.-butyl methyl ether; eluent B: methanol; isocratic: 50% A+50% B; flow 50.0 mL/min; UV 280 nm) yielded 42 mg N-[(cis)-4-hydroxytetrahydrofuran-3-yl]-2-(1-methyl-1H-pyrazol-4-yl)-3-oxo-6-[4-(trifluoro-methoxy)phenyl]-2,3-dihydropyridazine-4-carboxamide, enantiomer 1. Chiral HPLC: Rt=1.76 min (instrument: Agilent HPLC 1260; column: Chiralpak IE 3μ100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm)

Example 57

N-[(cis)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, Enantiomer 2

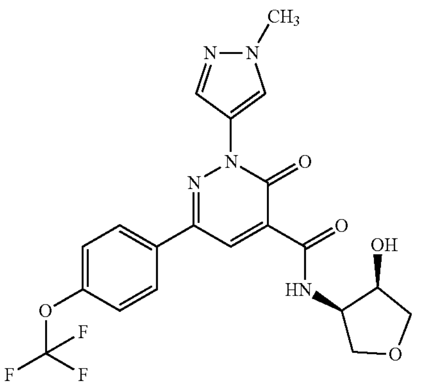 [SMILES: Cn1cc(-n2nc(-c3ccc(OC(F)(F)F)cc3)cc(C(=O)N[C@@H]3COC[C@@H]3O)c2=O)cn1]

HPLC-separation of 115 mg N-[(cis)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide (example 55) on a chiral column (instrument: Labomatic HD5000, Labocord-5000; Gilson GX-241, Labcol Vario 4000, column: Chiralpak IE 5μ 250×30 mm; eluent A: tert.-butyl methyl ether; eluent B: methanol; isocratic: 50% A+50% B; flow 50.0 mL/min; UV 280 nm) yielded 42 mg N-[(cis)-4-hydroxytetrahydrofuran-3-yl]-2-(1-methyl-1H-pyrazol-4-yl)-3-oxo-6-[4-(trifluoro-methoxy)phenyl]-2,3-dihydropyridazine-4-carboxamide, enantiomer 2. Chiral HPLC: Rt=2.19 min (instrument: Agilent HPLC 1260; column: Chiralpak IE 3μ100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm).

Example 58

6-[4-(Difluoromethyl)phenyl]-N-[(2S)-1-hydroxypropan-2-yl]-2-(1-methyl-1H-pyrazol-4-yl)-3-oxo-2,3-dihydropyridazine-4-carboxamide

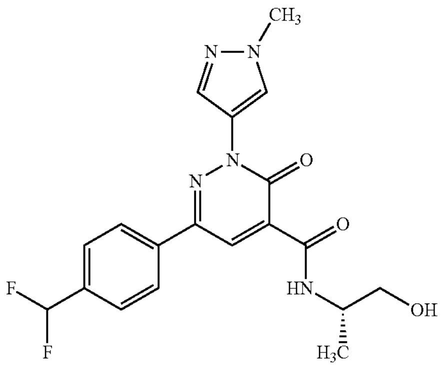 [SMILES: C[C@@H](CO)NC(=O)c1cc(-c2ccc(C(F)F)cc2)nn(-c2cnn(C)c2)c1=O]

A solution of 47 mg intermediate 6-[4-(difluoromethyl)phenyl]-2-(1-methyl-1H-pyrazol-4-yl)-3-oxo-2,3-dihydropyridazine-4-carboxylic acid, 20.4 mg (2S)-2-aminopropan-1-ol, 103 mg HATU, 0.1 mL ethyldiisopropylamine and 1 mg 4-dimethylaminopyridine in 1 mL of DMF was stirred at room temperature for 14 hours. Further 50 mg HATU, 0.05 mL ethyldiisopropylamine, 1 mg 4-dimethylaminopyridine and 10 mg (2S)-2-aminopropan-1-ol were added followed by stirring at 50° C. for 3 h. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 85%/B 15%→A 45%/B 55%; flow: 150 mL/min; UV-detection: 254 nm) to yield 41 mg 6-[4-(difluoromethyl)phenyl]-N-[(2S)-1-hydroxypropan-2-yl]-2-(1-methyl-1H-pyrazol-4-yl)-3-oxo-2,3-dihydropyridazine-4-carboxamide.

$^1$H NMR (400 MHz, DMSO-$d_6$) δ [ppm]=1.19 (d, 3H), 3.42-3.52 (m, 2H), 3.93 (s, 3H), 3.99-4.12 (m, 1H), 4.96 (t, 1H), 7.14 (t, 1H), 7.74 (d, 2H), 8.13 (s, 1H), 8.22 (d, 2H), 8.58 (s, 1H), 8.63 (s, 1H), 9.53 (d, 1H).

Example 59

N-(2-Hydroxy-2-methylpropyl)-2-(1-methyl-1H-pyrazol-4-yl)-3-oxo-6-[4-(trifluoromethoxy)phenyl]-2,3-dihydropyridazine-4-carboxamide

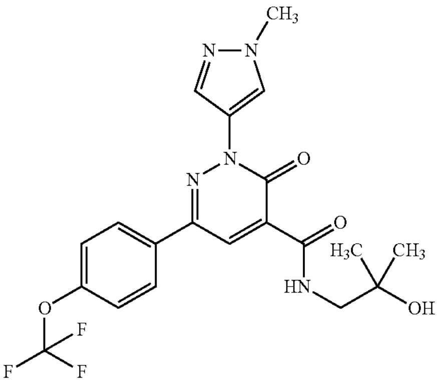 [SMILES: Cn1cc(-n2nc(-c3ccc(OC(F)(F)F)cc3)cc(C(=O)NCC(C)(C)O)c2=O)cn1]

A solution of 75 mg intermediate 2-(1-methyl-1H-pyrazol-4-yl)-3-oxo-6-[4-(trifluoromethoxy)phenyl]-2,3-dihydropyridazine-4-carboxylic acid, Si mg 1-amino-2-methylpropan-2-ol hydrochloride (1:1), 150 mg HATU, 0.14 mL ethyldiisopropylamine and 1.2 mg 4-dimethylaminopyridine in 1.5 mL of DMF was stirred at room temperature for 14 hours. Then the reaction mixture was filtered and subjected to RP-HPLC (Instrument: Waters Autopurification MS SingleQuad; Column: Waters XBridge C18 5μ100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 56 mg N-(2-hydroxy-2-methylpropyl)-2-(1-methyl-1H-pyrazol-4-yl)-3-oxo-6-[4-(trifluoromethoxy)phenyl]-2,3-dihydropyridazine-4-carboxamide.

$^1$H NMR (400 MHz, DMSO-$d_6$) δ[ppm]=1.15 (s, 6H), 3.33 (d, 2H), 3.93 (s, 3H), 4.70 (s, 1H), 7.48-7.55 (m, 2H), 8.12 (d, 1H), 8.16-8.23 (m, 2H), 8.56 (s, 1H), 8.61 (s, 1H), 9.65 (t, 1H).

Example 60

6-[4-(Difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide

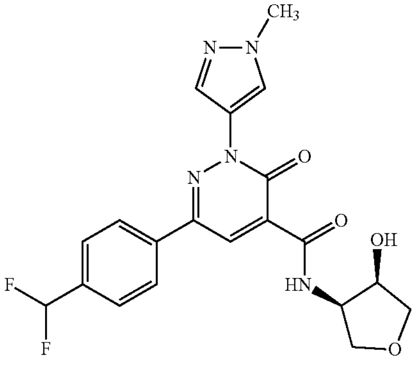 [SMILES: Cn1cc(-n2nc(-c3ccc(C(F)F)cc3)cc(C(=O)N[C@@H]3COC[C@@H]3O)c2=O)cn1]

A solution of 47 mg intermediate 6-[4-(difluoromethyl)phenyl]-2-(1-methyl-1H-pyrazol-4-yl)-3-oxo-2,3-dihydropyridazine-4-carboxylic acid, 38 mg cis-4-aminotetrahydro-3-furanol hydrochloride (1:1), 103 mg HATU, 0.1 mL ethyldiisopropylamine and 1 mg 4-dimethylaminopyridine in 1 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 38 mg 6-[4-(difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide.

$^1$H NMR (400 MHz, DMSO-$d_6$) δ[ppm]=3.48 (t, 1H), 3.65 (dd, 1H), 3.94 (s, 3H), 3.94-3.98 (m, 1H), 4.02 (t, 1H), 4.27-4.33 (m, 1H), 4.34-4.43 (m, 1H), 5.71 (d, 1H), 7.13 (t, 1H), 7.74 (d, 2H), 8.13 (s, 1H), 8.21 (d, 2H), 8.56 (s, 1H), 8.65 (s, 1H), 9.90 (d, 1H).

Example 61

1,5-Anhydro-2-({[6-(4-chlorophenyl)-2-(1-methyl-1H-pyrazol-4-yl)-3-oxo-2,3-dihydropyridazin-4-yl]carbonyl}amino)-2,4-dideoxy-D-erythro-pentitol

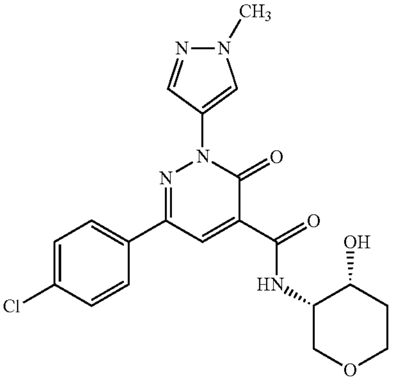 [SMILES: Cn1cc(-n2nc(-c3ccc(Cl)cc3)cc(C(=O)N[C@H]3COCC[C@H]3O)c2=O)cn1]

A solution of 95 mg intermediate 6-(4-chlorophenyl)-2-(1-methyl-1H-pyrazol-4-yl)-3-oxo-2,3-dihydropyridazine-4-carboxylic acid, 56 mg (3S,4R)-3-aminooxan-4-ol hydrochloride (1:1), 133.3 mg HATU, 0.12 mL ethyldiisopropylamine and 1.6 mg 4-dimethylaminopyridine in 2 mL of DMF was stirred at room temperature for 14 hours. Then the reaction mixture was filtered and subjected to RP-HPLC (instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 30 mg 1,5-anhydro-2-({[6-(4-chlorophenyl)-2-(1-methyl-1H-pyrazol-4-yl)-3-oxo-2,3-dihydropyridazin-4-yl]carbonyl}amino)-2,4-dideoxy-D-erythro-pentitol.

$^1$H NMR (400 MHz, DMSO-$d_6$) δ [ppm]=1.60-1.71 (m, 1H), 1.73-1.85 (m, 1H), 3.48-3.60 (m, 3H), 3.68-3.77 (m, 1H), 3.93 (s, 3H), 3.94-3.98 (m, 1H), 4.05-4.13 (m, 1H), 5.24 (d, 1H), 7.56-7.63 (m, 2H), 8.07-8.13 (m, 3H), 8.55 (s, 1H), 8.60 (s, 1H), 9.76 (d, 1H).

Example 62

6-[4-(Difluoromethyl)phenyl]-N-(2-hydroxy-2-methylpropyl)-2-(1-methyl-1H-pyrazol-4-yl)-3-oxo-2,3-dihydropyridazine-4-carboxamide

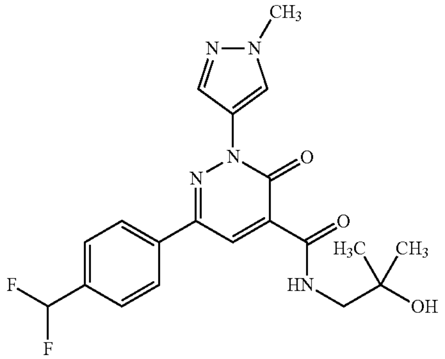 [SMILES: Cn1cc(-n2nc(-c3ccc(C(F)F)cc3)cc(C(=O)NCC(C)(C)O)c2=O)cn1]

A solution of 47 mg intermediate 6-[4-(difluoromethyl)phenyl]-2-(1-methyl-1H-pyrazol-4-yl)-3-oxo-2,3-dihydropyridazine-4-carboxylic acid, 24 mg 1-amino-2-methyl propan-2-ol, 103 mg HATU, 0.1 mL ethyldiisopropylamine and 1 mg 4-dimethylaminopyridine in 1 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 70%/B 30%→A 30%/B 70%; flow: 150 mL/min; UV-detection: 254 nm) to yield 27 mg 6-[4-(difluoromethyl)phenyl]-N-(2-hydroxy-2-methylpropyl)-2-(1-methyl-1H-pyrazol-4-yl)-3-oxo-2,3-dihydropyridazine-4-carboxamide.

$^1$H NMR (400 MHz, dichloromethane-$d_2$) δ [ppm]=1.13 (s, 6H), 3.91 (s, 3H), 4.68 (s, 1H), 7.11 (t, 1H), 7.71 (d, 2H), 8.11 (s, 1H), 8.19 (d, 2H), 8.54 (s, 1H), 8.61 (s, 1H), 9.62 (t, 1H).

Example 63

N-[(trans)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide

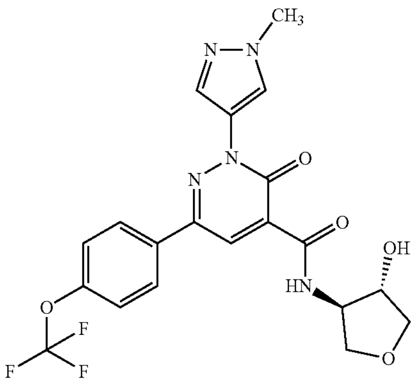 [SMILES: Cn1cc(-n2nc(-c3ccc(OC(F)(F)F)cc3)cc(C(=O)N[C@@H]3COC[C@H]3O)c2=O)cn1]

A solution of 122 mg intermediate 2-(1-methyl-1H-pyrazol-4-yl)-3-oxo-6-[4-(trifluoromethoxy)phenyl]-2,3-dihydropyridazine-4-carboxylic acid, 89.6 mg trans-4-aminotetrahydro-3-furanol hydrochloride (1:1), 244 mg HATU, 0.22 mL ethyldiisopropylamine and 3 mg 4-dimethylaminopyridine in 3 mL of DMF was stirred at room temperature for 14 hours. Then the reaction mixture was filtered and subjected to RP-HPLC (Instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 41 mg N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide.

$^1$H NMR (400 MHz, DMSO-$d_6$) δ [ppm]=3.56 (dd, 1H), 3.68 (dd, 1H), 3.90-3.95 (m, 4H), 3.99 (dd, 1H), 4.15-4.22 (m, 1H), 4.23-4.29 (m, 1H), 5.51 (d, 1H), 7.53 (d, 2H), 8.12 (s, 1H), 8.17-8.23 (m, 2H), 8.56-8.59 (m, 2H), 9.56 (d, 1H).

Example 64

N-[(trans)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, Enantiomer 1

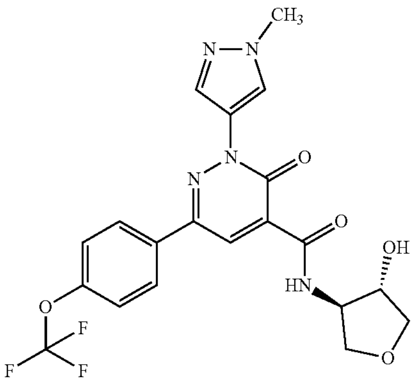 [SMILES: Cn1cc(-n2nc(-c3ccc(OC(F)(F)F)cc3)cc(C(=O)N[C@@H]3COC[C@H]3O)c2=O)cn1]

HPLC-separation of 39 mg N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide (example 63) on a chiral column (instrument: Labomatic HD5000, Labocord-5000; Gilson GX-241, Labcol Vario 4000, column: Chiralpak IE 5μ 250×30 mm; eluent A: tert.-butyl methyl ether; eluent B: methanol; isocratic: 50% A+50% B; flow 50.0 mL/min; UV 280 nm) yielded 16 mg N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, enantiomer 1. Chiral HPLC: Rt=1.91 min (instrument: Agilent HPLC 1260; column: Chiralpak IE 3μ100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm)

Example 65

N-[(trans)-4-Hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, Enantiomer 2

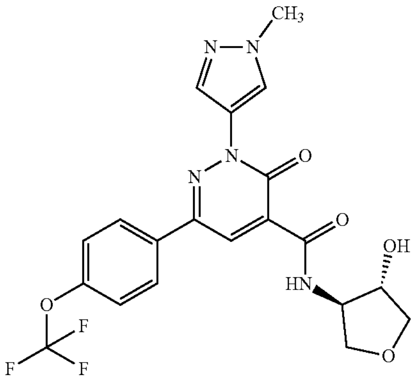 [SMILES: Cn1cc(-n2nc(-c3ccc(OC(F)(F)F)cc3)cc(C(=O)N[C@@H]3COC[C@H]3O)c2=O)cn1]

The separation of 38 mg N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide (example 63), according to example 64, additionally yielded 15 mg N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide, enantiomer 2. Chiral HPLC: Rt=2.33 min (instrument: Agilent HPLC 1260; column: Chiralpak IE 3μ 100×4.6 mm; eluent A: tert.-butyl methyl ether+0.1 vol-% diethylamine (99%); eluent B: methanol; isocratic: 50% A+50% B; flow 1.4 mL/min; temperature: 25° C.; DAD 280 nm).

Example 66

6-[6-(Difluoromethyl)pyridin-3-yl]-N-[(2S)-1-hydroxypropan-2-yl]-2-(1-methyl-1H-pyrazol-4-yl)-3-oxo-2,3-dihydropyridazine-4-carboxamide

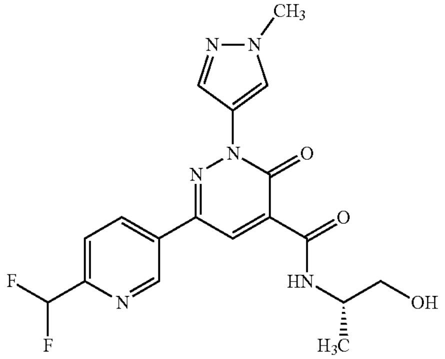 [SMILES: C[C@@H](CO)NC(=O)c1cc(-c2ccc(C(F)F)nc2)nn(-c2cnn(C)c2)c1=O]

A solution of 55 mg intermediate 6-[6-(difluoromethyl)pyridin-3-yl]-2-(1-methyl-1H-pyrazol-4-yl)-3-oxo-2,3-dihydropyridazine-4-carboxylic acid, 23.8 mg (S)-(+)-2-amino-1-propanol, 120 mg HATU, 0.11 mL ethyldiisopropylamine and 1.5 mg 4-dimethylaminopyridine in 1 mL of DMF was stirred at room temperature for 14 hours. Then the reaction mixture was filtered and subjected to RP-HPLC (Instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 90%/B 10%→A 50%/B 50%; flow: 150 mL/min; UV-detection: 254 nm) to yield 22 mg 6-[6-(difluoromethyl)pyridin-3-yl]-N-[(2S)-1-hydroxypropan-2-yl]-2-(1-methyl-1H-pyrazol-4-yl)-3-oxo-2,3-dihydropyridazine-4-carboxamide.

$^1$H NMR (400 MHz, DMSO-$d_6$) δ [ppm]=1.19 (d, 3H), 3.43-3.51 (m, 2H and water signal), 3.93 (s, 3H), 4.00-4.11 (m, 1H), 5.00 (t, 1H), 7.06 (t, 1H), 7.85 (d, 1H), 8.17 (s, 1H), 8.60 (s, 1H), 8.66 (dd, 1H), 8.69 (s, 1H), 9.35 (d, 1H), 9.50 (d, 1H).

Example 67

N-(2-Hydroxy-2-methylpropyl)-2-(1-methyl-1H-pyrazol-4-yl)-3-oxo-6-[4-(trifluoromethyl)phenyl]-2,3-dihydropyridazine-4-carboxamide

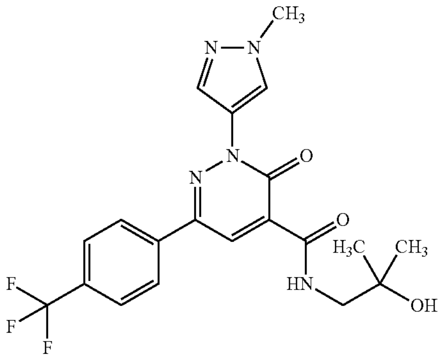 [SMILES: Cn1cc(-n2nc(-c3ccc(C(F)(F)F)cc3)cc(C(=O)NCC(C)(C)O)c2=O)cn1]

2-(1-Methyl-1H-pyrazol-4-yl)-3-oxo-6-[4-(trifluoromethyl)phenyl]-2,3-dihydropyridazine-4-carboxylic acid (50 mg, 0.137 mmol) was dissolved in anhydrous DMF (1.5 mL). 1-Amino-2-methylpropan-2-ol (24.5 mg, 0.28 mmol), N-ethyl-N-isopropylpropan-2-amine (0.108 mL, 0.62 mmol), and propane phosphonic acid anhydride (T3P, 121 μL, 50% in DMF, 207 μmol) were successively added. After stirring for 5.5 h at rt 1-amino-2-methylpropan-2-ol (12.5 mg, 0.14 mmol), N-ethyl-N-isopropylpropan-2-amine (72 μL, 0.41 mmol), and propane phosphonic acid anhydride (T3P, 80 μL, 50% in DMF, 137 μmol) were successively added. It was stirred at rt overnight. The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient, twice) to yield 8 mg (13%) of the title compound.

$^1$H-NMR (400 MHz, DMSO-$d_6$): δ [ppm]=1.15 (s, 6H), 3.31-3.36 (m, 2H and water signal), 3.94 (s, 3H), 4.71 (s, 1H), 7.89 (d, 2H), 8.14 (s, 1H), 8.30 (d, 2H), 8.58 (s, 1H), 8.66 (s, 1H), 9.63 (t, 1H).

Example 68

6-(4-Chlorophenyl)-N-[(2S)-1-hydroxypropan-2-yl]-3-oxo-2-(pyridin-3-yl)-2,3-dihydropyridazine-4-carboxamide

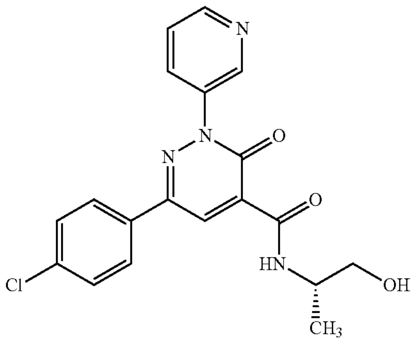 [SMILES: C[C@@H](CO)NC(=O)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2S)-2-Aminopropan-1-ol (32.1 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 31 mg (38%) of the title compound.

$^1$H-NMR (400 MHz, DMSO-$d_6$): δ [ppm]=1.16 (d, 3H), 3.39-3.49 (m, 2H), 3.98-4.09 (m, 1H), 4.94 (t, 1H), 7.57-7.61 (m, 2H), 7.63 (ddd, 1H), 7.99-8.03 (m, 2H), 8.16 (ddd, 1H), 8.67 (s, 1H), 8.69 (dd, 1H), 8.91 (d, 1H), 9.41 (d, 1H). $[\alpha]_D^{20}$=+13.8° (c=1.00, DMSO).

Example 69

6-(4-Chlorophenyl)-N-[(2R)-1-hydroxypropan-2-yl]-3-oxo-2-(pyridin-3-yl)-2,3-dihydropyridazine-4-carboxamide

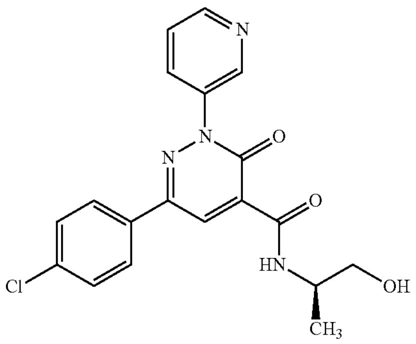 [SMILES: C[C@H](CO)NC(=O)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2R)-2-Aminopropan-1-ol (32.1 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 29 mg (35%) of the title compound.

$^1$H-NMR (400 MHz, DMSO-$d_6$): δ [ppm]=1.16 (d, 3H), 3.40-3.49 (m, 2H), 3.98-4.09 (m, 1H), 4.94 (t, 1H), 7.57-7.61 (m, 2H), 7.63 (dd, 1H), 7.99-8.03 (m, 2H), 8.16 (ddd, 1H), 8.67 (s, 1H), 8.69 (br d, 1H), 8.91 (br s, 1H), 9.41 (d, 1H).

$[\alpha]_D^{20}$=−5.5° (c=1.00, DMSO).

Example 70

6-(4-Chlorophenyl)-N-(1,3-dihydroxypropan-2-yl)-3-oxo-2-(pyridin-3-yl)-2,3-dihydropyridazine-4-carboxamide

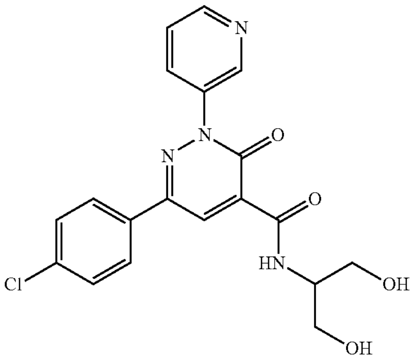 [SMILES: O=C(NC(CO)CO)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). 2-Aminopropane-1,3-diol (38.9 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 39 mg (46%) of the title compound.

$^1$H-NMR (400 MHz, DMSO-$d_6$): δ [ppm]=3.44-3.52 (m, 2H), 3.54-3.61 (m, 2H), 3.92-4.00 (m, 1H), 4.87 (t, 2H), 7.57-7.61 (m, 2H), 7.63 (dd, 1H), 7.99-8.03 (m, 2H), 8.16 (ddd, 1H), 8.66-8.73 (m, 2H), 8.91 (br s, 1H), 9.51 (d, 1H).

Example 71

6-(4-Chlorophenyl)-N-(2-hydroxy-2-methylpropyl)-3-oxo-2-(pyridin-3-yl)-2,3-dihydropyridazine-4-carboxamide

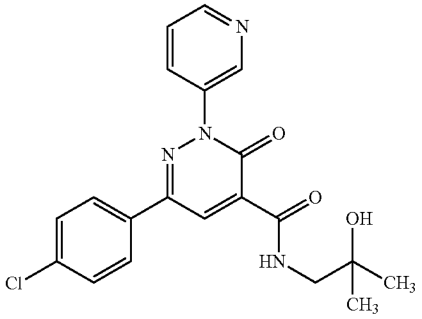 [SMILES: CC(C)(O)CNC(=O)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). 1-Amino-2-methylpropan-2-ol (38.1 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 27 mg (32%) of the title compound.

$^1$H-NMR (400 MHz, DMSO-$d_6$): δ [ppm]=1.13 (s, 6H), 3.31 (d, 2H), 4.67 (s, 1H), 7.56-7.61 (m, 2H), 7.63 (ddd, 1H), 7.99-8.03 (m, 2H), 8.17 (ddd, 1H), 8.68 (s, 1H), 8.69 (dd, 1H), 8.92 (d, 1H), 9.52 (t, 1H).

Example 72

(−)-6-(4-Chlorophenyl)-N-[(2S)-2,3-dihydroxypropyl]-3-oxo-2-(pyridin-3-yl)-2,3-dihydropyridazine-4-carboxamide

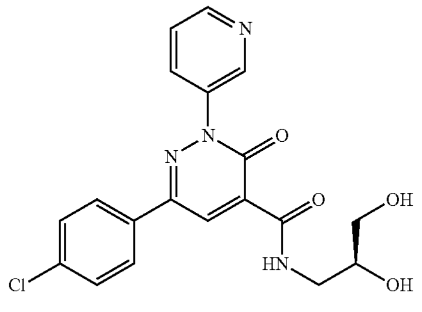 [SMILES: O=C(NC[C@H](O)CO)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2S)-3-Aminopropane-1,2-diol (38.9 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 34 mg (40%) of the title compound.

$^1$H-NMR (400 MHz, DMSO-$d_6$): δ [ppm]=3.19-3.32 (m, 2H), 3.36-3.43 (m, 1H), 3.55-3.64 (m, 2H), 4.69 (t, 1H), 5.00 (d, 1H), 7.56-7.61 (m, 2H), 7.63 (dd, 1H), 8.01 (d, 2H), 8.14-8.19 (m, 1H), 8.67 (s, 1H), 8.69 (br s, 1H), 8.92 (br s, 1H), 9.51 (t, 1H).

$[\alpha]_D^{20}$=−10.0° (c=1.00, DMSO).

Example 73

(+)-6-(4-Chlorophenyl)-N-[(2R)-2,3-dihydroxypropyl]-3-oxo-2-(pyridin-3-yl)-2,3-dihydropyridazine-4-carboxamide

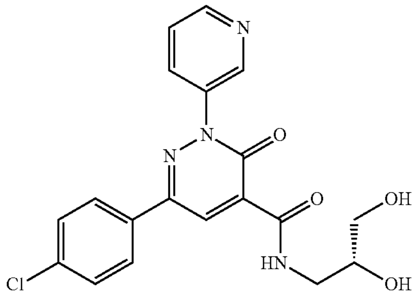 [SMILES: O=C(NC[C@@H](O)CO)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2R)-3-Aminopropane-1,2-diol (38.9 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 26 mg (30%) of the title compound.

$^1$H-NMR (400 MHz, DMSO-$d_6$): δ [ppm]=3.19-3.32 (m, 2H), 3.36-3.42 (m, 1H), 3.56-3.64 (m, 2H), 4.69 (t, 1H), 5.00 (d, 1H), 7.57-7.61 (m, 2H), 7.63 (ddd, 1H), 7.99-8.03 (m, 2H), 8.17 (ddd, 1H), 8.67 (s, 1H), 8.69 (dd, 1H), 8.92 (d, 1H), 9.51 (t, 1H).

$[\alpha]_D^{20}$=+20.2° (c=1.00, DMSO).

Example 74

(+)-6-(4-Chlorophenyl)-N-[(2S)-1-hydroxy-3-methoxypropan-2-yl]-3-oxo-2-(pyridin-3-yl)-2,3-dihydropyridazine-4-carboxamide

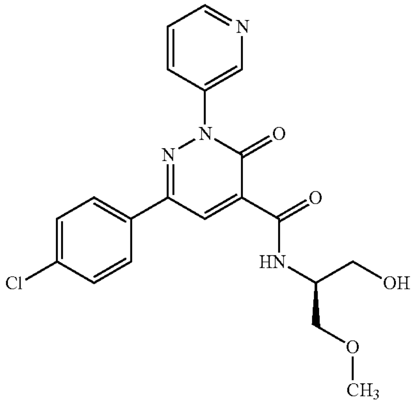 [SMILES: COC[C@H](CO)NC(=O)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2S)-2-Amino-3-methoxypropan-1-ol (44.9 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 40 mg (30%) of the title compound.

$^1$H-NMR (400 MHz, DMSO-$d_6$): δ [ppm]=3.28 (s, 3H), 3.41-3.58 (m, 4H), 4.08-4.17 (m, 1H), 4.97 (t, 1H), 7.57-7.61 (m, 2H), 7.63 (dd, 1H), 7.99-8.03 (m, 2H), 8.16 (ddd, 1H), 8.66-8.73 (m, 2H), 8.91 (br s, 1H), 9.51 (d, 1H).

$[\alpha]_D^{20}$=+2.2° (c=1.00, DMSO).

Example 75

(−)-6-(4-Chlorophenyl)-N-[(2R)-1-hydroxy-3-methoxypropan-2-yl]-3-oxo-2-(pyridin-3-yl)-2,3-dihydropyridazine-4-carboxamide

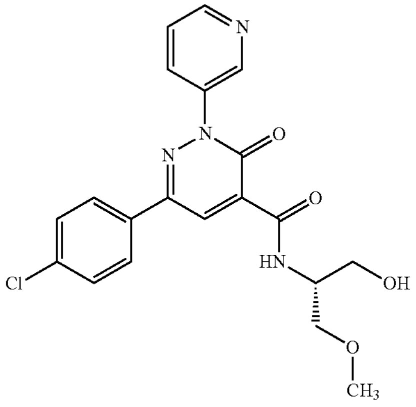 [SMILES: COC[C@@H](CO)NC(=O)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (70 mg, 0.21 mmol) was dissolved in anhydrous DMF (1.6 mL). (2R)-2-Amino-3-methoxypropan-1-ol (44.9 mg, 0.43 mmol), N-ethyl-N-isopropylpropan-2-amine (0.167 mL, 0.96 mmol), and propane phosphonic acid anhydride (T3P, 187 μL, 50% in DMF, 320 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 40 mg (30%) of the title compound.

$^1$H-NMR (400 MHz, DMSO-$d_6$): δ [ppm]=3.28 (s, 3H), 3.41-3.59 (m, 4H), 4.08-4.17 (m, 1H), 4.97 (t, 1H), 7.56-7.61 (m, 2H), 7.63 (br dd, 1H), 7.98-8.03 (m, 2H), 8.16 (br d, 1H), 8.66-8.75 (m, 2H), 8.91 (br s, 1H), 9.51 (d, 1H).

$[\alpha]_D^{20}$=−6.1° (c=1.00, DMSO).

Example 76

6-(4-Chlorophenyl)-3-oxo-2-(pyridin-3-yl)-N-[(2RS)-1,1,1-trifluoro-3-hydroxypropan-2-yl]-2,3-dihydropyridazine-4-carboxamide

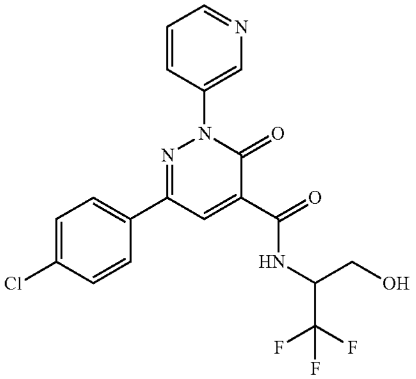

6-(4-Chlorophenyl)-3-oxo-2-(pyridin-3-yl)-2,3-dihydropyridazine-4-carboxylic acid (100 mg, 0.31 mmol) was dissolved in anhydrous DMF (2.3 mL). (2RS)-2-Amino-3,3,3-trifluoropropan-1-ol hydrochloride (1:1) (101 mg, 0.61 mmol), N-ethyl-N-isopropylpropan-2-amine (0.345 mL, 1.98 mmol), and propane phosphonic acid anhydride (T3P, 267 μL, 50% in DMF, 458 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 33 mg (25%) of the title compound.

$^1$H-NMR (400 MHz, DMSO-$d_6$): δ [ppm]=3.65-3.73 (m, 1H), 3.78-3.86 (m, 1H), 4.79-4.92 (m, 1H), 5.43 (t, 1H), 7.59 (d, 2H), 7.64 (br dd, 1H), 8.03 (d, 2H), 8.18 (br d, 1H), 8.63-8.79 (s, 2H), 8.93 (br s, 1H), 9.97 (d, 1H).

Example 77

6-(4-Chlorophenyl)-N-[(1RS)-1-cyclopropyl-2-hydroxyethyl]-3-oxo-2-(pyridin-3-yl)-2,3-dihydropyridazine-4-carboxamide

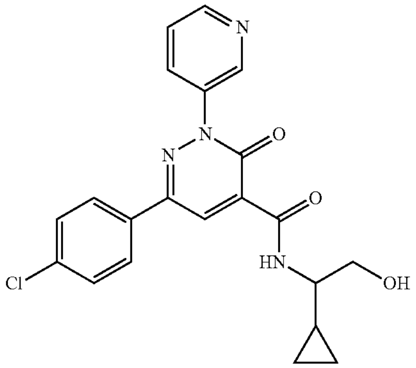 [SMILES: O=C(NC(CO)C1CC1)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (100 mg, 0.31 mmol) was dissolved in anhydrous DMF (2.3 mL). (2RS)-2-Amino-2-cyclopropylethanol hydrochloride (1:1) (84 mg, 0.61 mmol), N-ethyl-N-isopropylpropan-2-amine (0.345 mL, 1.98 mmol), and propane phosphonic acid anhydride (T3P, 267 μL, 50% in DMF, 458 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 37.5 mg (30%) of the title compound.

$^1$H-NMR (400 MHz, DMSO-$d_6$): δ [ppm]=0.26-0.50 (m, 4H), 1.03-1.13 (m, 1H), 3.40-3.47 (m, 1H), 3.52-3.62 (m, 2H), 4.92 (t, 1H), 7.56-7.61 (m, 2H), 7.63 (dd, 1H), 7.99-8.03 (m, 2H), 8.17 (ddd, 1H), 8.68 (s, 1H), 8.70 (br d, 1H), 8.92 (br s, 1H), 9.53 (d, 1H).

Example 78

6-(4-Chlorophenyl)-3-oxo-2-(pyridin-3-yl)-N-[(2RS)-3,3,3-trifluoro-2-hydroxypropyl]-2,3-dihydropyridazine-4-carboxamide

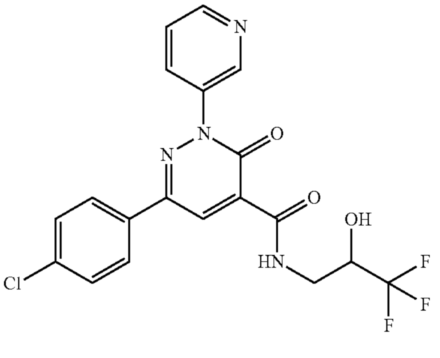 [SMILES: O=C(NCC(O)C(F)(F)F)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (100 mg, 0.31 mmol) was dissolved in anhydrous DMF (2.3 mL). (2RS)-3-Amino-1,1,1-trifluoropropan-2-ol (78.8 mg, 0.61 mmol), N-ethyl-N-isopropylpropan-2-amine (0.239 mL, 1.37 mmol), and propane phosphonic acid anhydride (T3P, 267 μL, 50% in DMF, 458 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 23 mg (23%) of the title compound.

$^1$H-NMR (400 MHz, DMSO-$d_6$): δ [ppm]=3.43-3.52 (m, 1H), 3.71-3.79 (m, 1H), 4.17-4.28 (m, 1H), 6.66 (d, 1H), 7.57-7.61 (m, 2H), 7.64 (dd, 1H), 7.99-8.04 (m, 2H), 8.17 (ddd, 1H), 8.66-8.73 (m, 2H), 8.92 (br s, 1H), 9.61 (t, 1H).

Example 79

6-(4-Chlorophenyl)-N-[(2RS)-3,3-difluoro-2-hydroxypropyl]-3-oxo-2-(pyridin-3-yl)-2,3-dihydropyridazine-4-carboxamide

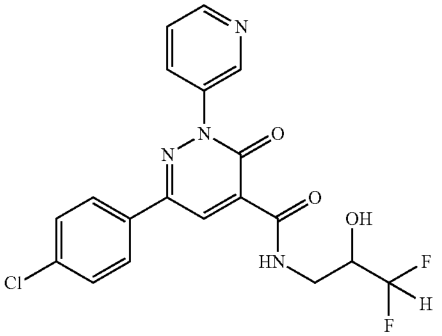 [SMILES: O=C(NCC(O)C(F)F)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (100 mg, 0.31 mmol) was dissolved in anhydrous DMF (2.3 mL). (2RS)-3-Amino-1,1-difluoropropan-2-ol hydrochloride (1:1) (90 mg, 0.61 mmol), N-ethyl-N-isopropylpropan-2-amine (0.345 mL, 1.98 mmol), and propane phosphonic acid anhydride (T3P, 267 μL, 50% in DMF, 458 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 28.3 mg (22%) of the title compound.

$^1$H-NMR (400 MHz, DMSO-$d_6$): δ [ppm]=3.36-3.43 (m, 1H), 3.66 (dt, 1H), 3.78-3.91 (m, 1H), 5.94 (d, 1H), 5.99 (d, 1H), 7.59 (d, 2H), 7.64 (br dd, 1H), 8.02 (d, 2H), 8.17 (br d, 1H), 8.64-8.75 (m, 2H), 8.93 (br s, 1H), 9.54 (t, 1H).

Example 80

6-(4-Chlorophenyl)-2-(5-fluoropyridin-3-yl)-N-[(2S)-1-hydroxypropan-2-yl]-3-oxo-2,3-dihydropyridazine-4-carboxamide

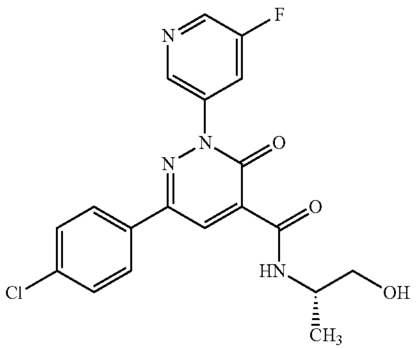 [SMILES: C[C@@H](CO)NC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). (2S)-2-Aminopropan-1-ol (18 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 31 mg (51%) of the title compound.

$^1$H-NMR (400 MHz, DMSO-d$_6$): δ [ppm]=1.16 (d, 3H), 3.40-3.50 (m, 2H), 3.99-4.09 (m, 1H), 4.95 (t, 1H), 7.57-7.61 (m, 2H), 8.01-8.05 (m, 2H), 8.25 (dt, 1H), 8.67 (s, 1H), 8.76 (d, 1H), 8.85 (t, 1H), 9.34 (d, 1H). $[\alpha]_D^{20}$=+9.5° (c=1.00, methanol).

Example 81

6-(4-Chlorophenyl)-2-(5-fluoropyridin-3-yl)-N-[(2R)-1-hydroxypropan-2-yl]-3-oxo-2,3-dihydropyridazine-4-carboxamide

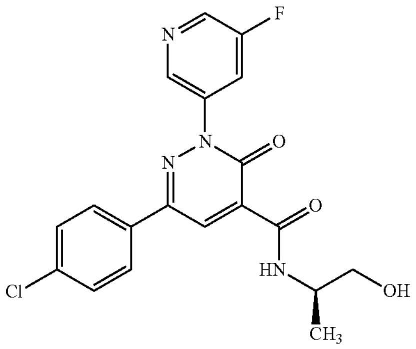 [SMILES: C[C@H](CO)NC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). (2R)-2-Aminopropan-1-ol (18 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 27 mg (46%) of the title compound.

$^1$H-NMR (400 MHz, DMSO-d$_6$): δ [ppm]=1.17 (d, 3H), 3.40-3.50 (m, 2H), 3.99-4.09 (m, 1H), 4.95 (t, 1H), 7.57-7.61 (m, 2H), 8.01-8.05 (m, 2H), 8.25 (dt, 1H), 8.67 (s, 1H), 8.76 (d, 1H), 8.85 (t, 1H), 9.34 (d, 1H).

$[\alpha]_D^{20}$=8.90 (c=1.00, methanol).

Example 82

6-(4-Chlorophenyl)-2-(5-fluoropyridin-3-yl)-N-(2-hydroxy-2-methyl propyl)-3-oxo-2,3-dihydropyridazine-4-carboxamide

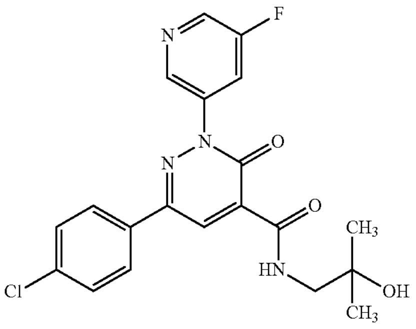 [SMILES: CC(C)(O)CNC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). 1-Amino-2-methylpropan-2-ol (22 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 35 mg (58%) of the title compound.

$^1$H-NMR (400 MHz, DMSO-d$_6$): δ [ppm]=1.13 (s, 6H), 3.32 (d, 2H), 4.68 (s, 1H), 7.57-7.61 (m, 2H), 8.01-8.06 (m, 2H), 8.25 (dt, 1H), 8.68 (s, 1H), 8.76 (d, 1H), 8.87 (t, 1H), 9.45 (t, 1H).

Example 83

6-(4-Chlorophenyl)-2-(5-fluoropyridin-3-yl)-N-[(2S)-1-hydroxy-3-methylbutan-2-yl]-3-oxo-2,3-dihydropyridazine-4-carboxamide

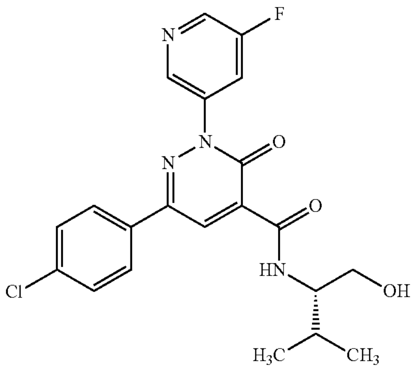 [SMILES: CC(C)[C@@H](CO)NC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). (2S)-2-Amino-3-methylbutan-1-ol (25 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 33 mg (53%) of the title compound.

$^1$H-NMR (400 MHz, DMSO-$d_6$): δ [ppm]=0.89 (d, 3H), 0.93 (d, 3H), 1.91-2.03 (m, 1H), 3.41-3.48 (m, 1H), 3.52-3.59 (m, 1H), 3.81-3.89 (m, 1H), 4.82 (t, 1H), 7.57-7.62 (m, 2H), 8.01-8.05 (m, 2H), 8.26 (dt, 1H), 8.68 (s, 1H), 8.76 (d, 1H), 8.86 (t, 1H), 9.30 (d, 1H). $[\alpha]_D^{20}$=−20.2° (c=1.00, methanol).

Example 84

6-(4-Chlorophenyl)-N-(1,3-dihydroxypropan-2-yl)-2-(5-fluoropyridin-3-yl)-3-oxo-2,3-dihydropyridazine-4-carboxamide

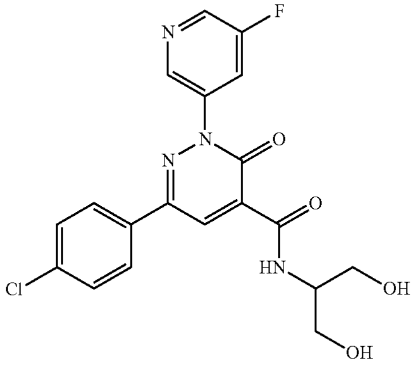 [SMILES: O=C(NC(CO)CO)c1cc(-c2ccc(Cl)cc2)nn(-c2cncc(F)c2)c1=O]

6-(4-Chlorophenyl)-2-(5-fluoropyridin-3-yl-3-oxo-2,3-dihydropyridazine-4-carboxylic acid (50 mg, 0.15 mmol) was dissolved in anhydrous DMF (1.5 mL). 2-Aminopropane-1,3-diol (22 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred at rt overnight. The crude reaction mixture was purified by RP-HPLC (column: X-Bridge C18 5 μm 100×30 mm, mobile phase: (water+0.2 vol % aqueous ammonia (32%))/acetonitrile, gradient) to yield 45 mg (74%) of the title compound.

$^1$H-NMR (400 MHz, DMSO-$d_6$): δ [ppm]=3.44-3.52 (m, 2H), 3.55-3.62 (m, 2H), 3.92-4.01 (m, 1H), 4.88 (t, 2H), 7.57-7.62 (m, 2H), 8.01-8.05 (m, 2H), 8.25 (br d, 1H), 8.69 (s, 1H), 8.79 (br s, 1H), 8.87 (br s, 1H), 9.45 (d, 1H).

Example 85

6-(4-Chlorophenyl)-2-(5-fluoropyridin-3-yl)-N-[(2R)-1-hydroxy-3-methoxypropan-2-yl]-3-oxo-2,3-dihydropyridazine-4-carboxamide

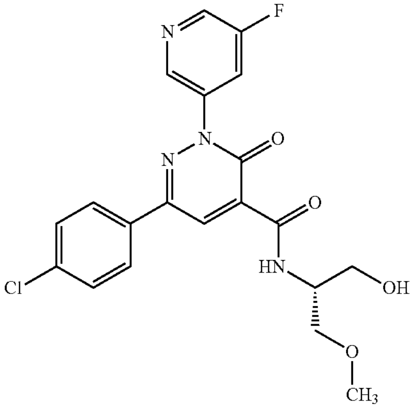 [SMILES: COC[C@@H](CO)NC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). (2R)-2-Amino-3-methoxypropan-1-ol (26 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred for 2 h at rt. The crude reaction mixture was purified by RP-HPLC (column: X-Bridge C18 5 μm 100×30 mm, mobile phase: (water+0.2 vol % aqueous ammonia (32%))/acetonitrile, gradient) to give 40 mg (64%) of the title compound.

$^1$H-NMR (400 MHz, DMSO-$d_6$): δ [ppm]=3.28 (s, 3H), 3.42-3.58 (m, 4H), 4.09-4.17 (m, 1H), 4.98 (t, 1H), 7.57-7.62 (m, 2H), 8.01-8.05 (m, 2H), 8.25 (ddd, 1H), 8.69 (s, 1H), 8.76 (d, 1H), 8.85 (t, 1H), 9.44 (d, 1H).

$[\alpha]_D^{20}$=−0.94° (c=1.00, methanol).

Example 86

6-(4-Chlorophenyl)-2-(5-fluoropyridin-3-yl)-N-[(2S)-1-hydroxy-3-methoxypropan-2-yl]-3-oxo-2,3-dihydropyridazine-4-carboxamide

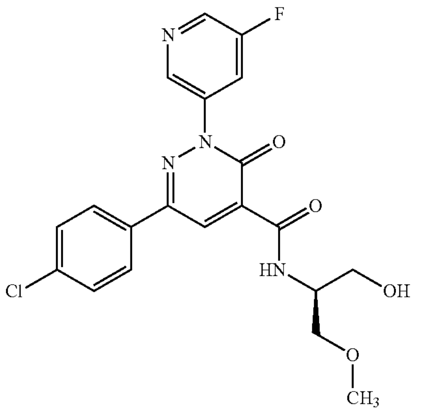 [SMILES: COC[C@H](CO)NC(=O)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.15 mmol) was dissolved in anhydrous DMF (1.5 mL). (2S)-2-Amino-3-methoxypropan-1-ol (26 mg, 0.25 mmol), N-ethyl-N-isopropylpropan-2-amine (0.113 mL, 0.65 mmol), and propane phosphonic acid anhydride (T3P, 127 μL, 50% in DMF, 217 μmol) were successively added. It was stirred for 1 h at rt. The crude reaction mixture was purified by RP-HPLC (column: X-Bridge C18 5 μm 100×30 mm, mobile phase: (water+0.2 vol % aqueous ammonia (32%))/acetonitrile, gradient) to give 41 mg (65%) of the title compound.

$^1$H-NMR (400 MHz, DMSO-$d_6$): δ [ppm]=3.28 (s, 3H), 3.42-3.59 (m, 4H), 4.09-4.17 (m, 1H), 4.98 (t, 1H), 7.57-7.62 (m, 2H), 8.01-8.05 (m, 2H), 8.25 (dt, 1H), 8.69 (s, 1H), 8.76 (d, 1H), 8.85 (t, 1H), 9.44 (d, 1H).

$[\alpha]_D^{20}$=+0.47° (c=1.00, methanol).

Example 87

(−)-6-(4-Chlorophenyl)-N-(3,3-difluoro-2-hydroxypropyl)-3-oxo-2-(pyridin-3-yl)-2,3-dihydropyridazine-4-carboxamide

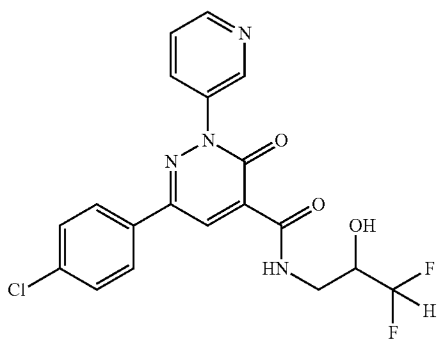 [SMILES: O=C(NCC(O)C(F)F)c1cc(-c2ccc(Cl)cc2)nn(-c2cccnc2)c1=O]

6-(4-Chlorophenyl)-N-[(2RS)-3,3-difluoro-2-hydroxypropyl]-3-oxo-2-(pyridin-3-yl)-2,3-dihydropyridazine-4-carboxamide (23.7 mg) was separated by chiral HPLC (column: YMC Amylose SA 5μ 250×30 mm, mobile phase: isocratic (1:1) of methanol/ethanol, 40 mL/min, UV: 254 nm) to yield 9.4 mg (40%) of the title compound.

$^1$H-NMR (400 MHz, DMSO-$d_6$): δ [ppm]=3.35-3.41 (m, 1H), 3.62-3.69 (m, 1H), 3.78-3.91 (m, 1H), 5.94 (dt, 1H), 6.00 (d, 1H), 7.57-7.61 (m, 2H), 7.64 (ddd, 1H), 7.99-8.04 (m, 2H), 8.17 (ddd, 1H), 8.68 (s, 1H), 8.69 (dd, 1H), 8.92 (d, 1H), 9.54 (t, 1H).

Chiral HPLC: Rt=3.34 min

Instrument: Agilent HPLC 1260: YMC Amylose SA 3μ 100×4.6 mm; eluent: (A: methanol+0.1 vol % diethylamine (99%))/B: ethanol, isocratic: 1:1, flow: 1.4 mL/min, temperature: 25° C., UV: 254 nm.

$[\alpha]_D^{20}$=−11.8° (c=1.00, methanol).

Example 88

(+)-6-(4-Chlorophenyl)-N-(3,3-difluoro-2-hydroxypropyl)-3-oxo-2-(pyridin-3-yl)-2,3-dihydropyridazine-4-carboxamide

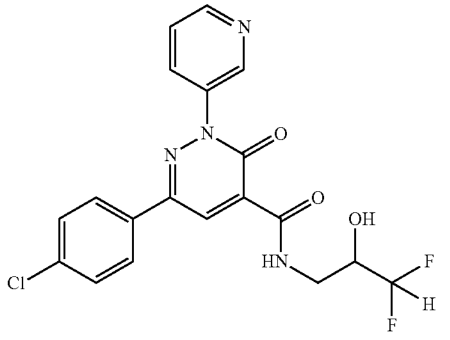 [SMILES: O=C(NCC(O)C(F)F)c1cc(-c2ccc(Cl)cc2)nn(-c2cccnc2)c1=O]

6-(4-Chlorophenyl)-N-[(2RS)-3,3-difluoro-2-hydroxypropyl]-3-oxo-2-(pyridin-3-yl)-2,3-dihydropyridazine-4-carboxamide (23.7 mg) was separated by chiral HPLC (column: YMC Amylose SA 5μ 250×30 mm, mobile phase: methanol/ethanol, isocratic: 1:1, 40 mL/min, UV: 254 nm) to yield 9.4 mg (40%) of the title compound.

$^1$H-NMR (400 MHz, DMSO-$d_6$): δ [ppm]=3.35-3.41 (m, 1H), 3.62-3.69 (m, 1H), 3.78-3.91 (m, 1H), 5.94 (dt, 1H), 6.00 (br d, 1H), 7.57-7.61 (m, 2H), 7.64 (ddd, 1H), 7.99-8.04 (m, 2H), 8.17 (ddd, 1H), 8.68 (s, 1H), 8.69 (dd, 1H), 8.92 (d, 1H), 9.54 (t, 1H).

Chiral HPLC: Rt=4.33 min

Instrument: Agilent HPLC 1260: YMC Amylose SA 3μ 100×4.6 mm; eluent: (A: methanol+0.1 vol % diethylamine (99%))/B: ethanol, isocratic: 1:1, flow: 1.4 mL/min, temperature: 25° C., UV: 254 nm.

$[\alpha]_D^{20}$=+11.0° (c=1.00, methanol).

Example 89

(−)-6-(4-Chlorophenyl)-3-oxo-2-(pyridin-3-yl)-N-(3,3,3-trifluoro-2-hydroxypropyl)-2,3-dihydropyridazine-4-carboxamide

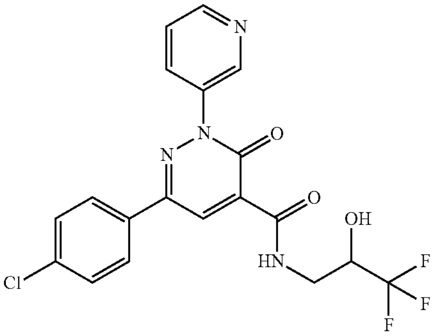 [SMILES: O=C(NCC(O)C(F)(F)F)c1cc(-c2ccc(Cl)cc2)nn(-c2cccnc2)c1=O]

6-(4-Chlorophenyl)-3-oxo-2-(pyridin-3-yl)-N-[(2RS)-3,3,3-trifluoro-2-hydroxypropyl]-2,3-dihydropyridazine-4-carboxamide (19.3 mg) was separated by chiral HPLC (column: YMC Amylose SA 5μ 250×30 mm, mobile phase: methanol/ethanol, isocratic: 1:1, 40 mL/min, UV: 254 nm) to yield 7.3 mg (38%) of the title compound.

$^1$H-NMR (400 MHz, DMSO-$d_6$): δ [ppm]=3.48 (ddd, 1H), 3.75 (ddd, 1H), 4.17-4.28 (m, 1H), 6.67 (br s, 1H), 7.57-7.61 (m, 2H), 7.64 (ddd, 1H), 7.99-8.04 (m, 2H), 8.17 (ddd, 1H), 8.67-8.71 (m, 2H), 8.92 (d, 1H), 9.61 (t, 1H).

Chiral HPLC: Rt=2.23 min

Instrument: Agilent HPLC 1260: YMC Amylose SA 3μ 100×4.6 mm; eluent: (A: methanol+0.1 vol % diethylamine (99%))/B: ethanol, isocratic: 1:1, flow: 1.4 mL/min, temperature: 25° C., UV: 254 nm.

$[\alpha]_D^{20}$=−13.2° (c=1.00, methanol).

Example 90

(+)-6-(4-Chlorophenyl)-3-oxo-2-(pyridin-3-yl)-N-(3,3,3-trifluoro-2-hydroxypropyl)-2,3-dihydropyridazine-4-carboxamide

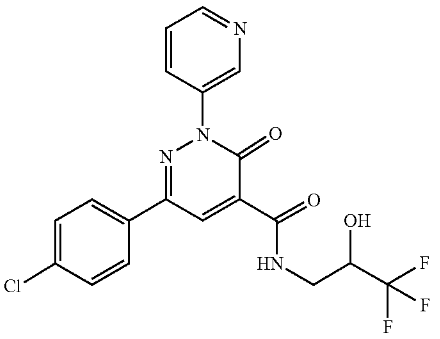 [SMILES: O=C(NCC(O)C(F)(F)F)c1cc(-c2ccc(Cl)cc2)nn(-c2cccnc2)c1=O]

6-(4-Chlorophenyl)-3-oxo-2-(pyridin-3-yl)-N-[(2RS)-3,3,3-trifluoro-2-hydroxypropyl]-2,3-dihydropyridazine-4-carboxamide (19.3 mg) was separated by chiral HPLC (column: YMC Amylose SA 5μ 250×30 mm, mobile phase: methanol/ethanol, isocratic: 1:1, 40 mL/min, UV: 254 nm) to yield 7.5 mg (39%) of the title compound.

$^1$H-NMR (400 MHz, DMSO-$d_6$): δ [ppm]=3.48 (ddd, 1H), 3.75 (ddd, 1H), 4.28-4.18 (m, 1H), 6.67 (br d, 1H), 7.57-7.61 (m, 2H), 7.64 (ddd, 1H), 7.99-8.04 (m, 2H), 8.17 (ddd, 1H), 8.67-8.72 (m, 2H), 8.92 (d, 1H), 9.61 (t, 1H).

Chiral HPLC: Rt=3.70 min

Instrument: Agilent HPLC 1260: YMC Amylose SA 3μ 100×4.6 mm; eluent: (A: methanol+0.1 vol % diethylamine (99%))/B: ethanol, isocratic: 1:1, flow: 1.4 mL/min, temperature: 25° C., UV: 254 nm.

$[\alpha]_D^{20}$=+12.7° (c=1.00, methanol).

Example 91

(+)-6-(4-Chlorophenyl)-N-(1-cyclopropyl-2-hydroxyethyl)-3-oxo-2-(pyridin-3-yl)-2,3-dihydropyridazine-4-carboxamide

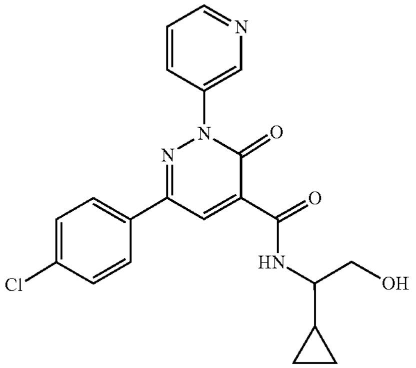 [SMILES: O=C(NC(CO)C1CC1)c1cc(-c2ccc(Cl)cc2)nn(-c2cccnc2)c1=O]

6-(4-Chlorophenyl)-N-[(1RS)-1-cyclopropyl-2-hydroxyethyl]-3-oxo-2-(pyridin-3-yl)-2,3-dihydropyridazine-4-carboxamide (32 mg) was separated by chiral HPLC (column: Cellulose SC 5μ 250×30 mm, mobile phase: methanol/ethanol, isocratic: 1:1, 30 mL/min, UV: 280 nm) to yield 14 mg (47%) of the title compound.

$^1$H-NMR (400 MHz, DMSO-$d_6$): δ [ppm]=0.25-0.50 (m, 4H), 1.03-1.11 (m, 1H), 3.40-3.48 (m, 1H), 3.63 (ddd, 2H), 4.93 (t, 1H), 7.56-7.61 (m, 2H), 7.61-7.65 (m, 1H), 7.99-8.03 (m, 2H), 8.17 (ddd, 1H), 8.68 (s, 1H), 8.70 (dd, 1H), 8.91 (d, 1H), 9.53 (d, 1H).

Chiral HPLC: Rt=1.75 min

Instrument: Agilent HPLC 1260: Cellulose SC 3μ 100×4.6 mm; eluent: (A: methanol+0.1 vol % diethylamine (99%))/B: ethanol, isocratic: 1:1, flow: 1.4 mL/min, temperature: 25° C., UV: 280 nm.

$[\alpha]_D^{20}$=+29.2° (c=1.00, methanol).

Example 92

(−)-6-(4-Chlorophenyl)-N-(1-cyclopropyl-2-hydroxyethyl)-3-oxo-2-(pyridin-3-yl)-2,3-dihydropyridazine-4-carboxamide

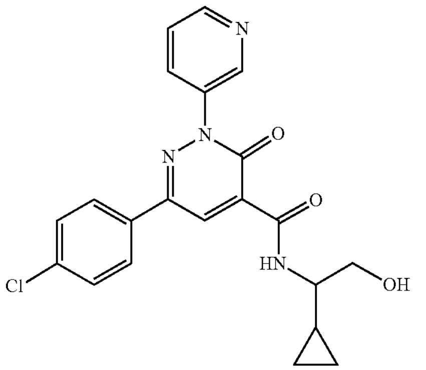 [SMILES: O=C(NC(CO)C1CC1)c1cc(-c2ccc(Cl)cc2)nn(-c2cccnc2)c1=O]

6-(4-Chlorophenyl)-N-[(1RS)-1-cyclopropyl-2-hydroxyethyl]-3-oxo-2-(pyridin-3-yl)-2,3-dihydropyridazine-4-carboxamide (32 mg) was separated by chiral HPLC (column: Cellulose SC 5μ 250×30 mm, mobile phase: methanol/ethanol, isocratic: 1:1, 30 mL/min, UV: 280 nm) to yield 13 mg (41%) of the title compound.

$^1$H-NMR (400 MHz, DMSO-$d_6$): δ [ppm]=0.26-0.50 (m, 4H), 1.03-1.11 (m, 1H), 3.40-3.48 (m, 1H), 3.52-3.62 (m, 2H), 4.93 (t, 1H), 7.56-7.61 (m, 2H), 7.63 (ddd, 1H), 7.99-8.03 (m, 2H), 8.17 (ddd, 1H), 8.68 (s, 1H), 8.70 (dd, 1H), 8.91 (d, 1H), 9.53 (d, 1H).

Chiral HPLC: Rt=2.75 min

Instrument: Agilent HPLC 1260: Cellulose SC 3μ 100×4.6 mm; eluent: (A: methanol+0.1 vol % diethylamine (99%))/B: ethanol, isocratic: 1:1, flow: 1.4 mL/min, temperature: 25° C., UV: 280 nm.

$[\alpha]_D^{20}$=−26.7° (c=1.00, methanol).

Example 93

(+)-6-(4-Chlorophenyl)-N-[(2R)-1-fluoro-3-hydroxypropan-2-yl]-3-oxo-2-(pyridin-3-yl)-2,3-dihydropyridazine-4-carboxamide

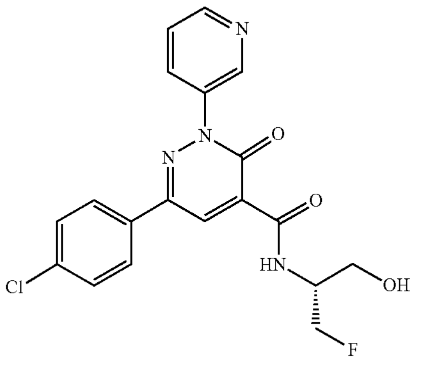 [SMILES: O=C(N[C@H](CO)CF)c1cc(-c2ccc(Cl)cc2)nn(-c2cccnc2)c1=O]

6-(4-Chlorophenyl)-3-oxo-2-(pyridin-3-yl)-2,3-dihydropyridazine-4-carboxylic acid (50 mg, 0.15 mmol) was dissolved in anhydrous DMF (1.5 mL). (2R)-2-Amino-3-fluoropropan-1-ol hydrochloride (1:1) (36 mg, 0.28 mmol), N-ethyl-N-isopropylpropan-2-amine (167 μL, 0.96 mmol), and propane phosphonic acid anhydride (T3P, 134 μL, 50% in DMF, 229 μmol) were successively added. It was stirred for 1 h at rt. The crude reaction mixture was purified by RP-HPLC (column: X-Bridge C18 5 μm 100×30 mm, mobile phase: (water+0.2 vol % aqueous ammonia (32%))/acetonitrile, gradient) and RP-HPLC (column: X-Bridge C18 5 μm 100×30 mm, mobile phase: (water+0.1 vol % formic acid (99%))/acetonitrile, gradient) to yield 3 mg (5%) of the title compound.

$^1$H-NMR (400 MHz, DMSO-$d_6$): δ [ppm]=3.48-3.56 (m, 1H), 3.57-3.64 (m, 1H), 4.18-4.32 (m, 1H), 4.46-4.55 (m, 1H), 4.58-4.67 (m, 1H), 5.16 (t, 1H), 7.57-7.61 (m, 2H), 7.63 (ddd, 1H), 7.99-8.04 (m, 2H), 8.16 (ddd, 1H), 8.67-8.71 (m, 2H), 8.91 (dd, 1H), 9.59 (d, 1H).

$[\alpha]_D^{20}$=+10.0° (c=1.00, methanol).

Example 94

N-[(1S)-1-Cyclopropyl-2-hydroxyethyl]-3-oxo-2-(pyridin-3-yl)-6-[4-(trifluoromethyl)phenyl]-2,3-dihydropyridazine-4-carboxamide

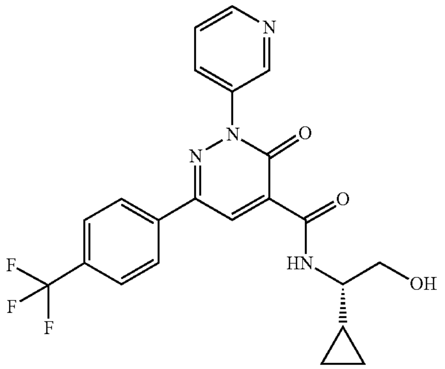 [SMILES: O=C(N[C@H](CO)C1CC1)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (150 mg, 0.42 mmol) was dissolved in anhydrous DMF (3.0 mL). (2S)-2-Amino-2-cyclopropylethanol hydrochloride (1:1) (114 mg, 0.83 mmol), N-ethyl-N-isopropylpropan-2-amine (470 μL, 2.70 mmol), and propane phosphonic acid anhydride (T3P, 364 μL, 50% in DMF, 624 μmol) were successively added. It was stirred for 2 h at rt. The reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient) affording an oil to which tert-butyl methyl ether was added. The mixture was treated for 10 minutes with ultrasound obtaining a white solid. The solvent was removed under vacuum, the solid was dried under vacuum at 50° C. overnight affording 84 mg (46%) of the title compound.

$^1$H-NMR (400 MHz, DMSO-$d_6$): δ [ppm]=0.26-0.50 (m, 4H), 1.04-1.13 (m, 1H), 3.41-3.49 (m, 1H), 3.53-3.62 (m, 2H), 4.93 (t, 1H), 7.64 (ddd, 1H), 7.88 (d, 2H), 8.16-8.24 (m, 3H), 8.71 (dd, 1H), 8.74 (s, 1H), 8.93 (d, 1H), 9.52 (d, 1H).

$[\alpha]_D^{20}$=+30.4 (c=1.00, methanol).

Example 95

(−)-6-(4-Chlorophenyl)-3-oxo-2-(pyridin-3-yl)-N-[(2S)-1,1,1-trifluoro-3-hydroxypropan-2-yl]-2,3-dihydropyridazine-4-carboxamide

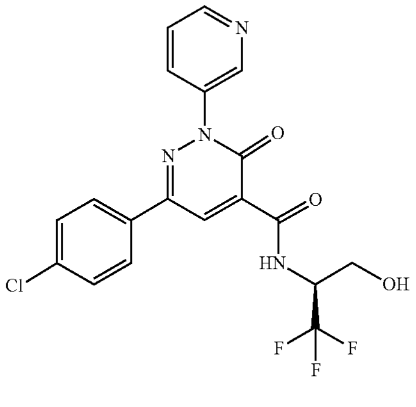 [SMILES: O=C(N[C@@H](CO)C(F)(F)F)c1cc(-c2ccc(Cl)cc2)nn(-c2cccnc2)c1=O]

6-(4-Chlorophenyl)-3-oxo-2-(pyridin-3-yl)-N-[(2RS)-1,1,1-trifluoro-3-hydroxypropan-2-yl]-2,3-dihydropyridazine-4-carboxamide (29 mg) was separated by chiral HPLC (column: Chiralpak IB 5μ 250×30 mm, mobile phase: isocratic (80:20) of carbon dioxide/2-propanol, 80 mL/min, temperature 40° C., BPR: 150 bar, UV: 254 nm) to yield 12.3 mg (42%) of the title compound.

$^1$H-NMR (400 MHz, DMSO-$d_6$): δ [ppm]=3.66-3.73 (m, 1H), 3.82 (dt, 1H), 4.80-4.91 (m, 1H), 5.43 (t, 1H), 7.57-7.61 (m, 2H), 7.64 (ddd, 1H), 8.01-8.05 (m, 2H), 8.18 (ddd, 1H), 8.70 (dd, 1H), 8.74 (s, 1H), 8.92 (dd, 1H), 9.97 (d, 1H).

Chiral HPLC: Rt=2.54 min

Instrument: Agilent HPLC 1260: Chiralpak IB 5μ 100×4.6 mm; eluent: carbon dioxide/2-propanol, isocratic: 80:20, flow: 4 mL/min, temperature: 37.5° C., BPR: 100 bar, UV: 254 nm.

$[\alpha]_D^{20}$=−8.5° (c=1.00, methanol).

Example 96

(+)-6-(4-Chlorophenyl)-3-oxo-2-(pyridin-3-yl)-N-[(2R)-1,1,1-trifluoro-3-hydroxypropan-2-yl]-2,3-dihydropyridazine-4-carboxamide

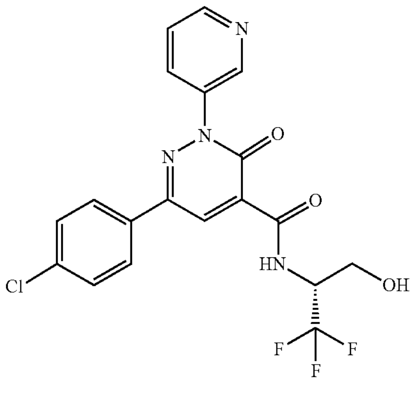 [SMILES: O=C(N[C@H](CO)C(F)(F)F)c1cc(-c2ccc(Cl)cc2)nn(-c2cccnc2)c1=O]

6-(4-Chlorophenyl)-3-oxo-2-(pyridin-3-yl)-N-[(2RS)-1,1,1-trifluoro-3-hydroxypropan-2-yl]-2,3-dihydropyridazine-4-carboxamide (29 mg) was separated by chiral HPLC (column: Chiralpak IB 5μ 250×30 mm, mobile phase: isocratic (80:20) of carbon dioxide/2-propanol, 80 mL/min, temperature 40° C., BPR: 150 bar, UV: 254 nm) to yield 11.5 mg (40%) of the title compound.

$^1$H-NMR (400 MHz, DMSO-$d_6$): δ [ppm]=3.65-3.73 (m, 1H), 3.82 (dt, 1H), 4.80-4.91 (m, 1H), 5.44 (t, 1H), 7.57-7.62 (m, 2H), 7.64 (ddd, 1H), 8.01-8.06 (m, 2H), 8.18 (ddd, 1H), 8.70 (dd, 1H), 8.74 (s, 1H), 8.92 (dd, 1H), 9.97 (d, 1H).

Chiral HPLC: Rt=3.40 min

Instrument: Agilent HPLC 1260: Chiralpak IB 5μ 100×4.6 mm; eluent: carbon dioxide/2-propanol, isocratic: 80:20, flow: 4 mL/min, temperature: 37.5° C., BPR: 100 bar, UV: 254 nm.

$[\alpha]_D^{20}$=+14.4° (c=1.00, methanol).

Example 97

6-(4-Chlorophenyl)-N-[(1RS)-1-cyclopropyl-2-hydroxyethyl]-2-(5-fluoropyridin-3-yl)-3-oxo-2,3-dihydropyridazine-4-carboxamide

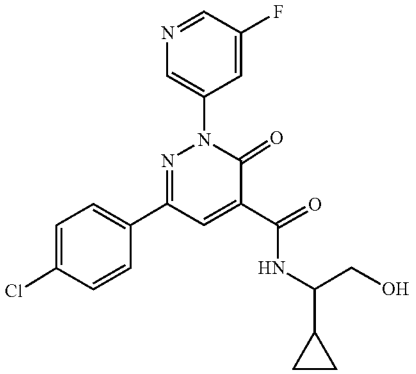 [SMILES: O=C(NC(CO)C1CC1)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (100 mg, 0.29 mmol) was dissolved in anhydrous DMF (2.2 mL). (2RS)-2-Amino-2-cyclopropylethanol hydrochloride (1:1) (80 mg, 0.58 mmol), N-ethyl-N-isopropylpropan-2-amine (328 μL, 1.88 mmol), and propane phosphonic acid anhydride (T3P, 254 μL, 50% in DMF, 434 μmol) were successively added. It was stirred at rt overnight. The reaction mixture was diluted with methanol and concentrated under vacuum. The residue was purified by RP-HPLC (column: X-Bridge C18 5 μm 100×30 mm, mobile phase: (water+0.1 vol % formic acid (99%))/acetonitrile, gradient) to yield 43.8 mg (35%) of the title compound.

$^1$H-NMR (400 MHz, DMSO-$d_6$): δ [ppm]=0.26-0.50 (m, 4H), 1.03-1.13 (m, 1H), 3.40-3.47 (m, 1H), 3.52-3.63 (m, 2H), 4.93 (t, 1H), 7.57-7.61 (m, 2H), 8.01-8.06 (m, 2H), 8.26 (ddd, 1H), 8.68 (s, 1H), 8.77 (d, 1H), 8.86 (d, 1H), 9.47 (t, 1H).

Example 98

6-(4-Chlorophenyl)-N-[(2R)-2,3-dihydroxypropyl]-2-(5-fluoropyridin-3-yl)-3-oxo-2,3-dihydro-pyridazine-4-carboxamide

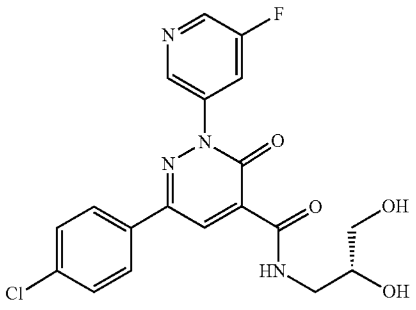 [SMILES: O=C(NC[C@@H](O)CO)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.145 mmol) was dissolved in anhydrous DMF (1.1 mL). (2R)-3-Amino-propane-1,2-diol (26.4 mg, 0.29 mmol), N-ethyl-N-isopropylpropan-2-amine (164 µL, 0.94 mmol), and propane phosphonic acid anhydride (T3P, 127 µL, 50% in DMF, 217 µmol) were successively added. It was stirred at rt overnight. The reaction mixture was diluted with methanol and concentrated under vacuum. The residue was purified by RP-HPLC (column: X-Bridge C18 5 µm 100×30 mm, mobile phase: (water+0.1 vol % formic acid (99%))/acetonitrile, gradient) to obtain 19.2 mg (32%) of the title compound.

$^1$H-NMR (400 MHz, DMSO-$d_6$): δ [ppm]=3.19-3.43 (m, 3H and water signal), 3.55-3.64 (m, 2H), 4.69 (br s, 1H), 5.00 (br s, 1H), 7.57-7.62 (m, 2H), 8.01-8.06 (m, 2H), 8.25 (ddd, 1H), 8.68 (s, 1H), 8.76 (d, 1H), 8.86 (t, 1H), 9.44 (t, 1H).

$[\alpha]_D^{20}$=+13.4° (c=1.00, methanol).

Example 99

6-(4-Chlorophenyl)-N-[(2S)-2,3-dihydroxypropyl]-2-(5-fluoropyridin-3-yl)-3-oxo-2,3-dihydro-pyridazine-4-carboxamide

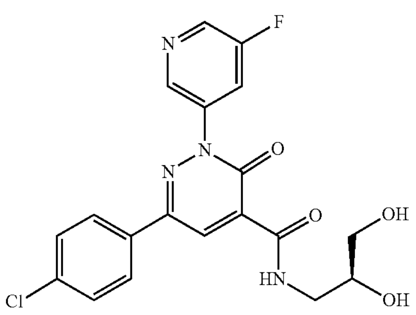 [SMILES: O=C(NC[C@H](O)CO)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.145 mmol) was dissolved in anhydrous DMF (1.1 mL). (2S)-3-Amino-propane-1,2-diol (26.4 mg, 0.29 mmol), N-ethyl-N-isopropylpropan-2-amine (164 µL, 0.94 mmol), and propane phosphonic acid anhydride (T3P, 127 µL, 50% in DMF, 217 µmol) were successively added. It was stirred at rt overnight. The reaction mixture was diluted with methanol and concentrated under vacuum. The residue was purified by RP-HPLC (column: X-Bridge C18 5 µm 100×30 mm, mobile phase: (water+0.1 vol % formic acid (99%))/acetonitrile, gradient) to afford 9.2 mg (15%) of the title compound.

$^1$H-NMR (400 MHz, DMSO-$d_6$): δ [ppm]=3.20-3.43 (m, 3H and water signal), 3.56-3.64 (m, 2H), 4.69 (br t, 1H), 5.01 (br d, 1H), 7.57-7.62 (m, 2H), 8.02-8.06 (m, 2H), 8.25 (ddd, 1H), 8.68 (s, 1H), 8.76 (d, 1H), 8.86 (s, 1H), 9.44 (t, 1H). $[\alpha]_D^{20}$=−8.4° (c=1.00, methanol).

Example 100

6-(4-Chlorophenyl)-2-(5-fluoropyridin-3-yl)-3-oxo-N-[(2R)-1,1,1-trifluoro-3-hydroxypropan-2-yl]-2,3-dihydropyridazine-4-carboxamide

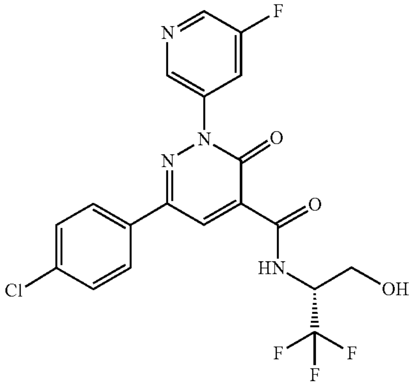 [SMILES: O=C(N[C@H](CO)C(F)(F)F)c1cc(-c2ccc(Cl)cc2)nn(-c2cncc(F)c2)c1=O]

6-(4-Chlorophenyl)-2-(5-fluoropyridin-3-yl)-3-oxo-2,3-dihydropyridazine-4-carboxylic acid (50 mg, 0.145 mmol) was dissolved in anhydrous DMF (1.1 mL). (2R)-2-Amino-3,3,3-trifluoropropan-1-ol hydrochloride (1:1) (47.9 mg, 0.29 mmol), N-ethyl-N-isopropylpropan-2-amine (164 µL, 0.94 mmol), and propane phosphonic acid anhydride (T3P, 127 µL, 50% in DMF, 217 µmol) were successively added. It was stirred at rt overnight. The reaction mixture was diluted with methanol and concentrated under vacuum. The residue was purified by RP-HPLC (column: X-Bridge C18 5 µm 100×30 mm, mobile phase: (water+0.1 vol % formic acid (99%))/acetonitrile, gradient) to afford 27.9 mg (42%) of the title compound.

$^1$H-NMR (400 MHz, DMSO-$d_6$): δ [ppm]=3.66-3.73 (m, 1H), 3.79-3.86 (m, 1H), 4.80-4.92 (m, 1H), 5.45 (br s, 1H), 7.58-7.62 (m, 2H), 8.03-8.07 (m, 2H), 8.26 (ddd, 1H), 8.74 (s, 1H), 8.77 (d, 1H), 8.86 (t, 1H), 9.90 (d, 1H).

$[\alpha]_D^{20}$=+11.0° (c=1.00, methanol).

Example 101

N-[(2RS)-3,3-Difluoro-2-hydroxypropyl]-3-oxo-2-(pyridin-3-yl)-6-[4-(trifluoromethyl)phenyl]-2,3-dihydropyridazine-4-carboxamide

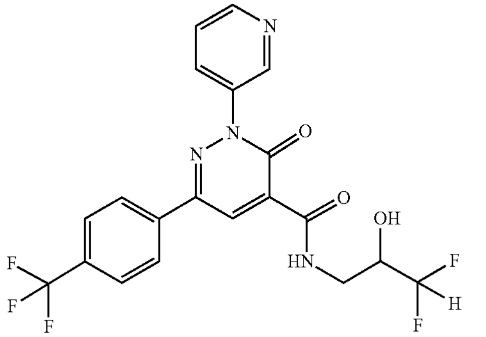 [SMILES: O=C(NCC(O)C(F)F)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (100 mg, 0.277 mmol) was dissolved in anhydrous DMF (2.1 mL). (2RS)-3-amino-1,1-difluoropropan-2-ol hydrochloride (1:1) (81.7 mg, 0.55 mmol), N-ethyl-N-isopropylpropan-2-amine (314 μL, 1.80 mmol), and propane phosphonic acid anhydride (T3P, 243 μL, 50% in DMF, 415 μmol) were successively added. It was stirred for 2 h at rt. The reaction mixture was diluted with methanol and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 90.1 mg (72%) of the title compound.

$^{1}$H-NMR (400 MHz, DMSO-$d_6$): δ [ppm]=3.36-3.44 (m, 1H), 3.66 (dt, 1H), 3.79-3.91 (m, 1H), 5.94 (dt, 1H), 6.00 (d, 1H), 7.65 (dd, 1H), 7.89 (d, 2H), 8.16-8.25 (m, 3H), 8.71 (dd, 1H), 8.74 (s, 1H), 8.93 (d, 1H), 9.53 (t, 1H).

Example 102

N-[(1S,2S)-2-Hydroxycyclopentyl]-3-oxo-2-(pyridin-3-yl)-6-[4-(trifluoromethyl)phenyl]-2,3-dihydropyridazine-4-carboxamide

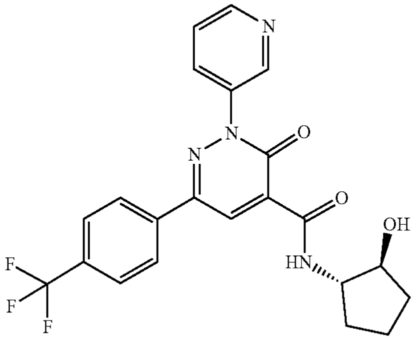 [SMILES: O=C(N[C@H]1CCC[C@@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (1S,2S)-2-Aminocyclopentanol hydrochloride (1:1) (38 mg, 0.28 mmol), N-ethyl-N-isopropylpropan-2-amine (157 μL, 0.90 mmol), and propane phosphonic acid anhydride (T3P, 122 μL, 50% in DMF, 208 μmol) were successively added. It was stirred for 2 h at rt. The reaction mixture was diluted with methanol and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 22.2 mg (36%) of the title compound.

$^{1}$H-NMR (400 MHz, DMSO-$d_6$): δ [ppm]=1.41-1.56 (m, 2H), 1.57-1.87 (m, 3H), 2.04-2.14 (m, 1H), 3.94 (quin, 1H), 3.99-4.07 (m, 1H), 4.95 (d, 1H), 7.64 (dd, 1H), 7.89 (d, 2H), 8.17 (ddd, 1H), 8.21 (d, 2H), 8.69-8.73 (m, 2H), 8.92 (d, 1H), 9.29 (d, 1H).

$[\alpha]_D^{20}$=+40.10 (c=1.00, methanol).

Example 103

N-[(1R,2S)-2-Hydroxycyclopentyl]-3-oxo-2-(pyridin-3-yl)-6-[4-(trifluoromethyl)phenyl]-2,3-dihydropyridazine-4-carboxamide

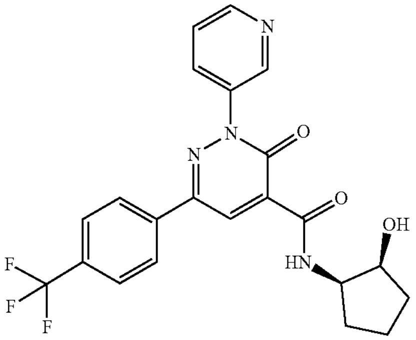 [SMILES: O=C(N[C@@H]1CCC[C@@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (1S,2R)-2-Aminocyclopentanol hydrochloride (1:1) (38 mg, 0.28 mmol), N-ethyl-N-isopropylpropan-2-amine (157 μL, 0.90 mmol), and propane phosphonic acid anhydride (T3P, 122 μL, 50% in DMF, 208 μmol) were successively added. It was stirred for 2 h at rt. The reaction mixture was diluted with methanol and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 36.5 mg (59%) of the title compound.

$^{1}$H-NMR (400 MHz, DMSO-$d_6$): δ [ppm]=1.46-1.65 (m, 3H), 1.70-1.88 (m, 2H), 1.92-2.04 (m, 1H), 3.99-4.12 (m, 2H), 5.05 (d, 1H), 7.64 (ddd, 1H), 7.89 (d, 2H), 8.18 (ddd, 1H), 8.21 (d, 2H), 8.70 (dd, 1H), 8.75 (s, 1H), 8.92 (d, 1H), 9.66 (d, 1H).

$[\alpha]_D^{20}$=−2.1° (c=1.00, methanol).

Example 104

N-[(1R,2R)-2-Hydroxycyclopentyl]-3-oxo-2-(pyridin-3-yl)-6-[4-(trifluoromethyl)phenyl]-2,3-dihydropyridazine-4-carboxamide

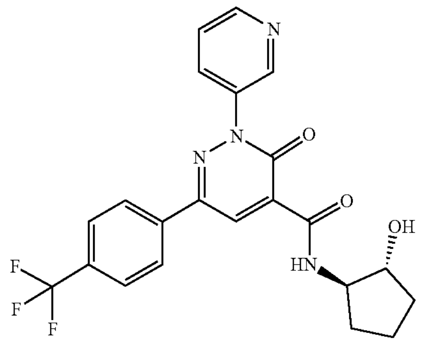 [SMILES: O=C(N[C@@H]1CCC[C@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (1R,2R)-2-Aminocyclopentanol hydrochloride (1:1) (38 mg, 0.28 mmol), N-ethyl-N-isopropylpropan-2-amine (157 μL, 0.90 mmol), and propane phosphonic acid anhydride (T3P, 122 μL, 50% in DMF, 208 μmol) were successively added. It was stirred for 2 h at rt. The reaction mixture was diluted with methanol and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 19 mg (31%) of the title compound.

$^1$H-NMR (400 MHz, DMSO-$d_6$): δ [ppm]=1.41-1.56 (m, 2H), 1.57-1.87 (m, 3H), 2.04-2.14 (m, 1H), 3.91-3.97 (m, 1H), 3.99-4.06 (m, 1H), 4.95 (d, 1H), 7.64 (ddd, 1H), 7.89 (d, 2H), 8.18 (ddd, 1H), 8.21 (d, 2H), 8.69-8.72 (m, 2H), 8.92 (d, 1H), 9.29 (d, 1H).

$[\alpha]_D^{20}$=−32.6° (c=1.00, methanol).

Example 105

N-[(1S,2R)-2-Hydroxycyclopentyl]-3-oxo-2-(pyridin-3-yl)-6-[4-(trifluoromethyl)phenyl]-2,3-dihydropyridazine-4-carboxamide

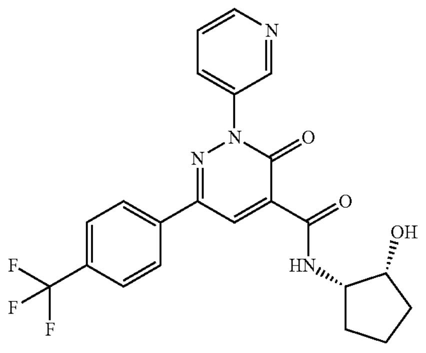 [SMILES: O=C(N[C@H]1CCC[C@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (1R,2S)-2-Aminocyclopentanol hydrochloride (1:1) (38 mg, 0.28 mmol), N-ethyl-N-isopropylpropan-2-amine (157 μL, 0.90 mmol), and propane phosphonic acid anhydride (T3P, 122 μL, 50% in DMF, 208 μmol) were successively added. It was stirred for 2 h at rt. The reaction mixture was diluted with methanol and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 19 mg (31%) of the title compound.

$^1$H-NMR (400 MHz, DMSO-$d_6$): δ [ppm]=1.47-1.64 (m, 3H), 1.70-1.88 (m, 2H), 1.93-2.03 (m, 1H), 3.99-4.12 (m, 2H), 5.05 (d, 1H), 7.64 (ddd, 1H), 7.89 (d, 2H), 8.17 (ddd, 1H), 8.21 (d, 2H), 8.70 (dd, 1H), 8.74 (s, 1H), 8.92 (d, 1H), 9.66 (d, 1H).

$[\alpha]_D^{20}$=+3.7° (c=1.00, methanol).

Example 106

N-[(1S,2R)-2-Hydroxycyclohexyl]-3-oxo-2-(pyridin-3-yl)-6-[4-(trifluoromethyl)phenyl]-2,3-dihydropyridazine-4-carboxamide

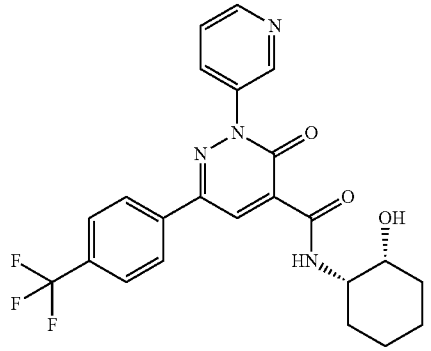 [SMILES: O=C(N[C@H]1CCCC[C@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (1R,2S)-2-Aminocyclohexanol hydrochloride (1:1) (44.2 mg, 0.28 mmol), N-ethyl-N-isopropylpropan-2-amine (157 μL, 0.90 mmol), and propane phosphonic acid anhydride (T3P, 122 μL, 50% in DMF, 208 μmol) were successively added. It was stirred at rt overnight.

The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) affording 30.1 mg (47%) of the title compound.

$^1$H-NMR (400 MHz, DMSO-$d_6$): δ [ppm]=1.25-1.38 (m, 2H), 1.48-1.69 (m, 6H), 3.75-3.80 (m, 1H), 3.88-3.96 (m, 1H), 4.88 (d, 1H), 7.64 (ddd, 1H), 7.88 (d, 2H), 8.16-8.23 (m, 3H), 8.71 (dd, 1H), 8.74 (s, 1H), 8.92 (dd, 1H), 9.60 (d, 1H).

$[\alpha]_D^{20}$=+5.0° (c=1.00, methanol).

Example 107

N-[(3RS,4RS)-4-Hydroxytetrahydrofuran-3-yl]-3-oxo-2-(pyridin-3-yl)-6-[4-(trifluoromethyl)phenyl]-2,3-dihydropyridazine-4-carboxamide

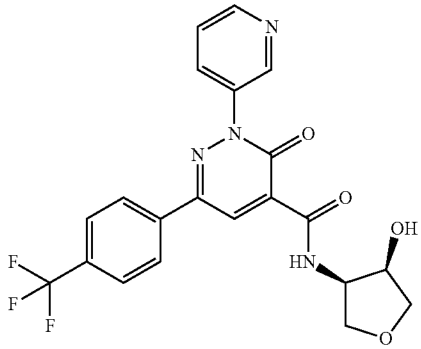 [SMILES: O=C(N[C@@H]1COC[C@@H]1O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (100 mg, 0.277 mmol) was dissolved in anhydrous DMF (2.1 mL). (3RS,4RS)-4-Aminotetrahydrofuran-3-ol hydrochloride (1:1) (77.3 mg, 0.55 mmol), N-ethyl-N-isopropylpropan-2-amine (314 μL, 1.80 mmol), and propane phosphonic acid anhydride (T3P, 243 μL, 50% in DMF, 415 μmol) were successively added. It was stirred at rt overnight.

The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) to afford 70.2 mg (57%) of the title compound.

$^1$H-NMR (400 MHz, DMSO-$d_6$): δ [ppm]=3.46 (t, 1H), 3.61 (dd, 1H), 3.93 (dd, 1H), 4.01 (dd, 1H), 4.25-4.31 (m, 1H), 4.32-4.40 (m, 1H), 5.70 (br s, 1H), 7.65 (ddd, 1H), 7.89 (d, 2H), 8.18 (ddd, 1H), 8.21 (d, 2H), 8.71 (dd, 1H), 8.76 (s, 1H), 8.92 (d, 1H), 9.80 (d, 1H).

Example 108

3-Oxo-2-(pyridin-3-yl)-N-[(2RS)-3,3,3-trifluoro-2-hydroxypropyl]-6-[4-(trifluoromethyl)phenyl]-2,3-dihydropyridazine-4-carboxamide

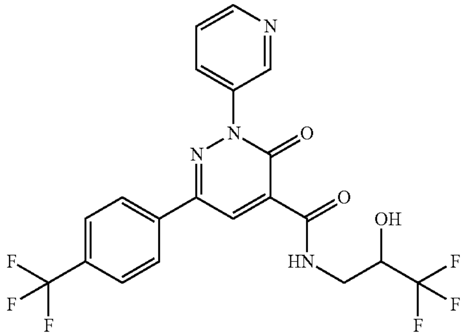

3-Oxo-2-(pyridin-3-yl)-6-[4-(trifluoromethyl)phenyl]-2,3-dihydropyridazine-4-carboxylic acid (100 mg, 0.277 mmol) was dissolved in anhydrous DMF (2.1 mL). (2RS)-3-Amino-1,1,1-trifluoropropan-2-ol (71.5 mg, 0.55 mmol), N-ethyl-N-isopropylpropan-2-amine (314 μL, 1.80 mmol), and propane phosphonic acid anhydride (T3P, 243 μL, 50% in DMF, 415 μmol) were successively added. It was stirred at rt overnight. The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) yielding 57.3 mg (44%) of the title compound.

$^1$H-NMR (400 MHz, DMSO-$d_6$): δ [ppm]=3.49 (ddd, 1H), 3.76 (ddd, 1H), 4.18-4.29 (m, 1H), 6.68 (br s, 1H), 7.65 (ddd, 1H), 7.89 (d, 2H), 8.18 (ddd, 1H), 8.22 (d, 2H), 8.71 (dd, 1H), 8.75 (s, 1H), 8.93 (d, 1H), 9.59 (t, 1H).

Example 109

N-[(1RS)-1-Cyclopropyl-2-hydroxyethyl]-3-oxo-2-(pyridin-3-yl)-6-[4-(trifluoromethyl)phenyl]-2,3-dihydropyridazine-4-carboxamide

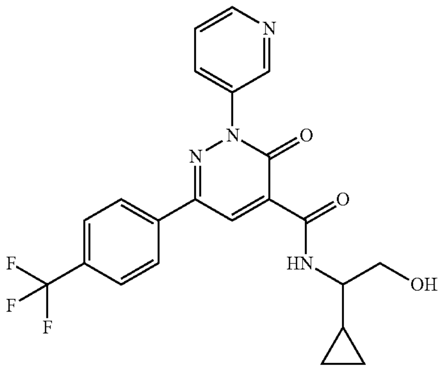 [SMILES: O=C(NC(CO)C1CC1)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (100 mg, 0.277 mmol) was dissolved in anhydrous DMF (2.1 mL). (2RS)-2-Amino-2-cyclopropylethanol hydrochloride (1:1) (76.2 mg, 0.55 mmol), N-ethyl-N-isopropylpropan-2-amine (314 μL, 1.80 mmol), and propane phosphonic acid anhydride (T3P, 243 μL, 50% in DMF, 415 μmol) were successively added. It was stirred at rt overnight. The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) affording 52.5 mg (43%) of the title compound.

$^1$H-NMR (400 MHz, DMSO-$d_6$): δ [ppm]=0.26-0.50 (m, 4H), 1.03-1.13 (m, 1H), 3.41-3.49 (m, 1H), 3.52-3.68 (m, 2H), 4.94 (t, 1H), 7.64 (ddd, 1H), 7.88 (d, 2H), 8.16-8.24 (m, 3H), 8.71 (dd, 1H), 8.74 (s, 1H), 8.93 (d, 1H), 9.52 (d, 1H).

Example 110

3-Oxo-2-(pyridin-3-yl)-N-[(2RS)-1,1,1-trifluoro-3-hydroxypropan-2-yl]-6-[4-(trifluoromethyl)phenyl]-2,3-dihydropyridazine-4-carboxamide

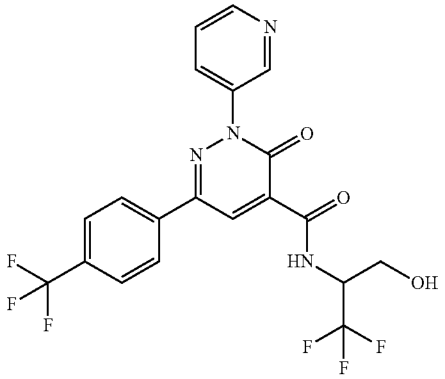

3-Oxo-2-(pyridin-3-yl)-6-[4-(trifluoromethyl)phenyl]-2,3-dihydropyridazine-4-carboxylic acid (100 mg, 0.277 mmol) was dissolved in anhydrous DMF (2.1 mL). (2RS)-2-Amino-3,3,3-trifluoropropan-1-ol (71.5 mg, 0.55 mmol), N-ethyl-N-isopropylpropan-2-amine (217 μL, 1.25 mmol), and propane phosphonic acid anhydride (T3P, 243 μL, 50% in DMF, 415 μmol) were successively added. It was stirred at rt overnight. The reaction mixture was diluted with dichloromethane and concentrated under vacuum. The residue was purified by RP-HPLC (column: X-Bridge C18 5 μm 100x30 mm, mobile phase: (water+0.2 vol % aqueous ammonia (32%))/acetonitrile, gradient) affording 64.4 mg (49%) of the title compound.

$^1$H-NMR (400 MHz, DMSO-$d_6$): δ [ppm]=3.66-3.75 (m, 1H), 3.83 (dd, 1H), 4.81-4.91 (m, 1H), 5.43 (br s, 1H), 7.65 (ddd, 1H), 7.89 (d, 2H), 8.19 (ddd, 1H), 8.23 (d, 2H), 8.72 (dd, 1H), 8.80 (s, 1H), 8.93 (d, 1H), 9.96 (d, 1H).

Example 111

N-[(2S)-1-Hydroxy-3-methoxypropan-2-yl]-3-oxo-2-(pyridin-3-yl)-6-[4-(trifluoromethyl)phenyl]-2,3-dihydropyridazine-4-carboxamide

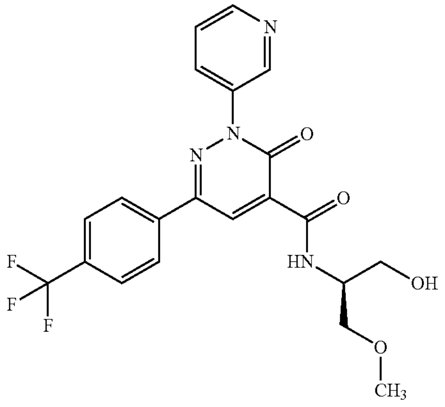 [SMILES: COC[C@H](CO)NC(=O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (2S)-2-Amino-3-methoxypropan-1-ol (29.1 mg, 0.28 mmol), N-ethyl-N-isopropylpropan-2-amine (109 μL, 0.62 mmol), and propane phosphonic acid anhydride (T3P, 122 μL, 50% in DMF, 208 μmol) were successively added. It was stirred at rt overnight. The reaction mixture was diluted with dichloromethane and concentrated under vacuum. The residue was purified by RP-HPLC (column: X-Bridge C18 5 μm 100x30 mm, mobile phase: (water+0.1 vol % formic acid (99%))/acetonitrile, gradient) yielding 26 mg (42%) of the title compound.

$^1$H-NMR (400 MHz, DMSO-$d_6$): δ [ppm]=3.28 (s, 3H), 3.42-3.59 (m, 4H), 4.09-4.18 (m, 1H), 4.98 (t, 1H), 7.64 (ddd, 1H), 7.89 (d, 2H), 8.18 (ddd, 1H), 8.21 (d, 2H), 8.71 (dd, 1H), 8.75 (s, 1H), 8.92 (dd, 1H), 9.50 (d, 1H).

$[\alpha]_D^{20}$=+15.1° (c=1.00, methanol).

Example 112

3-Oxo-2-(pyridin-3-yl)-N-[(2R)-1,1,1-trifluoro-3-hydroxypropan-2-yl]-6-[4-(trifluoromethyl)phenyl]-2,3-dihydropyridazine-4-carboxamide

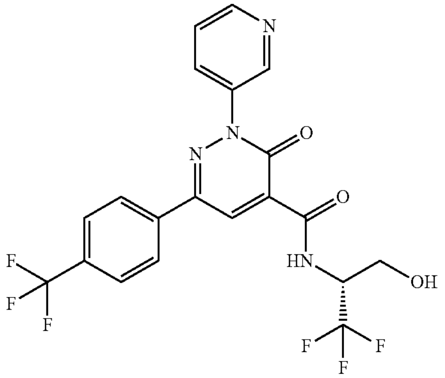 [SMILES: O=C(N[C@H](CO)C(F)(F)F)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (2R)-2-Amino-3,3,3-trifluoropropan-1-ol hydrochloride (1:1) (45.8 mg, 0.28 mmol), N-ethyl-N-isopropylpropan-2-amine (108.5 μL, 0.62 mmol), and propane phosphonic acid anhydride (T3P, 121.2 μL, 50% in DMF, 208 μmol) were successively added. It was stirred at rt overnight. The reaction mixture was diluted with dichloromethane and concentrated under vacuum. The residue was purified by RP-HPLC (column: X-Bridge C18 5 μm 100x30 mm, mobile phase: (water+0.2 vol % aqueous ammonia (32%))/acetonitrile, gradient) to obtain 17 mg (26%) of the title compound.

$^1$H-NMR (400 MHz, DMSO-$d_6$): δ [ppm]=3.66-3.74 (m, 1H), 3.79-3.86 (m, 1H), 4.81-4.92 (m, 1H), 5.45 (br t, 1H), 7.65 (ddd, 1H), 7.89 (d, 2H), 8.19 (ddd, 1H), 8.23 (d, 2H), 8.72 (dd, 1H), 8.80 (s, 1H), 8.93 (d, 1H), 9.96 (d, 1H).

$[\alpha]_D^{20}$=+13.2° (c=1.00, methanol).

Example 113

N-[(2R)-2,3-Dihydroxypropyl]-3-oxo-2-(pyridin-3-yl)-6-[4-(trifluoromethyl)phenyl]-2,3-dihydropyridazine-4-carboxamide

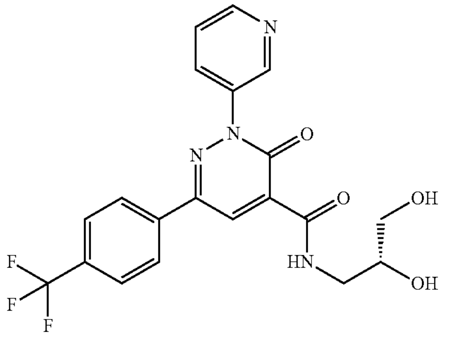 [SMILES: O=C(NC[C@@H](O)CO)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (2R)-3-Aminopropane-1,2-diol (25.2 mg, 0.28 mmol), N-ethyl-N-isopropylpropan-2-amine (108.5 μL, 0.62 mmol), and propane phosphonic acid anhydride (T3P, 121.2 μL, 50% in DMF, 208 μmol) were successively added. It was stirred at rt overnight. The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) giving 24.5 mg (41%) of the title compound.

$^1$H-NMR (400 MHz, DMSO-$d_6$): δ [ppm]=3.20-3.32 (m, 2H), 3.37-3.43 (m, 1H), 3.56-3.65 (m, 2H), 4.70 (t, 1H), 5.01 (d, 1H), 7.64 (ddd, 1H), 7.89 (d, 2H), 8.18 (ddd, 1H), 8.21 (d, 2H), 8.70 (dd, 1H), 8.74 (s, 1H), 8.93 (dd, 1H), 9.50 (t, 1H).

$[\alpha]_D^{20}$=+0.6° (c=1.00, methanol).

Example 114

N-[(2S)-2,3-Dihydroxypropyl]-3-oxo-2-(pyridin-3-yl)-6-[4-(trifluoromethyl)phenyl]-2,3-dihydropyridazine-4-carboxamide

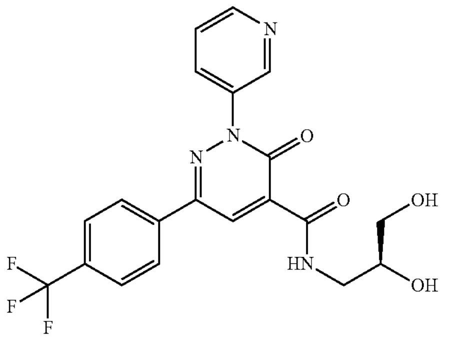 [SMILES: O=C(NC[C@H](O)CO)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.05 mL). (2S)-3-Aminopropane-1,2-diol (25.2 mg, 0.28 mmol), N-ethyl-N-isopropylpropan-2-amine (109 μL, 0.62 mmol), and propane phosphonic acid anhydride (T3P, 122 μL, 50% in DMF, 208 μmol) were successively added. It was stirred at rt overnight. The reaction mixture was diluted with dichloromethane and concentrated under vacuum. The residue was purified by RP-HPLC (column: X-Bridge C18 5 μm 100×30 mm, mobile phase: (water+0.2 vol % aqueous ammonia (32%))/acetonitrile, gradient) giving 17.3 mg (29%) of the title compound.

$^1$H-NMR (400 MHz, DMSO-$d_6$): δ [ppm]=3.20-3.30 (m, 2H), 3.36-3.43 (m, 1H), 3.56-3.65 (m, 2H), 4.70 (br t, 1H), 5.01 (br d, 1H), 7.64 (ddd, 1H), 7.89 (d, 2H), 8.18 (ddd, 1H), 8.21 (d, 2H), 8.70 (dd, 1H), 8.74 (s, 1H), 8.93 (dd, 1H), 9.50 (t, 1H).

$[\alpha]_D^{20}$=−9.7° (c=1.00, methanol).

Example 115

N-(2-Hydroxy-2-methylpropyl)-3-oxo-2-(pyridin-3-yl)-6-[4-(trifluoromethyl)phenyl]-2,3-dihydropyridazine-4-carboxamide

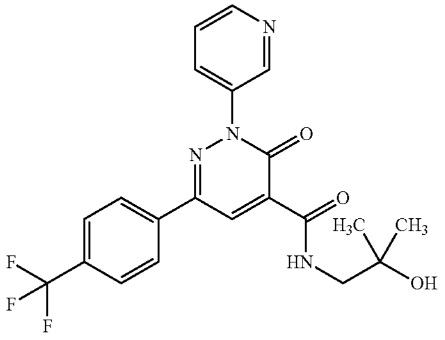 [SMILES: CC(C)(O)CNC(=O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.5 mL). 1-Amino-2-methylpropan-2-ol (21 mg, 0.24 mmol), N-ethyl-N-isopropylpropan-2-amine (108 μL, 0.62 mmol), and propane phosphonic acid anhydride (T3P, 121 μL, 50% in DMF, 208 μmol) were successively added. It was stirred at rt overnight. The reaction mixture was purified by RP-HPLC (column: X-Bridge C18 5 μm 100×30 mm, mobile phase: (water+0.2 vol % aqueous ammonia (32%))/acetonitrile, gradient and column: X-Bridge C18 5 μm 100×30 mm, mobile phase: (water+0.1 vol % formic acid (99%))/acetonitrile, gradient) giving 25 mg (42%) of the title compound.

$^1$H-NMR (400 MHz, DMSO-$d_6$): δ [ppm]=1.13 (s, 6H), 3.31-3.33 (m, 2H and water signal), 4.68 (s, 1H), 7.65 (ddd, 1H), 7.88 (d, 2H), 8.17-8.24 (m, 3H), 8.70 (dd, 1H), 8.74 (s, 1H), 8.93 (d, 1H), 9.50 (t, 1H).

Example 116

N-(1,3-Dihydroxypropan-2-yl)-3-oxo-2-(pyridin-3-yl)-6-[4-(trifluoromethyl)phenyl]-2,3-dihydropyridazine-4-carboxamide

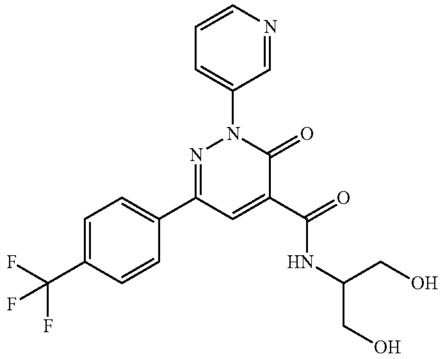 [SMILES: O=C(NC(CO)CO)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.5 mL). 2-Aminopropane-1,3-diol (21 mg, 0.24 mmol), N-ethyl-N-isopropylpropan-2-amine (108 μL, 0.62 mmol), and propane phosphonic acid anhydride (T3P, 121 μL, 50% in DMF, 208 μmol) were successively added. It was stirred at rt overnight. The reaction mixture was purified by RP-HPLC (column: X-Bridge C18 5 μm 100×30 mm, mobile phase: (water+0.2 vol % aqueous ammonia (32%))/acetonitrile, gradient) to afford 33 mg (55%) of the title compound.

$^1$H-NMR (400 MHz, DMSO-$d_6$): δ [ppm]=3.45-3.52 (m, 2H), 3.55-3.62 (m, 2H), 3.93-4.01 (m, 1H), 4.89 (t, 2H), 7.64 (dd, 1H), 7.89 (d, 2H), 8.17 (ddd, 1H), 8.21 (d, 2H), 8.70 (dd, 1H), 8.75 (s, 1H), 8.92 (d, 1H), 9.50 (d, 1H).

Example 117

3-Oxo-2-(pyridin-3-yl)-N-[(2S)-3,3,3-trifluoro-2-hydroxypropyl]-6-[4-(trifluoromethyl)phenyl]-2,3-dihydropyridazine-4-carboxamide

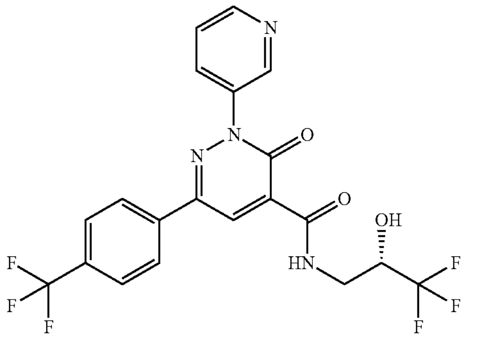

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.5 mL). (2S)-3-Amino-1,1,1-trifluoropropan-2-ol (30 mg, 0.24 mmol), N-ethyl-N-isopropylpropan-2-amine (108 μL, 0.62 mmol), and propane phosphonic acid anhydride (T3P, 121 μL, 50% in DMF, 208 μmol) were successively added. It was stirred at rt overnight. The reaction mixture was purified by RP-HPLC (column: X-Bridge C18 5 μm 100×30 mm, mobile phase: (water+0.2 vol % aqueous ammonia (32%))/acetonitrile, gradient) to yield 32 mg (49%) of the title compound.

$^1$H-NMR (400 MHz, DMSO-$d_6$): δ [ppm]=3.49 (ddd, 1H), 3.72-3.80 (m, 1H), 4.18-4.29 (m, 1H), 6.67 (d, 1H), 7.65 (ddd, 1H), 7.89 (d, 2H), 8.18 (ddd, 1H), 8.22 (d, 2H), 8.71 (dd, 1H), 8.76 (s, 1H), 8.93 (d, 1H), 9.59 (t, 1H).

$[\alpha]_D^{20}$=−12.3° (c=1.00, methanol).

Example 118

N-[(2R)-1-Hydroxypropan-2-yl]-3-oxo-2-(pyridin-3-yl)-6-[4-(trifluoromethyl)phenyl]-2,3-dihydropyridazine-4-carboxamide

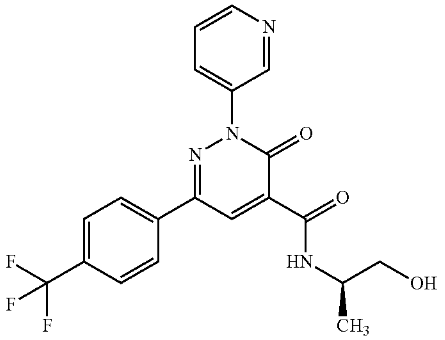 [SMILES: C[C@H](CO)NC(=O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.5 mL). (2R)-2-Aminopropan-1-ol (18 mg, 0.24 mmol), N-ethyl-N-isopropylpropan-2-amine (108 μL, 0.62 mmol), and propane phosphonic acid anhydride (T3P, 121 μL, 50% in DMF, 208 μmol) were successively added. It was stirred at rt overnight. The reaction mixture was purified by RP-HPLC (column: X-Bridge C18 5 μm 100×30 mm, mobile phase: (water+0.2 vol % aqueous ammonia (32%))/acetonitrile, gradient and column: X-Bridge C18 5 μm 100×30 mm, mobile phase: (water+0.1 vol % formic acid (99%))/acetonitrile, gradient) to yield 22 mg (38%) of the title compound.

$^1$H-NMR (400 MHz, DMSO-$d_6$): δ [ppm]=1.17 (d, 3H), 3.40-3.50 (m, 2H), 3.99-4.10 (m, 1H), 4.95 (t, 1H), 7.64 (ddd, 1H), 7.89 (d, 2H), 8.18 (ddd, 1H), 8.21 (d, 2H), 8.70 (dd, 1H), 8.73 (s, 1H), 8.92 (d, 1H), 9.39 (d, 1H).

$[\alpha]_D^{20}$=−8.9° (c=1.00, methanol).

Example 119

N-[(2S)-1-Hydroxypropan-2-yl]-3-oxo-2-(pyridin-3-yl)-6-[4-(trifluoromethyl)phenyl]-2,3-dihydropyridazine-4-carboxamide

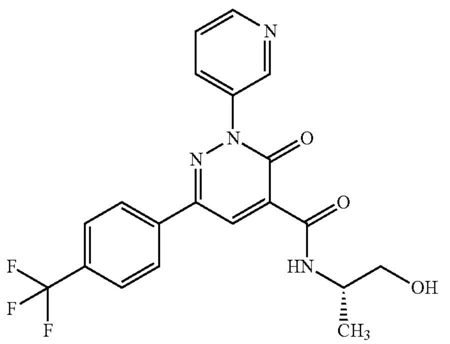 [SMILES: C[C@@H](CO)NC(=O)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (50 mg, 0.138 mmol) was dissolved in anhydrous DMF (1.5 mL). (2S)-2-Aminopropan-1-ol (18 mg, 0.24 mmol), N-ethyl-N-isopropylpropan-2-amine (108 μL, 0.62 mmol), and propane phosphonic acid anhydride (T3P, 121 μL, 50% in DMF, 208 μmol) were successively added. It was stirred at rt overnight. The reaction mixture was purified by RP-HPLC (column: X-Bridge C18 5 μm 100×30 mm, mobile phase: (water+0.2 vol % aqueous ammonia (32%))/acetonitrile, gradient and column: X-Bridge C18 5 μm 100×30 mm, mobile phase: (water+0.1 vol % formic acid (99%))/acetonitrile, gradient) to yield 25 mg (43%) of the title compound.

$^1$H-NMR (400 MHz, DMSO-$d_6$): δ [ppm]=1.17 (d, 3H), 3.40-3.50 (m, 2H), 4.00-4.09 (m, 1H), 4.95 (t, 1H), 7.64 (ddd, 1H), 7.89 (d, 2H), 8.18 (ddd, 1H), 8.21 (d, 2H), 8.70 (dd, 1H), 8.73 (s, 1H), 8.92 (d, 1H), 9.39 (d, 1H).

$[\alpha]_D^{20}$=+12.1 (c=1.00, methanol).

Example 120

6-(4-Chlorophenyl)-N-[(2S)-1-hydroxypropan-2-yl]-3-oxo-2-(pyrimidin-5-yl)-2,3-dihydropyridazine-4-carboxamide

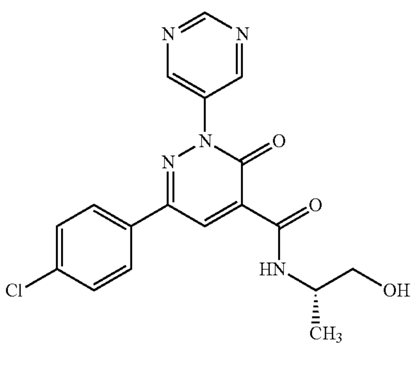 [SMILES: C[C@@H](CO)NC(=O)c1cc(-c2ccc(Cl)cc2)nn(-c2cncnc2)c1=O]

6-(4-Chlorophenyl)-3-oxo-2-(pyrimidin-5-yl)-2,3-dihydropyridazine-4-carboxylic acid (60 mg, 0.183 mmol) was dissolved in anhydrous DMF (1.4 mL). (2S)-2-Aminopropan-1-ol (27.4 mg, 0.37 mmol), N-ethyl-N-isopropylpropan-2-amine (143 μL, 0.82 mmol), and propane phosphonic acid anhydride (T3P, 160 μL, 50% in DMF, 274 μmol) were successively added. It was stirred for 24 h at 55° C. The reaction mixture was purified by RP-HPLC (column: X-Bridge C18 5 μm 100×30 mm, mobile phase: (water+0.2 vol % aqueous ammonia (32%))/acetonitrile, gradient and column: X-Bridge C18 5 μm 100×30 mm, mobile phase: (water+0.1 vol % formic acid (99%))/acetonitrile, gradient) to yield 5.3 mg (8%) of the title compound.

$^1$H-NMR (400 MHz, DMSO-$d_6$): δ [ppm]=1.17 (d, 3H), 3.40-3.50 (m, 2H), 3.99-4.10 (m, 1H), 4.96 (t, 1H), 7.58-7.62 (m, 2H), 8.03-8.07 (m, 2H), 8.68 (s, 1H), 9.25 (s, 2H), 9.29-9.32 (m, 2H).

$[\alpha]_D^{20}$=+1.1 (c=1.00, methanol).

Example 121

6-(4-Chlorophenyl)-3-oxo-2-(pyridin-3-yl)-N-(1,1,1-trifluoro-3-hydroxy-3-methyl butan-2-yl)-2,3-dihydropyridazine-4-carboxamide

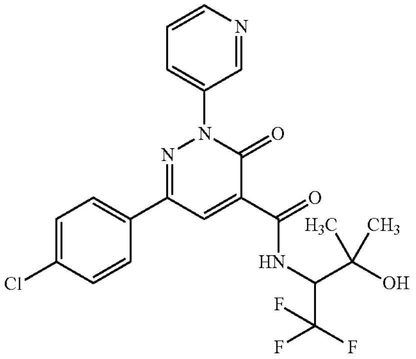 [SMILES: CC(C)(O)C(NC(=O)c1cc(-c2ccc(Cl)cc2)nn(-c2cccnc2)c1=O)C(F)(F)F]

A solution of 150 mg intermediate 6-(4-chlorophenyl)-3-oxo-2-(pyridin-3-yl)-2,3-dihydropyridazine-4-carboxylic acid, 177 mg 3-amino-4,4,4-trifluoro-2-methylbutan-2-ol hydrochloride (1:1), 348 mg HATU, 0.32 mL ethyldiisopropylamine and 4 mg 4-dimethylaminopyridine in 3 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 98 mg of the title compound.

$^1$H NMR (400 MHz, DMSO-$d_6$) δ [ppm]=1.19 (s, 3H), 1.34 (s, 3H), 4.66 (quin, 1H), 5.21 (s, 1H), 7.56-7.61 (m, 2H), 7.64 (dd, 1H), 8.00-8.06 (m, 2H), 8.16-8.22 (m, 1H), 8.70 (dd, 1H), 8.74 (s, 1H), 8.93 (d, 1H), 10.01 (d, 1H).

Example 122

6-(4-Chlorophenyl)-3-oxo-2-(pyridin-3-yl)-N-(1,1,1-trifluoro-3-hydroxy-3-methylbutan-2-yl)-2,3-dihydropyridazine-4-carboxamide, Enantiomer 1

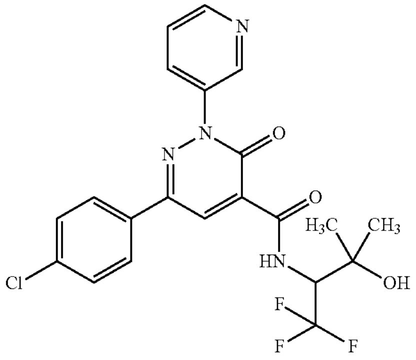 [SMILES: CC(C)(O)C(NC(=O)c1cc(-c2ccc(Cl)cc2)nn(-c2cccnc2)c1=O)C(F)(F)F]

HPLC-separation of 92 mg 6-(4-chlorophenyl)-3-oxo-2-(pyridin-3-yl)-N-(1,1,1-trifluoro-3-hydroxy-3-methylbutan-2-yl)-2,3-dihydropyridazine-4-carboxamide (example 121) on a chiral column (instrument: Labomatic HD5000, Labocord-5000; Gilson GX-241, Labcol Vario 4000, column: Chiralpak IA 5μ 250×30 mm; eluent A: methanol; eluent B: ethanol; isocratic: 50% A+50% B; flow 40.0 mL/min; UV 254 nm) yielded 36 mg 6-(4-chlorophenyl)-3-oxo-2-(pyridin-3-yl)-N-(1,1,1-trifluoro-3-hydroxy-3-methylbutan-2-yl)-2,3-dihydropyridazine-4-carboxamide, enantiomer 1.

Chiral HPLC: Rt=1.74 min (instrument: Agilent HPLC 1260; column: Chiralpak IA 3μ100×4.6 mm; eluent A: methanol+0.1 vol-% diethylamine (99%); eluent B: ethanol; isocratic: 50% A+50% B; flow 1.4 mL/min; temperature: 25° C.; DAD 254 nm).

Example 123

6-(4-Chlorophenyl)-3-oxo-2-(pyridin-3-yl)-N-(1,1,1-trifluoro-3-hydroxy-3-methylbutan-2-yl)-2,3-dihydropyridazine-4-carboxamide, Enantiomer 2

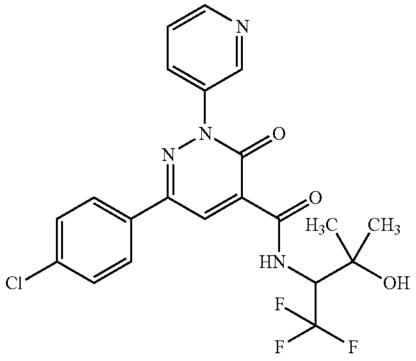 [SMILES: CC(C)(O)C(NC(=O)c1cc(-c2ccc(Cl)cc2)nn(-c2cccnc2)c1=O)C(F)(F)F]

HPLC-separation of 92 mg 6-(4-chlorophenyl)-3-oxo-2-(pyridin-3-yl)-N-(1,1,1-trifluoro-3-hydroxy-3-methylbutan-2-yl)-2,3-dihydropyridazine-4-carboxamide (example 121) on a chiral column (instrument: Labomatic HD5000, Labocord-5000; Gilson GX-241, Labcol Vario 4000, column: Chiralpak IA 5μ 250×30 mm; eluent A: methanol; eluent B: ethanol; isocratic: 50% A+50% B; flow 40.0 mL/min; UV 254 nm) yielded 37.5 mg 6-(4-chlorophenyl)-3-oxo-2-(pyridin-3-yl)-N-(1,1,1-trifluoro-3-hydroxy-3-methylbutan-2-yl)-2,3-dihydropyridazine-4-carboxamide, enantiomer 2.

Chiral HPLC: Rt=2.27 min (instrument: Agilent HPLC 1260; column: Chiralpak IA 3μ 100×4.6 mm; eluent A: methanol+0.1 vol-% diethylamine (99%); eluent B: ethanol; isocratic: 50% A+50% B; flow 1.4 mL/min; temperature: 25° C.; DAD 254 nm).

Example 124

6-(4-Chlorophenyl)-2-(5-fluoropyridin-3-yl)-N-[(1S,2R)-2-hydroxycyclohexyl]-3-oxo-2,3-dihydropyridazine-4-carboxamide

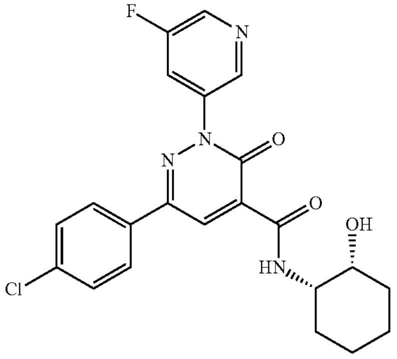 [SMILES: O=C(N[C@H]1CCCC[C@H]1O)c1cc(-c2ccc(Cl)cc2)nn(-c2cncc(F)c2)c1=O]

A solution of 75 mg intermediate 6-(4-chlorophenyl)-2-(5-fluoropyridin-3-yl)-3-oxo-2,3-dihydropyridazine-4-carboxylic acid, 66 mg (1R,2S)-2-aminocyclohexanol hydrochloride (1:1), 165 mg HATU, 0.11 mL ethyldiisopropylamine and 1.5 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 12 mg 6-(4-chlorophenyl)-2-(5-fluoropyridin-3-yl)-N-[(1S,2R)-2-hydroxycyclohexyl]-3-oxo-2,3-dihydropyridazine-4-carboxamide.

$^1H$ NMR (400 MHz, DMSO-$d_6$) δ [ppm]=1.33 (br d, 2H), 1.47-1.70 (m, 6H), 3.77 (br d, 1H), 3.86-3.95 (m, 1H), 4.89 (d, 1H), 7.55-7.62 (m, 2H), 7.99-8.05 (m, 2H), 8.22-8.28 (m, 1H), 8.68 (s, 1H), 8.76 (d, 1H), 8.85 (t, 1H), 9.55 (d, 1H).

Example 125

6-(4-Chlorophenyl)-N-[(1S,2R)-2-hydroxycyclohexyl]-3-oxo-2-(pyridin-3-yl)-2,3-dihydropyridazine-4-carboxamide

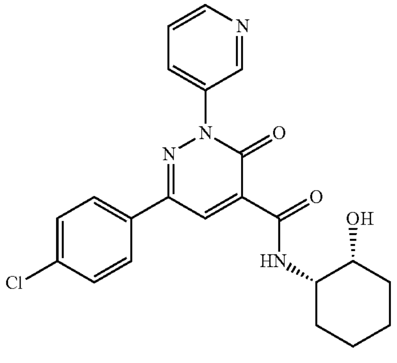 [SMILES: O=C(N[C@H]1CCCC[C@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 69 mg (1R,2S)-2-aminocyclohexanol hydrochloride (1:1), 165 mg HATU, 0.16 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 31 mg 6-(4-chlorophenyl)-N-[(1S,2R)-2-hydroxycyclohexyl]-3-oxo-2-(pyridin-3-yl)-2,3-dihydropyridazine-4-carboxamide.

$^1$H NMR (400 MHz, DMSO-$d_6$) δ [ppm]=1.24-1.38 (m, 2H), 1.47-1.70 (m, 6H), 3.77 (br s, 1H), 3.87-3.96 (m, 1H), 4.87 (d, 1H), 7.58 (d, 2H), 7.63 (dd, 1H), 8.00 (d, 2H), 8.13-8.19 (m, 1H), 8.67 (s, 1H), 8.69 (br d, 1H), 8.91 (s, 1H), 9.62 (d, 1H).

Example 126

N-[(1S,2R)-2-Hydroxycyclohexyl]-3-oxo-2-(pyridin-3-yl)-6-[4-(trifluoromethoxy)phenyl]-2,3-dihydropyridazine-4-carboxamide

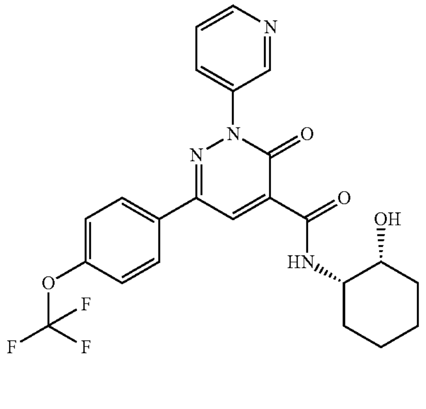 [SMILES: O=C(N[C@H]1CCCC[C@H]1O)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 60 mg (1R,2S)-2-aminocyclohexanol hydrochloride (1:1), 151 mg HATU, 0.14 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 17 mg N-[(1S,2R)-2-hydroxycyclohexyl]-3-oxo-2-(pyridin-3-yl)-6-[4-(trifluoromethoxy)phenyl]-2,3-dihydropyridazine-4-carboxamide.

$^1$H NMR (400 MHz, DMSO-$d_6$) δ [ppm]=1.32 (br s, 2H), 1.46-1.69 (m, 6H), 3.77 (br s, 1H), 3.87-3.98 (m, 1H), 4.88 (d, 1H), 7.51 (d, 2H), 7.63 (dd, 1H), 8.08-8.13 (m, 2H), 8.14-8.19 (m, 1H), 8.67-8.72 (m, 2H), 8.91 (d, 1H), 9.62 (d, 1H).

Example 127

6-[4-(Difluoromethyl)phenyl]-3-oxo-2-(pyridin-3-yl)-N-[(2R)-1,1,1-trifluoro-3-hydroxypropan-2-yl]-2,3-dihydropyridazine-4-carboxamide

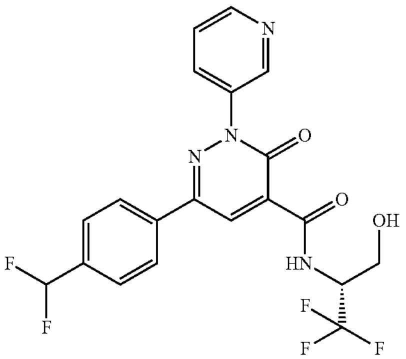 [SMILES: O=C(N[C@H](CO)C(F)(F)F)c1cc(-c2ccc(C(F)F)cc2)nn(-c2cccnc2)c1=O]

A solution of 65 mg intermediate 6-[4-(difluoromethyl)phenyl]-3-oxo-2-(pyridin-3-yl)-2,3-dihydropyridazine-4-carboxylic acid, 60 mg (2R)-2-amino-3,3,3-trifluoropropan-1-ol hydrochloride (1:1), 144 mg HATU, 0.1 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 37 mg 6-[4-(difluoromethyl)phenyl]-3-oxo-2-(pyridin-3-yl)-N-[(2R)-1,1,1-trifluoro-3-hydroxypropan-2-yl]-2,3-dihydropyridazine-4-carboxamide.

$^1$H NMR (400 MHz, DMSO-$d_6$) δ [ppm]=3.65-3.75 (m, 1H), 3.83 (dt, 1H), 4.81-4.92 (m, 1H), 5.44 (t, 1H), 7.13 (t, 1H), 7.65 (dd, 1H), 7.73 (d, 2H), 8.15 (d, 2H), 8.17-8.22 (m, 1H), 8.69-8.74 (m, 1H), 8.78 (s, 1H), 8.93 (d, 1H), 9.97 (d, 1H).

Example 128

6-(4-Chlorophenyl)-2-(5-fluoropyridin-3-yl)-3-oxo-N-[(2S)-3,3,3-trifluoro-2-hydroxypropyl]-2,3-dihydropyridazine-4-carboxamide

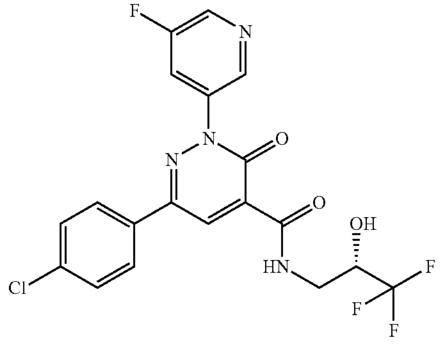 [SMILES: O=C(NC[C@H](O)C(F)(F)F)c1cc(-c2ccc(Cl)cc2)nn(-c2cncc(F)c2)c1=O]

A solution of 75 mg intermediate 6-(4-chlorophenyl)-2-(5-fluoropyridin-3-yl)-3-oxo-2,3-dihydropyridazine-4-carboxylic acid, 56 mg (2S)-3-amino-1,1,1-trifluoropropan-2-ol, 165 mg HATU, 0.11 mL ethyldiisopropylamine and 1.5 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 14 mg 6-(4-chlorophenyl)-2-(5-fluoropyridin-3-yl)-3-oxo-N-[(2S)-3,3,3-trifluoro-2-hydroxypropyl]-2,3-dihydropyridazine-4-carboxamide.

$^1$H NMR (400 MHz, DMSO-$d_6$) δ [ppm]=3.48 (ddd, 1H), 3.69-3.80 (m, 1H), 4.23 (br s, 1H), 6.67 (d, 1H), 7.55-7.63 (m, 2H), 8.00-8.07 (m, 2H), 8.23-8.27 (m, 1H), 8.69 (s, 1H), 8.77 (d, 1H), 8.87 (d, 1H), 9.54 (t, 1H).

Example 129

6-(4-Chlorophenyl)-2-(5-fluoropyridin-3-yl)-N-[(1S,2R)-2-hydroxycyclopentyl]-3-oxo-2,3-dihydropyridazine-4-carboxamide

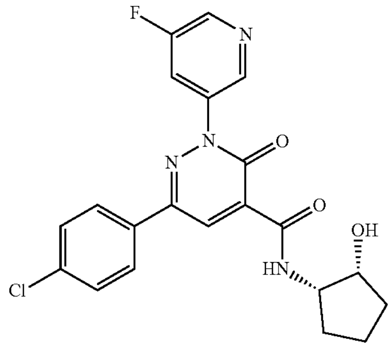 [SMILES: O=C(N[C@H]1CCC[C@H]1O)c1cc(-c2ccc(Cl)cc2)nn(-c2cncc(F)c2)c1=O]

A solution of 75 mg intermediate 6-(4-chlorophenyl)-2-(5-fluoropyridin-3-yl)-3-oxo-2,3-dihydropyridazine-4-carboxylic acid, 60 mg (1R,2S)-2-aminocyclopentanol hydrochloride (1:1), 165 mg HATU, 0.11 mL ethyldiisopropylamine and 1.5 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 18 mg 6-(4-chlorophenyl)-2-(5-fluoropyridin-3-yl)-N-[(1S,2R)-2-hydroxycyclopentyl]-3-oxo-2,3-dihydropyridazine-4-carboxamide.

$^1$H NMR (400 MHz, DMSO-$d_6$) δ[ppm]=1.47-1.64 (m, 3H), 1.70-1.89 (m, 2H), 1.93-2.04 (m, 1H), 3.99-4.12 (m, 2H), 5.06 (d, 1H), 7.56-7.61 (m, 2H), 7.99-8.06 (m, 2H), 8.24 (dt, 1H), 8.68 (s, 1H), 8.76 (d, 1H), 8.85 (t, 1H), 9.62 (d, 1H).

Example 130

6-(4-Chlorophenyl)-N-[(1S,2S)-2-hydroxycyclopentyl]-3-oxo-2-(pyridin-3-yl)-2,3-dihydropyridazine-4-carboxamide

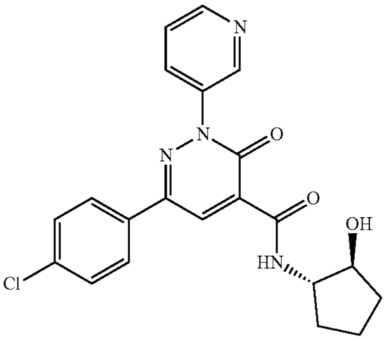 [SMILES: O=C(N[C@H]1CCC[C@@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 62 mg (1S,2S)-2-aminocyclopentanol hydrochloride (1:1), 174 mg HATU, 0.16 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 31 mg 6-(4-chlorophenyl)-N-[(1S,2S)-2-hydroxycyclopentyl]-3-oxo-2-(pyridin-3-yl)-2,3-dihydropyridazine-4-carboxamide.

$^1$H NMR (400 MHz, DMSO-$d_6$) δ [ppm]=1.39-1.55 (m, 2H), 1.58-1.76 (m, 2H), 1.77-1.88 (m, 1H), 2.03-2.14 (m, 1H), 3.90-3.96 (m, 1H), 3.98-4.06 (m, 1H), 4.94 (d, 1H), 7.56-7.61 (m, 2H), 7.63 (dd, 1H), 7.98-8.03 (m, 2H), 8.16 (ddd, 1H), 8.65 (s, 1H), 8.69 (dd, 1H), 8.91 (d, 1H), 9.31 (d, 1H).

$[\alpha]_D^{20}$=+34.5 (c=1.00, DMSO).

Example 131

3-Oxo-2-(pyridin-3-yl)-N-[(2S)-3,3,3-trifluoro-2-hydroxypropyl]-6-[4-(trifluoromethoxy)phenyl]-2,3-dihydropyridazine-4-carboxamide

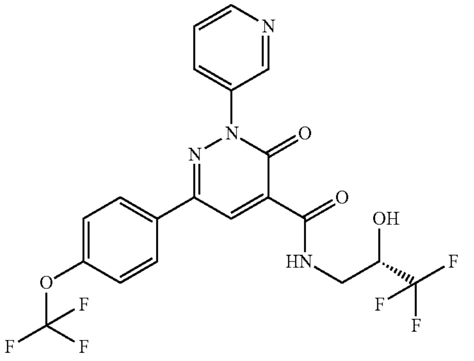 [SMILES: O=C(NC[C@H](O)C(F)(F)F)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 51 mg (2S)-3-amino-1,1,1-trifluoropropan-2-ol, 151 mg HATU, 0.14 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 24 mg 3-oxo-2-(pyridin-3-yl)-N-[(2S)-3,3,3-trifluoro-2-hydroxypropyl]-6-[4-(trifluoromethoxy)phenyl]-2,3-dihydropyridazine-4-carboxamide.

$^1$H NMR (400 MHz, DMSO-$d_6$) δ [ppm]=3.48 (ddd, 1H), 3.72-3.80 (m, 1H), 4.18-4.28 (m, 1H), 6.66 (d, 1H), 7.52 (d, 2H), 7.64 (dd, 1H), 8.08-8.15 (m, 2H), 8.15-8.20 (m, 1H), 8.67-8.72 (m, 2H), 8.93 (d, 1H), 9.61 (t, 1H).

Chiral HPLC: Rt=1.74 min (instrument: Agilent HPLC 1260; column: YMC Amylose SA 3μ 100×4.6 mm; eluent A: methanol+0.1 Vol-% diethylamine (99%), eluent B: ethanol; isocratic: 50% A+50% B; flow 1.4 ml/min; temperature: 25° C.; DAD 254 nm.

$[\alpha]_D^{20}$=−8.4 (c=1.00, DMSO).

Example 132

N-[(1S,2S)-2-Hydroxycyclopentyl]-3-oxo-2-(pyridin-3-yl)-6-[4-(trifluoromethoxy)phenyl]-2,3-dihydropyridazine-4-carboxamide

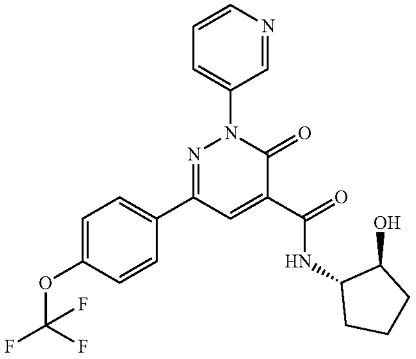 [SMILES: O=C(N[C@H]1CCC[C@@H]1O)c1cc(-c2ccc(OC(F)(F)F)cc2)nn(-c2cccnc2)c1=O]

A solution of 150 mg intermediate 3-oxo-2-(pyridin-3-yl)-6-[4-(trifluoromethoxy)phenyl]-2,3-dihydropyridazine-4-carboxylic acid, 109 mg (1S,2S)-2-amino-cyclopentanol, 302 mg HATU, 0.28 mL ethyldiisopropylamine and 2 mg 4-dimethylaminopyridine in 3 mL of DMF was stirred at 40° C. for 3 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 75 mg N-[(1S,2S)-2-hydroxycyclopentyl]-3-oxo-2-(pyridin-3-yl)-6-[4-(trifluoromethoxy)phenyl]-2,3-dihydropyridazine-4-carboxamide.

$^1$H NMR (400 MHz, DMSO-$d_6$) δ[ppm]=1.39-1.55 (m, 2H), 1.57-1.67 (m, 1H), 1.67-1.76 (m, 1H), 1.77-1.87 (m, 1H), 2.03-2.14 (m, 1H), 3.90-3.97 (m, 1H), 3.98-4.06 (m, 1H), 4.95 (d, 1H), 7.51 (d, 2H), 7.63 (dd, 1H), 8.09-8.13 (m, 2H), 8.14-8.19 (m, 1H), 8.66 (s, 1H), 8.69 (d, 1H), 8.91 (d, 1H), 9.31 (d, 1H).

Example 133

6-(4-Chlorophenyl)-N-[(cis)-2-hydroxycyclohexyl]-3-oxo-2-(pyridin-3-yl)-2,3-dihydropyridazine-4-carboxamide

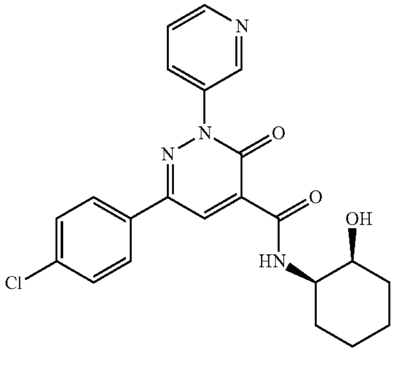 [SMILES: O=C(N[C@@H]1CCCC[C@@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 69 mg cis-2-amino-1-cyclohexanol hydrochloride (1:1), 174 mg HATU, 0.16 mL ethyldiisopropylamine and 1 mg 4-dimethylaminopyridine in 2 mL of DMF was stirred at room temperature for 48 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 39 mg 6-(4-chlorophenyl)-N-[(cis)-2-hydroxycyclohexyl]-3-oxo-2-(pyridin-3-yl)-2,3-dihydropyridazine-4-carboxamide.

$^1H$ NMR (400 MHz, DMSO-$d_6$) δ [ppm]=1.26-1.37 (m, 2H), 1.46-1.69 (m, 6H), 3.77 (m, 1H), 3.86-3.97 (m, 1H), 4.88 (d, 1H), 7.55-7.60 (m, 2H), 7.63 (dd, 1H), 7.97-8.03 (m, 2H), 8.13-8.19 (m, 1H), 8.67 (s, 1H), 8.69 (dd, 1H), 8.91 (d, 1H), 9.62 (d, 1H).

Example 134

3-Oxo-2-(pyridin-3-yl)-N-[(2R)-1,1,1-trifluoro-3-hydroxypropan-2-yl]-6-[4-(trifluoromethoxy)phenyl]-2,3-dihydropyridazine-4-carboxamide

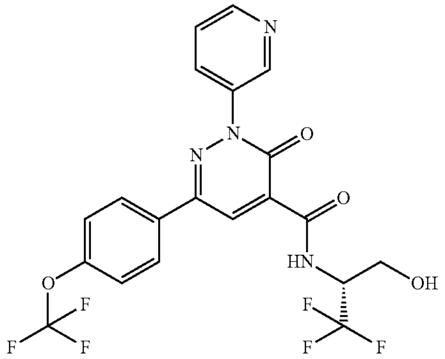 [SMILES: O=C(N[C@H](CO)C(F)(F)F)c1cc(-c2ccc(OC(F)(F)F)cc2)nn(-c2cccnc2)c1=O]

A solution of 52 mg intermediate 3-oxo-2-(pyridin-3-yl)-6-[4-(trifluoromethoxy)phenyl]-2,3-dihydropyridazine-4-carboxylic acid, 46.6 mg (2R)-2-amino-3,3,3-trifluoropropan-1-ol hydrochloride (1:1), 105 mg HATU, 0.07 mL ethyldiisopropylamine and 1 mg 4-dimethylaminopyridine in 1 mL of DMF was stirred at 40° C. for 3 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 70%/B 30%→A 30%/B 70%; flow: 150 mL/min; UV-detection: 254 nm) to yield 24 mg 3-oxo-2-(pyridin-3-yl)-N-[(2R)-1,1,1-trifluoro-3-hydroxypropan-2-yl]-6-[4-(trifluoro-methoxy)phenyl]-2,3-dihydropyridazine-4-carboxamide.

$^1H$ NMR (400 MHz, DMSO-$d_6$) δ [ppm]=3.65-3.74 (m, 1H), 3.82 (dt, 1H), 4.80-4.91 (m, 1H), 5.44 (t, 1H), 7.52 (d, 2H), 7.64 (dd, 1H), 8.10-8.16 (m, 2H), 8.16-8.21 (m, 1H), 8.71 (dd, 1H), 8.75 (s, 1H), 8.92 (d, 1H), 9.98 (d, 1H).

$[\alpha]_D^{20}$=10.2° (c=1.00, DMSO).

Example 135

3-Oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide

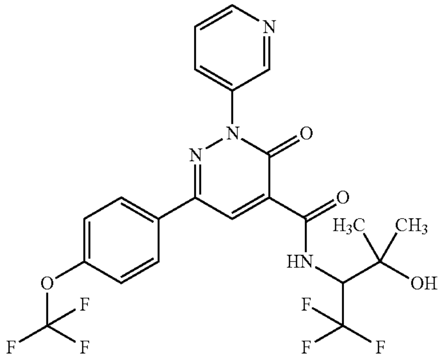 [SMILES: CC(C)(O)C(NC(=O)c1cc(-c2ccc(OC(F)(F)F)cc2)nn(-c2cccnc2)c1=O)C(F)(F)F]

A solution of 150 mg intermediate 3-oxo-2-(pyridin-3-yl)-6-[4-(trifluoromethoxy)phenyl]-2,3-dihydropyridazine-4-carboxylic acid, 154 mg 3-amino-4,4,4-trifluoro-2-methylbutan-2-ol hydrochloride (1:1), 302 mg HATU, 0.3 mL ethyldiisopropylamine and 4 mg 4-dimethylaminopyridine in 3 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 70%/B 30%→A 30%/B 70%; flow: 150 mL/min; UV-detection: 254 nm) to yield 63 mg 3-oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide.

$^1H$ NMR (400 MHz, DMSO-$d_6$) δ [ppm]=1.20 (s, 3H), 1.34 (s, 3H), 4.67 (quin, 1H), 5.22 (s, 1H), 7.51 (d, 2H), 7.61-7.67 (m, 1H), 8.11-8.15 (m, 2H), 8.19 (ddd, 1H), 8.70 (dd, 1H), 8.75 (s, 1H), 8.93 (d, 1H), 10.02 (d, 1H).

Example 136

3-Oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide, Enantiomer 1

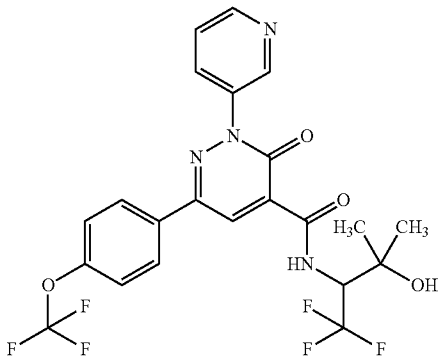 [SMILES: CC(C)(O)C(NC(=O)c1cc(-c2ccc(OC(F)(F)F)cc2)nn(-c2cccnc2)c1=O)C(F)(F)F]

HPLC-separation of 58 mg 3-oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide (example 135) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 50.0 mL/min; UV 254 nm) yielded 23 mg 3-oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide, enantiomer 1.

Chiral HPLC: Rt=1.57 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

Example 137

3-Oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide, Enantiomer 2

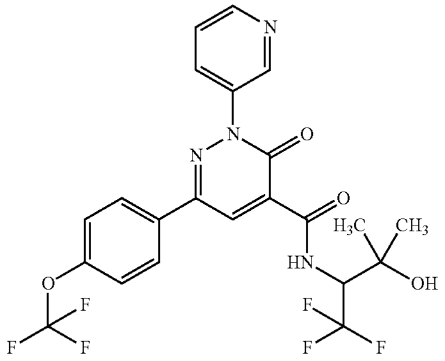 [SMILES: CC(C)(O)C(NC(=O)c1cc(-c2ccc(OC(F)(F)F)cc2)nn(-c2cccnc2)c1=O)C(F)(F)F]

HPLC-separation of 58 mg 3-oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide (example 135) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 50.0 mL/min; UV 254 nm) yielded 20 mg 3-oxo-2-(pyridin-3-yl)-N-[1,1,1-trifluoro-3-hydroxy-3-methylbutan-2-yl]-6-[4-(trifluoromethoxy)phenyl]-2,3-dihydropyridazine-4-carboxamide, enantiomer 2.

Chiral HPLC: Rt=3.29 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

Example 138

6-(4-Chlorophenyl)-N-[(1R,2S)-2-hydroxycyclopentyl]-3-oxo-2-(pyridin-3-yl)-2,3-dihydropyridazine-4-carboxamide

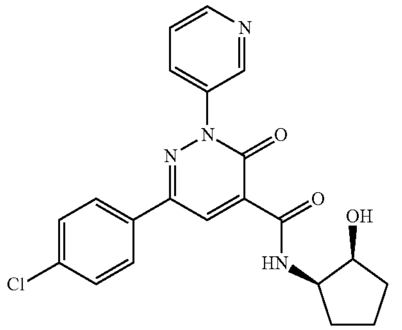 [SMILES: O=C(N[C@@H]1CCC[C@@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 63 mg (1S,2R)-2-aminocyclopentanol hydrochloride (1:1), 174 mg HATU, 0.16 mL ethyldiisopropylamine and 1 mg 4-dimethylaminopyridine in 2 mL of DMF was stirred at room temperature for 90 min. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 35 mg 6-(4-chlorophenyl)-N-[(1R,2S)-2-hydroxycyclopentyl]-3-oxo-2-(pyridin-3-yl)-2,3-dihydropyridazine-4-carboxamide.

$^1H$ NMR (400 MHz, DMSO-$d_6$) δ[ppm]=1.46-1.64 (m, 3H), 1.70-1.88 (m, 2H), 1.92-2.03 (m, 1H), 3.99-4.12 (m, 2H), 5.04 (d, 1H), 7.56-7.61 (m, 2H), 7.61-7.66 (m, 1H), 7.97-8.03 (m, 2H), 8.16 (ddd, 1H), 8.66-8.70 (m, 2H), 8.91 (d, 1H), 9.67 (d, 1H).

Example 139

6-[4-(Difluoromethyl)phenyl]-N-[(1S,2S)-2-hydroxycyclopentyl]-3-oxo-2-(pyridin-3-yl)-2,3-dihydropyridazine-4-carboxamide

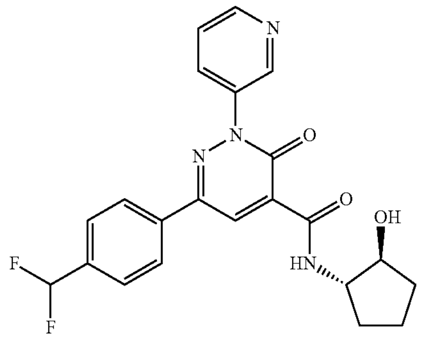 [SMILES: O=C(N[C@H]1CCC[C@@H]1O)c1cc(-c2ccc(C(F)F)cc2)nn(-c2cccnc2)c1=O]

A solution of 65 mg intermediate 6-[4-(difluoromethyl)phenyl]-3-oxo-2-(pyridin-3-yl)-2,3-dihydropyridazine-4-carboxylic acid, 60 mg (1S,2S)-2-aminocyclopentanol hydrochloride (1:1), 144 mg HATU, 0.1 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 13 mg 6-[4-(difluoromethyl)phenyl]-N-[(1S,2S)-2-hydroxycyclopentyl]-3-oxo-2-(pyridin-3-yl)-2,3-dihydropyridazine-4-carboxamide.

$^1$H NMR (400 MHz, DMSO-$d_6$) δ [ppm]=1.39-1.56 (m, 2H), 1.58-1.76 (m, 2H), 1.77-1.87 (m, 1H), 2.04-2.14 (m, 1H), 3.94 (br d, 1H), 3.98-4.07 (m, 1H), 4.95 (br d, 1H), 7.13 (t, 1H), 7.64 (dd, 1H), 7.72 (d, 2H), 8.13 (d, 2H), 8.15-8.20 (m, 1H), 8.66-8.72 (m, 2H), 8.92 (d, 1H), 9.31 (d, 1H).

Example 140

N-[(trans)-3,3-Difluoro-2-hydroxycyclohexyl]-3-oxo-2-(pyridin-3-yl)-6-[4-(trifluoromethoxy)phenyl]-2,3-dihydropyridazine-4-carboxamide

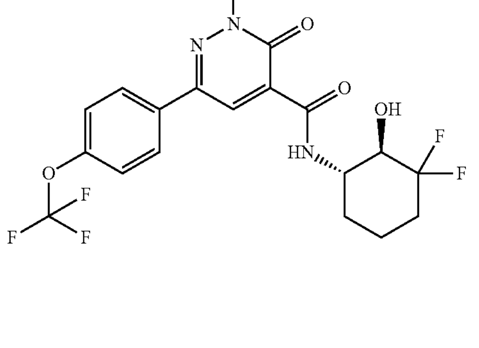

A solution of 150 mg intermediate 3-oxo-2-(pyridin-3-yl)-6-[4-(trifluoromethoxy)phenyl]-2,3-dihydropyridazine-4-carboxylic acid, 149 mg trans-6-amino-2,2-difluorocyclohexan-1-ol hydrochloride (1:1), 302 mg HATU, 0.3 mL ethyldiisopropylamine and 4 mg 4-dimethylaminopyridine in 3 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 70%/B 30%→A 30%/B 70%; flow: 150 mL/min; UV-detection: 254 nm) to yield 66 mg N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide.

$^1$H NMR (400 MHz, DMSO-$d_6$) δ [ppm]=1.40-1.54 (m, 2H), 1.66 (br s, 1H), 1.72-1.90 (m, 1H), 1.94-2.11 (m, 2H), 3.69-3.82 (m, 1H), 3.97 (br s, 1H), 5.78 (d, 1H), 7.52 (d, 2H), 7.64 (dd, 1H), 8.08-8.14 (m, 2H), 8.15-8.20 (m, 1H), 8.68-8.72 (m, 2H), 8.92 (d, 1H), 9.52 (d, 1H).

Example 141

N-[(trans)-3,3-Difluoro-2-hydroxycyclohexyl]-3-oxo-2-(pyridin-3-yl)-6-[4-(trifluoromethoxy)phenyl]-2,3-dihydropyridazine-4-carboxamide, Enantiomer 1

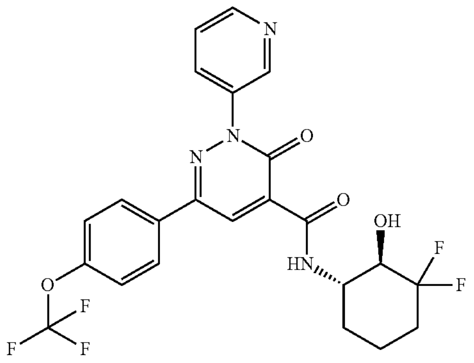 [SMILES: O=C(N[C@H]1CCCC(F)(F)[C@@H]1O)c1cc(-c2ccc(OC(F)(F)F)cc2)nn(-c2cccnc2)c1=O]

HPLC-separation of 58 mg N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide (example 140) on a chiral column (instrument: Labomatic HD5000, Labocord-5000; Gilson GX-241, Labcol Vario 4000, column: Chiralpak IA 5μ 250×30 mm; eluent A: ethanol+0.1 vol-% diethylamine (99%); eluent B: methanol; isocratic: 50% A+50% B; flow 40.0 mL/min; UV 254 nm) yielded 21 mg N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide, enantiomer 1. Chiral HPLC: Rt=1.48 min (instrument: Agilent HPLC 1260; column: Chiralpak IA 3μ100×4.6 mm; eluent A: ethanol+0.1 vol-% diethylamine (99%); eluent B: ethanol; isocratic: 90% A+10% B; flow 1.4 mL/min; temperature: 25° C.; DAD 254 nm).

Example 142

N-[(trans)-3,3-Difluoro-2-hydroxycyclohexyl]-3-oxo-2-(pyridin-3-yl)-6-[4-(trifluoromethoxy)phenyl]-2,3-dihydropyridazine-4-carboxamide, Enantiomer 2

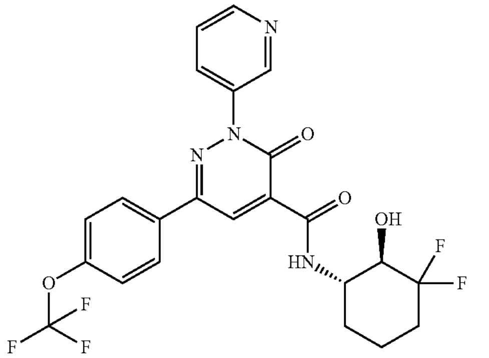 [SMILES: O=C(N[C@H]1CCCC(F)(F)[C@@H]1O)c1cc(-c2ccc(OC(F)(F)F)cc2)nn(-c2cccnc2)c1=O]

HPLC-separation of 58 mg N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide (example 140) on a chiral column (instrument: Labomatic HD5000, Labocord-5000; Gilson GX-241, Labcol Vario 4000, column: Chiralpak IA 5μ 250×30 mm; eluent A: ethanol+0.1 vol-% diethylamine (99%); eluent B: methanol; isocratic: 50% A+50% B; flow 40.0 mL/min; UV 254 nm) yielded 23 mg N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide, enantiomer 2. Chiral HPLC: Rt=1.78 min (instrument: Agilent HPLC 1260; column: Chiralpak IA 3μ100×4.6 mm; eluent A: ethanol+0.1 vol-% diethylamine (99%); eluent B: ethanol; isocratic: 90% A+10% B; flow 1.4 mL/min; temperature: 25° C.; DAD 254 nm).

Example 143

6-(4-Chlorophenyl)-N-[(trans)-3,3-difluoro-2-hydroxycyclohexyl]-3-oxo-2-(pyridin-3-yl)-2,3-dihydropyridazine-4-carboxamide

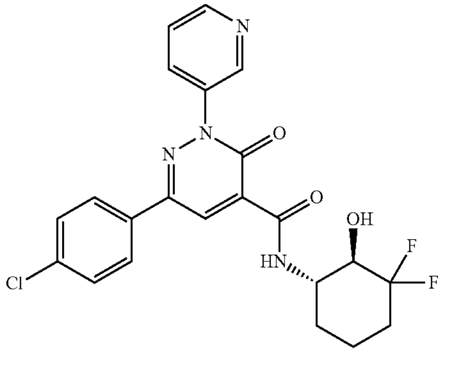 [SMILES: O=C(N[C@H]1CCCC(F)(F)[C@@H]1O)c1cc(-c2ccc(Cl)cc2)nn(-c2cccnc2)c1=O]

A solution of 150 mg intermediate 6-(4-chlorophenyl)-3-oxo-2-(pyridin-3-yl)-2,3-dihydropyridazine-4-carboxylic acid, 172 mg (trans)-6-amino-2,2-difluorocyclohexan-1-ol hydrochloride (1:1), 348 mg HATU, 0.3 mL ethyldiisopropylamine and 4 mg 4-dimethylaminopyridine in 3 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 66 mg rac-6-(4-Chlorophenyl)-N-[(trans)-3,3-difluoro-2-hydroxycyclohexyl]-3-oxo-2-(pyridin-3-yl)-2,3-dihydropyridazine-4-carboxamide.

$^1H$ NMR (400 MHz, DMSO-$d_6$) δ [ppm]=1.40-1.53 (m, 2H), 1.66 (br s, 1H), 1.72-1.89 (m, 1H), 1.92-2.11 (m, 2H), 3.69-3.80 (m, 1H), 3.96 (br s, 1H), 5.77 (d, 1H), 7.56-7.61 (m, 2H), 7.63 (dd, 1H), 7.98-8.02 (m, 2H), 8.14-8.18 (m, 1H), 8.67 (s, 1H), 8.70 (dd, 1H), 8.91 (d, 1H), 9.51 (d, 1H).

Example 144

6-(4-Chlorophenyl)-N-[(trans)-3,3-difluoro-2-hydroxycyclohexyl]-3-oxo-2-(pyridin-3-yl)-2,3-dihydropyridazine-4-carboxamide, Enantiomer 1

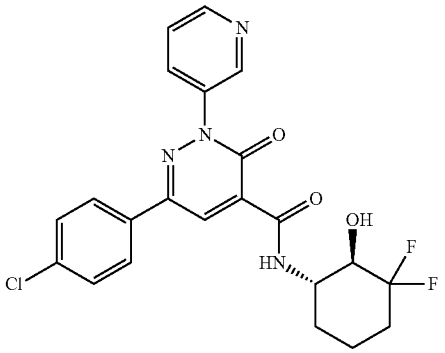 [SMILES: O=C(N[C@H]1CCCC(F)(F)[C@@H]1O)c1cc(-c2ccc(Cl)cc2)nn(-c2cccnc2)c1=O]

HPLC-separation of 58 mg 6-(4-chlorophenyl)-N-[(trans)-3,3-difluoro-2-hydroxycyclohexyl]-3-oxo-2-(pyridin-3-yl)-2,3-dihydropyridazine-4-carboxamide (example 143) on a chiral column (instrument: Labomatic HD5000, Labocord-5000; Gilson GX-241, Labcol Vario 4000, column: YMC Cellulose SC 5μ 250×30 mm; eluent A: methanol; Eluent B: ethanol; isocratic: 50% A+10% B; flow 40.0 mL/min; UV 254 nm) yielded 20 mg 6-(4-chlorophenyl)-N-[(trans)-3,3-difluoro-2-hydroxycyclohexyl]-3-oxo-2-(pyridin-3-yl)-2,3-dihydropyridazine-4-carboxamide, enantiomer 1.

Chiral HPLC: Rt=1.74 min (instrument: Agilent HPLC 1260; column: YMC Cellulose SC 3μ 100×4.6 mm; eluent A: methanol+0.1 vol-% diethylamine (99%); eluent B: ethanol; isocratic: 50% A+50% B; flow 1.4 mL/min; temperature: 25° C.; DAD 254 nm).

Example 145

6-(4-Chlorophenyl)-N-[(trans)-3,3-difluoro-2-hydroxycyclohexyl]-3-oxo-2-(pyridin-3-yl)-2,3-dihydropyridazine-4-carboxamide, Enantiomer 2

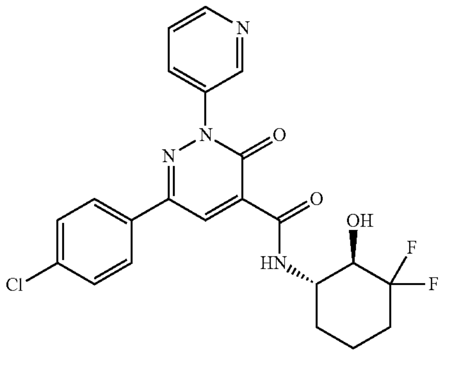 [SMILES: O=C(N[C@H]1CCCC(F)(F)[C@@H]1O)c1cc(-c2ccc(Cl)cc2)nn(-c2cccnc2)c1=O]

HPLC-separation of 58 mg 6-(4-chlorophenyl)-N-[(trans)-3,3-difluoro-2-hydroxycyclohexyl]-3-oxo-2-(pyridin-3-yl)-2,3-dihydropyridazine-4-carboxamide (example 143) on a chiral column (instrument: Labomatic HD5000, Labocord-5000; Gilson GX-241, Labcol Vario 4000, column: YMC Cellulose SC 5μ 250×30 mm; eluent A: methanol; Eluent B: ethanol; isocratic: 50% A+10% B; flow 40.0 mL/min; UV 254 nm) yielded 19 mg 6-(4-chlorophenyl)-N-[(trans)-3,3-difluoro-2-hydroxycyclohexyl]-3-oxo-2-(pyridin-3-yl)-2,3-dihydropyridazine-4-carboxamide, enantiomer 2.

Chiral HPLC: Rt=2.29 min (instrument: Agilent HPLC 1260; column: YMC Cellulose SC 3μ 100×4.6 mm; eluent A: methanol+0.1 vol-% diethylamine (99%); eluent B: ethanol; isocratic: 50% A+50% B; flow 1.4 mL/min; temperature: 25° C.; DAD 254 nm).

Example 146

3-Oxo-2-(pyridin-3-yl)-N-[3,3,3-trifluoro-2-hydroxypropyl]-6-[4-(trifluoromethoxy)phenyl]-2,3-dihydropyridazine-4-carboxamide

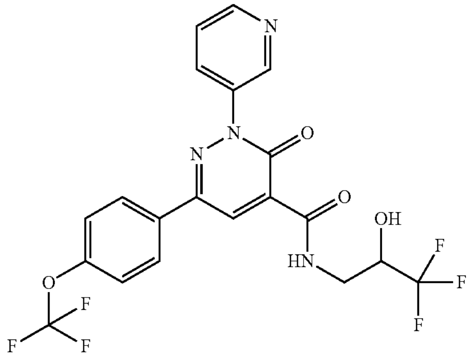 [SMILES: O=C(NCC(O)C(F)(F)F)c1cc(-c2ccc(OC(F)(F)F)cc2)nn(-c2cccnc2)c1=O]

A solution of 50 mg intermediate 3-oxo-2-(pyridin-3-yl)-6-[4-(trifluoromethoxy)phenyl]-2,3-dihydropyridazine-4-carboxylic acid, 34 mg 3-amino-1,1,1-trifluoro-2-propanol, 101 mg HATU, 0.1 mL ethyldiisopropylamine and 1 mg 4-dimethylaminopyridine in 1 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 70%/B 30%→A 30%/B 70%; flow: 150 mL/min; UV-detection: 254 nm) to yield 8 mg rac-3-oxo-2-(pyridin-3-yl)-N-[3,3,3-trifluoro-2-hydroxypropyl]-6-[4-(trifluoromethoxy)phenyl]-2,3-dihydropyridazine-4-carboxamide.

$^1H$ NMR (400 MHz, DMSO-$d_6$) δ [ppm]=3.48 (ddd, 1H), 3.70-3.79 (m, 1H), 4.16-4.29 (m, 1H), 6.66 (d, 1H), 7.52 (d, 2H), 7.64 (dd, 1H), 8.09-8.14 (m, 2H), 8.15-8.20 (m, 1H), 8.67-8.72 (m, 2H), 8.93 (d, 1H), 9.61 (t, 1H).

Example 147

N-[(1S,2R)-2-Hydroxycyclopentyl]-3-oxo-2-(pyridin-3-yl)-6-[4-(trifluoromethoxy)phenyl]-2,3-dihydropyridazine-4-carboxamide

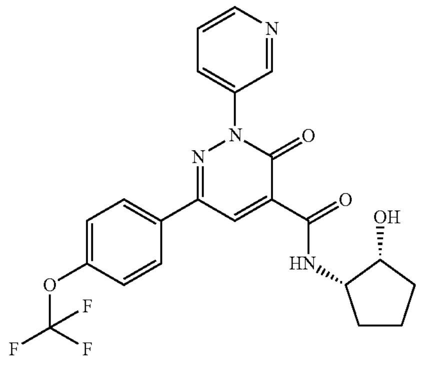 [SMILES: O=C(N[C@H]1CCC[C@H]1O)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 54 mg (1R,2S)-2-aminocyclopentanol hydrochlorid (1:1), 151 mg HATU, 0.14 mL ethyldiisopropylamine and 1 mg 4-dimethylaminopyridine in 2 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 19 mg N-[(1S,2R)-2-hydroxycyclopentyl]-3-oxo-2-(pyridin-3-yl)-6-[4-(trifluoromethoxy)phenyl]-2,3-dihydropyridazine-4-carboxamide.

$^1H$ NMR (400 MHz, DMSO-$d_6$) δ[ppm]=1.46-1.64 (m, 3H), 1.69-1.88 (m, 2H), 1.92-2.02 (m, 1H), 3.99-4.09 (m, 2H), 5.04 (d, 1H), 7.51 (d, 2H), 7.60-7.66 (m, 1H), 8.07-8.14 (m, 2H), 8.17 (ddd, 1H), 8.67-8.71 (m, 2H), 8.91 (d, 1H), 9.68 (d, 1H).

Example 148

6-(4-Chlorophenyl)-N-[(trans)-2-hydroxycyclopentyl]-3-oxo-2-(pyridin-3-yl)-2,3-dihydropyridazine-4-carboxamide

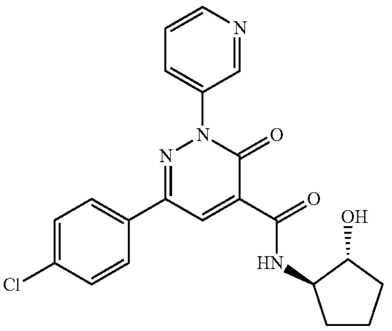 [SMILES: O=C(N[C@@H]1CCC[C@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 63 mg trans-2-aminocyclopentanol hydrochloride (1:1), 174 mg HATU, 0.16 mL ethyldiisopropylamine and 1 mg 4-dimethylaminopyridine in 2 mL of DMF was stirred at rt for 48 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×mm, eluent A: 0.1 vol % formic acid in water, eluent B: acetonitrile; gradient: A 70%/B 30%→A 30%/B 70%; flow: 150 mL/min; UV-detection: 254 nm) to yield 26 mg 6-(4-chlorophenyl)-N-[(trans)-2-hydroxycyclopentyl]-3-oxo-2-(pyridin-3-yl)-2,3-dihydropyridazine-4-carboxamide.

$^1$H NMR (400 MHz, DMSO-$d_6$) δ [ppm]=1.39-1.56 (m, 2H), 1.59-1.67 (m, 1H), 1.67-1.75 (m, 1H), 1.77-1.86 (m, 1H), 2.03-2.13 (m, 1H), 3.93 (quin, 1H), 3.98-4.06 (m, 1H), 4.94 (d, 1H), 7.56-7.60 (m, 2H), 7.63 (dd, 1H), 7.98-8.03 (m, 2H), 8.16 (ddd, 1H), 8.65 (s, 1H), 8.69 (dd, 1H), 8.91 (d, 1H), 9.31 (d, 1H).

Example 149

3-Oxo-2-(pyridin-3-yl)-N-(1,1,1-trifluoro-3-hydroxypropan-2-yl)-6-[4-(trifluoromethoxy)phenyl]-2,3-dihydropyridazine-4-carboxamide

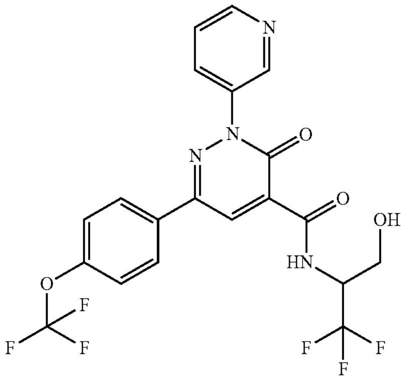 [SMILES: O=C(NC(CO)C(F)(F)F)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 68 mg 2-amino-3,3,3-trifluoropropan-1 of hydrochloride (1:1), 151 mg HATU, 0.14 mL ethyldiisopropylamine and 1 mg 4-dimethylaminopyridine in 2 mL of DMF was stirred at rt for 14 hours. Then the reaction mixture was filtered and subjected to RP-HPLC (instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 46 mg 3-oxo-2-(pyridin-3-yl)-N-(1,1,1-trifluoro-3-hydroxypropan-2-yl)-6-[4-(trifluoromethoxy)phenyl]-2,3-dihydropyridazine-4-carboxamide.

$^1$H NMR (400 MHz, DMSO-$d_6$) δ [ppm] 3.66-3.74 (m, 1H), 3.79-3.85 (m, 1H), 4.86 (dt, 1H), 5.44 (t, 1H), 7.52 (d, 2H), 7.64 (dd, 1H), 8.11-8.16 (m, 2H), 8.16-8.21 (m, 1H), 8.68-8.72 (m, 1H), 8.75 (s, 1H), 8.92 (d, 1H), 9.98 (d, 1H).

Example 150

N-[(1S)-1-Cyclopropyl-2-hydroxyethyl]-6-[4-(difluoromethyl)phenyl]-3-oxo-2-(pyridin-3-yl)-2,3-dihydropyridazine-4-carboxamide

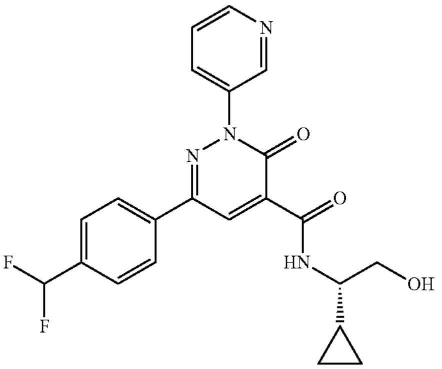 [SMILES: O=C(N[C@H](CO)C1CC1)c1cc(-c2ccc(C(F)F)cc2)nn(-c2cccnc2)c1=O]

A solution of 85 mg intermediate 6-[4-(difluoromethyl) phenyl]-3-oxo-2-(pyridin-3-yl)-2,3-dihydropyridazine-4-carboxylic acid, 69 mg (2S)-2-aminocyclopropylethan-1-ol hydrochloride (1:1), 190 mg HATU, 0.17 mL ethyldiisopropylamine and 1.5 mg 4-dimethylaminopyridine in 3 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 43 mg N-[(1S)-1-cyclopropyl-2-hydroxyethyl]-6-[4-(difluoromethyl)phenyl]-3-oxo-2-(pyridin-3-yl)-2,3-dihydropyridazine-4-carboxamide.

$^1$H NMR (400 MHz, DMSO-$d_6$) δ [ppm]=0.25-0.32 (m, 1H), 0.32-0.39 (m, 1H), 0.40-0.50 (m, 2H), 1.03-1.13 (m, 1H), 3.45 (tt, 1H), 3.58 (tq, 2H), 4.93 (t, 1H), 7.13 (t, 1H), 7.61-7.66 (m, 1H), 7.72 (d, 2H), 8.13 (d, 2H), 8.16-8.21 (m, 1H), 8.70 (dd, 1H), 8.72 (s, 1H), 8.93 (d, 1H), 9.53 (d, 1H).

Example 151

6-[4-(Difluoromethyl)phenyl]-N-[(2S)-1-hydroxy-propan-2-yl]-3-oxo-2-(pyridin-3-yl)-2,3-dihydro-pyridazine-4-carboxamide

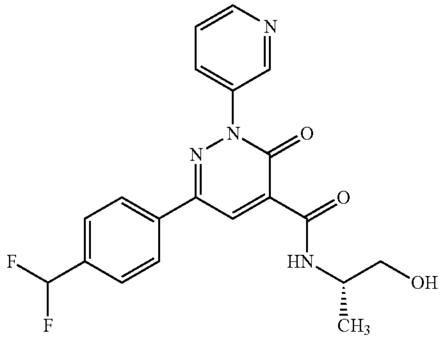 [SMILES: C[C@@H](CO)NC(=O)c1cc(-c2ccc(C(F)F)cc2)nn(-c2cccnc2)c1=O]

A solution of 65 mg intermediate 6-[4-(difluoromethyl) phenyl]-3-oxo-2-(pyridin-3-yl)-2,3-dihydropyridazine-4-carboxylic acid, 28 mg (2S)-2-amino-1-propanol, 144 mg HATU, 0.1 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 14 mg 6-[4-(difluoromethyl)phenyl]-N-[(2S)-1-hydroxypropan-2-yl]-3-oxo-2-(pyridin-3-yl)-2,3-dihydropyridazine-4-carboxamide.

$^1$H NMR (400 MHz, DMSO-$d_6$) δ [ppm]=1.17 (d, 3H), 3.41-3.49 (m, 2H), 3.99-4.09 (m, 1H), 4.94 (t, 1H), 7.13 (t, 1H), 7.61-7.66 (m, 1H), 7.72 (d, 2H), 8.13 (d, 2H), 8.15-8.19 (m, 1H), 8.68-8.72 (m, 2H), 8.92 (d, 1H), 9.41 (d, 1H).

Example 152

N-[(2S)-1-Hydroxypropan-2-yl]-6-(4-methyl phenyl)-3-oxo-2-(pyridin-3-yl)-2,3-dihydropyridazine-4-carboxamide

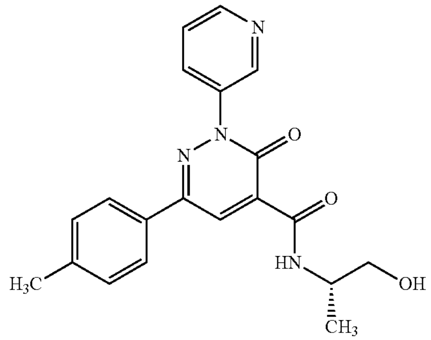 [SMILES: Cc1ccc(-c2cc(C(=O)N[C@@H](C)CO)c(=O)n(-c3cccnc3)n2)cc1]

A solution of 17 mg intermediate 6-(4-methylphenyl)-3-oxo-2-(pyridin-3-yl)-2,3-dihydropyridazine-4-carboxylic acid, 28 mg (2S)-2-amino-1-propanol, 43 mg HATU, 0.03 mL ethyldiisopropylamine and 1 mg 4-dimethylaminopyridine in 0.5 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 85%/B 15%→A 45%/B 55%; flow: 150 mL/min; UV-detection: 254 nm) to yield 14 mg N-[(2S)-1-hydroxypropan-2-yl]-6-(4-methylphenyl)-3-oxo-2-(pyridin-3-yl)-2,3-dihydropyridazine-4-carboxamide.

$^1$H NMR (400 MHz, DMSO-$d_6$) δ[ppm]=1.16 (d, 3H), 2.37 (s, 3H), 3.40-3.49 (m, 2H), 3.99-4.08 (m, 1H), 4.94 (t, 1H), 7.34 (d, 2H), 7.60-7.65 (m, 1H), 7.86 (d, 2H), 8.16 (ddd, 1H), 8.64 (s, 1H), 8.68 (dd, 1H), 8.90 (d, 1H), 9.44 (d, 1H).

Example 153

N-[(2S)-1-Hydroxypropan-2-yl]-3-oxo-2-(pyridin-3-yl)-6-[4-(trifluoromethoxy)phenyl]-2,3-dihydro-pyridazine-4-carboxamide

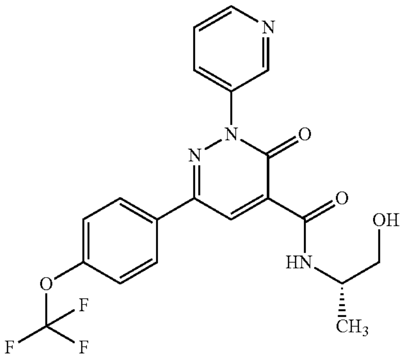 [SMILES: C[C@@H](CO)NC(=O)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 30 mg (S)-(+)-2-amino-1-propanol, 151 mg HATU, 0.14 mL ethyldiisopropylamine and 1 mg 4-dimethylaminopyridine in 2 mL of DMF was stirred at rt for 14 hours. Then the reaction mixture was filtered and subjected to RP-HPLC (instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 54 mg N-[(2S)-1-hydroxypropan-2-yl]-3-oxo-2-(pyridin-3-yl)-6-[4-(trifluoromethoxy)phenyl]-2,3-dihydropyridazine-4-carboxamide.

$^1$H NMR (400 MHz, DMSO-$d_6$) δ [ppm]=1.16 (d, 3H), 3.42-3.50 (m, 2H), 3.99-4.09 (m, 1H), 4.95 (t, 1H), 7.51 (d, 2H), 7.63 (dd, 1H), 8.09-8.14 (m, 2H), 8.17 (ddd, 1H), 8.67-8.71 (m, 2H), 8.91 (d, 1H), 9.41 (d, 1H).

Example 154

6-(4-Chlorophenyl)-2-(5-fluoropyridin-3-yl)-N-[(trans)-4-hydroxytetrahydrofuran-3-yl]-3-oxo-2,3-dihydropyridazine-4-carboxamide

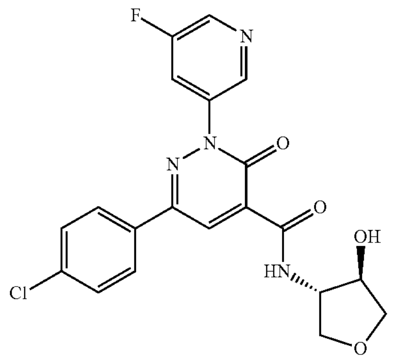 [SMILES: O=C(N[C@H]1COC[C@@H]1O)c1cc(-c2ccc(Cl)cc2)nn(-c2cncc(F)c2)c1=O]

A solution of 150 mg intermediate 6-(4-chlorophenyl)-2-(5-fluoropyridin-3-yl)-3-oxo-2,3-dihydropyridazine-4-carboxylic acid, 124 mg trans-4-aminotetrahydro-3-furanol hydrochloride (1:1), 330 mg HATU, 0.23 mL ethyldiisopropylamine and 2.6 mg 4-dimethylaminopyridine in 3 mL of DMF was stirred at room temperature for 48 hours. Then water was added and the precipitate subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 55 mg 6-(4-chlorophenyl)-2-(5-fluoropyridin-3-yl)-N-[(trans)-4-hydroxytetrahydrofuran-3-yl]-3-oxo-2,3-dihydropyridazine-4-carboxamide.

$^1$H NMR (400 MHz, DMSO-$d_6$) δ [ppm]=3.54 (dd, 1H), 3.65 (dd, 1H), 3.90 (dd, 1H), 3.98 (dd, 1H), 4.18 (dt, 1H), 4.25 (td, 1H), 5.49 (d, 1H), 7.58-7.61 (m, 2H), 8.01-8.06 (m, 2H), 8.22-8.27 (m, 1H), 8.65 (s, 1H), 8.76 (d, 1H), 8.85 (s, 1H), 9.34 (d, 1H).

Example 155

6-(4-Chlorophenyl)-2-(5-fluoropyridin-3-yl)-N-[(trans)-4-hydroxytetrahydrofuran-3-yl]-3-oxo-2,3-dihydropyridazine-4-carboxamide, Enantiomer 1

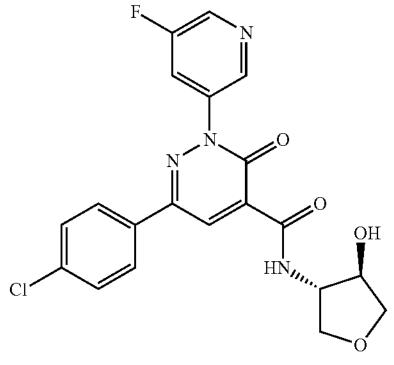 [SMILES: O=C(N[C@H]1COC[C@@H]1O)c1cc(-c2ccc(Cl)cc2)nn(-c2cncc(F)c2)c1=O]

HPLC-separation of 49 mg 6-(4-chlorophenyl)-2-(5-fluoropyridin-3-yl)-N-[(trans)-4-hydroxytetrahydrofuran-3-yl]-3-oxo-2,3-dihydropyridazine-4-carboxamide (example 154) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 40.0 mL/min; UV 254 nm) yielded 14 mg 6-(4-chlorophenyl)-2-(5-fluoropyridin-3-yl)-N-[(trans)-4-hydroxytetrahydrofuran-3-yl]-3-oxo-2,3-dihydropyridazine-4-carboxamide, enantiomer 1.

Chiral HPLC: Rt=2.36 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=−21.2° (c=1.00, DMSO).

Example 156

6-(4-Chlorophenyl)-2-(5-fluoropyridin-3-yl)-N-[(trans)-4-hydroxytetrahydrofuran-3-yl]-3-oxo-2,3-dihydropyridazine-4-carboxamide, Enantiomer 2

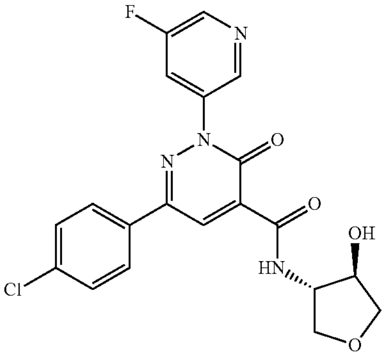 [SMILES: O=C(N[C@H]1COC[C@@H]1O)c1cc(-c2ccc(Cl)cc2)nn(-c2cncc(F)c2)c1=O]

HPLC-separation of 49 mg 6-(4-chlorophenyl)-2-(5-fluoropyridin-3-yl)-N-[(trans)-4-hydroxytetrahydrofuran-3-yl]-3-oxo-2,3-dihydropyridazine-4-carboxamide (example 154) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 40.0 mL/min; UV 254 nm) yielded 11 mg 6-(4-chlorophenyl)-2-(5-fluoropyridin-3-yl)-N-[(trans)-4-hydroxytetrahydrofuran-3-yl]-3-oxo-2,3-dihydropyridazine-4-carboxamide, enantiomer 2.

Chiral HPLC: Rt=2.72 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=27.2° (c=1.00, DMSO).

Example 157

N-[(cis)-4-Hydroxytetrahydrofuran-3-yl]-3-oxo-2-(pyridin-3-yl)-6-[4-(trifluoromethoxy)phenyl]-2,3-dihydropyridazine-4-carboxamide

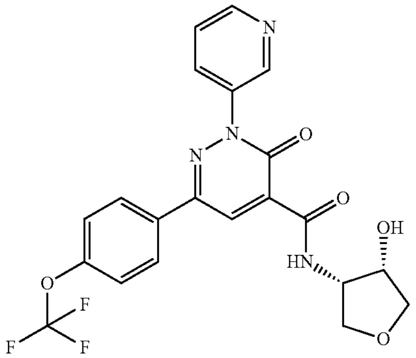 [SMILES: O=C(N[C@H]1COC[C@H]1O)c1cc(-c2ccc(OC(F)(F)F)cc2)nn(-c2cccnc2)c1=O]

A solution of 200 mg intermediate 3-oxo-2-(pyridin-3-yl)-6-[4-(trifluoromethoxy)phenyl]-2,3-dihydropyridazine-4-carboxylic acid, 148 mg cis-4-aminotetrahydro-3-furanol hydrochloride (1:1), 403 mg HATU, 0.37 mL ethyldiisopropylamine and 3 mg 4-dimethylaminopyridine in 4 mL of DMF was stirred at rt for 14 hours. Then the reaction mixture was filtered and subjected to RP-HPLC (HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 89 mg N-[(cis)-4-hydroxytetrahydrofuran-3-yl]-3-oxo-2-(pyridin-3-yl)-6-[4-(trifluoromethoxy)phenyl]-2,3-dihydropyridazine-4-carboxamide.

$^1H$ NMR (400 MHz, DMSO-$d_6$) δ [ppm]=3.45 (dd, 1H), 3.61 (dd, 1H), 3.93 (dd, 1H), 4.01 (dd, 1H), 4.24-4.31 (m, 1H), 4.31-4.40 (m, 1H), 5.69 (d, 1H), 7.48-7.54 (m, 2H), 7.64 (br dd, 1H), 8.09-8.14 (m, 2H), 8.17 (br d, 1H), 8.71 (m, 2H), 8.93 (br s, 1H), 9.81 (d, 1H).

Example 158

N-[(cis)-4-Hydroxytetrahydrofuran-3-yl]-3-oxo-2-(pyridin-3-yl)-6-[4-(trifluoromethoxy)phenyl]-2,3-dihydropyridazine-4-carboxamide, Enantiomer 1

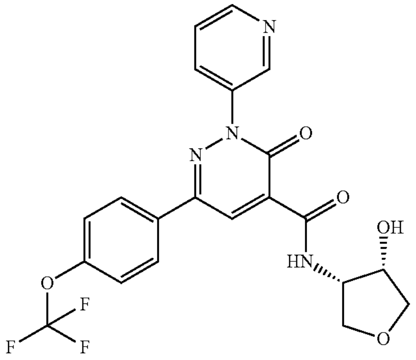 [SMILES: O=C(N[C@H]1COC[C@H]1O)c1cc(-c2ccc(OC(F)(F)F)cc2)nn(-c2cccnc2)c1=O]

HPLC-separation of 89 mg N-[(cis)-4-hydroxytetrahydrofuran-3-yl]-3-oxo-2-(pyridin-3-yl)-6-[4-(trifluoromethoxy)phenyl]-2,3-dihydropyridazine-4-carboxamide (example 157) on a chiral column (instrument: Labomatic HD5000, Labocord-5000; Gilson GX-241, Labcol Vario 4000, column: Chiralpak ID 5μ 250×30 mm; eluent A: tert.-butyl methyl ether+0.1 vol-% diethylamine (99%); Eluent B: methanol; isocratic: 50% A+50% B; flow 50.0 mL/min; UV 254 nm) yielded 18 mg N-[(cis)-4-hydroxytetrahydrofuran-3-yl]-3-oxo-2-(pyridin-3-yl)-6-[4-(trifluoromethoxy)phenyl]-2,3-dihydropyridazine-4-carboxamide, enantiomer 1.

Chiral HPLC: Rt=1.73 min (instrument: Agilent HPLC 1260; column: Chiralpak ID 3μ 100×4.6 mm; eluent A: tert.-butyl methyl ether+0.1 vol-% diethylamine (99%); eluent B: methanol; isocratic: 90% A+10% B; flow 1.4 mL/min; temperature: 25° C.; DAD 254 nm).

Example 159

N-[(cis)-4-Hydroxytetrahydrofuran-3-yl]-3-oxo-2-(pyridin-3-yl)-6-[4-(trifluoromethoxy)phenyl]-2,3-dihydropyridazine-4-carboxamide, Enantiomer 2

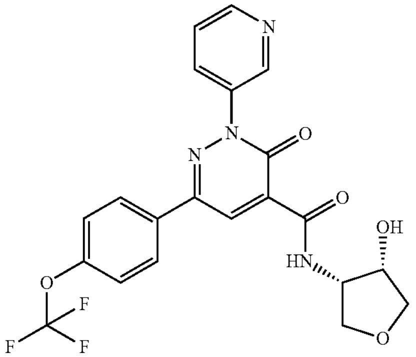 [SMILES: O=C(N[C@H]1COC[C@H]1O)c1cc(-c2ccc(OC(F)(F)F)cc2)nn(-c2cccnc2)c1=O]

HPLC-separation of 89 mg N-[(cis)-4-hydroxytetrahydrofuran-3-yl]-3-oxo-2-(pyridin-3-yl)-6-[4-(trifluoromethoxy)phenyl]-2,3-dihydropyridazine-4-carboxamide (example 157) on a chiral column (instrument: Labomatic HD5000, Labocord-5000; Gilson GX-241, Labcol Vario 4000, column: Chiralpak ID 5μ 250×30 mm; eluent A: tert.-butyl methyl ether+0.1 vol-% diethylamine (99%); Eluent B: methanol; isocratic: 50% A+50% B; flow 50.0 mL/min; UV 254 nm) yielded 18 mg N-[(cis)-4-hydroxytetrahydrofuran-3-yl]-3-oxo-2-(pyridin-3-yl)-6-[4-(trifluoromethoxy)phenyl]-2,3-dihydropyridazine-4-carboxamide, enantiomer 2.

Chiral HPLC: Rt=2.58 min (instrument: Agilent HPLC 1260; column: Chiralpak ID 3μ100×4.6 mm; eluent A: tert.-butyl methyl ether+0.1 vol-% diethylamine (99%); eluent B: methanol; isocratic: 90% A+10% B; flow 1.4 mL/min; temperature: 25° C.; DAD 254 nm).

Example 160

N-[(trans)-4-Hydroxytetrahydrofuran-3-yl]-3-oxo-2-(pyridin-3-yl)-6-[4-(trifluoromethoxy)phenyl]-2,3-dihydropyridazine-4-carboxamide

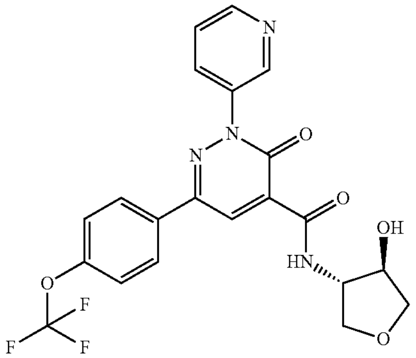 [SMILES: O=C(N[C@H]1COC[C@@H]1O)c1cc(-c2ccc(OC(F)(F)F)cc2)nn(-c2cccnc2)c1=O]

A solution of 150 mg intermediate 3-oxo-2-(pyridin-3-yl)-6-[4-(trifluoromethoxy)phenyl]-2,3-dihydropyridazine-4-carboxylic acid, 113 mg trans-4-aminotetrahydro-3-furanol hydrochloride (1:1), 302 mg HATU, 0.2 mL ethyldiisopropylamine and 2.5 mg 4-dimethylaminopyridine in 3 mL of DMF was stirred at rt for 48 hours. Then the reaction mixture was filtered and subjected to RP-HPLC (HPLC (Instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 56 mg N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide.

$^1H$ NMR (400 MHz, DMSO-$d_6$) δ[ppm]=3.54 (dd, 1H), 3.65 (dd, 1H), 3.89 (dd, 1H), 3.98 (dd, 1H), 4.18 (br s, 1H), 4.25 (td, 1H), 5.50 (d, 1H), 7.51 (d, 2H), 7.63 (dd, 1H), 8.08-8.14 (m, 2H), 8.15-8.19 (m, 1H), 8.66 (s, 1H), 8.70 (br d, 1H), 8.92 (br s, 1H), 9.42 (d, 1H).

Example 161

N-[(trans)-4-Hydroxytetrahydrofuran-3-yl]-3-oxo-2-(pyridin-3-yl)-6-[4-(trifluoromethoxy)phenyl]-2,3-dihydropyridazine-4-carboxamide, Enantiomer 1

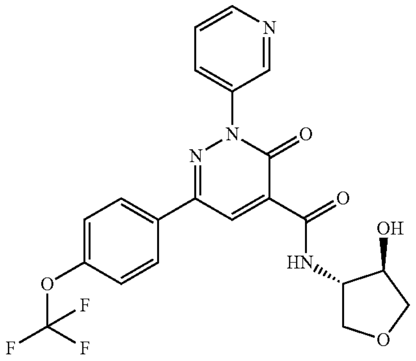 [SMILES: O=C(N[C@H]1COC[C@@H]1O)c1cc(-c2ccc(OC(F)(F)F)cc2)nn(-c2cccnc2)c1=O]

HPLC-separation of 49 mg N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide (example 160) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 40.0 mL/min; UV 254 nm) yielded 20 mg N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide, enantiomer 1.

Chiral HPLC: Rt=2.37 min (instrument: Agilent HPLC 1260; column: Chiralpak IB 3μ100×4.6 mm; eluent A: tert.-butyl methyl ether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=−30.1° (c=1.00, MeOH).

Example 162

N-[(trans)-4-Hydroxytetrahydrofuran-3-yl]-3-oxo-2-(pyridin-3-yl)-6-[4-(trifluoromethoxy)phenyl]-2,3-dihydropyridazine-4-carboxamide, Enantiomer 2

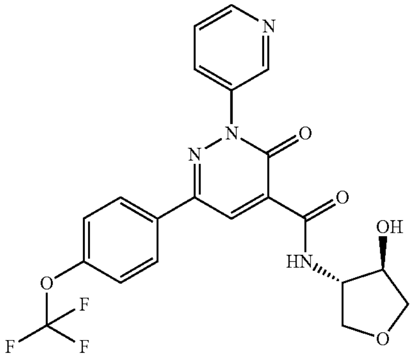 [SMILES: O=C(N[C@H]1COC[C@@H]1O)c1cc(-c2ccc(OC(F)(F)F)cc2)nn(-c2cccnc2)c1=O]

HPLC-separation of 49 mg N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide (example 160) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 40.0 mL/min; UV 254 nm) yielded 20 mg N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide, enantiomer 2.

Chiral HPLC: Rt=2.94 min (instrument: Agilent HPLC 1260; column: Chiralpak IB 3μ100×4.6 mm; eluent A: tert.-butyl methyl ether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=30.5° (c=1.00, MeOH).

Example 163

6-(4-Chloro-2-fluorophenyl)-N-[(2S)-1-hydroxypropan-2-yl]-3-oxo-2-(pyridin-3-yl)-2,3-dihydropyridazine-4-carboxamide

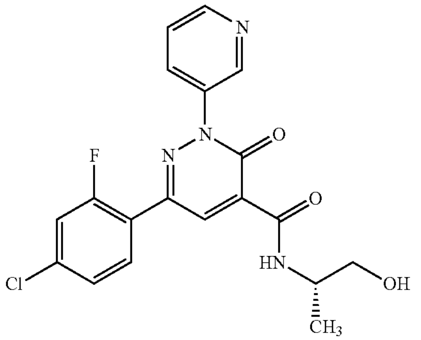 [SMILES: C[C@@H](CO)NC(=O)c1cc(-c2ccc(Cl)cc2F)nn(-c2cccnc2)c1=O]

A solution of 75 mg intermediate 6-(4-chloro-2-fluorophenyl)-3-oxo-2-(pyridin-3-yl)-2,3-dihydropyridazine-4-carboxylic acid, 32.5 mg (2S)-2-amino-1-propanol, 164 mg HATU, 0.15 mL ethyldiisopropylamine and 1.5 mg 4-dimethylaminopyridine in 3 mL of DMF was stirred at 40° C. for 4 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 43 mg 6-(4-chloro-2-fluorophenyl)-N-[(2S)-1-hydroxypropan-2-yl]-3-oxo-2-(pyridin-3-yl)-2,3-dihydropyridazine-4-carboxamide.

$^1$H NMR (400 MHz, DMSO-$d_6$) δ [ppm]=1.15 (d, 3H), 3.44 (br d, 2H), 3.97-4.08 (m, 1H), 7.45 (dd, 1H), 7.63 (dd, 1H), 7.69 (dd, 1H), 7.86 (t, 1H), 8.16 (dt, 1H), 8.51 (d, 1H), 8.69 (dd, 1H), 8.91 (d, 1H), 9.39 (d, 1H).

Example 164

3-(4-Chlorophenyl)-N-[(1S,2R)-2-hydroxycyclohexyl]-6-oxo-6H-1,4'-bipyridazine-5-carboxamide

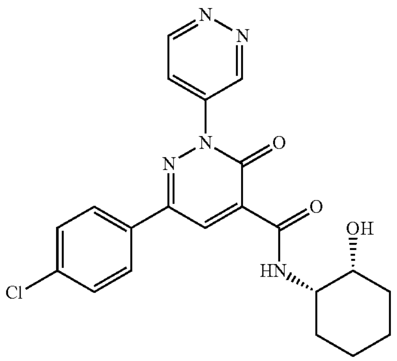 [SMILES: O=C(N[C@H]1CCCC[C@H]1O)c1cc(-c2ccc(Cl)cc2)nn(-c2ccnnc2)c1=O]

A solution of 80 mg intermediate 3-(4-chlorophenyl)-6-oxo-6H-1,4'-bipyridazine-5-carboxylic acid, 66 mg (1R,2S)-2-aminocyclohexanol hydrochloride (1:1), 185 mg HATU, 0.17 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 12 mg 3-(4-chlorophenyl)-N-[(1S,2R)-2-hydroxycyclohexyl]-6-oxo-6H-1,4'-bipyridazine-5-carboxamide.

$^1$H NMR (400 MHz, DMSO-$d_6$) δ [ppm]=1.34 (br d, 2H), 1.48-1.73 (m, 6H), 3.78 (br d, 1H), 3.87-3.95 (m, 1H), 4.91 (d, 1H), 7.59-7.63 (m, 2H), 8.04-8.10 (m, 2H), 8.21 (dd, 1H), 8.67 (s, 1H), 9.45 (d, 1H), 9.48 (dd, 1H), 9.74 (dd, 1H).

Example 165

6-[6-(Difluoromethyl)pyridin-3-yl]-N-[(1S,2S)-2-hydroxycyclopentyl]-3-oxo-2-(pyridin-3-yl)-2,3-dihydropyridazine-4-carboxamide

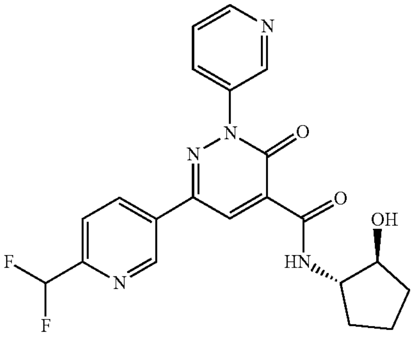 [SMILES: O=C(N[C@H]1CCC[C@@H]1O)c1cc(-c2ccc(C(F)F)nc2)nn(-c2cccnc2)c1=O]

A solution of 75 mg intermediate 6-[6-(difluoromethyl)pyridin-3-yl]-3-oxo-2-(pyridin-3-yl)-2,3-dihydropyridazine-4-carboxylic acid, 60 mg (1S,2S)-2-aminocyclopentanol hydrochloride (1:1), 166 mg HATU, 0.15 mL ethyldiisopropylamine and 1 mg 4-dimethylaminopyridine in 2 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 54 mg 6-[6-(difluoromethyl)pyridin-3-yl]-N-[(1S,2S)-2-hydroxycyclopentyl]-3-oxo-2-(pyridin-3-yl)-2,3-dihydropyridazine-4-carboxamide.

$^1$H NMR (400 MHz, DMSO-$d_6$) δ [ppm]=1.39-1.56 (m, 2H), 1.58-1.67 (m, 1H), 1.67-1.76 (m, 1H), 1.77-1.87 (m, 1H), 2.03-2.15 (m, 1H), 3.94 (quin, 1H), 3.98-4.07 (m, 1H), 4.95 (d, 1H), 7.06 (t, 1H), 7.62-7.67 (m, 1H), 7.84 (d, 1H), 8.19 (ddd, 1H), 8.58 (dd, 1H), 8.70 (dd, 1H), 8.76 (s, 1H), 8.94 (d, 1H), 9.24-9.29 (m, 2H).

Example 166

N-[(2S)-1-Hydroxypropan-2-yl]-3-oxo-2-(pyridin-3-yl)-6-[6-(trifluoromethyl)pyridin-3-yl]-2,3-dihydropyridazine-4-carboxamide

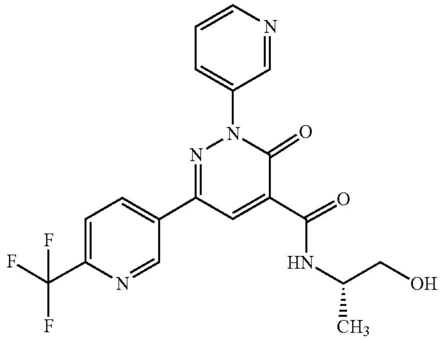 [SMILES: C[C@@H](CO)NC(=O)c1cc(-c2ccc(C(F)(F)F)nc2)nn(-c2cccnc2)c1=O]

A solution of N-[(2S)-1-hydroxypropan-2-yl]-3-oxo-6-[6-(trifluoromethyl)pyridin-3-yl]-2,3-dihydropyridazine-4-carboxamide (48 mg, 140 μmol) and 3-(4,4,5,5-tetramethyl-1,3,2-dioxaborolan-2-yl)pyridine (CAS No. [329214-79-1]; 2.0 eq, 57 mg, 279 μmol) in DMF (5 mL) under argon was treated with 2,2'-bipyridine (CAS No. [366-18-7]; 2.5 eq, 55 mg, 349 μmol), sodium hydrogen carbonate (2.0 eq, 30 mg, 279 μmol) and copper acetate (1.3 eq, 32 mg, 175 μmol) and stirred at room temperature for three days. The reaction mixture was diluted with water (2 mL), adjusted to pH 3 with 2 M aqueous hydrochloric acid and subjected to preparative reversed-phase HPLC followed by lyophilization to give the title compound (7 mg).

$^1$H-NMR (400 MHz, DMSO-$d_6$) δ[ppm]=1.17 (d, 3H), 3.42-3.49 (m, 2H), 4.00-4.10 (m, 1H), 4.95 (br s, 1H), 7.65 (dd, 1H), 8.05 (d, 1H), 8.20 (ddd, 1H), 8.67 (dd, 1H), 8.71 (dd, 1H), 8.81 (s, 1H), 8.95 (d, 1H), 9.35-9.37 (m, 2H).

Example 167

3-(4-Chlorophenyl)-N-[(1S,2R)-2-hydroxycyclopentyl]-6-oxo-6H-1,4'-bipyridazine-5-carboxamide

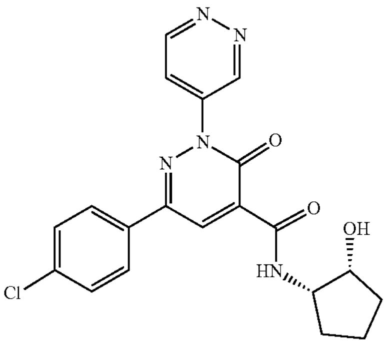 [SMILES: O=C(N[C@H]1CCC[C@H]1O)c1cc(-c2ccc(Cl)cc2)nn(-c2ccnnc2)c1=O]

A solution of 65 mg intermediate 3-(4-chlorophenyl)-6-oxo-6H-1,4'-bipyridazine-5-carboxylic acid, 54 mg (1R,2S)-2-aminocyclopentanol-hydrochlorid (1:1), 150 mg HATU, 0.14 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 12 mg 3-(4-chlorophenyl)-N-[(1S,2R)-2-hydroxycyclopentyl]-6-oxo-6H-1,4'-bipyridazine-5-carboxamide.

$^1$H NMR (400 MHz, DMSO-$d_6$) δ [ppm]=1.47-1.66 (m, 3H), 1.70-1.89 (m, 2H), 1.94-2.04 (m, 1H), 4.00-4.12 (m, 2H), 5.08 (d, 1H), 7.58-7.63 (m, 2H), 8.06-8.10 (m, 2H), 8.21 (dd, 1H), 8.68 (s, 1H), 9.48 (dd, 1H), 9.53 (d, 1H), 9.74 (dd, 1H).

Example 168

6-(4-Chlorophenyl)-N-[(trans)-4-hydroxytetrahydrofuran-3-yl]-3-oxo-2-(pyridin-3-yl)-2,3-dihydropyridazine-4-carboxamide

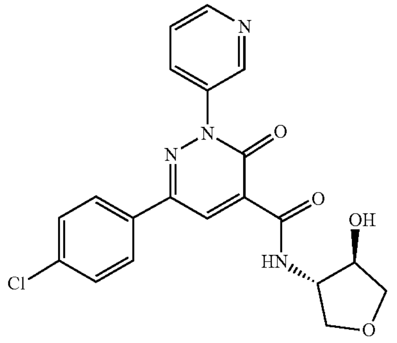 [SMILES: O=C(N[C@H]1COC[C@@H]1O)c1cc(-c2ccc(Cl)cc2)nn(-c2cccnc2)c1=O]

A solution of 150 mg intermediate 6-(4-chlorophenyl)-3-oxo-2-(pyridin-3-yl)-2,3-dihydropyridazine-4-carboxylic acid, 130 mg trans-4-aminotetrahydro-3-furanol hydrochloride (1:1), 348 mg HATU, 0.24 mL ethyldiisopropylamine and 2.8 mg 4-dimethylaminopyridine in 3.5 mL of DMF was stirred at room temperature for 48 hours. Then water was added and the precipitate subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 68 mg 6-(4-chlorophenyl)-N-[(trans)-4-hydroxytetrahydrofuran-3-yl]-3-oxo-2-(pyridin-3-yl)-2,3-dihydropyridazine-4-carboxamide.

$^1$H NMR (400 MHz, DMSO-$d_6$) δ [ppm]=3.54 (dd, 1H), 3.64 (dd, 1H), 3.89 (dd, 1H), 3.98 (dd, 1H), 4.17 (tt, 1H), 4.25 (tt, 1H), 5.49 (d, 1H), 7.56-7.61 (m, 2H), 7.61-7.65 (m, 1H), 7.99-8.03 (m, 2H), 8.16 (ddd, 1H), 8.65 (s, 1H), 8.69 (dd, 1H), 8.91 (d, 1H), 9.42 (d, 1H).

Example 169

6-(4-Chlorophenyl)-N-[(trans)-4-hydroxytetrahydrofuran-3-yl]-3-oxo-2-(pyridin-3-yl)-2,3-dihydropyridazine-4-carboxamide, Enantiomer 1

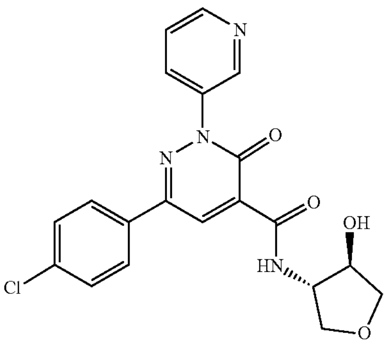 [SMILES: O=C(N[C@H]1COC[C@@H]1O)c1cc(-c2ccc(Cl)cc2)nn(-c2cccnc2)c1=O]

HPLC-separation of 61 mg rac-6-(4-chlorophenyl)-2-(5-fluoropyridin-3-yl)-N-[(trans)-4-hydroxytetrahydrofuran-3-yl]-3-oxo-2,3-dihydropyridazine-4-carboxamide (example 168) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 50.0 mL/min; UV 254 nm) yielded 19 mg 6-(4-chlorophenyl)-N-[(trans)-4-hydroxytetrahydrofuran-3-yl]-3-oxo-2-(pyridin-3-yl)-2,3-dihydropyridazine-4-carboxamide, enantiomer 1.

Chiral HPLC: Rt=2.36 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=−29.4° (c=1.00, MeOH).

Example 170

6-(4-Chlorophenyl)-N-[(trans)-4-hydroxytetrahydrofuran-3-yl]-3-oxo-2-(pyridin-3-yl)-2,3-dihydropyridazine-4-carboxamide, Enantiomer 2

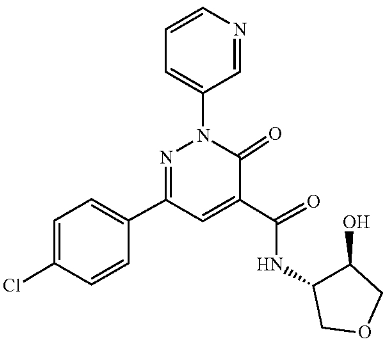 [SMILES: O=C(N[C@H]1COC[C@@H]1O)c1cc(-c2ccc(Cl)cc2)nn(-c2cccnc2)c1=O]

HPLC-separation of 49 mg rac-6-(4-chlorophenyl)-2-(5-fluoropyridin-3-yl)-N-[(trans)-4-hydroxytetrahydrofuran-3-yl]-3-oxo-2,3-dihydropyridazine-4-carboxamide (example 168) on a chiral column (instrument: Labomatic HD5000, Labocord-5000; Gilson GX-241, Labcol Vario 4000, column: Chiralpak IB 5μ 250×30 mm; eluent A: methyl tert.-butylether+0.1 vol-% diethylamine (99%); eluent B: ethanol; isocratic: 90% A+10% B; flow 50.0 mL/min; UV 254 nm) yielded 20 mg 6-(4-chlorophenyl)-N-[(trans)-4-hydroxytetrahydrofuran-3-yl]-3-oxo-2-(pyridin-3-yl)-2,3-dihydropyridazine-4-carboxamide, enantiomer 2.

Chiral HPLC: Rt=2.72 min (instrument: Agilent HPLC 1260; column: Chiralpak IB 3μ100×4.6 mm; eluent A: methyl tert.-butylether+0.1 vol-% diethylamine (99%); eluent B: ethanol; isocratic: 90% A+10% B; flow 1.4 mL/min; temperature: 25° C.; DAD 254 nm).

$[\alpha]_D^{20}$=30.2° (c=1.00, MeOH).

Example 171

6-(4-Chlorophenyl)-N-[(cis)-4-hydroxytetrahydrofuran-3-yl]-3-oxo-2-(pyridin-3-yl)-2,3-dihydropyridazine-4-carboxamide

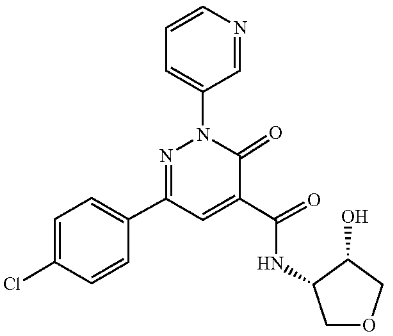 [SMILES: O=C(N[C@H]1COC[C@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 64 mg cis-4-aminotetrahydro-3-furanol hydrochloride (1:1), 174 mg HATU, 0.16 mL ethyldiisopropylamine and 1 mg 4-dimethylaminopyridine in 2 mL of DMF was stirred at room temperature for 48 hours. Then water was added and the precipitate subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 70%/B 30%→A 30%/B 70%; flow: 150 mL/min; UV-detection: 254 nm) to yield 31 mg 6-(4-chlorophenyl)-N-[(cis)-4-hydroxytetrahydrofuran-3-yl]-3-oxo-2-(pyridin-3-yl)-2,3-dihydropyridazine-4-carboxamide.

$^1$H NMR (400 MHz, DMSO-$d_6$) δ [ppm]=3.45 (t, 1H), 3.61 (dd, 1H), 3.93 (dd, 1H), 4.01 (dd, 1H), 4.24-4.29 (m, 1H), 4.31-4.40 (m, 1H), 5.68 (d, 1H), 7.57-7.61 (m, 2H), 7.61-7.65 (m, 1H), 8.00-8.03 (m, 2H), 8.15-8.18 (m, 1H), 8.67-8.73 (m, 2H), 8.91 (d, 1H), 9.81 (d, 1H).

Example 172

6-(4-Chlorophenyl)-N-[(cis)-4-hydroxytetrahydrofuran-3-yl]-3-oxo-2-(pyridin-3-yl)-2,3-dihydropyridazine-4-carboxamide, Enantiomer 1

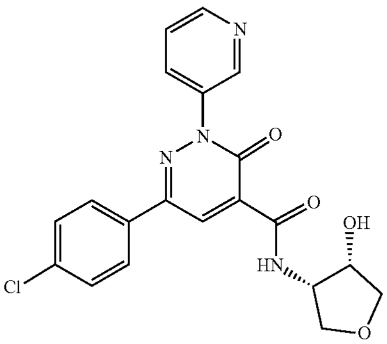 [SMILES: O=C(N[C@H]1COC[C@H]1O)c1cc(-c2ccc(Cl)cc2)nn(-c2cccnc2)c1=O]

HPLC-separation of 25 mg rac-6-(4-chlorophenyl)-N-[(cis)-4-hydroxytetrahydrofuran-3-yl]-3-oxo-2-(pyridin-3-yl)-2,3-dihydropyridazine-4-carboxamide (example 171) on a chiral column (instrument: Labomatic HD5000, Labocord-5000; Gilson GX-241, Labcol Vario 4000, column: Chiralpak IA 5μ 250×30 mm; eluent A: acetonitrile+0.1 vol-% diethylamine (99%); eluent B: ethanol; isocratic: 90% A+10% B; flow 50.0 mL/min; UV 254 nm) yielded 5 mg 6-(4-chlorophenyl)-N-[(cis)-4-hydroxytetrahydrofuran-3-yl]-3-oxo-2-(pyridin-3-yl)-2,3-dihydropyridazine-4-carboxamide, enantiomer 1.

Chiral HPLC: Rt=2.46 min (instrument: Agilent HPLC 1260; column: Chiralpak IA 3μ100×4.6 mm; eluent A: acetonitrile+0.1 vol-% diethylamine (99%); eluent B: ethanol; isocratic: 90% A+10% B; flow 1.4 mL/min; temperature: 25° C.; DAD 254 nm).

Example 173

6-(4-Chlorophenyl)-N-[(cis)-4-hydroxytetrahydrofuran-3-yl]-3-oxo-2-(pyridin-3-yl)-2,3-dihydropyridazine-4-carboxamide, Enantiomer 2

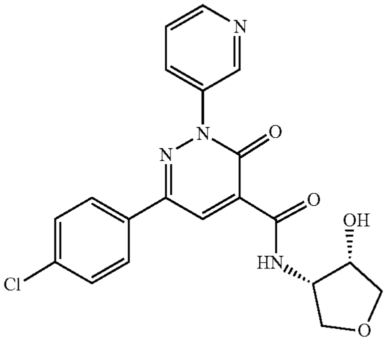 [SMILES: O=C(N[C@H]1COC[C@H]1O)c1cc(-c2ccc(Cl)cc2)nn(-c2cccnc2)c1=O]

HPLC-separation of 25 mg 6-(4-chlorophenyl)-N-[(cis)-4-hydroxytetrahydrofuran-3-yl]-3-oxo-2-(pyridin-3-yl)-2,3-dihydropyridazine-4-carboxamide (example 171) on a chiral column (instrument: Labomatic HD5000, Labocord-5000; Gilson GX-241, Labcol Vario 4000, column: Chiralpak IA 5μ 250×30 mm; eluent A: acetonitrile+0.1 vol-% diethylamine (99%); eluent B: ethanol; isocratic: 90% A+10% B; flow 50.0 mL/min; UV 254 nm) yielded 5 mg 6-(4-chlorophenyl)-N-[(cis)-4-hydroxytetrahydrofuran-3-yl]-3-oxo-2-(pyridin-3-yl)-2,3-dihydropyridazine-4-carboxamide, enantiomer 2. Chiral HPLC: Rt=3.63 min (instrument: Agilent HPLC 1260; column: Chiralpak IA 3μ 100×4.6 mm; eluent A: acetonitrile+0.1 vol-% diethylamine (99%); eluent B: ethanol; isocratic: 90% A+10% B; flow 1.4 mL/min; temperature: 25° C.; DAD 254 nm).

Example 174

3-(4-Chlorophenyl)-N-[(1S,2S)-2-hydroxycyclopentyl]-6-oxo-6H-1,4'-bipyridazine-5-carboxamide

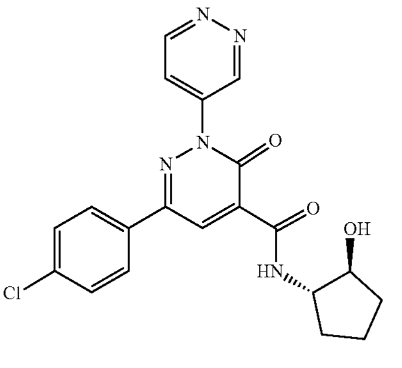 [SMILES: O=C(N[C@H]1CCC[C@@H]1O)c1cc(-c2ccc(Cl)cc2)nn(-c2ccnnc2)c1=O]

A solution of 65 mg intermediate 3-(4-chlorophenyl)-6-oxo-6H-1,4'-bipyridazine-5-carboxylic acid, 54 mg (1S,2S)-2-aminocyclopentanol hydrochlorid (1:1), 150 mg HATU, 0.14 mL ethyldiisopropylamine and 1 mg 4-dimethylaminopyridine in 2 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 14 mg 3-(4-chlorophenyl)-N-[(1S,2S)-2-hydroxycyclopentyl]-6-oxo-6H-1,4'-bipyridazine-5-carboxamide.

$^1$H NMR (400 MHz, DMSO-$d_6$) δ [ppm]=1.41-1.57 (m, 2H), 1.60-1.76 (m, 2H), 1.79-1.88 (m, 1H), 2.07-2.14 (m, 1H), 3.90-3.98 (m, 1H), 3.98-4.06 (m, 1H), 4.95 (d, 1H), 7.59-7.64 (m, 2H), 8.05-8.11 (m, 2H), 8.22 (dd, 1H), 8.63 (s, 1H), 9.10 (d, 1H), 9.48 (dd, 1H), 9.75 (dd, 1H).

Example 175

1,5-Anhydro-2-({[6-(4-chlorophenyl)-3-oxo-2-(pyridin-3-yl)-2,3-dihydropyridazin-4-yl]carbonyl}amino)-2,4-dideoxy-D-erythro-pentitol

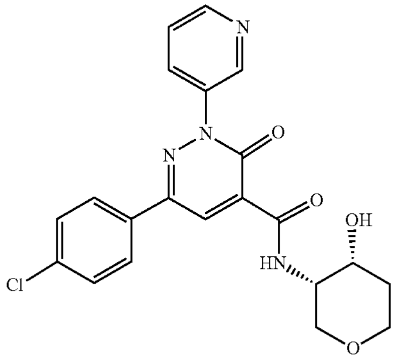 [SMILES: O=C(N[C@H]1COCC[C@H]1O)c1cc(-c2ccc(Cl)cc2)nn(-c2cccnc2)c1=O]

A solution of 75 mg intermediate 6-(4-chlorophenyl)-3-oxo-2-(pyridin-3-yl)-2,3-dihydropyridazine-4-carboxylic acid, 73 mg (3S,4R)-3-aminooxan-4-ol hydrochloride (1:1), 174 mg HATU, 0.16 mL ethyldiisopropylamine and 1 mg 4-dimethylaminopyridine in 2 mL of DMF was stirred at room temperature for 14 hours. Then water was added and the precipitate subjected to RP-HPLC (instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 43 mg 1,5-anhydro-2-({[6-(4-chlorophenyl)-3-oxo-2-(pyridin-3-yl)-2,3-dihydropyridazin-4-yl]carbonyl}amino)-2,4-dideoxy-D-erythro-pentitol.

$^1$H NMR (400 MHz, DMSO-$d_6$) δ [ppm]=1.57-1.65 (m, 1H), 1.72-1.81 (m, 1H), 3.47-3.54 (m, 1H), 3.56 (d, 2H), 3.64-3.73 (m, 1H), 3.88-3.95 (m, 1H), 4.02-4.12 (m, 1 H), 5.23 (br s, 1H), 7.56-7.61 (m, 2H), 7.64 (dd, 1H), 7.98-8.03 (m, 2H), 8.14-8.19 (m, 1H), 8.68-8.71 (m, 2H), 8.91 (s, 1H), 9.66 (d, 1H).

$[\alpha]_D^{20}$=41.9° (c=1.00, DMSO).

Example 176

1,5-Anhydro-2,4-dideoxy-2-[({3-oxo-2-(pyridin-3-yl)-6-[4-(trifluoromethoxy)phenyl]-2,3-dihydropyridazin-4-yl}carbonyl)amino]-D-erythro-pentitol

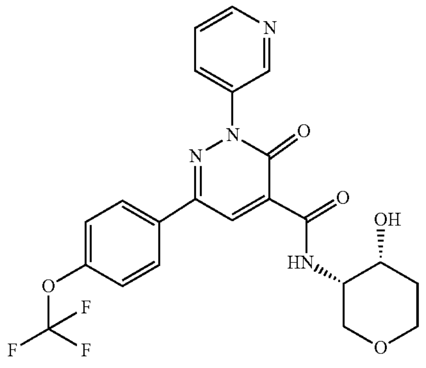 [SMILES: O=C(N[C@H]1COCC[C@H]1O)c1cc(-c2ccc(OC(F)(F)F)cc2)nn(-c2cccnc2)c1=O]

A solution of 75 mg intermediate 3-oxo-2-(pyridin-3-yl)-6-[4-(trifluoromethoxy)phenyl]-2,3-dihydropyridazine-4-carboxylic acid, 64 mg (3S,4R)-3-aminooxan-4-ol hydrochloride (1:1), 151 mg HATU, 0.1 mL ethyldiisopropylamine and 2 mg 4-dimethylaminopyridine in 1.5 mL of DMF was stirred at rt for 14 hours. Then the reaction mixture was filtered and subjected to RP-HPLC (HPLC (Instrument: Waters Autopurification MS SingleQuad; Column: Waters XBridge C18 5μ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm) to yield 26 mg 1,5-anhydro-2,4-dideoxy-2-[({3-oxo-2-(pyridin-3-yl)-6-[4-(trifluoromethoxy)phenyl]-2,3-dihydropyridazin-4-yl}carbonyl)amino]-D-erythro-pentitol.

$^1$H NMR (400 MHz, DMSO-$d_6$) δ [ppm]=1.57-1.66 (m, 1H), 1.77 (td, 1H), 3.47-3.53 (m, 1H), 3.56 (d, 2H), 3.65-3.73 (m, 1H), 3.92 (dq, 1H), 4.03-4.11 (m, 1H), 5.23 (d, 1H), 7.51 (d, 2H), 7.64 (dd, 1H), 8.08-8.13 (m, 2H), 8.15-8.19 (m, 1H), 8.67-8.72 (m, 2H), 8.91 (s, 1H), 9.66 (d, 1H).

Example 177

3-(4-Chlorophenyl)-N-[(2S)-1-hydroxypropan-2-yl]-6-oxo-6H-1,4'-bipyridazine-5-carboxamide

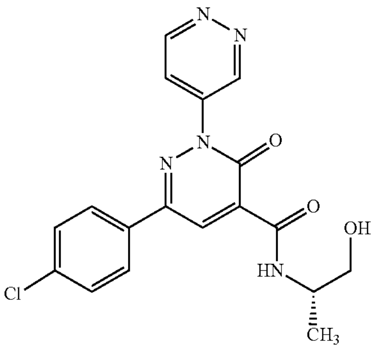 [SMILES: C[C@@H](CO)NC(=O)c1cc(-c2ccc(Cl)cc2)nn(-c2ccnnc2)c1=O]

A solution of 65 mg intermediate 3-(4-chlorophenyl)-6-oxo-6H-1,4'-bipyridazine-5-carboxylic acid, 30 mg (2S)-2-aminopropan-1-ol, 150 mg HATU, 0.14 mL ethyldiisopropylamine and 1 mg 4-dimethylaminopyridine in 2 mL of DMF was stirred at room temperature for 14 hours and at 50° C. for 1 h. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 4 mg 3-(4-chlorophenyl)-N-[(2S)-1-hydroxypropan-2-yl]-6-oxo-6H-1,4'-bipyridazine-5-carboxamide.

$^1$H NMR (400 MHz, DMSO-$d_6$) δ [ppm]=1.17 (d, 3H), 3.42-3.50 (m, 2H), 3.99-4.09 (m, 1H), 4.96 (t, 1H), 7.58-7.64 (m, 2H), 8.07-8.11 (m, 2H), 8.22 (dd, 1H), 8.66 (s, 1H), 9.23 (d, 1H), 9.48 (dd, 1H), 9.75 (dd, 1H).

Example 178

3-(4-Chlorophenyl)-N-(2-hydroxy-2-methylpropyl)-6-oxo-6H-1,4'-bipyridazine-5-carboxamide

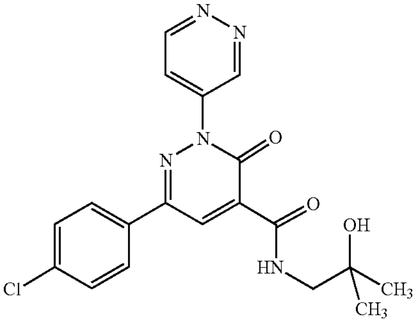 [SMILES: CC(C)(O)CNC(=O)c1cc(-c2ccc(Cl)cc2)nn(-c2ccnnc2)c1=O]

A solution of 80 mg intermediate 3-(4-chlorophenyl)-6-oxo-6H-1,4'-bipyridazine-5-carboxylic acid, 43 mg 1-amino-2-methylpropan-2-ol, 185 mg HATU, 0.17 mL ethyldiisopropylamine and 1 mg 4-dimethylaminopyridine in 2 mL of DMF was stirred at room temperature for 14 hours and at 50° C. for 1 h. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 28 mg 3-(4-chlorophenyl)-N-(2-hydroxy-2-methylpropyl)-6-oxo-6H-1,4'-bipyridazine-5-carboxamide.

$^1$H NMR (400 MHz, DMSO-d$_6$) δ [ppm]=1.14 (s, 6H), 3.32 (s, 2H), 4.70 (s, 1H), 7.58-7.63 (m, 2H), 8.06-8.11 (m, 2H), 8.22 (dd, 1H), 8.68 (s, 1H), 9.34 (t, 1H), 9.48 (dd, 1H), 9.75 (dd, 1H).

Example 179

6-(4-Cyanophenyl)-N-[(2S)-1-hydroxypropan-2-yl]-3-oxo-2-(pyridin-3-yl)-2,3-dihydropyridazine-4-carboxamide

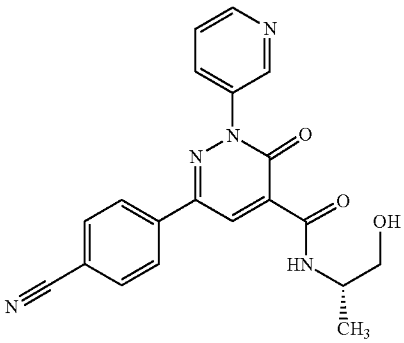 [SMILES: C[C@@H](CO)NC(=O)c1cc(-c2ccc(C#N)cc2)nn(-c2cccnc2)c1=O]

A solution of 150 mg intermediate 6-(4-cyanophenyl)-3-oxo-2-(pyridin-3-yl)-2,3-dihydropyridazine-4-carboxylic acid, 71 mg (2S)-2-aminopropan-1-ol, 358 mg HATU, 0.33 mL ethyldiisopropylamine and 3 mg 4-dimethylaminopyridine in 6 mL of DMF was stirred at 40° C. for 4 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 15 mg 6-(4-cyanophenyl)-N-[(2S)-1-hydroxypropan-2-yl]-3-oxo-2-(pyridin-3-yl)-2,3-dihydropyridazine-4-carboxamide.

$^1$H NMR (400 MHz, DMSO-d$_6$) δ[ppm]=1.16 (d, 3H), 3.41-3.50 (m, 2H), 3.99-4.09 (m, 1H), 4.94 (t, 1H), 7.61-7.66 (m, 1H), 7.97-8.01 (m, 2H), 8.16-8.22 (m, 3H), 8.70 (dd, 1H), 8.73 (s, 1H), 8.92 (d, 1H), 9.37 (d, 1H).

Example 180

6-[6-(Difluoromethyl)pyridin-3-yl]-N-[(2S)-1-hydroxypropan-2-yl]-3-oxo-2-(pyridin-3-yl)-2,3-dihydropyridazine-4-carboxamide

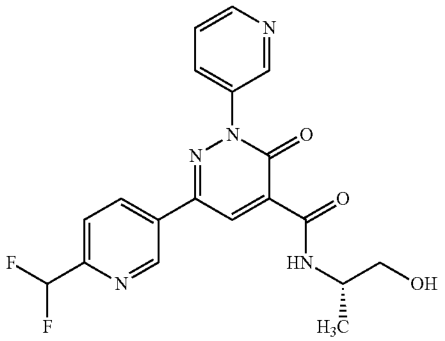 [SMILES: C[C@@H](CO)NC(=O)c1cc(-c2ccc(C(F)F)nc2)nn(-c2cccnc2)c1=O]

A solution of 85 mg intermediate 6-[6-(difluoromethyl)pyridin-3-yl]-3-oxo-2-(pyridin-3-yl)-2,3-dihydropyridazine-4-carboxylic acid, 37 mg (2S)-2-aminopropan-1-ol, 188 mg HATU, 0.17 mL ethyldiisopropylamine and 1.5 mg 4-dimethylaminopyridine in 3 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 40 mg 6-[6-(difluoromethyl)pyridin-3-yl]-N-[(2S)-1-hydroxypropan-2-yl]-3-oxo-2-(pyridin-3-yl)-2,3-dihydropyridazine-4-carboxamide.

$^1$H NMR (400 MHz, DMSO-d$_6$) δ [ppm]=1.17 (d, 3H), 3.40-3.50 (m, 2H), 3.99-4.10 (m, 1H), 4.95 (t, 1H), 7.06 (t, 1H), 7.61-7.66 (m, 1H), 7.84 (d, 1H), 8.16-8.21 (m, 1H), 8.58 (dd, 1H), 8.70 (dd, 1H), 8.78 (s, 1H), 8.94 (d, 1H), 9.27 (d, 1H), 9.37 (d, 1H).

Example 181

3-(4-Chlorophenyl)-N-[(cis)-4-hydroxytetrahydro-furan-3-yl]-6-oxo-6H-1,4'-bipyridazine-5-carboxamide

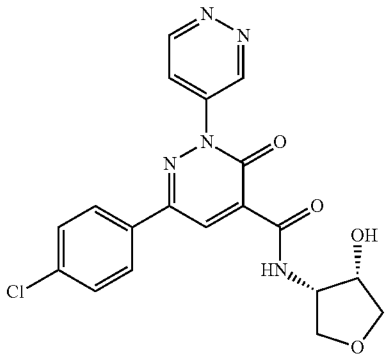 [SMILES: O=C(N[C@H]1COC[C@H]1O)c1cc(-c2ccc(Cl)cc2)nn(-c2ccnnc2)c1=O]

A solution of 125 mg intermediate 3-(4-chlorophenyl)-6-oxo-6H-1,4'-bipyridazine-5-carboxylic acid, 106 mg cis-4-aminotetrahydro-3-furanol hydochloride, 289 mg HATU, 0.19 mL ethyldiisopropylamine and 3 mg 4-dimethylaminopyridine in 3 mL of DMF was stirred at room temperature for 14 hours and at 50° C. for 1 h. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 17 mg 3-(4-chlorophenyl)-N-[(cis)-4-hydroxytetrahydrofuran-3-yl]-6-oxo-6H-1,4'-bipyridazine-5-carboxamide.

$^1$H NMR (400 MHz, DMSO-$d_6$) δ [ppm]=3.47 (dd, 1H), 3.63 (dd, 1H), 3.94 (dd, 1H), 4.02 (dd, 1H), 4.29 (ddt, 1H), 4.32-4.41 (m, 1H), 5.73 (d, 1H), 7.58-7.63 (m, 2H), 8.05-8.10 (m, 2H), 8.22 (dd, 1H), 8.70 (s, 1H), 9.48 (dd, 1H), 9.66 (d, 1H), 9.74 (dd, 1H).

Example 182

6-[6-(Difluoromethyl)pyridin-3-yl]-N-[(cis)-4-hydroxytetrahydrofuran-3-yl]-3-oxo-2-(pyridin-3-yl)-2,3-dihydropyridazine-4-carboxamide

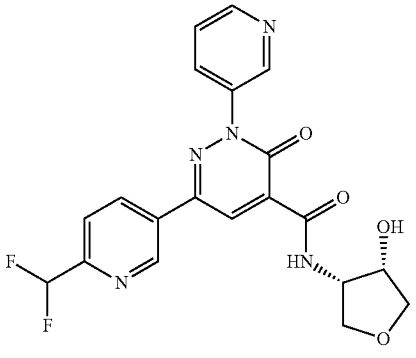 [SMILES: O=C(N[C@H]1COC[C@H]1O)c1cc(-c2ccc(C(F)F)nc2)nn(-c2cccnc2)c1=O]

A solution of 125 mg intermediate 6-[6-(difluoromethyl)pyridin-3-yl]-3-oxo-2-(pyridin-3-yl)-2,3-dihydropyridazine-4-carboxylic acid, 101 mg cis-4-aminotetrahydro-3-furanol hydrochlorid (1:1), 276 mg HATU, 0.25 mL ethyldiisopropylamine and 2 mg 4-dimethylaminopyridine in 3 mL of DMF was stirred at rt for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: water+0.2 vol % aqueous ammonia (32%), eluent B: acetonitrile; gradient: A 85%/B 15%→A 45%/B 55%; flow: 150 mL/min; UV-detection: 254 nm) to yield 86 mg 6-[6-(difluoromethyl)pyridin-3-yl]-N-[(cis)-4-hydroxytetrahydrofuran-3-yl]-3-oxo-2-(pyridin-3-yl)-2,3-dihydropyridazine-4-carboxamide.

$^1$H NMR (400 MHz, DMSO-$d_6$) δ[ppm]=3.46 (t, 1H), 3.61 (dd, 1H), 3.93 (dd, 1H), 4.02 (dd, 1H), 4.25-4.31 (m, 1H), 4.32-4.40 (m, 1H), 5.70 (d, 1H), 7.06 (t, 1H), 7.62-7.67 (m, 1H), 7.84 (d, 1H), 8.19 (ddd, 1H), 8.58 (dd, 1H), 8.71 (dd, 1H), 8.81 (s, 1H), 8.94 (d, 1H), 9.28 (d, 1H), 9.78 (d, 1H).

Example 183

6-[6-(Difluoromethyl)pyridin-3-yl]-N-[(cis)-4-hydroxytetrahydrofuran-3-yl]-3-oxo-2-(pyridin-3-yl)-2,3-dihydropyridazine-4-carboxamide, Enantiomer 1

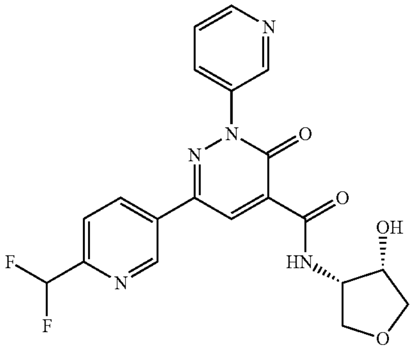 [SMILES: O=C(N[C@H]1COC[C@H]1O)c1cc(-c2ccc(C(F)F)nc2)nn(-c2cccnc2)c1=O]

HPLC-separation of 81 mg 6-[6-(difluoromethyl)pyridin-3-yl]-N-[(cis)-4-hydroxytetrahydrofuran-3-yl]-3-oxo-2-(pyridin-3-yl)-2,3-dihydropyridazine-4-carboxamide (example 182) on a chiral column (instrument: Labomatic HD5000, Labocord-5000; Gilson GX-241, Labcol Vario 4000, column: Amylose SA 5μ 250×30 mm; eluent A: acetonitrile+0.1 vol-% diethylamine (99%); eluent B: methanol+0.1 vol-% diethylamine (99%); isocratic: 50% A+50% B; flow 50.0 mL/min; UV 254 nm) yielded 35 mg 6-[6-(difluoromethyl)pyridin-3-yl]-N-[(cis)-4-hydroxytetrahydrofuran-3-yl]-3-oxo-2-(pyridin-3-yl)-2,3-dihydropyridazine-4-carboxamide, enantiomer 1.

Chiral HPLC: Rt=1.33 min (instrument: Agilent HPLC 1260; column: Amylose SA 3μ 100×4.6 mm; eluent A: acetonitrile+0.1 vol-% diethylamine (99%); eluent B: methanol; isocratic: 50% A+50% B; flow 1.4 mL/min; temperature: 25° C.; DAD 254 nm).

Example 184

6-[6-(Difluoromethyl)pyridin-3-yl]-N-[(cis)-4-hydroxytetrahydrofuran-3-yl]-3-oxo-2-(pyridin-3-yl)-2,3-dihydropyridazine-4-carboxamide, Enantiomer 2

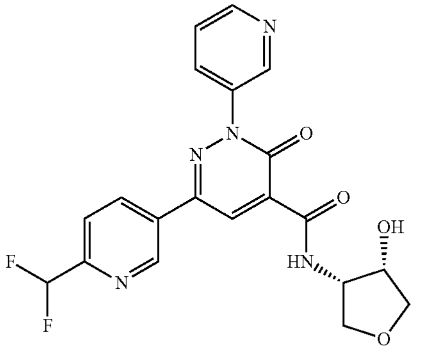 [SMILES: O=C(N[C@H]1COC[C@H]1O)c1cc(-c2ccc(C(F)F)nc2)nn(-c2cccnc2)c1=O]

HPLC-separation of 81 mg 6-[6-(difluoromethyl)pyridin-3-yl]-N-[(cis)-4-hydroxytetrahydrofuran-3-yl]-3-oxo-2-(pyridin-3-yl)-2,3-dihydropyridazine-4-carboxamide (example 182) on a chiral column (instrument: Labomatic HD5000, Labocord-5000; Gilson GX-241, Labcol Vario 4000, column: Amylose SA 5µ 250×30 mm; eluent A: acetonitrile+0.1 vol-% diethylamine (99%); eluent B: methanol+0.1 vol-% diethylamine (99%); isocratic: 50% A+50% B; flow 50.0 mL/min; UV 254 nm) yielded 35 mg 6-[6-(difluoromethyl)pyridin-3-yl]-N-[(cis)-4-hydroxytetrahydrofuran-3-yl]-3-oxo-2-(pyridin-3-yl)-2,3-dihydropyridazine-4-carboxamide, enantiomer 2.

Chiral HPLC: Rt=1.74 min (instrument: Agilent HPLC 1260; column: Amylose SA 3µ100×4.6 mm; eluent A: acetonitrile+0.1 vol-% diethylamine (99%); eluent B: methanol; isocratic: 50% A+50% B; flow 1.4 mL/min; temperature: 25° C.; DAD 254 nm).

Example 185

6-(4-Chlorophenyl)-3-oxo-2-(pyrimidin-5-yl)-N-(1,1,1-trifluoro-3-hydroxy-3-methyl butan-2-yl)-2,3-dihydropyridazine-4-carboxamide

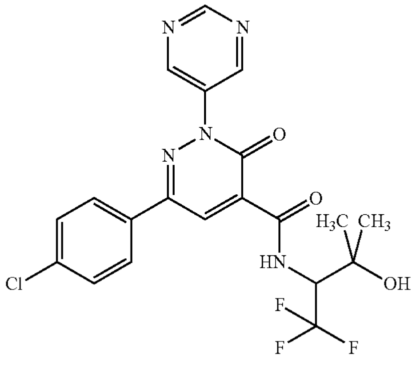 [SMILES: CC(C)(O)C(NC(=O)c1cc(-c2ccc(Cl)cc2)nn(-c2cncnc2)c1=O)C(F)(F)F]

A solution of 130 mg intermediate 6-(4-chlorophenyl)-3-oxo-2-(pyrimidin-5-yl)-2,3-dihydropyridazine-4-carboxylic acid, 153 mg 3-amino-4,4,4-trifluoro-2-methylbutan-2-ol hydochloride, 301 mg HATU, 0.21 mL ethyldiisopropylamine and 3.6 mg 4-dimethylaminopyridine in 3 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1 vol % formic acid in water, eluent B: acetonitrile; gradient: A 85%/B 15%→A 45%/B 55%; flow: 150 mL/min; UV-detection: 254 nm) to yield 20 mg 6-(4-chlorophenyl)-3-oxo-2-(pyrimidin-5-yl)-N-(1,1,1-trifluoro-3-hydroxy-3-methylbutan-2-yl)-2,3-dihydropyridazine-4-carboxamide.

$^1H$ NMR (400 MHz, DMSO-$d_6$) δ[ppm]=1.19 (s, 3H), 1.35 (s, 3H), 4.60-4.73 (m, 1H), 5.23 (s, 1H), 7.57-7.63 (m, 2H), 8.08 (d, 2H), 8.75 (s, 1H), 9.26 (s, 2H), 9.31 (s, 1H), 9.90 (d, 1H).

Example 186

6-(4-Chlorophenyl)-3-oxo-2-(pyrimidin-5-yl)-N-(1,1,1-trifluoro-3-hydroxy-3-methyl butan-2-yl)-2,3-dihydropyridazine-4-carboxamide, Enantiomer 1

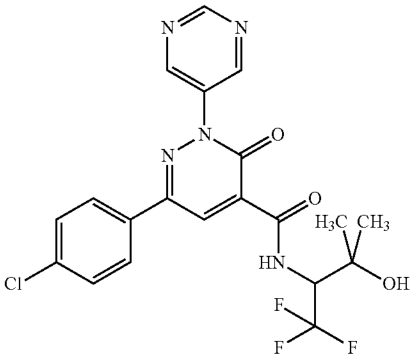 [SMILES: CC(C)(O)C(NC(=O)c1cc(-c2ccc(Cl)cc2)nn(-c2cncnc2)c1=O)C(F)(F)F]

HPLC-separation of 17 mg 6-(4-chlorophenyl)-3-oxo-2-(pyrimidin-5-yl)-N-(1,1,1-trifluoro-3-hydroxy-3-methylbutan-2-yl)-2,3-dihydropyridazine-4-carboxamide (example 185) on a chiral column (instrument: Sepiatec: Prep SFC100; column: Chiralpak IB 5 µm 250×30 mm; eluent A: CO2, eluent B: isopropanol; isocratic: 30% B; flow 100.0 mL/min; temperature: 40° C.; BPR: 150 bar; MWD @ 254 nm) yielded 4 mg 6-(4-chlorophenyl)-3-oxo-2-(pyrimidin-5-yl)-N-(1,1,1-trifluoro-3-hydroxy-3-methylbutan-2-yl)-2,3-dihydropyridazine-4-carboxamide, enantiomer 1.

Chiral HPLC: Rt=1.62 min (instrument: Agilent HPLC 1260; column: Chiralpak IB 5 µm 100×4.6 mm; eluent A: CO2; eluent B: ethanol; isocratic: 80% A+20% B; flow 4.0 mL/min; temperature: 37.5° C.; BPR: 100 bar; MWD @254 nm).

Example 187

6-(4-Chlorophenyl)-3-oxo-2-(pyrimidin-5-yl)-N-(1,1,1-trifluoro-3-hydroxy-3-methyl butan-2-yl)-2,3-dihydropyridazine-4-carboxamide, Enantiomer 2

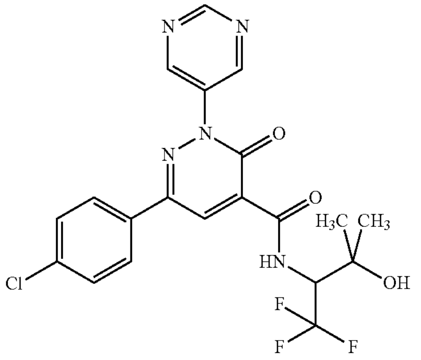 [SMILES: CC(C)(O)C(NC(=O)c1cc(-c2ccc(Cl)cc2)nn(-c2cncnc2)c1=O)C(F)(F)F]

HPLC-separation of 17 mg 6-(4-chlorophenyl)-3-oxo-2-(pyrimidin-5-yl)-N-(1,1,1-trifluoro-3-hydroxy-3-methylbutan-2-yl)-2,3-dihydropyridazine-4-carboxamide (example 185) on a chiral column (instrument: Sepiatec: Prep SFC100; column: Chiralpak IB 5 μm 250×30 mm; eluent A: CO2, eluent B: isopropanol; isocratic: 30% B; flow 100.0 mL/min; temperature: 40° C.; BPR: 150 bar; MWD @ 254 nm) yielded 4 mg 6-(4-chlorophenyl)-3-oxo-2-(pyrimidin-5-yl)-N-(1,1,1-trifluoro-3-hydroxy-3-methylbutan-2-yl)-2,3-dihydropyridazine-4-carboxamide, enantiomer 2.

Chiral HPLC: Rt=3.68 min (instrument: Agilent HPLC 1260; column: Chiralpak IB 5 μm 100×4.6 mm; eluent A: CO2; eluent B: ethanol; isocratic: 80% A+20% B; flow 4.0 mL/min; temperature: 37.5° C.; BPR: 100 bar; MWD @254 nm).

Example 188

N-[(1-Hydroxycyclopropyl)methyl]-3-oxo-2-(pyridin-3-yl)-6-[4-(trifluoromethyl)phenyl]-2,3-dihydropyridazine-4-carboxamide

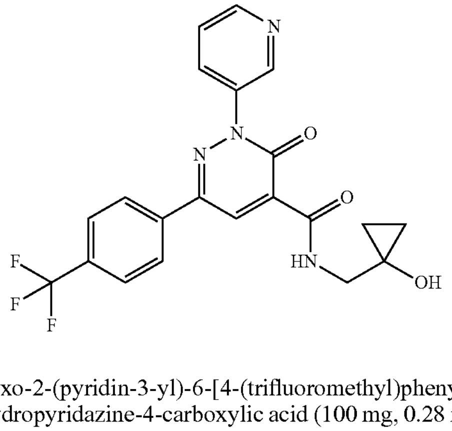

3-Oxo-2-(pyridin-3-yl)-6-[4-(trifluoromethyl)phenyl]-2,3-dihydropyridazine-4-carboxylic acid (100 mg, 0.28 mmol) was dissolved in anhydrous DMF (2.0 mL). 1-(Aminomethyl)cyclopropanol (48.2 mg, 0.55 mmol), N-ethyl-N-isopropylpropan-2-amine (217 μL, 1.25 mmol), and propane phosphonic acid anhydride (T3P, 243 μL, 50% in DMF, 416 μmol) were successively added. It was stirred for 3 h at rt. The reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient) yielding 67 mg (51%) of the title compound.

$^1$H-NMR (400 MHz, DMSO-$d_6$): δ [ppm]=0.52-0.57 (m, 2H), 0.59-0.64 (m, 2H), 3.47 (d, 2H), 5.52 (s, 1H), 7.65 (ddd, 1H), 7.89 (d, 2H), 8.17-8.24 (m, 3H), 8.71 (dd, 1H), 8.75 (s, 1H), 8.94 (dd, 1H), 9.58 (t, 1H).

Example 189

N-[(1-Hydroxycyclobutyl)methyl]-3-oxo-2-(pyridin-3-yl)-6-[4-(trifluoromethyl)phenyl]-2,3-dihydropyridazine-4-carboxamide

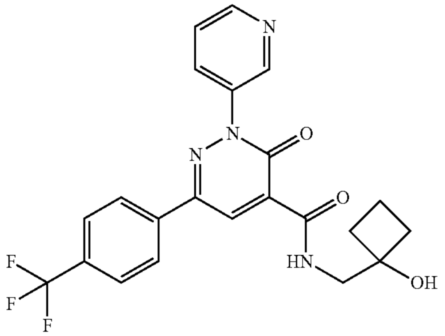 [SMILES: O=C(NCC1(O)CCC1)c1cc(-c2ccc(C(F)(F)F)cc2)nn(-c2cccnc2)c1=O]

3-Oxo-2-(pyridin-3-yl)-6-[4-(trifluoromethyl)phenyl]-2,3-dihydropyridazine-4-carboxylic acid (100 mg, 0.28 mmol) was dissolved in anhydrous DMF (2.0 mL). 1-(Aminomethyl)cyclobutanol (59.0 mg, 0.55 mmol), N-ethyl-N-isopropylpropan-2-amine (217 μL, 1.25 mmol), and propane phosphonic acid anhydride (T3P, 243 μL, 50% in DMF, 416 μmol) were successively added. It was stirred for 3 h at rt. The reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient) yielding 81 mg (66%) of the title compound.

$^1$H-NMR (400 MHz, DMSO-$d_6$): δ [ppm]=1.44-1.57 (m, 1H), 1.59-1.68 (m, 1H), 1.92-2.00 (m, 4H), 3.49 (d, 2H), 5.41 (s, 1H), 7.64 (ddd, 1H), 7.89 (d, 2H), 8.16-8.24 (m, 3H), 8.70 (dd, 1H), 8.76 (s, 1H), 8.92 (d, 1H), 9.49 (t, 1H).

Example 190

(+)-6-(4-Chlorophenyl)-N-[(2S)-1-hydroxypropan-2-yl]-3-oxo-2-(1H-pyrazol-4-yl)-2,3-dihydropyridazine-4-carboxamide

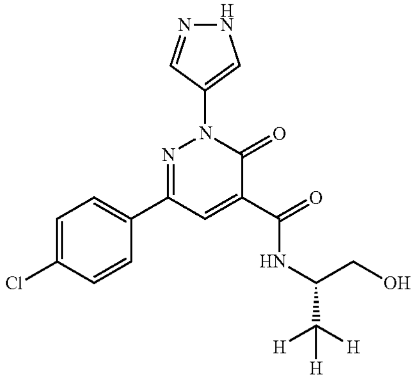 [SMILES: C[C@@H](CO)NC(=O)c1cc(-c2ccc(Cl)cc2)nn(-c2cn[nH]c2)c1=O]

6-(4-Chlorophenyl)-3-oxo-2-(1H-pyrazol-4-yl)-2,3-dihydropyridazine-4-carboxylic acid (75 mg) was dissolved in anhydrous DMF (2 mL). (2S)-2-Aminopropan-1-ol (36 mg), N-ethyl-N-isopropylpropan-2-amine (0.186 mL), and propane phosphonic acid anhydride (T3P, 207 μL, 50% in DMF) were successively added. It was stirred 1 h at rt. The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient) to yield 46 mg of the title compound $^1$H-NMR (400 MHz, DMSO-$d_6$): δ [ppm]=1.19 (d, 3H), 3.42-3.52 (m, 2H), 4.00-4.11 (m, 1H), 4.96 (br s, 1H), 7.57-7.62 (m, 2H), 8.07-8.13 (m, 2H), 8.14-8.55 (m, 2H), 8.59 (s, 1H), 9.52 (d, 1H), 13.24 (br s, 1H).

$[\alpha]_D^{20}$=+18.4° (c=1.00, methanol).

Example 191

6-[4-(Dimethylamino)phenyl]-N-[(2S)-1-hydroxypropan-2-yl]-3-oxo-2-(pyridin-3-yl)-2,3-dihydropyridazine-4-carboxamide

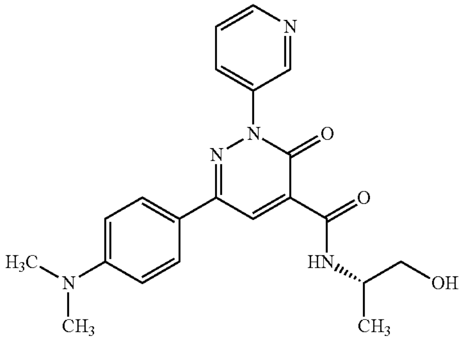 [SMILES: C[C@@H](CO)NC(=O)c1cc(-c2ccc(N(C)C)cc2)nn(-c2cccnc2)c1=O]

6-[4-(Dimethylamino)phenyl]-N-[(2S)-1-hydroxypropan-2-yl]-3-oxo-2,3-dihydropyridazine-4-carboxamide (14 mg) was dissolved in DMF (0.6 mL). Pyridin-3-yl boronic acid (11 mg), 2,2'-bipyridine (35 mg), sodium carbonate (5.6 mg), and anhydrous copper diacetate (20 mg) were added. The reaction mixture was stirred for 14 h at 80° C., cooled down and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 5 mg 6-[4-(dimethylamino)phenyl]-N-[(2S)-1-hydroxypropan-2-yl]-3-oxo-2-(pyridin-3-yl)-2,3-dihydropyridazine-4-carboxamide.

$^1$H NMR (400 MHz, DMSO-$d_6$) δ [ppm] 1.16 (d, 3H), 2.98 (s, 6H), 3.39-3.49 (m, 2H), 3.97-4.09 (m, 1H), 4.93 (t, 1H), 6.78-6.83 (m, 2H), 7.58-7.64 (m, 1H), 7.75-7.81 (m, 2H), 8.14 (ddd, 1H), 8.59 (s, 1H), 8.67 (dd, 1H), 8.89 (d, 1H), 9.49 (d, 1H).

Example 192

6-(4-Chlorophenyl)-N-[(2S)-1-hydroxypropan-2-yl]-2-(1-methyl-1H-pyrazol-3-yl)-3-oxo-2,3-dihydropyridazine-4-carboxamide

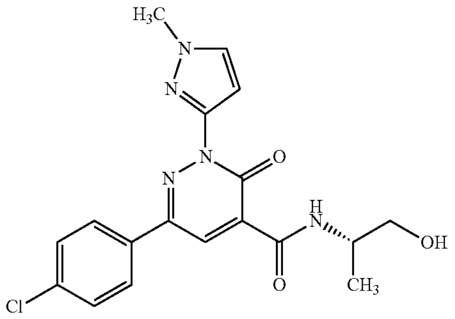 [SMILES: C[C@@H](CO)NC(=O)c1cc(-c2ccc(Cl)cc2)nn(-c2ccn(C)n2)c1=O]

A solution of 94 mg intermediate 6-(4-chlorophenyl)-2-(1-methyl-1H-pyrazol-3-yl)-3-oxo-2,3-dihydropyridazine-4-carboxylic acid, 43 mg (2S)-2-amino-1-propanol, 216 mg HATU, 0.20 mL ethyldiisopropylamine and 2 mg 4-dimethylaminopyridine in 4 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×mm, eluent A: 0.1% formic acid in water, eluent B: acetonitrile; gradient: A 70%/B 30%→A 30%/B 70%; flow: 150 mL/min; UV-detection: 254 nm) to yield 62 mg 6-(4-chlorophenyl)-N-[(2S)-1-hydroxypropan-2-yl]-2-(1-methyl-1H-pyrazol-3-yl)-3-oxo-2,3-dihydropyridazine-4-carboxamide.

$^1$H NMR (400 MHz, DMSO-$d_6$) δ [ppm]=1.16 (d, 3H), 3.40-3.48 (m, 2H), 3.91 (s, 3H), 3.98-4.08 (m, 1H), 4.93 (t, 1H), 6.57 (d, 1H), 7.55-7.60 (m, 2H), 7.86 (d, 1H), 7.92-7.98 (m, 2H), 8.62 (s, 1H), 9.41 (d, 1H).

Example 193

6-(4-Chlorophenyl)-N-[(2S)-1-hydroxypropan-2-yl]-2-(3-methyl-1H-pyrazol-5-yl)-3-oxo-2,3-dihydropyridazine-4-carboxamide

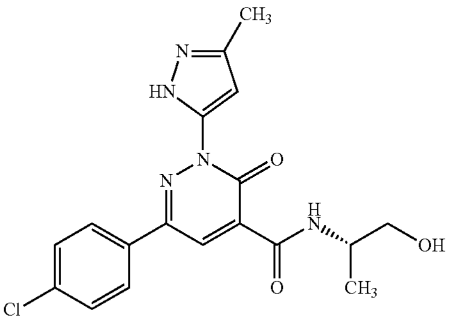 [SMILES: Cc1cc(-n2nc(-c3ccc(Cl)cc3)cc(C(=O)N[C@@H](C)CO)c2=O)[nH]n1]

A solution of 75 mg intermediate 6-(4-chlorophenyl)-2-(3-methyl-1H-pyrazol-5-yl)-3-oxo-2,3-dihydropyridazine-4-carboxylic acid, 34 mg (2S)-2-amino-1-propanol, 172 mg HATU, 0.16 mL ethyldiisopropylamine and 1 mg 4-dimethylaminopyridine in 4 mL of DMF was stirred at room temperature for 14 hours. Then the reaction mixture was filtered and subjected to RP-HPLC (instrument: Labomatic HD-3000 HPLC gradient pump, Labomatic Labocol Vario-2000 fraction collector; column: Chromatorex C-18 125 mm×30 mm, eluent A: 0.1% formic acid in water, eluent B: acetonitrile; gradient: A 85%/B 15%→A 45%/B 55%; flow: 150 mL/min; UV-detection: 254 nm) to yield 44 mg 6-(4-chlorophenyl)-N-[(2S)-1-hydroxypropan-2-yl]-2-(3-methyl-1H-pyrazol-5-yl)-3-oxo-2,3-dihydropyridazine-4-carboxamide.

δ[ppm]=1.16 (d, 3H), 2.31 (s, 3H), 3.40-3.49 (m, 2H), 3.97-$^1$H-NMR (400 MHz, DMSO-$d_6$): 4.08 (m, 1H), 4.93 (t, 1H), 6.33 (d, 1H), 7.55-7.60 (m, 2H), 7.95 (d, 2H), 8.61 (s, 1H), 9.45 (d, 1H), 12.85 (s, 1H).

Example 194

(+)-6-(4-Chlorophenyl)-N-[(2S)-1-hydroxypropan-2-yl]-3-oxo-2-(1,2-thiazol-4-yl)-2,3-dihydropyridazine-4-carboxamide

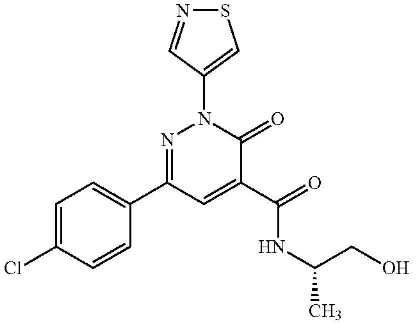 [SMILES: C[C@@H](CO)NC(=O)c1cc(-c2ccc(Cl)cc2)nn(-c2cnsc2)c1=O]

6-(4-Chlorophenyl)-3-oxo-2-(1,2-thiazol-4-yl)-2,3-dihydropyridazine-4-carboxylic acid (70 mg) was dissolved in anhydrous DMF (2 mL). (2S)-2-Aminopropan-1-ol (31.5 mg), N-ethyl-N-isopropylpropan-2-amine (0.164 mL), and propane phosphonic acid anhydride (T3P, 184 μL, 50% in DMF) were successively added. It was stirred for 2 h at rt.

The crude reaction mixture was concentrated under vacuum and purified by RP-HPLC (column: X-Bridge C18 5 μm 100×30 mm, mobile phase: (water+0.2 vol % aqueous ammonia (32%))/acetonitrile, gradient) to yield 47 mg of the title compound $^1$H-NMR (400 MHz, DMSO-$d_6$): δ [ppm]=1.18 (d, 3H), 3.42-3.52 (m, 2H), 3.99-4.10 (m, 1H), 4.97 (t, 1H), 7.58-7.63 (m, 2H), 8.07-8.12 (m, 2H), 8.64 (s, 1H), 9.13 (s, 1H), 9.39 (d, 1H), 9.61 (s, 1H).

$[\alpha]_D^{20}$=+9.55° (c=1.00, DMSO).

The following examples were prepared from the starting materials stated in the table using the procedure described in example 107 or 127. Enantiomers were separated from their racemate by chiral HPLC using the column and solvent conditions stated.

TABLE 2

Examples 195-345

| Expl. | Structure | IUPAC name | Starting materials | analytics |
|---|---|---|---|---|
| 195 | 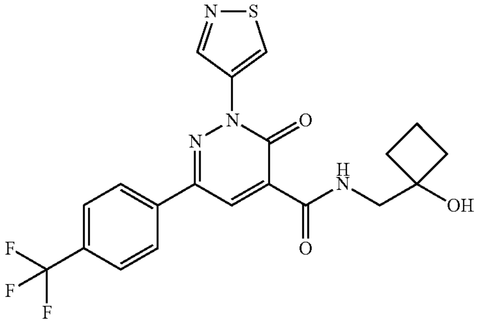 [SMILES: O=C(NCC1(O)CCC1)c1cc(-c2ccc(C(F)(F)F)cc2)nn(-c2cnsc2)c1=O] | N-[(1-Hydroxycyclobutyl)methyl]-3-oxo-2-(1,2-thiazol-4-yl)-6-[4-(trifluoromethyl)phenyl]-2,3-dihydropyridazine-4-carboxamide | 3-Oxo-2-(1,2-thiazol-4-yl)-6-[4-(trifluoromethyl)phenyl]-2,3-dihydropyridazine-4-carboxylic acid, 1-(aminomethyl)cyclobutanol | $^1$H-NMR (400 MHz, DMSO-$d_6$): δ [ppm] = 1.44-1.57 (m, 1H), 1.59-1.70 (m, 1H), 1.94-2.02 (m, 4H), 3.51 (d, 2H), 5.45 (s, 1H), 7.90 (d, 2H), 8.29 (d, 2H), 8.73 (s, 1H), 9.14 (s, 1H), 9.49 (t, 1H), 9.62 (s, 1H). |

TABLE 2-continued

Examples 195-345

| Expl. | Structure | IUPAC name | Starting materials | analytics |
|---|---|---|---|---|
| 196 | 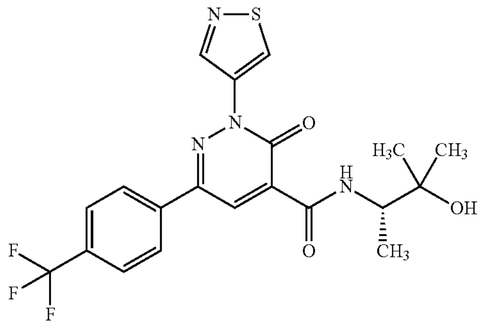 [SMILES: C[C@H](NC(=O)c1cc(-c2ccc(C(F)(F)F)cc2)nn(-c2cnsc2)c1=O)C(C)(C)O] | N-[(2S)-3-Hydroxy-3-methylbutan-2-yl]-3-oxo-2-(1,2-thiazol-4-yl)-6-[4-(trifluoromethyl)phenyl]-2,3-dihydropyridazine-4-carboxamide, $[\alpha]_D^{20}$ = +29.8° (c = 1.00, DMSO) | 3-Oxo-2-(1,2-thiazol-4-yl)-6-[4-(trifluoromethyl)phenyl]-2,3-dihydropyridazine-4-carboxylic acid, (3S)-3-amino-2-methylbutan-2-ol | $^1$H-NMR (400 MHz, DMSO-$d_6$): δ [ppm] = 1.12 (s, 3H), 1.15 (d, 3H), 1.18 (s, 3H), 3.89-3.97 (m, 1H), 4.69 (s, 1H), 7.90 (d, 2H), 8.29 (d, 2H), 8.71 (s, 1H), 9.13 (s, 1H), 9.49 (d, 1H), 9.62 (s, 1H). |
| 197 | 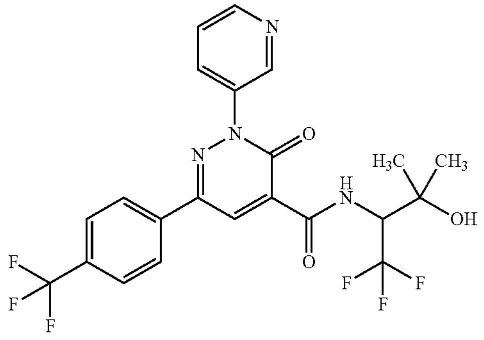 [SMILES: CC(C)(O)C(NC(=O)c1cc(-c2ccc(C(F)(F)F)cc2)nn(-c2cccnc2)c1=O)C(F)(F)F] | (+)-3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide, enantiomer 2, $[\alpha]_D^{20}$ = +35.8° (c = 1.00, methanol) | 3-Oxo-2-(pyridin-3-yl)-6-[4-(trifluoromethyl)phenyl]-2,3-dihydropyridazine 4-carboxylic acid, 3-amino-4,4,4-trifluoro-2-methylbutan-2-ol hydrochloride, Chiralpak IB 5µ 250 × 30 mm, eluent A: $CO_2$, eluent B: ethanol, isocratic: 22% B, 100 mL/min, 40° C., BPR: 150 bar, 254 nm | $^1$H-NMR (400 MHz, DMSO-$d_6$): δ [ppm] = 1.20 (s, 3H), 1.35 (s, 3H), 4.67 (quin, 1H), 5.22 (s, 1H), 7.65 (ddd, 1H), 7.89 (d, 2H), 8.18-8.25 (m, 3H), 8.71 (dd, 1H), 8.80 (s, 1H), 8.94 (dd, 1H), 10.00 (d, 1H). Rt = 3.69 min, Chiralpak IB 5 µm 100 × 4.6 mm, eluent A: $CO_2$, eluent B: ethanol, isocratic: 22% B, 4 mL/min, 37.5° C., BPR: 100 bar, 254 nm |
| 198 | 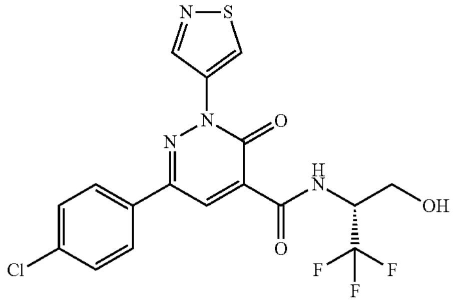 [SMILES: O=C(N[C@H](CO)C(F)(F)F)c1cc(-c2ccc(Cl)cc2)nn(-c2cnsc2)c1=O] | 6-(4-Chlorophenyl)-3-oxo-2-(1,2-thiazol-4-yl)-N-[(2R)-1,1,1-trifluoro-3-hydroxypropan-2-yl]-2,3-dihydropyridazine-4-carboxamide, $[\alpha]_D^{20}$ = +29.8° (c = 1.00, methanol) | 6-(4-Chlorophenyl)-3-oxo-2-(1,2-thiazol-4-yl)-2,3-dihydropyridazine 4-carboxylic acid, (2R)-2-amino-3,3,3-trifluoropropan-1-ol hydrochloride | $^1$H-NMR (400 MHz, DMSO-$d_6$): δ [ppm] = 3.67-3.75 (m, 1H), 3.85 (dt, 1H), 4.81-4.93 (m, 1H), 5.47 (t, 1H), 7.58-7.63 (m, 2H), 8.09-8.13 (m, 2H), 8.70 (s, 1H), 9.13 (s, 1H), 9.63 (s, 1H), 9.97 (d, 1H). |
| 199 | 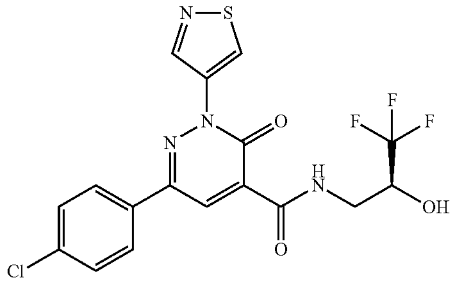 [SMILES: O=C(NC[C@H](O)C(F)(F)F)c1cc(-c2ccc(Cl)cc2)nn(-c2cnsc2)c1=O] | 6-(4-Chlorophenyl)-3-oxo-2-(1,2-thiazol-4-yl)-N-[(2S)-3,3,3-trifluoro-2-hydroxypropyl]-2,3-dihydropyridazine-4-carboxamide, $[\alpha]_D^{20}$ = −6.9° = 1.00, methanol) | 6-(4-Chlorophenyl)-3-oxo-2-(1,2-thiazol-4-yl)-2,3-dihydropyridazine 4-carboxylic acid, (2S)-3-amino-1,1,1-trifluoropropan-2-ol | $^1$H-NMR (400 MHz, DMSO-$d_6$): δ [ppm] = 3.49 (ddd, 1H), 3.76 (ddd, 1H), 4.19-4.30 (m, 1H), 6.69 (br d, 1H), 7.58-7.63 (m, 2H), 8.07-8.12 (m, 2H), 8.66 (s, 1H), 9.14 (s, 1H), 9.60 (s, 1H), 9.60 (t, 1H). |

TABLE 2-continued

| Examples 195-345 | | | | |
|---|---|---|---|---|
| Expl. | Structure | IUPAC name | Starting materials | analytics |
| 200 | 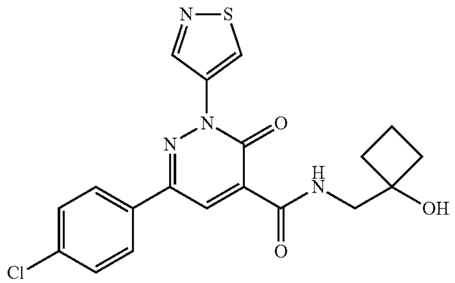 [SMILES: O=C(NCC1(O)CCC1)c1cc(-c2ccc(Cl)cc2)nn(-c2cnsc2)c1=O] | 6-(4-Chlorophenyl)-N-[(1-hydroxycyclobutyl)methyl]-3-oxo-2-(1,2-thiazol-4-yl)-2,3-dihydropyridazine-4-carboxamide | 6-(4-Chlorophenyl)-3-oxo-2-(1,2-thiazol-4-yl)-2,3-dihydropyridazine 4-carboxylic acid, 1-(aminomethyl) cyclobutanol | $^1$H-NMR (400 MHz, DMSO-$d_6$): δ [ppm] = 1.44-1.57 (m, 1H), 1.59-1.69 (m, 1H), 1.93-2.01 (m, 4H), 3.50 (d, 2H), 5.44 (s, 1H), 7.58-7.62 (m, 2H), 8.07-8.11 (m, 2H), 8.66 (s, 1H), 9.13 (s, 1H), 9.50 (t, 1H), 9.60 (s, 1H). |
| 201 | 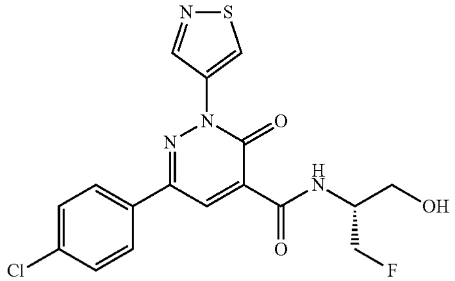 [SMILES: O=C(N[C@H](CO)CF)c1cc(-c2ccc(Cl)cc2)nn(-c2cnsc2)c1=O] | 6-(4-Chlorophenyl)-N-[(2R)-1-fluoro-3-hydroxypropan-2-yl]-3-oxo-2-(1,2-thiazol-4-yl)-2,3-dihydropyridazine-4-carboxamide, $[\alpha]_D^{20}$ = +10.0° (c = 1.00, DMSO) | 6-(4-Chlorophenyl)-3-oxo-2-(1,2-thiazol-4-yl)-2,3-dihydropyridazine-4-carboxylic acid, (2R)-2-amino-3-fluoropropan-1-ol hydrochloride | $^1$H-NMR (400 MHz, DMSO-$d_6$): δ [ppm] = 3.50-3.58 (m, 1H), 3.59-3.66 (m, 1H), 4.19-4.33 (m, 1H), 4.49-4.57 (m, 1H), 4.60-4.69 (m, 1H), 5.18 (t, 1H), 7.58-7.63 (m, 2H), 8.07-8.13 (m, 2H), 8.66 (s, 1H), 9.13 (s, 1H), 9.58 (d, 1H), 9.61 (s, 1H). |
| 202 | 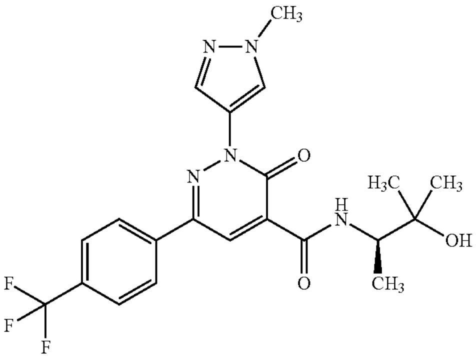 [SMILES: C[C@@H](NC(=O)c1cc(-c2ccc(C(F)(F)F)cc2)nn(-c2cnn(C)c2)c1=O)C(C)(C)O] | N-[(2R)-3-Hydroxy-3-methylbutan-2-yl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = −32.4° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (3R)-3-amino-2-methylbutan-2-ol hydrochloride | $^1$H-NMR (400 MHz, DMSO-$d_6$): δ [ppm] = 1.13 (s, 3H), 1.15 (d, 3H), 1.18 (s, 3H), 3.90-3.99 (m, 4H), 4.68 (s, 1H), 7.89 (d, 2H), 8.12 (s, 1H), 8.29 (d, 2H), 8.58 (s, 1H), 8.66 (s, 1H), 9.62 (d, 1H). |
| 203 | 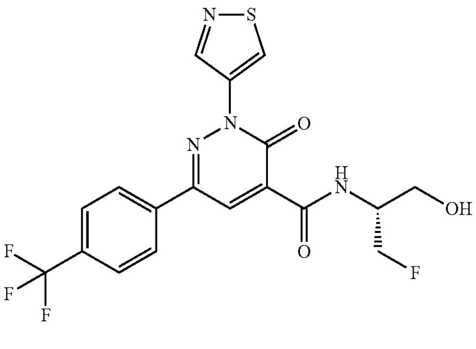 [SMILES: O=C(N[C@H](CO)CF)c1cc(-c2ccc(C(F)(F)F)cc2)nn(-c2cnsc2)c1=O] | N-[(2R)-1-Fluoro-3-hydroxypropan-2-yl]-3-oxo-2-(1,2-thiazol-4-yl)-6-[4-(trifluoromethyl)phenyl]-2,3-dihydropyridazine-4-carboxamide, $[\alpha]_D^{20}$ = +6.2° (c = 1.00, DMSO) | 3-Oxo-2-(1,2-thiazol-4-yl)-6-[4-(trifluoromethyl)phenyl]-2,3-dihydropyridazine-4-carboxylic acid, (2R)-2-amino-3-fluoropropan-1-ol hydrochloride | $^1$H-NMR (400 MHz, DMSO-$d_6$): δ [ppm] = 3.51-3.58 (m, 1H), 3.60-3.67 (m, 1H), 4.20-4.34 (m, 1H), 4.49-4.57 (m, 1H), 4.61-4.69 (m, 1H), 5.19 (t, 1H), 7.90 (d, 2H), 8.30 (d, 2H), 8.73 (s, 1H), 9.14 (s, 1H), 9.57 (d, 1H), 9.63 (s, 1H). |

TABLE 2-continued

| Examples 195-345 | | | | |
|---|---|---|---|---|
| Expl. | Structure | IUPAC name | Starting materials | analytics |
| 204 | 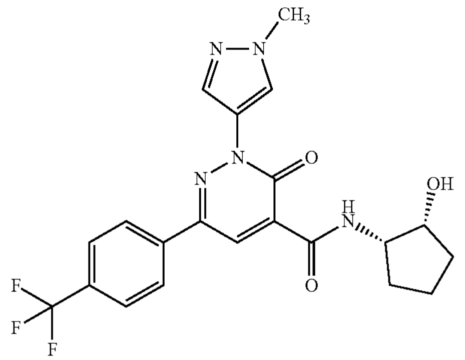 [SMILES: Cn1cc(-n2nc(-c3ccc(C(F)(F)F)cc3)cc(C(=O)N[C@H]3CCC[C@H]3O)c2=O)cn1] | N-[(1S,2R)-2-Hydroxycyclopentyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = +11.0° (c = 1.00, methanol) | 2-(1-Methyl-1H-pyrazol-4-yl)-3-oxo-6-[4-(trifluoromethyl)phenyl]-2,3-dihydropyridazine 4-carboxylic acid, (1R,2S)-2-aminocyclopentanol hydrochloride | $^1$H-NMR (400 MHz, DMSO-$d_6$): δ [ppm] = 1.49-1.67 (m, 3H), 1.72-1.92 (m, 2H), 1.93-2.03 (m, 1H), 3.94 (s, 3H), 4.02-4.14 (m, 2H), 5.06 (d, 1H), 7.90 (d, 2H), 8.13 (s, 1H), 8.30 (d, 2H), 8.57 (s, 1H), 8.67 (s, 1H), 9.76 (d, 1H). |
| 205 | 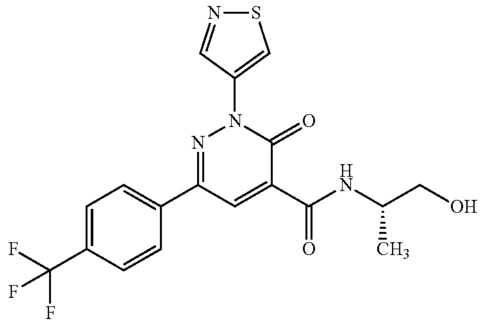 [SMILES: C[C@@H](CO)NC(=O)c1cc(-c2ccc(C(F)(F)F)cc2)nn(-c2cnsc2)c1=O] | N-[(2S)-1-Hydroxypropan-2-yl]-3-oxo-2-(1,2-thiazol-4-yl)-6-[4-(trifluoromethyl)phenyl]-2,3-dihydropyridazine-4-carboxamide, $[\alpha]_D^{20}$ = +24.3° (c = 1.00, methanol) | 3-Oxo-2-(1,2-thiazol-4-yl)-6-[4-(trifluoromethyl)phenyl]-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.52 (m, 2H), 4.00-4.11 (m, 1H), 4.97 (t, 1H), 7.90 (d, 2H), 8.29 (d, 2H), 8.70 (s, 1H), 9.14 (s, 1H), 9.38 (d, 1H), 9.62 (s, 1H). |
| 206 | 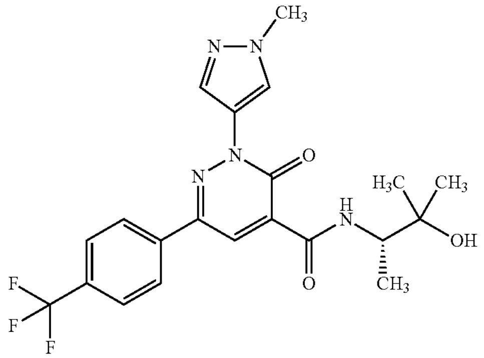 [SMILES: C[C@H](NC(=O)c1cc(-c2ccc(C(F)(F)F)cc2)nn(-c2cnn(C)c2)c1=O)C(C)(C)O] | N-[(2S)-3-Hydroxy-3-methylbutan-2-yl]-2-(1-methyl-1H-pyrazol-4-yl)-3-oxo-6-[4-(trifluoromethyl)phenyl]-2,3-dihydropyridazine-4-carboxamide, [α]20 = +36.7° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (3S)-3-amino-2-methylbutan-2-ol | $^1$H-NMR (400 MHz, DMSO-$d_6$): δ [ppm] = 1.13 (s, 3H), 1.15 (d, 3H), 1.18 (s, 3H), 3.90-3.99 (m, 4H), 4.68 (s, 1H), 7.89 (d, 2H), 8.12 (s, 1H), 8.29 (d, 2H), 8.58 (s, 1H), 8.66 (s, 1H), 9.62 (d, 1H). |
| 207 | 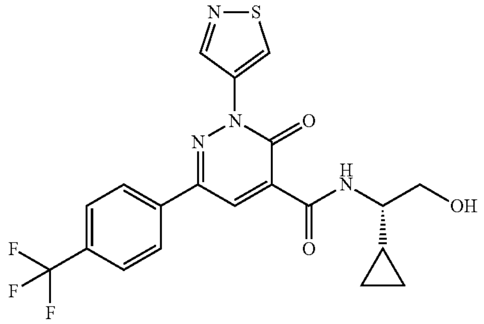 [SMILES: O=C(N[C@H](CO)C1CC1)c1cc(-c2ccc(C(F)(F)F)cc2)nn(-c2cnsc2)c1=O] | N-[(1S)-1-Cyclopropyl-2-hydroxyethyl]-3-oxo-2-(1,2-thiazol-4-yl)-6-[4-(trifluoromethyl)phenyl]-2,3-dihydropyridazine-4-carboxamide, $[\alpha]_D^{20}$ = +23.3° (c = 1.00, DMSO) | 3-Oxo-2-(1,2-thiazol-4-yl)-6-[4-(trifluoromethyl)phenyl]-2,3-dihydropyridazine-4-carboxylic acid, (2S)-2-amino-2-cyclopropylethanol hydrochloride | $^1$H-NMR (400 MHz, DMSO-$d_6$): δ [ppm] = 0.27-0.52 (m, 4H), 1.06-1.16 (m, 1H), 3.42-3.50 (m, 1H), 3.54-3.65 (m, 2H), 4.96 (t, 1H), 7.90 (d, 2H), 8.29 (d, 2H), 8.71 (s, 1H), 9.14 (s, 1H), 9.51 (d, 1H), 9.63 (s, 1H). |

TABLE 2-continued

Examples 195-345

| Expl. | Structure | IUPAC name | Starting materials | analytics |
|---|---|---|---|---|
| 208 | 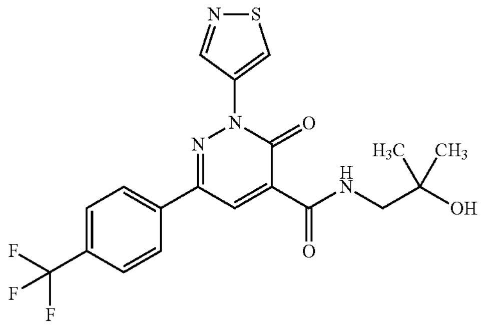 [SMILES: CC(C)(O)CNC(=O)c1cc(-c2ccc(C(F)(F)F)cc2)nn(-c2cnsc2)c1=O] | N-(2-Hydroxy-2-methylpropyl)-3-oxo-2-(1,2-thiazol-4-yl)-6-[4-(trifluoromethyl)phenyl]-2,3-dihydropyridazine-4-carboxamide | 3-Oxo-2-(1,2-thiazol-4-yl)-6-[4-(trifluoromethyl)phenyl]-2,3-dihydropyridazine 4-carboxylic acid, 1-amino-2-methylpropan-2-ol | $^1$H-NMR (400 MHz, DMSO-$d_6$): δ [ppm] = 1.15 (s, 6H), 3.33-3.35 (m, 2H and water signal), 4.71 (s, 1H), 7.90 (d, 2H), 8.29 (d, 2H), 8.72 (s, 1H), 9.15 (s, 1H), 9.50 (t, 1H), 9.63 (s, 1H). |
| 209 | 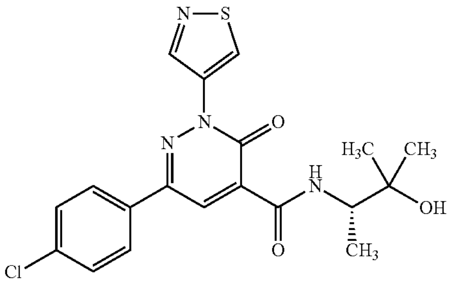 [SMILES: C[C@H](NC(=O)c1cc(-c2ccc(Cl)cc2)nn(-c2cnsc2)c1=O)C(C)(C)O] | 6-(4-Chlorophenyl)-N-[(2S)-3-hydroxy-3-methylbutan-2-yl]-3-oxo-2-(1,2-thiazol-4-yl)-2,3-dihydropyridazine-4-carboxamide, $[\alpha]_D^{20}$ = +38.4° (c = 1.00, methanol) | 6-(4-Chlorophenyl)-3-oxo-2-(1,2-thiazol-4-yl)-2,3-dihydropyridazine 4-carboxylic acid, (3S)-3-amino-2-methylbutan-2-ol | $^1$H-NMR (400 MHz, DMSO-$d_6$): δ [ppm] = 1.12 (s, 3H), 1.15 (d, 3H), 1.17 (s, 3H), 3.89-3.97 (m, 1H), 4.68 (s, 1H), 7.58-7.62 (m, 2H), 8.07-8.11 (m, 2H), 8.64 (s, 1H), 9.12 (s, 1H), 9.50 (d, 1H), 9.61 (s, 1H). |
| 210 | 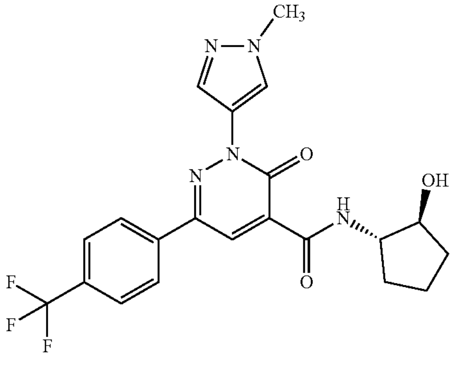 [SMILES: Cn1cc(-n2nc(-c3ccc(C(F)(F)F)cc3)cc(C(=O)N[C@H]3CCC[C@@H]3O)c2=O)cn1] | N-[(1S,2S)-2-Hydroxycyclopentyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = +48.9° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (1S,2S)-2-aminocyclopentanol hydrochloride | $^1$H-NMR (400 MHz, DMSO-$d_6$): δ [ppm] = 1.43-1.58 (m, 2H), 1.60-1.81 (m, 2H), 1.81-1.91 (m, 1H), 2.06-2.16 (m, 1H), 3.93 (s, 3H), 3.94-4.07 (m, 2H), 4.97 (d, 1H), 7.89 (d, 2H), 8.13 (s, 1H), 8.30 (d, 2H), 8.57 (s, 1H), 8.63 (s, 1H), 9.42 (d, 1H). |
| 211 | 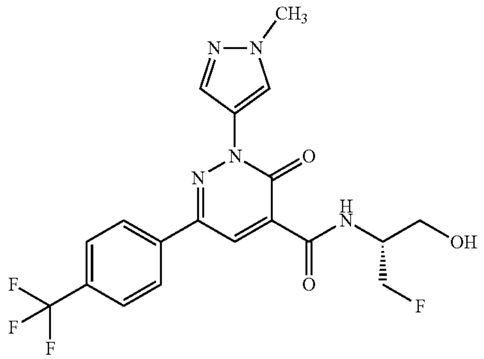 [SMILES: Cn1cc(-n2nc(-c3ccc(C(F)(F)F)cc3)cc(C(=O)N[C@H](CO)CF)c2=O)cn1] | N-[(2R)-1-Fluoro-3-hydroxypropan-2-yl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = +18.0° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (2R)-2-amino-3-fluoropropan-1-ol hydrochloride | $^1$H-NMR (400 MHz, DMSO-$d_6$): δ [ppm] = 3.52-3.59 (m, 1H), 3.60-3.67 (m, 1H), 3.94 (s, 3H), 4.20-4.34 (m, 1H), 4.49-4.58 (m, 1H), 4.61-4.70 (m, 1H), 5.19 (t, 1H), 7.90 (d, 2H), 8.14 (s, 1H), 8.31 (d, 2H), 8.59 (s, 1H), 8.68 (s, 1H), 9.71 (d, 1H). |

TABLE 2-continued

| Examples 195-345 | | | | |
|---|---|---|---|---|
| Expl. | Structure | IUPAC name | Starting materials | analytics |
| 212 | 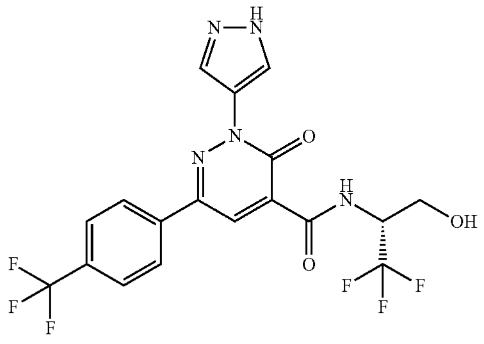 [SMILES: O=C(N[C@H](CO)C(F)(F)F)c1cc(-c2ccc(C(F)(F)F)cc2)nn(-c2cn[nH]c2)c1=O] | 3-Oxo-2-(1H-pyrazol-4-yl)-N-[(2R)-1,1,1-trifluoro-3-hydroxypropan-2-yl]-6-[4-(trifluoromethyl)phenyl]-2,3-dihydropyridazine-4-carboxamide, $[\alpha]_D^{20}$ = +34.0° (c = 1.00, DMSO) | 3-Oxo-2-(1H-pyrazol-4-yl)-6-[4-(trifluoromethyl)phenyl]-2,3-dihydropyridazine-4-carboxylic acid, (2R)-2-amino-3,3,3-trifluoropropan-1-ol hydrochloride | $^1$H-NMR (400 MHz, DMSO-$d_6$): δ [ppm] = 3.69-3.77 (m, 1H), 3.85 (dt, 1H), 4.83-4.93 (m, 1H), 5.48 (t, 1H), 7.90 (d, 2H), 8.09-8.36 (m, 3H), 8.37-8.66 (m, 1H), 8.72 (s, 1H), 10.09 (d, 1H), 13.29 (br s, 1H). |
| 213 | 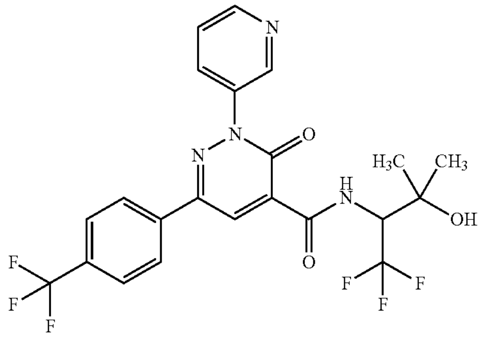 [SMILES: CC(C)(O)C(NC(=O)c1cc(-c2ccc(C(F)(F)F)cc2)nn(-c2cccnc2)c1=O)C(F)(F)F] | 3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide | 3-Oxo-2-(pyridin-3-yl)-6-[4-(trifluoromethyl)phenyl]-2,3-dihydropyridazine-4-carboxylic acid, 3-amino-4,4,4-trifluoro-2-methylbutan-2-ol hydrochloride | $^1$H-NMR (400 MHz, DMSO-$d_6$): δ [ppm] = 1.20 (s, 3H), 1.35 (s, 3H), 4.67 (quin, 1H), 5.22 (s, 1H), 7.65 (ddd, 1H), 7.89 (d, 2H), 8.18-8.25 (m, 3H), 8.71 (dd, 1H), 8.80 (s, 1H), 8.94 (d, 1H), 10.00 (d, 1H). |
| 214 | 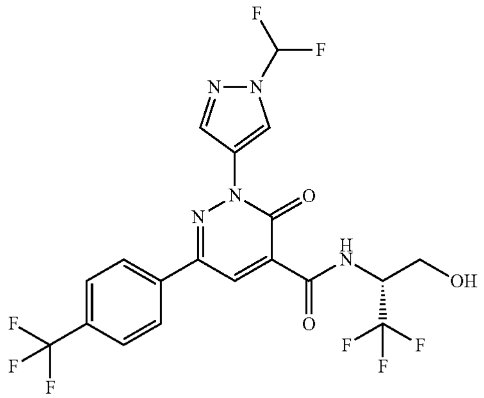 [SMILES: O=C(N[C@H](CO)C(F)(F)F)c1cc(-c2ccc(C(F)(F)F)cc2)nn(-c2cnn(C(F)F)c2)c1=O] | 2-[1-(Difluoromethyl)-1H-pyrazol-4-yl]-3-oxo-N-[(2R)-1,1,1-trifluoro-3-hydroxypropan-2-yl]-6-[4-(trifluoromethyl)phenyl]-2,3-dihydropyridazine-4-carboxamide, $[\alpha]_D^{20}$ = +29.9° (c = 1.00, DMSO) | 2-[1-(Difluoromethyl)-1H-pyrazol-4-yl]-3-oxo-6-[4-(trifluoromethyl)phenyl]-2,3-dihydropyridazine-4-carboxylic acid, (2R)-2-amino-3,3,3-trifluoropropan-1-ol hydrochloride | $^1$H-NMR (400 MHz, DMSO-$d_6$): δ [ppm] = 3.70-3.76 (m, 1H), 3.83-3.89 (m, 1H), 4.82-4.95 (m, 1H), 5.48 (br s, 1H), 7.91 (d, 2H), 7.93 (t, 1H), 8.36 (d, 2H), 8.55 (s, 1H), 8.75 (s, 1H), 9.10 (s, 1H), 9.99 (d, 1H). |
| 215 | 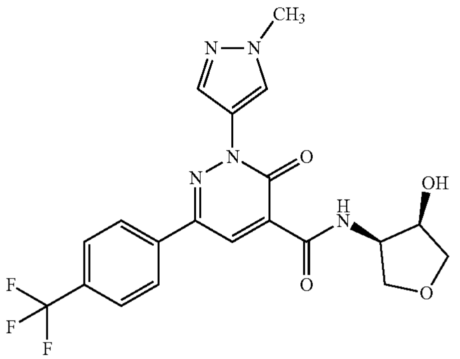 [SMILES: Cn1cc(-n2nc(-c3ccc(C(F)(F)F)cc3)cc(C(=O)N[C@@H]3COC[C@@H]3O)c2=O)cn1] | N-cis-4-Hydroxytetrahydrofuran-3-yl-2-(1-methyl-1H-pyrazol-4-yl)-3-oxo-6-[4-(trifluoromethyl)phenyl]-2,3-dihydropyridazine-4-carboxamide | 2-(1-Methyl-1H-pyrazol-4-yl)-3-oxo-6-[4-(trifluoromethyl)phenyl]-2,3-dihydropyridazine-4-carboxylic acid, cis-4-aminotetrahydro-furan-3-ol hydrochloride | $^1$H-NMR (400 MHz, DMSO-$d_6$): δ [ppm] = 3.48 (t, 1H), 3.65 (dd, 1H), 3.94-3.98 (m, 4H), 4.02 (t, 1H), 4.27-4.33 (m, 1H), 4.35-4.43 (m, 1H), 5.71 (d, 1H), 7.90 (d, 2H), 8.14 (s, 1H), 8.30 (d, 2H), 8.58 (s, 1H), 8.68 (s, 1H), 9.89 (d, 1H). |

TABLE 2-continued

| Examples 195-345 | | | | |
|---|---|---|---|---|
| Expl. | Structure | IUPAC name | Starting materials | analytics |
| 216 | 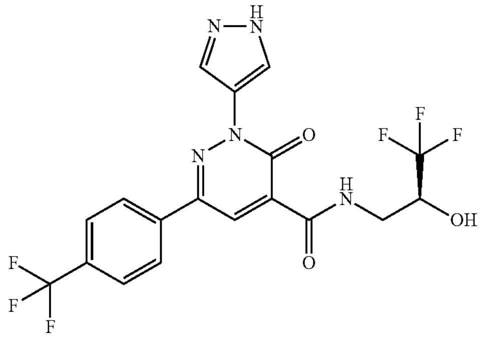 [SMILES: O=C(NC[C@H](O)C(F)(F)F)c1cc(-c2ccc(C(F)(F)F)cc2)nn(-c2cn[nH]c2)c1=O] | 3-Oxo-2-(1H-pyrazol-4-yl)-N-[(2S)-3,3,3-trifluoro-2-hydroxypropyl]-6-[4-(trifluoromethyl)phenyl]-2,3-dihydropyridazine-4-carboxamide, $[\alpha]_D^{20}$ = −2.0° = 1.00, DMSO) | 3-Oxo-2-(1H-pyrazol-4-yl)-6-[4-(trifluoromethyl)phenyl]-2,3-dihydropyridazine 4-carboxylic acid, (2S)-3-amino-1,1,1-trifluoropropan-2-ol | $^1$H-NMR (400 MHz, DMSO-$d_6$): δ [ppm] = 3.50 (ddd, 1H), 3.78 (ddd, 1H), 4.20-4.30 (m, 1H), 6.69 (br d, 1H), 7.90 (d, 2H), 8.10-8.60 (m, 4H), 8.68 (s, 1H), 9.73 (t, 1H), 13.27 (br s, 1H). |
| 217 | 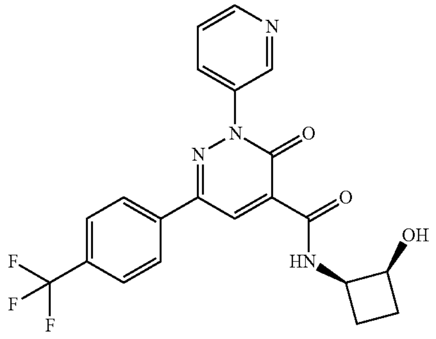 [SMILES: O=C(N[C@@H]1CC[C@@H]1O)c1cc(-c2ccc(C(F)(F)F)cc2)nn(-c2cccnc2)c1=O] | (+)-N-cis-2-Hydroxycyclobutyl-3-oxo-2-(pyridin-3-yl)-6-[4-(trifluoromethyl)phenyl]-2,3-dihydropyridazine-4-carboxamide, enantiomer 1, $[\alpha]_D^{20}$ = +34.0° (c = 1.00, DMSO) | 3-Oxo-2-(pyridin-3-yl)-6-[4-(trifluoromethyl)phenyl]-2,3-dihydropyridazine-4-carboxylic acid, cis-2-aminocyclobutanol hydrochloride Chiralpak IB 5μ 250 × 30 mm, eluent A: $CO_2$, eluent B: isopropanol, isocratic: 24% B, 100 mL/min, 40° C., BPR: 150 bar, 220 nm | $^1$H-NMR (400 MHz, DMSO-$d_6$): δ [ppm] = 1.74-1.92 (m, 2H), 2.06-2.16 (m, 2H), 4.33-4.41 (m, 2H), 5.51-5.54 (m, 1H), 7.65 (dd, 1H), 7.89 (d, 2H), 8.17-8.23 (m, 3H), 8.71 (dd, 1H), 8.73 (s, 1H), 8.93 (d, 1H), 9.88 (br d, 1H). Rt = 2.13 min, Chiralpak IB 5 μm 100 × 4.6 mm, eluent A: $CO_2$, eluent B: isopropanol, isocratic: 24% B, 4 mL/min, 37.5° C., BPR: 100 bar, 220 nm |
| 218 | 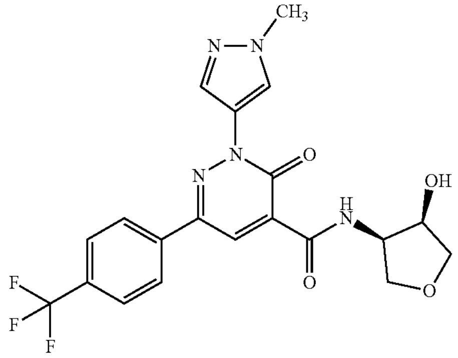 [SMILES: Cn1cc(-n2nc(-c3ccc(C(F)(F)F)cc3)cc(C(=O)N[C@@H]3COC[C@@H]3O)c2=O)cn1] | (+)-N-cis-4-Hydroxytetrahydrofuran-3-yl-2-(1-methyl-1H-pyrazol-4-yl)-3-oxo-6-[4-(trifluoromethyl)phenyl]-2,3-dihydropyridazine-4-carboxamide, enantiomer 2, $[\alpha]_D^{20}$ = +27.8° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, cis-4-aminotetrahydro-furan-3-ol hydrochloride Chiralpak IC 5μ 250 × 30 mm, eluent A: $CO_2$, eluent B: isopropanol, isocratic: 36% B, 100 mL/min, 40° C., BPR: 150 bar, 254 nm | $^1$H-NMR (400 MHz, DMSO-$d_6$): δ [ppm] = 3.48 (t, 1H), 3.65 (dd, 1H), 3.92-3.98 (m, 4H), 4.02 (t, 1H), 4.27-4.33 (m, 1H), 4.35-4.43 (m, 1H), 5.71 (d, 1H), 7.90 (d, 2H), 8.14 (s, 1H), 8.30 (d, 2H), 8.58 (s, 1H), 8.68 (s, 1H), 9.89 (d, 1H). Rt = 2.55 min, Chiralpak IC 5 μm 100 × 4.6 mm, eluent A: $CO_2$, eluent B: isopropanol, isocratic: 36% B, 4 mL/min, 37.5° C., BPR: 100 bar, 254 nm |
| 219 | 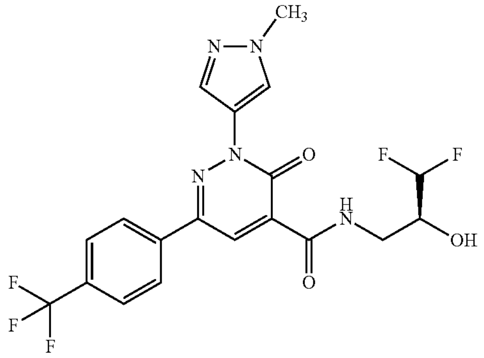 [SMILES: Cn1cc(-n2nc(-c3ccc(C(F)(F)F)cc3)cc(C(=O)NC[C@H](O)C(F)F)c2=O)cn1] | N-[(2S)-3,3-Difluoro-2-hydroxypropyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = −0.1° +/−0.33° = 1.00, DMSO) | 2-(1-Methyl-1H-pyrazol-4-yl)-3-oxo-6-[4-(trifluoromethyl)phenyl]-2,3-dihydropyridazine-4-carboxylic acid, (2S)-3-amino-1,1-difluoropropan-2-ol hydrochloride | $^1$H-NMR (400 MHz, DMSO-$d_6$): δ [ppm] = 3.42 (ddd, 1H), 3.68 (dt, 1H), 3.81-3.96 (m, 4H), 5.96 (dt, 1H), 6.03 (d, 1H), 7.90 (d, 2H), 8.14 (s, 1H), 8.30 (d, 2H), 8.56 (s, 1H), 8.66 (s, 1H), 9.65 (t, 1H). |

TABLE 2-continued

| Examples 195-345 | | | | |
|---|---|---|---|---|
| Expl. | Structure | IUPAC name | Starting materials | analytics |
| 220 | 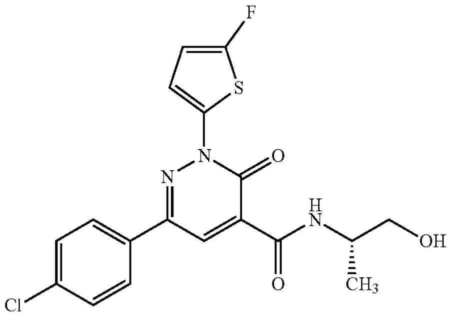 [SMILES: C[C@@H](CO)NC(=O)c1cc(-c2ccc(Cl)cc2)nn(-c2ccc(F)s2)c1=O] | 6-(4-Chlorophenyl)-2-(5-fluoro-2-thienyl)-N-[(2S)-1-hydroxypropan-2-yl]-3-oxo-2,3-dihydropyridazine-4-carboxamide, $[\alpha]_D^{20}$ = +6.4° +/−0.33° = 1.00, DMSO) | 6-(4-Chlorophenyl)-2-(5-fluoro-2-thienyl)-3-oxo-2,3-dihydropyridazine-4-carboxylic acid, (2S)-3-amino-1,1-difluoropropan-2-ol hydrochloride | $^1$H-NMR (400 MHz, DMSO-$d_6$): δ [ppm] = 1.19 (d, 3H), 3.43-3.53 (m, 2H), 4.00-4.11 (m, 1H), 4.98 (t, 1H), 6.84 (dd, 1H), 7.56 (t, 1H), 7.62 (d, 2H), 8.11 (d, 2H), 8.60 (s, 1H), 9.22 (d, 1H). |
| 221 | 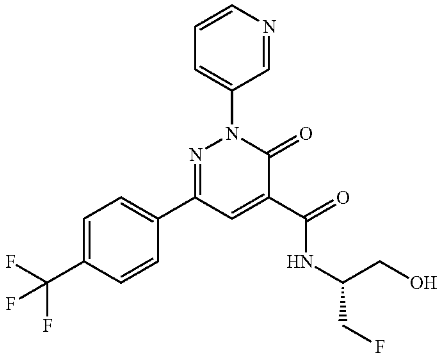 [SMILES: O=C(N[C@H](CO)CF)c1cc(-c2ccc(C(F)(F)F)cc2)nn(-c2cccnc2)c1=O] | N-[(2R)-1-Fluoro-3-hydroxypropan-2-yl]-3-oxo-2-(pyridin-3-yl)-6-[4-(trifluoromethyl) phenyl]-2,3-dihydropyridazine-4-carboxamide, $[\alpha]_D^{20}$ = +9.4° (c = 1.00, methanol) | 3-Oxo-2-(pyridin-3-yl)-6-[4-(trifluoromethyl) phenyl]-2,3-dihydropyridazine-4-carboxylic acid, (2R)-2-amino-3-fluoropropan-1-ol hydrochloride | $^1$H-NMR (400 MHz, DMSO-$d_6$): δ [ppm] = 3.49-3.56 (m, 1H), 3.58-3.64 (m, 1H), 4.19-4.33 (m, 1H), 4.47-4.55 (m, 1H), 4.59-4.67 (m, 1H), 5.17 (t, 1H), 7.64 (ddd, 1H), 7.89 (d, 2H), 8.18 (ddd, 1H), 8.22 (d, 2H), 8.71 (dd, 1H), 8.76 (s, 1H), 8.92 (d, 1H), 9.57 (d, 1H). |
| 222 | 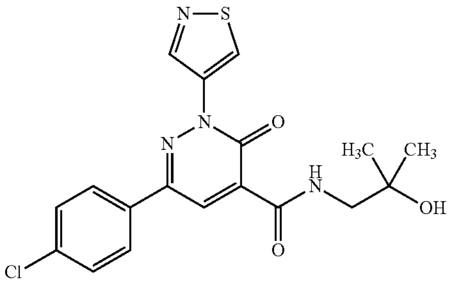 | 6-(4-Chlorophenyl)-N-(2-hydroxy-2-methylpropyl)-3-oxo-2-(1,2-thiazol-4-yl)-2,3-dihydropyridazine-4-carboxamide | 6-(4-Chlorophenyl)-3-oxo-2-(1,2-thiazol-4-yl)-2,3-dihydropyridazine-4-carboxylic acid, 1-amino-2-methylpropan-2-ol | $^1$H-NMR (400 MHz, DMSO-$d_6$): δ [ppm] = 1.15 (s, 6H), 3.31-3.35 (m, 2H and water signal), 4.70 (s, 1H), 7.58-7.63 (m, 2H), 8.07-8.12 (m, 2H), 8.65 (s, 1H), 9.14 (s, 1H), 9.51 (t, 1H), 9.61 (s, 1H). |
| 223 | 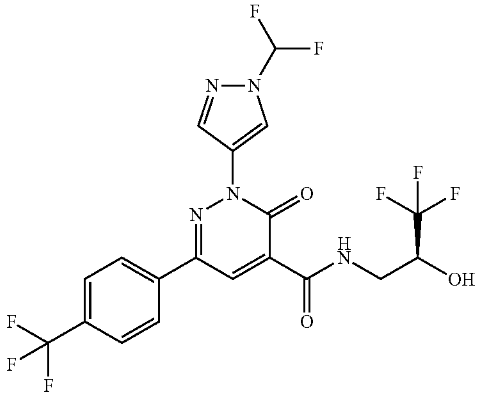 [SMILES: O=C(NC[C@H](O)C(F)(F)F)c1cc(-c2ccc(C(F)(F)F)cc2)nn(-c2cnn(C(F)F)c2)c1=O] | 2-[1-(Difluoromethyl)-1H-pyrazol-4-yl]-3-oxo-N-[(2S)-3,3,3-trifluoro-2-hydroxypropyl]-6-[4-(trifluoromethyl) phenyl]-2,3-dihydropyridazine-4-carboxamide, $[\alpha]_D^{20}$ = −0.7° +/−0.39 (c = 1.00, DMSO) | 2-[1-(Difluoromethyl)-1H-pyrazol-4-yl]-3-oxo-6-[4-(trifluoromethyl) phenyl]-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.51 (ddd, 1H), 3.78 (ddd, 1H), 4.20-4.32 (m, 1H), 6.70 (br s, 1H), 7.91 (d, 2H), 7.94 (t, 1H), 8.35 (d, 2H), 8.54 (s, 1H), 8.71 (s, 1H), 9.04 (s, 1H), 9.62 (t, 1H). |

TABLE 2-continued

| Examples 195-345 | | | | |
|---|---|---|---|---|
| Expl. | Structure | IUPAC name | Starting materials | analytics |
| 224 | 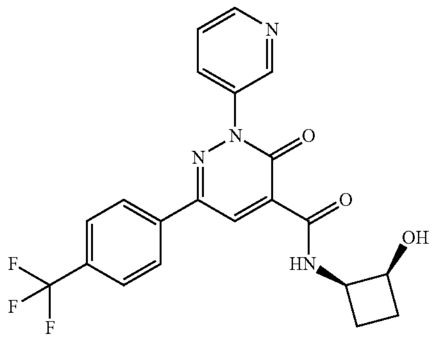 [SMILES: O=C(N[C@@H]1CC[C@@H]1O)c1cc(-c2ccc(C(F)(F)F)cc2)nn(-c2cccnc2)c1=O] | N-cis-2-Hydroxycyclobutyl-3-oxo-2-(pyridin-3-yl)-6-[4-(trifluoromethyl)phenyl]-2,3-dihydropyridazine-4-carboxamide | 3-Oxo-2-(pyridin-3-yl)-6-[4-(trifluoromethyl)phenyl]-2,3-dihydropyridazine-4-carboxylic acid, cis-2-aminocyclobutanol hydrochloride | $^1$H-NMR (400 MHz, DMSO-$d_6$): δ [ppm] = 1.74-1.92 (m, 2H), 2.06-2.16 (m, 2H), 4.33-4.41 (m, 2H), 5.53 (br s, 1H), 7.65 (dd, 1H), 7.89 (d, 2H), 8.16-8.23 (m, 3H), 8.71 (dd, 1H), 8.73 (s, 1H), 8.93 (d, 1H), 9.88 (br d, 1H). |
| 225 | 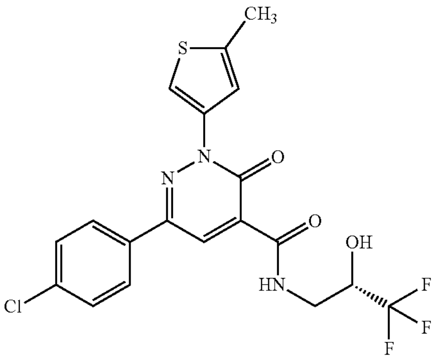 | 6-(4-Chlorophenyl)-2-(5-methyl-3-thienyl)-3-oxo-N-[(2S)-3,3,3-trifluoro-2-hydroxypropyl]-2,3-dihydropyridazine-4-carboxamide, $[\alpha]_D^{20}$ = −4.4° = 1.00, DMSO) | 6-(4-Chlorophenyl)-2-(5-methyl-3-thienyl)-3-oxo-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.48 (ddd, 1H), 3.76 (ddd, 1H), 4.18-4.29 (m, 1H), 6.68 (br d, 1H), 7.37 (t, 1H), 7.58-7.63 (m, 2H), 7.94 (d, 1H), 8.02-8.07 (m, 2H), 8.62 (s, 1H), 9.70 (t, 1H). |
| 226 | 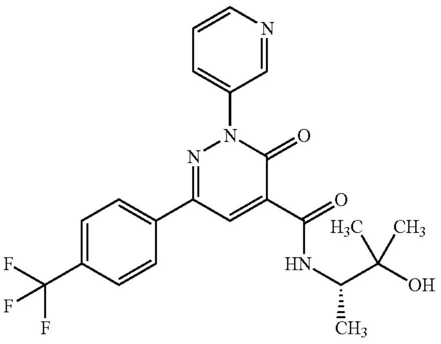 [SMILES: C[C@H](NC(=O)c1cc(-c2ccc(C(F)(F)F)cc2)nn(-c2cccnc2)c1=O)C(C)(C)O] | N-[(2S)-3-Hydroxy-3-methylbutan-2-yl]-3-oxo-2-(pyridin-3-yl)-6-[4-(trifluoromethyl)phenyl]-2,3-dihydropyridazine-4-carboxamide, $[\alpha]_D^{20}$ = +32.6° (c = 1.00, DMSO) | 3-Oxo-2-(pyridin-3-yl)-6-[4-(trifluoromethyl)phenyl]-2,3-dihydropyridazine-4-carboxylic acid, (3S)-3-amino-2-methylbutan-2-ol | $^1$H-NMR (400 MHz, DMSO-$d_6$): δ [ppm] = 1.10 (s, 3H), 1.13 (d, 3H), 1.16 (s, 3H), 3.88-3.96 (m, 1H), 4.66 (s, 1H), 7.64 (ddd, 1H), 7.88 (d, 2H), 8.17-8.23 (m, 3H), 8.70 (dd, 1H), 8.74 (s, 1H), 8.92 (d, 1H), 9.50 (d, 1H). |
| 227 | 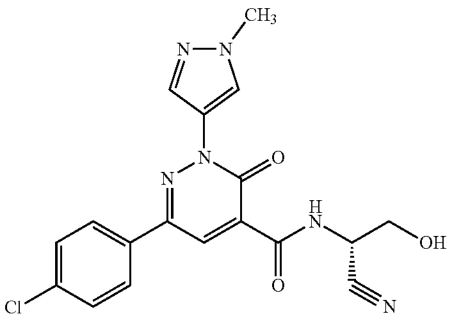 [SMILES: Cn1cc(-n2nc(-c3ccc(Cl)cc3)cc(C(=O)N[C@@H](C#N)CO)c2=O)cn1] | 6-(4-Chlorophenyl)-N-[(1S)-1-cyano-2-hydroxyethyl]-2-(1-methyl-1H-pyrazol-4-yl)-3-oxo-2,3-dihydropyridazine-4-carboxamide, $[\alpha]_D^{20}$ = −19.8° (c = 1.00, DMSO) | 6-(4-Chlorophenyl)-2-(1-methyl-1H-pyrazol-4-yl)-3-oxo-2,3-dihydropyridazine-4-carboxylic acid, (2S)-2-amino-3-hydroxy-propanenitrile hydrochloride | $^1$H-NMR (400 MHz, DMSO-$d_6$): δ [ppm] = 3.73-3.80 (m, 1H), 3.81-3.87 (m, 1H), 3.94 (s, 3H), 5.05-5.11 (m, 1H), 5.85 (t, 1H), 7.58-7.63 (m, 2H), 8.10-8.15 (m, 3H), 8.57 (s, 1H), 8.62 (s, 1H), 10.08 (d, 1H). |

TABLE 2-continued

| Examples 195-345 | | | | |
|---|---|---|---|---|
| Expl. | Structure | IUPAC name | Starting materials | analytics |
| 228 | 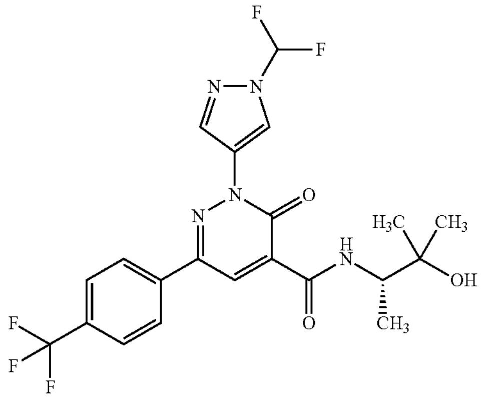 [SMILES: C[C@H](NC(=O)c1cc(-c2ccc(C(F)(F)F)cc2)nn(-c2cnn(C(F)F)c2)c1=O)C(C)(C)O] | 2-[1-(Difluoromethyl)-1H-pyrazol-4-yl]-N-[(2S)-3-hydroxy-3-methylbutan-2-yl]-3-oxo-6-[4-(trifluoromethyl)phenyl]-2,3-dihydropyridazine-4-carboxamide, $[\alpha]_D^{20}$ = +20.3° (c = 1.00, DMSO) | 2-[1-(Difluoromethyl)-1H-pyrazol-4-yl]-3-oxo-6-[4-(trifluoromethyl)phenyl]-2,3-dihydropyridazine-4-carboxylic acid, (3S)-3-amino-2-methylbutan-2-ol | $^1$H-NMR (400 MHz, DMSO-$d_6$): δ [ppm] = 1.13 (s, 3H), 1.16 (d, 3H), 1.19 (s, 3H), 3.90-3.99 (m, 1H), 4.69 (s, 1H), 7.90 (d, 2H), 7.93 (t, 1H), 8.34 (d, 2H), 8.53 (s, 1H), 8.69 (s, 1H), 9.07 (s, 1H), 9.52 (d, 1H). |
| 229 | 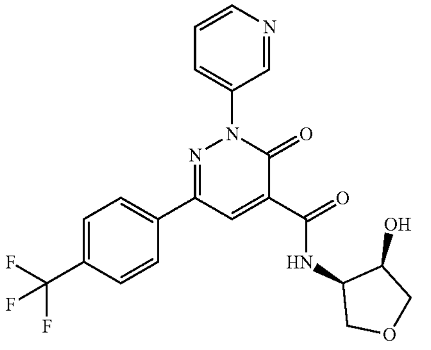 [SMILES: O=C(N[C@@H]1COC[C@@H]1O)c1cc(-c2ccc(C(F)(F)F)cc2)nn(-c2cccnc2)c1=O] | (+)-N-cis-4-Hydroxytetra-hydrofuran-3-yl-3-oxo-2-(pyridin-3-yl)-6-[4-(trifluoromethyl)phenyl]-2,3-dihydropyridazine-4-carboxamide, enantiomer 1, $[\alpha]_D^{20}$ = +24.8° (c = 1.00, methanol) | 3-Oxo-2-(pyridin-3-yl)-6-[4-(trifluoromethyl)phenyl]-2,3-dihydropyridazine-4-carboxylic acid, cis-4-aminotetrahydro-furan-3-ol hydrochloride Chiralpak IA 5µ 250 × 30 mm, eluent A: $CO_2$, eluent B: methanol, isocratic: 27% B, 100 mL/min, 40° C., BPR: 150 bar, 54 nm | $^1$H-NMR (400 MHz, DMSO-$d_6$): δ [ppm] = 3.46 (t, 1H), 3.61 (dd, 1H), 3.93 (dd, 1H), 4.01 (t, 1H), 4.25-4.31 (m, 1H), 4.32-4.40 (m, 1H), 5.70 (br d, 1H), 7.65 (ddd, 1H), 7.89 (d, 2H), 8.18 (ddd, 1H), 8.21 (d, 2H), 8.71 (dd, 1H), 8.76 (s, 1H), 8.92 (d, 1H), 9.80 (d, 1H). Rt = 3.36 min, Chiralpak IA 5 µm 100 × 4.6 mm, eluent A: $CO_2$, eluent B: methanol, isocratic: 27% B, 4.0 mL/min, 37.5° C., BPR: 100 bar, 254 nm |
| 230 | 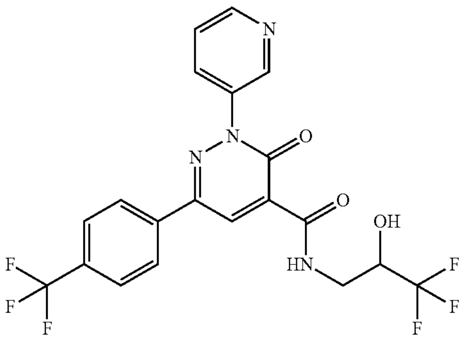 [SMILES: O=C(NCC(O)C(F)(F)F)c1cc(-c2ccc(C(F)(F)F)cc2)nn(-c2cccnc2)c1=O] | (−)-N-(3,3-Difluoro-2-hydroxypropyl)-3-oxo-2-(pyridin-3-yl)-6-[4-(trifluoromethyl)phenyl]-2,3-dihydropyridazine-4-carboxamide, enantiomer 2, $[\alpha]_D^{20}$ = −8.3° = 1.00, methanol) | 3-Oxo-2-(pyridin-3-yl)-6-[4-(trifluoromethyl)phenyl]-2,3-dihydropyridazine 4-carboxylic acid, 3-amino-1,1-difluoropropan-2-ol hydrochloride Chiralpak IE 5µ 250 × 30 mm, eluent A: 2-methoxy-2-methylpropane and 0.1 vol % diethylamine (99%), eluent B: methanol, isocratic: 50% B, 40 mL/min, 254 nm | $^1$H-NMR (400 MHz, DMSO-$d_6$): δ [ppm] = 3.40 (ddd, 1H), 3.66 (ddd, 1H), 3.79-3.91 (m, 1H), 5.94 (dt, 1H), 6.00 (d, 1H), 7.65 (ddd, 1H), 7.89 (d, 2H), 8.18 (ddd, 1H), 8.22 (d, 2H), 8.71 (dd, 1H), 8.74 (s, 1H), 8.93 (d, 1H), 9.53 (t, 1H). Rt = 1.76 min, Chiralpak IE 3um 100 × 4.6 mm, eluent A: 2-methoxy-2-methylpropane and 0.1 vol % diethylamine (99%), eluent B: methanol, isocratic: 50% B, 1.4 mL/min, 25° C., 254 nm |

TABLE 2-continued

| Examples 195-345 | | | | |
|---|---|---|---|---|
| Expl. | Structure | IUPAC name | Starting materials | analytics |
| 231 | 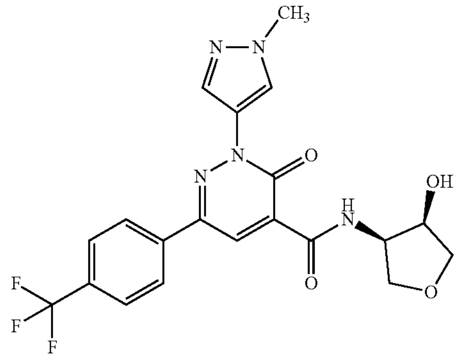 [SMILES: Cn1cc(-n2nc(-c3ccc(C(F)(F)F)cc3)cc(C(=O)N[C@@H]3COC[C@@H]3O)c2=O)cn1] | (−)-N-cis-4-Hydroxytetra-hydrofuran-3-yl-2-(1-methyl-1H-pyrazol-4-yl)-3-oxo-6-[4-(trifluoromethyl) phenyl]-2,3-dihydropyridazine-4-carboxamide, enantiomer 1, $[\alpha]_D^{20}$ = −23.2° (c = 1.00, methanol) | 2-(1-Methyl-1H-pyrazol-4-yl)-3-oxo-6-[4-(trifluoromethyl) phenyl]-2,3-dihydropyridazine-4-carboxylic acid, cis-4-aminotetrahydro-furan-3-ol hydrochloride Chiralpak IC 5μ 250 x 30 mm, eluent A: $CO_2$, eluent B: isopropanol, isocratic: 36% B, 100 mL/min, 40° C., BPR: 150 bar, 254 nm | $^1$H-NMR (400 MHz, DMSO-$d_6$): δ [ppm] = 3.48 (t, 1H), 3.65 (dd, 1H), 3.92-3.98 (m, 4H), 4.02 (t, 1H), 4.27-4.33 (m, 1H), 4.35-4.43 (m, 1H), 5.71 (d, 1H), 7.90 (d, 2H), 8.14 (s, 1H), 8.30 (d, 2H), 8.58 (s, 1H), 8.68 (s, 1H), 9.89 (d, 1H). Rt = 1.67 min, Chiralpak IC 5 μm 100 x 4.6 mm, eluent A: $CO_2$, eluent B: isopropanol, isocratic: 36% B, 4 mL/min, 37.5° C., BPR: 100 bar, 254 nm |
| 232 | 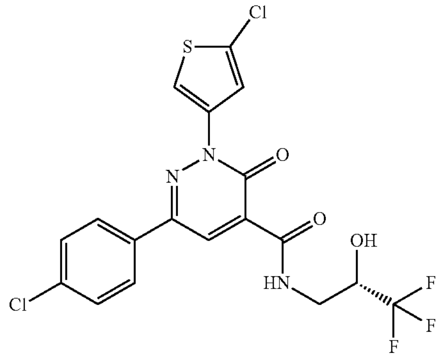 [SMILES: O=C(NC[C@H](O)C(F)(F)F)c1cc(-c2ccc(Cl)cc2)nn(-c2csc(Cl)c2)c1=O] | 6-(4-Chlorophenyl)-2-(5-chloro-3-thienyl)-3-oxo-N-[(2S)-3,3,3-trifluoro-2-hydroxypropyl]-2,3-dihydropyridazine-4-carboxamide, $[\alpha]_D^{20}$ = −2.9° = 1.00, DMSO) | 6-(4-Chlorophenyl)-2-(5-chloro-3-thienyl)-3-oxo-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.48 (ddd, 1H), 3.76 (ddd, 1H), 4.18-4.29 (m, 1H), 6.68 (d, 1H), 7.58-7.62 (m, 2H), 7.69 (d, 1H), 8.05-8.09 (m, 2H), 8.10 (d, 1H), 8.63 (s, 1H), 9.61 (t, 1H). |
| 233 | 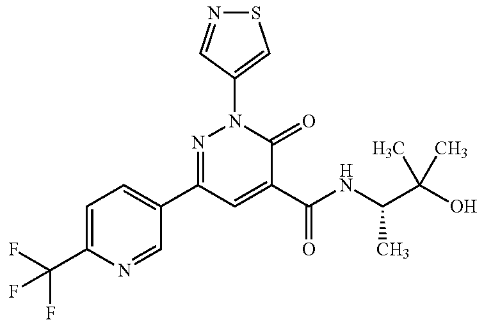 [SMILES: C[C@H](NC(=O)c1cc(-c2ccc(C(F)(F)F)nc2)nn(-c2cnsc2)c1=O)C(C)(C)O] | N-[(2S)-3-Hydroxy-3-methylbutan-2-yl]-3-oxo-2-(1,2-thiazol-4-yl)-6-[6-(trifluoromethyl) pyridin-3-yl]-2,3-dihydropyridazine-4-carboxamide, $[\alpha]_D^{20}$ = +25.2° (c = 1.00, DMSO) | 3-Oxo-2-(1,2-thiazol-4-yl)-6-[6-(trifluoromethyl) pyridin-3-yl]-2,3-dihydropyridazine-4-carboxylic acid, (3S)-3-amino-2-methylbutan-2-ol hydrochloride | $^1$H-NMR (400 MHz, DMSO-$d_6$): δ [ppm] = 1.13 (s, 3H), 1.15 (d, 3H), 1.18 (s, 3H), 3.90-3.98 (m, 1H), 4.70 (s, 1H), 8.06 (d, 1H), 8.75 (dd, 1H), 8.79 (s, 1H), 9.18 (s, 1H), 9.44 (d, 1H), 9.46 (d, 1H), 9.66 (s, 1H). |
| 234 | 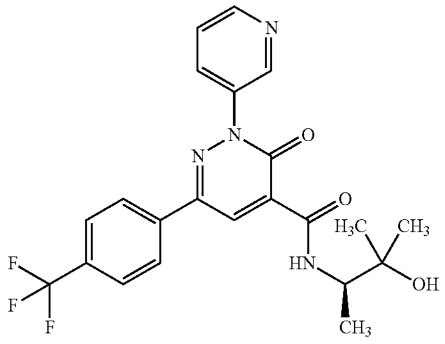 | N-[(2R)-3-Hydroxy-3-methylbutan-2-yl]-3-oxo-2-(pyridin-3-yl)-6-[4-(trifluoromethyl) phenyl]-2,3-dihydropyridazine-4-carboxamide, $[\alpha]_D^{20}$ = −29.2° (c = 1.00, methanol) | 3-Oxo-2-(pyridin-3-yl)-6-[4-(trifluoromethyl) phenyl]-2,3-dihydropyridazine-4-carboxylic acid, (3R)-3-amino-2-methylbutan-2-ol hydrochloride | $^1$H-NMR (400 MHz, DMSO-$d_6$): δ [ppm] = 1.10 (s, 3H), 1.13 (d, 3H), 1.16 (s, 3H), 3.88-3.96 (m, 1H), 4.66 (s, 1H), 7.64 (ddd, 1H), 7.88 (d, 2H), 8.17-8.23 (m, 3H), 8.70 (dd, 1H), 8.74 (s, 1H), 8.92 (d, 1H), 9.50 (d, 1H). |

TABLE 2-continued

| Expl. | Structure | IUPAC name | Starting materials | analytics |
|---|---|---|---|---|
| Examples 195-345 | | | | |
| 235 | 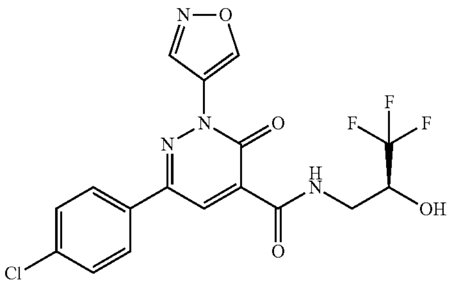 | 6-(4-Chlorophenyl)-2-(1,2-oxazol-4-yl)-3-oxo-N-[(2S)-3,3,3-trifluoro-2-hydroxypropyl]-2,3-dihydropyridazine-4-carboxamide, $[\alpha]_D^{20}$ = −7.5° = 1.00, DMSO) | 6-(4-Chlorophenyl)-2-(1,2-oxazol-4-yl)-3-oxo-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.50 (ddd, 1H), 3.77 (ddd, 1H), 4.18-4.30 (m, 1H), 6.70 (d, 1H), 7.59-7.64 (m, 2H), 8.16-8.20 (m, 2H), 8.66 (s, 1H), 9.46 (s, 1H), 9.53 (t, 1H), 9.78 (s, 1H). |
| 236 | 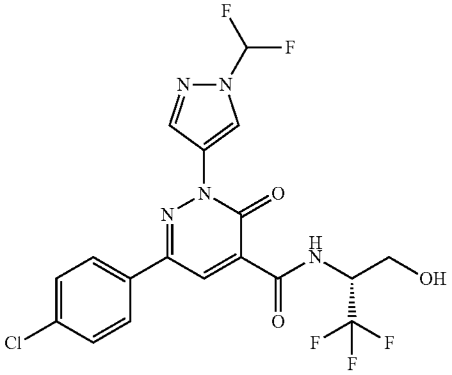 [SMILES: O=C(N[C@H](CO)C(F)(F)F)c1cc(-c2ccc(Cl)cc2)nn(-c2cnn(C(F)F)c2)c1=O] | 6-(4-Chlorophenyl)-2-[1-(difluoromethyl)-1H-pyrazol-4-yl]-3-oxo-N-[(2R)-1,1, 1-trifluoro-3-hydroxypropan-2-yl]-2,3-dihydropyridazine-4-carboxamide, $[\alpha]_D^{20}$ = +26.8° (c = 1.00, DMSO) | 6-(4-Chlorophenyl)-2-[1-(difluoromethyl)-1H-pyrazol-4-yl]-3-oxo-2,3-dihydropyridazine-4-carboxylic acid, (2R)-2-amino-3,3,3-trifluoropropan-1-ol hydrochloride | $^1$H-NMR (400 MHz, DMSO-$d_6$): δ [ppm] = 3.69-3.75 (m, 1H), 3.85 (dt, 1H), 4.82-4.94 (m, 1H), 5.47 (t, 1H), 7.59-7.64 (m, 2H), 7.92 (t, 1H), 8.14-8.19 (m, 2H), 8.54 (s, 1H), 8.69 (s, 1H), 9.08 (s, 1H), 10.01 (d, 1H). |
| 237 | 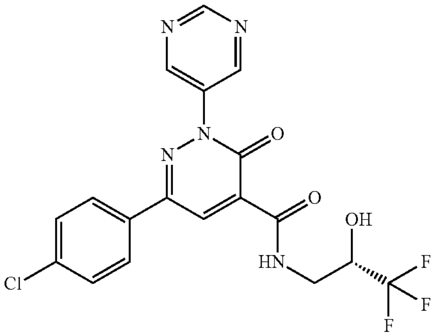 [SMILES: O=C(NC[C@H](O)C(F)(F)F)c1cc(-c2ccc(Cl)cc2)nn(-c2cncnc2)c1=O] | 6-(4-Chlorophenyl)-3-oxo-2-(pyrimidin-5-yl)-N-[(2S)-3,3,3-trifluoro-2-hydroxypropyl]-2,3-dihydropyridazine-4-carboxamide, $[\alpha]_D^{20}$ = −15.8° (c = 1.00, methanol) | 6-(4-Chlorophenyl)-3-oxo-2-(pyrimidin-5-yl)-2,3-dihydropyridazine-4-carboxylic acid, (2S)-3-amino-1,1,1-trifluoropropan-2-ol hydrochloride | $^1$H-NMR (400 MHz, DMSO-$d_6$): δ [ppm] = 3.49 (ddd, 1H), 3.75 (ddd, 1H), 4.18-4.29 (m, 1H), 6.67 (d, 1H), 7.58-7.63 (m, 2H), 8.04-8.08 (m, 2H), 8.70 (s, 1H), 9.26 (s, 2H), 9.31 (s, 1H), 9.50 (t, 1H). |
| 238 | 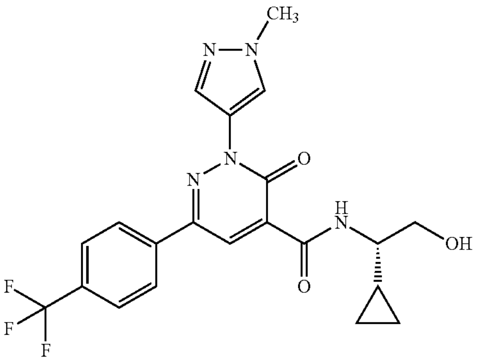 [SMILES: Cn1cc(-n2nc(-c3ccc(C(F)(F)F)cc3)cc(C(=O)N[C@H](CO)C3CC3)c2=O)cn1] | N-[(1S)-1-Cyclopropyl-2-hydroxyethyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = +27.3° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (2S)-2-amino-2-cyclopropylethanol hydrochloride | $^1$H-NMR (400 MHz, DMSO-$d_6$): δ [ppm] = 0.28-0.52 (m, 4H), 1.07-1.17 (m, 1H), 3.43-3.49 (m, 1H), 3.55-3.65 (m, 2H), 3.94 (s, 3H), 4.96 (t, 1H), 7.89 (d, 2H), 8.14 (d, 1H), 8.30 (d, 2H), 8.60 (s, 1H), 8.66 (s, 1H), 9.65 (d, 1H). |

TABLE 2-continued

| Examples 195-345 | | | | |
|---|---|---|---|---|
| Expl. | Structure | IUPAC name | Starting materials | analytics |
| 239 | 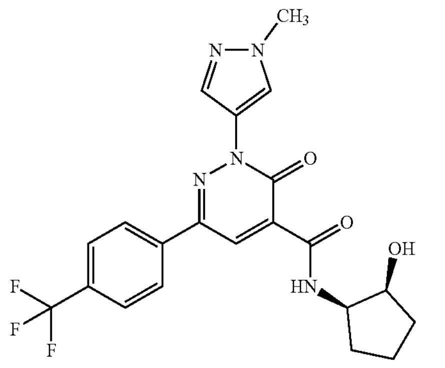 [SMILES: Cn1cc(-n2nc(-c3ccc(C(F)(F)F)cc3)cc(C(=O)N[C@@H]3CCC[C@@H]3O)c2=O)cn1] | N-[(1R,2S)-2-Hydroxycyclopentyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = −7.1° = 1.00, methanol) | 2-(1-Methyl-1H-pyrazol-4-yl)-3-oxo-6-[4-(trifluoromethyl)phenyl]-2,3-dihydropyridazine-4-carboxylic acid, (1S,2R)-2-aminocyclopentanol hydrochloride | $^1$H-NMR (400 MHz, DMSO-$d_6$): δ [ppm] = 1.48-1.67 (m, 3H), 1.72-1.91 (m, 2H), 1.93-2.03 (m, 1H), 3.94 (s, 3H), 4.02-4.14 (m, 2H), 5.06 (d, 1H), 7.90 (d, 2H), 8.13 (d, 1H), 8.30 (d, 2H), 8.57 (s, 1H), 8.67 (s, 1H), 9.76 (d, 1H). |
| 240 | 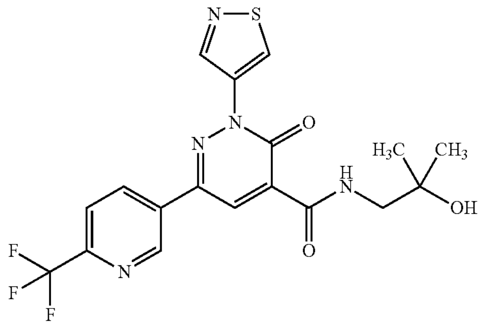 [SMILES: CC(C)(O)CNC(=O)c1cc(-c2ccc(C(F)(F)F)nc2)nn(-c2cnsc2)c1=O] | N-(2-Hydroxy-2-methylpropyl)-3-oxo-2-(1,2-thiazol-4-yl)-6-[6-(trifluoromethyl)pyridin-3-yl]-2,3-dihydropyridazine-4-carboxamide | 3-Oxo-2-(1,2-thiazol-4-yl)-6-[6-(trifluoromethyl)pyridin-3-yl]-2,3-dihydropyridazine-4-carboxylic acid, 1-amino-2-methylpropan-2-ol | $^1$H-NMR (400 MHz, DMSO-$d_6$): δ [ppm] = 1.15 (s, 6H), 3.32-3.36 (m, 2H and water signal), 4.72 (s, 1H), 8.06 (d, 1H), 8.76 (dd, 1H), 8.79 (s, 1H), 9.19 (s, 1H), 9.45 (d, 1H), 9.47 (t, 1H), 9.66 (s, 1H). |
| 241 | 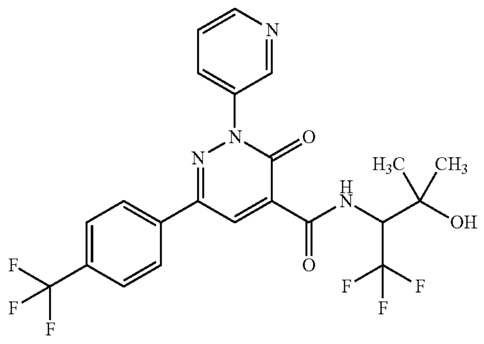 [SMILES: CC(C)(O)C(NC(=O)c1cc(-c2ccc(C(F)(F)F)cc2)nn(-c2cccnc2)c1=O)C(F)(F)F] | (−)-3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide, enantiomer 1, $[\alpha]_D^{20}$ = −20.0° (c = 1.00, methanol) | 3-Oxo-2-(pyridin-3-yl)-6-[4-(trifluoromethyl)phenyl]-2,3-dihydropyridazine-4-carboxylic acid, 3-amino-4,4,4-trifluoro-2-methylbutan-2-ol hydrochloride, Chiralpak IB 5μ 250 × 30 mm, eluent A: $CO_2$, eluent B: ethanol, isocratic: 22% B, 100 mL/min, 40° C., BPR: 150 bar, 254 nm | $^1$H-NMR (400 MHz, DMSO-$d_6$): δ [ppm] = 1.20 (s, 3H), 1.35 (s, 3H), 4.67 (quin, 1H), 5.22 (s, 1H), 7.65 (ddd, 1H), 7.89 (d, 2H), 8.18-8.25 (m, 3H), 8.71 (dd, 1H), 8.80 (s, 1H), 8.94 (dd, 1H), 10.00 (d, 1H). Rt = 1.10 min, Chiralpak IB 5 μm 100 × 4.6 mm, eluent A: $CO_2$, eluent B: ethanol, isocratic: 22% B, 4 mL/min, 37.5° C., BPR: 100 bar, 254 nm |
| 242 | 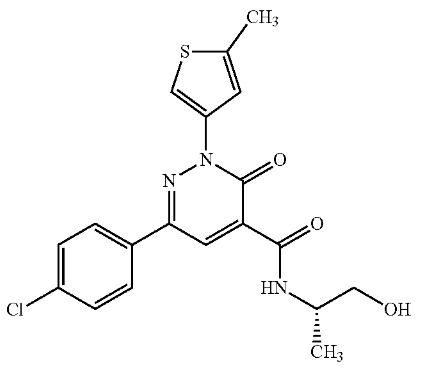 | 6-(4-Chlorophenyl)-N-[(2S)-1-hydroxypropan-2-yl]-2-(5-methyl-3-thienyl)-3-oxo-2,3-dihydropyridazine-4-carboxamide, $[\alpha]_D^{20}$ = +12.0° (c = 1.00, DMSO) | 6-(4-Chlorophenyl)-2-(5-methyl-3-thienyl)-3-oxo-2,3-dihydropyridazine-4-carboxylic acid, (2S)-2-aminopropan-1-ol | $^1$H-NMR (400 MHz, DMSO-$d_6$): δ [ppm] = 1.17 (d, 3H), 3.41-3.51 (m, 2H), 3.99-4.09 (m, 1H), 4.95 (t, 1H), 7.36 (t, 1H), 7.58-7.62 (m, 2H), 7.93 (d, 1H), 8.01-8.07 (m, 2H), 8.60 (s, 1H), 9.48 (d, 1H). |

TABLE 2-continued

| Examples 195-345 | | | | |
|---|---|---|---|---|
| Expl. | Structure | IUPAC name | Starting materials | analytics |
| 243 | 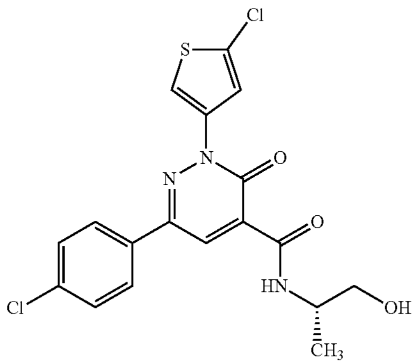 [SMILES: C[C@@H](CO)NC(=O)c1cc(-c2ccc(Cl)cc2)nn(-c2csc(Cl)c2)c1=O] | 6-(4-Chlorophenyl)-2-(5-chloro-3-thienyl)-N-[(2S)-1-hydroxypropan-2-yl]-3-oxo-2,3-dihydropyridazine-4-carboxamide, $[\alpha]_D^{20}$ = +13.6° (c = 1.00, DMSO) | 6-(4-Chlorophenyl)-2-(5-chloro-3-thienyl)-3-oxo-2,3-dihydropyridazine-4-carboxylic acid, (2S)-2-aminopropan-1-ol | $^1$H-NMR (400 MHz, DMSO-$d_6$): δ [ppm] = 1.17 (d, 3H), 3.41-3.51 (m, 2H), 3.99-4.09 (m, 1H), 4.95 (t, 1H), 7.58-7.62 (m, 2H), 7.68 (d, 1H), 8.04-8.08 (m, 2H), 8.09 (d, 1H), 8.60 (s, 1H), 9.40 (d, 1H). |
| 244 | 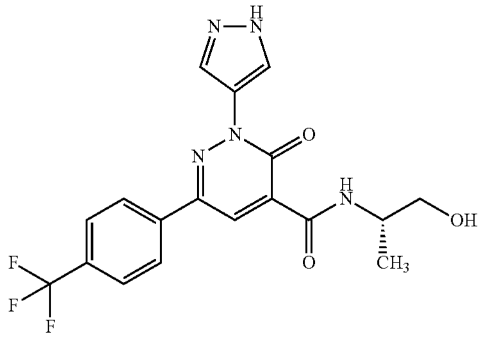 [SMILES: C[C@@H](CO)NC(=O)c1cc(-c2ccc(C(F)(F)F)cc2)nn(-c2cn[nH]c2)c1=O] | N-[(2S)-1-Hydroxypropan-2-yl]-3-oxo-2-(1H-pyrazol-4-yl)-6-[4-(trifluoromethyl) phenyl]-2,3-dihydropyridazine-4-carboxamide, $[\alpha]_D^{20}$ = +11.8° (c = 1.00, DMSO) | 3-Oxo-2-(1H-pyrazol-4-yl)-6-[4-(trifluoromethyl) phenyl]-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.53 (m, 2H), 4.01-4.12 (m, 1H), 4.97 (t, 1H), 7.89 (d, 2H), 8.27-8.47 (m, 4H), 8.66 (s, 1H), 9.51 (d, 1H), 13.26 (br s, 1H). |
| 245 | 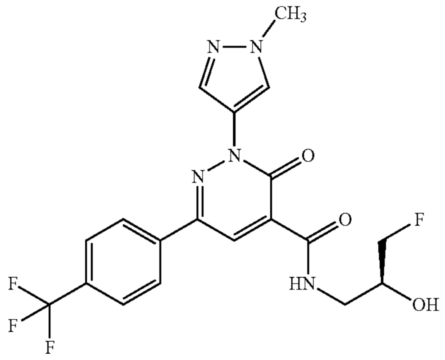 [SMILES: Cn1cc(-n2nc(-c3ccc(C(F)(F)F)cc3)cc(C(=O)NC[C@H](O)CF)c2=O)cn1] | N-[(2S)-3-Fluoro-2-hydroxypropyl]-2-(1-methyl-1H-pyrazol-4-yl)-3-oxo-6-[4-(trifluoromethyl) phenyl]-2,3-dihydropyridazine-4-carboxamide, $[\alpha]_D^{20}$ = +1.4 +/−0.47° = 1.00, DMSO) | 2-(1-Methyl-1H-pyrazol-4-yl)-3-oxo-6-[4-(trifluoromethyl) phenyl]-2,3-dihydropyridazine-4-carboxylic acid, (2S)-1-amino-3-fluoropropan-2-ol hydrochloride | $^1$H-NMR (400 MHz, DMSO-$d_6$): δ [ppm] = 3.34-3.41 (m, 1H), 3.56 (dt, 1H), 3.84-3.94 (m, 4H), 4.32 (ddd, 1H), 4.44 (ddd, 1H), 5.50 (d, 1H), 7.89 (d, 2H), 8.14 (d, 1H), 8.30 (d, 2H), 8.56 (s, 1H), 8.65 (s, 1H), 9.60 (t, 1H). |
| 246 | 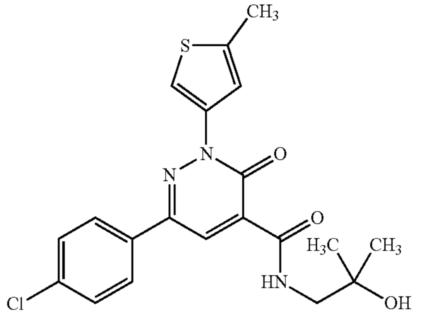 [SMILES: Cc1cc(-n2nc(-c3ccc(Cl)cc3)cc(C(=O)NCC(C)(C)O)c2=O)cs1] | 6-(4-Chlorophenyl)-N-(2-hydroxy-2-methylpropyl)-2-(5-methyl-3-thienyl)-3-oxo-2,3-dihydropyridazine-4-carboxamide | 6-(4-Chlorophenyl)-2-(5-methyl-3-thienyl)-3-oxo-2,3-dihydropyridazine-4-carboxylic acid, 1-amino-2-methylpropan-2-ol | $^1$H-NMR (400 MHz, DMSO-$d_6$): δ [ppm] = 1.14 (s, 6H), 3.30-3.33 (m, 2H and water signal), 4.69 (s, 1H), 7.35-7.38 (m, 1H), 7.57-7.62 (m, 2H), 7.93 (d, 1H), 8.02-8.06 (m, 2H), 8.61 (s, 1H), 9.60 (t, 1H). |

TABLE 2-continued

| Examples 195-345 | | | | |
|---|---|---|---|---|
| Expl. | Structure | IUPAC name | Starting materials | analytics |
| 247 | 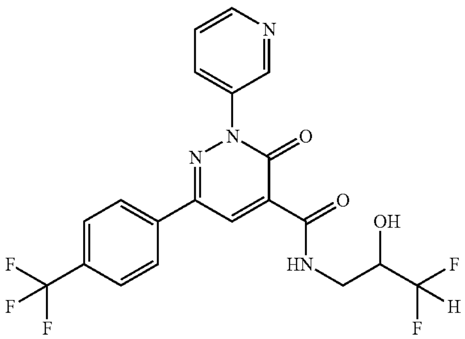 [SMILES: O=C(NCC(O)C(F)F)c1cc(-c2ccc(C(F)(F)F)cc2)nn(-c2cccnc2)c1=O] | (+)-N-(3,3-Difluoro-2-hydroxypropyl)-3-oxo-2-(pyridin-3-yl)-6-[4-(trifluoromethyl)phenyl]-2,3-dihydropyridazine-4-carboxamide, enantiomer 1, $[\alpha]_D^{20}$ = +15.8° (c = 1.00, methanol) | 3-Oxo-2-(pyridin-3-yl)-6-[4-(trifluoromethyl)phenyl]-2,3-dihydropyridazine-4-carboxylic acid, 3-amino-1,1-difluoropropan-2-ol hydrochloride Chiralpak IE 5µ 250 × 30 mm, eluent A: 2-methoxy-2-methylpropane and 0.1 vol % diethylamine (99%), eluent B: methanol, isocratic: 50% B, 40 mL/min, 254 nm | $^1$H-NMR (400 MHz, DMSO-$d_6$): δ [ppm] = 3.40 (ddd, 1H), 3.66 (ddd, 1H), 3.79-3.91 (m, 1H), 5.94 (dt, 1H), 6.01 (br d, 1H), 7.65 (ddd, 1H), 7.89 (d, 2H), 8.18 (ddd, 1H), 8.22 (d, 2H), 8.71 (dd, 1H), 8.74 (s, 1H), 8.93 (d, 1H), 9.53 (t, 1H). Rt = 1.28 min, Chiralpak IE 3um 100 × 4.6 mm, eluent A: 2-methoxy-2-methylpropane and 0.1 vol % diethylamine (99%), eluent B: methanol, isocratic: 50% B, 1.4 mL/min, 25° C., 254 nm |
| 248 | 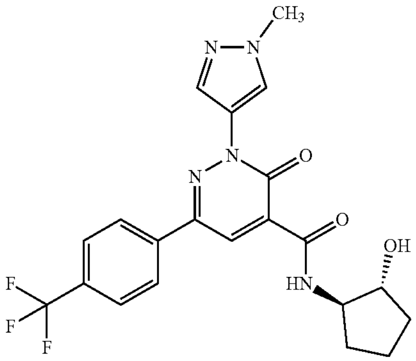 [SMILES: Cn1cc(-n2nc(-c3ccc(C(F)(F)F)cc3)cc(C(=O)N[C@@H]3CCC[C@H]3O)c2=O)cn1] | N-[(1R,2R)-2-Hydroxycyclopentyl]-2-(1-methyl-1H-pyrazol-4-yl)-3-oxo-6-[4-(trifluoromethyl)phenyl]-2,3-dihydropyridazine-4-carboxamide, $[\alpha]_D^{20}$ = −32.7° (c = 1.00, methanol) | 2-(1-Methyl-1H-pyrazol-4-yl)-3-oxo-6-[4-(trifluoromethyl)phenyl]-2,3-dihydropyridazine-4-carboxylic acid, (1R,2R)-2-aminocyclopentanol hydrochloride | $^1$H-NMR (400 MHz, DMSO-$d_6$): δ [ppm] = 1.43-1.58 (m, 2H), 1.60-1.81 (m, 2H), 1.81-1.91 (m, 1H), 2.06-2.16 (m, 1H), 3.91-3.99 (m, 4H), 4.00-4.07 (m, 1H), 4.97 (d, 1H), 7.89 (d, 2H), 8.13 (s, 1H), 8.30 (d, 2H), 8.57 (s, 1H), 8.63 (s, 1H), 9.42 (d, 1H). |
| 249 | 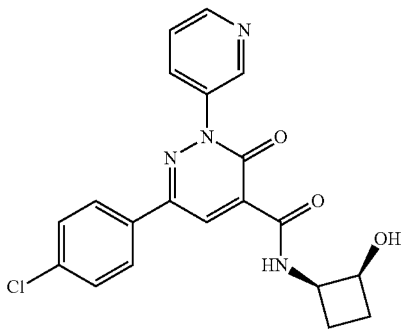 [SMILES: O=C(N[C@@H]1CC[C@@H]1O)c1cc(-c2ccc(Cl)cc2)nn(-c2cccnc2)c1=O] | (+)-6-(4-Chlorophenyl)-N-cis-2-hydroxycyclobutyl-3-oxo-2-(pyridin-3-yl)-2,3-dihydropyridazine-4-carboxamide, enantiomer 1, $[\alpha]_D^{20}$ = +13.9° (c = 1.00, methanol) | 6-(4-Chlorophenyl)-3-oxo-2-(pyridin-3-yl)-2,3-dihydropyridazine-4-carboxylic acid, cis-2-aminocyclobutanol hydrochloride Chiralpak IB 5µ 250 × 30 mm, eluent A: $CO_2$, eluent B: isopropanol, isocratic: 28% B, 100 mL/min, 40° C., BPR: 150 bar, 220 nm | $^1$H-NMR (400 MHz, DMSO-$d_6$): δ [ppm] = 1.74-1.92 (m, 2H), 2.06-2.16 (m, 2H), 4.33-4.41 (m, 2H), 5.52 (d, 1H), 7.57-7.61 (m, 2H), 7.64 (ddd, 1H), 7.99-8.03 (m, 2H), 8.17 (ddd, 1H), 8.67 (s, 1H), 8.70 (dd, 1H), 8.91-8.92 (m, 1H), 9.89 (br d, 1H). Rt = 2.98 min, Chiralpak IB 5 µm 100 × 4.6 mm, eluent A: $CO_2$, eluent B: ethanol, isocratic: 24% B, 4 mL/min, 37.5° C., BPR: 100 bar, 220 nm |

TABLE 2-continued

| Examples 195-345 | | | | |
|---|---|---|---|---|
| Expl. | Structure | IUPAC name | Starting materials | analytics |
| 250 | 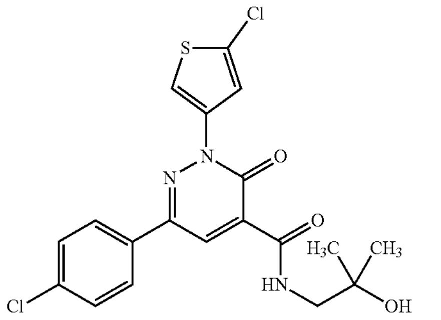 [SMILES: CC(C)(O)CNC(=O)c1cc(-c2ccc(Cl)cc2)nn(-c2csc(Cl)c2)c1=O] | 6-(4-Chlorophenyl)-2-(5-chloro-3-thienyl)-N-(2-hydroxy-2-methylpropyl)-3-oxo-2,3-dihydropyridazine-4-carboxamide | 6-(4-Chlorophenyl)-2-(5-chloro-3-thienyl)-3-oxo-2,3-dihydropyridazine-4-carboxylic acid, 1-amino-2-methylpropan-2-ol | $^1$H-NMR (400 MHz, DMSO-$d_6$): δ [ppm] = 1.14 (s, 6H), 3.30-3.33 (m, 2H and part of water signal), 4.69 (s, 1H), 7.57-7.62 (m, 2H), 7.68 (d, 1H), 8.04-8.08 (m, 2H), 8.10 (d, 1H), 8.61 (s, |
| 251 | 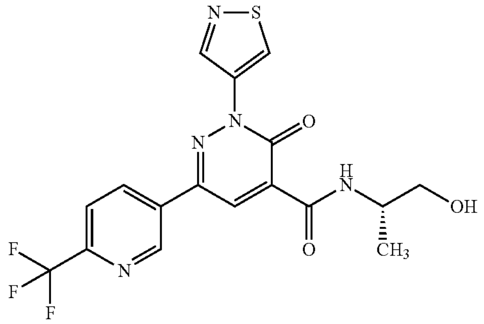 | N-[(2S)-1-Hydroxypropan-2-yl]-3-oxo-2-(1,2-thiazol-4-yl)-6-[6-(trifluoromethyl) pyridin-3-yl]-2,3-dihydropyridazine-4-carboxamide, $[\alpha]_D^{20}$ = +9.3° (c = 1.00, DMSO) | 3-Oxo-2-(1,2-thiazol-4-yl)-6-[6-(trifluoromethyl) pyridin-3-yl]-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.53 (m, 2H), 4.01-4.11 (m, 1H), 4.98 (t, 1H), 8.07 (d, 1H), 8.75 (dd, 1H), 8.78 (s, 1H), 9.19 (s, 1H), 9.35 (d, 1H), 9.44 (d, 1H), 9.66 (s, 1H). |
| 252 | 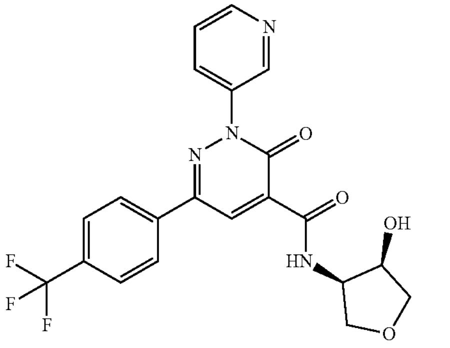 | (−)-N-cis-4-Hydroxytetra-hydrofuran-3-yl-3-oxo-2-(pyridin-3-yl)-6-[4-(trifluoromethyl) phenyl]-2,3-dihydropyridazine-4-carboxamide, enantiomer 2, $[\alpha]_D^{20}$ = −16.6° (c = 1.00, methanol) | 3-Oxo-2-(pyridin-3-yl)-6-[4-(trifluoromethyl) phenyl]-2,3-dihydropyridazine-4-carboxylic acid, cis-4-aminotetrahydro-furan-3-ol hydrochloride Chiralpak IA 5μ 250 × 30 mm, eluent A: $CO_2$, eluent B: methanol, isocratic: 27% B, 100 mL/min, 40° C., BPR: 150 bar, 254 nm | $^1$H-NMR (400 MHz, DMSO-$d_6$): δ [ppm] = 3.46 (t, 1H), 3.61 (dd, 1H), 3.93 (dd, 1H), 4.01 (t, 1H), 4.25-4.31 (m, 1H), 4.32-4.40 (m, 1H), 5.70 (br d, 1H), 7.64 (ddd, 1H), 7.89 (d, 2H), 8.18 (ddd, 1H), 8.21 (d, 2H), 8.71 (dd, 1H), 8.76 (s, 1H), 8.92 (d, 1H), 9.80 (d, 1H). Rt = 5.97 min, Chiralpak IA 5 μm 100 × 4.6 mm, eluent A: $CO_2$, eluent B: methanol, isocratic: 27% B, 4.0 mL/min, 37.5° C., BPR: 100 bar, 254 nm |
| 253 | 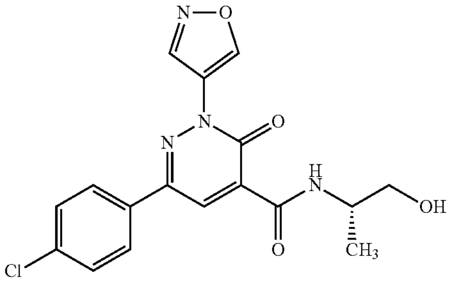 [SMILES: C[C@@H](CO)NC(=O)c1cc(-c2ccc(Cl)cc2)nn(-c2cnoc2)c1=O] | 6-(4-Chlorophenyl)-N-[(2S)-1-hydroxypropan-2-yl]-2-(1,2-oxazol-4-yl)-3-oxo-2,3-dihydropyridazine-4-carboxamide, $[\alpha]_D^{20}$ = +96.8° (c = 1.00, DMSO) | 6-(4-Chlorophenyl)-2-(1,2-oxazol-4-yl)-3-oxo-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.52 (m, 2H), 4.01-4.12 (m, 1H), 4.98 (br s, 1H), 7.58-7.63 (m, 2H), 8.15-8.20 (m, 2H), 8.63 (s, 1H), 9.31 (d, 1H), 9.45 (s, 1H), 9.80 (s, 1H). |

TABLE 2-continued

| Examples 195-345 | | | | |
|---|---|---|---|---|
| Expl. | Structure | IUPAC name | Starting materials | analytics |
| 254 | 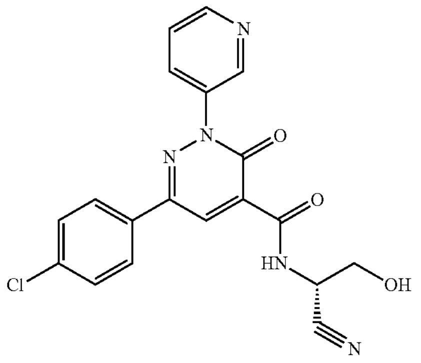 [SMILES: N#C[C@@H](CO)NC(=O)c1cc(-c2ccc(Cl)cc2)nn(-c2cccnc2)c1=O] | 6-(4-Chlorophenyl)-N-[(1S)-1-cyano-2-hydroxyethyl]-3-oxo-2-(pyridin-3-yl)-2,3-dihydropyridazine-4-carboxamide, $[\alpha]_D^{20}$ = −16.5° (c = 1.00, DMSO) | 6-(4-Chlorophenyl)-3-oxo-2-(pyridin-3-yl)-2,3-dihydropyridazine-4-carboxylic acid, (2S)-2-amino-3-hydroxypropanenitrile hydrochloride | $^1$H-NMR (400 MHz, DMSO-$d_6$): δ [ppm] = 3.71-3.78 (m, 1H), 3.78-3.84 (m, 1H), 5.06 (dt, 1H), 5.82 (t, 1H), 7.57-7.61 (m, 2H), 7.64 (ddd, 1H), 8.01-8.06 (m, 2H), 8.18 (ddd, 1H), 8.70 (dd, 1H), 8.72 (s, 1H), 8.92 (d, 1H), 9.96 (d, 1H). |
| 255 | 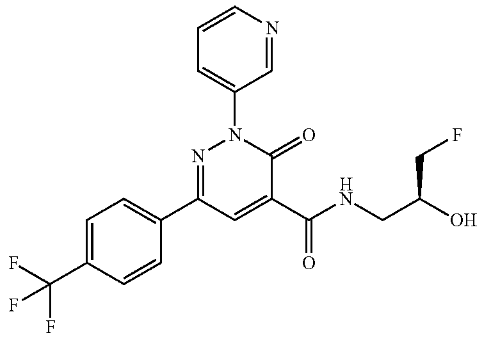 [SMILES: O=C(NC[C@H](O)CF)c1cc(-c2ccc(C(F)(F)F)cc2)nn(-c2cccnc2)c1=O] | N-[(2S)-3-Fluoro-2-hydroxypropyl]-3-oxo-2-(pyridin-3-yl)-6-[4-(trifluoromethyl)phenyl]-2,3-dihydropyridazine-4-carboxamide, $[\alpha]_D^{20}$ = −3.9° = 1.00, DMSO) | 3-Oxo-2-(pyridin-3-yl)-6-[4-(trifluoromethyl)phenyl]-2,3-dihydropyridazine-4-carboxylic acid, (2S)-1-amino-3-fluoropropan-2-ol hydrochloride | $^1$H-NMR (400 MHz, DMSO-$d_6$): δ [ppm] = 3.34-3.39 (m, 1H), 3.55 (dt, 1H), 3.82-3.95 (m, 1H), 4.30 (ddd, 1H), 4.42 (ddd, 1H), 5.48 (d, 1H), 7.65 (ddd, 1H), 7.89 (d, 2H), 8.16-8.24 (m, 3H), 8.70 (dd, 1H), 8.73 (s, 1H), 8.93 (d, 1H), 9.48 (t, 1H). |
| 256 | 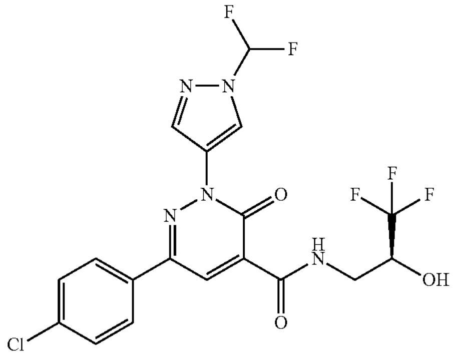 [SMILES: O=C(NC[C@H](O)C(F)(F)F)c1cc(-c2ccc(Cl)cc2)nn(-c2cnn(C(F)F)c2)c1=O] | 6-(4-Chlorophenyl)-2-[1-(difluoromethyl)-1H-pyrazol-4-yl]-3-oxo-N-[(2S)-3,3,3-trifluoro-2-hydroxypropyl]-2,3-dihydropyridazine-4-carboxamide, $[\alpha]_D^{20}$ = −2.5° = 1.00, DMSO) | 6-(4-Chlorophenyl)-2-[1-(difluoromethyl)-1H-pyrazol-4-yl]-3-oxo-2,3-dihydropyridazine-4-carboxylic acid, (2S)-3-amino-1, 1,1-trifluoropropan-2-ol | $^1$H-NMR (400 MHz, DMSO-$d_6$): δ [ppm] = 3.50 (ddd, 1H), 3.77 (ddd, 1H), 4.19-4.31 (m, 1H), 6.70 (d, 1H), 7.58-7.64 (m, 2H), 7.94 (t, 1H), 8.12-8.17 (m, 2H), 8.53 (s, 1H), 8.64 (s, 1H), 9.02 (s, 1H), 9.63 (t, 1H). |
| 257 | 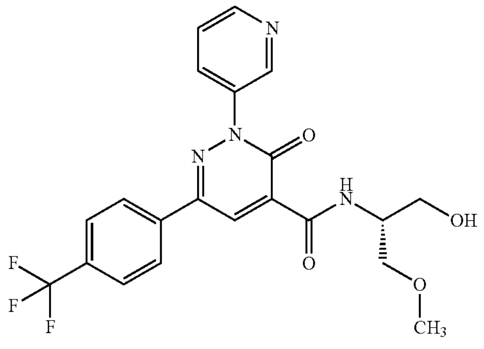 [SMILES: COC[C@@H](CO)NC(=O)c1cc(-c2ccc(C(F)(F)F)cc2)nn(-c2cccnc2)c1=O] | N-[(2R)-1-Hydroxy-3-methoxypropan-2-yl]-3-oxo-2-(pyridin-3-yl)-6-[4-(trifluoromethyl)phenyl]-2,3-dihydropyridazine-4-carboxamide, $[\alpha]_D^{20}$ = −0.95° +/−0.33° = 1.00, MeOH) | 3-Oxo-2-(pyridin-3-yl)-6-[4-(trifluoromethyl)phenyl]-2,3-dihydropyridazine-4-carboxylic acid, (2R)-2-amino-3-methoxypropan-1-ol | $^1$H-NMR (400 MHz, DMSO-$d_6$): δ [ppm] = 3.28 (s, 3H), 3.42-3.59 (m, 4H), 4.09-4.18 (m, 1H), 4.98 (t, 1H), 7.64 (ddd, 1H), 7.89 (d, 2H), 8.18 (ddd, 1H), 8.21 (d, 2H), 8.71 (dd, 1H), 8.75 (s, 1H), 8.92 (d, 1H), 9.50 (d, 1H). |

TABLE 2-continued

Examples 195-345

| Expl. | Structure | IUPAC name | Starting materials | analytics |
|---|---|---|---|---|
| 258 | 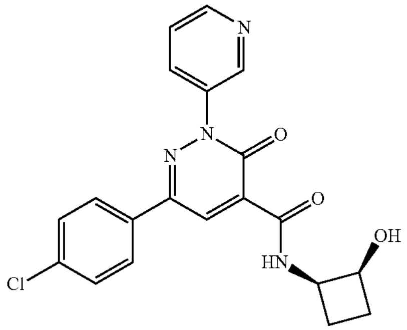 [SMILES: O=C(N[C@@H]1CC[C@@H]1O)c1cc(-c2ccc(Cl)cc2)nn(-c2cccnc2)c1=O] | 6-(4-Chlorophenyl)-N-cis-2-hydroxycyclobutyl-3-oxo-2-(pyridin-3-yl)-2,3-dihydropyridazine-4-carboxamide | 6-(4-Chlorophenyl)-3-oxo-2-(pyridin-3-yl)-2,3-dihydropyridazine-4-carboxylic acid, cis-2-aminocyclobutanol hydrochloride | $^1$H-NMR (400 MHz, DMSO-$d_6$): δ [ppm] = 1.74-1.91 (m, 2H), 2.05-2.16 (m, 2H), 4.33-4.41 (m, 2H), 5.49-5.54 (m, 1H), 7.57-7.61 (m, 2H), 7.64 (ddd, 1H), 7.98-8.03 (m, 2H), 8.17 (ddd, 1H), 8.67 (s, 1H), 8.70 (dd, 1H), 8.92 (d, 1H), 9.89 (br d, 1H). |
| 259 | 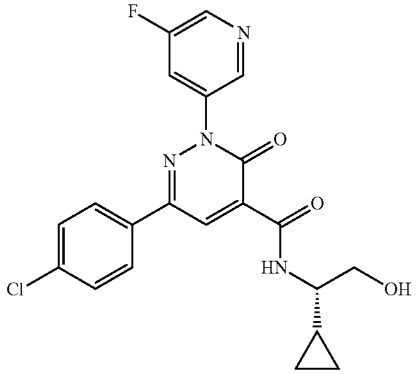 [SMILES: O=C(N[C@H](CO)C1CC1)c1cc(-c2ccc(Cl)cc2)nn(-c2cncc(F)c2)c1=O] | 6-(4-Chlorophenyl)-N-[(1S)-1-cyclopropyl-2-hydroxyethyl]-2-(5-fluoropyridin-3-yl)-3-oxo-2,3-dihydropyridazine-4-carboxamide, $[\alpha]_D^{20}$ = +30.5° (c = 1.00, MeOH) | 6-(4-Chlorophenyl)-2-(5-fluoropyridin-3-yl)-3-oxo-2,3-dihydropyridazine-4-carboxylic acid, (2S)-2-amino-2-cyclopropylethanol hydrochloride | $^1$H-NMR (400 MHz, DMSO-$d_6$): δ [ppm] = 0.26-0.50 (m, 4H), 1.03-1.13 (m, 1H), 3.40-3.48 (m, 1H), 3.52-3.63 (m, 2H), 4.94 (t, 1H), 7.57-7.61 (m, 2H), 8.01-8.05 (m, 2H), 8.26 (ddd, 1H), 8.68 (s, 1H), 8.77 (d, 1H), 8.86 (t, 1H), 9.47 (d, 1H). |
| 260 | 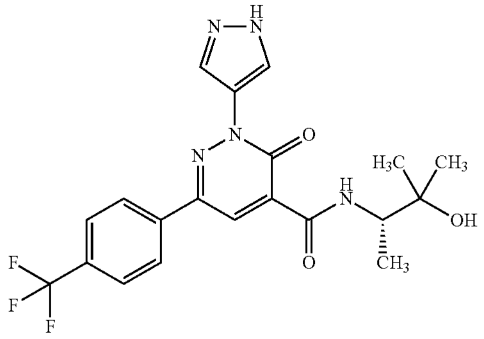 [SMILES: C[C@H](NC(=O)c1cc(-c2ccc(C(F)(F)F)cc2)nn(-c2cn[nH]c2)c1=O)C(C)(C)O] | N-[(2S)-3-Hydroxy-3-methylbutan-2-yl]-3-oxo-2-(1H-pyrazol-4-yl)-6-[4-(trifluoromethyl)phenyl]-2,3-dihydropyridazine-4-carboxamide, $[\alpha]_D^{20}$ = +30.1° (c = 1.00, DMSO) | 3-Oxo-2-(1H-pyrazol-4-yl)-6-[4-(trifluoromethyl)phenyl]-2,3-dihydropyridazine-4-carboxylic acid, (3S)-3-amino-2-methylbutan-2-ol | $^1$H-NMR (400 MHz, DMSO-$d_6$): δ [ppm]= 1.13 (s, 3H), 1.16 (d, 3H), 1.18 (s, 3H), 3.90-3.99 (m, 1H), 4.69 (s, 1H), 7.89 (d, 2H), 8.30 (d, 4H), 8.66 (s, 1H), 9.62 (d, 1H), 13.26 (br s, 1H). |
| 261 | 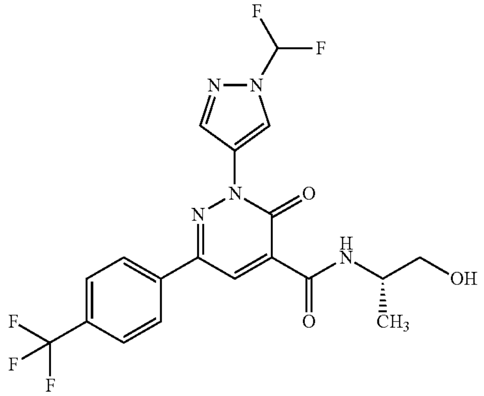 [SMILES: C[C@@H](CO)NC(=O)c1cc(-c2ccc(C(F)(F)F)cc2)nn(-c2cnn(C(F)F)c2)c1=O] | 2-[1-(Difluoromethyl)-1H-pyrazol-4-yl]-N-[(2S)-1-hydroxypropan-2-yl]-3-oxo-6-[4-(trifluoromethyl)phenyl]-2,3-dihydropyridazine-4-carboxamide, $[\alpha]_D^{20}$ = +13.2° (c = 1.00, methanol) | 2-[1-(Difluoromethyl)-1H-pyrazol-4-yl]-3-oxo-6-[4-(trifluoromethyl)phenyl]-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.53 (m, 2H), 4.01-4.12 (m, 1H), 4.98 (t, 1H), 7.90 (d, 2H), 7.93 (t, 1H), 8.34 (d, 2H), 8.54 (s, 1H), 8.69 (s, 1H), 9.07 (s, 1H), 9.42 (d, 1H). |

TABLE 2-continued

| Examples 195-345 | | | | |
|---|---|---|---|---|
| Expl. | Structure | IUPAC name | Starting materials | analytics |
| 262 | 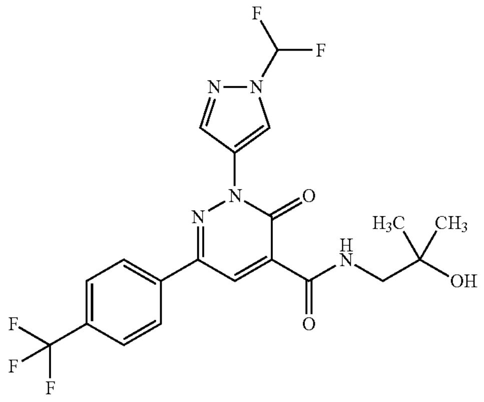 [SMILES: CC(C)(O)CNC(=O)c1cc(-c2ccc(C(F)(F)F)cc2)nn(-c2cnn(C(F)F)c2)c1=O] | 2-[1-(Difluoromethyl)-1H-pyrazol-4-yl]-N-(2-hydroxy-2-methylpropyl)-3-oxo-6-[4-(trifluoromethyl)phenyl]-2,3-dihydropyridazine-4-carboxamide | 2-[1-(Difluoromethyl)-1H-pyrazol-4-yl]-3-oxo-6-[4-(trifluoromethyl)phenyl]-2,3-dihydropyridazine-4-carboxylic acid, 1-amino-2-methylpropan-2-ol | $^1$H-NMR (400 MHz, DMSO-$d_6$): δ [ppm] = 1.16 (s, 6H), 3.33-3.36 (m, 2H and water signal), 4.71 (s, 1H), 7.90 (d, 2H), 7.94 (t, 1H), 8.34 (d, 2H), 8.54 (s, 1H), 8.70 (s, 1H), 9.06 (s, 1H), 9.53 (t, 1H). |
| 263 | 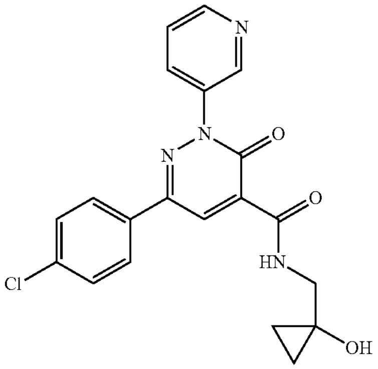 [SMILES: O=C(NCC1(O)CC1)c1cc(-c2ccc(Cl)cc2)nn(-c2cccnc2)c1=O] | 6-(4-Chlorophenyl)-N-[(1-hydroxycyclopropyl)methyl]-3-oxo-2-(pyridin-3-yl)-2,3-dihydropyridazine-4-carboxamide | 6-(4-Chlorophenyl)-3-oxo-2-(pyridin-3-yl)-2,3-dihydropyridazine-4-carboxylic acid, 1-(aminomethyl)cyclopropanol | $^1$H-NMR (400 MHz, DMSO-$d_6$): δ [ppm] = 0.52-0.57 (m, 2H), 0.58-0.64 (m, 2H), 3.46 (d, 2H), 5.52 (s, 1H), 7.59 (d, 2H), 7.64 (dd, 1H), 8.02 (d, 2H), 8.18 (ddd, 1H), 8.67-8.71 (m, 2H), 8.93 (d, 1H), 9.60 (t, 1H). |
| 264 | 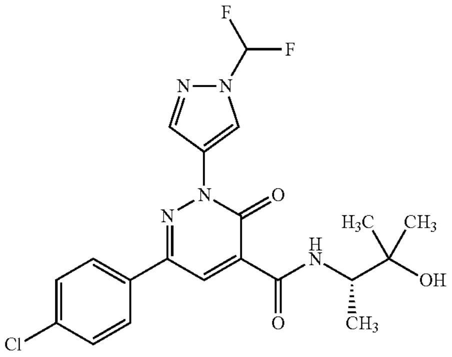 [SMILES: C[C@H](NC(=O)c1cc(-c2ccc(Cl)cc2)nn(-c2cnn(C(F)F)c2)c1=O)C(C)(C)O] | 6-(4-Chlorophenyl)-2-[1-(difluoromethyl)-1H-pyrazol-4-yl]-N-[(2S)-3-hydroxy-3-methylbutan-2-yl]-3-oxo-2,3-dihydropyridazine-4-carboxamide, $[\alpha]_D^{20}$ = +22.8° (c = 1.00, DMSO) | 6-(4-Chlorophenyl)-2-[1-(difluoromethyl)-1H-pyrazol-4-yl]-3-oxo-2,3-dihydropyridazine-4-carboxylic acid, (3S)-3-amino-2-methylbutan-2-ol | $^1$H-NMR (400 MHz, DMSO-$d_6$): δ [ppm] = 1.13 (s, 3H), 1.15 (d, 3H), 1.18 (s, 3H), 3.89-3.98 (m, 1H), 4.68 (s, 1H), 7.57-7.64 (m, 2H), 7.92 (t, 1H), 8.11-8.17 (m, 2H), 8.52 (s, 1H), 8.63 (s, 1H), 9.05 (s, 1H), 9.53 (d, 1H). |
| 265 | 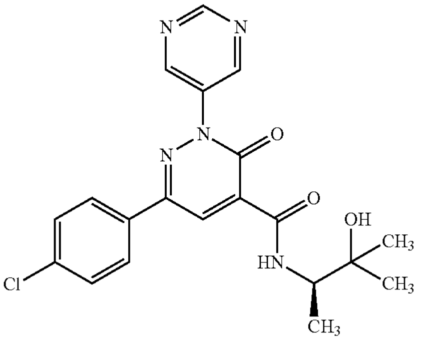 [SMILES: C[C@@H](NC(=O)c1cc(-c2ccc(Cl)cc2)nn(-c2cncnc2)c1=O)C(C)(C)O] | 6-(4-Chlorophenyl)-N-[(2R)-3-hydroxy-3-methylbutan-2-yl]-3-oxo-2-(pyrimidin-5-yl)-2,3-dihydropyridazine-4-carboxamide, $[\alpha]_D^{20}$ = −27.7° (c = 1.00, methanol) | 6-(4-Chlorophenyl)-3-oxo-2-(pyrimidin-5-yl)-2,3-dihydropyridazine-4-carboxylic acid, (3R)-3-amino-2-methylbutan-2-ol hydrochloride | $^1$H-NMR (400 MHz, DMSO-$d_6$): δ [ppm] = 1.10 (s, 3H), 1.13 (d, 3H), 1.16 (s, 3H), 3.87-3.96 (m, 1H), 4.67 (br s, 1H), 7.57-7.62 (m, 2H), 8.03-8.07 (m, 2H), 8.69 (s, 1H), 9.25 (s, 2H), 9.30 (s, 1H), 9.41 (d, 1H). |

TABLE 2-continued

Examples 195-345

| Expl. | Structure | IUPAC name | Starting materials | analytics |
|---|---|---|---|---|
| 266 | 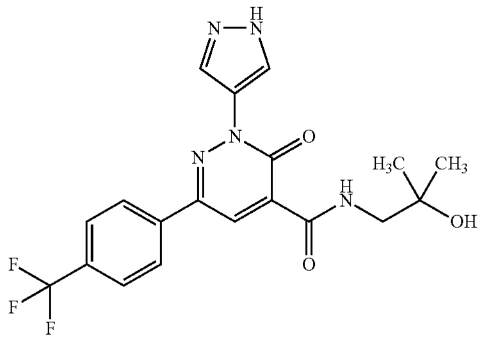 [SMILES: CC(C)(O)CNC(=O)c1cc(-c2ccc(C(F)(F)F)cc2)nn(-c2cn[nH]c2)c1=O] | N-(2-Hydroxy-2-methylpropyl)-3-oxo-2-(1H-pyrazol-4-yl)-6-[4-(trifluoromethyl)phenyl]-2,3-dihydropyridazine-4-carboxamide | 3-Oxo-2-(1H-pyrazol-4-yl)-6-[4-(trifluoromethyl)phenyl]-2,3-dihydropyridazine-4-carboxylic acid, 1-amino-2-methylpropan-2-ol | $^1$H-NMR (400 MHz, DMSO-$d_6$): δ [ppm] = 1.15 (s, 6H), 3.33-3.36 (m, 2H and water signal), 4.71 (s, 1H), 7.89 (d, 2H), 8.11-8.61 (m, 4H), 8.67 (s, 1H), 9.64 (t, 1H), 13.27 (br s, 1H). |
| 267 | 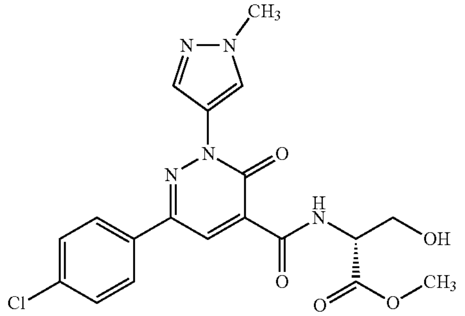 [SMILES: COC(=O)[C@@H](CO)NC(=O)c1cc(-c2ccc(Cl)cc2)nn(-c2cnn(C)c2)c1=O] | Methyl N-{[6-(4-chlorophenyl)-2-(1-methyl-1H-pyrazol-4-yl)-3-oxo-2,3-dihydropyridazine-4-yl]carbonyl}-D-serinate, $[\alpha]_D^{20}$ = −6.8° = 1.00, DMSO) | 6-(4-Chlorophenyl)-2-(1-methyl-1H-pyrazol-4-yl)-3-oxo-2,3-dihydropyridazine-4-carboxylic acid, methyl D-serinate hydrochloride | $^1$H-NMR (400 MHz, DMSO-$d_6$): δ [ppm] = 3.70 (s, 3H), 3.75 (ddd, 1H), 3.88-3.95 (m, 4H), 4.65-4.70 (m, 1H), 5.34 (t, 1H), 7.58-7.62 (m, 2H), 8.09-8.13 (m, 2H), 8.14 (d, 1H), 8.59 (s, 1H), 8.62 (s, 1H), 10.11 (d, 1H). |
| 268 | 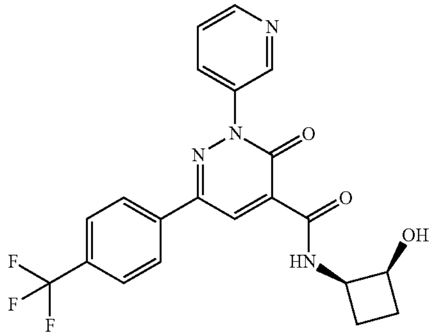 [SMILES: O=C(N[C@@H]1CC[C@@H]1O)c1cc(-c2ccc(C(F)(F)F)cc2)nn(-c2cccnc2)c1=O] | (−)-N-cis-2-Hydroxycyclobutyl-3-oxo-2-(pyridin-3-yl)-6-[4-(trifluoromethyl)phenyl]-2,3-dihydropyridazine-4-carboxamide, enantiomer 2, $[\alpha]_D^{20}$ = −26.8° (c = 1.00, MeOH) | 3-Oxo-2-(pyridin-3-yl)-6-[4-(trifluoromethyl)phenyl]-2,3-dihydropyridazine-4-carboxylic acid, cis-2-aminocyclobutanol hydrochloride Chiralpak IB 5µ 250 × 30 mm, eluent A: $CO_2$, eluent B: isopropanol, isocratic: 24% B, 100 mL/min, 40° C., BPR: 150 bar, 220 nm | $^1$H-NMR (400 MHz, DMSO-$d_6$): δ [ppm] = 1.74-1.93 (m, 2H), 2.06-2.17 (m, 2H), 4.33-4.41 (m, 2H), 5.53 (d, 1H), 7.65 (dd, 1H), 7.89 (d, 2H), 8.16-8.23 (m, 3H), 8.71 (br d, 1H), 8.73 (s, 1H), 8.93 (br s, 1H), 9.88 (br d, 1H). Rt = 3.98 min, Chiralpak IB 5 µm 100 × 4.6 mm, eluent A: $CO_2$, eluent B: isopropanol, isocratic: 24% B, 4 mL/min, 37.5° C., BPR: 100 bar, 220 nm |
| 269 | 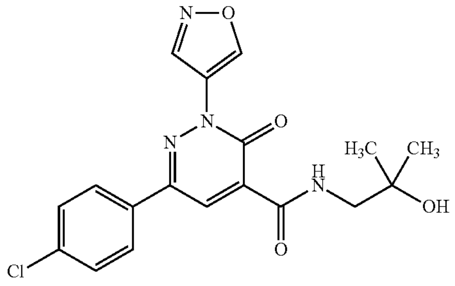 [SMILES: CC(C)(O)CNC(=O)c1cc(-c2ccc(Cl)cc2)nn(-c2cnoc2)c1=O] | 6-(4-Chlorophenyl)-N-(2-hydroxy-2-methylpropyl)-2-(1,2-oxazol-4-yl)-3-oxo-2,3-dihydropyridazine-4-carboxamide | 6-(4-Chlorophenyl)-2-(1,2-oxazol-4-yl)-3-oxo-2,3-dihydropyridazine-4-carboxylic acid, 1-amino-2-methylpropan-2-ol | $^1$H-NMR (400 MHz, DMSO-$d_6$): δ [ppm] = 1.15 (s, 6H), 3.33-3.35 (m, 2H and water signal), 4.71 (s, 1H), 7.58-7.63 (m, 2H), 8.15-8.21 (m, 2H), 8.65 (s, 1H), 9.41-9.46 (m, 2H), 9.80 (s, 1H). |

TABLE 2-continued

Examples 195-345

| Expl. | Structure | IUPAC name | Starting materials | analytics |
| --- | --- | --- | --- | --- |
| 270 | 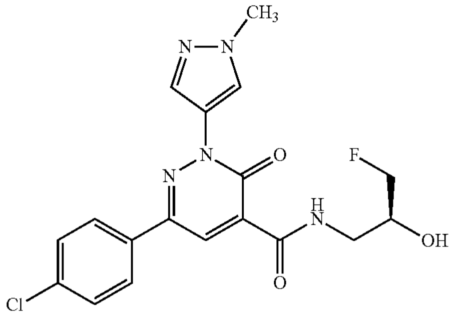 [SMILES: Cn1cc(-n2nc(-c3ccc(Cl)cc3)cc(C(=O)NC[C@H](O)CF)c2=O)cn1] | 6-(4-Chlorophenyl)-N-[(2S)-3-fluoro-2-hydroxypropyl]-2-(1-methyl-1H-pyrazol-4-yl)-3-oxo-2,3-dihydropyridazine-4-carboxamide, $[\alpha]_D^{20}$ = +1.7° +/−0.6° = 1.00, DMSO) | 6-(4-Chlorophenyl)-2-(1-methyl-1H-pyrazol-4-yl)-3-oxo-2,3-dihydropyridazine-4-carboxylic acid, (2S)-1-amino-3-fluoropropan-2-ol hydrochloride | $^1$H-NMR (400 MHz, DMSO-$d_6$): δ [ppm] = 3.34-3.40 (m, 1H), 3.56 (dt, 1H), 3.84-3.96 (m, 4H), 4.27-4.36 (m, 1H), 4.39-4.48 (m, 1H), 5.50 (d, 1H), 7.58-7.62 (m, 2H), 8.08-8.13 (m, 3H), 8.55 (s, 1H), 8.58 (s, 1H), 9.62 (t, 1H). |
| 271 | 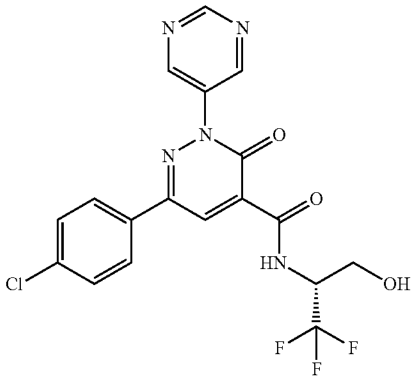 [SMILES: O=C(N[C@H](CO)C(F)(F)F)c1cc(-c2ccc(Cl)cc2)nn(-c2cncnc2)c1=O] | 6-(4-Chlorophenyl)-3-oxo-2-(pyrimidin-5-yl)-N-[(2R)-1,1,1-trifluoro-3-hydroxypropan-2-yl]-2,3-dihydropyridazine-4-carboxamide, $[\alpha]_D^{20}$ = +8.9° (c = 1.00, methanol) | 6-(4-Chlorophenyl)-3-oxo-2-(pyrimidin-5-yl)-2,3-dihydropyridazine-4-carboxylic acid, (2R)-2-amino-3,3,3-trifluoropropan-1-ol hydrochloride | $^1$H-NMR (400 MHz, DMSO-$d_6$): δ [ppm] = 3.66-3.74 (m, 1H), 3.83 (dt, 1H), 4.80-4.93 (m, 1H), 5.45 (t, 1H), 7.58-7.63 (m, 2H), 8.05-8.10 (m, 2H), 8.75 (s, 1H), 9.26 (s, 2H), 9.32 (s, 1H), 9.86 (d, 1H). |
| 272 | 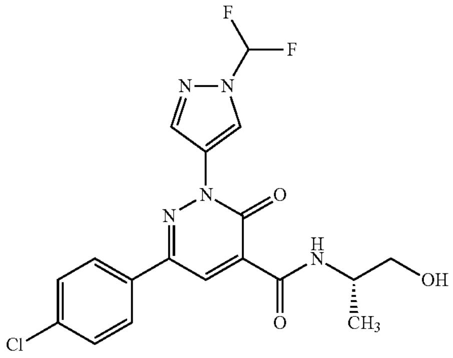 [SMILES: C[C@@H](CO)NC(=O)c1cc(-c2ccc(Cl)cc2)nn(-c2cnn(C(F)F)c2)c1=O] | 6-(4-Chlorophenyl)-2-[1-(difluoromethyl)-1H-pyrazol-4-yl]-N-[(2S)-1-hydroxypropan-2-yl]-3-oxo-2,3-dihydropyridazine-4-carboxamide, $[\alpha]_D^{20}$ = +13.7° (c = 1.00, methanol) | 6-(4-Chlorophenyl)-2-[1-(difluoromethyl)-1H-pyrazol-4-yl]-3-oxo-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.52 (m, 2H), 4.00-4.11 (m, 1H), 4.97 (t, 1H), 7.59-7.63 (m, 2H), 7.92 (t, 1H), 8.12-8.17 (m, 2H), 8.52 (s, 1H), 8.62 (s, 1H), 9.05 (s, 1H), 9.43 (d, 1H). |
| 273 | 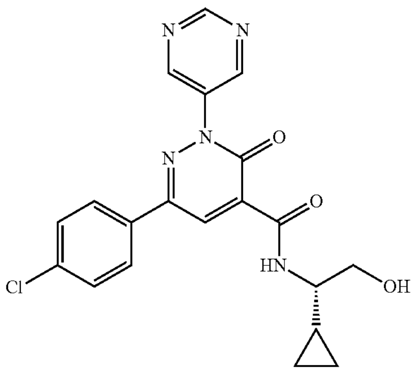 [SMILES: O=C(N[C@H](CO)C1CC1)c1cc(-c2ccc(Cl)cc2)nn(-c2cncnc2)c1=O] | 6-(4-Chlorophenyl)-N-[(1S)-1-cyclopropyl-2-hydroxyethyl]-3-oxo-2-(pyrimidin-5-yl)-2,3-dihydropyridazine-4-carboxamide, $[\alpha]_D^{20}$ = +24.9° (c = 1.00, methanol) | 6-(4-Chlorophenyl)-3-oxo-2-(pyrimidin-5-yl)-2,3-dihydropyridazine-4-carboxylic acid, (2S)-2-amino-2-cyclopropylethanol hydrochloride | $^1$H-NMR (400 MHz, DMSO-$d_6$): δ [ppm] = 0.26-0.51 (m, 4H), 1.04-1.14 (m, 1H), 3.40-3.48 (m, 1H), 3.52-3.64 (m, 2H), 4.94 (t, 1H), 7.57-7.62 (m, 2H), 8.03-8.08 (m, 2H), 8.69 (s, 1H), 9.26 (s, 2H), 9.31 (s, 1H), 9.43 (d, 1H). |

TABLE 2-continued

Examples 195-345

| Expl. | Structure | IUPAC name | Starting materials | analytics |
| --- | --- | --- | --- | --- |
| 274 | 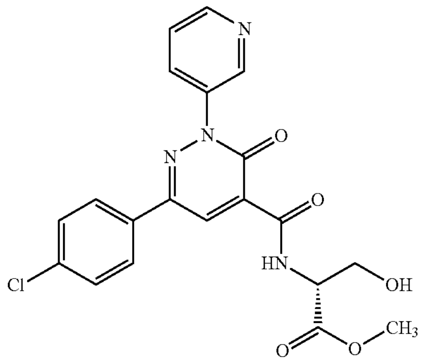 [SMILES: COC(=O)[C@@H](CO)NC(=O)c1cc(-c2ccc(Cl)cc2)nn(-c2cccnc2)c1=O] | Methyl N-{[6-(4-chlorophenyl)-3-oxo-2-(pyridin-3-yl)-2,3-dihydropyridazine-4-yl]carbonyl}-D-serinate | 6-(4-Chlorophenyl)-3-oxo-2-(pyridin-3-yl)-2,3-dihydropyridazine-4-carboxylic acid, methyl D-serinate hydrochloride | $^1$H-NMR (400 MHz, DMSO-$d_6$): δ [ppm] = 3.68 (s, 3H), 3.73 (ddd, 1H), 3.88 (ddd, 1H), 4.63-4.67 (m, 1H), 5.32 (t, 1H), 7.57-7.61 (m, 2H), 7.64 (ddd, 1H), 8.00-8.04 (m, 2H), 8.18 (ddd, 1H), 8.69-8.71 (m, 2H), 8.93 (d, 1H), 9.96 (d, 1H). |
| 275 | 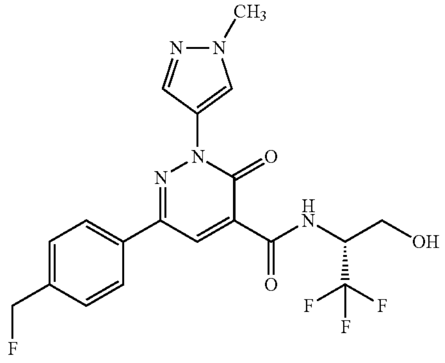 [SMILES: Cn1cc(-n2nc(-c3ccc(CF)cc3)cc(C(=O)N[C@H](CO)C(F)(F)F)c2=O)cn1] | 6-[4-(Fluoromethyl) phenyl]-2-(1-methyl-1H-pyrazol-4-yl)-3-oxo-N-[(2R)-1,1,1-trifluoro-3-hydroxypropan-2-yl]-2,3-dihydropyridazine-4-carboxamide, $[\alpha]_D^{20}$ = +38.6° (c = 1.00, DMSO) | 6-[4-(Fluoromethyl) phenyl]-2-(1-methyl-1H-pyrazol-4-yl)-3-oxo-2,3-dihydropyridazine-4-carboxylic acid, (2R)-2-amino-3,3,3-trifluoropropan-1-ol | $^1$H-NMR (400 MHz, DMSO-$d_6$): δ [ppm] = 3.68-3.76 (m, 1H), 3.85 (br dd, 1H), 3.94 (s, 3H), 4.81-4.93 (m, 1H), 5.46 (s, 2H), 5.58 (s, 1H), 7.59 (dd, 2H), 8.11-8.16 (m, 3H), 8.60 (s, 1H), 8.67 (s, 1H), 10.14 (d, 1H). |
| 276 | 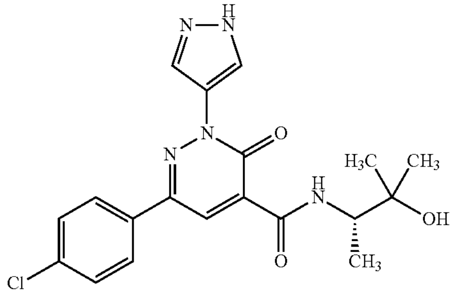 [SMILES: C[C@H](NC(=O)c1cc(-c2ccc(Cl)cc2)nn(-c2cn[nH]c2)c1=O)C(C)(C)O] | 6-(4-Chlorophenyl)-N-[(2S)-3-hydroxy-3-methylbutan-2-yl]-3-oxo-2-(1H-pyrazol-4-yl)-2,3-dihydropyridazine-4-carboxamide, $[\alpha]_D^{20}$ = +37.0° (c = 1.00, methanol) | 6-(4-Chlorophenyl)-3-oxo-2-(1H-pyrazol-4-yl)-2,3-dihydropyridazine-4-carboxylic acid, (3S)-3-amino-2-methylbutan-2-ol | $^1$H-NMR (400 MHz, DMSO-$d_6$): δ [ppm] = 1.12 (s, 3H), 1.15 (d, 3H), 1.18 (s, 3H), 3.90-3.98 (m, 1H), 4.68 (s, 1H), 7.57-7.62 (m, 2H), 8.08-8.12 (m, 2H), 8.19 (br s, 1H), 8.50 (br s, 1H), 8.60 (s, 1H), 9.63 (d, 1H), 13.24 (br s, 1H). |
| 277 | 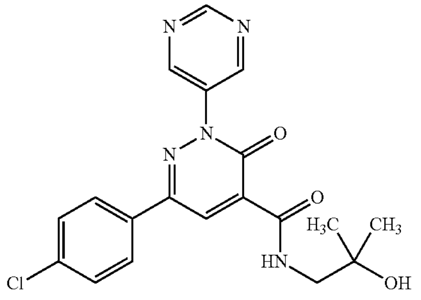 [SMILES: CC(C)(O)CNC(=O)c1cc(-c2ccc(Cl)cc2)nn(-c2cncnc2)c1=O] | 6-(4-Chlorophenyl)-N-(2-hydroxy-2-methylpropyl)-3-oxo-2-(pyrimidin-5-yl)-2,3-dihydropyridazine-4-carboxamide, $[\alpha]_D^{20}$ = +24.9° (c = 1.00, methanol) | 6-(4-Chlorophenyl)-3-oxo-2-(pyrimidin-5-yl)-2,3-dihydropyridazine-4-carboxylic acid, 1-amino-2-methylpropan-2-ol | $^1$H-NMR (400 MHz, DMSO-$d_6$): δ [ppm] = 1.13 (s, 6H), 3.31-3.33 (m, 2H and water signal), 4.69 (s, 1H), 7.57-7.62 (m, 2H), 8.03-8.08 (m, 2H), 8.69 (s, 1H), 9.26 (s, 2H), 9.30 (s, 1H), 9.41 (t, 1H). |

TABLE 2-continued

| Examples 195-345 | | | | |
|---|---|---|---|---|
| Expl. | Structure | IUPAC name | Starting materials | analytics |
| 278 | 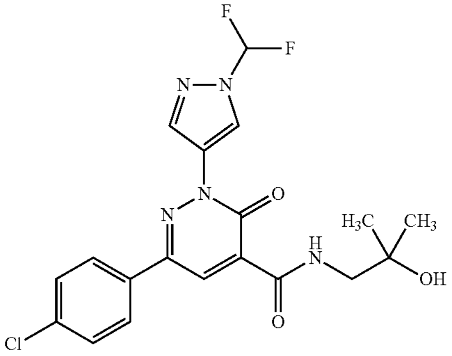 [SMILES: CC(C)(O)CNC(=O)c1cc(-c2ccc(Cl)cc2)nn(-c2cnn(C(F)F)c2)c1=O] | 6-(4-Chlorophenyl)-2-[1-(difluoromethyl)-1H-pyrazol-4-yl]-N-(2-hydroxy-2-methylpropyl)-3-oxo-2,3-dihydropyridazine-4-carboxamide | 6-(4-Chlorophenyl)-2-[1-(difluoromethyl)-1H-pyrazol-4-yl]-3-oxo-2,3-dihydropyridazine-4-carboxylic acid, 1-amino-2-methylpropan-2-ol | $^1$H-NMR (400 MHz, DMSO-$d_6$): δ [ppm] = 1.15 (s, 6H), 3.33-3.34 (m, 2H and water signal), 4.71 (s, 1H), 7.58-7.63 (m, 2H), 7.93 (t, 1H), 8.12-8.17 (m, 2H), 8.53 (s, 1H), 8.63 (s, 1H), 9.05 (s, 1H), 9.54 (t, 1H). |
| 279 | 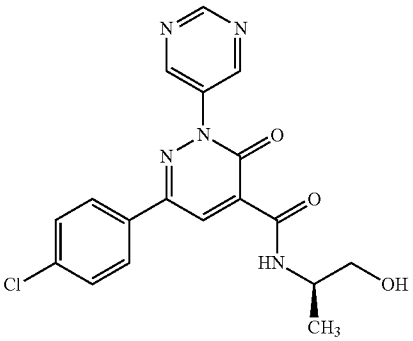 [SMILES: C[C@H](CO)NC(=O)c1cc(-c2ccc(Cl)cc2)nn(-c2cncnc2)c1=O] | 6-(4-Chlorophenyl)-N-[(2R)-1-hydroxypropan-2-yl]-3-oxo-2-(pyrimidin-5-yl)-2,3-dihydropyridazine-4-carboxamide, $[\alpha]_D^{20}$ = −0.8° +/−0.2° (c = 1.00, methanol) | 6-(4-Chlorophenyl)-3-oxo-2-(pyrimidin-5-yl)-2,3-dihydropyridazine-4-carboxylic acid, (2R)-2-aminopropan-1-ol hydrochloride | $^1$H-NMR (400 MHz, DMSO-$d_6$): δ [ppm] = 1.17 (d, 3H), 3.40-3.51 (m, 2H), 3.99-4.10 (m, 1H), 4.96 (t, 1H), 7.58-7.62 (m, 2H), 8.03-8.08 (m, 2H), 8.68 (s, 1H), 9.25 (s, 2H), 9.28-9.32 (m, 2H). |
| 280 | 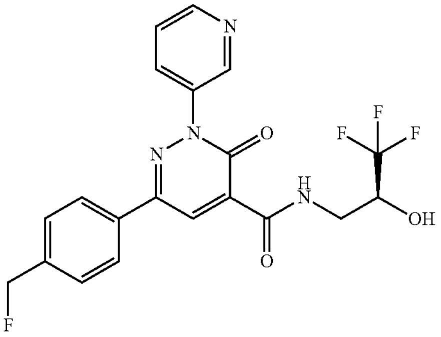 [SMILES: O=C(NC[C@H](O)C(F)(F)F)c1cc(-c2ccc(CF)cc2)nn(-c2cccnc2)c1=O] | 6-[4-(Fluoromethyl) phenyl]-3-oxo-2-(pyridin-3-yl)-N-[(2S)-3,3,3-trifluoro-2-hydroxypropyl]-2,3-dihydropyridazine-4-carboxamide, $[\alpha]_D^{20}$ = −11.7° (c = 1.00, DMSO) | 6-[4-(Fluoromethyl) phenyl]-3-oxo-2-(pyridin-3-yl)-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.48 (ddd, 1H), 3.76 (ddd, 1H), 4.18-4.28 (m, 1H), 5.51 (d, 2H), 6.68 (s, 1H), 7.57 (dd, 2H), 7.64 (ddd, 1H), 8.03 (d, 2H), 8.17 (ddd, 1H), 8.68-8.71 (m, 2H), 8.93 (d, 1H), 9.62 (t, 1H). |
| 281 | 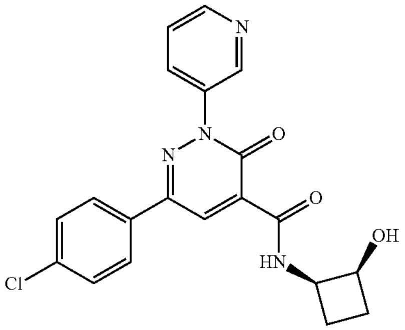 [SMILES: O=C(N[C@@H]1CC[C@@H]1O)c1cc(-c2ccc(Cl)cc2)nn(-c2cccnc2)c1=O] | (−)-6-(4-Chlorophenyl)-N-cis-2-hydroxycyclobutyl-3-oxo-2-(pyridin-3-yl)-2,3-dihydropyridazine-4-carboxamide, enantiomer 2, $[\alpha]_D^{20}$ = −18.3° (c = 1.00, methanol) | 6-(4-Chlorophenyl)-3-oxo-2-(pyridin-3-yl)-2,3-dihydropyridazine-4-carboxylic acid, cis-2-aminocyclobutanol hydrochloride Chiralpak IB 5μ 250 × 30 mm, eluent A: $CO_2$, eluent B: isopropanol, isocratic: 28% B, 100 mL/min, 40° C., BPR: 150 bar, 220 nm | $^1$H-NMR (400 MHz, DMSO-$d_6$): δ [ppm] = 1.73-1.91 (m, 2H), 2.06-2.15 (m, 2H), 4.34-4.40 (m, 2H), 5.51 ( br d, 1H), 7.57-7.61 (m, 2H), 7.64 (ddd, 1H), 7.99-8.03 (m, 2H), 8.17 (ddd, 1H), 8.67 (s, 1H), 8.70 (dd, 1H), 8.92 (d, 1H), 9.89 (br d, 1H). Rt = 5.00 min, Chiralpak IB 5 μm 100 × 4.6 mm, eluent A: $CO_2$, eluent B: ethanol, isocratic: 24% B, 4 mL/min, 37.5° C., BPR: 100 bar, 220 nm |

TABLE 2-continued

| Examples 195-345 | | | | |
|---|---|---|---|---|
| Expl. | Structure | IUPAC name | Starting materials | analytics |
| 282 | 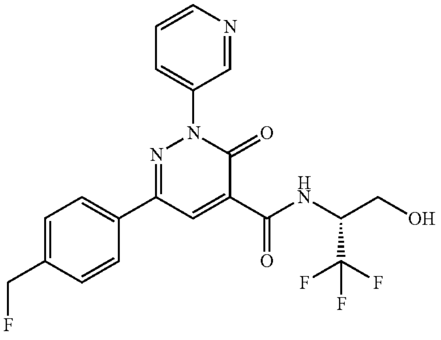 [SMILES: O=C(N[C@H](CO)C(F)(F)F)c1cc(-c2ccc(CF)cc2)nn(-c2cccnc2)c1=O] | 6-[4-(Fluoromethyl)phenyl]-3-oxo-2-(pyridin-3-yl)-N-[(2R)-1,1,1-trifluoro-3-hydroxypropan-2-yl]-2,3-dihydropyridazine-4-carboxamide, $[\alpha]_D^{20}$ = +11.7° (c = 1.00, DMSO) | 6-[4-(Fluoromethyl)phenyl]-3-oxo-2-(pyridin-3-yl)-2,3-dihydropyridazine-4-carboxylic acid, (2R)-2-amino-3,3,3-trifluoropropan-1-ol hydrochloride | $^1$H-NMR (400 MHz, DMSO-$d_6$): δ [ppm] = 3.66-3.74 (m, 1H), 3.83 (dt, 1H), 4.80-4.92 (m, 1H), 5.41-5.46 (m, 2H), 5.57 (s, 1H), 7.55-7.59 (m, 2H), 7.64 (dd, 1H), 8.05 (d, 2H), 8.18 (ddd, 1H), 8.71 (dd, 1H), 8.75 (s, 1H), 8.93 (d, 1H), 9.99 (d, 1H). |
| 283 | 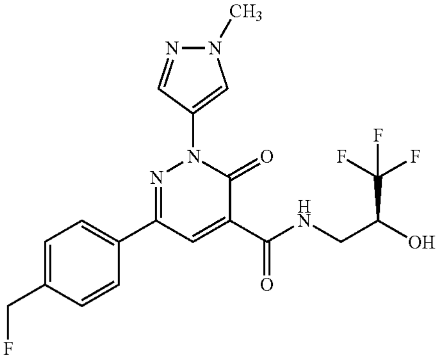 [SMILES: Cn1cc(-n2nc(-c3ccc(CF)cc3)cc(C(=O)NC[C@H](O)C(F)(F)F)c2=O)cn1] | 6-[4-(Fluoromethyl)phenyl]-2-(1-methyl-1H-pyrazol-4-yl)-3-oxo-N-[(2S)-3,3,3-trifluoro-2-hydroxypropyl]-2,3-dihydropyridazine-4-carboxamide, $[\alpha]_D^{20}$ = +1.2° +/−0.5° = 1.00, DMSO) | 6-[4-(Fluoromethyl)phenyl]-2-(1-methyl-1H-pyrazol-4-yl)-3-oxo-2,3-dihydropyridazine-4-carboxylic acid, (2S)-3-amino-1,1,1-trifluoropropan-2-ol | $^1$H-NMR (400 MHz, DMSO-$d_6$): δ [ppm] = 3.49 (ddd, 1H), 3.78 (dt, 1H), 3.94 (s, 3H), 4.19-4.30 (m, 1H), 5.52 (d, 2H), 6.69 (d, 1H), 7.59 (br d, 2H), 8.09-8.15 (m, 3H), 8.55 (s, 1H), 8.63 (s, 1H), 9.76 (br t, 1H). |
| 284 | 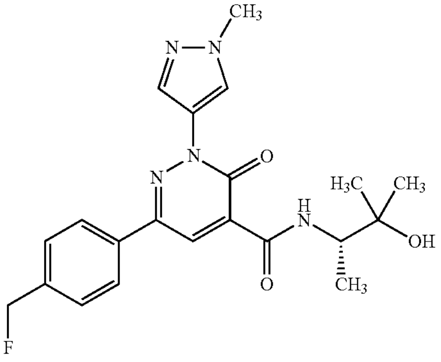 [SMILES: C[C@H](NC(=O)c1cc(-c2ccc(CF)cc2)nn(-c2cnn(C)c2)c1=O)C(C)(C)O] | 6-[4-(Fluoromethyl)phenyl]-N-[(2S)-3-hydroxy-3-methylbutan-2-yl]-2-(1-methyl-1H-pyrazol-4-yl)-3-oxo-2,3-dihydropyridazine-4-carboxamide, $[\alpha]_D^{20}$ = +26.1° (c = 1.00, DMSO) | 6-[4-(Fluoromethyl)phenyl]-2-(1-methyl-1H-pyrazol-4-yl)-3-oxo-2,3-dihydropyridazine-4-carboxylic acid, (3S)-3-amino-2-methylbutan-2-ol | $^1$H-NMR (400 MHz, DMSO-$d_6$): δ [ppm] = 1.13 (s, 3H), 1.15 (d, 3H), 1.18 (s, 3H), 3.89-3.99 (m, 4H), 4.67 (s, 1H), 5.52 (d, 2H), 7.58 (dd, 2H), 8.09-8.13 (m, 3H), 8.57 (s, 1H), 8.61 (s, 1H), 9.65 (d, 1H). |
| 285 | 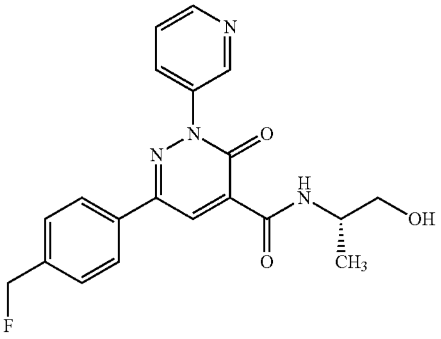 [SMILES: C[C@@H](CO)NC(=O)c1cc(-c2ccc(CF)cc2)nn(-c2cccnc2)c1=O] | 6-[4-(Fluoromethyl)phenyl]-N-[(2S)-1-hydroxypropan-2-yl]-3-oxo-2-(pyridin-3-yl)-2,3-dihydropyridazine-4-carboxamide, $[\alpha]_D^{20}$ = +7.5° (c = 1.00, DMSO) | 6-[4-(Fluoromethyl)phenyl]-3-oxo-2-(pyridin-3-yl)-2,3-dihydropyridazine-4-carboxylic acid, (2S)-2-aminopropan-1-ol | $^1$H-NMR (400 MHz, DMSO-$d_6$): δ [ppm] = 1.17 (d, 3H), 3.40-3.49 (m, 2H), 3.99-4.09 (m, 1H), 4.94 (t, 1H), 5.50 (d, 2H), 7.55-7.58 (m, 2H), 7.63 (ddd, 1H), 8.03 (d, 2H), 8.17 (ddd, 1H), 8.68-8.71 (m, 2H), 8.91 (d, 1H), 9.42 (d, 1H). |

TABLE 2-continued

Examples 195-345

| Expl. | Structure | IUPAC name | Starting materials | analytics |
|---|---|---|---|---|
| 286 | 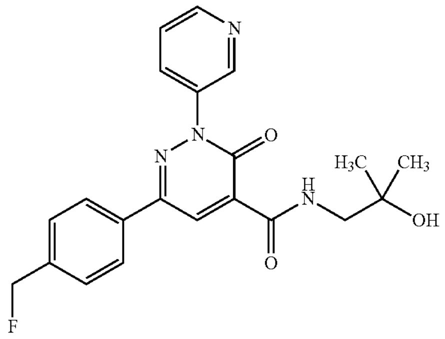 [SMILES: CC(C)(O)CNC(=O)c1cc(-c2ccc(CF)cc2)nn(-c2cccnc2)c1=O] | 6-[4-(Fluoromethyl) phenyl]-N-(2-hydroxy-2-methylpropyl)-3-oxo-2-(pyridin-3-yl)-2,3-dihydropyridazine-4-carboxamide | 6-[4-(Fluoromethyl) phenyl]-3-oxo-2-(pyridin-3-yl)-2,3-dihydropyridazine-4-carboxylic acid, 1-amino-2-methylpropan-2-ol | $^1$H-NMR (400 MHz, DMSO-$d_6$): δ [ppm] = 1.13 (s, 6H), 3.31-3.33 (m, 2H and water signal), 4.67 (s, 1H), 5.50 (d, 2H), 7.55-7.58 (m, 2H), 7.64 (dd, 1H), 8.03 (d, 2H), 8.18 (ddd, 1H), 8.70 (s, 2H), 8.93 (d, 1H), 9.53 (t, 1H). |
| 287 | 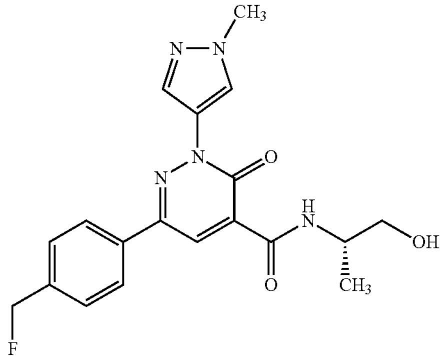 [SMILES: C[C@@H](CO)NC(=O)c1cc(-c2ccc(CF)cc2)nn(-c2cnn(C)c2)c1=O] | 6-[4-(Fluoromethyl) phenyl]-N-[(2S)-1-hydroxypropan-2-yl]-2-(1-methyl-1H-pyrazol-4-yl)-3-oxo-2,3-dihydropyridazine-4-carboxamide, $[\alpha]_D^{20}$ = +13.5° (c = 1.00, DMSO) | 6-[4-(Fluoromethyl) phenyl]-2-(1-methyl-1H-pyrazol-4-yl)-3-oxo-2,3-dihydropyridazine-4-carboxylic acid, (2S)-2-aminopropan-1-ol | $^1$H-NMR (400 MHz, DMSO-$d_6$): δ [ppm] = 1.19 (d, 3H), 3.43-3.52 (br d, 2H), 3.93 (s, 3H), 4.00-4.12 (m, 1H), 4.96 (br s, 1H), 5.52 (d, 2H), 7.56-7.60 (m, 2H), 8.09-8.14 (m, 3H), 8.57 (s, 1H), 8.61 (s, 1H), 9.55 (d, 1H). |
| 288 | 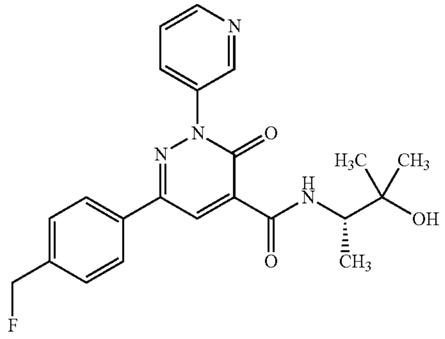 [SMILES: C[C@H](NC(=O)c1cc(-c2ccc(CF)cc2)nn(-c2cccnc2)c1=O)C(C)(C)O] | 6-[4-(Fluoromethyl) phenyl]-N-[(2S)-3-hydroxy-3-methylbutan-2-yl]-3-oxo-2-(pyridin-3-yl)-2,3-dihydropyridazine-4-carboxamide, $[\alpha]_D^{20}$ = +20.0° (c = 1.00, DMSO) | 6-[4-(Fluoromethyl) phenyl]-3-oxo-2-(pyridin-3-yl)-2,3-dihydropyridazine-4-carboxylic acid, (3S)-3-amino-2-methylbutan-2-ol | $^1$H-NMR (400 MHz, DMSO-$d_6$): δ [ppm] = 1.10 (s, 3H), 1.13 (d, 3H), 1.15 (s, 3H), 3.87-3.96 (m, 1H), 4.65 (s, 1H), 5.50 (d, 2H), 7.56 (dd, 2H), 7.63 (ddd, 1H), 8.00-8.04 (m, 2H), 8.18 (ddd, 1H), 8.68-8.71 (m, 2H), 8.92 (d, 1H), 9.53 (d, 1H). |
| 289 | 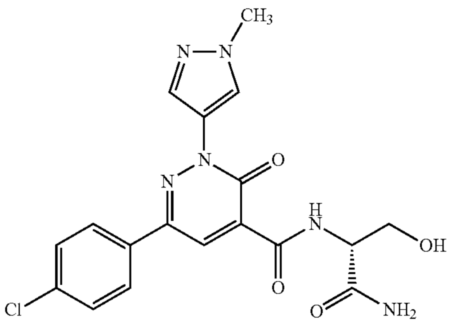 [SMILES: Cn1cc(-n2nc(-c3ccc(Cl)cc3)cc(C(=O)N[C@H](CO)C(N)=O)c2=O)cn1] | N-[(2R)-1-Amino-3-hydroxy-1-oxopropan-2-yl]-6-(4-chlorophenyl)-2-(1-methyl-1H-pyrazol-4-yl)-3-oxo-2,3-dihydropyridazine-4-carboxamide, $[\alpha]_D^{20}$ = −64.5° (c = 1.00, DMSO) | 6-(4-Chlorophenyl)-2-(1-methyl-1H-pyrazol-4-yl)-3-oxo-2,3-dihydropyridazine-4-carboxylic acid, D-serinamide hydrochloride | $^1$H-NMR (400 MHz, DMSO-$d_6$): δ [ppm] = 3.64-3.71 (m, 1H), 3.76-3.82 (m, 1H), 3.94 (s, 3H), 4.45-4.50 (m, 1H), 5.11 (t, 1H), 7.23 (s, 1H), 7.54 (s, 1H), 7.58-7.63 (m, 2H), 8.09-8.13 (m, 2H), 8.14 (d, 1H), 8.59 (s, 1H), 8.60 (s, 1H), 9.96 (d, 1H). |

TABLE 2-continued

| Examples 195-345 | | | | |
|---|---|---|---|---|
| Expl. | Structure | IUPAC name | Starting materials | analytics |
| 290 | 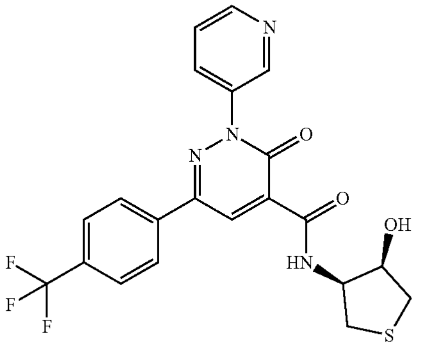 | N-cis-4-Hydroxytetra-hydrothiophen-3-yl-3-oxo-2-(pyridin-3-yl)-6-[4-(trifluoromethyl)phenyl]-2,3-dihydropyridazine-4-carboxamide | 3-Oxo-2-(pyridin-3-yl)-6-[4-(trifluoromethyl)phenyl]-2,3-dihydropyridazine-4-carboxylic acid, cis-4-aminotetrahydro-thiophene-3-ol hydrochloride | $^1$H-NMR (400 MHz, DMSO-$d_6$): δ [ppm] = 2.68-2.76 (m, 2H), 3.03 (dd, 1H), 3.10 (dd, 1H), 4.30-4.38 (m, 2H), 5.67 (d, 1H), 7.64 (dd, 1H), 7.89 (d, 2H), 8.18 (ddd, 1H), 8.22 (d, 2H), 8.71 (dd, 1H), 8.76 (s, 1H), 8.92 (d, 1H), 9.76 (d, 1H). |
| 291 | 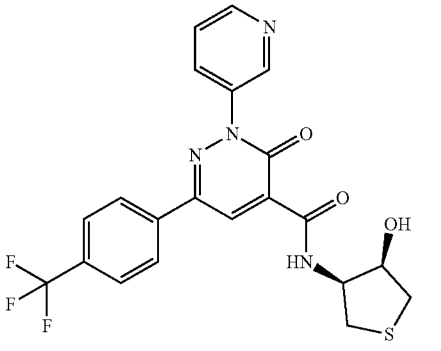 [SMILES: O=C(N[C@@H]1CSC[C@@H]1O)c1cc(-c2ccc(C(F)(F)F)cc2)nn(-c2cccnc2)c1=O] | (−)-N-cis-4-hydroxy-tetrahydrothiophen-3-yl-3-oxo-2-(pyridin-3-yl)-6-[4-(trifluoromethyl)phenyl]-2,3-dihydropyridazine-4-carboxamide, enantiomer 2, $[\alpha]_D^{20}$ = −2.0° = 1.00, DMSO) | 3-Oxo-2-(pyridin-3-yl)-6-[4-(trifluoromethyl)phenyl]-2,3-dihydropyridazine-4-carboxylic acid, cis-4-aminotetrahydro-thiophene-3-ol hydrochloride Chiralpak ID 5μ 250 × 30 mm, eluent A: $CO_2$, eluent B: ethanol, isocratic: 30% B, 100 mL/min, 40° C., BPR: 150 bar, 254 nm | $^1$H-NMR (400 MHz, DMSO-$d_6$): δ [ppm] = 2.69-2.76 (m, 2H), 2.99-3.06 (m, 1H), 3.11 (dd, 1H), 4.30-4.39 (m, 2H), 5.67 (d, 1H), 7.64 (ddd, 1H), 7.89 (d, 2H), 8.18 (ddd, 1H), 8.22 (d, 2H), 8.71 (dd, 1H), 8.77 (s, 1H), 8.92 (dd, 1H), 9.76 (d, 1H). Rt = 5.53 min, Chiralpak ID 5 μm 100 × 4.6 mm, eluent A: $CO_2$, eluent B: ethanol, isocratic: 30% B, 4 mL/min, 37.5° C., BPR: 100 bar, 254 nm |
| 292 | 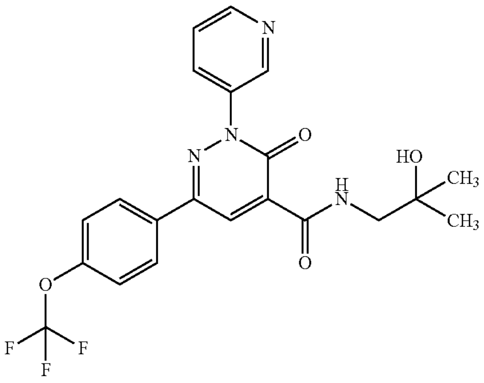 [SMILES: CC(C)(O)CNC(=O)c1cc(-c2ccc(OC(F)(F)F)cc2)nn(-c2cccnc2)c1=O] | N-(2-Hydroxy-2-methylpropyl)-3-oxo-2-(pyridin-3-yl)-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, 1-amino-2-methylpropan-2-ol | $^1$H NMR (400 MHz, DMSO-$d_6$) δ pm = 1.13 (s, 6 H), 3.30-3.33 (m, 2 H), 4.68 (s, 1 H), 7.51 (br d, 2 H), 7.63 (dd, 1 H), 8.12 (d, 2 H), 8.18 (br d, 1 H), 8.69 (m, 2 H), 8.90-8.95 (m, 1 H), 9.49-9.55 (m, 1 H). |
| 293 | 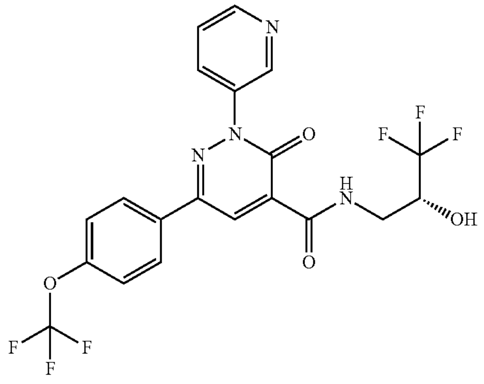 [SMILES: O=C(NC[C@@H](O)C(F)(F)F)c1cc(-c2ccc(OC(F)(F)F)cc2)nn(-c2cccnc2)c1=O] | 3-Oxo-2-(pyridin-3-yl)-N-[(2R)-3,3,3-trifluoro-2-hydroxypropyl]-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, (2R)-3-amino-1,1,1-trifluoropropan-2-ol | $^1$H NMR (400 MHz, DMSO-$d_6$) δ [ppm] = 3.43-3.53 (m, 1 H), 3.71-3.79 (m, 1 H), 4.17-4.28 (m, 1 H), 6.66 (d, 1 H), 7.52 (d, 2 H), 7.64 (dd, 1 H), 8.13 (d, 2 H), 8.17 (ddd, 1 H), 8.67-8.73 (m, 2 H), 8.93 (d, 1 H), 9.60 (t, 1 H). |

TABLE 2-continued

Examples 195-345

| Expl. | Structure | IUPAC name | Starting materials | analytics |
|---|---|---|---|---|
| 294 | 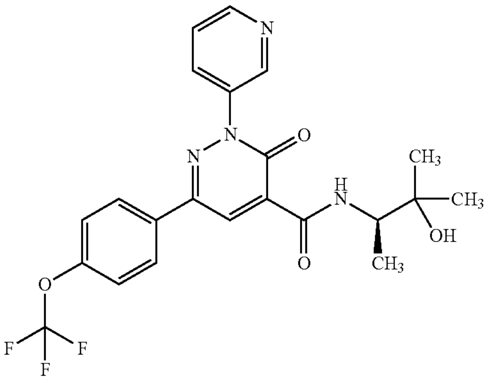 [SMILES: C[C@@H](NC(=O)c1cc(-c2ccc(OC(F)(F)F)cc2)nn(-c2cccnc2)c1=O)C(C)(C)O] | N-[(2R)-3-Hydroxy-3-methylbutan-2-yl]-3-oxo-2-(pyridin-3-yl)-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, (3R)-3-amino-2-methylbutan-2-ol | $^{1}$H NMR (400 MHz, DMSO-$d_6$) δ [ppm] = 1.10 (s, 3 H), 1.13 (d, 3 H), 1.15 (s, 3 H), 3.89-3.96 (dd, 1 H), 4.66 (s, 1 H), 7.51 (d, 2 H), 7.63 (dd, 1 H), 8.09-8.14 (m, 2 H), 8.15-8.20 (m, 1 H), 8.67-8.72 (m, 2 H), 8.92 (d, 1 H), 9.52 (t, 1 H). |
| 295 | 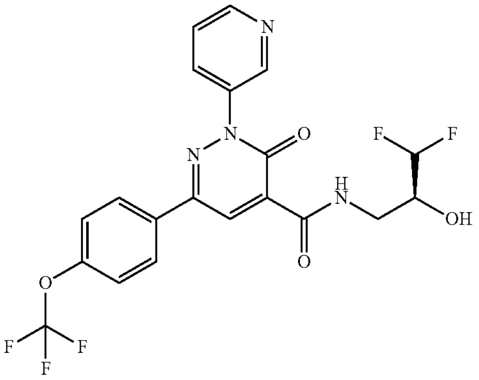 [SMILES: O=C(NC[C@H](O)C(F)F)c1cc(-c2ccc(OC(F)(F)F)cc2)nn(-c2cccnc2)c1=O] | N-[(2S)-3,3-Difluoro-2-hydroxypropyl]-3-oxo-2-(pyridin-3-yl)-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, (2S)-3-amino-1,1-difluoropropan-2-ol | $^{1}$H NMR (400 MHz, DMSO-$d_6$) δ [ppm] = 3.36-3.44 (m, 1 H), 3.62-3.70 (m, 1 H), 3.78-3.91 (m, 1 H), 5.94 (dt, 1H), 6.00 (d, 1 H), 7.52 (d, 2 H), 7.64 (dd, 1 H), 8.09-8.15 (m, 2 H), 8.15-8.19 (m, 1 H), 8.67-8.71 (m, 2 H), 8.93 (d, 1 H), 9.55 (t, 1 H). |
| 296 | 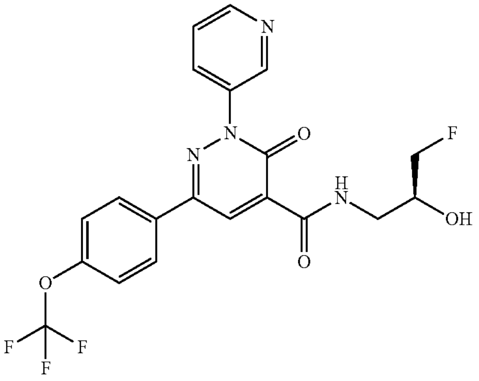 [SMILES: O=C(NC[C@H](O)CF)c1cc(-c2ccc(OC(F)(F)F)cc2)nn(-c2cccnc2)c1=O] | N-[(2S)-3-Fluoro-2-hydroxypropyl]-3-oxo-2-(pyridin-3-yl)-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, (2S)-1-amino-3-fluoropropan-2-ol | $^{1}$H NMR (400 MHz, DMSO-$d_6$) δ [ppm] = 3.30-3.40 (m, 1H and water signal), 3.50-3.59 (m, 1 H), 3.82-3.94 (m, 1 H), 4.26-4.46 (m, 2 H), 5.48 (br d, 1 H), 7.51 (d, 2 H), 7.63 (dd, 1 H), 8.09-8.14 (m, 2 H), 8.15-8.19 (m, 1 H), 8.65-8.72 (m, 2 H), 8.93 (br s, 1 H), 9.50 (t, 1 H). |
| 297 | 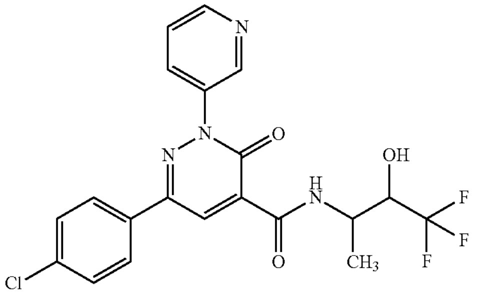 [SMILES: CC(NC(=O)c1cc(-c2ccc(Cl)cc2)nn(-c2cccnc2)c1=O)C(O)C(F)(F)F] | 6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 1 | 6-(4-Chlorophenyl)-3-oxo-2-(pyridin-3-yl)-N-(4,4,4-trifluoro-3-hydroxybutan-2-yl)-2,3-dihydropyridazine-4-carboxamide | Analytical chiral HPLC: Rt = 1.62 min Instrument: Agilent HPLC 1260; column: YMC Amylose SA 3 μ 100 × 4.6 mm; eluent: tert.-butylmethylether + 0.1 vol % diethylamine (99%)/ethanol 90:10, flow 1.4 mL/min; temperature: 25° C.; DAD scan: 254 nm. |

TABLE 2-continued

Examples 195-345

| Expl. | Structure | IUPAC name | Starting materials | analytics |
|---|---|---|---|---|
| 298 | 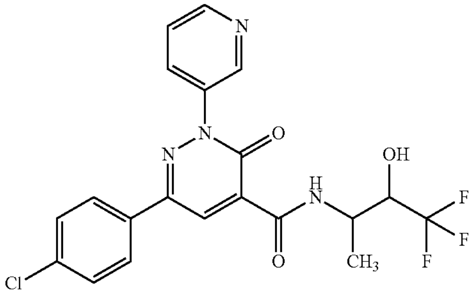 [SMILES: CC(NC(=O)c1cc(-c2ccc(Cl)cc2)nn(-c2cccnc2)c1=O)C(O)C(F)(F)F] | 6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 2 | 6-(4-Chlorophenyl)-3-oxo-2-(pyridin-3-yl)-N-(4,4,4-trifluoro-3-hydroxybutan-2-yl)-2,3-dihydropyridazine-4-carboxamide | Analytical chiral HPLC: Rt = 2.31 min Instrument: Agilent HPLC 1260; column: YMC Amylose SA 3 μ 100 × 4.6 mm; eluent: tert.- butylmethylether + 0.1 vol % diethylamine (99%)/ ethanol 90:10, flow 1.4 mL/min; temperature: 25° C.; DAD scan: 254 nm. |
| 299 | 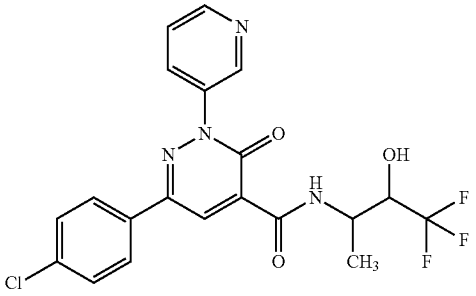 [SMILES: CC(NC(=O)c1cc(-c2ccc(Cl)cc2)nn(-c2cccnc2)c1=O)C(O)C(F)(F)F] | 6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 3 | 6-(4-Chlorophenyl)-3-oxo-2-(pyridin-3-yl)-N-(4,4,4-trifluoro-3-hydroxybutan-2-yl)-2,3-dihydropyridazine-4-carboxamide | Analytical chiral HPLC: Rt = 1.38 min Instrument: Agilent HPLC 1260; column: YMC Amylose SA 3 μ 100 × 4.6 mm; eluent: tert.- butylmethylether + 0.1 vol % diethylamine (99%)/ ethanol 90:10, flow 1.4 mL/min; temperature: 25° C.; DAD scan: 254 nm. |
| 300 | 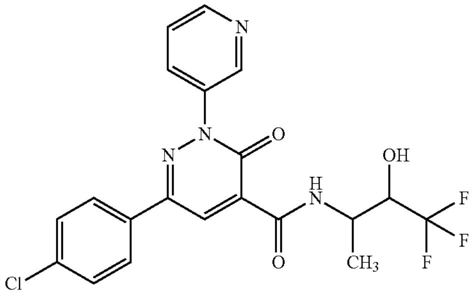 [SMILES: CC(NC(=O)c1cc(-c2ccc(Cl)cc2)nn(-c2cccnc2)c1=O)C(O)C(F)(F)F] | 6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 4 | 6-(4-Chlorophenyl)-3-oxo-2-(pyridin-3-yl)-N-(4,4,4-trifluoro-3-hydroxybutan-2-yl)-2,3-dihydropyridazine-4-carboxamide | Analytical chiral HPLC: Rt = 2.86 min Instrument: Agilent HPLC 1260; column: YMC Amylose SA 3 μ 100 × 4.6 mm; eluent: tert.- butylmethylether + 0.1 vol % diethylamine (99%)/ ethanol 90:10, flow 1.4 mL/min; temperature: 25° C.; DAD scan: 254 nm. |
| 301 | 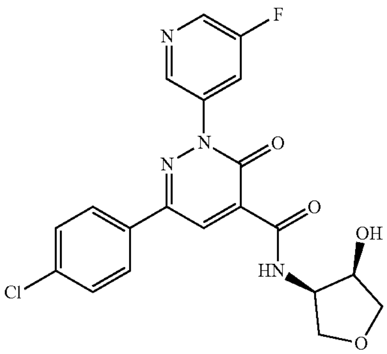 [SMILES: O=C(N[C@@H]1COC[C@@H]1O)c1cc(-c2ccc(Cl)cc2)nn(-c2cncc(F)c2)c1=O] | 6-(4-Chlorophenyl)-2-(5-fluoropyridin-3-yl)-N-[(cis)-4-hydroxytetrahydro-furan-3-yl]-3-oxo-2,3-dihydropyridazine-4-carboxamide | 6-(4-Chlorophenyl)-2-(5-fluoropyridin-3-yl)-3-oxo-2,3-dihydropyridazine-4-carboxylic acid, cis-4-aminotetrahydro-3-furanol hydrochloride 1:1 | $^{1}H$ NMR (400 MHz, DMSO-$d_6$) δ [ppm] = 3.45 (t, 1 H), 3.61 (dd, 1 H), 3.93 (dd, 1 H), 3.98-4.04 (m, 1 H), 4.25-4.30 (m, 1 H), 4.31-4.40 (m, 1 H), 5.71 (d, 1 H), 7.57-7.62 (m, 2 H), 8.01-8.06 (m, 2 H), 8.25 (dt, 1 H), 8.70 (s, 1 H), 8.77 (d, 1 H), 8.85 (d, 1 H), 9.73-9.77 (m, 1 H). |
| 302 | 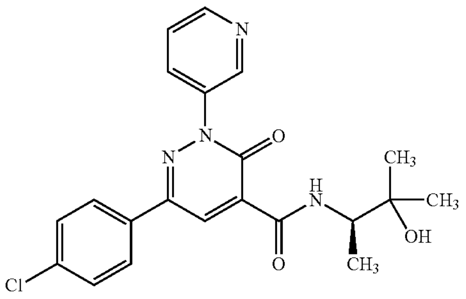 [SMILES: C[C@@H](NC(=O)c1cc(-c2ccc(Cl)cc2)nn(-c2cccnc2)c1=O)C(C)(C)O] | 6-(4-Chlorophenyl)-N-[(2R)-3-hydroxy-3-methylbutan-2-yl]-3-oxo-2-(pyridin-3-yl)-2,3-dihydropyridazine-4-carboxamide | 6-(4-Chlorophenyl)-3-oxo-2-(pyridin-3-yl)-2,3-dihydropyridazine-4-carboxylic acid, (3R)-3-amino-2-methylbutan-2-ol | $^{1}H$ NMR (400 MHz, DMSO-$d_6$) δ [ppm] = 1.10 (s, 3 H), 1.13 (d, 3 H), 1.15 (s, 3 H), 3.91 (dd, 1 H), 4.55-4.75 (m, 1H), 7.56-7.61 (m, 2 H), 7.61-7.66 (m, 1 H), 7.98-8.03 (m, 2 H), 8.17 (br d, 1 H), 8.67 (s, 1 H), 8.68-8.75 (m, 1 H), 8.88-8.98 (m, 1 H), 9.51 (d, 1 H). |

TABLE 2-continued

| Expl. | Structure | IUPAC name | Starting materials | analytics |
|---|---|---|---|---|
| | Examples 195-345 | | | |
| 303 | 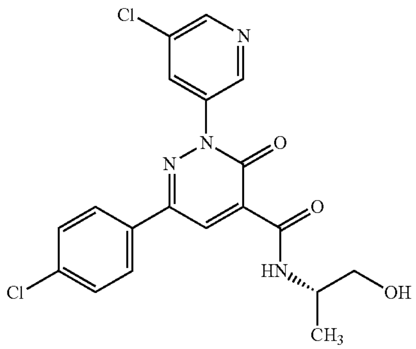 [SMILES: C[C@@H](CO)NC(=O)c1cc(-c2ccc(Cl)cc2)nn(-c2cncc(Cl)c2)c1=O] | 6-(4-Chlorophenyl)-2-(5-chloropyridin-3-yl)-N-[(2S)-1-hydroxypropan-2-yl]-3-oxo-2,3-dihydropyridazine-4-carboxamide | 6-(4-Chlorophenyl)-2-(5-chloropyridin-3-yl)-3-oxo-2,3-dihydropyridazine-4-carboxylic acid, (2S)-2-aminopropan-1-ol | $^1$H NMR (400 MHz, DMSO-$d_6$) δ [ppm] = 1.16 (d, 3 H), 3.40-3.50 (m, 2 H), 3.98-4.09 (m, 1 H), 4.95 (t, 1 H), 7.59 (d, 2 H), 8.03 (d, 2 H), 8.41 (t, 1 H), 8.67 (s, 1 H), 8.79 (d, 1 H), 8.92 (d, 1 H), 9.31-9.36 (m, 1 H). |
| 304 | 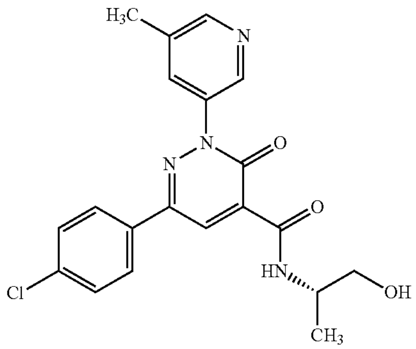 [SMILES: Cc1cncc(-n2nc(-c3ccc(Cl)cc3)cc(C(=O)N[C@@H](C)CO)c2=O)c1] | 6-(4-Chlorophenyl)-N-[(2S)-1-hydroxypropan-2-yl]-2-(5-methylpyridin-3-yl)-3-oxo-2,3-dihydropyridazine-4-carboxamide | 6-(4-Chlorophenyl)-2-(5-methylpyridin-3-yl)-3-oxo-2,3-dihydropyridazine-4-carboxylic acid, (2S)-2-aminopropan-1-ol | $^1$H NMR (400 MHz, DMSO-$d_6$) δ [ppm] = 1.16 (d, 3 H), 2.41 (s, 3 H), 3.39-3.50 (m, 2 H), 3.98-4.09 (m, 1 H), 4.94 (t, 1 H), 7.56-7.61 (m, 2 H), 7.96-8.02 (m, 3 H), 8.54 (d, 1 H), 8.65 (s, 1 H), 8.69 (d, 1 H), 9.41 (d, 1 H). |
| 305 | 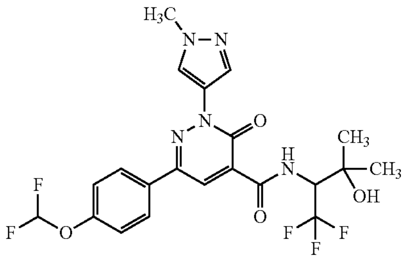 [SMILES: Cn1cc(-n2nc(-c3ccc(OC(F)F)cc3)cc(C(=O)NC(C(C)(C)O)C(F)(F)F)c2=O)cn1] | 6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide | 6-[4-(Difluoromethoxy)phenyl]-2-(1-methyl-1H-pyrazol-4-yl)-3-oxo-2,3-dihydropyridazine-4-carboxylic acid, 3-amino-4,4,4-trifluoro-2-methylbutan-2-ol hydrochloride (1:1) | $^1$H NMR (400 MHz, DMSO-$d_6$) δ [ppm] = 1.21 (s, 3 H), 1.37 (s, 3 H), 3.93 (s, 3 H), 4.63-4.74 (m, 1 H), 5.23 (s, 1 H), 7.33 (d, 2 H), 7.38 (t, 1H), 8.11-8.13 (m, 1 H), 8.13-8.17 (m, 2 H), 8.58 (s, 1 H), 8.64 (s, 1 H), 10.18 (d, 1 H). |
| 306 | 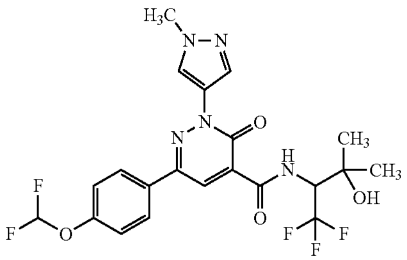 [SMILES: Cn1cc(-n2nc(-c3ccc(OC(F)F)cc3)cc(C(=O)NC(C(C)(C)O)C(F)(F)F)c2=O)cn1] | 6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide Isomer 1 | 6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide; preparative chiral HPLC: instrument: Labomatic HD5000, Labocord-5000; Gilson GX-241, Labcol Vario 4000, column: YMC Cellulose SB 5µ 250 × 30 mm; eluent A: tert.-butylmethylether + 0.1 Vol-% | Analytical chiral HPLC: Rt = 3.87 min Instrument: Agilent HPLC 1260; column: YMC Amylose SA 3µ 100 × 4.6 mm; eluent: tert.- butylmethylether + 0.1 vol % diethylamine (99%)/ methanol 50:50, flow 1.4 mL/min; temperature: 25° C.; DAD scan: 254 nm. $[a]_D^{20}$ = 43.2° = 1.00, MeOH) |

TABLE 2-continued

| Examples 195-345 | | | | |
|---|---|---|---|---|
| Expl. | Structure | IUPAC name | Starting materials | analytics |
| | | | diethylamin (99%); eluent B: methanol; isocratic: 50% A + 50% B; flow 40.0 ml/min; UV 254 nm. | |
| 307 | 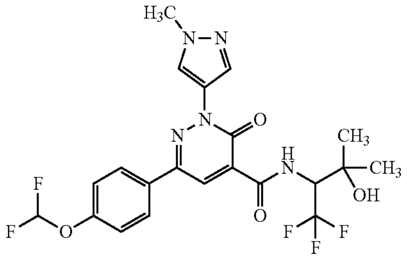 [SMILES: Cn1cc(-n2nc(-c3ccc(OC(F)F)cc3)cc(C(=O)NC(C(C)(C)O)C(F)(F)F)c2=O)cn1] | 6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide Isomer 2 | 6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide; chiral HPLC see example 306 | Analytical chiral HPLC: Rt = 2.67 min Instrument: Agilent HPLC 1260; column: YMC Amylose SA 3μ 100 × 4.6 mm; eluent: tert.- butylmethylether + 0.1 vol % diethylamine (99%)/methanol 50:50, flow 1.4 mL/min; temperature: 25° C.; DAD scan: 254 nm. $[a]_D^{20}$ = −40.4° = 1.00, MeOH) |
| 308 | 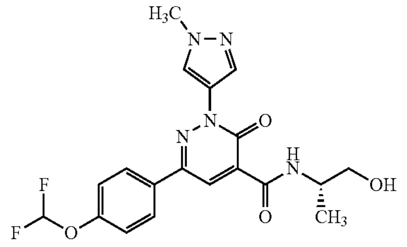 [SMILES: C[C@@H](CO)NC(=O)c1cc(-c2ccc(OC(F)F)cc2)nn(-c2cnn(C)c2)c1=O] | 6-[4-(Difluoromethoxy)phenyl]-N-[(2S)-1-hydroxypropan-2-yl]-2-(1-methyl-1H-pyrazol-4-yl)-3-oxo-2,3-dihydropyridazine-4-carboxamide | 6-[4-(Difluoromethoxy)phenyl]-2-(1-methyl-1H-pyrazol-4-yl)-3-oxo-2,3-dihydropyridazine-4-carboxylic acid, (2S)-2-aminopropan-1-ol | $^1$H NMR (400 MHz, DMSO-$d_6$) δ [ppm] = 1.19 (d, 3 H), 3.40-3.53 (m, 2 H), 3.93 (s, 3 H), 3.98-4.13 (m, 1 H), 4.96 (t, 1 H), 7.30-7.35 (m, 2 H), 7.38 (t, 1H), 8.11-8.16 (m, 3 H), 8.56 (s, 1 H), 8.58 (s, 1 H), 9.55 (d, 1 H). |
| 309 | 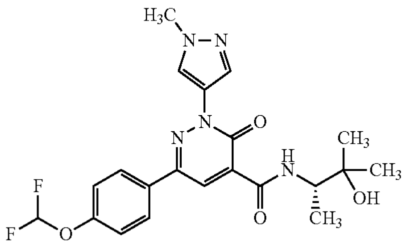 [SMILES: C[C@H](NC(=O)c1cc(-c2ccc(OC(F)F)cc2)nn(-c2cnn(C)c2)c1=O)C(C)(C)O] | 6-[4-(Difluoromethoxy)phenyl]-N-[(2S)-3-hydroxy-3-methylbutan-2-yl]-2-(1-methyl-1H-pyrazol-4-yl)-3-oxo-2,3-dihydropyridazine-4-carboxamide | 6-[4-(Difluoromethoxy)phenyl]-2-(1-methyl-1H-pyrazol-4-yl)-3-oxo-2,3-dihydropyridazine-4-carboxylic acid, (3S)-3-amino-2-methylbutan-2-ol hydrochloride 1:1 | $^1$H NMR (400 MHz, DMSO-d6) δ [ppm] = 1.12 (s, 3 H), 1.15 (d, 3 H), 1.18 (s, 3 H), 3.88-3.99 (m, 4 H), 4.68 (s, 1 H), 7.33 (d, 2 H), 7.38 (t, 1H), 8.09-8.17 (m, 3 H), 8.56 (s, 1 H), 8.59 (s, 1 H), 9.62-9.68 (d, 1 H). |
| 310 | 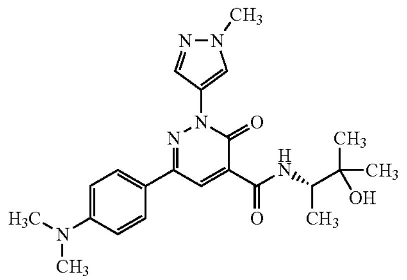 [SMILES: C[C@H](NC(=O)c1cc(-c2ccc(N(C)C)cc2)nn(-c2cnn(C)c2)c1=O)C(C)(C)O] | 6-[4-(Dimethylamino)phenyl]-N-[(2S)-3-hydroxy-3-methylbutan-2-yl]-2-(1-methyl-1H-pyrazol-4-yl)-3-oxo-2,3-dihydropyridazine-4-carboxamide | 6-[4-(Dimethylamino)phenyl]-2-(1-methyl-1H-pyrazol-4-yl)-3-oxo-2,3-dihydropyridazine-4-carboxylic acid, (3S)-3-amino-2-methylbutan-2-ol hydrochloride 1:1 | $^1$H NMR (400 MHz, DMSO-d6) δ [ppm] = 1.12 (s, 3 H), 1.15 (d, 3 H), 1.17 (s, 3 H), 3.00 (s, 6 H), 3.89-3.98 (m, 4 H), 4.65 (s, 1 H), 6.80-6.86 (m, 2 H), 7.85-7.91 (m, 2 H), 8.07 (s, 1 H), 8.52 (s, 2 H), 9.69-9.75 (m, 1 H). |

TABLE 2-continued

| Examples 195-345 | | | | |
|---|---|---|---|---|
| Expl. | Structure | IUPAC name | Starting materials | analytics |
| 311 | 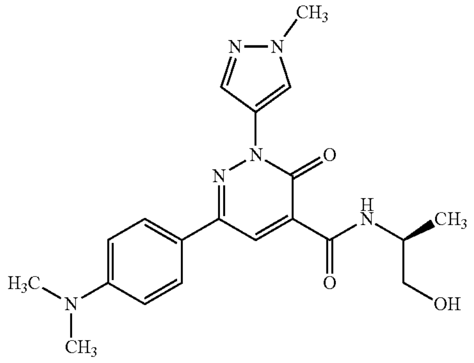 [SMILES: C[C@@H](CO)NC(=O)c1cc(-c2ccc(N(C)C)cc2)nn(-c2cnn(C)c2)c1=O] | 6-[4-(Dimethylamino)phenyl]-N-[(2S)-1-hydroxypropan-2-yl]-2-(1-methyl-1H-pyrazol-4-yl)-3-oxo-2,3-dihydropyridazine-4-carboxamide | 6-[4-(Dimethylamino)phenyl]-2-(1-methyl-1H-pyrazol-4-yl)-3-oxo-2,3-dihydropyridazine-4-carboxylic acid, (2S)-2-aminopropan-1-ol | $^1$H NMR (400 MHz, DMSO-$d_6$) δ [ppm] = 1.18 (d, 3 H), 3.00 (s, 6 H), 3.42-3.52 (m, 2 H), 3.92 (s, 3 H), 4.00-4.10 (m, 1 H), 4.95 (t, 1 H), 6.82 (d, 2 H), 7.87 (d, 2 H), 8.08 (d, 1 H), 8.51 (s, 1 H), 8.52 (s, 1 H), 9.59-9.65 (m, 1 H). |
| 312 | 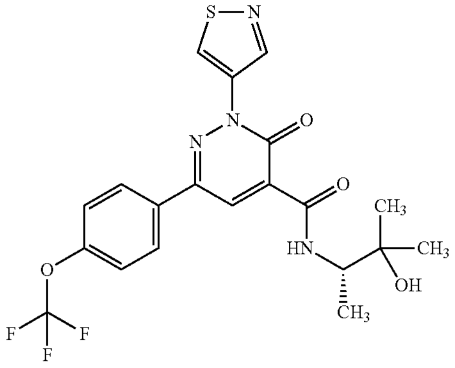 [SMILES: C[C@H](NC(=O)c1cc(-c2ccc(OC(F)(F)F)cc2)nn(-c2cnsc2)c1=O)C(C)(C)O] | N-[(2S)-3-Hydroxy-3-methylbutan-2-yl]-3-oxo-2-(1,2-thiazol-4-yl)-6-[4-(trifluoromethoxy)phenyl]-2,3-dihydropyridazine-4-carboxamide | 3-Oxo-2-(1,2-thiazol-4-yl)-6-[4-(trifluoromethoxy)phenyl]-2,3-dihydropyridazine-4-carboxylic acid, (3S)-3-amino-2-methylbutan-2-ol hydrochloride 1:1 | $^1$H NMR (400 MHz, DMSO-$d_6$) δ [ppm] = 1.12 (s, 3 H), 1.15 (d, 3 H), 1.17 (s, 3 H), 3.87-3.98 (m, 1 H), 4.68 (s, 1 H), 7.53 (d, 2 H), 8.17-8.21 (m, 2 H), 8.66 (s, 1 H), 9.13 (s, 1 H), 9.51 (d, 1 H), 9.61 (s, 1 H). |
| 313 | 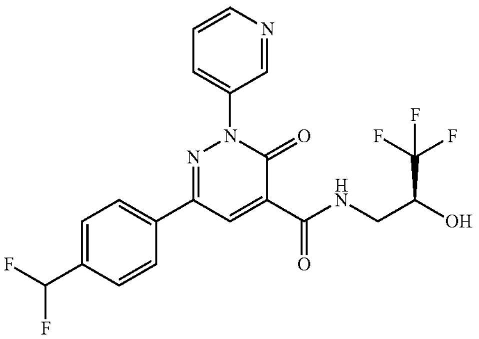 [SMILES: O=C(NC[C@H](O)C(F)(F)F)c1cc(-c2ccc(C(F)F)cc2)nn(-c2cccnc2)c1=O] | 6-[4-(Difluoromethyl)phenyl]-3-oxo-2-(pyridin-3-yl)-N-[(2S)-3,3,3-trifluoro-2-hydroxypropyl]-2,3-dihydropyridazine-4-carboxamide | 6-[4-(Difluoromethyl)phenyl]-3-oxo-2-(pyridin-3-yl)-2,3-dihydropyridazine-4-carboxylic acid, (2S)-3-amino-1,1,1-trifluoropropan-2-ol | $^1$H NMR (400 MHz, DMSO-$d_6$) δ [ppm] = 3.44-3.53 (m, 1 H), 3.72-3.80 (m, 1 H), 4.23 (qd, 1 H), 6.67 (d, 1 H), 7.13 (t, 1 H), 7.62-7.67 (m, 1 H), 7.73 (d, 2 H), 8.13 (d, 2 H), 8.18 (ddd, 1 H), 8.70 (dd, 1 H), 8.73 (s, 1 H), 8.93 (d, 1 H), 9.57-9.64 (m, 1 H). |
| 314 | 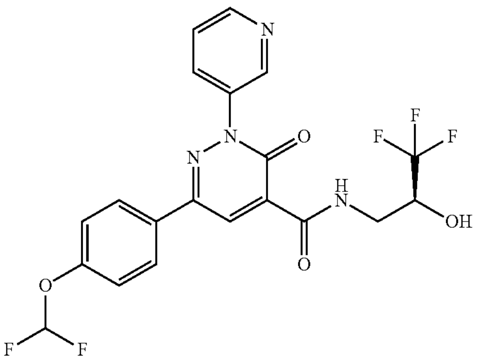 [SMILES: O=C(NC[C@H](O)C(F)(F)F)c1cc(-c2ccc(OC(F)F)cc2)nn(-c2cccnc2)c1=O] | 6-[4-(Difluoromethoxy)phenyl]-3-oxo-2-(pyridin-3-yl)-N-[(2S)-3,3,3-trifluoro-2-hydroxypropyl]-2,3-dihydropyridazine-4-carboxamide | 6-[4-(Difluoromethoxy)phenyl]-3-oxo-2-(pyridin-3-yl)-2,3-dihydropyridazine-4-carboxylic acid, (2S)-3-amino-1,1,1-trifluoropropan-2-ol | $^1$H NMR (400 MHz, DMSO-$d_6$) δ [ppm] = 3.42-3.52 (m, 1 H), 3.69-3.80 (m, 1 H), 4.17-4.29 (m, 1 H), 6.67 (d, 1 H), 7.32 (d, 2 H), 7.36 (t, 1H), 7.65 (br d, 1 H), 8.03-8.07 (m, 2 H), 8.15-8.19 (m, 1 H), 8.65-8.71 (m, 2 H), 8.92 (d, 1 H), 9.62 (t, 1 H). |

TABLE 2-continued

| Examples 195-345 | | | | |
|---|---|---|---|---|
| Expl. | Structure | IUPAC name | Starting materials | analytics |
| 315 | 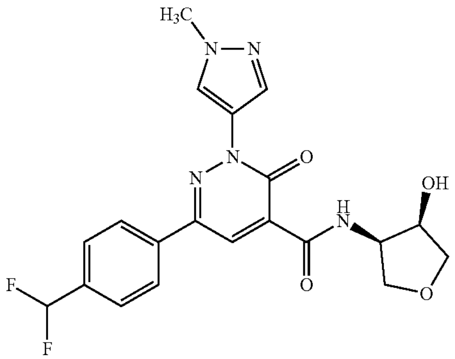 [SMILES: Cn1cc(-n2nc(-c3ccc(C(F)F)cc3)cc(C(=O)N[C@@H]3COC[C@@H]3O)c2=O)cn1] | 6-[4-(Difluoromethyl)phenyl]-N-[(cis)-4-hydroxytetrahydro-furan-3-yl]-2-(1-methyl-1H-pyrazol-4-yl)-3-oxo-2,3-dihydropyridazine-4-carboxamide Isomere 1 | 6-[4-(Difluoromethyl)phenyl]-N-[(cis)-4-hydroxytetrahydro-furan-3-yl]-2-(1-methyl-1H-pyrazol-4-yl)-3-oxo-2,3-dihydropyridazine-4-carboxamide; preparative chiral HPLC: instrument: Sepiatec: Prep SFC100; column: Chiralpak IC 5 µm 250 × 30 mm; eluent A: $CO_2$, eluent B: 2-propanol + 0.4 Vol-% diethylamine (99%); isocratic: 42% B; flow 100.0 ml/min temperature: 40° C.; BPR: 150 bar; MWD@ 254 nm. | Analytical chiral HPLC: Rt = 2.72 min Instrument: Agilent: 1260, Aurora SFC-module; column: Chiralpak IC 5 µm 100 × 4.6 mm; eluent A: $CO_2$, eluent B: 2-propanol + 0.2 Vol-% diethylamine (99%); isocratic: 42% B; flow 4.0 ml/min; temperature: 37.5° C.; BPR: 100 bar; MWD @ 254 nm. $^1$H NMR (400 MHz, DMSO-$d_6$) δ [ppm] = 3.48 (t, 1 H), 3.65 (dd, 1 H), 3.92-3.98 (m, 4 H), 4.02 (t, 1 H), 4.26-4.33 (m, 1 H), 4.33-4.43 (m, 1 H), 5.71 (d, 1 H), 7.14 (m, 1 H), 7.74 (d, 2 H), 8.13 (s, 1 H), 8.21 (d, 2 H), 8.56-8.57 (m, 1 H), 8.65 (s, 1 H), 9.90 (d, 1 H). |
| 316 | 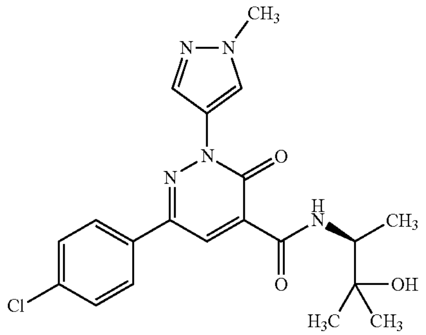 [SMILES: C[C@H](NC(=O)c1cc(-c2ccc(Cl)cc2)nn(-c2cnn(C)c2)c1=O)C(C)(C)O] | 6-(4-Chlorophenyl)-N-[(2S)-3-hydroxy-3-methylbutan-2-yl]-2-(1-methyl-1H-pyrazol-4-yl)-3-oxo-2,3-dihydropyridazine-4-carboxamide | 6-(4-Chlorophenyl)-2-(1-methyl-1H-pyrazol-4-yl)-3-oxo-2,3-dihydropyridazine-4-carboxylic acid, (3S)-3-amino-2-methylbutan-2-ol hydrochloride 1:1 | $^1$H NMR (400 MHz, DMSO-$d_6$) δ [ppm] = 1.12 (s, 3 H), 1.15 (d, 3 H), 1.18 (s, 3 H), 3.87-3.98 (m, 4 H), 4.67 (s, 1 H), 7.55-7.63 (m, 2 H), 8.06-8.14 (m, 3 H), 8.56 (s, 1 H), 8.59 (s, 1 H), 9.60-9.66 (m, 1 H). |
| 317 | 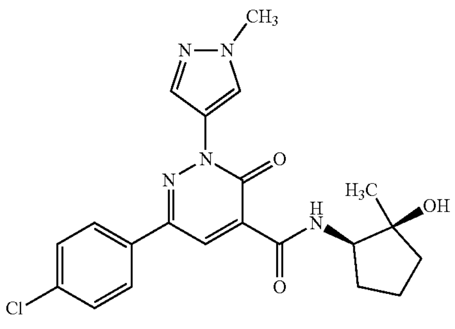 [SMILES: Cn1cc(-n2nc(-c3ccc(Cl)cc3)cc(C(=O)N[C@@H]3CCC[C@]3(C)O)c2=O)cn1] | 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide | 6-(4-Chlorophenyl)-2-(1-methyl-1H-pyrazol-4-yl)-3-oxo-2,3-dihydropyridazine-4-carboxylic acid; cis-2-amino-1-methylcyclo-pentanol trifluoroacetic acid 1:1 | $^1$H NMR (400 MHz, DMSO-$d_6$) δ [ppm] = 1.21 (s, 3 H), 1.39-1.51 (m, 1 H), 1.57-1.78 (m, 4 H), 2.15-2.24 (m, 1 H), 3.93 (s, 3 H), 4.10-4.18 (m, 1 H), 4.72 (s, 1 H), 7.57-7.63 (m, 2 H), 8.08-8.13 (m, 3 H), 8.55 (s, 1 H), 8.58 (s, 1 H), 9.50 (d, 1 H). |

TABLE 2-continued

Examples 195-345

| Expl. | Structure | IUPAC name | Starting materials | analytics |
|---|---|---|---|---|
| 318 | 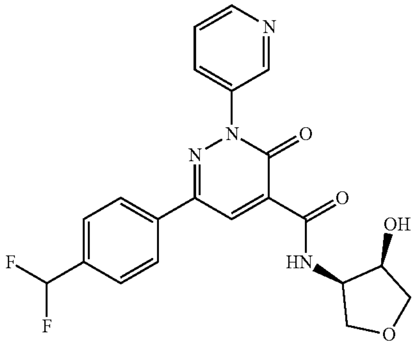 [SMILES: O=C(N[C@@H]1COC[C@@H]1O)c1cc(-c2ccc(C(F)F)cc2)nn(-c2cccnc2)c1=O] | 6-[4-(Difluoromethyl)phenyl]-N-[(cis)-4-hydroxy-tetrahydrofuran-3-yl]-3-oxo-2-(pyridin-3-yl)-2,3-dihydropyridazine-4-carboxamide Isomere 1 | 6-[4-(Difluoromethyl)phenyl]-3-oxo-2-(pyridin-3-yl)-2,3-dihydropyridazine-4-carboxylic acid, cis-4-aminotetrahydro-3-furanol hydrochloride 1:1; preparative chiral HPLC: instrument: Labomatic HD5000, Labocord-5000; Gilson GX-241, Labcol Vario 4000, column: Chiralpak IA 5μ 250 × 30 mm; eluent A: acetonitrile + 0.1 Vol-% diethylamine (99%); eluent B: ethanol; isocratic: 92% A + 08% B; flow 50.0 ml/min; UV 254 nm. | Analytical chiral HPLC: Rt = 1.89 min instrument: Agilent HPLC 1260; column: Chiralpak IA 3μ 100 × 4.6 mm; eluent A: acetonitrile + 0.1 Vol-% diethylamine (99%); eluent B: ethanol; isocratic: 90% A + 10% B; flow 1.4 ml/min; temperature: 25° C.; DAD 254 nm. |
| 319 | 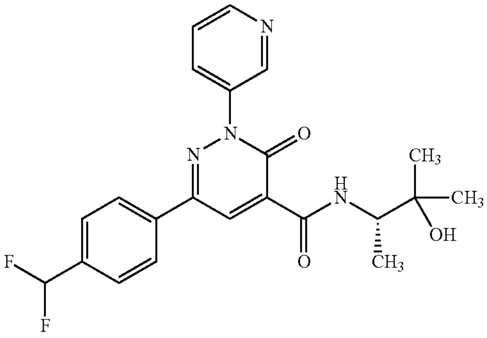 [SMILES: C[C@H](NC(=O)c1cc(-c2ccc(C(F)F)cc2)nn(-c2cccnc2)c1=O)C(C)(C)O] | 6-[4-(Difluoromethyl)phenyl]-N-[(2S)-3-hydroxy-3-methylbutan-2-yl]-3-oxo-2-(pyridin-3-yl)-2,3-dihydropyridazine-4-carboxamide | 6-[4-(Difluoromethyl)phenyl]-3-oxo-2-(pyridin-3-yl)-2,3-dihydropyridazine-4-carboxylic acid, (3S)-3-amino-2-methylbutan-2-ol hydrochloride 1:1 | $^1$H NMR (400 MHz, DMSO-$d_6$) δ [ppm] = 1.10 (s, 3 H), 1.13 (d, 3 H), 1.15 (s, 3 H), 3.85-3.98 (m, 1 H), 4.66 (s, 1 H), 7.13 (t, 1H), 7.63 (ddd, 1 H), 7.72 (d, 2 H), 8.13 (d, 2 H), 8.18 (ddd, 1 H), 8.70 (dd, 1 H), 8.72 (s, 1 H), 8.92 (d, 1 H), 9.51 (d, 1 H). $[a]_D^{20}$ = 34.1° = 1.00, DMSO) |
| 320 | 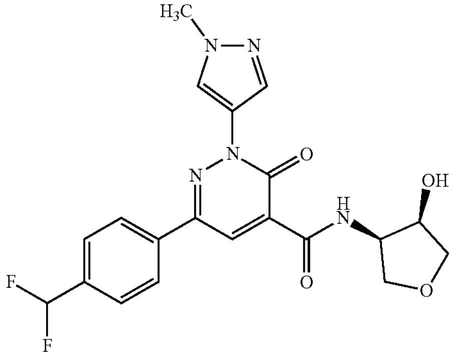 [SMILES: Cn1cc(-n2nc(-c3ccc(C(F)F)cc3)cc(C(=O)N[C@@H]3COC[C@@H]3O)c2=O)cn1] | 6-[4-(Difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide Isomere 2 | 6-[4-(Difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide; preparative chiral HPLC: instrument: Sepiatec: Prep SFC100; column: Chiralpak IC 5 μm 250 × 30 mm; eluent A: $CO_2$, eluent B: 2-propanol + 0.4vol-% diethylamine (99%); isocratic: 42% B; flow 100.0 ml/min temperature: | Analytical chiral HPLC: Rt = 1.71 min Instrument: Agilent: 1260, Aurora SFC-module; column: Chiralpak IC 5 μm 100 × 4.6 mm; eluent A: $CO_2$, eluent B: 2-propanol + 0.2vol-% diethylamine (99%); isocratic: 42% B; flow 4.0 ml/min; temperature: 37.5° C.; BPR: 100 bar; MWD @ 254 nm. |

TABLE 2-continued

| Examples 195-345 | | | | |
|---|---|---|---|---|
| Expl. | Structure | IUPAC name | Starting materials | analytics |
| | | | 40° C.; BPR: 150 bar; MWD @ 254 nm. | |
| 321 | 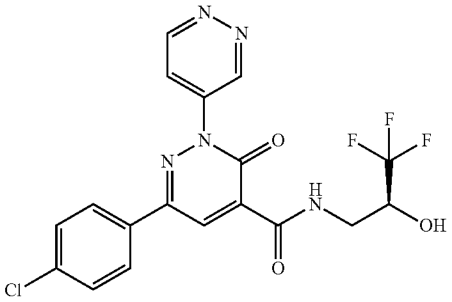 [SMILES: O=C(NC[C@H](O)C(F)(F)F)c1cc(-c2ccc(Cl)cc2)nn(-c2ccnnc2)c1=O] | 3-(4-Chlorophenyl)-6-oxo-N-[(2S)-3,3,3-trifluoro-2-hydroxypropyl]-6H-1,4'-bipyridazine-5-carboxamide | 3-(4-Chlorophenyl)-6-oxo-6H-[1,4'-bipyridazine-]-5-carboxylic acid, (2S)-3-amino-1,1,1-trifluoropropan-2-ol | $^1$H NMR (400 MHz, DMSO-$d_6$) δ [ppm] = 3.49 (ddd, 1 H), 3.70-3.79 (m, 1 H), 4.24 (qd, 1 H), 6.67 (d, 1 H), 7.59-7.64 (m, 2 H), 8.06-8.12 (m, 2 H), 8.22 (dd, 1 H), 8.66-8.71 (m, 1 H), 9.41-9.47 (m, 1 H), 9.49 (dd, 1 H), 9.73-9.77 (m, 1 H). |
| 322 | 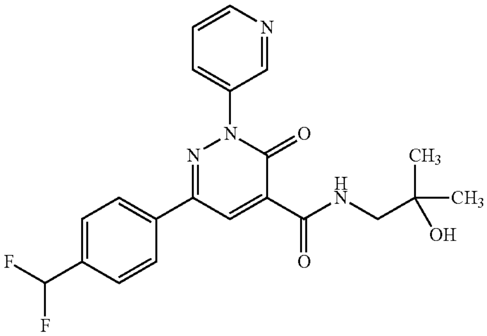 [SMILES: CC(C)(O)CNC(=O)c1cc(-c2ccc(C(F)F)cc2)nn(-c2cccnc2)c1=O] | 6-[4-(Difluoromethyl) phenyl]-N-(2-hydroxy-2-methylpropyl)-3-oxo-2-(pyridin-3-yl)-2,3-dihydropyridazine-4-carboxamide | 6-[4-(Difluoromethyl) phenyl]-3-oxo-2-(pyridin-3-yl)-2,3-dihydropyridazine-4-carboxylic acid, 1-amino-2-methylpropan-2-ol | $^1$H NMR (400 MHz, DMSO-$d_6$) δ [ppm] = 1.13 (s, 6 H), 3.31 (s, 2H), 4.68 (s, 1 H), 7.13 (t, 1H), 7.61-7.67 (m, 1 H), 7.72 (d, 2 H), 8.13 (d, 2 H), 8.19 (ddd, 1 H), 8.70 (br d, 1 H), 8.72 (s, 1 H), 8.93 (d, 1 H), 9.49-9.54 (m, 1 H). |
| 323 | 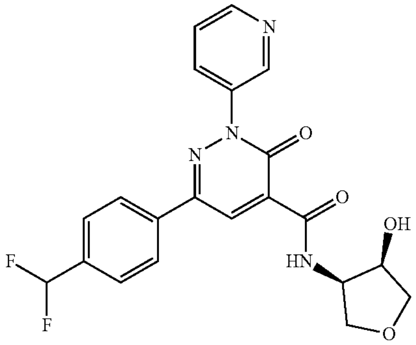 [SMILES: O=C(N[C@@H]1COC[C@@H]1O)c1cc(-c2ccc(C(F)F)cc2)nn(-c2cccnc2)c1=O] | 6-[4-(Difluoromethyl) phenyl]-N-[(cis)-4-hydroxy-tetrahydrofuran-3-yl]-3-oxo-2-(pyridin-3-yl)-2,3-dihydropyridazine-4-carboxamide Isomere 2 | 6-[4-(Difluoromethyl) phenyl]-3-oxo-2-(pyridin-3-yl)-2,3-dihydropyridazine-4-carboxylic acid, cis-4-aminotetrahydro-3-furanol hydrochloride 1:1; preparative chiral HPLC: instrument: Labomatic HD5000, Labocord-5000; Gilson GX-241, Labcol Vario 4000, column: Chiralpak IA 5μ 250 x 30 mm; eluent A: acetonitrile + 0.1 vol-% diethylamine (99%); eluent B: ethanol; isocratic: 92% A + 08% B; flow 50.0 ml/min; UV 254 nm. | Analytical chiral HPLC: Rt = 2.61 min Instrument: Agilent: 1260, Aurora SFC-module; column: Chiralpak IC 5 μm 100 x 4.6 mm; eluent A: $CO_2$, eluent B: 2-propanol + 0.2vol-% diethylamine (99%); isocratic: 42% B; flow 4.0 ml/min; temperature: 37.5° C.; BPR: 100 bar; MWD @ 254 nm. |

TABLE 2-continued

| Examples 195-345 | | | | |
|---|---|---|---|---|
| Expl. | Structure | IUPAC name | Starting materials | analytics |
| 324 | 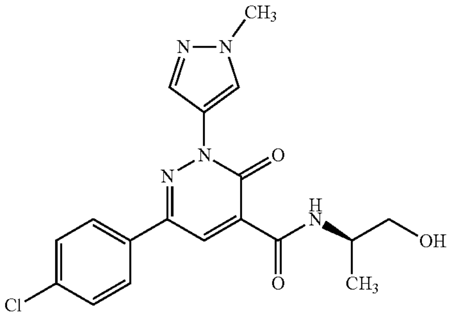 [SMILES: C[C@H](CO)NC(=O)c1cc(-c2ccc(Cl)cc2)nn(-c2cnn(C)c2)c1=O] | 6-(4-Chlorophenyl)-N-[(2R)-1-hydroxypropan-2-yl]-2-(1-methyl-1H-pyrazol-4-yl)-3-oxo-2,3-dihydropyridazine-4-carboxamide | 6-(4-Chlorophenyl)-2-(1-methyl-1H-pyrazol-4-yl)-3-oxo-2,3-dihydropyridazine-4-carboxylic acid; (2R)-2-aminopropan-1-ol | $^1$H NMR (400 MHz, DMSO-$d_6$) δ [ppm] = 1.19 (d, 3 H), 3.42-3.52 (m, 2 H), 3.93 (s, 3 H), 3.99-4.12 (m, 1 H), 4.94 (br s, 1H), 7.58-7.62 (m, 2 H), 8.08-8.12 (m, 3 H), 8.56 (s, 1 H), 8.58 (s, 1 H), 9.49-9.56 (m, 1 H). $[\alpha]_D^{20}$ = −10.9° = 1.00, DMSO) |
| 325 | 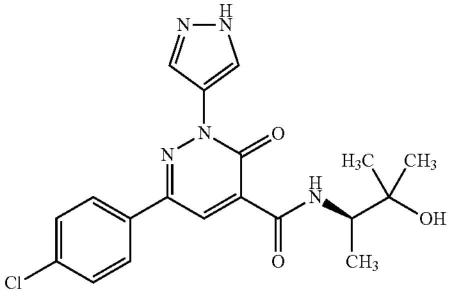 [SMILES: C[C@@H](NC(=O)c1cc(-c2ccc(Cl)cc2)nn(-c2cn[nH]c2)c1=O)C(C)(C)O] | 6-(4-Chlorophenyl)-N-[(2R)-3-hydroxy-3-methylbutan-2-yl]-3-oxo-2-(1H-pyrazol-4-yl)-2,3-dihydropyridazine-4-carboxamide | 6-(4-Chlorophenyl)-3-oxo-2-(1H-pyrazol-4-yl)-2,3-dihydropyridazine-4-carboxylic acid, (3R)-3-amino-2-methylbutan-2-ol | $^1$H NMR (400 MHz, DMSO-$d_6$) δ [ppm] = 1.13 (s, 3 H), 1.15 (d, 3 H), 1.18 (s, 3 H), 3.86-4.00 (m, 1 H), 4.68 (s, 1 H), 7.57-7.62 (m, 2 H), 8.07-8.12 (m, 2 H), 8.17 (br s, 1 H), 8.51 (br s, 1 H), 8.59 (s, 1 H), 9.58-9.68 (m, 1 H), 13.23 (br s, 1 H). $[\alpha]_D^{20}$ = −24.7° = 1.00, DMSO) |

The following examples were prepared from the starting materials stated in the table using the procedure described as in intermediate 119. Enantiomers were separated from their racemate by chiral HPLC using the column and solvent conditions stated.

| | | | | |
|---|---|---|---|---|
| 326 | 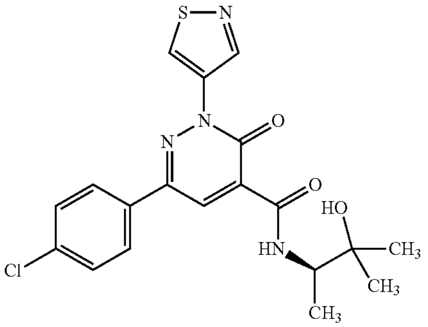 [SMILES: C[C@@H](NC(=O)c1cc(-c2ccc(Cl)cc2)nn(-c2cnsc2)c1=O)C(C)(C)O] | 6-(4-Chlorophenyl)-N-[(2R)-3-hydroxy-3-methylbutan-2-yl]-3-oxo-2-(1,2-thiazol-4-yl)-2,3-dihydropyridazine-4-carboxamide | 6-(4-Chlorophenyl)-N-[(2R)-3-hydroxy-3-methylbutan-2-yl]-3-oxo-2,3-dihydropyridazine-4-carboxamide, 4-(4,4,5,5-tetramethyl-1,3,2-dioxaborolan-2-yl)-1,2-thiazole | $^1$H NMR (400 MHz, DMSO-$d_6$) δ ppm = 1.12 (s, 3 H), 1.15 (d, 3 H), 1.17 (s, 3 H), 3.85-3.98 (m, 1 H), 4.68 (s, 1 H), 7.57-7.62 (m, 2 H), 8.06-8.11 (m, 2 H), 8.64 (s, 1 H), 9.12 (s, 1 H), 9.50 (d, 1 H), 9.61 (s, 1 H). |
| 327 | 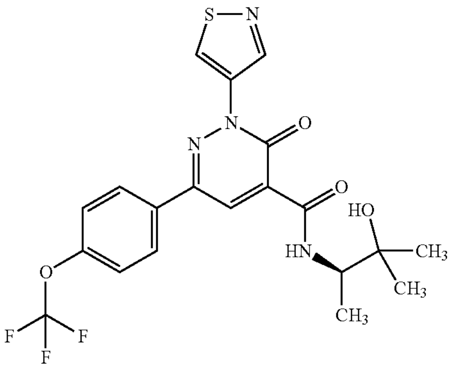 [SMILES: C[C@@H](NC(=O)c1cc(-c2ccc(OC(F)(F)F)cc2)nn(-c2cnsc2)c1=O)C(C)(C)O] | N-[(2R)-3-Hydroxy-3-methylbutan-2-yl]-3-oxo-2-(1,2-thiazol-4-yl)-6-[4-(trifluoromethoxy)phenyl]-2,3-dihydropyridazine-4-carboxamide | N-[(2R)-3-hydroxy-3-methylbutan-2-yl]-3-oxo-6-[4-(trifluoromethoxy)phenyl]-2,3-dihydropyridazine-4-carboxamide, 4-(4,4,5,5-tetramethyl-1,3,2-dioxaborolan-2-yl)-1,2-thiazole | $^1$H NMR (400 MHz, DMSO-$d_6$) δ ppm = 1.12 (s, 3 H), 1.15 (d, 3 H), 1.17 (s, 3 H), 3.88-3.97 (m, 1 H), 4.69 (s, 1 H), 7.52 (d, 2 H), 8.17-8.21 (m, 2 H), 8.66 (s, 1 H), 9.12 (s, 1 H), 9.51 (d, 1 H), 9.61 (s, 1 H). |

-continued

| | | | | |
|---|---|---|---|---|
| 328 | 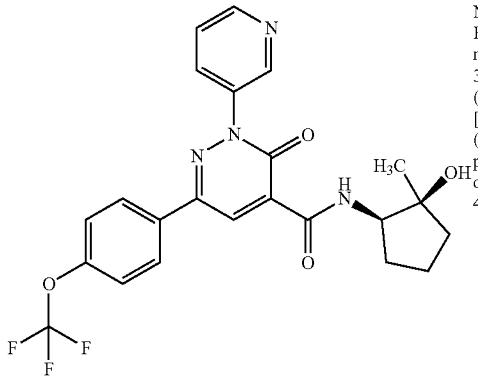 | N-[(cis)-2-Hydroxy-2-methylcyclopentyl]-3-oxo-2-(pyridin-3-yl)-6-[4-(trifluoromethoxy)phenyl]-2,3-dihydropyridazine-4-carboxamide | 3-Oxo-2-(pyridin-3-yl)-6-[4-(trifluoromethoxy)phenyl]-2,3-dihydropyridazine-4-carboxylic acid, cis-2-amino-1-methylcyclopentan-1-ol trifluoroacetic acid | $^1$H NMR (400 MHz, DMSO-$d_6$) δ ppm = 1.17 (s, 3 H), 1.37-1.47 (m, 1 H), 1.53-1.64 (m, 2 H), 1.65-1.76 (m, 2 H), 2.13-2.23 (m, 1 H), 4.10-4.17 (m, 1 H), 4.70 (s, 1 H), 7.51 (d, 2 H), 7.61-7.66 (m, 1 H), 8.09-8.14 (m, 2 H), 8.17 (ddd, 1 H), 8.68 (s, 1 H), 8.70 (dd, 1 H), 8.91 (d, 1 H), 9.37 (d, 1 H). |
| 329 | 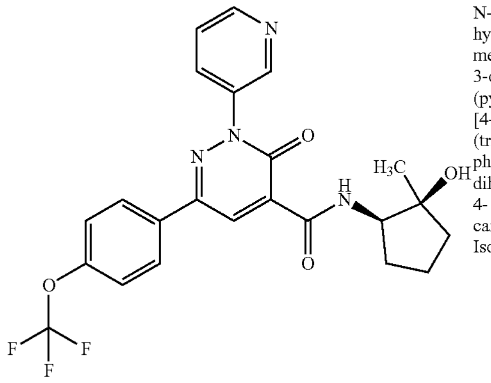 | N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide, Isomer 1 | N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide; preparative chiral HPLC: instrument: Labomatic HD5000, Labocord-5000; Gilson GX-241, Labcol Vario 4000, column: Chiralpak IA 5μ 250 × 30 mm; eluent A: hexane + 0.1 vol-% diethylamine (99%) eluent B: 2-propanol; isocratic: 60% A + 40% B; flow 40.0 mL/min; UV 254 nm. | Analytical chiral HPLC: Rt = 2.80 min Instrument: Agilent HPLC 1260; column: Chiralpak IA 3μ 100 × 4,6 mm; eluent: hexane + 0.1 vol% diethylamine (99%)/ 2-propanol 60:40, flow 1.4 mL/min; temperature: 25° C.; UV 254 nm. |
| 330 | 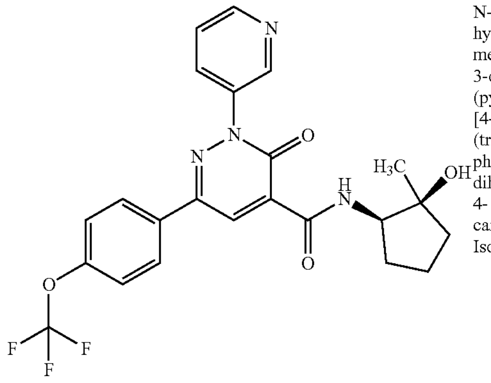 | N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide, Isomer 2 | N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide; preparative chiral HPLC: instrument: Labomatic HD5000, Labocord-5000; Gilson GX-241, Labcol Vario 4000, column: Chiralpak IA 5μ 250 × 30 mm; eluent A: hexane + 0.1 vol-% diethylamine (99%) eluent B: 2-propanol; isocratic: 60% A + 40% B; flow 40.0 mL/min; UV 254 nm. | Analytical chiral HPLC: Rt = 3.50 min Instrument: Agilent HPLC 1260; column: Chiralpak IA 3μ 100 × 4,6 mm; eluent: hexane + 0.1 vol % diethylamine (99%)/ 2-propanol 60:40, flow 1.4 mL/min; temperature: 25° C.; UV 254 nm. |

-continued

| | | | | |
|---|---|---|---|---|
| 331 | 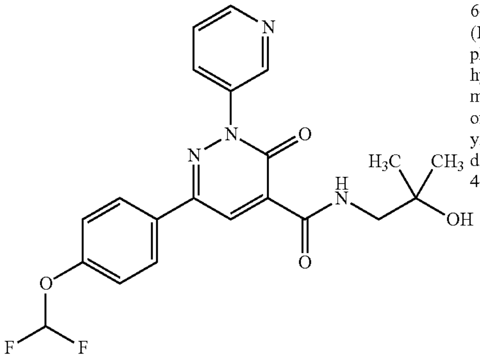 | 6-[4-(Difluoromethoxy)phenyl]-N-(2-hydroxy-2-methylpropyl)-3-oxo-2-(pyridin-3-yl)-2,3-dihydropyridazine-4-carboxamide | 6-[4-(Difluoromethoxy)phenyl]-3-oxo-2-(pyridin-3-yl)-2,3-dihydropyridazine-4-carboxylic acid, 1-amino-2-methylpropan-2-ol | $^1$H NMR (400 MHz, DMSO-$d_6$) δ ppm = 1.13 (s, 6 H), 3.30-3.32 (m, 2 H), 4.68 (s, 1 H), 7.31 (d, 2 H), 7.36 (t, 1 H), 7.60-7.66 (m, 1 H), 8.02-8.06 (m, 2 H), 8.15-8.20 (m, 1 H), 8.67 (s, 1 H), 8.69 (dd, 1 H), 8.92 (d, 1 H), 9.53 (t, 1 H). |
| 332 | 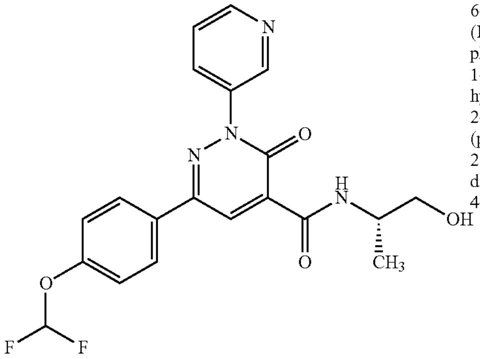 | 6-[4-(Difluoromethoxy)phenyl]-N-[(2S)-1-hydroxypropan-2-yl]-3-oxo-2-(pyridin-3-yl)-2,3-dihydropyridazine-4-carboxamide | 6-[4-(Difluoromethoxy)phenyl]-3-oxo-2-(pyridin-3-yl)-2,3-dihydropyridazine-4-carboxylic acid, (S)-(+)-2-amino-1-propanol | $^1$H NMR (400 MHz, DMSO-$d_6$) δ ppm = 1.16 (d, 3 H), 3.41-3.51 (m, 2 H), 3.98-4.10 (m, 1 H), 4.94 (s br, 1 H), 7.29-7.34 (m, 2 H), 7.36 (t, 1 H), 7.60-7.65 (m, 1 H), 8.02-8.07 (m, 2 H), 8.16 (ddd, 1 H), 8.66 (s, 1 H), 8.69 (dd, 1 H), 8.91 (d, 1 H), 9.42 (d, 1 H). |
| 333 | 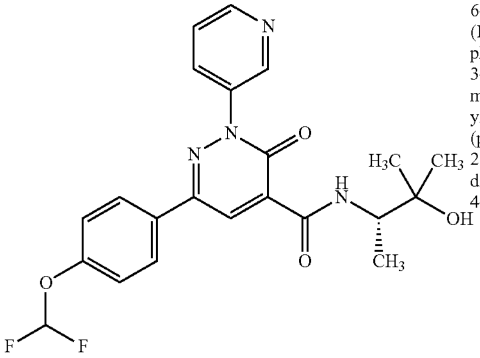 | 6-[4-(Difluoromethoxy)phenyl]-N-[(2S)-3-hydroxy-3-methylbutan-2-yl]-3-oxo-2-(pyridin-3-yl)-2,3-dihydropyridazine-4-carboxamide | 6-[4-(Difluoromethoxy)phenyl]-3-oxo-2-(pyridin-3-yl)-2,3-dihydropyridazine-4-carboxylic acid, (S)-3-amino-2-methylbutan-2-ol | $^1$H NMR (400 MHz, DMSO-$d_6$) δ ppm = 1.10 (s, 3 H), 1.13 (d, 3 H), 1.15 (s, 3 H), 3.86-3.96 (m, 1 H), 4.65 (s, 1 H), 7.29-7.34 (m, 2 H), 7.36 (t, 1 H), 7.60-7.65 (m, 1 H), 8.02-8.06 (m, 2 H), 8.17-8.19 (ddd, 1 H), 8.67 (s, 1 H), 8.69 (dd, 1 H), 8.91 (d, 1 H), 9.53 (d, 1 H). |
| 334 | 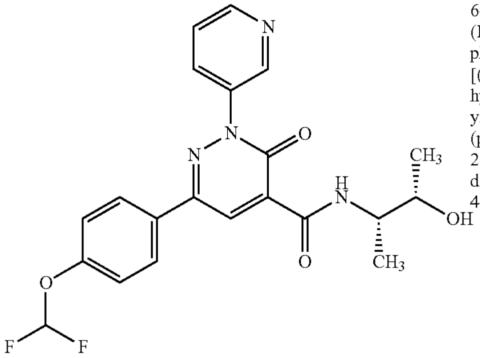 | 6-[4-(Difluoromethoxy)phenyl]-N-[(2S,3S)-3-hydroxybutan-2-yl]-3-oxo-2-(pyridin-3-yl)-2,3-dihydropyridazine-4-carboxamide | 6-[4-(Difluoromethoxy)phenyl]-3-oxo-2-(pyridin-3-yl)-2,3-dihydropyridazine-4-carboxylic acid, (2S,3S)-3-aminobutan-2-ol hydrochloride (1:1) | $^1$H NMR (400 MHz, DMSO-$d_6$) δ ppm = 1.04 (d, 3 H), 1.15 (d, 3 H), 3.67-3.75 (m, 1 H), 3.89-3.98 (m, 1 H), 4.95 (d, 1 H), 7.29-7.34 (m, 2 H), 7.36 (t, 1 H), 7.60-7.65 (m, 1 H), 8.02-8.06 (m, 2 H), 8.17 (ddd, 1 H), 8.67 (s, 1 H), 8.69 (dd, 1 H), 8.91 (d, 1 H), 9.44 (d, 1 H). |

-continued

| | | | | |
|---|---|---|---|---|
| 335 | 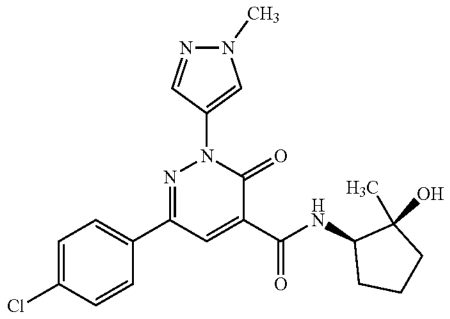 [SMILES: Cn1cc(-n2nc(-c3ccc(Cl)cc3)cc(C(=O)N[C@@H]3CCC[C@]3(C)O)c2=O)cn1] | 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide; Isomer 1 | 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide; preparative chiral HPLC: instrument: Labomatic HD5000, Labocord-5000; Gilson GX-241, Labcol Vario 4000, column: Chiralpak IA 5μ 250 × 30 mm; eluent A: hexane + 0.1 vol-% diethylamine (99%) eluent B: ethanol; isocratic: 50% A + 50% B; flow 40.0 mL/min; UV 254 nm. | Analytical chiral HPLC: Rt = 2.96 min Instrument: Agilent HPLC 1260; column: Chiralpak IA 3μ 100 × 4,6 mm; eluent: hexane + 0.1 vol % diethylamine (99%)/ethanol 50:50, flow 1.4 mL/min; temperature: 25° C.; UV 254 nm. |
| 336 | 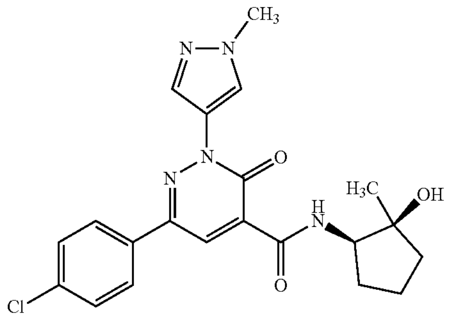 [SMILES: Cn1cc(-n2nc(-c3ccc(Cl)cc3)cc(C(=O)N[C@@H]3CCC[C@]3(C)O)c2=O)cn1] | 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide; Isomer 2 | 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide; preparative chiral HPLC: instrument: Labomatic HD5000, Labocord-5000; Gilson GX-241, Labcol Vario 4000, column: Chiralpak IA 5μ 250 × 30 mm; eluent A: hexane + 0.1 vol-% diethylamine (99%) eluent B: ethanol; isocratic: 50% A + 50% B; flow 40.0 mL/min; UV 254 nm. | Analytical chiral HPLC: Rt = 5.10 min Instrument: Agilent HPLC 1260; column: Chiralpak IA 3μ 100 × 4,6 mm; eluent: hexane + 0.1 vol % diethylamine (99%)/ethanol 50:50, flow 1.4 mL/min; temperature: 25° C.; UV: 254 nm. |
| 337 | 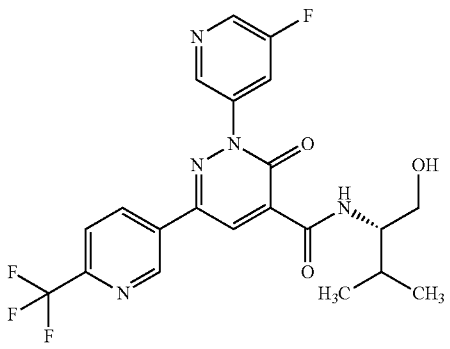 [SMILES: CC(C)[C@@H](CO)NC(=O)c1cc(-c2ccc(C(F)(F)F)nc2)nn(-c2cncc(F)c2)c1=O] | 2-(5-Fluoropyridin-3-yl)-N-[(2S)-1-hydroxy-3-methylbutan-2-yl]-3-oxo-6-[6-(trifluoromethyl)pyridin-3-yl]-2,3-dihydropyridazine-4-carboxamide | 2-(5-Fluoropyridin-3-yl)-3-oxo-6-[6-(trifluoromethyl)pyridin-3-yl]-2,3-dihydropyridazine-4-carboxylic acid, (2S)-2-amino-3-methylbutan-1-ol | $^1$H NMR (400 MHz, DMSO-$d_6$) δ ppm = 0.90 (d, 3 H), 0.93 (d, 3 H), 1.93-2.03 (m, 1 H), 3.41-3.49 (m, 1 H), 3.52-3.60 (m, 1 H), 3.82-3.90 (m, 1 H), 4.83 (t br, 1 H), 8.06 (d, 1 H), 8.27-8.32 (m, 1 H), 8.70 (dd, 1 H), 8.78 (d, 1 H), 8.83 (s, 1 H), 8.89-8.91 (m, 1 H), 9.26 (d, 1 H), 9.39 (d, 1 H). |

-continued

| | | | | |
|---|---|---|---|---|
| 338 | 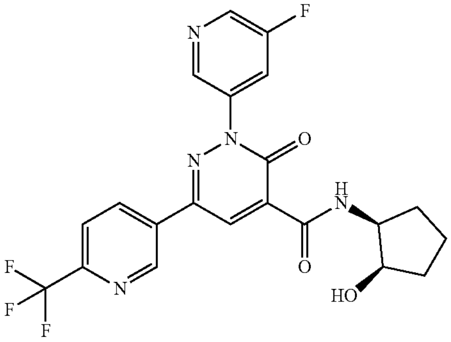 [SMILES: O=C(N[C@H]1CCC[C@H]1O)c1cc(-c2ccc(C(F)(F)F)nc2)nn(-c2cncc(F)c2)c1=O] | 2-(5-Fluoropyridin-3-yl)-N-[(1S,2R)-2-hydroxycyclopentyl]-3-oxo-6-[6-(trifluoromethyl) pyridin-3-yl]-2,3-dihydropyridazine-4-carboxamide | 2-(5-Fluoropyridin-3-yl)-3-oxo-6-[6-(trifluoromethyl) pyridin-3-yl]-2,3-dihydropyridazine-4-carboxylic acid, cis-(1R,2S)-2-aminocyclopentanol hydrochloride (1:1) | $^1$H NMR (400 MHz, DMSO-$d_6$) δ ppm = 1.47-1.65 (m, 3 H), 1.70-1.88 (m, 2 H), 1.93-2.04 (m, 1 H), 3.99-4.12 (m, 2 H), 5.07 (d, 1 H), 8.05 (d, 1 H), 8.29 (ddd, 1 H), 8.69 (dd, 1 H), 8.78 (d, 1 H), 8.83 (s, 1 H), 8.89 (t, 1 H), 9.38 (d, 1 H), 9.58 (d, 1 H). |
| 339 | 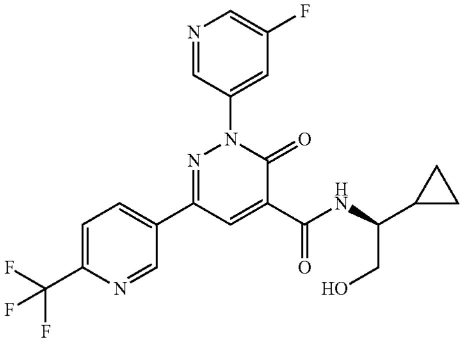 [SMILES: O=C(N[C@H](CO)C1CC1)c1cc(-c2ccc(C(F)(F)F)nc2)nn(-c2cncc(F)c2)c1=O] | N-[(1S)-1-Cyclopropyl-2-hydroxyethyl]-2-(5-fluoropyridin-3-yl)-3-oxo-6-[6-(trifluoromethyl) pyridin-3-yl]-2,3-dihydropyridazine-4-carboxamide | 2-(5-Fluoropyridin-3-yl)-3-oxo-6-[6-(trifluoromethyl) pyridin-3-yl]-2,3-dihydropyridazine-4-carboxylic acid, (2S)-2-amino-2-cyclopropylethan-1-ol hydrochloride (1:1) | $^1$H NMR (400 MHz, DMSO-$d_6$) δ ppm = 0.26-0.33 (m, 1 H), 0.33-0.40 (m, 1 H), 0.41-0.51 (m, 2 H), 1.04-1.15 (m, 1 H), 3.41-3.49 (m, 1 H), 3.53-3.64 (m, 2 H), 4.95 (t, 1 H), 8.05 (d, 1 H), 8.28-8.32 (m, 1 H), 8.70 (dd, 1 H), 8.78 (d, 1 H), 8.83 (s, 1 H), 8.90 (t, 1 H), 9.39 (d, 1 H), 9.44 (d, 1 H). |
| 340 | 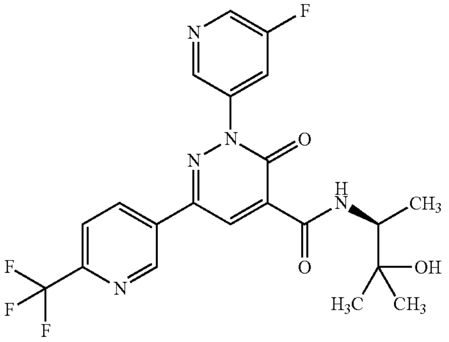 [SMILES: C[C@H](NC(=O)c1cc(-c2ccc(C(F)(F)F)nc2)nn(-c2cncc(F)c2)c1=O)C(C)(C)O] | 2-(5-Fluoropyridin-3-yl)-N-[(2S)-3-hydroxy-3-methylbutan-2-yl]-3-oxo-6-[6-(trifluoromethyl) pyridin-3-yl]-2,3-dihydropyridazine-4-carboxamide | 2-(5-Fluoropyridin-3-yl)-3-oxo-6-[6-(trifluoromethyl) pyridin-3-yl]-2,3-dihydropyridazine-4-carboxylic acid, (S)-3-amino-2-methylbutan-2-ol hydrochloride (1:1) | $^1$H NMR (400 MHz, DMSO-$d_6$) δ ppm = 1.11 (d, 3 H), 1.14 (d, 3 H), 1.16 (s, 3 H), 3.88-3.97 (m, 1 H), 4.68 (s, 1 H), 8.05 (d, 1 H), 8.29 (ddd, 1 H), 8.68 (dd, 1 H), 8.78 (d, 1 H), 8.82 (s, 1 H), 8.90 (t, 1 H), 9.37-9.42 (m, 2 H). |
| 341 | 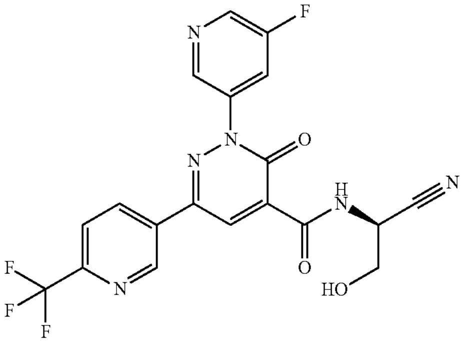 [SMILES: N#C[C@@H](CO)NC(=O)c1cc(-c2ccc(C(F)(F)F)nc2)nn(-c2cncc(F)c2)c1=O] | N-[(1S)-1-Cyano-2-hydroxyethyl]-2-(5-fluoropyridin-3-yl)-3-oxo-6-[6-(trifluoromethyl) pyridin-3-yl]-2,3-dihydropyridazine-4-carboxamide | 2-(5-Fluoropyridin-3-yl)-3-oxo-6-[6-(trifluoromethyl) pyridin-3-yl]-2,3-dihydropyridazine-4-carboxylic acid, (2S)-2-amino-3-hydroxypropane nitrile | $^1$H NMR (400 MHz, DMSO-$d_6$) δ ppm = 3.73-3.86 (m, 2 H), 5.03-5.10 (m, 1 H), 5.84 (t, 1 H), 8.07 (d, 1 H), 8.27-8.32 (m, 1 H), 8.72 (dd, 1 H), 8.79 (d, 1 H), 8.88 (s, 1 H), 8.91 (t, 1 H), 9.41 (d, 1 H), 9.84 (d, 1 H). |

-continued

| | | | | |
|---|---|---|---|---|
| 342 | 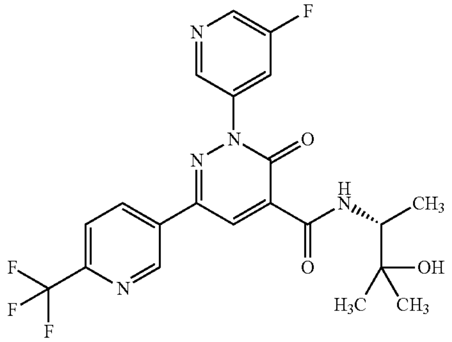 [SMILES: C[C@@H](NC(=O)c1cc(-c2ccc(C(F)(F)F)nc2)nn(-c2cncc(F)c2)c1=O)C(C)(C)O] | 2-(5-Fluoropyridin-3-yl)-N-[(2R)-3-hydroxy-3-methylbutan-2-yl]-3-oxo-6-[6-(trifluoromethyl)pyridin-3-yl]-2,3-dihydropyridazine-4-carboxamide | 2-(5-Fluoropyridin-3-yl)-3-oxo-6-[6-(trifluoromethyl)pyridin-3-yl]-2,3-dihydropyridazine-4-carboxylic acid, (3R)-3-amino-2-methylbutan-2-ol hydrochloride (1:1) | $^1$H NMR (400 MHz, DMSO-$d_6$) δ ppm = 1.11 (s, 3 H), 1.14 (d, 3 H), 1.16 (s, 3 H), 3.88-3.97 (m, 1 H), 4.68 (s, 1 H), 8.05 (d, 1 H), 8.27-8.32 (m, 1 H), 8.69 (dd, 1 H), 8.78 (d, 1 H), 8.82 (s, 1 H), 8.90 (t, 1 H), 9.37-9.44 (m, 2 H). |
| 343 | 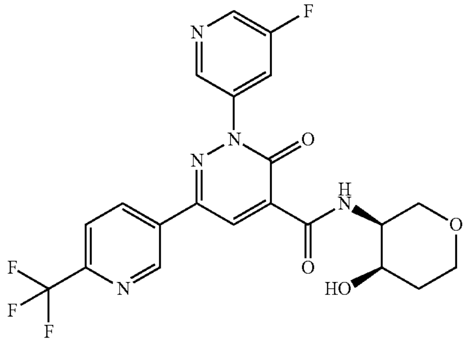 [SMILES: O=C(N[C@H]1COCC[C@H]1O)c1cc(-c2ccc(C(F)(F)F)nc2)nn(-c2cncc(F)c2)c1=O] | 1,5-Anhydro-2,4-dideoxy-2-[({2-(5-fluoropyridin-3-yl)-3-oxo-6-[6-(trifluoromethyl)pyridin-3-yl]-2,3-dihydropyridazine-4-yl}carbonyl)amino]-D-erythro-pentitol | 2-(5-Fluoropyridin-3-yl)-3-oxo-6-[6-(trifluoromethyl)pyridin-3-yl]-2,3-dihydropyridazine-4-carboxylic acid, (3S,4R)-3-aminooxan-4-ol hydrochloride (1:1) | $^1$H NMR (400 MHz, DMSO-$d_6$) δ ppm = 1.59-1.68 (m, 1 H), 1.73-1.83 (m, 1 H), 3.47-3.54 (m, 1 H), 3.57 (d, 2 H), 3.66-3.74 (m, 1 H), 3.91-3.97 (m, 1 H), 4.04-4.12 (m, 1 H), 5.25 (d, 1 H), 8.03-8.08 (m, 1 H), 8.26-8.32 (m, 1 H), 8.70 (dd, 1 H), 8.78 (d, 1 H), 8.85 (s, 1 H), 8.88-8.91 (m, 1 H), 9.39 (d, 1 H), 9.55 (d, 1 H). |
| 344 | 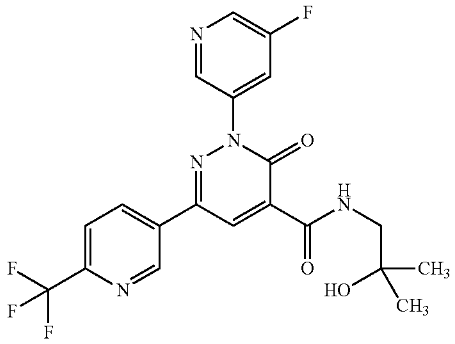 [SMILES: CC(C)(O)CNC(=O)c1cc(-c2ccc(C(F)(F)F)nc2)nn(-c2cncc(F)c2)c1=O] | 2-(5-Fluoropyridin-3-yl)-N-(2-hydroxy-2-methylpropyl)-3-oxo-6-[6-(trifluoromethyl)pyridin-3-yl]-2,3-dihydropyridazine-4-carboxamide | 2-(5-Fluoropyridin-3-yl)-3-oxo-6-[6-(trifluoromethyl)pyridin-3-yl]-2,3-dihydropyridazine-4-carboxylic acid, 1-amino-2-methylpropan-2-ol | $^1$H NMR (400 MHz, DMSO-$d_6$) δ ppm = 1.14 (s, 6 H), 4.68-4.71 (s, 1 H), 8.04-8.07 (m, 1 H), 8.27-8.32 (m, 1 H), 8.70 (dd, 1 H), 8.78 (d, 1 H), 8.83 (s, 1 H), 8.89-8.92 (m, 1 H), 9.37-9.43 (m, 2 H). |
| 345 | 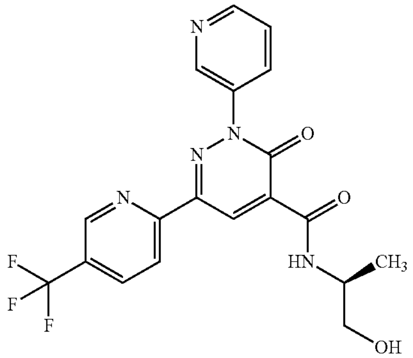 [SMILES: C[C@@H](CO)NC(=O)c1cc(-c2ccc(C(F)(F)F)cn2)nn(-c2cccnc2)c1=O] | N-[(2S)-1-Hydroxypropan-2-yl]-3-oxo-2-(pyridin-3-yl)-6-[5-(trifluoromethyl)pyridin-2-yl]-2,3-dihydropyridazine-4-carboxamide | N-[(2S)-1-Hydroxypropan-2-yl]-3-oxo-6-[5-(trifluoromethyl)pyridin-2-yl]-2,3-dihydropyridazine-4-carboxamide, pyridin-3-ylboronic acid | $^1$H NMR (400 MHz, DMSO-$d_6$) δ ppm = 1.16 (d, 3 H), 3.41-3.49 (m, 2 H), 4.00-4.10 (m, 1 H), 4.96 (t, 1 H), 7.65 (dd, 1 H), 8.18-8.22 (m, 1 H), 8.32-8.38 (m, 2 H), 8.72 (d br, 1 H), 8.92-8.95 (m, 1 H), 9.09 (s, 1 H), 9.17-9.19 (m, 1 H), 9.36 (d, 1 H). |

DESCRIPTION OF THE FIGURES

FIG. 1 describes the sequence listing of the light chain of the TPP-3911 antibody (anti-PD-L1-mIgG1Kappa_RG7446chimera|light_chain|pTT5-anti-PD-L1-huVH-mulgG1-CH1-CH3-kappa-chimera)

FIG. 2 describes the sequence listing of the heavy chain of the TPP-3911 antibody (anti-PD-L1-mIgG1Kappa_RG7446chimera|heavy_chain|pTT5-anti-PD-L1-huVH-mulgG1-CH1-CH3-kappa-chimera

EXPERIMENTAL SECTION—BIOLOGICAL ASSAYS

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Transactivation Assay in Human Cell Line (In Vitro Assays 1 and 2)

Transactivation assays were carried out in U87 glioblastoma cells (ATCC) endogenously expressing AHR. In addition the cells were stably transfected with an AHR inducible firefly luciferase reporter gene construct that carried AHR-binding sites (DRE) in its promoter and a *renilla* reporter gene construct with constitutively active promoter. Kynurenic acid is an endogenous AHR activating ligand and was used to prestimulate test cells prior to testing the antagonistic properties of compounds.

In Vitro Assay 1: Antagonism in Human Cell Line

Cells in medium (tryptophan free RPMI, 1% FCS, 2 mM Glutamine) supplemented with 150 uM kynurenic acid were grown for 20 hours in absence (negative control) or presence of increasing concentrations of test compounds (typical dilutions: 72 μmol/L, 0.25 nmol/L, 0.89 nmol/L; 3.1 nmol/L, 11 nmol/L, 38 nmol/L, 130 nmol/L, 470 nmol/L, 1.6 μmol/L, 5.7 μmol/L and 20 μmol/L in duplicates). As positive inhibition control cells supplemented with 150 uM kynurenic acid were incubated in presence of 5 uM Staurosporin. Normalization was done by positive and negative controls.

Firefly luciferase and *Renilla* activity was determined by the DualGlo Luciferase Assay System (Promega, #2920). *Renilla* activity was used to assess toxic effects of compounds.

In Vitro Assay 2: Agonism in Human Cell Line

Cells in medium (tryptophan free RPMI, 1% FCS, 2 mM Glutamine) were grown for 20 hours in absence (negative control) or presence of increasing concentrations of test compounds (typical dilutions: 72 μmol/L, 0.25 nmol/L, 0.89 nmol/L; 3.1 nmol/L, 11 nmol/L, 38 nmol/L, 130 nmol/L, 470 nmol/L, 1.6 μmol/L, 5.7 μmol/L and 20 μmol/L in duplicates). As positive activation control cells were incubated with 300 uM kynurenic acid. Normalization was done by positive and negative controls.

Firefly luciferase activity was determined by the SteadyGlo Luciferase Assay System (Promega, #2520).

In Vitro Assay 3: AHR-Regulated CYP1A1 Expression in Human Cell Line

To assess the AHR inhibitory activity of the substances described in this application, the ability thereof to antagonise ligand-induced AHR gene regulation in a dose-dependent manner was quantified. For this purpose, quantitative PCR analysis was used to determine expression of the AHR-regulated gene CYP1A1 in a human monocytic U937 cell line upon stimulation with 200 uM KA in the presence and absence of AHR inhibitor. U937 cells were sown at a concentration of $2\times10^5$ cells/well in 100 ul of growth medium (RPMI 1640, 20% FCS) in 96-well microtitre plates. CYP1A1 expression was induced with 200 uM KA (positive control) in the presence or absence of the substances for 6 hours. Human U937 cells were typically incubated with eight different concentrations of the substances (1 nM, 3 nM, 10 nM, 30 nM, 100 nM, 300 nM, 1 uM and 3 uM) and analyzed in duplicate on the same microtitre plate. After stimulation, cells were lysed with Nucleic Acid Lysis Solution (#4305895, Applied Biosystems) and RNA was isolated using the 6100 Nucleic Acid Preparation Station (Applied Biosystems) and reverse-transcribed to cDNA using SuperScript VILO cDNA synthesis kit (#11754-250, Invitrogen). Unstimulated cells were used as the negative control. Taqman probes for human CYP1A1 (Hs01054797_g1) and human HPRT (Hs02800695_m1) were used to analyze fold expression of CYP1A1 of HPRT. Quantitation was performed on a Taqman SDS7900HT.

TABLE 3

$IC_{50}$ values of examples in in vitro assays 1-3

| Example | Assay 1: AHR-luc Hum Antagonism $IC_{50}$ [M] | Assay 2: AHR-luc Hum Agonism $IC_{50}$ [M] | Assay 3: Hum CYP1A1 Antagonism $IC_{50}$ [M] |
|---|---|---|---|
| 1 | 7.38 E−9 | >2.00 E−5 | 4.30 E−9 |
| 2 | 2.57 E−9 | >2.00 E−5 | 3.03 E−9 |
| 3 | 1.05 E−7 | >2.00 E−5 | |
| 4 | 9.52 E−9 | >2.00 E−5 | |
| 5 | 5.99 E−9 | >2.00 E−5 | 3.45 E−9 |
| 6 | 1.81 E−7 | >2.00 E−5 | |
| 7 | 2.05 E−8 | >2.00 E−5 | |
| 8 | 1.90 E−8 | >2.00 E−5 | 1.58 E−8 |
| 9 | 1.64 E−7 | >2.00 E−5 | |
| 10 | 4.25 E−9 | >2.00 E−5 | 1.02 E−8 |
| 11 | 4.55 E−9 | >2.00 E−5 | 1.50 E−10 |
| 12 | 2.32 E−8 | >2.00 E−5 | 1.85 E−8 |
| 13 | 3.25 E−8 | >2.00 E−5 | 2.00 E−8 |
| 14 | 1.21 E−8 | >2.00 E−5 | 2.55 E−8 |
| 15 | 2.65 E−8 | >2.00 E−5 | 1.22 E−7 |
| 16 | 3.69 E−9 | >2.00 E−5 | 2.49 E−9 |
| 17 | 1.50 E−8 | >2.00 E−5 | 2.50 E−8 |
| 18 | 1.42 E−8 | >2.00 E−5 | 1.13 E−8 |
| 19 | 3.92 E−9 | >2.00 E−5 | 6.43 E−9 |
| 20 | 2.67 E−8 | >2.00 E−5 | 6.31 E−8 |
| 21 | 2.80 E−8 | >2.00 E−5 | 1.82 E−8 |
| 22 | 2.00 E−8 | >2.00 E−5 | 1.12 E−8 |
| 23 | 4.57 E−8 | >2.00 E−5 | |
| 24 | 8.75 E−8 | >2.00 E−5 | |
| 25 | 6.82 E−8 | >2.00 E−5 | 9.11 E−8 |
| 26 | 8.75 E−8 | >2.00 E−5 | |
| 27 | 1.77 E−7 | >2.00 E−5 | |
| 28 | 2.93 E−7 | >2.00 E−5 | |
| 29 | 7.61 E−8 | >2.00 E−5 | |
| 30 | 6.08 E−8 | >2.00 E−5 | |
| 31 | 2.44 E−7 | >2.00 E−5 | |
| 32 | 3.56 E−8 | >2.00 E−5 | 2.19 E−8 |
| 33 | 2.66 E−9 | >2.00 E−5 | |
| 34 | 1.30 E−7 | >2.00 E−5 | |
| 35 | 1.50 E−9 | >2.00 E−5 | 4.10 E−8 |
| 36 | | >2.00 E−5 | |
| 37 | 2.64 E−9 | >2.00 E−5 | 4.23 E−10 |
| 38 | 3.43 E−8 | >2.00 E−5 | 3.62 E−8 |
| 39 | 2.08 E−9 | >2.00 E−5 | 3.39 E−9 |
| 40 | 1.10 E−6 | >2.00 E−5 | |
| 41 | 1.65 E−6 | >2.00 E−5 | |
| 42 | 1.57 E−6 | >2.00 E−5 | |
| 43 | 2.30 E−8 | >2.00 E−5 | |
| 44 | 1.16 E−8 | >2.00 E−5 | 9.43 E−9 |
| 45 | 4.15 E−8 | >2.00 E−5 | 8.35 E−8 |
| 46 | 1.48 E−9 | >2.00 E−5 | 1.36 E−9 |
| 47 | 1.52 E−9 | >2.00 E−5 | 1.66 E−9 |
| 48 | 2.49 E−9 | >2.00 E−5 | |
| 49 | 6.50 E−9 | >2.00 E−5 | 7.55 E−9 |
| 50 | 8.39 E−9 | >2.00 E−5 | 6.74 E−9 |
| 51 | 9.54 E−9 | >2.00 E−5 | |
| 52 | 1.15 E−8 | >2.00 E−5 | |
| 53 | 1.16 E−8 | >2.00 E−5 | 1.11 E−8 |

TABLE 3-continued $IC_{50}$ values of examples in in vitro assays 1-3

| Example | Assay 1: AHR-luc Hum Antagonism $IC_{50}$ [M] | Assay 2: AHR-luc Hum Agonism $IC_{50}$ [M] | Assay 3: Hum CYP1A1 Antagonism $IC_{50}$ [M] |
|---|---|---|---|
| 54 | 1.43 E−8 | >2.00 E−5 | |
| 55 | 1.79 E−8 | >2.00 E−5 | |
| 56 | 2.56 E−8 | >2.00 E−5 | |
| 57 | 7.48 E−9 | >2.00 E−5 | |
| 58 | 1.86 E−8 | >2.00 E−5 | 1.08 E−8 |
| 59 | 2.00 E−8 | >2.00 E−5 | |
| 60 | 2.18 E−8 | >2.00 E−5 | |
| 61 | 2.84 E−8 | >2.00 E−5 | 3.89 E−8 |
| 62 | 2.95 E−8 | >2.00 E−5 | 1.91 E−8 |
| 63 | 8.10 E−8 | >2.00 E−5 | |
| 64 | 8.16 E−8 | >2.00 E−5 | |
| 65 | 2.55 E−8 | >2.00 E−5 | |
| 66 | 2.59 E−7 | >2.00 E−5 | |
| 67 | 4.30 E−9 | >2.00 E−5 | |
| 68 | 2.42 E−8 | >2.00 E−5 | 2.18 E−8 |
| 69 | 2.14 E−7 | >2.00 E−5 | |
| 70 | 1.59 E−7 | >2.00 E−5 | |
| 71 | 3.80 E−8 | >2.00 E−5 | 6.07 E−8 |
| 72 | 1.82 E−7 | >2.00 E−5 | 4.95 E−7 |
| 73 | 2.83 E−7 | >2.00 E−5 | 3.55 E−7 |
| 74 | 1.52 E−7 | >2.00 E−5 | |
| 75 | 8.34 E−8 | >2.00 E−5 | |
| 76 | 1.19 E−8 | >2.00 E−5 | 1.38 E−8 |
| 77 | 1.12 E−8 | >2.00 E−5 | 8.70 E−9 |
| 78 | 6.68 E−9 | >2.00 E−5 | 4.81 E−9 |
| 79 | 3.95 E−8 | >2.00 E−5 | 8.04 E−8 |
| 80 | 2.71 E−8 | >2.00 E−5 | 3.26 E−8 |
| 81 | 1.06 E−7 | >2.00 E−5 | |
| 82 | 3.76 E−8 | >2.00 E−5 | 3.45 E−8 |
| 83 | 4.61 E−9 | >2.00 E−5 | |
| 84 | 1.63 E−7 | >2.00 E−5 | |
| 85 | 3.60 E−8 | >2.00 E−5 | |
| 86 | 5.59 E−8 | >2.00 E−5 | |
| 87 | 2.96 E−8 | >2.00 E−5 | 2.15 E−8 |
| 88 | 7.80 E−8 | >2.00 E−5 | |
| 89 | 4.80 E−9 | >2.00 E−5 | 2.64 E−9 |
| 90 | 2.17 E−8 | >2.00 E−5 | 4.02 E−8 |
| 91 | 4.81 E−8 | >2.00 E−5 | |
| 92 | 1.90 E−8 | >2.00 E−5 | 2.76 E−9 |
| 93 | 2.48 E−8 | >2.00 E−5 | 4.32 E−9 |
| 94 | 8.44 E−9 | >2.00 E−5 | 1.65 E−8 |
| 95 | 6.23 E−8 | >2.00 E−5 | |
| 96 | 3.67 E−9 | >2.00 E−5 | 3.77 E−9 |
| 97 | 7.06 E−9 | >2.00 E−5 | |
| 98 | 2.51 E−7 | >2.00 E−5 | |
| 99 | 1.29 E−7 | >2.00 E−5 | |
| 100 | 1.27 E−8 | >2.00 E−5 | |
| 101 | 9.54 E−9 | >2.00 E−5 | |
| 102 | 1.88 E−9 | >2.00 E−5 | 1.69 E−9 |
| 103 | 1.33 E−8 | >2.00 E−5 | 2.45 E−8 |
| 104 | 2.02 E−8 | >2.00 E−5 | 1.48 E−8 |
| 105 | 2.37 E−9 | >2.00 E−5 | 1.86 E−9 |
| 106 | | >2.00 E−5 | |
| 107 | 1.23 E−8 | >2.00 E−5 | |
| 108 | | >2.00 E−5 | |
| 109 | 1.63 E−9 | >2.00 E−5 | |
| 110 | 3.31 E−9 | >2.00 E−5 | |
| 111 | 2.65 E−8 | >2.00 E−5 | |
| 112 | 1.15 E−9 | >2.00 E−5 | 9.05 E−10 |
| 113 | 4.83 E−8 | >2.00 E−5 | 1.05 E−7 |
| 114 | 8.55 E−8 | >2.00 E−5 | |
| 115 | 2.63 E−9 | >2.00 E−5 | 1.09 E−8 |
| 116 | 1.15 E−7 | >2.00 E−5 | |
| 117 | | >2.00 E−5 | |
| 118 | 4.51 E−8 | >2.00 E−5 | 5.70 E−8 |
| 119 | 3.06 E−9 | >2.00 E−5 | 5.72 E−9 |
| 120 | 6.79 E−8 | >2.00 E−5 | |
| 121 | 2.54 E−9 | >2.00 E−5 | |
| 122 | 2.65 E−8 | >2.00 E−5 | |
| 123 | 5.70 E−9 | >2.00 E−5 | |
| 124 | 3.64 E−9 | >2.00 E−5 | |
| 125 | 3.82 E−9 | >2.00 E−5 | 4.40 E−9 |
| 126 | 4.60 E−9 | >2.00 E−5 | 5.15 E−9 |
| 127 | 4.17 E−9 | >2.00 E−5 | |
| 128 | 5.05 E−9 | >2.00 E−5 | |
| 129 | 5.53 E−9 | >2.00 E−5 | |
| 130 | 6.54 E−9 | >2.00 E−5 | 6.42 E−9 |
| 131 | 6.23 E−9 | >2.00 E−5 | 7.29 E−9 |
| 132 | 6.88 E−9 | >2.00 E−5 | |
| 133 | 7.52 E−9 | >2.00 E−5 | |
| 134 | 7.68 E−9 | >2.00 E−5 | 9.89 E−9 |
| 135 | 7.91 E−9 | >2.00 E−5 | |
| 136 | 6.04 E−8 | >2.00 E−5 | |
| 137 | 4.23 E−9 | >2.00 E−5 | |
| 138 | 9.04 E−9 | >2.00 E−5 | 7.61 E−9 |
| 139 | 9.20 E−9 | >2.00 E−5 | 9.16 E−9 |
| 140 | 9.55 E−9 | >2.00 E−5 | |
| 141 | 1.48 E−7 | >2.00 E−5 | |
| 142 | 8.32 E−9 | >2.00 E−5 | |
| 143 | 9.61 E−9 | >2.00 E−5 | |
| 144 | 3.14 E−8 | >2.00 E−5 | |
| 145 | 6.90 E−9 | >2.00 E−5 | |
| 146 | 1.03 E−8 | >2.00 E−5 | |
| 147 | 1.22 E−8 | >2.00 E−5 | 1.11 E−8 |
| 148 | 1.53 E−8 | >2.00 E−5 | |
| 149 | 1.88 E−8 | >2.00 E−5 | 1.12 E−8 |
| 150 | 1.99 E−8 | >2.00 E−5 | |
| 151 | 2.11 E−8 | >2.00 E−5 | |
| 152 | 2.41 E−8 | >2.00 E−5 | 2.13 E−8 |
| 153 | 2.42 E−8 | >2.00 E−5 | 2.17 E−8 |
| 154 | 3.68 E−8 | >2.00 E−5 | |
| 155 | 9.05 E−8 | >2.00 E−5 | |
| 156 | 2.50 E−8 | >2.00 E−5 | |
| 157 | 3.93 E−8 | >2.00 E−5 | |
| 158 | 2.18 E−8 | >2.00 E−5 | 2.52 E−8 |
| 159 | 5.70 E−8 | >2.00 E−5 | 9.79 E−8 |
| 160 | 7.92 E−8 | >2.00 E−5 | |
| 161 | 1.03 E−7 | >2.00 E−5 | |
| 162 | 2.73 E−8 | >2.00 E−5 | 3.73 E−8 |
| 163 | 1.34 E−7 | >2.00 E−5 | |
| 164 | 1.57 E−7 | >2.00 E−5 | |
| 165 | 2.09 E−7 | >2.00 E−5 | |
| 166 | 1.80 E−7 | | |
| 167 | 2.39 E−7 | >2.00 E−5 | |
| 168 | 2.40 E−7 | | |
| 169 | 3.17 E−8 | >2.00 E−5 | |
| 170 | 5.73 E−8 | >2.00 E−5 | 2.24 E−8 |
| 171 | 5.84 E−8 | >2.00 E−5 | |
| 172 | 2.95 E−8 | >2.00 E−5 | 2.34 E−8 |
| 173 | 5.49 E−8 | >2.00 E−5 | 1.40 E−7 |
| 174 | 6.15 E−8 | >2.00 E−5 | |
| 175 | 6.61 E−8 | >2.00 E−5 | 1.12 E−7 |
| 176 | 6.61 E−8 | >2.00 E−5 | 3.88 E−8 |
| 177 | 4.65 E−7 | >2.00 E−5 | |
| 178 | 5.94 E−7 | >2.00 E−5 | |
| 179 | 7.36 E−7 | >2.00 E−5 | |
| 180 | 7.94 E−7 | >2.00 E−5 | |
| 181 | 9.11 E−7 | >2.00 E−5 | |
| 182 | 6.11 E−6 | >2.00 E−5 | |
| 183 | 1.97 E−6 | >2.00 E−5 | |
| 184 | 3.81 E−6 | >2.00 E−5 | |
| 185 | 3.71 E−8 | >2.00 E−5 | |
| 186 | 1.31 E−7 | >2.00 E−5 | |
| 187 | 3.35 E−8 | >2.00 E−5 | |
| 188 | 1.25 E−8 | >2.00 E−5 | |
| 189 | 3.03 E−9 | >2.00 E−5 | |
| 190 | 6.56 E−8 | >2.00 E−5 | |
| 191 | 3.35 E−9 | >2.00 E−5 | |
| 192 | 3.41 E−7 | >2.00 E−5 | 4.30 E−9 |
| 193 | 3.52 E−7 | >2.00 E−5 | 3.03 E−9 |
| 194 | 3.09 E−9 | >2.00 E−5 | 7.60 E−9 |
| 195 | 3.63 E−10 | >2.00 E−5 | |
| 196 | 4.18 E−10 | >2.00 E−5 | |
| 197 | 5.02 E−10 | >2.00 E−5 | |
| 198 | 5.99 E−10 | >2.00 E−5 | |
| 199 | 6.94 E−10 | >2.00 E−5 | |

TABLE 3-continued

| IC$_{50}$ values of examples in in vitro assays 1-3 | | | |
|---|---|---|---|
| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
| 200 | 7.34 E−10 | >2.00 E−5 | |
| 201 | 8.23 E−10 | >2.00 E−5 | |
| 202 | 8.25 E−10 | >2.00 E−5 | |
| 203 | 8.52 E−10 | >2.00 E−5 | |
| 204 | 1.00 E−9 | >2.00 E−5 | 1.55 E−9 |
| 205 | 1.06 E−9 | >2.00 E−5 | |
| 206 | 1.07 E−9 | >2.00 E−5 | |
| 207 | 1.21 E−9 | >2.00 E−5 | |
| 208 | 1.22 E−9 | >2.00 E−5 | |
| 209 | 1.24 E−9 | >2.00 E−5 | |
| 210 | 1.46 E−9 | >2.00 E−5 | 2.02 E−9 |
| 211 | 1.62 E−9 | >2.00 E−5 | 2.67 E−9 |
| 212 | 1.69 E−9 | >2.00 E−5 | |
| 213 | 1.92 E−9 | >2.00 E−5 | |
| 214 | 2.07 E−9 | >2.00 E−5 | |
| 215 | 2.21 E−9 | >2.00 E−5 | |
| 216 | 2.38 E−9 | >2.00 E−5 | |
| 217 | 2.44 E−9 | >2.00 E−5 | 7.01 E−9 |
| 218 | 2.78 E−9 | >2.00 E−5 | 4.01 E−9 |
| 219 | 3.21 E−9 | >2.00 E−5 | |
| 220 | 3.36 E−9 | >2.00 E−5 | 1.96 E−9 |
| 221 | 3.63 E−9 | >2.00 E−5 | |
| 222 | 4.27 E−9 | >2.00 E−5 | |
| 223 | 4.31 E−9 | >2.00 E−5 | |
| 224 | 4.37 E−9 | >2.00 E−5 | |
| 225 | 5.04 E−9 | >2.00 E−5 | |
| 226 | 5.91 E−9 | >2.00 E−5 | |
| 227 | 5.99 E−9 | >2.00 E−5 | 1.16 E−8 |
| 228 | 1.33 E−8 | >2.00 E−5 | |
| 229 | 7.09 E−9 | >2.00 E−5 | 1.22 E−8 |
| 230 | 7.57 E−9 | >2.00 E−5 | 1.04 E−8 |
| 23- | 7.89 E−9 | >2.00 E−5 | 9.93 E−9 |
| 232 | 8.16 E−9 | >2.00 E−5 | 7.38 E−9 |
| 233 | 8.23 E−9 | 1.72 E−5 | |
| 234 | 8.42 E−9 | >2.00 E−5 | 9.60 E−9 |
| 235 | 8.87 E−9 | >2.00 E−5 | |
| 236 | 9.03 E−9 | >2.00 E−5 | |
| 237 | 9.38 E−9 | >2.00 E−5 | 7.86 E−9 |
| 238 | 9.88 E−9 | >2.00 E−5 | 1.47 E−8 |
| 239 | 1.00 E−8 | >2.00 E−5 | |
| 240 | 1.06 E−8 | >2.00 E−5 | 2.27 E−8 |
| 241 | 1.09 E−8 | >2.00 E−5 | 3.63 E−8 |
| 242 | 1.11 E−8 | >2.00 E−5 | |
| 243 | 1.18 E−8 | >2.00 E−5 | |
| 244 | 1.19 E−8 | >2.00 E−5 | |
| 245 | 1.28 E−8 | >2.00 E−5 | |
| 246 | 1.32 E−8 | >2.00 E−5 | |
| 247 | 1.39 E−8 | >2.00 E−5 | |
| 248 | 1.41 E−8 | >2.00 E−5 | 3.13 E−8 |
| 249 | 1.53 E−8 | >2.00 E−5 | |
| 250 | 1.69 E−8 | >2.00 E−5 | 1.05 E−8 |
| 251 | 1.79 E−8 | >2.00 E−5 | |
| 252 | 1.80 E−8 | >2.00 E−5 | |
| 253 | 1.94 E−8 | >2.00 E−5 | |
| 254 | 2.29 E−8 | >2.00 E−5 | |
| 255 | 2.58 E−8 | >2.00 E−5 | |
| 256 | 2.60 E−8 | >2.00 E−5 | |
| 257 | 2.63 E−8 | >2.00 E−5 | |
| 258 | 2.75 E−8 | >2.00 E−5 | |
| 259 | 2.81 E−8 | >2.00 E−5 | |
| 260 | 2.94 E−8 | >2.00 E−5 | 1.44 E−8 |
| 261 | 3.30 E−8 | >2.00 E−5 | |
| 262 | 4.12 E−8 | >2.00 E−5 | |
| 263 | 4.19 E−8 | >2.00 E−5 | |
| 264 | 4.44 E−8 | >2.00 E−5 | 8.56 E−8 |
| 265 | 4.88 E−8 | >2.00 E−5 | |
| 266 | 5.68 E−8 | >2.00 E−5 | |
| 267 | 5.69 E−8 | >2.00 E−5 | |
| 268 | 5.69 E−8 | >2.00 E−5 | |
| 269 | 6.17 E−8 | >2.00 E−5 | |
| 270 | 6.45 E−8 | >2.00 E−5 | |
| 271 | 7.20 E−8 | >2.00 E−5 | |
| 272 | 9.11 E−8 | >2.00 E−5 | |
| 273 | 1.01 E−7 | >2.00 E−5 | |
| 274 | 1.11 E−7 | >2.00 E−5 | |
| 275 | 1.30 E−7 | >2.00 E−5 | |
| 276 | 1.31 E−7 | >2.00 E−5 | |
| 277 | 1.39 E−7 | >2.00 E−5 | |
| 278 | 1.40 E−7 | >2.00 E−5 | |
| 279 | 1.68 E−7 | >2.00 E−5 | |
| 280 | 1.78 E−7 | >2.00 E−5 | |
| 281 | 2.61 E−7 | >2.00 E−5 | |
| 282 | 3.04 E−7 | >2.00 E−5 | |
| 283 | 4.30 E−7 | >2.00 E−5 | |
| 284 | 5.71 E−7 | >2.00 E−5 | |
| 285 | 6.02 E−7 | >2.00 E−5 | |
| 286 | 6.72 E−7 | >2.00 E−5 | |
| 287 | 7.21 E−7 | >2.00 E−5 | |
| 288 | 8.20 E−7 | >2.00 E−5 | |
| 289 | 8.75 E−7 | >2.00 E−5 | |
| 290 | 2.82 E−9 | >2.00 E−5 | |
| 291 | 4.38 E−9 | >2.00 E−5 | |
| 292 | 4.59 E−8 | >2.00 E−5 | 4.33 E−8 |
| 293 | 8.22 E−8 | >2.00 E−5 | |
| 294 | 4.98 E−8 | >2.00 E−5 | |
| 295 | 3.19 E−8 | >2.00 E−5 | 8.99 E−8 |
| 296 | 1.18 E−7 | >2.00 E−5 | |
| 297 | 1.49 E−9 | >2.00 E−5 | |
| 298 | 3.69 E−9 | >2.00 E−5 | |
| 299 | 1.33 E−8 | >2.00 E−5 | |
| 300 | | >2.00 E−5 | |
| 301 | 3.10 E−8 | >2.00 E−5 | |
| 302 | 8.15 E−8 | >2.00 E−5 | |
| 303 | 1.33 E−7 | >2.00 E−5 | |
| 304 | 3.49 E−7 | >2.00 E−5 | |
| 305 | 1.64 E−9 | >2.00 E−5 | |
| 306 | 1.33 E−9 | >2.00 E−5 | |
| 307 | 7.39 E−8 | >2.00 E−5 | |
| 308 | 2.19 E−8 | >2.00 E−5 | 3.37 E−8 |
| 309 | 1.64 E−8 | >2.00 E−5 | 4.03 E−8 |
| 310 | 1.70 E−9 | >2.00 E−5 | 1.69 E−9 |
| 311 | 1.82 E−9 | >2.00 E−5 | 1.03 E−9 |
| 312 | 1.85 E−9 | >2.00 E−5 | |
| 313 | 2.63 E−9 | >2.00 E−5 | 3.81 E−9 |
| 314 | 5.80 E−9 | >2.00 E−5 | 1.09 E−8 |
| 315 | 1.59 E−8 | >2.00 E−5 | 1.19 E−8 |
| 316 | 2.06 E−8 | >2.00 E−5 | |
| 317 | 3.03 E−8 | >2.00 E−5 | 3.73 E−8 |
| 318 | 3.20 E−8 | >2.00 E−5 | |
| 319 | 3.55 E−8 | >2.00 E−5 | 2.23 E−8 |
| 320 | 4.41 E−8 | >2.00 E−5 | |
| 321 | 5.06 E−8 | >2.00 E−5 | |
| 322 | 5.67 E−8 | >2.00 E−5 | 3.11 E−8 |
| 323 | 6.04 E−8 | >2.00 E−5 | |
| 324 | 1.22 E−7 | >2.00 E−5 | |
| 325 | 2.42 E−7 | >2.00 E−5 | |
| 326 | 5.04 E−10 | >2.00 E−5 | |
| 327 | 2.58 E−9 | >2.00 E−5 | |
| 328 | 3.06 E−8 | >2.00 E−5 | |
| 329 | 2.94 E−8 | >2.00 E−5 | |
| 330 | 9.27 E−8 | >2.00 E−5 | |
| 331 | 2.34 E−7 | >2.00 E−5 | |
| 332 | 9.45 E−8 | >2.00 E−5 | |
| 333 | 7.49 E−8 | >2.00 E−5 | |
| 334 | 6.02 E−8 | >2.00 E−5 | |
| 335 | 1.13 E−8 | >2.00 E−5 | |
| 336 | 4.29 E−8 | >2.00 E−5 | |
| 337 | 2.08 E−8 | >2.00 E−5 | |
| 338 | 2.41 E−8 | >2.00 E−5 | |
| 339 | 2.76 E−8 | >2.00 E−5 | |
| 340 | 4.97 E−8 | >2.00 E−5 | |
| 341 | 1.02 E−7 | >2.00 E−5 | |
| 342 | 1.32 E−7 | >2.00 E−5 | |

TABLE 3-continued

| IC$_{50}$ values of examples in in vitro assays 1-3 | | | |
|---|---|---|---|
| Example | Assay 1: AHR-luc Hum Antagonism IC$_{50}$ [M] | Assay 2: AHR-luc Hum Agonism IC$_{50}$ [M] | Assay 3: Hum CYP1A1 Antagonism IC$_{50}$ [M] |
| 343 | 1.71 E−7 | >2.00 E−5 | |
| 344 | 1.74 E−7 | >2.00 E−5 | |
| 345 | 5.53 E−8 | >2.00 E−5 | |

In Vitro Assay 4: Rescue of TNFα Production from Human Primary Monocytes

The ability of the substances to enhance immune cell activity was determined. The substances were tested for their capacity to reverse KA-induced inhibition of TNFα production by LPS-stimulated human monocytes. Human monocytes were purified by negative selection from donor PBMCs using Miltenyi beads and seeded at $2\times10^5$ cells/well in complete growth medium (RPMI 1640, 10% FCS). Monocytes were incubated with 10 ng/mL LPS (O127:B8, #L4516, Sigma) and 200 uM KA (#3375, Sigma) and substances were added at concentrations of 1 uM, 0.3 uM and 0.1 uM and cultured for 18 hours. LPS alone served as the positive control. TNFα production in the supernatant was measured by Meso Scale Discovery immunoassay and the ability of the substances to rescue TNFα production was calculated as a percentage of LPS stimulation and KA-induced inhibition and normalized to the donor-specific response with the reference AHR antagonist compound GNF-351 (Smith et al., J Pharmacol Exp Ther, 2011, 338 (1):318-27). Table 4 shows highest percent TNFα rescue relative to highest percent rescue with GNF-351 (observed predominantly at 0.3 and 0.1 uM) and the concentration at which highest rescue was observed with the test compound.

TABLE 4

| Human monocytes: efficacy of selected examples in in vitro assay 4 | | |
|---|---|---|
| Example | Individual Donors % rescue TNFα normalised to ref cmpd | Individual Donors Conc of highest rescue |
| 5 | 67 | 1 μM |
| | 99 | 1 μM |
| | 61 | 1 μM |
| 7 | 126 | 0.1 μM |
| | 63 | 1 μM |
| | 49 | 1 μM |
| 8 | 99 | 1 μM |
| | 55 | 1 μM |
| | 104 | 1 μM |
| | 109 | 1 μM |
| | 36 | 0.1 μM |
| 12 | 74 | 0.1 μM |
| | 122 | 1 μM |
| | 213 | 0.1 μM |
| | 109 | 0.3 μM |
| 13 | 24 | 1 μM |
| | 85 | 1 μM |
| 16 | 249 | 1 μM |
| | 165 | 1 μM |
| 17 | 438 | 1 μM |
| | 296 | 1 μM |

TABLE 4-continued

| Human monocytes: efficacy of selected examples in in vitro assay 4 | | |
|---|---|---|
| Example | Individual Donors % rescue TNFα normalised to ref cmpd | Individual Donors Conc of highest rescue |
| 18 | 83 | 1 μM |
| | 73 | 1 μM |
| | 76 | 0.3 μM |
| | 105 | 0.3 μM |
| 21 | 87 | 0.3 μM |
| | 77 | 1 μM |
| 22 | 66 | 1 μM |
| | 71 | 1 μM |
| 23 | 274 | 1 μM |
| | 81 | 1 μM |
| 24 | 84 | 0.3 μM |
| | 59 | 1 μM |
| 25 | 46 | 1 μM |
| | 53 | 1 μM |
| 27 | 87 | 1 μM |
| | 105 | 0.3 μM |
| 29 | 66 | 1 μM |
| | 88 | 1 μM |
| 36 | 74 | 1 μM |
| | 65 | 1 μM |
| 47 | 68 | 1 μM |
| | 64 | 1 μM |
| 69 | 88 | 0.1 μM |
| | 97 | 0.1 μM |
| 79 | 76 | 0.3 μM |
| | 63 | 0.1 μM |
| 88 | 69 | 1 μM |
| | 35 | 1 μM |
| 110 | 85 | 0.1 μM |
| | 42 | 0.3 μM |
| 113 | 91 | 1 μM |
| | 51 | 1 μM |
| 138 | 49 | 0.1 μM |
| | 84 | 0.3 μM |
| 147 | 50 | 0.1 μM |
| | 89 | 0.3 μM |
| 184 | 63 | 0.1 μM |
| | 62 | 1 μM |
| 186 | 65 | 0.1 μM |
| | 108 | 0.3 μM |

In Vivo Assay: Efficacy of Compositions Comprising an Example Compound and a PD-1/-L1 Axis Antagonist Animals are ordered from Charles River Sulzfeld, Germany and assigned to the study at the age of 7 weeks. Animal husbandry, feeding and health conditions are according to animal welfare guidelines. B16F10-OVA cells are B16F10 mouse melanoma cells that were virally transduced to express ovalbumin. B16F10-OVA cells were cultivated with RPMI 1640 with 10% FCS+2.5 μg/ml blasticidin and splitted at least 3 times before inoculation. The antibiotic blasticidin is removed 1 passage before inoculation. Female C57/BL6N mice were inoculated with 100000 B16F100VA tumor cells in 50% medium/50% matrigel subcutaneously in the flank. After 5 days the animals were randomized and therapeutic treatment started. The AhR antagonist was dissolved in Ethanol/Solutol/Water (10/40/50) and given at 30 mg/kg, QD, p.o. The anti-PD-L1 antibody (TPP-3911) was dosed at 10 mg/kg, q3d, i.p. The isotype control mIgG1 was given 10 mg/kg q3d (TPP-3267), i.p.

The anti-PDL1 antibody is a chimera of the variable domain of atezolizumab with murine IgG1 CH1, 2 and 3 domains. TPP-3911. The isotype antibody is a mouse IgG1 (clone MOPC-21, BioXCell BE0083).

Tumor size was measured using calipers determining length (a) and width (b). Tumor volume was calculated according to:

$$v = \frac{a \times b^2}{2}$$

Based on tumor volume efficacy was calculated dividing tumor volume of the respective treatment group by tumor volume of the control group (T/C).

| | Control: Isotype + vehicle | aPDL1 + vehicle | Example 17 + isotype | Example 17 + aPDL1 |
|---|---|---|---|---|
| T/C | 1.00 | 0.96 | 0.92 | 0.71 |

In Vivo Assay: Efficacy of Compositions Comprising an Example Compound and a CTLA4 Axis Antagonist Animals are ordered from Charles River Sulzfeld, Germany and assigned to the study at the age of 8 weeks. Animal husbandry, feeding and health conditions are according to animal welfare guidelines. B16F10-OVA cells are B16F10 mouse melanoma cells that were virally transduced to express ovalbumin. B16F10-OVA cells were cultivated with RPMI 1640 with 10% FCS+2.5 μg/ml blasticidin and splitted at least 3 times before inoculation. The antibiotic blasticidin is removed 1 passage before inoculation. Female C57/BL6J mice were inoculated with 10000 B16F10-OVA tumor cells in 50% medium/50% matrigel subcutaneously in the flank. After 7 days the animals were randomized and therapeutic treatment started on day 8. The AhR antagonists were dissolved in Ethanol/Solutol/Water (10/40/50) and given at 30 mg/kg, QD, p.o. The anti-CTLA4 antibody was dosed at 1 mg/kg, q3d, i.p. The anti-CTLA4 antibody is mouse-specific with syrian hamster IgG1 isotype (Clone: 9H10 (anti mouse CTLA4), Fa. BioXCell BE0131). The isotype antibody is a syrian hamster IgG1 (TPP-9833).

Tumor size was measured using calipers determining length (a) and width (b). Tumor volume was calculated according to:

$$v = \frac{a \times b^2}{2}$$

Based on tumor volume efficacy was calculated dividing tumor volume of the respective treatment group by tumor volume of the control group (T/C).

| | Control: Isotype + vehicle | aCTLA4(1 mg/kg) + vehicle | Example 17 + isotype | Example 131 + isotype | Example 17 + aCTLA4(1 mg/kg) | Example 131 + aCTLA4(1 mg/kg) |
|---|---|---|---|---|---|---|
| T/C | 1.00 | 0.81 | 0.90 | 1.05 | 0.64 | 0.59 |

The clones MOPC-21 and 9H10 (anti mouse CTLA4) can, for example, be purchased via the company Bio X Cell, 10 Technology Dr., Suit 2B, West Lebanon, NH 03784-1671 USA (Catalog #:BE0083 (invivoMab quality) #BP0083 (in vivo Plus quality), respectively Catalog #: BE0131).

The invention claimed is:

1. A compound of formula (I):

(I)

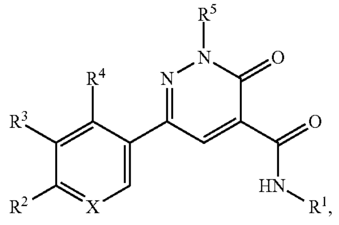

wherein $R^1$ is $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally once with $C_1$-$C_3$-alkyl and/or one to three times with halogen, or $C_3$-$C_6$-cycloalkyl-$C_1$-$C_3$-alkyl substituted once with hydroxy and optionally once with $C_1$-$C_3$-alkyl and/or one to three times with halogen, or ($C_3$-$C_6$-cycloalkyl)$_2$-$C_1$-$C_3$-alkyl substituted once with hydroxy and optionally once with $C_1$-$C_3$-alkyl and/or one to three times with halogen, or 4- to 6-membered heterocycloalkyl substituted once with hydroxy and optionally once with $C_1$-$C_3$-alkyl and/or one to three times with halogen;

$R^2$ is chloro, cyano, dimethylamino, methyl, fluoromethyl, difluoromethyl, trifluoromethyl, methoxy, difluoromethoxy or trifluoromethoxy;

$R^3$ is hydrogen, fluoro, chloro or methyl;

$R^4$ is hydrogen or fluoro;

$R^5$ is monocyclic heteroaryl, which is optionally substituted one to three times, independently from each other, with $R^6$;

$R^6$ is $C_1$-$C_4$-alkyl, $C_1$-$C_4$-haloalkyl, $C_3$-$C_6$-cycloalkyl, $C_1$-$C_4$-alkoxy, halogen or cyano;

X is CH;

$R^{10}$ is $C_1$-$C_4$-alkyl; and $R^{11}$ and $R^{12}$ are the same or different and are independently hydrogen or $C_1$-$C_3$-alkyl, or $R^{11}$ and $R^{12}$ together with the nitrogen atom to which they are attached form a 4- to 6-membered nitrogen containing heterocyclic ring, said ring optionally containing one additional heteroatom selected from O, S, NH, NRa in which Ra represents a C1-C4-alkyl group, or a polymorph, an enantiomer, a diastereomer, a racemate, a tautomer, an N-oxide, a hydrate, a solvate, a physiologically acceptable salt, a solvate of the physiologically acceptable salt, or a mixture of the same.

2. The compound according to claim 1, wherein:

$R^1$ is $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_2$-alkoxy or cyclopropyl and optionally one to three times with halogen, or $C_4$-$C_6$-cycloalkyl substituted once with hydroxy and optionally once with $C_1$-$C_3$-alkyl and/or one to three times with halogen, or $C_3$-$C_6$-cycloalkyl-methyl substituted once with hydroxy and optionally once with $C_1$-$C_3$-alkyl and/or one to three times with halogen, or ($C_3$-$C_6$-cycloalkyl)$_2$-methyl substituted once with hydroxy and optionally once with $C_1$-$C_3$-alkyl and/or one to three times with halogen, or 5- or 6-membered heterocycloalkyl substituted once with hydroxy and optionally once with $C_1$-$C_3$-alkyl and/or one to three times with halogen;

$R^2$ is chloro, cyano, dimethylamino, methyl, fluoromethyl, difluoromethyl, trifluoromethyl, methoxy, difluoromethoxy or trifluoromethoxy;

$R^3$ is hydrogen or fluoro;

$R^4$ is hydrogen or fluoro;

$R^5$ is monocyclic heteroaryl, which is optionally substituted one to three times, independently from each other, with $R^6$;

$R^6$ is methyl, difluoromethyl, methoxy, halogen or cyano;

X is CH;

$R^{10}$ is $C_1$-$C_4$-alkyl; and $R^{11}$ and $R^{12}$ are the same or different and are independently hydrogen or $C_1$-$C_3$-alkyl, or $R^{11}$ and $R^{12}$ together with the nitrogen atom to which they are attached form a 4- to 6-membered nitrogen containing heterocyclic ring, said ring optionally containing one additional heteroatom selected from O, S, NH, NRa in which Ra represents a C1-C4-alkyl group, or a polymorph, an enantiomer, a diastereomer, a racemate, a tautomer, an N-oxide, a hydrate, a solvate, a physiologically acceptable salt, a solvate of the physiologically acceptable salt, or a mixture of the same.

3. The compound according to claim 1, wherein:

$R^1$ is $C_2$-$C_5$-hydroxyalkyl, wherein said $C_2$-$C_5$-hydroxyalkyl groups are optionally substituted once with cyano, —$COOCH_3$, —$CONH_2$, methoxy or cyclopropyl and optionally one to three times with fluoro, or $C_4$-$C_6$-cycloalkyl substituted once with hydroxy and optionally once with methyl and/or one to two times with fluoro, or $C_3$-$C_4$-cycloalkyl-methyl substituted once with hydroxy, or 5- or 6-membered heterocycloalkyl substituted once with hydroxy, said heterocycloalkyl contains one oxygen atom;

$R^2$ is chloro, dimethylamino, methyl, fluoromethyl, difluoromethyl, trifluoromethyl, difluoromethoxy or trifluoromethoxy;

$R^3$ is hydrogen;

$R^4$ is hydrogen or fluoro;

$R^5$ is a group selected from:

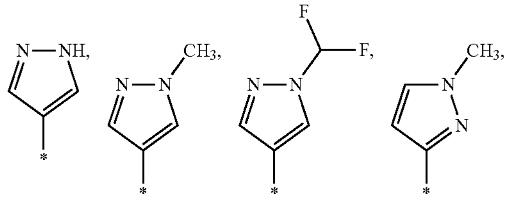

-continued

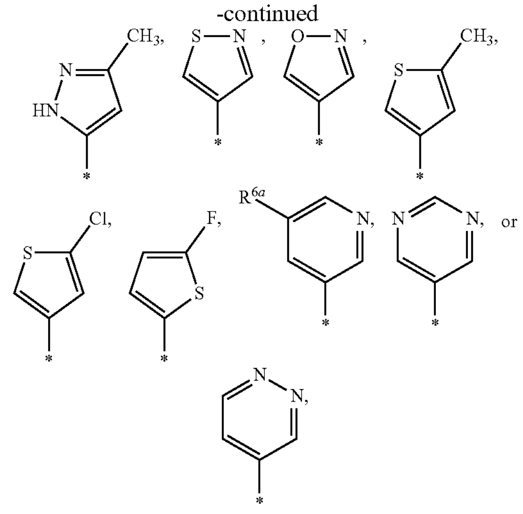

wherein * indicates the point of attachment of said group with the rest of the molecule;

R6a is hydrogen, methyl, fluoro or chloro; and

X is CH, or a polymorph, an enantiomer, a diastereomer, a racemate, a tautomer, an N-oxide, a hydrate, a solvate, a physiologically acceptable salt, a solvate of the physiologically acceptable salt, or a mixture of the same.

4. The compound according to claim 1, wherein the compound is selected from the group consisting of:

N-(1-hydroxy-3-methylbutan-2-yl)-6-(4-methylphenyl)-2-(1-methyl-1H-pyrazol-4-yl)-3-oxo-2,3-dihydropyridazine-4-carboxamide;

N-[(2R)-1-hydroxy-3-methylbutan-2-yl]-6-(4-methylphenyl)-2-(1-methyl-1H-pyrazol-4-yl)-3-oxo-2,3-dihydropyridazine-4-carboxamide;

N-[(2S)-1-hydroxy-3-methylbutan-2-yl]-6-(4-methylphenyl)-2-(1-methyl-1H-pyrazol-4-yl)-3-oxo-2,3-dihydropyridazine-4-carboxamide;

N-(1-hydroxybutan-2-yl)-6-(4-methylphenyl)-2-(1-methyl-1H-pyrazol-4-yl)-3-oxo-2,3-dihydropyridazine-4-carboxamide;

N-[(2R)-1-hydroxybutan-2-yl]-6-(4-methylphenyl)-2-(1-methyl-1H-pyrazol-4-yl)-3-oxo-2,3-dihydropyridazine-4-carboxamide;

N-[(2S)-1-hydroxybutan-2-yl]-6-(4-methylphenyl)-2-(1-methyl-1H-pyrazol-4-yl)-3-oxo-2,3-dihydropyridazine-4-carboxamide;

N-(1-hydroxypropan-2-yl)-6-(4-methylphenyl)-2-(1-methyl-1H-pyrazol-4-yl)-3-oxo-2,3-dihydropyridazine-4-carboxamide;

N-[(2R)-1-hydroxypropan-2-yl]-6-(4-methylphenyl)-2-(1-methyl-1H-pyrazol-4-yl)-3-oxo-2,3-dihydropyridazine-4-carboxamide;

N-[(2S)-1-hydroxypropan-2-yl]-6-(4-methylphenyl)-2-(1-methyl-1H-pyrazol-4-yl)-3-oxo-2,3-dihydropyridazine-4-carboxamide;

6-(4-methylphenyl)-2-(1-methyl-1H-pyrazol-4-yl)-3-oxo-N-(3,3,3-trifluoro-2-hydroxypropyl)-2,3-dihydropyridazine-4-carboxamide;

6-(4-methylphenyl)-2-(1-methyl-1H-pyrazol-4-yl)-3-oxo-N-[(2R)-3,3,3-trifluoro-2-hydroxypropyl]-2,3-dihydropyridazine-4-carboxamide;

6-(4-methylphenyl)-2-(1-methyl-1H-pyrazol-4-yl)-3-oxo-N-[(2S)-3,3,3-trifluoro-2-hydroxypropyl]-2,3-dihydropyridazine-4-carboxamide;

N-(3,3-difluoro-2-hydroxypropyl)-6-(4-methylphenyl)-2-(1-methyl-1H-pyrazol-4-yl)-3-oxo-2,3-dihydropyridazine-4-carboxamide;

N-[(2R)-3,3-difluoro-2-hydroxypropyl]-6-(4-methylphenyl)-2-(1-methyl-1H-pyrazol-4-yl)-3-oxo-2,3-dihydropyridazine-4-carboxamide;

N-[(2S)-3,3-difluoro-2-hydroxypropyl]-6-(4-methylphenyl)-2-(1-methyl-1H-pyrazol-4-yl)-3-oxo-2,3-dihydropyridazine-4-carboxamide;

6-(4-chlorophenyl)-N-(1-hydroxy-3-methylbutan-2-yl)-2-(1-methyl-1H-pyrazol-4-yl)-3-oxo-2,3-dihydropyridazine-4-carboxamide;

6-(4-chlorophenyl)-N-[(2S)-1-hydroxy-3-methylbutan-2-yl]-2-(1-methyl-1H-pyrazol-4-yl)-3-oxo-2,3-dihydropyridazine-4-carboxamide;

6-(4-chlorophenyl)-N-(1-hydroxypropan-2-yl)-2-(1-methyl-1H-pyrazol-4-yl)-3-oxo-2,3-dihydropyridazine-4-carboxamide;

6-(4-chlorophenyl)-N-[(2S)-1-hydroxypropan-2-yl]-2-(1-methyl-1H-pyrazol-4-yl)-3-oxo-2,3-dihydropyridazine-4-carboxamide;

6-(4-chlorophenyl)-2-(1-methyl-1H-pyrazol-4-yl)-3-oxo-N-(3,3,3-trifluoro-2-hydroxypropyl)-2,3-dihydropyridazine-4-carboxamide;

6-(4-chlorophenyl)-2-(1-methyl-1H-pyrazol-4-yl)-3-oxo-N-[(2R)-3,3,3-trifluoro-2-hydroxypropyl]-2,3-dihydropyridazine-4-carboxamide;

6-(4-chlorophenyl)-2-(1-methyl-1H-pyrazol-4-yl)-3-oxo-N-[(2S)-3,3,3-trifluoro-2-hydroxypropyl]-2,3-dihydropyridazine-4-carboxamide;

6-(4-chlorophenyl)-N-(3,3-difluoro-2-hydroxypropyl)-2-(1-methyl-1H-pyrazol-4-yl)-3-oxo-2,3-dihydropyridazine-4-carboxamide;

6-(4-chlorophenyl)-N-[(2R)-3,3-difluoro-2-hydroxypropyl]-2-(1-methyl-1H-pyrazol-4-yl)-3-oxo-2,3-dihydropyridazine-4-carboxamide;

6-(4-chlorophenyl)-N-[(2S)-3,3-difluoro-2-hydroxypropyl]-2-(1-methyl-1H-pyrazol-4-yl)-3-oxo-2,3-dihydropyridazine-4-carboxamide;

6-(4-chlorophenyl)-N-(2-hydroxy-3-methoxypropyl)-2-(1-methyl-1H-pyrazol-4-yl)-3-oxo-2,3-dihydropyridazine-4-carboxamide;

6-(4-chlorophenyl)-N-[(2R)-2-hydroxy-3-methoxypropyl]-2-(1-methyl-1H-pyrazol-4-yl)-3-oxo-2,3-dihydropyridazine-4-carboxamide;

6-(4-chlorophenyl)-N-[(2S)-2-hydroxy-3-methoxypropyl]-2-(1-methyl-1H-pyrazol-4-yl)-3-oxo-2,3-dihydropyridazine-4-carboxamide;

6-(4-chlorophenyl)-N-(2,3-dihydroxypropyl)-2-(1-methyl-1H-pyrazol-4-yl)-3-oxo-2,3-dihydropyridazine-4-carboxamide;

6-(4-chlorophenyl)-N-[(2R)-2,3-dihydroxypropyl]-2-(1-methyl-1H-pyrazol-4-yl)-3-oxo-2,3-dihydropyridazine-4-carboxamide;

6-(4-chlorophenyl)-N-[(2S)-2,3-dihydroxypropyl]-2-(1-methyl-1H-pyrazol-4-yl)-3-oxo-2,3-dihydropyridazine-4-carboxamide;

6-(4-chlorophenyl)-N-(1-hydroxy-3-methoxypropan-2-yl)-2-(1-methyl-1H-pyrazol-4-yl)-3-oxo-2,3-dihydropyridazine-4-carboxamide;

6-(4-chlorophenyl)-N-[(2R)-1-hydroxy-3-methoxypropan-2-yl]-2-(1-methyl-1H-pyrazol-4-yl)-3-oxo-2,3-dihydropyridazine-4-carboxamide;

6-(4-chlorophenyl)-N-[(2S)-1-hydroxy-3-methoxypropan-2-yl]-2-(1-methyl-1H-pyrazol-4-yl)-3-oxo-2,3-dihydropyridazine-4-carboxamide;

6-(4-chlorophenyl)-N-(1,3-dihydroxypropan-2-yl)-2-(1-methyl-1H-pyrazol-4-yl)-3-oxo-2,3-dihydropyridazine-4-carboxamide;

6-(4-chlorophenyl)-N-(2-hydroxy-2-methylpropyl)-2-(1-methyl-1H-pyrazol-4-yl)-3-oxo-2,3-dihydropyridazine-4-carboxamide;

6-(4-chlorophenyl)-2-(1-methyl-1H-pyrazol-4-yl)-3-oxo-N-(1,1,1-trifluoro-3-hydroxypropan-2-yl)-2,3-dihydropyridazine-4-carboxamide;

6-(4-chlorophenyl)-2-(1-methyl-1H-pyrazol-4-yl)-3-oxo-N-[(2R)-1,1,1-trifluoro-3-hydroxypropan-2-yl]-2,3-dihydropyridazine-4-carboxamide;

6-(4-chlorophenyl)-2-(1-methyl-1H-pyrazol-4-yl)-3-oxo-N-[(2S)-1,1,1-trifluoro-3-hydroxypropan-2-yl]-2,3-dihydropyridazine-4-carboxamide;

2-(1-methyl-1H-pyrazol-4-yl)-3-oxo-N-(1,1,1-trifluoro-3-hydroxypropan-2-yl)-6-[4-(trifluoromethyl)phenyl]-2,3-dihydropyridazine-4-carboxamide;

2-(1-methyl-1H-pyrazol-4-yl)-3-oxo-N-[(2R)-1,1,1-trifluoro-3-hydroxypropan-2-yl]-6-[4-(trifluoromethyl)phenyl]-2,3-dihydropyridazine-4-carboxamide;

2-(1-methyl-1H-pyrazol-4-yl)-3-oxo-N-(3,3,3-trifluoro-2-hydroxypropyl)-6-[4-(trifluoromethyl)phenyl]-2,3-dihydropyridazine-4-carboxamide;

2-(1-methyl-1H-pyrazol-4-yl)-3-oxo-N-[(2S)-3,3,3-trifluoro-2-hydroxypropyl]-6-[4-(trifluoromethyl)phenyl]-2,3-dihydropyridazine-4-carboxamide;

N-(1-hydroxypropan-2-yl)-2-(1-methyl-1H-pyrazol-4-yl)-3-oxo-6-[4-(trifluoromethyl)phenyl]-2,3-dihydropyridazine-4-carboxamide;

N-[(2R)-1-hydroxypropan-2-yl]-2-(1-methyl-1H-pyrazol-4-yl)-3-oxo-6-[4-(trifluoromethyl)phenyl]-2,3-dihydropyridazine-4-carboxamide;

N-[(2S)-1-hydroxypropan-2-yl]-2-(1-methyl-1H-pyrazol-4-yl)-3-oxo-6-[4-(trifluoromethyl)phenyl]-2,3-dihydropyridazine-4-carboxamide;

6-(4-chlorophenyl)-2-(1-cyclobutyl-1H-pyrazol-4-yl)-3-oxo-N-(3,3,3-trifluoro-2-hydroxypropyl)-2,3-dihydropyridazine-4-carboxamide;

6-(4-chlorophenyl)-2-(1-cyclobutyl-1H-pyrazol-4-yl)-3-oxo-N-[(2S)-3,3,3-trifluoro-2-hydroxypropyl]-2,3-dihydropyridazine-4-carboxamide;

6-(4-chlorophenyl)-2-(1-cyclobutyl-1H-pyrazol-4-yl)-3-oxo-N-(1,1,1-trifluoro-3-hydroxypropan-2-yl)-2,3-dihydropyridazine-4-carboxamide;

6-(4-chlorophenyl)-2-(1-cyclobutyl-1H-pyrazol-4-yl)-3-oxo-N-[(2R)-1,1,1-trifluoro-3-hydroxypropan-2-yl]-2,3-dihydropyridazine-4-carboxamide;

6-(4-chlorophenyl)-2-(1-cyclobutyl-1H-pyrazol-4-yl)-N-(1-hydroxypropan-2-yl)-3-oxo-2,3-dihydropyridazine-4-carboxamide;

6-(4-chlorophenyl)-2-(1-cyclobutyl-1H-pyrazol-4-yl)-N-[(2S)-1-hydroxypropan-2-yl]-3-oxo-2,3-dihydropyridazine-4-carboxamide;

6-(4-chlorophenyl)-N-[(cis)-4-hydroxytetrahydrofuran-3-yl]-2-(1-methyl-1H-pyrazol-4-yl)-3-oxo-2,3-dihydropyridazine-4-carboxamide;

6-(4-chlorophenyl)-N-[(3R,4R)-4-hydroxytetrahydrofuran-3-yl]-2-(1-methyl-1H-pyrazol-4-yl)-3-oxo-2,3-dihydropyridazine-4-carboxamide;

6-(4-chlorophenyl)-N-[(3S,4S)-4-hydroxytetrahydrofuran-3-yl]-2-(1-methyl-1H-pyrazol-4-yl)-3-oxo-2,3-dihydropyridazine-4-carboxamide;

N-[(cis)-2-hydroxycyclohexyl]-2-(1-methyl-1H-pyrazol-4-yl)-3-oxo-6-[4-(trifluoromethoxy)phenyl]-2,3-dihydropyridazine-4-carboxamide;
N-[(1S,2R)-2-hydroxycyclohexyl]-2-(1-methyl-1H-pyrazol-4-yl)-3-oxo-6-[4-(trifluoromethoxy)phenyl]-2,3-dihydropyridazine-4-carboxamide;
2-(1-methyl-1H-pyrazol-4-yl)-3-oxo-N-(1,1,1-trifluoro-3-hydroxypropan-2-yl)-6-[4-(trifluoromethoxy)phenyl]-2,3-dihydropyridazine-4-carboxamide;
2-(1-methyl-1H-pyrazol-4-yl)-3-oxo-N-[(2R)-1,1,1-trifluoro-3-hydroxypropan-2-yl]-6-[4-(trifluoromethoxy)phenyl]-2,3-dihydropyridazine-4-carboxamide;
6-(4-chlorophenyl)-N-[(cis)-2-hydroxycyclohexyl]-2-(1-methyl-1H-pyrazol-4-yl)-3-oxo-2,3-dihydropyridazine-4-carboxamide;
6-(4-chlorophenyl)-N-[(1S,2R)-2-hydroxycyclohexyl]-2-(1-methyl-1H-pyrazol-4-yl)-3-oxo-2,3-dihydropyridazine-4-carboxamide;
6-(4-chlorophenyl)-N-[(trans)-2-hydroxycyclopentyl]-2-(1-methyl-1H-pyrazol-4-yl)-3-oxo-2,3-dihydropyridazine-4-carboxamide;
6-(4-chlorophenyl)-N-[(1S,2S)-2-hydroxycyclopentyl]-2-(1-methyl-1H-pyrazol-4-yl)-3-oxo-2,3-dihydropyridazine-4-carboxamide;
6-(4-chlorophenyl)-N-[(cis)-2-hydroxycyclopentyl]-2-(1-methyl-1H-pyrazol-4-yl)-3-oxo-2,3-dihydropyridazine-4-carboxamide;
6-(4-chlorophenyl)-N-[(1S,2R)-2-hydroxycyclopentyl]-2-(1-methyl-1H-pyrazol-4-yl)-3-oxo-2,3-dihydropyridazine-4-carboxamide;
6-[4-(difluoromethyl)phenyl]-N-[(trans)-2-hydroxycyclopentyl]-2-(1-methyl-1H-pyrazol-4-yl)-3-oxo-2,3-dihydropyridazine-4-carboxamide;
N-(1-hydroxypropan-2-yl)-2-(1-methyl-1H-pyrazol-4-yl)-3-oxo-6-[4-(trifluoromethoxy)phenyl]-2,3-dihydropyridazine-4-carboxamide;
N-[(2S)-1-hydroxypropan-2-yl]-2-(1-methyl-1H-pyrazol-4-yl)-3-oxo-6-[4-(trifluoromethoxy)phenyl]-2,3-dihydropyridazine-4-carboxamide;
N-[(cis)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
N-[(3R,4R)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
N-[(3S,4S)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
6-[4-(difluoromethyl)phenyl]-N-(1-hydroxypropan-2-yl)-2-(1-methyl-1H-pyrazol-4-yl)-3-oxo-2,3-dihydropyridazine-4-carboxamide;
6-[4-(difluoromethyl)phenyl]-N-[(2S)-1-hydroxypropan-2-yl]-2-(1-methyl-1H-pyrazol-4-yl)-3-oxo-2,3-dihydropyridazine-4-carboxamide;
N-(2-hydroxy-2-methylpropyl)-2-(1-methyl-1H-pyrazol-4-yl)-3-oxo-6-[4-(trifluoromethoxy)phenyl]-2,3-dihydropyridazine-4-carboxamide;
6-[4-(difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide;
1,5-anhydro-2-({[6-(4-chlorophenyl)-2-(1-methyl-1H-pyrazol-4-yl)-3-oxo-2,3-dihydropyridazin-4-yl]carbonyl}amino)-2,4-dideoxy-D-erythro-pentitol;
6-[4-(difluoromethyl)phenyl]-N-(2-hydroxy-2-methylpropyl)-2-(1-methyl-1H-pyrazol-4-yl)-3-oxo-2,3-dihydropyridazine-4-carboxamide;
N-[(trans)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
N-[(3R,4S)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
N-[(3S,4R)-4-hydroxytetrahydrofuran-3-yl]-2-(1-methyl-1H-pyrazol-4-yl)-3-oxo-6-[4-(trifluoromethoxy)phenyl]-2,3-dihydropyridazine-4-carboxamide;
N-(2-hydroxy-2-methylpropyl)-2-(1-methyl-1H-pyrazol-4-yl)-3-oxo-6-[4-(trifluoromethyl)phenyl]-2,3-dihydropyridazine-4-carboxamide;
6-(4-chlorophenyl)-N-(1-hydroxypropan-2-yl)-3-oxo-2-(pyridin-3-yl)-2,3-dihydropyridazine-4-carboxamide;
6-(4-chlorophenyl)-N-[(2R)-1-hydroxypropan-2-yl]-3-oxo-2-(pyridin-3-yl)-2,3-dihydropyridazine-4-carboxamide;
6-(4-chlorophenyl)-N-[(2S)-1-hydroxypropan-2-yl]-3-oxo-2-(pyridin-3-yl)-2,3-dihydropyridazine-4-carboxamide;
6-(4-chlorophenyl)-N-(1,3-dihydroxypropan-2-yl)-3-oxo-2-(pyridin-3-yl)-2,3-dihydropyridazine-4-carboxamide;
6-(4-chlorophenyl)-N-(2-hydroxy-2-methylpropyl)-3-oxo-2-(pyridin-3-yl)-2,3-dihydropyridazine-4-carboxamide;
6-(4-chlorophenyl)-N-(2,3-dihydroxypropyl)-3-oxo-2-(pyridin-3-yl)-2,3-dihydropyridazine-4-carboxamide;
6-(4-chlorophenyl)-N-[(2R)-2,3-dihydroxypropyl]-3-oxo-2-(pyridin-3-yl)-2,3-dihydropyridazine-4-carboxamide;
6-(4-chlorophenyl)-N-[(2S)-2,3-dihydroxypropyl]-3-oxo-2-(pyridin-3-yl)-2,3-dihydropyridazine-4-carboxamide;
6-(4-chlorophenyl)-N-(1-hydroxy-3-methoxypropan-2-yl)-3-oxo-2-(pyridin-3-yl)-2,3-dihydropyridazine-4-carboxamide;
6-(4-chlorophenyl)-N-[(2R)-1-hydroxy-3-methoxypropan-2-yl]-3-oxo-2-(pyridin-3-yl)-2,3-dihydropyridazine-4-carboxamide;
6-(4-chlorophenyl)-N-[(2S)-1-hydroxy-3-methoxypropan-2-yl]-3-oxo-2-(pyridin-3-yl)-2,3-dihydropyridazine-4-carboxamide;
6-(4-chlorophenyl)-3-oxo-2-(pyridin-3-yl)-N-(1,1,1-trifluoro-3-hydroxypropan-2-yl)-2,3-dihydropyridazine-4-carboxamide;
6-(4-chlorophenyl)-3-oxo-2-(pyridin-3-yl)-N-[(2R)-1,1,1-trifluoro-3-hydroxypropan-2-yl]-2,3-dihydropyridazine-4-carboxamide;
6-(4-chlorophenyl)-3-oxo-2-(pyridin-3-yl)-N-[(2S)-1,1,1-trifluoro-3-hydroxypropan-2-yl]-2,3-dihydropyridazine-4-carboxamide;
6-(4-chlorophenyl)-N-(1-cyclopropyl-2-hydroxyethyl)-3-oxo-2-(pyridin-3-yl)-2,3-dihydropyridazine-4-carboxamide;
6-(4-chlorophenyl)-N-[(1R)-1-cyclopropyl-2-hydroxyethyl]-3-oxo-2-(pyridin-3-yl)-2,3-dihydropyridazine-4-carboxamide;
6-(4-chlorophenyl)-N-[(1S)-1-cyclopropyl-2-hydroxyethyl]-3-oxo-2-(pyridin-3-yl)-2,3-dihydropyridazine-4-carboxamide;
6-(4-chlorophenyl)-3-oxo-2-(pyridin-3-yl)-N-(3,3,3-trifluoro-2-hydroxypropyl)-2,3-dihydropyridazine-4-carboxamide;
6-(4-chlorophenyl)-3-oxo-2-(pyridin-3-yl)-N-[(2R)-3,3,3-trifluoro-2-hydroxypropyl]-2,3-dihydropyridazine-4-carboxamide;

6-(4-chlorophenyl)-3-oxo-2-(pyridin-3-yl)-N-[(2S)-3,3,3-trifluoro-2-hydroxypropyl]-2,3-dihydropyridazine-4-carboxamide;

6-(4-chlorophenyl)-N-(3,3-difluoro-2-hydroxypropyl)-3-oxo-2-(pyridin-3-yl)-2,3-dihydropyridazine-4-carboxamide;

6-(4-chlorophenyl)-N-[(2R)-3,3-difluoro-2-hydroxypropyl]-3-oxo-2-(pyridin-3-yl)-2,3-dihydropyridazine-4-carboxamide;

6-(4-chlorophenyl)-N-[(2S)-3,3-difluoro-2-hydroxypropyl]-3-oxo-2-(pyridin-3-yl)-2,3-dihydropyridazine-4-carboxamide;

6-(4-chlorophenyl)-2-(5-fluoropyridin-3-yl)-N-(1-hydroxypropan-2-yl)-3-oxo-2,3-dihydropyridazine-4-carboxamide;

6-(4-chlorophenyl)-2-(5-fluoropyridin-3-yl)-N-[(2R)-1-hydroxypropan-2-yl]-3-oxo-2,3-dihydropyridazine-4-carboxamide;

6-(4-chlorophenyl)-2-(5-fluoropyridin-3-yl)-N-[(2S)-1-hydroxypropan-2-yl]-3-oxo-2,3-dihydropyridazine-4-carboxamide;

6-(4-chlorophenyl)-2-(5-fluoropyridin-3-yl)-N-(2-hydroxy-2-methylpropyl)-3-oxo-2,3-dihydropyridazine-4-carboxamide;

6-(4-chlorophenyl)-2-(5-fluoropyridin-3-yl)-N-(1-hydroxy-3-methylbutan-2-yl)-3-oxo-2,3-dihydropyridazine-4-carboxamide;

6-(4-chlorophenyl)-2-(5-fluoropyridin-3-yl)-N-[(2S)-1-hydroxy-3-methylbutan-2-yl]-3-oxo-2,3-dihydropyridazine-4-carboxamide;

6-(4-chlorophenyl)-N-(1,3-dihydroxypropan-2-yl)-2-(5-fluoropyridin-3-yl)-3-oxo-2,3-dihydropyridazine-4-carboxamide;

6-(4-chlorophenyl)-2-(5-fluoropyridin-3-yl)-N-(1-hydroxy-3-methoxypropan-2-yl)-3-oxo-2,3-dihydropyridazine-4-carboxamide;

6-(4-chlorophenyl)-2-(5-fluoropyridin-3-yl)-N-[(2R)-1-hydroxy-3-methoxypropan-2-yl]-3-oxo-2,3-dihydropyridazine-4-carboxamide;

6-(4-chlorophenyl)-2-(5-fluoropyridin-3-yl)-N-[(2S)-1-hydroxy-3-methoxypropan-2-yl]-3-oxo-2,3-dihydropyridazine-4-carboxamide;

6-(4-chlorophenyl)-N-(1-fluoro-3-hydroxypropan-2-yl)-3-oxo-2-(pyridin-3-yl)-2,3-dihydropyridazine-4-carboxamide;

6-(4-chlorophenyl)-N-[(2R)-1-fluoro-3-hydroxypropan-2-yl]-3-oxo-2-(pyridin-3-yl)-2,3-dihydropyridazine-4-carboxamide;

N-(1-cyclopropyl-2-hydroxyethyl)-3-oxo-2-(pyridin-3-yl)-6-[4-(trifluoromethyl)phenyl]-2,3-dihydropyridazine-4-carboxamide;

N-[(1S)-1-cyclopropyl-2-hydroxyethyl]-3-oxo-2-(pyridin-3-yl)-6-[4-(trifluoromethyl)phenyl]-2,3-dihydropyridazine-4-carboxamide;

6-(4-chlorophenyl)-N-(1-cyclopropyl-2-hydroxyethyl)-2-(5-fluoropyridin-3-yl)-3-oxo-2,3-dihydropyridazine-4-carboxamide;

6-(4-chlorophenyl)-N-(2,3-dihydroxypropyl)-2-(5-fluoropyridin-3-yl)-3-oxo-2,3-dihydropyridazine-4-carboxamide;

6-(4-chlorophenyl)-N-[(2R)-2,3-dihydroxypropyl]-2-(5-fluoropyridin-3-yl)-3-oxo-2,3-dihydropyridazine-4-carboxamide;

6-(4-chlorophenyl)-N-[(2S)-2,3-dihydroxypropyl]-2-(5-fluoropyridin-3-yl)-3-oxo-2,3-dihydropyridazine-4-carboxamide;

6-(4-chlorophenyl)-2-(5-fluoropyridin-3-yl)-3-oxo-N-(1,1,1-trifluoro-3-hydroxypropan-2-yl)-2,3-dihydropyridazine-4-carboxamide;

6-(4-chlorophenyl)-2-(5-fluoropyridin-3-yl)-3-oxo-N-[(2R)-1,1,1-trifluoro-3-hydroxypropan-2-yl]-2,3-dihydropyridazine-4-carboxamide;

N-(3,3-difluoro-2-hydroxypropyl)-3-oxo-2-(pyridin-3-yl)-6-[4-(trifluoromethyl)phenyl]-2,3-dihydropyridazine-4-carboxamide;

N-(2-hydroxycyclopentyl)-3-oxo-2-(pyridin-3-yl)-6-[4-(trifluoromethyl)phenyl]-2,3-dihydropyridazine-4-carboxamide;

N-[(1S,2S)-2-hydroxycyclopentyl]-3-oxo-2-(pyridin-3-yl)-6-[4-(trifluoromethyl)phenyl]-2,3-dihydropyridazine-4-carboxamide;

N-[(1R,2R)-2-hydroxycyclopentyl]-3-oxo-2-(pyridin-3-yl)-6-[4-(trifluoromethyl)phenyl]-2,3-dihydropyridazine-4-carboxamide;

N-[(1R,2S)-2-hydroxycyclopentyl]-3-oxo-2-(pyridin-3-yl)-6-[4-(trifluoromethyl)phenyl]-2,3-dihydropyridazine-4-carboxamide;

N-[(1S,2R)-2-hydroxycyclopentyl]-3-oxo-2-(pyridin-3-yl)-6-[4-(trifluoromethyl)phenyl]-2,3-dihydropyridazine-4-carboxamide;

N-[(cis)-2-hydroxycyclohexyl]-3-oxo-2-(pyridin-3-yl)-6-[4-(trifluoromethyl)phenyl]-2,3-dihydropyridazine-4-carboxamide;

N-[(1S,2R)-2-hydroxycyclohexyl]-3-oxo-2-(pyridin-3-yl)-6-[4-(trifluoromethyl)phenyl]-2,3-dihydropyridazine-4-carboxamide;

N-[(cis)-4-hydroxytetrahydrofuran-3-yl]-3-oxo-2-(pyridin-3-yl)-6-[4-(trifluoromethyl)phenyl]-2,3-dihydropyridazine-4-carboxamide;

3-oxo-2-(pyridin-3-yl)-N-(3,3,3-trifluoro-2-hydroxypropyl)-6-[4-(trifluoromethyl)phenyl]-2,3-dihydropyridazine-4-carboxamide;

3-oxo-2-(pyridin-3-yl)-N-[(2S)-3,3,3-trifluoro-2-hydroxypropyl]-6-[4-(trifluoromethyl)phenyl]-2,3-dihydropyridazine-4-carboxamide;

3-oxo-2-(pyridin-3-yl)-N-(1,1,1-trifluoro-3-hydroxypropan-2-yl)-6-[4-(trifluoromethyl)phenyl]-2,3-dihydropyridazine-4-carboxamide;

3-oxo-2-(pyridin-3-yl)-N-(1,1,1-trifluoro-3-hydroxypropan-2-yl)-6-[4-(trifluoromethyl)phenyl]-2,3-dihydropyridazine-4-carboxamide;

3-oxo-2-(pyridin-3-yl)-N-[(2R)-1,1,1-trifluoro-3-hydroxypropan-2-yl]-6-[4-(trifluoromethyl)phenyl]-2,3-dihydropyridazine-4-carboxamide;

N-(1-hydroxy-3-methoxypropan-2-yl)-3-oxo-2-(pyridin-3-yl)-6-[4-(trifluoromethyl)phenyl]-2,3-dihydropyridazine-4-carboxamide;

N-[(2S)-1-hydroxy-3-methoxypropan-2-yl]-3-oxo-2-(pyridin-3-yl)-6-[4-(trifluoromethyl)phenyl]-2,3-dihydropyridazine-4-carboxamide;

N-(2,3-dihydroxypropyl)-3-oxo-2-(pyridin-3-yl)-6-[4-(trifluoromethyl)phenyl]-2,3-dihydropyridazine-4-carboxamide;

N-[(2R)-2,3-dihydroxypropyl]-3-oxo-2-(pyridin-3-yl)-6-[4-(trifluoromethyl)phenyl]-2,3-dihydropyridazine-4-carboxamide;

N-[(2S)-2,3-dihydroxypropyl]-3-oxo-2-(pyridin-3-yl)-6-[4-(trifluoromethyl)phenyl]-2,3-dihydropyridazine-4-carboxamide;

N-(2-hydroxy-2-methylpropyl)-3-oxo-2-(pyridin-3-yl)-6-[4-(trifluoromethyl)phenyl]-2,3-dihydropyridazine-4-carboxamide;

N-(1,3-dihydroxypropan-2-yl)-3-oxo-2-(pyridin-3-yl)-6-[4-(trifluoromethyl)phenyl]-2,3-dihydropyridazine-4-carboxamide;

N-(1-hydroxypropan-2-yl)-3-oxo-2-(pyridin-3-yl)-6-[4-(trifluoromethyl)phenyl]-2,3-dihydropyridazine-4-carboxamide;

N-[(2R)-1-hydroxypropan-2-yl]-3-oxo-2-(pyridin-3-yl)-6-[4-(trifluoromethyl)phenyl]-2,3-dihydropyridazine-4-carboxamide;

N-[(2S)-1-hydroxypropan-2-yl]-3-oxo-2-(pyridin-3-yl)-6-[4-(trifluoromethyl)phenyl]-2,3-dihydropyridazine-4-carboxamide;

6-(4-chlorophenyl)-N-(1-hydroxypropan-2-yl)-3-oxo-2-(pyrimidin-5-yl)-2,3-dihydropyridazine-4-carboxamide;

6-(4-chlorophenyl)-N-[(2S)-1-hydroxypropan-2-yl]-3-oxo-2-(pyrimidin-5-yl)-2,3-dihydropyridazine-4-carboxamide;

6-(4-chlorophenyl)-3-oxo-2-(pyridin-3-yl)-N-(1,1,1-trifluoro-3-hydroxy-3-methylbutan-2-yl)-2,3-dihydropyridazine-4-carboxamide;

6-(4-chlorophenyl)-3-oxo-2-(pyridin-3-yl)-N-[(2R)-1,1,1-trifluoro-3-hydroxy-3-methylbutan-2-yl]-2,3-dihydropyridazine-4-carboxamide;

6-(4-chlorophenyl)-3-oxo-2-(pyridin-3-yl)-N-[(2S)-1,1,1-trifluoro-3-hydroxy-3-methylbutan-2-yl]-2,3-dihydropyridazine-4-carboxamide;

6-(4-chlorophenyl)-2-(5-fluoropyridin-3-yl)-N-[(cis)-2-hydroxycyclohexyl]-3-oxo-2,3-dihydropyridazine-4-carboxamide;

6-(4-chlorophenyl)-2-(5-fluoropyridin-3-yl)-N-[(1S,2R)-2-hydroxycyclohexyl]-3-oxo-2,3-dihydropyridazine-4-carboxamide;

6-(4-chlorophenyl)-2-(5-fluoropyridin-3-yl)-N-[(cis)-2-hydroxycyclohexyl]-3-oxo-2,3-dihydropyridazine-4-carboxamide;

6-(4-chlorophenyl)-2-(5-fluoropyridin-3-yl)-N-[(1S,2R)-2-hydroxycyclohexyl]-3-oxo-2,3-dihydropyridazine-4-carboxamide;

N-[(cis)-2-hydroxycyclohexyl]-3-oxo-2-(pyridin-3-yl)-6-[4-(trifluoromethoxy)phenyl]-2,3-dihydropyridazine-4-carboxamide;

N-[(1S,2R)-2-hydroxycyclohexyl]-3-oxo-2-(pyridin-3-yl)-6-[4-(trifluoromethoxy)phenyl]-2,3-dihydropyridazine-4-carboxamide;

6-[4-(difluoromethyl)phenyl]-3-oxo-2-(pyridin-3-yl)-N-(1,1,1-trifluoro-3-hydroxypropan-2-yl)-2,3-dihydropyridazine-4-carboxamide;

6-[4-(difluoromethyl)phenyl]-3-oxo-2-(pyridin-3-yl)-N-[(2R)-1,1,1-trifluoro-3-hydroxypropan-2-yl]-2,3-dihydropyridazine-4-carboxamide;

6-(4-chlorophenyl)-2-(5-fluoropyridin-3-yl)-3-oxo-N-(3,3,3-trifluoro-2-hydroxypropyl)-2,3-dihydropyridazine-4-carboxamide;

6-(4-chlorophenyl)-2-(5-fluoropyridin-3-yl)-3-oxo-N-[(2S)-3,3,3-trifluoro-2-hydroxypropyl]-2,3-dihydropyridazine-4-carboxamide;

6-(4-chlorophenyl)-2-(5-fluoropyridin-3-yl)-N-[(cis)-2-hydroxycyclopentyl]-3-oxo-2,3-dihydropyridazine-4-carboxamide;

6-(4-chlorophenyl)-2-(5-fluoropyridin-3-yl)-N-[(1S,2R)-2-hydroxycyclopentyl]-3-oxo-2,3-dihydropyridazine-4-carboxamide;

6-(4-chlorophenyl)-N-[(trans)-2-hydroxycyclopentyl]-3-oxo-2-(pyridin-3-yl)-2,3-dihydropyridazine-4-carboxamide;

6-(4-chlorophenyl)-N-[(1S,2S)-2-hydroxycyclopentyl]-3-oxo-2-(pyridin-3-yl)-2,3-dihydropyridazine-4-carboxamide;

3-oxo-2-(pyridin-3-yl)-N-(3,3,3-trifluoro-2-hydroxypropyl)-6-[4-(trifluoromethoxy)phenyl]-2,3-dihydropyridazine-4-carboxamide;

3-oxo-2-(pyridin-3-yl)-N-[(2S)-3,3,3-trifluoro-2-hydroxypropyl]-6-[4-(trifluoromethoxy)phenyl]-2,3-dihydropyridazine-4-carboxamide;

N-[(trans)-2-hydroxycyclopentyl]-3-oxo-2-(pyridin-3-yl)-6-[4-(trifluoromethoxy)phenyl]-2,3-dihydropyridazine-4-carboxamide;

N-[(1S,2S)-2-hydroxycyclopentyl]-3-oxo-2-(pyridin-3-yl)-6-[4-(trifluoromethoxy)phenyl]-2,3-dihydropyridazine-4-carboxamide;

6-(4-chlorophenyl)-N-[(cis)-2-hydroxycyclohexyl]-3-oxo-2-(pyridin-3-yl)-2,3-dihydropyridazine-4-carboxamide;

3-oxo-2-(pyridin-3-yl)-N-(1,1,1-trifluoro-3-hydroxypropan-2-yl)-6-[4-(trifluoromethoxy)phenyl]-2,3-dihydropyridazine-4-carboxamide;

3-oxo-2-(pyridin-3-yl)-N-[(2R)-1,1,1-trifluoro-3-hydroxypropan-2-yl]-6-[4-(trifluoromethoxy)phenyl]-2,3-dihydropyridazine-4-carboxamide;

3-oxo-2-(pyridin-3-yl)-N-(1,1,1-trifluoro-3-hydroxy-3-methylbutan-2-yl)-6-[4-(trifluoromethoxy)phenyl]-2,3-dihydropyridazine-4-carboxamide;

3-oxo-2-(pyridin-3-yl)-N-[(2R)-1,1,1-trifluoro-3-hydroxy-3-methylbutan-2-yl]-6-[4-(trifluoromethoxy)phenyl]-2,3-dihydropyridazine-4-carboxamide;

3-oxo-2-(pyridin-3-yl)-N-[(2S)-1,1,1-trifluoro-3-hydroxy-3-methylbutan-2-yl]-6-[4-(trifluoromethoxy)phenyl]-2,3-dihydropyridazine-4-carboxamide;

6-(4-chlorophenyl)-N-[(cis)-2-hydroxycyclopentyl]-3-oxo-2-(pyridin-3-yl)-2,3-dihydropyridazine-4-carboxamide;

6-(4-chlorophenyl)-N-[(1R,2S)-2-hydroxycyclopentyl]-3-oxo-2-(pyridin-3-yl)-2,3-dihydropyridazine-4-carboxamide;

6-[4-(difluoromethyl)phenyl]-N-[(trans)-2-hydroxycyclopentyl]-3-oxo-2-(pyridin-3-yl)-2,3-dihydropyridazine-4-carboxamide;

6-[4-(difluoromethyl)phenyl]-N-[(1S,2S)-2-hydroxycyclopentyl]-3-oxo-2-(pyridin-3-yl)-2,3-dihydropyridazine-4-carboxamide;

N-[(trans)-3,3-difluoro-2-hydroxycyclohexyl]-3-oxo-2-(pyridin-3-yl)-6-[4-(trifluoromethoxy)phenyl]-2,3-dihydropyridazine-4-carboxamide;

N-[(1S,2R)-3,3-difluoro-2-hydroxycyclohexyl]-3-oxo-2-(pyridin-3-yl)-6-[4-(trifluoromethoxy)phenyl]-2,3-dihydropyridazine-4-carboxamide;

N-[(1R,2S)-3,3-difluoro-2-hydroxycyclohexyl]-3-oxo-2-(pyridin-3-yl)-6-[4-(trifluoromethoxy)phenyl]-2,3-dihydropyridazine-4-carboxamide;

6-(4-chlorophenyl)-N-[(trans)-3,3-difluoro-2-hydroxycyclohexyl]-3-oxo-2-(pyridin-3-yl)-2,3-dihydropyridazine-4-carboxamide;

6-(4-chlorophenyl)-N-[(1S,2R)-3,3-difluoro-2-hydroxycyclohexyl]-3-oxo-2-(pyridin-3-yl)-2,3-dihydropyridazine-4-carboxamide;

6-(4-chlorophenyl)-N-[(1R,2S)-3,3-difluoro-2-hydroxycyclohexyl]-3-oxo-2-(pyridin-3-yl)-2,3-dihydropyridazine-4-carboxamide;

N-[(cis)-2-hydroxycyclopentyl]-3-oxo-2-(pyridin-3-yl)-6-[4-(trifluoromethoxy)phenyl]-2,3-dihydropyridazine-4-carboxamide;

N-[(1S,2R)-2-hydroxycyclopentyl]-3-oxo-2-(pyridin-3-yl)-6-[4-(trifluoromethoxy)phenyl]-2,3-dihydro-pyridazine-4-carboxamide;

N-(1-cyclopropyl-2-hydroxyethyl)-6-[4-(difluoromethyl)phenyl]-3-oxo-2-(pyridin-3-yl)-2,3-dihydropyridazine-4-carboxamide;

N-[(1S)-1-cyclopropyl-2-hydroxyethyl]-6-[4-(difluoromethyl)phenyl]-3-oxo-2-(pyridin-3-yl)-2,3-dihydro-pyridazine-4-carboxamide;

6-[4-(difluoromethyl)phenyl]-N-(1-hydroxypropan-2-yl)-3-oxo-2-(pyridin-3-yl)-2,3-dihydropyridazine-4-carboxamide;

6-[4-(difluoromethyl)phenyl]-N-[(2S)-1-hydroxypropan-2-yl]-3-oxo-2-(pyridin-3-yl)-2,3-dihydropyridazine-4-carboxamide;

N-(1-hydroxypropan-2-yl)-6-(4-methylphenyl)-3-oxo-2-(pyridin-3-yl)-2,3-dihydropyridazine-4-carboxamide;

N-[(2S)-1-hydroxypropan-2-yl]-6-(4-methylphenyl)-3-oxo-2-(pyridin-3-yl)-2,3-dihydropyridazine-4-carboxamide;

N-(1-hydroxypropan-2-yl)-3-oxo-2-(pyridin-3-yl)-6-[4-(trifluoromethoxy)phenyl]-2,3-dihydropyridazine-4-carboxamide;

N-[(2S)-1-hydroxypropan-2-yl]-3-oxo-2-(pyridin-3-yl)-6-[4-(trifluoromethoxy)phenyl]-2,3-dihydro-pyridazine-4-carboxamide;

6-(4-chlorophenyl)-2-(5-fluoropyridin-3-yl)-N-[(trans)-4-hydroxytetrahydrofuran-3-yl]-3-oxo-2,3-dihydro-pyridazine-4-carboxamide;

6-(4-chlorophenyl)-2-(5-fluoropyridin-3-yl)-N-[(3S,4R)-4-hydroxytetrahydrofuran-3-yl]-3-oxo-2,3-dihydro-pyridazine-4-carboxamide;

6-(4-chlorophenyl)-2-(5-fluoropyridin-3-yl)-N-[(3R,4S)-4-hydroxytetrahydrofuran-3-yl]-3-oxo-2,3-dihydro-pyridazine-4-carboxamide;

N-[(cis)-4-hydroxytetrahydrofuran-3-yl]-3-oxo-2-(pyridin-3-yl)-6-[4-(trifluoromethoxy)phenyl]-2,3-dihydro-pyridazine-4-carboxamide;

N-[(3S,4S)-4-hydroxytetrahydrofuran-3-yl]-3-oxo-2-(pyridin-3-yl)-6-[4-(trifluoromethoxy)phenyl]-2,3-dihydropyridazine-4-carboxamide;

N-[(3R,4R)-4-hydroxytetrahydrofuran-3-yl]-3-oxo-2-(pyridin-3-yl)-6-[4-(trifluoromethoxy)phenyl]-2,3-dihydropyridazine-4-carboxamide;

N-[(trans)-4-hydroxytetrahydrofuran-3-yl]-3-oxo-2-(pyridin-3-yl)-6-[4-(trifluoromethoxy)phenyl]-2,3-dihydropyridazine-4-carboxamide;

N-[(3S,4R)-4-hydroxytetrahydrofuran-3-yl]-3-oxo-2-(pyridin-3-yl)-6-[4-(trifluoromethoxy)phenyl]-2,3-dihydropyridazine-4-carboxamide;

N-[(3R,4S)-4-hydroxytetrahydrofuran-3-yl]-3-oxo-2-(pyridin-3-yl)-6-[4-(trifluoromethoxy)phenyl]-2,3-dihydropyridazine-4-carboxamide;

6-(4-chloro-2-fluorophenyl)-N-(1-hydroxypropan-2-yl)-3-oxo-2-(pyridin-3-yl)-2,3-dihydropyridazine-4-carboxamide;

6-(4-chloro-2-fluorophenyl)-N-[(2S)-1-hydroxypropan-2-yl]-3-oxo-2-(pyridin-3-yl)-2,3-dihydropyridazine-4-carboxamide;

3-(4-chlorophenyl)-N-[(cis)-2-hydroxycyclohexyl]-6-oxo-6H-1,4'-bipyridazine-5-carboxamide;

3-(4-chlorophenyl)-N-[(1S,2R)-2-hydroxycyclohexyl]-6-oxo-6H-1,4'-bipyridazine-5-carboxamide;

3-(4-chlorophenyl)-N-[(cis)-2-hydroxycyclopentyl]-6-oxo-6H-1,4'-bipyridazine-5-carboxamide;

3-(4-chlorophenyl)-N-[(1 S,2R)-2-hydroxycyclopentyl]-6-oxo-6H-1,4'-bipyridazine-5-carboxamide;

6-(4-chlorophenyl)-N-[(trans)-4-hydroxytetrahydrofuran-3-yl]-3-oxo-2-(pyridin-3-yl)-2,3-dihydropyridazine-4-carboxamide;

6-(4-chlorophenyl)-N-[(3S,4R)-4-hydroxytetrahydrofuran-3-yl]-3-oxo-2-(pyridin-3-yl)-2,3-dihydro-pyridazine-4-carboxamide;

6-(4-chlorophenyl)-N-[(3R,4S)-4-hydroxytetrahydrofuran-3-yl]-3-oxo-2-(pyridin-3-yl)-2,3-dihydro-pyridazine-4-carboxamide;

6-(4-chlorophenyl)-N-[(cis)-4-hydroxytetrahydrofuran-3-yl]-3-oxo-2-(pyridin-3-yl)-2,3-dihydropyridazine-4-carboxamide;

6-(4-chlorophenyl)-N-[(3R,4R)-4-hydroxytetrahydrofuran-3-yl]-3-oxo-2-(pyridin-3-yl)-2,3-dihydro-pyridazine-4-carboxamide;

6-(4-chlorophenyl)-N-[(3S,4S)-4-hydroxytetrahydrofuran-3-yl]-3-oxo-2-(pyridin-3-yl)-2,3-dihydro-pyridazine-4-carboxamide;

3-(4-chlorophenyl)-N-[(trans)-2-hydroxycyclopentyl]-6-oxo-6H-1,4'-bipyridazine-5-carboxamide;

3-(4-chlorophenyl)-N-[(1S,2S)-2-hydroxycyclopentyl]-6-oxo-6H-1,4'-bipyridazine-5-carboxamide;

1,5-anhydro-2-({[6-(4-chlorophenyl)-3-oxo-2-(pyridin-3-yl)-2,3-dihydropyridazin-4-yl]carbonyl}amino)-2,4-dideoxy-cis-pentitol;

1,5-anhydro-2-({[6-(4-chlorophenyl)-3-oxo-2-(pyridin-3-yl)-2,3-dihydropyridazin-4-yl]carbonyl}amino)-2,4-dideoxy-D-erythro-pentitol;

1,5-anhydro-2,4-dideoxy-2-[({3-oxo-2-(pyridin-3-yl)-6-[4-(trifluoromethoxy)phenyl]-2,3-dihydropyridazin-4-yl}carbonyl)amino]-cis-pentitol;

1,5-anhydro-2,4-dideoxy-2-[({3-oxo-2-(pyridin-3-yl)-6-[4-(trifluoromethoxy)phenyl]-2,3-dihydropyridazin-4-yl}carbonyl)amino]-D-erythro-pentitol;

3-(4-chlorophenyl)-N-(1-hydroxypropan-2-yl)-6-oxo-6H-1,4'-bipyridazine-5-carboxamide;

3-(4-chlorophenyl)-N-[(2S)-1-hydroxypropan-2-yl]-6-oxo-6H-1,4'-bipyridazine-5-carboxamide;

3-(4-chlorophenyl)-N-(2-hydroxy-2-methylpropyl)-6-oxo-6H-1,4'-bipyridazine-5-carboxamide;

6-(4-cyanophenyl)-N-(1-hydroxypropan-2-yl)-3-oxo-2-(pyridin-3-yl)-2,3-dihydropyridazine-4-carboxamide;

6-(4-cyanophenyl)-N-[(2S)-1-hydroxypropan-2-yl]-3-oxo-2-(pyridin-3-yl)-2,3-dihydropyridazine-4-carboxamide;

3-(4-chlorophenyl)-N-[(cis)-4-hydroxytetrahydrofuran-3-yl]-6-oxo-6H-1,4'-bipyridazine-5-carboxamide;

6-(4-chlorophenyl)-3-oxo-2-(pyrimidin-5-yl)-N-(1,1,1-trifluoro-3-hydroxy-3-methylbutan-2-yl)-2,3-dihydro-pyridazine-4-carboxamide;

6-(4-chlorophenyl)-3-oxo-2-(pyrimidin-5-yl)-N-[(2R)-1,1,1-trifluoro-3-hydroxy-3-methylbutan-2-yl]-2,3-dihydropyridazine-4-carboxamide;

6-(4-chlorophenyl)-3-oxo-2-(pyrimidin-5-yl)-N-[(2S)-1,1,1-trifluoro-3-hydroxy-3-methylbutan-2-yl]-2,3-dihydropyridazine-4-carboxamide;

N-[(1-hydroxycyclopropyl)methyl]-3-oxo-2-(pyridin-3-yl)-6-[4-(trifluoromethyl)phenyl]-2,3-dihydro-pyridazine-4-carboxamide;

N-[(1-hydroxycyclobutyl)methyl]-3-oxo-2-(pyridin-3-yl)-6-[4-(trifluoromethyl)phenyl]-2,3-dihydro-pyridazine-4-carboxamide;

6-(4-chlorophenyl)-N-(1-hydroxypropan-2-yl)-3-oxo-2-(1H-pyrazol-4-yl)-2,3-dihydropyridazine-4-carboxamide;

6-(4-chlorophenyl)-N-[(2S)-1-hydroxypropan-2-yl]-3-oxo-2-(1H-pyrazol-4-yl)-2,3-dihydropyridazine-4-carboxamide;

6-[4-(dimethylamino)phenyl]-N-(1-hydroxypropan-2-yl)-3-oxo-2-(pyridin-3-yl)-2,3-dihydropyridazine-4-carboxamide;

6-[4-(dimethylamino)phenyl]-N-[(2S)-1-hydroxypropan-2-yl]-3-oxo-2-(pyridin-3-yl)-2,3-dihydropyridazine-4-carboxamide;

6-(4-chlorophenyl)-N-(1-hydroxypropan-2-yl)-2-(1-methyl-1H-pyrazol-3-yl)-3-oxo-2,3-dihydropyridazine-4-carboxamide;

6-(4-chlorophenyl)-N-[(2S)-1-hydroxypropan-2-yl]-2-(1-methyl-1H-pyrazol-3-yl)-3-oxo-2,3-dihydropyridazine-4-carboxamide;

6-(4-chlorophenyl)-N-(1-hydroxypropan-2-yl)-2-(3-methyl-1H-pyrazol-5-yl)-3-oxo-2,3-dihydropyridazine-4-carboxamide;

6-(4-chlorophenyl)-N-[(2S)-1-hydroxypropan-2-yl]-2-(3-methyl-1H-pyrazol-5-yl)-3-oxo-2,3-dihydropyridazine-4-carboxamide;

6-(4-chlorophenyl)-N-(1-hydroxypropan-2-yl)-3-oxo-2-(1,2-thiazol-4-yl)-2,3-dihydropyridazine-4-carboxamide;

6-(4-chlorophenyl)-N-[(2S)-1-hydroxypropan-2-yl]-3-oxo-2-(1,2-thiazol-4-yl)-2,3-dihydropyridazine-4-carboxamide;

N-[(1-Hydroxycyclobutyl)methyl]-3-oxo-2-(1,2-thiazol-4-yl)-6-[4-(trifluoromethyl)phenyl]-2,3-dihydropyridazine-4-carboxamide;

N-[(2S)-3-Hydroxy-3-methylbutan-2-yl]-3-oxo-2-(1,2-thiazol-4-yl)-6-[4-(trifluoromethyl)phenyl]-2,3-dihydropyridazine-4-carboxamide;

(+)-3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide enantiomer 2;

6-(4-Chlorophenyl)-3-oxo-2-(1,2-thiazol-4-yl)-N-[(2R)-1,1,1-trifluoro-3-hydroxypropan-2-yl]-2,3-dihydropyridazine-4-carboxamide;

6-(4-Chlorophenyl)-3-oxo-2-(1,2-thiazol-4-yl)-N-[(2S)-3,3,3-trifluoro-2-hydroxypropyl]-2,3-dihydropyridazine-4-carboxamide;

6-(4-Chlorophenyl)-N-[(1-hydroxycyclobutyl)methyl]-3-oxo-2-(1,2-thiazol-4-yl)-2,3-dihydropyridazine-4-carboxamide;

6-(4-Chlorophenyl)-N-[(2R)-1-fluoro-3-hydroxypropan-2-yl]-3-oxo-2-(1,2-thiazol-4-yl)-2,3-dihydropyridazine-4-carboxamide;

N-[(2R)-3-Hydroxy-3-methylbutan-2-yl]-2-(1-methyl-1H-pyrazol-4-yl)-3-oxo-6-[4-(trifluoromethyl)phenyl]-2,3-dihydropyridazine-4-carboxamide;

N-[(2R)-1-Fluoro-3-hydroxypropan-2-yl]-3-oxo-2-(1,2-thiazol-4-yl)-6-[4-(trifluoromethyl)phenyl]-2,3-dihydropyridazine-4-carboxamide;

N-[(1S,2R)-2-Hydroxycyclopentyl]-2-(1-methyl-1H-pyrazol-4-yl)-3-oxo-6-[4-(trifluoromethyl)phenyl]-2,3-dihydropyridazine-4-carboxamide;

N-[(2S)-1-Hydroxypropan-2-yl]-3-oxo-2-(1,2-thiazol-4-yl)-6-[4-(trifluoromethyl)phenyl]-2,3-dihydropyridazine-4-carboxamide;

N-[(2S)-3-Hydroxy-3-methylbutan-2-yl]-2-(1-methyl-1H-pyrazol-4-yl)-3-oxo-6-[4-(trifluoromethyl)phenyl]-2,3-dihydropyridazine-4-carboxamide;

N-[(1S)-1-Cyclopropyl-2-hydroxyethyl]-3-oxo-2-(1,2-thiazol-4-yl)-6-[4-(trifluoromethyl)phenyl]-2,3-dihydropyridazine-4-carboxamide;

N-(2-Hydroxy-2-methylpropyl)-3-oxo-2-(1,2-thiazol-4-yl)-6-[4-(trifluoromethyl)phenyl]-2,3-dihydropyridazine-4-carboxamide;

6-(4-Chlorophenyl)-N-[(2S)-3-hydroxy-3-methylbutan-2-yl]-3-oxo-2-(1,2-thiazol-4-yl)-2,3-dihydropyridazine-4-carboxamide;

N-[(1S,2S)-2-Hydroxycyclopentyl]-2-(1-methyl-1H-pyrazol-4-yl)-3-oxo-6-[4-(trifluoromethyl)phenyl]-2,3-dihydropyridazine-4-carboxamide;

N-[(2R)-1-Fluoro-3-hydroxypropan-2-yl]-2-(1-methyl-1H-pyrazol-4-yl)-3-oxo-6-[4-(trifluoromethyl)phenyl]-2,3-dihydropyridazine-4-carboxamide;

3-Oxo-2-(1H-pyrazol-4-yl)-N-[(2R)-1,1,1-trifluoro-3-hydroxypropan-2-yl]-6-[4-(trifluoromethyl)phenyl]-2,3-dihydropyridazine-4-carboxamide;

3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide;

2-[1-(Difluoromethyl)-1H-pyrazol-4-yl]-3-oxo-N-1[(2R)-1,1,1-trifluoro-3-hydroxypropan-2-yl]-6-[4-(trifluoromethyl)phenyl]-2,3-dihydropyridazine-4-carboxamide;

N-cis-4-Hydroxytetrahydrofuran-3-yl-2-(1-methyl-1H-pyrazol-4-yl)-3-oxo-6-[4-(trifluoromethyl)phenyl]-2,3-dihydropyridazine-4-carboxamide;

3-Oxo-2-(1H-pyrazol-4-yl)-N-[(2S)-3,3,3-trifluoro-2-hydroxypropyl]-6-[4-(trifluoromethyl)phenyl]-2,3-dihydropyridazine-4-carboxamide;

(+)-N-cis-2-Hydroxycyclobutyl-3-oxo-2-(pyridin-3-yl)-6-[4-(trifluoromethyl)phenyl]-2,3-dihydropyridazine-4-carboxamide enantiomer 1;

(+)-N-cis-4-Hydroxytetrahydrofuran-3-yl-2-(1-methyl-1H-pyrazol-4-yl)-3-oxo-6-[4-(trifluoromethyl)phenyl]-2,3-dihydropyridazine-4-carboxamide enantiomer 2;

N-[(2S)-3,3-Difluoro-2-hydroxypropyl]-2-(1-methyl-1H-pyrazol-4-yl)-3-oxo-6-[4-(trifluoromethyl)phenyl]-2,3-dihydropyridazine-4-carboxamide;

6-(4-Chlorophenyl)-2-(5-fluoro-2-thienyl)-N-[(2S)-1-hydroxypropan-2-yl]-3-oxo-2,3-dihydropyridazine-4-carboxamide;

N-[(2R)-1-Fluoro-3-hydroxypropan-2-yl]-3-oxo-2-(pyridin-3-yl)-6-[4-(trifluoromethyl)phenyl]-2,3-dihydropyridazine-4-carboxamide;

6-(4-Chlorophenyl)-N-(2-hydroxy-2-methylpropyl)-3-oxo-2-(1,2-thiazol-4-yl)-2,3-dihydropyridazine-4-carboxamide;

2-[1-(Difluoromethyl)-1H-pyrazol-4-yl]-3-oxo-N-[(2S)-3,3,3-trifluoro-2-hydroxypropyl]-6-[4-(trifluoromethyl)phenyl]-2,3-dihydropyridazine-4-carboxamide;

N-cis-2-Hydroxycyclobutyl-3-oxo-2-(pyridin-3-yl)-6-[4-(trifluoromethyl)phenyl]-2,3-dihydropyridazine-4-carboxamide;

6-(4-Chlorophenyl)-2-(5-methyl-3-thienyl)-3-oxo-N-[(2S)-3,3,3-trifluoro-2-hydroxypropyl]-2,3-dihydropyridazine-4-carboxamide;

N-[(2S)-3-Hydroxy-3-methylbutan-2-yl]-3-oxo-2-(pyridin-3-yl)-6-[4-(trifluoromethyl)phenyl]-2,3-dihydropyridazine-4-carboxamide;

6-(4-Chlorophenyl)-N-[(1S)-1-cyano-2-hydroxyethyl]-2-(1-methyl-1H-pyrazol-4-yl)-3-oxo-2,3-dihydropyridazine-4-carboxamide;

2-[1-(Difluoromethyl)-1H-pyrazol-4-yl]-N-[(2S)-3-hydroxy-3-methylbutan-2-yl]-3-oxo-6-[4-(trifluoromethyl)phenyl]-2,3-dihydropyridazine-4-carboxamide;

(+)-N-cis-4-Hydroxytetrahydrofuran-3-yl-3-oxo-2-(pyridin-3-yl)-6-[4-(trifluoromethyl)phenyl]-2,3-dihydropyridazine-4-carboxamide enantiomer 1;

(−)-N-(3,3-Difluoro-2-hydroxypropyl)-3-oxo-2-(pyridin-3-yl)-6-[4-(trifluoromethyl)phenyl]-2,3-dihydropyridazine-4-carboxamide enantiomer 2;

(−)-N-cis-4-Hydroxytetrahydrofuran-3-yl-2-(1-methyl-1H-pyrazol-4-yl)-3-oxo-6-[4-(trifluoromethyl)phenyl]-2,3-dihydropyridazine-4-carboxamide enantiomer 1;

6-(4-Chlorophenyl)-2-(5-chloro-3-thienyl)-3-oxo-N-[(2S)-3,3,3-trifluoro-2-hydroxypropyl]-2,3-dihydropyridazine-4-carboxamide;

N-[(2S)-3-Hydroxy-3-methylbutan-2-yl]-3-oxo-2-(1,2-thiazol-4-yl)-6-[6-(trifluoromethyl)pyridin-3-yl]-2,3-dihydropyridazine-4-carboxamide;

N-[(2R)-3-Hydroxy-3-methylbutan-2-yl]-3-oxo-2-(pyridin-3-yl)-6-[4-(trifluoromethyl)phenyl]-2,3-dihydropyridazine-4-carboxamide;

6-(4-Chlorophenyl)-2-(1,2-oxazol-4-yl)-3-oxo-N-[(2S)-3,3,3-trifluoro-2-hydroxypropyl]-2,3-dihydropyridazine-4-carboxamide;

2-[1-(Difluoromethyl)-1H-pyrazol-4-yl]-3-oxo-N-[(2S)-3,3,3-trifluoro-2-hydroxypropyl]-6-[4-(trifluoromethyl)phenyl]-2,3-dihydropyridazine-4-carboxamide;

6-(4-Chlorophenyl)-3-oxo-2-(pyrimidin-5-yl)-N-[(2S)-3,3,3-trifluoro-2-hydroxypropyl]-2,3-dihydropyridazine-4-carboxamide;

N-[(1S)-1-Cyclopropyl-2-hydroxyethyl]-2-(1-methyl-1H-pyrazol-4-yl)-3-oxo-6-[4-(trifluoromethyl)phenyl]-2,3-dihydropyridazine-4-carboxamide;

N-[(1R,2S)-2-Hydroxycyclopentyl]-2-(1-methyl-1H-pyrazol-4-yl)-3-oxo-6-[4-(trifluoromethyl)phenyl]-2,3-dihydropyridazine-4-carboxamide;

(−)-3-Oxo-2-(pyridin-3-yl)-N-(1,1,1-trifluoro-3-hydroxy-3-methylbutan-2-yl)-6-[4-(trifluoromethyl)phenyl]-2,3-dihydropyridazine-4-carboxamide enantiomer 1;

6-(4-Chlorophenyl)-N-[(2S)-1-hydroxypropan-2-yl]-2-(5-methyl-3-thienyl)-3-oxo-2,3-dihydropyridazine-4-carboxamide;

6-(4-Chlorophenyl)-2-(5-chloro-3-thienyl)-N-[(2S)-1-hydroxypropan-2-yl]-3-oxo-2,3-dihydropyridazine-4-carboxamide;

N-[(2S)-1-Hydroxypropan-2-yl]-3-oxo-2-(1H-pyrazol-4-yl)-6-[4-(trifluoromethyl)phenyl]-2,3-dihydropyridazine-4-carboxamide;

N-[(2S)-3-Fluoro-2-hydroxypropyl]-2-(1-methyl-1H-pyrazol-4-yl)-3-oxo-6-[4-(trifluoromethyl)phenyl]-2,3-dihydropyridazine-4-carboxamide;

6-(4-Chlorophenyl)-N-(2-hydroxy-2-methylpropyl)-2-(5-methyl-3-thienyl)-3-oxo-2,3-dihydropyridazine-4-carboxamide;

N-(3,3-Difluoro-2-hydroxypropyl)-3-oxo-2-(pyridin-3-yl)-6-[4-(trifluoromethyl)phenyl]-2,3-dihydropyridazine-4-carboxamide enantiomer 1;

N-[(1R,2R)-2-Hydroxycyclopentyl]-2-(1-methyl-1H-pyrazol-4-yl)-3-oxo-6-[4-(trifluoromethyl)phenyl]-2,3-dihydropyridazine-4-carboxamide;

(+)-6-(4-Chlorophenyl)-N-cis-2-hydroxycyclobutyl-3-oxo-2-(pyridin-3-yl)-2,3-dihydropyridazine-4-carboxamide enantiomer 1;

6-(4-Chlorophenyl)-2-(5-chloro-3-thienyl)-N-(2-hydroxy-2-methylpropyl)-3-oxo-2,3-dihydropyridazine-4-carboxamide;

(−)-N-cis-4-Hydroxytetrahydrofuran-3-yl-3-oxo-2-(pyridin-3-yl)-6-[4-(trifluoromethyl)phenyl]-2,3-dihydropyridazine-4-carboxamide, enantiomer 2;

6-(4-Chlorophenyl)-N-[(2S)-1-hydroxypropan-2-yl]-2-(1,2-oxazol-4-yl)-3-oxo-2,3-dihydropyridazine-4-carboxamide;

6-(4-Chlorophenyl)-N-[(1S)-1-cyano-2-hydroxyethyl]-3-oxo-2-(pyridin-3-yl)-2,3-dihydropyridazine-4-carboxamide;

N-[(2S)-3-Fluoro-2-hydroxypropyl]-3-oxo-2-(pyridin-3-yl)-6-[4-(trifluoromethyl)phenyl]-2,3-dihydropyridazine-4-carboxamide;

6-(4-Chlorophenyl)-2-[1-(difluoromethyl)-1H-pyrazol-4-yl]-3-oxo-N-[(2S)-3,3,3-trifluoro-2-hydroxypropyl]-2,3-dihydropyridazine-4-carboxamide;

N-[(2R)-1-Hydroxy-3-methoxypropan-2-yl]-3-oxo-2-(pyridin-3-yl)-6-[4-(trifluoromethyl)phenyl]-2,3-dihydropyridazine-4-carboxamide;

6-(4-Chlorophenyl)-N-cis-2-hydroxycyclobutyl-3-oxo-2-(pyridin-3-yl)-2,3-dihydropyridazine-4-carboxamide;

6-(4-Chlorophenyl)-N-[(1S)-1-cyclopropyl-2-hydroxyethyl]-2-(5-fluoropyridin-3-yl)-3-oxo-2,3-dihydropyridazine-4-carboxamide;

N-[(2S)-3-Hydroxy-3-methylbutan-2-yl]-3-oxo-2-(1H-pyrazol-4-yl)-6-[4-(trifluoromethyl)phenyl]-2,3-dihydropyridazine-4-carboxamide;

2-[1-(Difluoromethyl)-1H-pyrazol-4-yl]-N-[(2S)-1-hydroxypropan-2-yl]-3-oxo-6-[4-(trifluoromethyl)phenyl]-2,3-dihydropyridazine-4-carboxamide;

2-[1-(Difluoromethyl)-1H-pyrazol-4-yl]-N-(2-hydroxy-2-methylpropyl)-3-oxo-6-[4-(trifluoromethyl)phenyl]-2,3-dihydropyridazine-4-carboxamide;

6-(4-Chlorophenyl)-N-[(1-hydroxycyclopropyl)methyl]-3-oxo-2-(pyridin-3-yl)-2,3-dihydropyridazine-4-carboxamide;

6-(4-Chlorophenyl)-2-[1-(difluoromethyl)-1H-pyrazol-4-yl]-N-[(2S)-3-hydroxy-3-methylbutan-2-yl]-3-oxo-2,3-dihydropyridazine-4-carboxamide;

6-(4-Chlorophenyl)-N-[(2R)-3-hydroxy-3-methylbutan-2-yl]-3-oxo-2-(pyrimidin-5-yl)-2,3-dihydropyridazine-4-carboxamide;

N-(2-Hydroxy-2-methylpropyl)-3-oxo-2-(1H-pyrazol-4-yl)-6-[4-(trifluoromethyl)phenyl]-2,3-dihydropyridazine-4-carboxamide;

Methyl N-{[6-(4-chlorophenyl)-2-(1-methyl-1H-pyrazol-4-yl)-3-oxo-2,3-dihydropyridazin-4-yl]carbonyl}-D-serinate;

(−)-N-cis-2-Hydroxycyclobutyl-3-oxo-2-(pyridin-3-yl)-6-[4-(trifluoromethyl)phenyl]-2,3-dihydropyridazine-4-carboxamide enantiomer 2;

6-(4-Chlorophenyl)-N-(2-hydroxy-2-methylpropyl)-2-(1,2-oxazol-4-yl)-3-oxo-2,3-dihydropyridazine-4-carboxamide;

6-(4-Chlorophenyl)-N-[(2S)-3-fluoro-2-hydroxypropyl]-2-(1-methyl-1H-pyrazol-4-yl)-3-oxo-2,3-dihydropyridazine-4-carboxamide;

6-(4-Chlorophenyl)-3-oxo-2-(pyrimidin-5-yl)-N-[(2R)-1,1,1-trifluoro-3-hydroxypropan-2-yl]-2,3-dihydropyridazine-4-carboxamide;

6-(4-Chlorophenyl)-2-[1-(difluoromethyl)-1H-pyrazol-4-yl]-N-[(2S)-1-hydroxypropan-2-yl]-3-oxo-2,3-dihydropyridazine-4-carboxamide;

6-(4-Chlorophenyl)-N-[(1S)-1-cyclopropyl-2-hydroxyethyl]-3-oxo-2-(pyrimidin-5-yl)-2,3-dihydropyridazine-4-carboxamide;

Methyl N-{[6-(4-chlorophenyl)-3-oxo-2-(pyridin-3-yl)-2,3-dihydropyridazin-4-yl]carbonyl}-D-serinate;

6-[4-(Fluoromethyl)phenyl]-2-(1-methyl-1H-pyrazol-4-yl)-3-oxo-N-[(2R)-1,1,1-trifluoro-3-hydroxypropan-2-yl]-2,3-dihydropyridazine-4-carboxamide;

6-(4-Chlorophenyl)-N-[(2S)-3-hydroxy-3-methylbutan-2-yl]-3-oxo-2-(1H-pyrazol-4-yl)-2,3-dihydropyridazine-4-carboxamide;

6-(4-Chlorophenyl)-N-(2-hydroxy-2-methylpropyl)-3-oxo-2-(pyrimidin-5-yl)-2,3-dihydropyridazine-4-carboxamide;

6-(4-Chlorophenyl)-2-[1-(difluoromethyl)-1H-pyrazol-4-yl]-N-(2-hydroxy-2-methylpropyl)-3-oxo-2,3-dihydropyridazine-4-carboxamide;

6-(4-Chlorophenyl)-N-[(2R)-1-hydroxypropan-2-yl]-3-oxo-2-(pyrimidin-5-yl)-2,3-dihydropyridazine-4-carboxamide;

6-[4-(Fluoromethyl)phenyl]-3-oxo-2-(pyridin-3-yl)-N-[(2S)-3,3,3-trifluoro-2-hydroxypropyl]-2,3-dihydropyridazine-4-carboxamide;

(−)-6-(4-Chlorophenyl)-N-cis-2-hydroxycyclobutyl-3-oxo-2-(pyridin-3-yl)-2,3-dihydropyridazine-4-carboxamide, enantiomer 2;

6-[4-(Fluoromethyl)phenyl]-3-oxo-2-(pyridin-3-yl)-N-[(2R)-1,1,1-trifluoro-3-hydroxypropan-2-yl]-2,3-dihydropyridazine-4-carboxamide;

6-[4-(Fluoromethyl)phenyl]-2-(1-methyl-1H-pyrazol-4-yl)-3-oxo-N-[(2S)-3,3,3-trifluoro-2-hydroxypropyl]-2,3-dihydropyridazine-4-carboxamide;

6-[4-(Fluoromethyl)phenyl]-N-[(2S)-3-hydroxy-3-methylbutan-2-yl]-2-(1-methyl-1H-pyrazol-4-yl)-3-oxo-2,3-dihydropyridazine-4-carboxamide;

6-[4-(Fluoromethyl)phenyl]-N-[(2S)-1-hydroxypropan-2-yl]-3-oxo-2-(pyridin-3-yl)-2,3-dihydropyridazine-4-carboxamide;

6-[4-(Fluoromethyl)phenyl]-N-(2-hydroxy-2-methylpropyl)-3-oxo-2-(pyridin-3-yl)-2,3-dihydropyridazine-4-carboxamide;

6-[4-(Fluoromethyl)phenyl]-N-[(2S)-1-hydroxypropan-2-yl]-2-(1-methyl-1H-pyrazol-4-yl)-3-oxo-2,3-dihydropyridazine-4-carboxamide;

6-[4-(Fluoromethyl)phenyl]-N-[(2S)-3-hydroxy-3-methylbutan-2-yl]-3-oxo-2-(pyridin-3-yl)-2,3-dihydropyridazine-4-carboxamide;

N-[(2R)-1-Amino-3-hydroxy-1-oxopropan-2-yl]-6-(4-chlorophenyl)-2-(1-methyl-1H-pyrazol-4-yl)-3-oxo-2,3-dihydropyridazine-4-carboxamide;

N-cis-4-Hydroxytetrahydrothiophen-3-yl-3-oxo-2-(pyridin-3-yl)-6-[4-(trifluoromethyl)phenyl]-2,3-dihydropyridazine-4-carboxamide;

(−)-N-cis-4-Hydroxytetrahydrothiophen-3-yl-3-oxo-2-(pyridin-3-yl)-6-[4-(trifluoromethyl)phenyl]-2,3-dihydropyridazine-4-carboxamide, enantiomer 2;

N-(2-Hydroxy-2-methylpropyl)-3-oxo-2-(pyridin-3-yl)-6-[4-(trifluoromethoxy)phenyl]-2,3-dihydropyridazine-4-carboxamide;

3-Oxo-2-(pyridin-3-yl)-N-[(2R)-3,3,3-trifluoro-2-hydroxypropyl]-6-[4-(trifluoromethoxy)phenyl]-2,3-dihydropyridazine-4-carboxamide;

N-[(2R)-3-Hydroxy-3-methylbutan-2-yl]-3-oxo-2-(pyridin-3-yl)-6-[4-(trifluoromethoxy)phenyl]-2,3-dihydropyridazine-4-carboxamide;

N-[(2S)-3,3-Difluoro-2-hydroxypropyl]-3-oxo-2-(pyridin-3-yl)-6-[4-(trifluoromethoxy)phenyl]-2,3-dihydropyridazine-4-carboxamide;

N-[(2S)-3-Fluoro-2-hydroxypropyl]-3-oxo-2-(pyridin-3-yl)-6-[4-(trifluoromethoxy)phenyl]-2,3-dihydropyridazine-4-carboxamide;

6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 1;

6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 2;

6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 3;

6-(4-Chlorophenyl)-3-oxo-2-(pyridin-3-yl)-N-(4,4,4-trifluoro-3-hydroxybutan-2-yl)-2,3-dihydropyridazine-4-carboxamide Isomer 4;

6-(4-Chlorophenyl)-2-(5-fluoropyridin-3-yl)-N-[(cis)-4-hydroxytetrahydrofuran-3-yl]-3-oxo-2,3-dihydropyridazine-4-carboxamide;

6-(4-Chlorophenyl)-N-[(2R)-3-hydroxy-3-methylbutan-2-yl]-3-oxo-2-(pyridin-3-yl)-2,3-dihydropyridazine-4-carboxamide;

6-(4-Chlorophenyl)-2-(5-chloropyridin-3-yl)-N-[(2S)-1-hydroxypropan-2-yl]-3-oxo-2,3-dihydropyridazine-4-carboxamide;

6-(4-Chlorophenyl)-N-[(2S)-1-hydroxypropan-2-yl]-2-(5-methylpyridin-3-yl)-3-oxo-2,3-dihydropyridazine-4-carboxamide;

6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide;

6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide Isomer 1;

6-[4-(Difluoromethoxy)phenyl]-2-(1-methyl-1H-pyrazol-4-yl)-3-oxo-N-(1,1,1-trifluoro-3-hydroxy-3-methylbutan-2-yl)-2,3-dihydropyridazine-4-carboxamide Isomer 2;

6-[4-(Difluoromethoxy)phenyl]-N-[(2S)-1-hydroxypropan-2-yl]-2-(1-methyl-1H-pyrazol-4-yl)-3-oxo-2,3-dihydropyridazine-4-carboxamide;

6-[4-(Difluoromethoxy)phenyl]-N-[(2S)-3-hydroxy-3-methylbutan-2-yl]-2-(1-methyl-1H-pyrazol-4-yl)-3-oxo-2,3-dihydropyridazine-4-carboxamide;

6-[4-(Dimethylamino)phenyl]-N-[(2S)-3-hydroxy-3-methylbutan-2-yl]-2-(1-methyl-1H-pyrazol-4-yl)-3-oxo-2,3-dihydropyridazine-4-carboxamide;

6-[4-(Dimethylamino)phenyl]-N-[(2S)-1-hydroxypropan-2-yl]-2-(1-methyl-1H-pyrazol-4-yl)-3-oxo-2,3-dihydropyridazine-4-carboxamide;

N-[(2S)-3-Hydroxy-3-methylbutan-2-yl]-3-oxo-2-(1,2-thiazol-4-yl)-6-[4-(trifluoromethoxy)phenyl]-2,3-dihydropyridazine-4-carboxamide;

6-[4-(Difluoromethyl)phenyl]-3-oxo-2-(pyridin-3-yl)-N-[(2S)-3,3,3-trifluoro-2-hydroxypropyl]-2,3-dihydropyridazine-4-carboxamide;

6-[4-(Difluoromethoxy)phenyl]-3-oxo-2-(pyridin-3-yl)-N-[(2S)-3,3,3-trifluoro-2-hydroxypropyl]-2,3-dihydropyridazine-4-carboxamide;

6-[4-(Difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide Isomer 1;

6-(4-Chlorophenyl)-N-[(2S)-3-hydroxy-3-methylbutan-2-yl]-2-(1-methyl-1H-pyrazol-4-yl)-3-oxo-2,3-dihydropyridazine-4-carboxamide;

6-(4-Chlorophenyl)-N-(2-hydroxy-2-methylcyclopentyl)-2-(1-methyl-1H-pyrazol-4-yl)-3-oxo-2,3-dihydropyridazine-4-carboxamide;

6-[4-(Difluoromethyl)phenyl]-N-[(cis)-4-hydroxytetrahydrofuran-3-yl]-3-oxo-2-(pyridin-3-yl)-2,3-dihydropyridazine-4-carboxamide Isomer 1;

6-[4-(Difluoromethyl)phenyl]-N-[(2S)-3-hydroxy-3-methylbutan-2-yl]-3-oxo-2-(pyridin-3-yl)-2,3-dihydropyridazine-4-carboxamide;

6-[4-(Difluoromethyl)phenyl]-N-[(cis)-4-hydroxytetrahydrofuran-3-yl]-2-(1-methyl-1H-pyrazol-4-yl)-3-oxo-2,3-dihydropyridazine-4-carboxamide Isomer 2;

3-(4-Chlorophenyl)-6-oxo-N-[(2S)-3,3,3-trifluoro-2-hydroxypropyl]-6H-1,4'-bipyridazine-5-carboxamide;

6-[4-(Difluoromethyl)phenyl]-N-(2-hydroxy-2-methylpropyl)-3-oxo-2-(pyridin-3-yl)-2,3-dihydropyridazine-4-carboxamide;

6-[4-(Difluoromethyl)phenyl]-N-[(cis)-4-hydroxytetrahydrofuran-3-yl]-3-oxo-2-(pyridin-3-yl)-2,3-dihydropyridazine-4-carboxamide Isomer 2;

6-(4-Chlorophenyl)-N-[(2R)-1-hydroxypropan-2-yl]-2-(1-methyl-1H-pyrazol-4-yl)-3-oxo-2,3-dihydropyridazine-4-carboxamide;

6-(4-Chlorophenyl)-N-[(2R)-3-hydroxy-3-methylbutan-2-yl]-3-oxo-2-(1H-pyrazol-4-yl)-2,3-dihydropyridazine-4-carboxamide;

6-(4-Chlorophenyl)-N-[(2R)-3-hydroxy-3-methylbutan-2-yl]-3-oxo-2-(1,2-thiazol-4-yl)-2,3-dihydropyridazine-4-carboxamide;

N-[(2R)-3-Hydroxy-3-methylbutan-2-yl]-3-oxo-2-(1,2-thiazol-4-yl)-6-[4-(trifluoromethoxy)phenyl]-2,3-dihydropyridazine-4-carboxamide;

N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide;

N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide, isomer 1;

N-[(cis)-2-hydroxy-2-methylcyclopentyl]-3-oxo-2-(pyridin-3-yl)-6-[4-(trifluoromethoxy)phenyl]-2,3-dihydropyridazine-4-carboxamide, isomer 2;

6-[4-(difluoromethoxy)phenyl]-N-(2-hydroxy-2-methylpropyl)-3-oxo-2-(pyridin-3-yl)-2,3-dihydropyridazine-4-carboxamide;

6-[4-(difluoromethoxy)phenyl]-N-[(2S)-1-hydroxypropan-2-yl]-3-oxo-2-(pyridin-3-yl)-2,3-dihydropyridazine-4-carboxamide;

6-[4-(difluoromethoxy)phenyl]-N-[(2S)-3-hydroxy-3-methylbutan-2-yl]-3-oxo-2-(pyridin-3-yl)-2,3-dihydropyridazine-4-carboxamide;

6-[4-(difluoromethoxy)phenyl]-N-[(2S,3S)-3-hydroxybutan-2-yl]-3-oxo-2-(pyridin-3-yl)-2,3-dihydropyridazine-4-carboxamide;

6-(4-chlorophenyl)-N-[(cis)-2-hydroxy-2-methylcyclopentyl]-2-(1-methyl-1H-pyrazol-4-yl)-3-oxo-2,3-dihydropyridazine-4-carboxamide; isomer 1; and 6-(4-Chlorophenyl)-N-[(cis)-2-hydroxy-2-methylcyclopentyl]-2-(1-methyl-1H-pyrazol-4-yl)-3-oxo-2,3-dihydropyridazine-4-carboxamide; Isomer 2;

or a polymorph, an enantiomer, a diastereomer, a racemate, a tautomer, an N-oxide, a hydrate, a solvate, a physiologically acceptable salt, a solvate of the physiologically acceptable salt, or a mixture of the same.

5. A method of preparing a compound of formula (I) according to claim 1, said method comprising reacting an intermediate compound of formula (VII):

(VII)

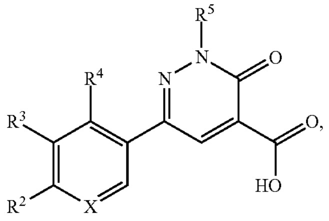

wherein X, $R^2$, $R^3$, $R^4$ and $R^5$ are as defined for the compound of formula (I) according to claim 1, with a compound of formula (VIII):

(VIII)

$H_2N-R^1$, wherein $R^1$ is as defined for the compound of formula (I) according to claim 1, thereby giving a compound of formula (I):

(I)

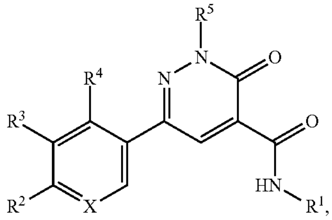

wherein X, $R^1$, $R^2$, $R^3$, $R^4$ and $R^5$ are as defined for the compound of formula (I) according to claim 1.

6. A method of preparing a compound of formula (I) according to claim 1, said method comprising reacting an intermediate compound of formula (XII):

(XII)

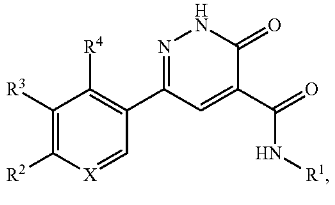

wherein X, $R^1$, $R^2$, $R^3$ and $R^4$ are as defined for the compound of formula (I) according to claim 1, with a compound of formula (XIV):

(XIV)

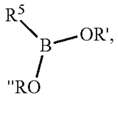

wherein $R^5$ is as defined for the compound of formula (I) according to claim 1, and R' and R" are simultaneously H or $C_1$-$C_4$-alkyl, or R' and R" form together a $C_2$-$C_7$-alkylene group as part of a 1,2- or 1,3-diol boronic ester or a —CO—$CH_2$—($NCH_3$)—$CH_2$—CO— group;

thereby giving a compound of formula (I):

(I)

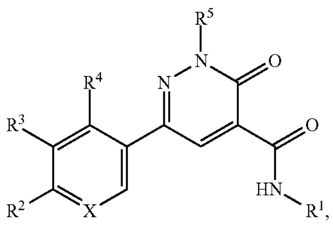

wherein X, $R^1$, $R^2$, $R^3$, $R^4$ and $R^5$ are as defined for the compound of formula (I) according to claim 1.

7. A pharmaceutical composition comprising a compound of formula (I) according to claim 1 and one or more pharmaceutically acceptable excipients.

8. A pharmaceutical combination comprising:

one or more first active ingredients, wherein the one or more first active ingredients are selected from the group consisting of compounds of formula (I) according to claim 1, and one or more pharmaceutical active anti cancer compounds or one or more pharmaceutical active immune checkpoint inhibitors.

9. The pharmaceutical combination according to claim 8, wherein the pharmaceutical active immune checkpoint inhibitor is an antibody.

10. The pharmaceutical combination according to claim 9, wherein the pharmaceutical active immune checkpoint inhibitor is the antibody TPP-3911.

11. A method for treating a disease to a human in need thereof, comprising administering a compound of formula (I) according to claim 1 to the human.

12. A method for treating a disease in a human or animal in need thereof, comprising administering a compound of formula (I) according to claim 1 to the human or animal, wherein the disease is cancer, a condition with dysregulated immune responses or a disorder associated with aberrant AHR signaling.

13. A compound of formula (VII):

(VII)

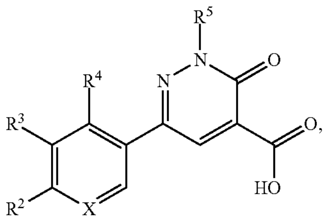

wherein $R^2$ is chloro, cyano, dimethylamino, methyl, fluoromethyl, difluoromethyl, trifluoromethyl, methoxy, difluoromethoxy or trifluoromethoxy;

$R^3$ is hydrogen, fluoro, chloro or methyl;

$R^4$ is hydrogen or fluoro;

$R^5$ is monocyclic heteroaryl, which is optionally substituted one to three times, independently from each other, with $R^6$;

$R^6$ is $C_1$-$C_4$-alkyl, $C_1$-$C_4$-haloalkyl, $C_3$-$C_6$-cycloalkyl, $C_1$-$C_4$-alkoxy, halogen or cyano, and X is CH.

14. A compound of formula (XII):

(XII)

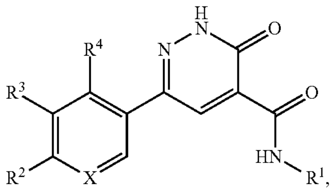

wherein $R^1$ is $C_2$-$C_6$-hydroxyalkyl, wherein said $C_2$-$C_6$-hydroxyalkyl groups are optionally substituted once with cyano, —$COOR^{10}$, —$CONR^{11}R^{12}$, $C_1$-$C_4$-alkoxy or $C_3$-$C_6$-cycloalkyl and optionally one to three times with halogen, or $C_3$-$C_6$-cycloalkyl substituted once with hydroxy and optionally once with $C_1$-$C_3$-alkyl and/or one to three times with halogen, or $C_3$-$C_6$-cycloalkyl-$C_1$-$C_3$-alkyl substituted once with hydroxy and optionally once with $C_1$-$C_3$-alkyl and/or one to three times with halogen, or ($C_3$-$C_6$-cycloalkyl)$_2$-$C_1$-$C_3$-alkyl substituted once with hydroxy and optionally once with $C_1$-$C_3$-alkyl and/or one to three times with halogen, or 4- to 6-membered heterocycloalkyl substituted once with hydroxy and optionally once with $C_1$-$C_3$-alkyl and/or one to three times with halogen;

$R^2$ is chloro, cyano, dimethylamino, methyl, fluoromethyl, difluoromethyl, trifluoromethyl, methoxy, difluoromethoxy or trifluoromethoxy;

$R^3$ is hydrogen, fluoro, chloro or methyl;

$R^4$ is hydrogen or fluoro; and

X is CH.

15. The method of claim 12, wherein the disease is a liquid or solid tumor.

* * * * *